US010189912B2

(12) United States Patent
Walker et al.

(10) Patent No.: US 10,189,912 B2
(45) Date of Patent: *Jan. 29, 2019

(54) CARRIER IMMUNOGLOBULINS

(71) Applicant: AMGEN INC., Thousand Oaks, CA (US)

(72) Inventors: Kenneth W. Walker, Newbury Park, CA (US); Yue-Sheng Li, Cambridge, MA (US); Thomas Charles Boone, Newbury Park, CA (US); George Doellgast, Asheville, NC (US); HoSung Min, Seoul (KR); Jane Talvenheimo, Seattle, WA (US); Taruna Arora, Palo Alto, CA (US); Frederick W. Jacobsen, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 15/405,233

(22) Filed: Jan. 12, 2017

(65) Prior Publication Data

US 2017/0190793 A1 Jul. 6, 2017

Related U.S. Application Data

(60) Continuation of application No. 14/285,576, filed on May 22, 2014, now Pat. No. 9,562,107, which is a division of application No. 13/258,668, filed as application No. PCT/US2010/028060 on Mar. 19, 2010, now Pat. No. 8,734,796.

(60) Provisional application No. 61/210,594, filed on Mar. 20, 2009.

(51) Int. Cl.
| | |
|---|---|
| *C07K 16/44* | (2006.01) |
| *A61K 39/395* | (2006.01) |
| *C07K 16/00* | (2006.01) |
| *C07K 16/18* | (2006.01) |
| *C07K 14/435* | (2006.01) |
| *C07K 14/575* | (2006.01) |
| *C07K 14/605* | (2006.01) |
| *C07K 16/24* | (2006.01) |
| *C07K 14/66* | (2006.01) |
| *A61K 47/68* | (2017.01) |

(52) U.S. Cl.
CPC ........ *C07K 16/44* (2013.01); *A61K 39/39591* (2013.01); *A61K 47/6817* (2017.08); *A61K 47/6843* (2017.08); *C07K 14/43504* (2013.01); *C07K 14/575* (2013.01); *C07K 14/605* (2013.01); *C07K 14/66* (2013.01); *C07K 16/00* (2013.01); *C07K 16/18* (2013.01); *C07K 16/248* (2013.01); *C07K 2317/21* (2013.01); *C07K 2317/24* (2013.01); *C07K 2317/56* (2013.01); *C07K 2317/565* (2013.01); *C07K 2317/92* (2013.01); *C07K 2317/94* (2013.01); *C07K 2319/00* (2013.01); *C07K 2319/30* (2013.01); *C07K 2319/55* (2013.01)

(58) Field of Classification Search
CPC .............. C07K 16/44; C07K 2317/565; A61K 39/39591
See application file for complete search history.

(56) References Cited

U.S. PATENT DOCUMENTS

| | | |
|---|---|---|
| 6,072,037 A | 6/2000 | Yao et al. |
| 6,932,969 B1 | 8/2005 | Bourel et al. |
| 7,067,131 B2 | 6/2006 | Gudas et al. |
| 7,326,414 B2 | 2/2008 | Bedian et al. |
| 7,521,048 B2 | 4/2009 | Gliniak et al. |
| 2006/0140948 A1 | 6/2006 | Foltz et al. |
| 2006/0246071 A1 | 11/2006 | Green et al. |
| 2007/0148180 A1 | 6/2007 | Fischer et al. |
| 2007/0166308 A1 | 7/2007 | Pullen et al. |
| 2007/0269369 A1 | 11/2007 | Gegg et al. |
| 2008/0152587 A1 | 6/2008 | Zhou et al. |
| 2008/0268462 A1 | 10/2008 | Kosmeder et al. |
| 2009/0155275 A1 | 6/2009 | Wu et al. |

FOREIGN PATENT DOCUMENTS

| | | |
|---|---|---|
| WO | WO 00/09730 | 2/2000 |
| WO | WO 01/62931 A2 | 8/2001 |
| WO | WO 03/080672 A1 | 10/2003 |
| WO | WO 2004/096271 A1 | 11/2004 |
| WO | WO 2005/037235 A2 | 4/2005 |
| WO | WO 2005/040229 A2 | 5/2005 |
| WO | WO 2006/055689 A2 | 5/2006 |
| WO | WO 2006/127040 A2 | 11/2006 |
| WO | WO 2007/027713 A2 | 3/2007 |
| WO | WO 2007/045463 A1 | 4/2007 |
| WO | WO 2008/054603 C2 | 5/2008 |

(Continued)

OTHER PUBLICATIONS

Davies, et al., "Structural Basis of Antibody Function", *Ann. Rev. Immunol*, 1: 87-117 (1983).

(Continued)

*Primary Examiner* — Prema M Mertz
(74) *Attorney, Agent, or Firm* — Angela L. Purcell

(57) ABSTRACT

Disclosed is an isolated antigen binding protein, such as but not limited to, an antibody or antibody fragment. Also disclosed are pharmaceutical compositions and medicaments comprising the antigen binding protein, isolated nucleic acid encoding it, vectors, host cells, and hybridomas useful in methods of making it. In some embodiments the antigen binding protein comprises one to twenty-four pharmacologically active chemical moieties conjugated thereto, such as a pharmacologically active polypeptide.

24 Claims, 55 Drawing Sheets

Specification includes a Sequence Listing.

(56) References Cited

FOREIGN PATENT DOCUMENTS

| WO | WO 2008/088422 A2 | 7/2008 |
|---|---|---|
| WO | WO 2009/086411 A2 | 7/2009 |
| WO | WO 2010/054007 A1 | 5/2010 |
| WO | WO 2010/088522 A2 | 8/2010 |
| WO | WO 2010/108153 A2 | 9/2010 |
| WO | WO 2010/108153 A3 | 9/2010 |
| WO | WO 2010/108154 A2 | 9/2010 |
| WO | WO 2010/108154 A3 | 9/2010 |
| WO | WO 2011/094593 A2 | 8/2011 |
| WO | WO 2012/040518 A2 | 3/2012 |
| WO | WO 2012/040518 A3 | 3/2012 |

OTHER PUBLICATIONS

Dougan, et al., "Effects of substitutions in binding surface of an antibody on antigen affinity", *Protein Engineering*, 11(1): 65-74 (1998).

Fagerstam, et al., "Detection of Antigen-Antibody Interactions by Surface Plasmon Resonance, Application to Epitope Mapping", *J of Molecular Recognition*, 3(5/6): 208-214 (1990).

He, et al., "Effects of mutation at the $D$-$J_h$ junction on affinity, specificity, and idiotypy of anti-progesterone antibody DB3", *Protein Science* 15: 2141-2148 (2006).

Hirayama et al., (Jan. 1982) "Biological activities of antitrinitrophenyl and antidinitrophenyl mouse monoclonal antibodies," Proc. Natl. Acad. Sci. USA, vol. 79, 613-615.

Igawa, et al., "Reduced elimination of IgG antibodies by engineering the variable region", *Protein Engineering, Design & Selection*, 23(5): 385-392 (2010).

Parhami-Seren, et al., "Structural Analysis of Mutants of High-Affinity and Low-Affinity p-Azophenylarsonal-Specific Antibodies Generated by Alanine Scanning of Heavy Chain Complementarity-Determining Region 2", *J of Immunol*, 167: 5129-5135 (2001).

Probes Product Information Sheet, entitled "Anti-Dinitrophenyl-KLH Antibodies", downloaded from the internet on Sep. 8, 2013 from the URL: http://probes.invitrogen.com/media/pis/mp06423.pdf>, 2 pgs.

Rudikoff et al., "Single amino acid substitution altering antigen-binding specificity", *PNSA USA*, 79: 1979-1983 (1982).

Sumida and Taniguchi, (Jun. 1985) "Novel mechanisms of specific suppression of anti-hapten antibody response mediated by monoclonal anti-carrier antibody," J. Immunol., vol. 134(6), 3675-3681.

Tamura et al., "Structural correlates of an anticarcinoma antibody: identification of specificity-determining residues (SDRs) and development of a minimally immunogenic antibody variant by retention of SDRs only", *J Immunol.*, 164: 1432-1441 (2000).

Tian, C. et al., (Mar. 2007) "Evidence for preferential Ig gene usage and differential TdT and exonuclease activities in human naïve and memory B cells," Mol. Immunol., vol. 44(9), 2173-2183.

Wang, X. et al., (Nov. 1999) "Immunoglobulin VH Gene Expression in Human Aging," Clin. Immunol., vol. 93(2), 132-142.

Yang, et al., "Preparation and Identification of anti-2, 4-dinitrophenyl monoclonal antibodies", *J of Immunol Methods*, 313: 20-28 (2006).

Zoon, FDA Document, "Points to Consider in the Manufacture and Testing of Monoclonal Products for Human Use", *U.S. Department of Health & Human Services, Food and Drug Administration, Center for Biologics Evaluation and Research*, 50 pgs, (1997).

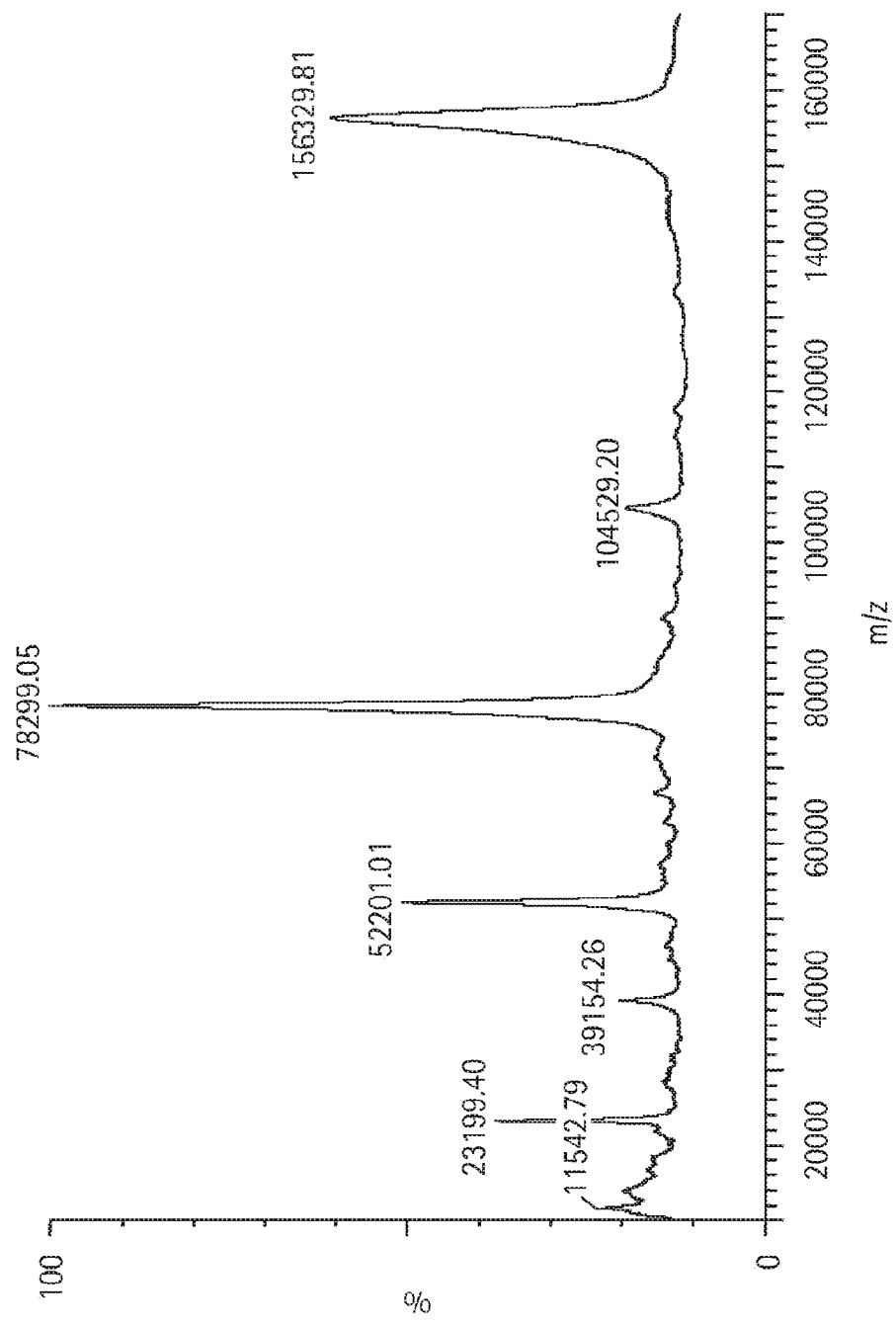

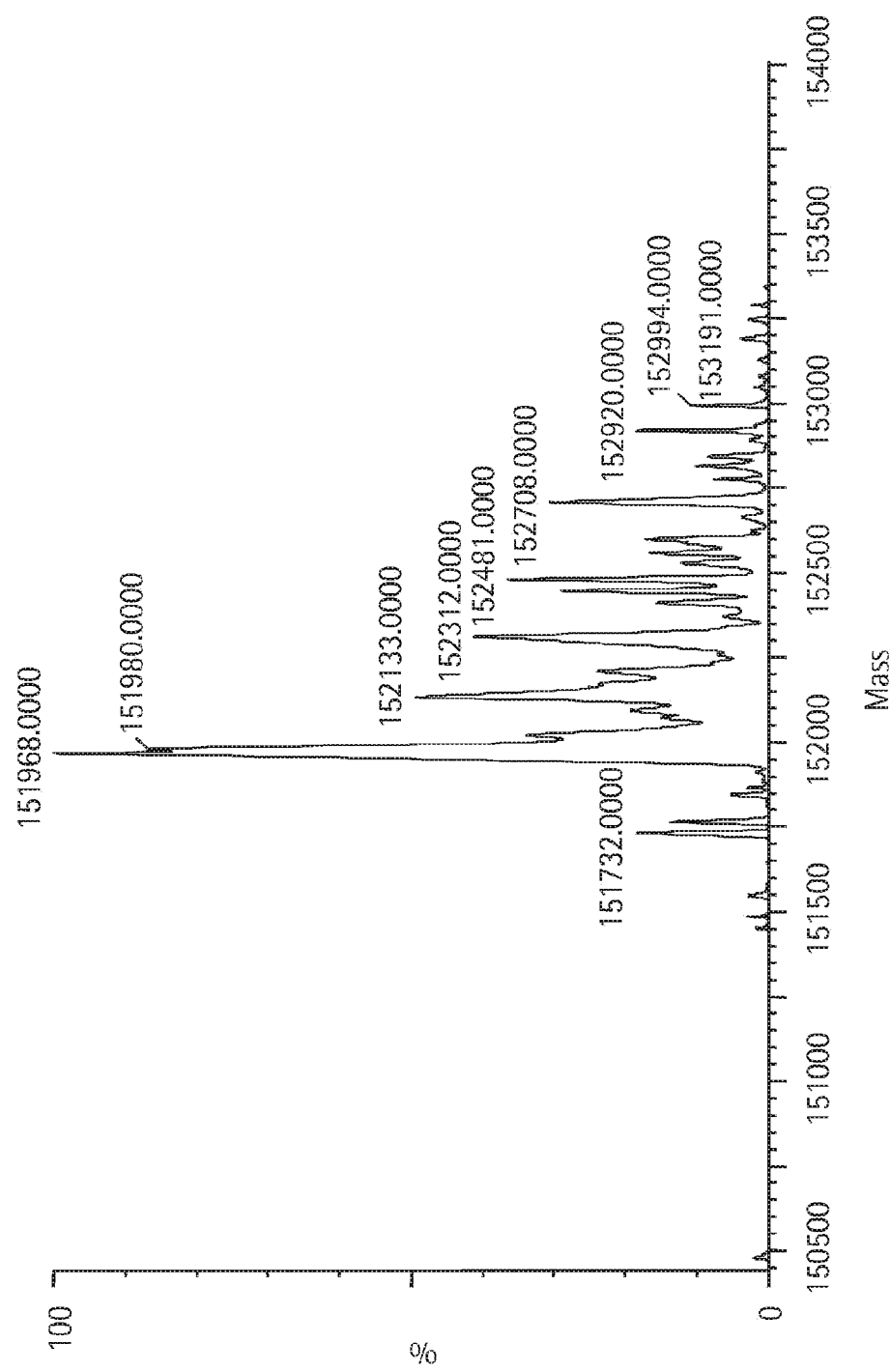

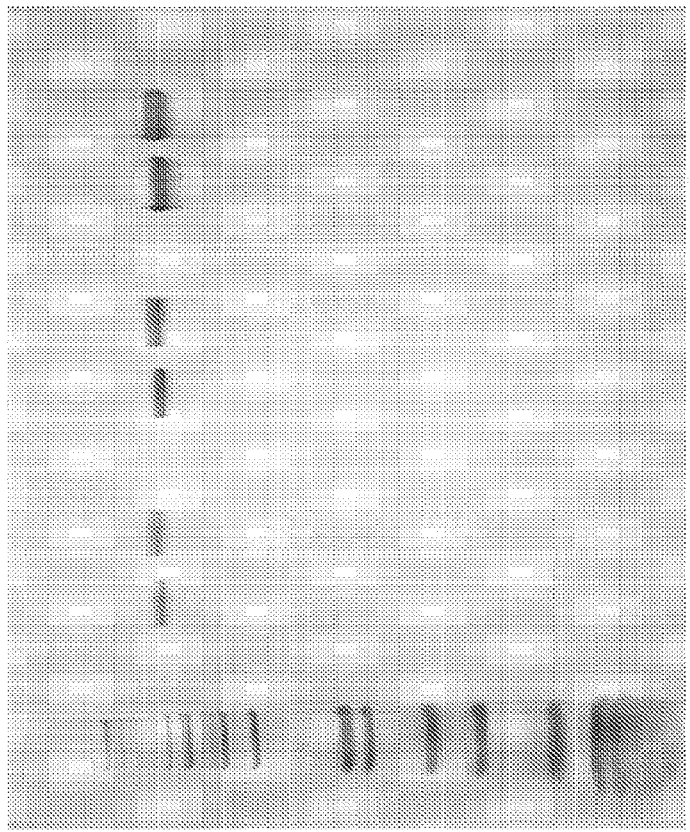
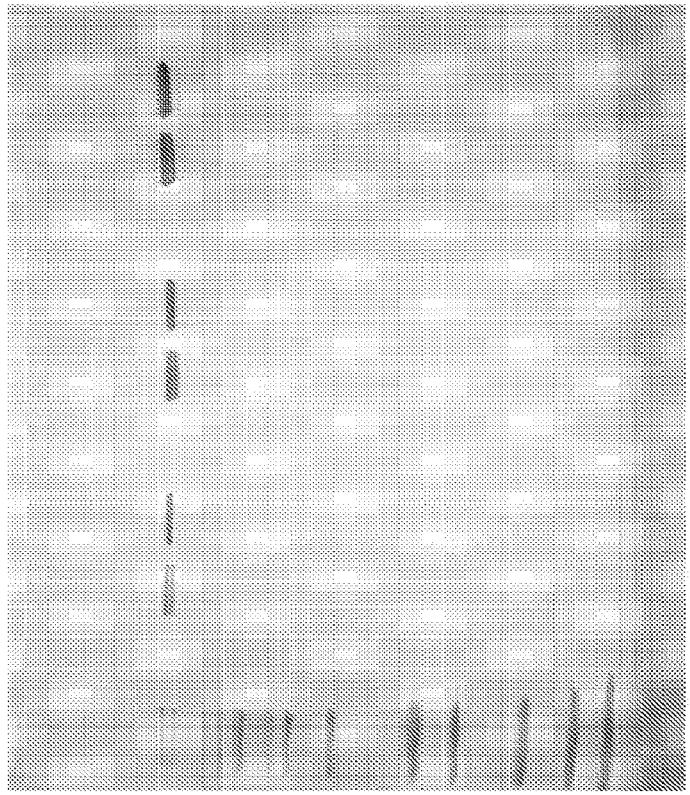
FIG. 13B
FIG. 13A

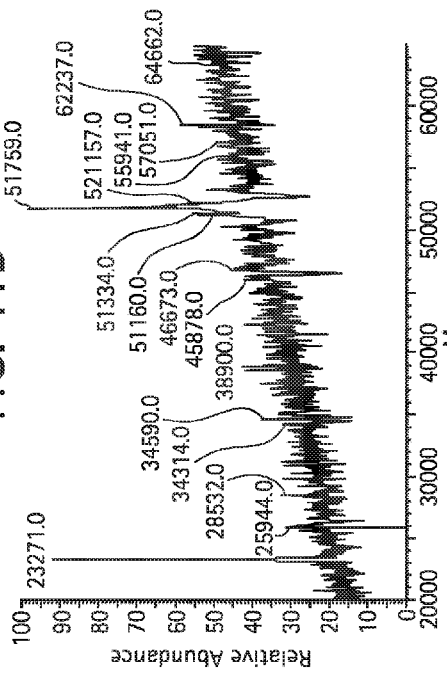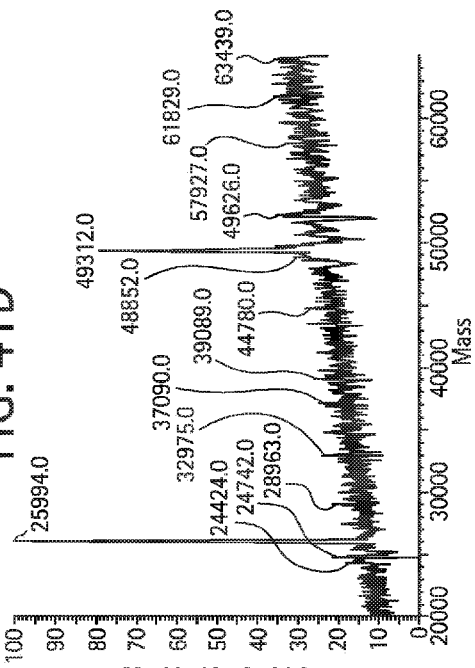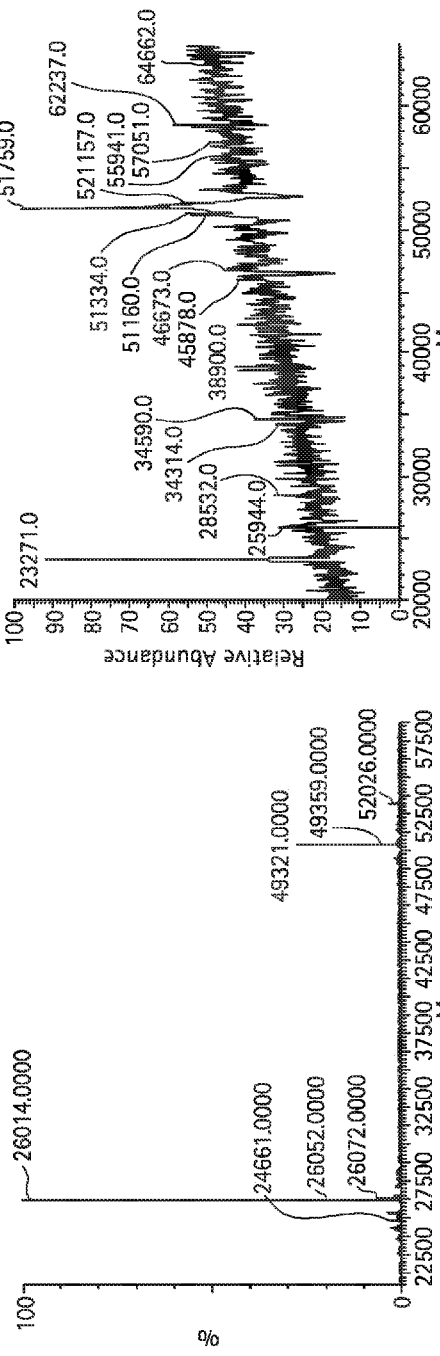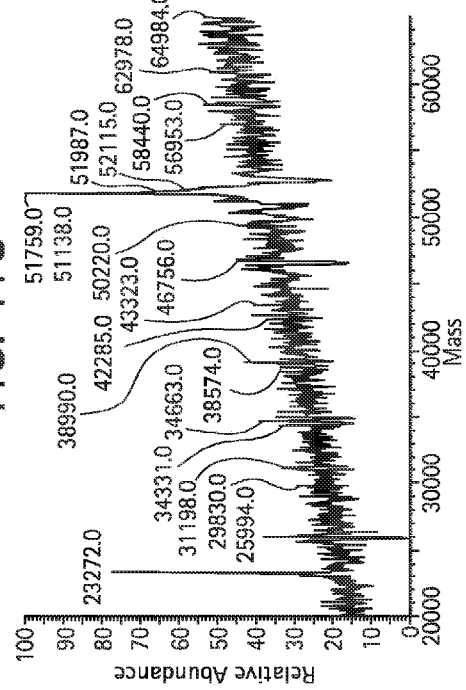

CARRIER IMMUNOGLOBULINS

This application is a continuation of U.S. application Ser. No. 14/285,576, filed May 22, 2014, which is a division of U.S. Nonprovisional application Ser. No. 13/258,668, filed Apr. 11, 2012, now U.S. Pat. No. 8,734,796, which is a national stage application under 35 U.S.C. 371 of International Application No. PCT/US10/28060, having an international filing date of Mar. 19, 2010, which claims the benefit of U.S. Provisional Application No. 61/210,594, filed Mar. 20, 2009, all of which are hereby incorporated by reference in their entireties.

The instant application contains an ASCII "txt" compliant sequence listing submitted via EFS-WEB on Jan. 12, 2017, which serves as both the computer readable form (CRF) and the paper copy required by 37 C.F.R. Section 1.821(c) and 1.821(e), and is hereby incorporated by reference in its entirety. The name of the "txt" file created on Jan. 10, 2017, is: A-1537-US-CNT_ST25 and is 549 kb in size.

Throughout this application various publications are referenced within parentheses or brackets. The disclosures of these publications in their entireties are hereby incorporated by reference in this application in order to more fully describe the state of the art to which this invention pertains.

BACKGROUND OF THE INVENTION

1. Field of the Invention

This invention relates to carrier antibodies to which one or more pharmacologically active chemical moieties can be conjugated for improved pharmacokinetic characteristics.

2. Discussion of the Related Art

A "carrier" moiety refers to a pharmacologically inactive molecule to which a pharmacologically active chemical moiety, such as a non-peptide organic moiety (i.e., "small molecule") or a polypeptide agent, can be covalently conjugated or fused. Effective carriers have been sought to prevent or mitigate in vivo degradation of pharmacologically active moieties by proteolysis or other in vivo activity-diminishing chemical modifications of the pharmacologically active chemical moiety, or to reduce renal clearance, to enhance in vivo half-life or other pharmacokinetic properties of a therapeutic, such as increasing the rate of absorption, reducing toxicity or immunogenicity, improving solubility, and/or increasing manufacturability or storage stability, compared to an unconjugated form of the pharmacologically active moiety.

Examples of such carrier moieties that have been employed in the pharmaceutical industry include polyethylene glycol (see, e.g., Burg et al., Erythropoietin conjugates with polyethylene glycol, WO 01/02017), immunoglobulin Fc domain (see, e.g., Feige et al., Modified peptides as therapeutic agents, U.S. Pat. No. 6,660,843), human serum albumin (see, e.g., Rosen et al., Albumin fusion proteins, U.S. Pat. No. 6,926,898 and US 2005/0054051; Bridon et al., Protection of endogenous therapeutic peptides from peptidase activity through conjugation to blood components, U.S. Pat. No. 6,887,470), transthyretin (see, e.g., Walker et al., Use of transthyretin peptide/protein fusions to increase the serum half-life of pharmacologically active peptides/proteins, US 2003/0195154 A1; 2003/0191056 A1), or thyroxine-binding globulin, or a combination such as immunoglobulin (light chain+heavy chain) and Fc domain (the heterotrimeric combination a so-called "hemibody"), (for example as described in Sullivan et al., Toxin Peptide Therapeutic Agents, PCT/US2007/022831, published as WO 2008/088422. Pharmacologically active moieties have also been conjugated to a peptide or small molecule that has an affinity for a long half-life serum protein. (See, e.g., Blaney et al., Method and compositions for increasing the serum half-life of pharmacologically active agents by binding to transthyretin-selective ligands, U.S. Pat. No. 5,714, 142; Sato et al., Serum albumin binding moieties, US 2003/0069395 A1; Jones et al., Pharmaceutical active conjugates, U.S. Pat. No. 6,342,225).

Fischer et al. described a peptide-immunoglobulin-conjugate, in which the immunoglobulin consisted of two heavy chains or two heavy chains and two light chains, in which the immunoglobulin was not a functionable immunoglobulin (Fischer et al., A peptide-immunoglobulin conjugate, WO 2007/045463 A1).

The present invention provides carrier immunoglobulins yielding exceptional uniformity and efficiency of recombinant expression, in vitro stability and non-aggregation, resistance to photodegradation and oxidation, non-cross-reactivity with human antigens, and good pharmacokinetic properties.

SUMMARY OF THE INVENTION

The invention relates to antigen binding proteins. The inventive antigen binding proteins, including antibodies and antibody fragments, have reliable expression and purification characteristics, resulting in products that are stable and relatively uniform, and have outstanding pharmacokinetic (PK) properties in rats and cynomolgous monkeys. The inventive antigen binding proteins are found to specifically bind to dinitrophenol (DNP) or keyhole limpet hemocynanin (KLH), but have not been detected to bind to human proteins, cells or tissues. These antigen binding prioteins can be used for many purposes, including, but not limited to, quality control or analytical standards for antibody-based drugs and as controls for biologically relevant isotype-matched antibodies.

In some embodiments, the antigen binding protein of the present invention is used as a carrier for pharmacologically active chemical moieties, e.g., small molecules, peptides, and/or proteins to enhance their PK properties. The pharmacologically active moieties can be conjugated, i.e., covalently bound, to the inventive immunoglobulin by a chemical conjugation reaction, or through recombinant genetic expression, they can be fused to the antigen binding protein.

The invention also provides materials and methods for producing such inventive immunoglobulins, including isolated nucleic acids that encode them, vectors and isolated host cells, and hybridomas. Also provided are isolated nucleic acids encoding any of the immunoglobulin heavy and/or light chain sequences and/or VH and/or VL sequences and/or CDR sequences disclosed herein. In a related embodiment, an expression vector comprising any of the aforementioned nucleic acids is provided. In still another embodiment, a host cell is provided comprising any of the aforementioned nucleic acids or expression vectors.

The inventive immunoglobulin can be used in the manufacture of a pharmaceutical composition or medicament. The inventive pharmaceutical composition or medicament comprises the immunoglobulin conjugated with a pharmacologically active agent, and a pharmaceutically acceptable diluent, carrier or excipient.

Numerous methods are contemplated in the present invention. For example, a method is provided involving culturing the aforementioned host cell comprising the expression vector of the invention such that the encoded antigen binding protein is expressed. A method is also provided involving culturing the aforementioned hybridoma in a culture medium under conditions permitting expression of the antigen binding protein by the hybridoma. Such methods can also comprise the step of recovering the antigen binding protein from the host cell culture. In a related embodiment, an isolated antigen binding protein produced by the aforementioned method is provided.

The foregoing summary is not intended to define every aspect of the invention, and additional aspects are described in other sections, such as the Detailed Description of Embodiments. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIG. 1A represents a monovalent heterodimeric Fc-toxin peptide analog fusion with the toxin peptide analog fused to the C-terminal end of one of the immunoglobulin Fc domain monomers. FIG. 1N represents a monovalent antibody with a toxin peptide analog moiety inserted into an internal loop of the immunoglobulin Fc domain of one of the HC monomers. Dimers or trimers will form spontaneously in certain host cells upon expression of a deoxyribonucleic acid (DNA) construct encoding a single chain. In other host cells, the cells can be placed in conditions favoring formation of dimers/trimers or the dimers/trimers can be formed in vitro. If more than one HC monomer, LC monomer, or immunoglobulin Fc domain monomer is part of a single embodiment, the individual monomers can be, if desired, identical or different from each other.

Part of the column effluent was diverted into a Waters LCT Premier ESI-TOF mass spectrometer for mass analysis. The instrument was run in the positive V mode. The capillary voltage was set at 3,200 V and the cone voltage at 80 V. The mass spectrum was acquired from 800 to 3000 tt m/z and deconvoluted using the MaxEnt1 software provided by the instrument manufacturer.

Figure 4A:
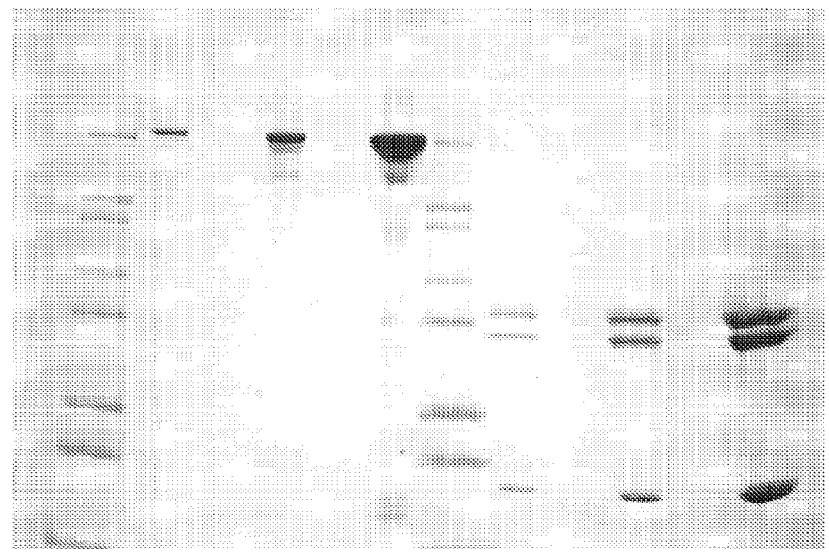

FIG. 4A shows a Coomassie brilliant blue stained Tris-glycine 4-20% SDS-PAGE of the final monovalent anti-KLH HC-L10-ShK[1-35, Q16K] Ab product described in Example 4. Lanes 1-12 were loaded as follows: lane 1: Novex Mark12 wide range protein standards (10 µl); lane 2: 0.5 µg product, non-reduced; lane 3: blank; lane 4: 2.0 µg product, non-reduced; lane 5: blank; lane 6: 10 µg product, non-reduced; lane 7: Novex Mark12 wide range protein standards (10 µl); lane 8: 0.5 µg product, reduced; lane 9: blank; lane 10: 2.0 µg product, reduced; lane 11: blank; lane 12: 10 µg product, reduced.

Figure 4B:
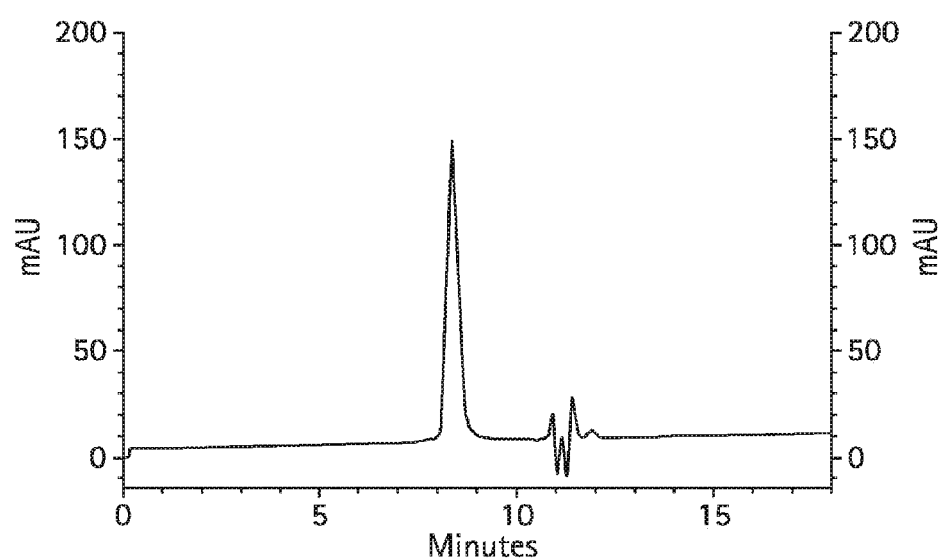

FIG. 4B shows size exclusion chromatography on 25 µg of the final monovalent anti-KLH 120.6 HC-L10-ShK[1-35, Q16K] antibody product, described in Example 4, injected onto a Phenomenex BioSep SEC-3000 column (7.8×300 mm) in 50 mM $NaH_2PO_4$, 250 mM NaCl, and pH 6.9 at 1 mL/min detecting the absorbance at 280 nm. The deflection observed at about 11 min is an injection-related artefact.

Figure 4C:
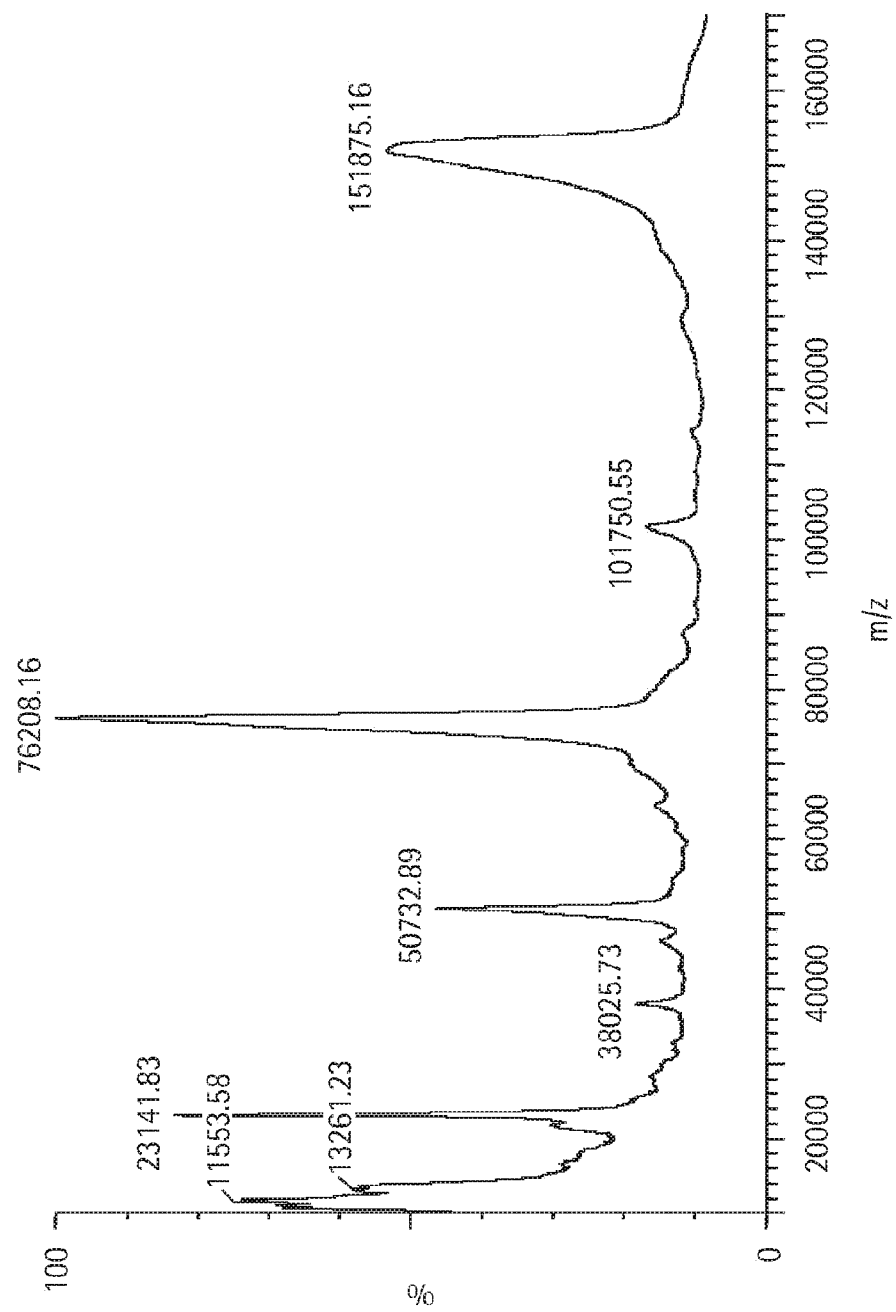

FIG. 4C shows a MALDI mass spectral analysis of the final sample of monovalent anti-KLH HC-L10-ShK[1-35, Q16K] Ab, described in Example 4, analyzed using a Micromass MALDI micro MX mass spectrometer equipped with a nitrogen laser. The sample was run at positive linear mode. The instrument's voltage was set at 12 kV and the high mass detector was set at 5 kV. Each spectrum was produced by accumulating data from about 200 laser shots. External mass calibration was achieved using purified proteins of known molecular masses.

Figure 5A:
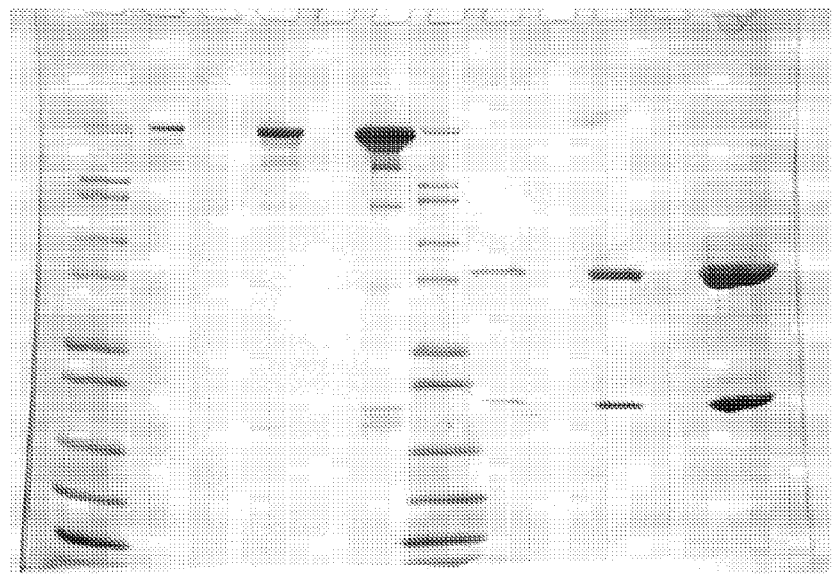

FIG. 5A shows a Coomassie brilliant blue stained Tris-glycine 4-20% SDS-PAGE of the final bivalent aKLH HC-L10-ShK [1-35 Q16K] Ab product, described in Example 4. Lanes 1-12 were loaded as follows: lane 1: Novex Mark12 wide range protein standards (10 µl); lane 2: 0.5 µg product, non-reduced; lane 3: blank; lane 4: 2.0 µg product, non-reduced; lane 5: blank; lane 6: 10 µg product, non-reduced; lane 7: Novex Mark12 wide range protein standards (10 µl); lane 8: 0.5 µg product, reduced; lane 9: blank; lane 10: 2.0 µg product, reduced; lane 11: blank; lane 12: 10 µg product, reduced.

Figure 5B:
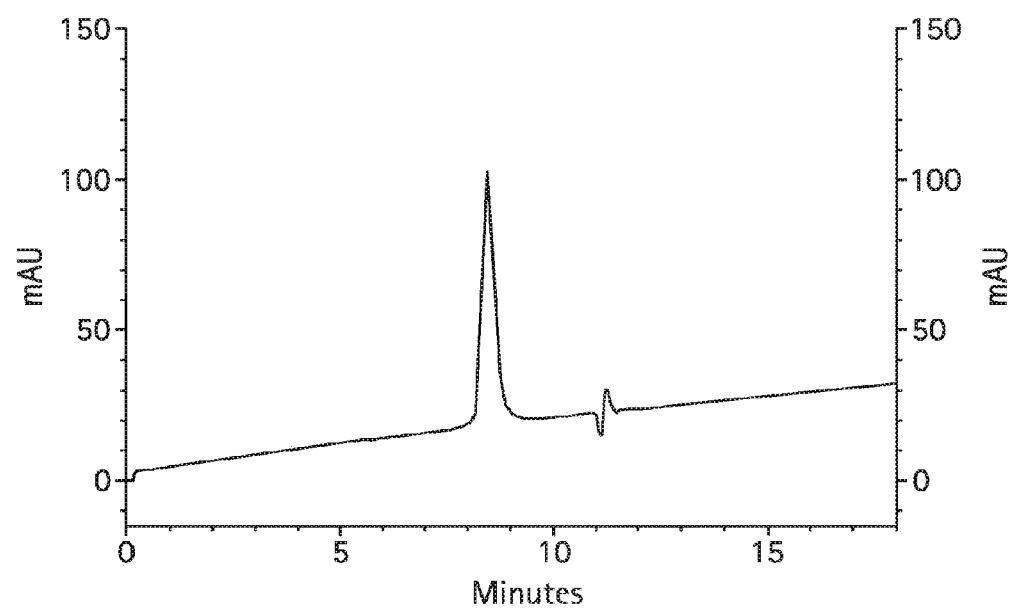

FIG. 5B shows size exclusion chromatography on 25 µg of the final bivalent anti-KLH HC-L10-ShK[1-35, Q16K] Ab product, described in Example 4, injected onto a Phenomenex BioSep SEC-3000 column (7.8×300 mm) in 50 mM $NaH_2PO_4$, 500 mM NaCl, and pH 6.9 at 1 mL/min detecting the absorbance at 280 nm. The deflection observed at about 11.5 min is an injection-related artefact.

FIG. 5C shows a MALDI mass spectral analysis of the final sample of bivalent anti-KLH HC-L10-ShK[1-35, Q16K] Ab, described in Example 4, analyzed using a Micromass MALDI micro MX mass spectrometer equipped with a nitrogen laser. The sample was run at positive linear mode. The instrument's voltage was set at 12 kV and the high mass detector was set at 5 kV. Each spectrum was produced by accumulating data from about 200 laser shots. External mass calibration was achieved using purified proteins of known molecular masses.

Figure 6A:
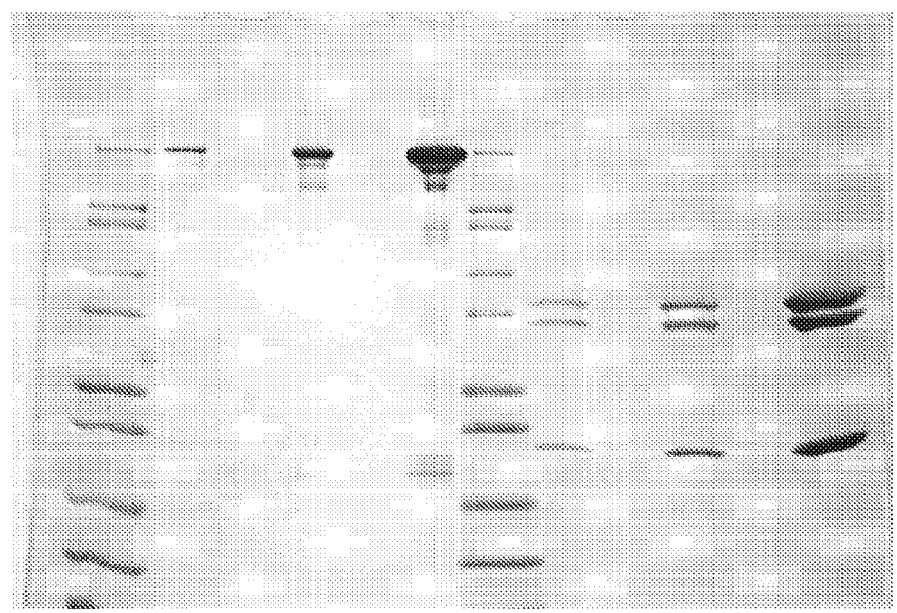

FIG. 6A shows a Coomassie brilliant blue stained Tris-glycine 4-20% SDS-PAGE of the final monovalent KLH HC-L10-ShK[2-35, Q16K] Ab product, described in Example 4. Lanes 1-12 were loaded as follows: lane 1: Novex Mark12 wide range protein standards (10 µl); lane 2: 0.5 µg product, non-reduced; lane 3: blank; lane 4: 2.0 µg product, non-reduced; lane 5: blank; lane 6: 10 µg product, non-reduced; lane 7: Novex Mark12 wide range protein standards (10 µl); lane 8: 0.5 µg product, reduced; lane 9: blank; lane 10: 2.0 µg product, reduced; lane 11: blank; lane 12: 10 µg product, reduced.

Figure 6B:
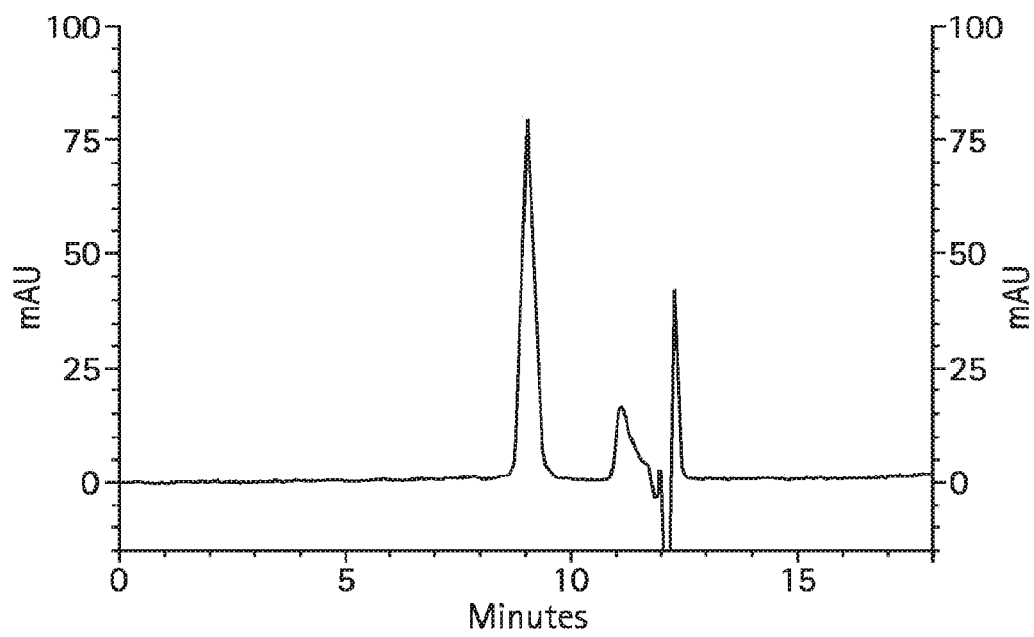

FIG. 6B shows size exclusion chromatography on 20 µg of the final monovalent anti-KLH HC-L10-ShK[2-35, Q16K] Ab product, described in Example 4, injected onto a Phenomenex BioSep SEC-3000 column (7.8×300 mm) in 50 mM $NaH_2PO_4$, 250 mM NaCl, and pH 6.9 at 1 mL/min detecting the absorbance at 280 nm. The deflection observed at about 11 min is an injection-related artefact.

FIG. 6C shows an LC-MS mass spectral analysis of the final sample of monovalent anti-KLH HC-L10-ShK[2-35, Q16K] Ab, described in Example 4. The product was chromatographed through a Waters MassPREP micro desalting column using a Waters ACQUITY UPLC system. The column was set at 80° C. and the protein eluted using a linear gradient of increasing acetonitrile concentration in 0.1% formic acid. Part of the column effluent was diverted into a Waters LCT Premier ESI-TOF mass spectrometer for mass analysis. The instrument was run in the positive V mode. The capillary voltage was set at 3,200 V and the cone voltage at 80 V. The mass spectrum was acquired from 800 to 3000 m/z and deconvoluted using the MaxEnt1 software provided by the instrument manufacturer.

Figure 7:
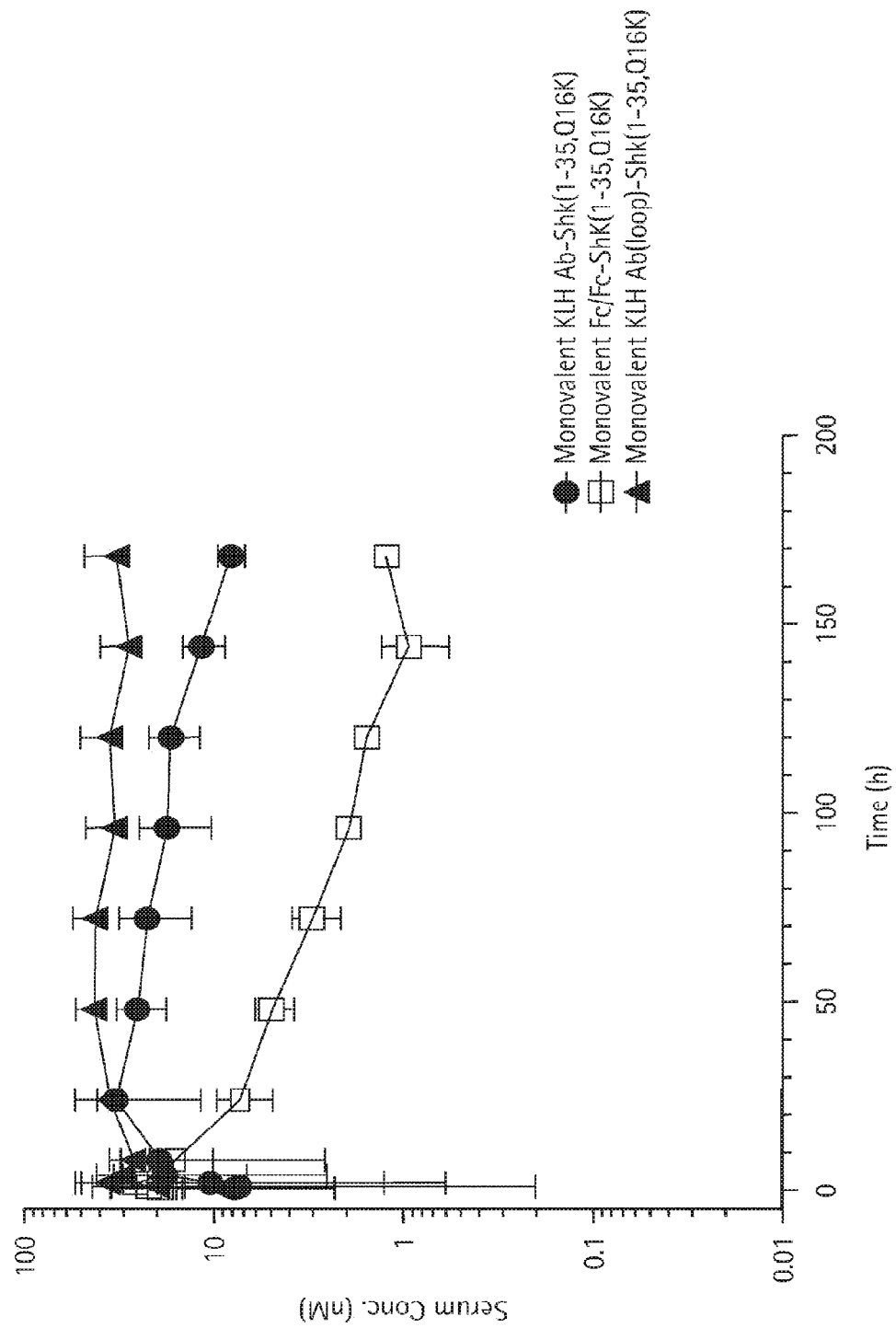

FIG. 7 shows results of pharmacokinetic studies (single-subcutaneous dose=6 mg/kg) performed in Sprague-Dawley rats. Open squares represent data for monovalent Fc/Fc-L10-ShK(1-35, Q16K) (heterodimer of SEQ ID NO: 1 and SEQ ID NO:26) closed circles represent data for monovalent anti-KLH antibody-ShK(1-35, Q16K) (tetramer of SEQ ID NO: 28, SEQ ID NO:29, SEQ ID NO:28, and SEQ ID NO:32); and closed triangles represent data for monovalent anti-KLH antibody (loop)-ShK(1-35, Q16K) (tetramer of SEQ ID NO: 28; SEQ ID NO:35; SEQ ID NO:28; and SEQ ID NO:34), described in Example 5 and Table 7H.

Figure 8:
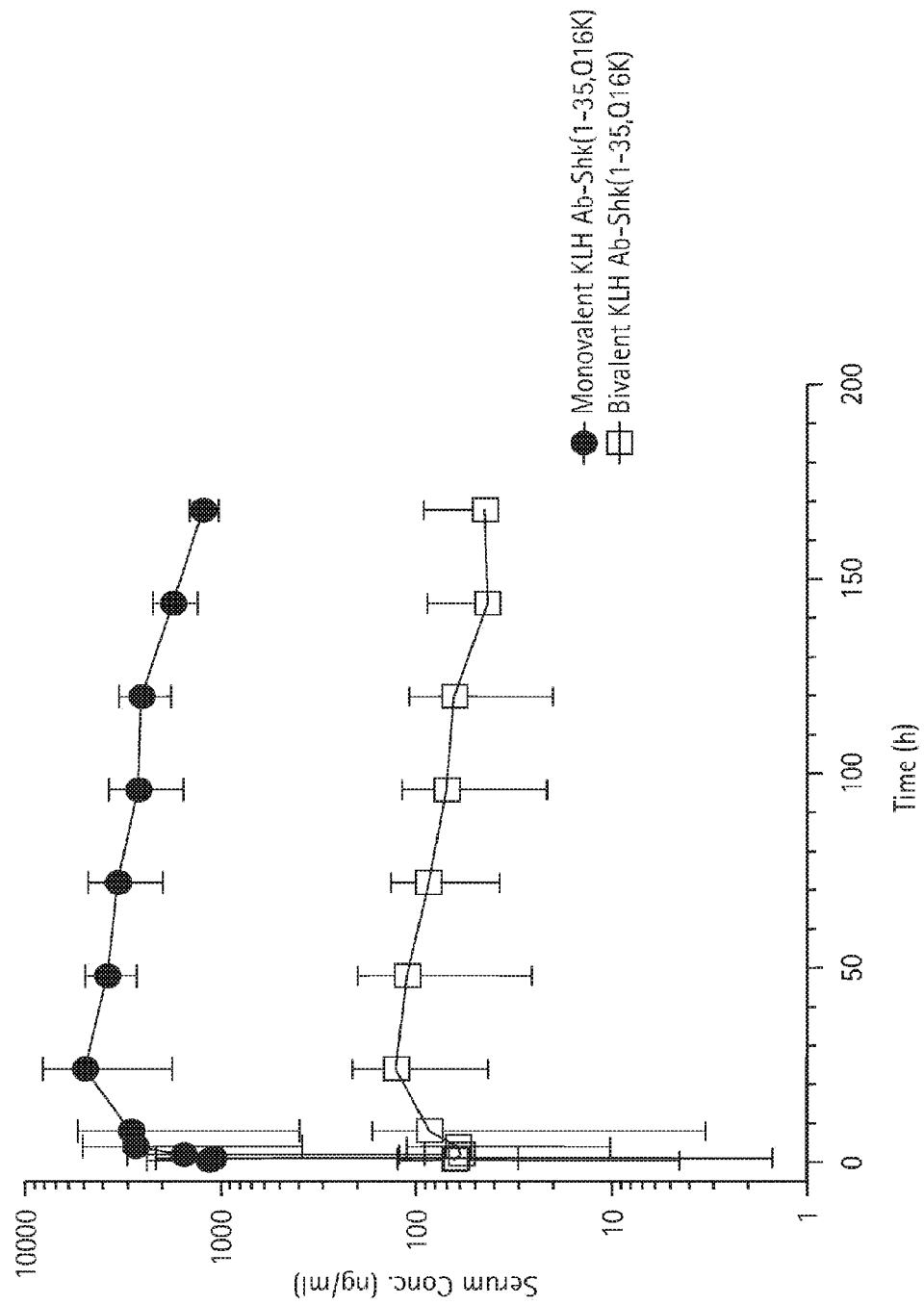

FIG. 8 shows results of pharmacokinetic studies (single-subcutaneous dose=6 mg/kg dose) performed in Sprague-Dawley rats for bivalent (open squares) and monovalent (closed circles) anti-KLH antibody-ShK(1-35, Q16K) (respectively, tetramers of [SEQ ID NO: 28, SEQ ID NO:32, SEQ ID NO:28, SEQ ID NO:32] and [SEQ ID NO: 28, SEQ ID NO:29, SEQ ID NO:28, SEQ ID NO:32]), as further described in Example 5, and Table 7J.

Figure 9:
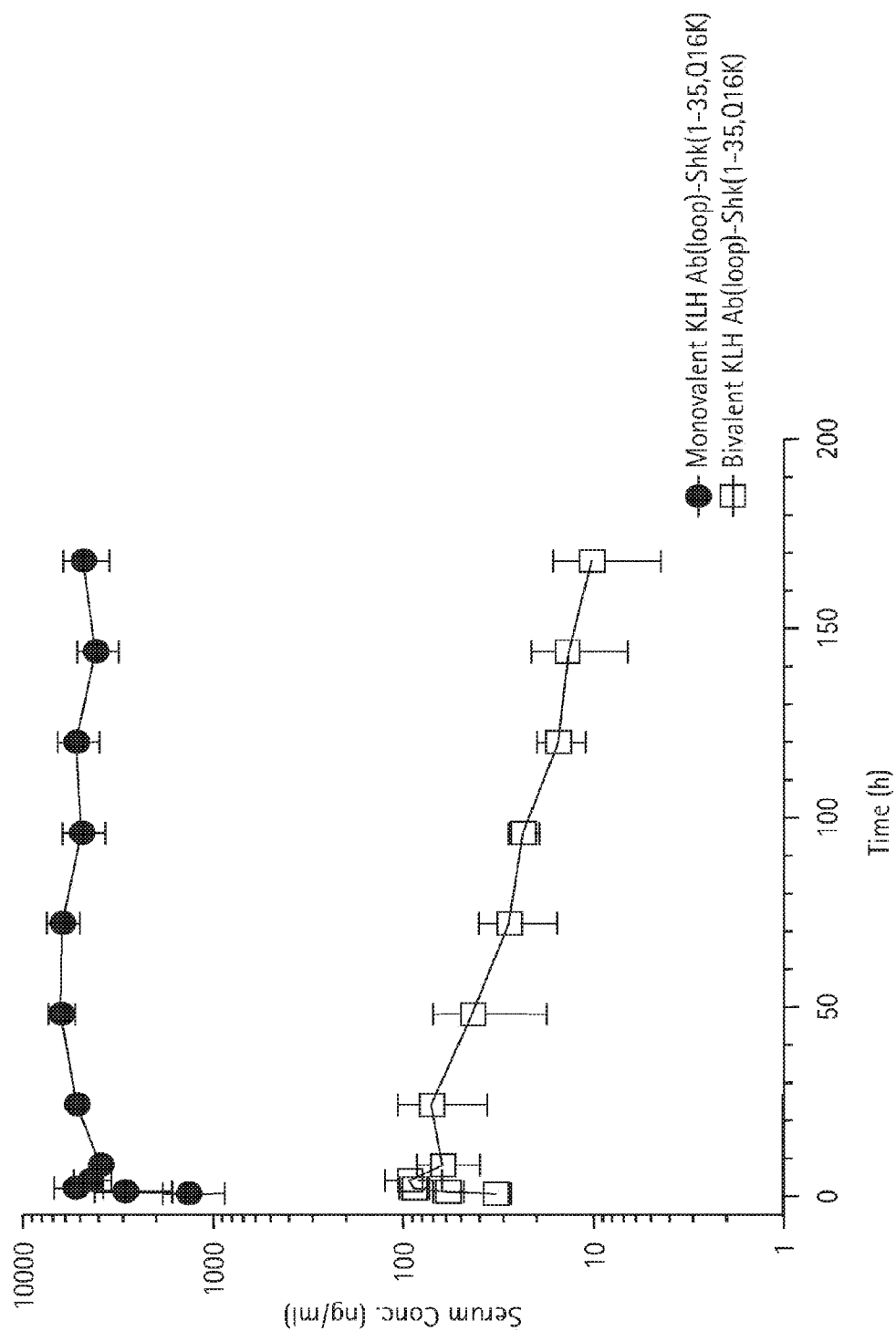

FIG. 9 shows results of pharmacokinetic studies (single-subcutaneous dose=6 mg/kg) performed in Sprague-Dawley rats for bivalent (open squares) and monovalent (closed circles) anti-KLH antibody (loop)-ShK(1-35, Q16K) (respectively, tetramers of [SEQ ID NO: 28, SEQ ID NO:35, SEQ ID NO:28, SEQ ID NO:35] and [SEQ ID NO: 28, SEQ ID NO:34, SEQ ID NO:28, SEQ ID NO:35]), as further described in Example 5, and Table 7L.

Figure 10:
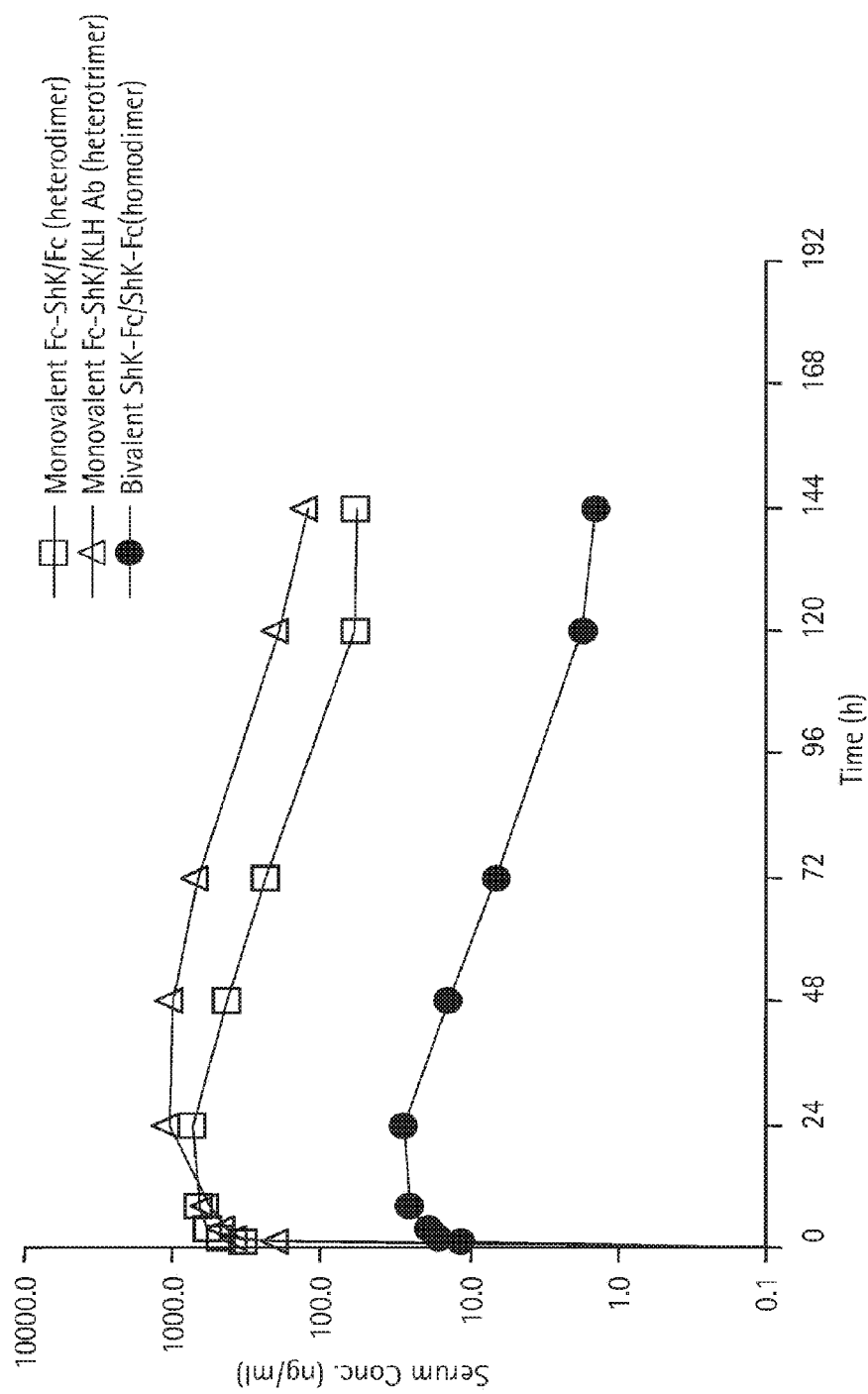

FIG. 10 shows the results of pharmacokinetic studies (single, 2 mg/kg subcutaneous dose) in SD rats of monovalent Fc-ShK/Fc heterodimer (open squares), monovalent Fc-ShK/KLH Ab (heterotrimer or hemibody) (open triangle) and the bivalent ShK-Fc/ShK-Fc homodimer (closed circles). The monovalent heterodimer and heterotrimer provided much greater exposure than the bivalent homodimer. Further details on this study, are provided in Example 5.

Figure 11:
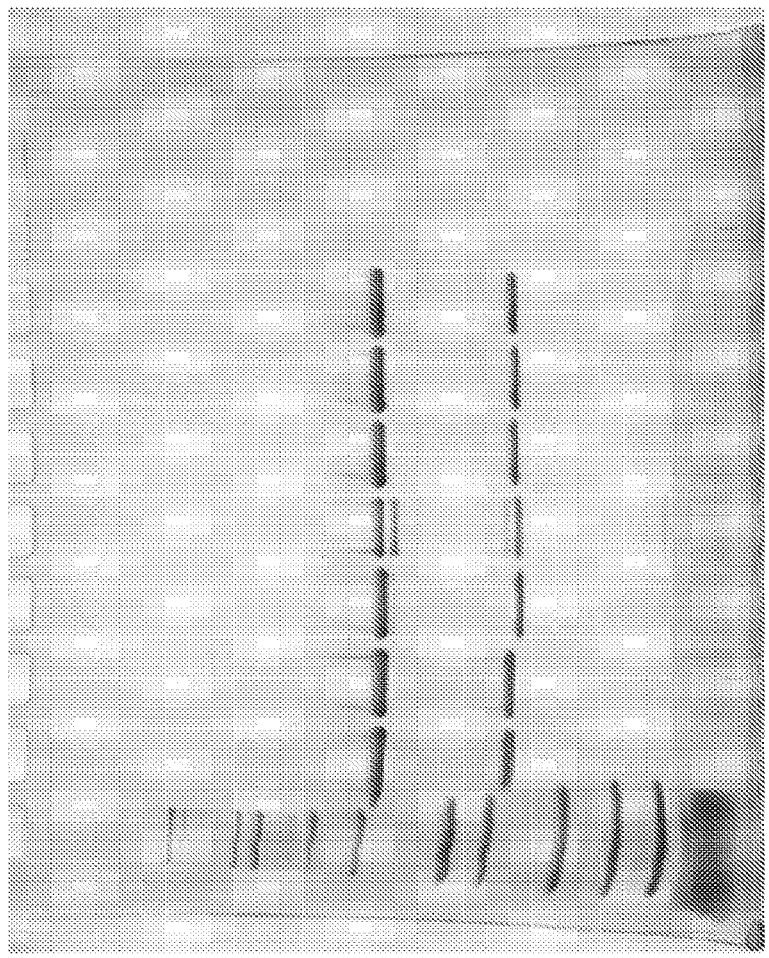

FIG. 11 shows analysis of antibodies on a 1.0 mm Tris-glycine 4-20% SDS-PAGE (Novex) developed at 220V using reducing loading buffer and staining with QuickBlue (Boston Biologicals). Lanes were loaded as follows (left to right): lane 1, Novex Mark 12 standards; lane 2, 2 µg aDNP 3B1 Ab from transient cell culture; lane 3, 2 µg aDNP-3B1 Ab from stable cell culture; lane 4, 2 µg aDNP 3H4 Ab from transient cell culture; lane 5, 2 µg aDNP 3H4 Ab from stable cell culture; lane 6, 2 µg aDNP 3A1 Ab from transient cell culture; lane 7, 2 µg aDNP 3C2 Ab from transient cell culture; and lane 8, 2 µg aDNP 3A4 Ab from transient cell culture.

Figure 12B:
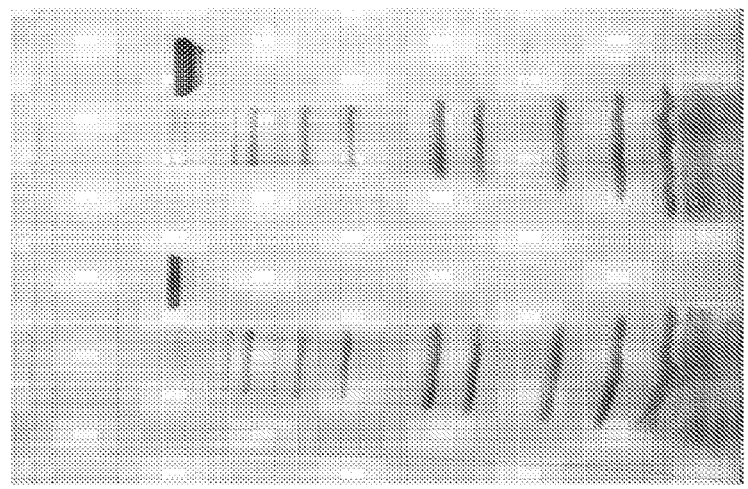
Figure 12A:
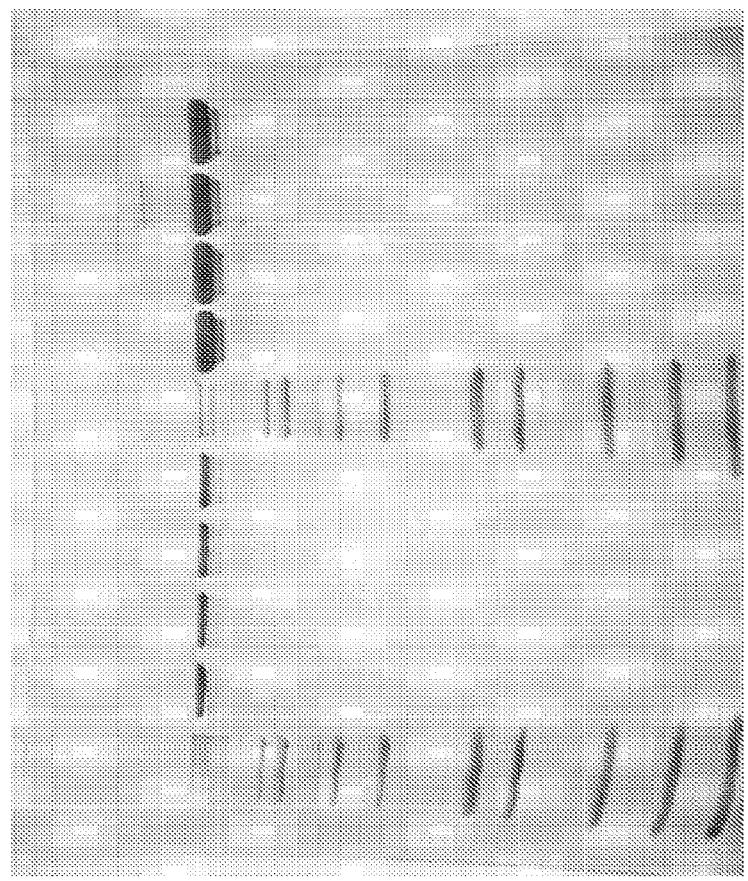

FIG. 12A-B shows analysis of antibodies on a 1.0 mm Tris-glycine 4-20% SDS-PAGE (Novex) developed at 220V using non-reducing loading buffer and staining with Quick-Blue (Boston Biologicals). Lanes were loaded as follows (left to right): (FIG. 12A): lane 1, Novex Mark 12 standards; lane 2, 0.5 µg aDNP 3A1 Ab; lane 3, 0.5 µg aDNP 3A4 Ab; lane 4, 0.5 µg aDNP 3C2 Ab; lane 5, 0.5 µg aKLH 120.6 Ab; lane 6, Novex Mark 12 standards; lane 7, 5 µg aDNP 3A1 Ab; lane 8, 5 µg aDNP 3A4 Ab; lane 9, 5 µg aDNP 3C2 Ab; lane 10, 5 µg aKLH 120.6 Ab; (FIG. 12B): lane 1, Novex Mark 12 standards; lane 2, 0.5 µg aDNP 3B1 Ab; lane 3, blank; lane 4, Novex Mark 12 standards; lane 5, 5 µg aDNP 3B1 Ab.

FIG. 13A shows analysis of antibodies on a 1.0 mm Tris-glycine 4-20% SDS-PAGE (Novex) developed at 220V using non-reducing loading buffer and staining with Quick-Blue (Boston Biologicals). Lanes were loaded as follows (left to right): lane 1, Novex Mark 12 standards; lane 2, blank; lane 3, 0.2 µg aDNP 3B1 Ab; lane 4, 0.2 µg aDNP 3A1 Ab, lane 5, blank; lane 6, 0.6 µg aDNP 3B1 Ab; lane 7, 0.6 µg aDNP 3A1 Ab; lane 8, blank; lane 9, 1.8 µg aDNP 3B1 Ab; lane 10, 1.8 µg aDNP 3A1 Ab.

FIG. 13B shows analysis of antibodies on a 1.0 mm Bis-Tris 4-12% NuPAGE (Novex) developed at 220V using non-reducing loading buffer and staining with QuickBlue (Boston Biologicals); Lanes were loaded as follows (left to right):: lane 1, Novex Mark 12 standards; lane 2, blank; lane 3, 0.2 µg aDNP 3B1 Ab; lane 4, 0.2 µg aDNP 3A1 Ab; lane 5, blank; lane 6, 0.6 µg aDNP 3B1 Ab; lane 7, 0.6 µg aDNP 3A1 Ab; lane 8, blank; lane 9, 1.8 µg aDNP 3B1 Ab; lane 10, 1.8 µg aDNP 3A1 Ab.

Figure 14A:
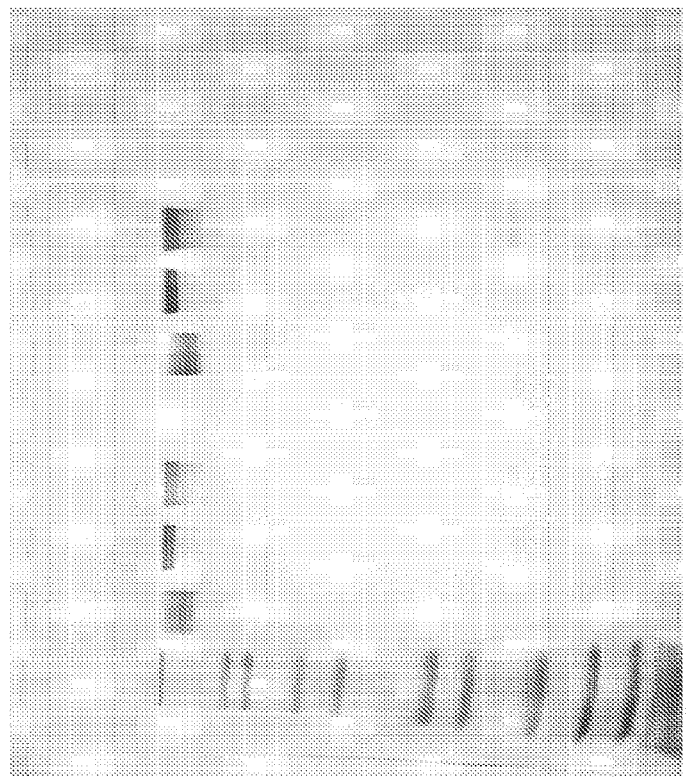
Figure 14B:
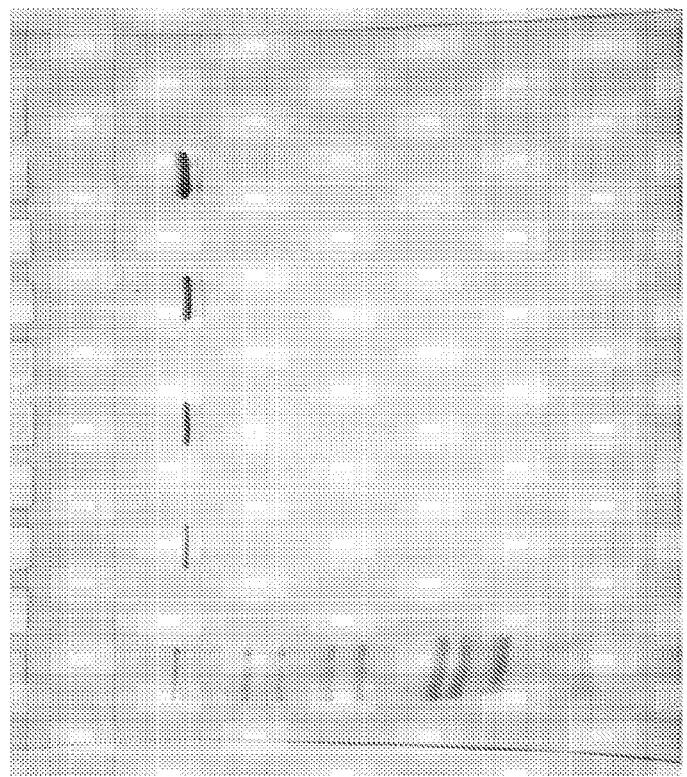

FIG. 14A-B shows analysis of antibodies on a 1.0 mm Tris-glycine 4-20% SDS-PAGE (Novex) developed at 220V using non-reducing loading buffer and staining with Quick-Blue (Boston Biologicals). Lanes were loaded as follows (left to right): (FIG. 14A: with 0.1% SDS in running buffer): lane 1, Novex Mark 12 standards; lane 2, 0.5 µg aDNP 3B1 Ab incubated at room temperature for 10 min; lane 3, 0.5 µg aDNP 3B1 Ab incubated at 85° C. for 5 min; lane 4, 0.5 µg aDNP 3B1 Ab incubated at 100° C. for 10 min; lane 5, blank; lane 6, 1 µg aDNP 3B1 Ab incubated at room temperature for 10 min; lane 7, 1 µg aDNP 3B1 Ab incubated at 85° C. for 5 min; lane 8, 1 µg aDNP 3B1 Ab incubated at 100° C. for 10 min; (FIG. 14B: 0.4% SDS in running buffer; 85° C. treatment for 5 min): lane 1, Novex Mark 12 standards, lane 2, blank; lane 3, 0.25 µg aDNP 3B1 Ab; lane 4, blank; lane 5, 0.5 µg aDNP 3B1 Ab; lane 6, blank; lane 7, 1.0 µg aDNP 3B1 Ab; lane 8, blank; lane 9, 2.0 µg aDNP 3B1 Ab.

Figure 15:
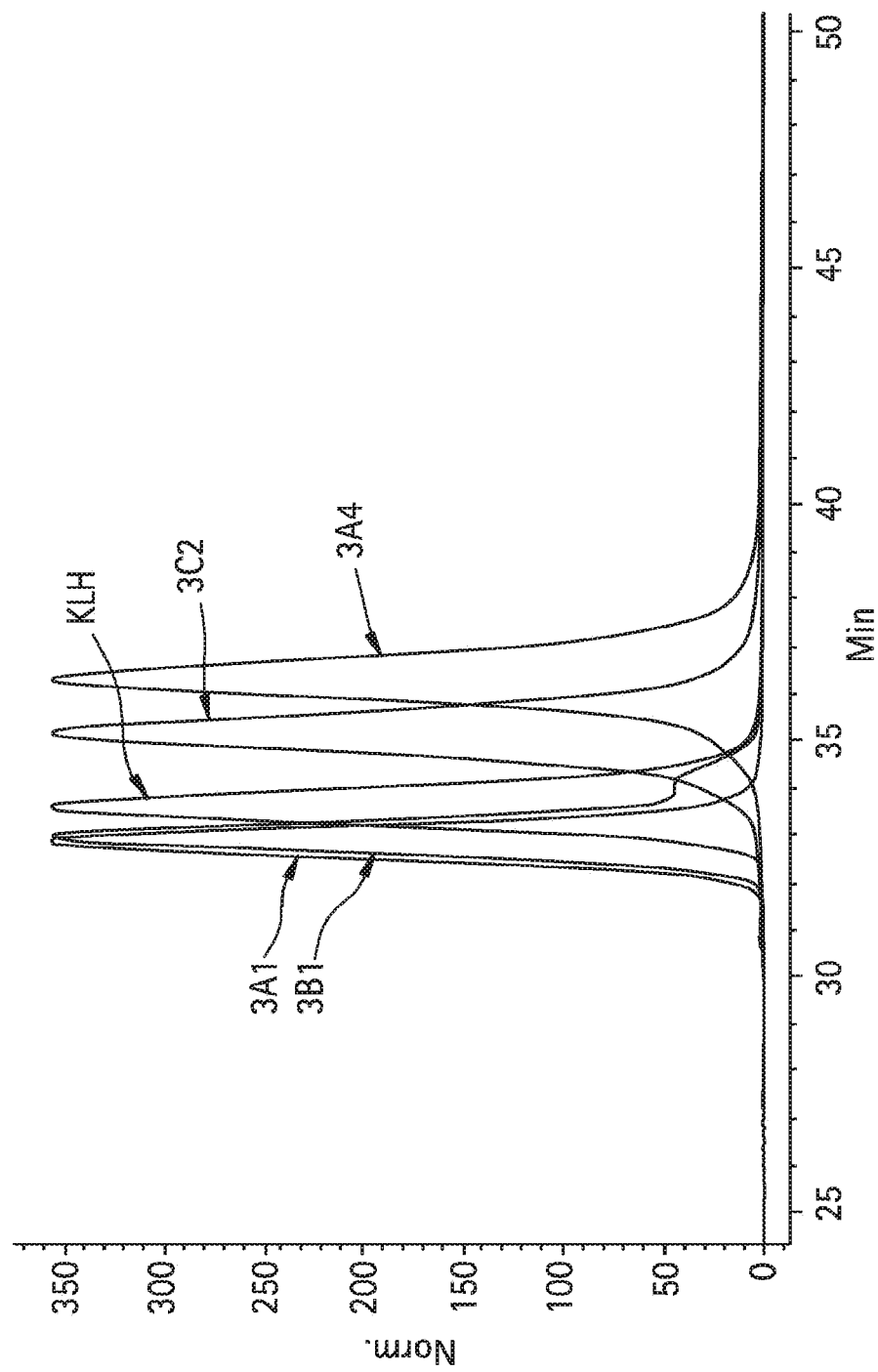

FIG. 15 shows analysis, using two size exclusion columns (TSK-GEL G3000SWXL, 5 mm particle size, 7.8×300 mm, TosohBioscience, 08541) in series with a 100 mM sodium phosphate, 250 mM NaCl at pH 6.8 mobile phase flowed at 0.5 mL/min., of antibodies: aDNP 3A1 ("3A1", darker trace with post shoulder); aDNP 3B1 ("3B1"); aKLH 120.6 ("KLH"); aDNP 3C2 ("3C2"), and aDNP 3A4 ("3A4").

Figure 16:
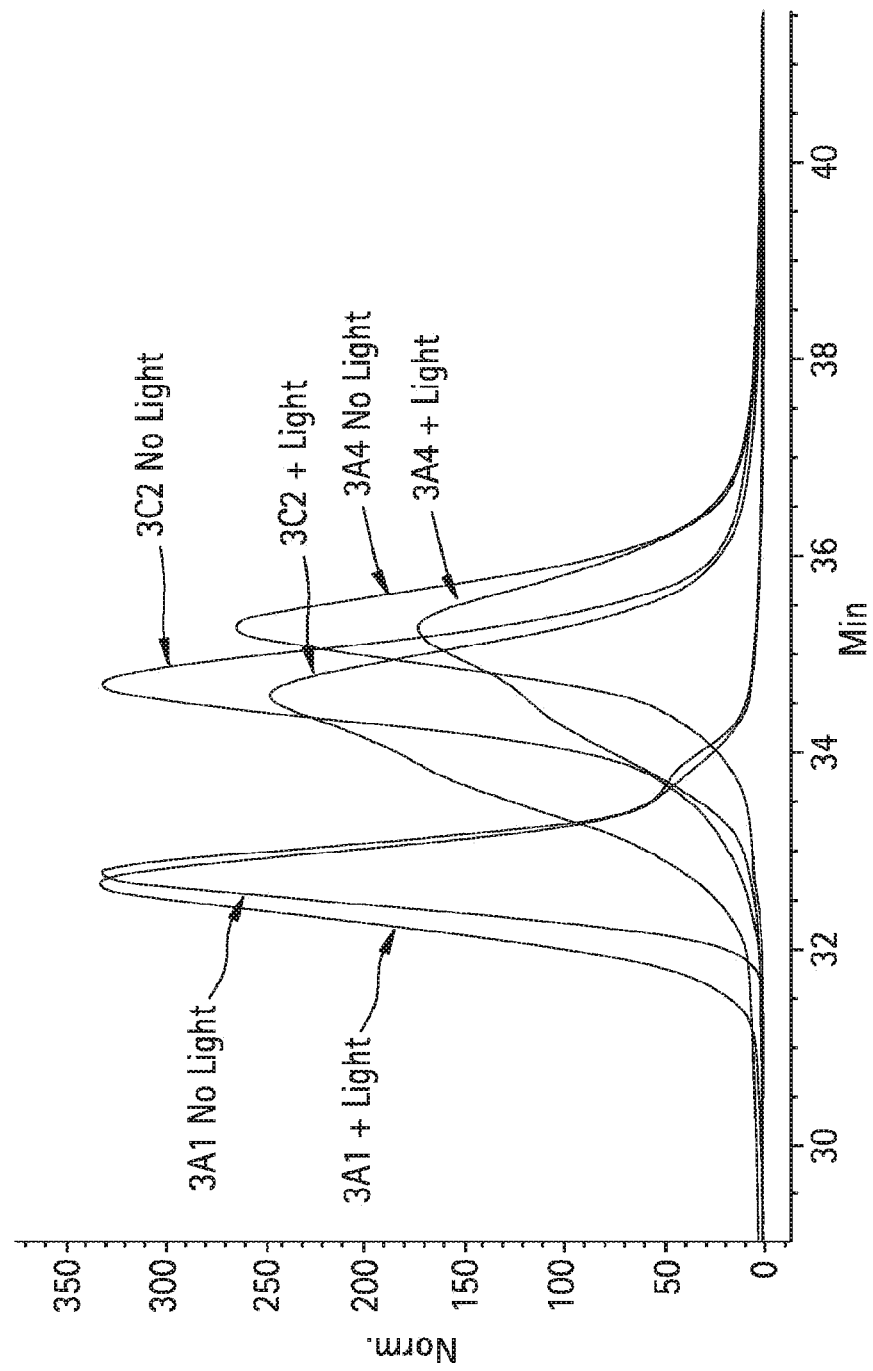

FIG. 16 shows analysis of antibodies aDNP 3A1 ("3A1"), aDNP 3C2 ("3C2") and DNP-3A4 before and after 3 weeks of light exposure, using two size exclusion columns (TSK-GEL G3000SWXL, 5 mm particle size, 7.8×300 mm, TosohBioscience, 08541) in series with a 100 mM sodium phosphate, 250 mM NaCl at pH 6.8 mobile phase flowed at 0.5 mL/min.

Figure 17A:
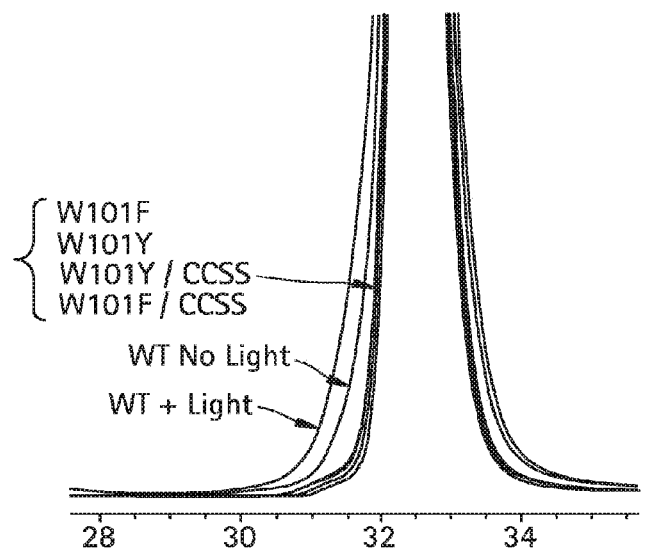
Figure 17B:
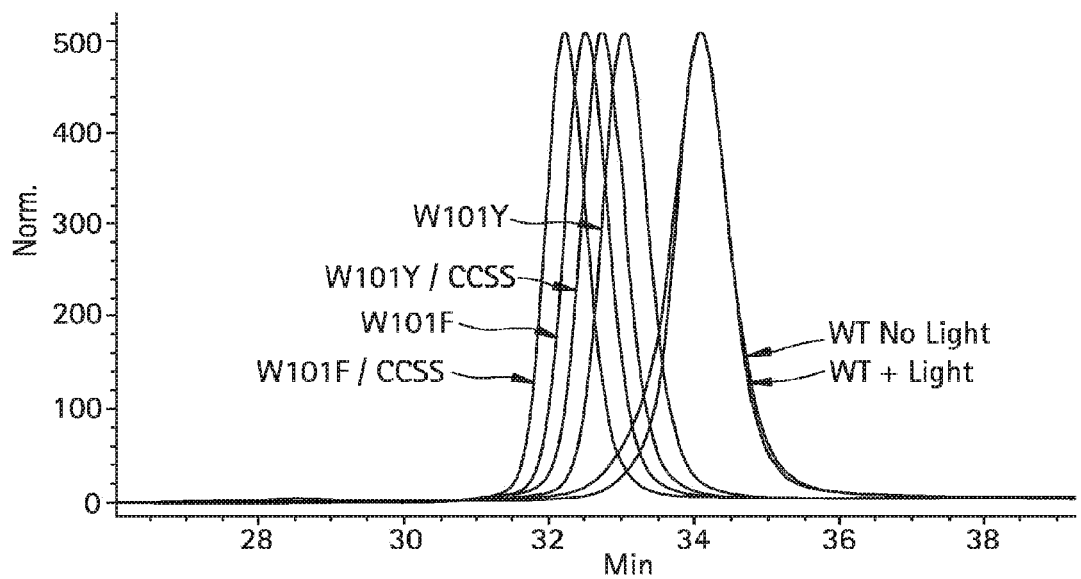

FIG. 17A-B show analysis, using two size exclusion columns (TSK-GEL G3000SWXL, 5 mm particle size, 7.8×300 mm, TosohBioscience, 08541) in series with a 100 mM sodium phosphate, 250 mM NaCl at pH 6.8 mobile phase flowed at 0.5 mL/min, of antibodies aDNP 3A4, aDNP 3A4-Y ("W1010Y"), aDNP 3A4-F ("W101F"), aDNP 3A4 YSS ("W101Y/CCSS"), and aDNP-3A4-FSS ("W101F/CCSS") before (FIG. 17A) and after (FIG. 17B) 2 days of light exposure.

Figure 18:
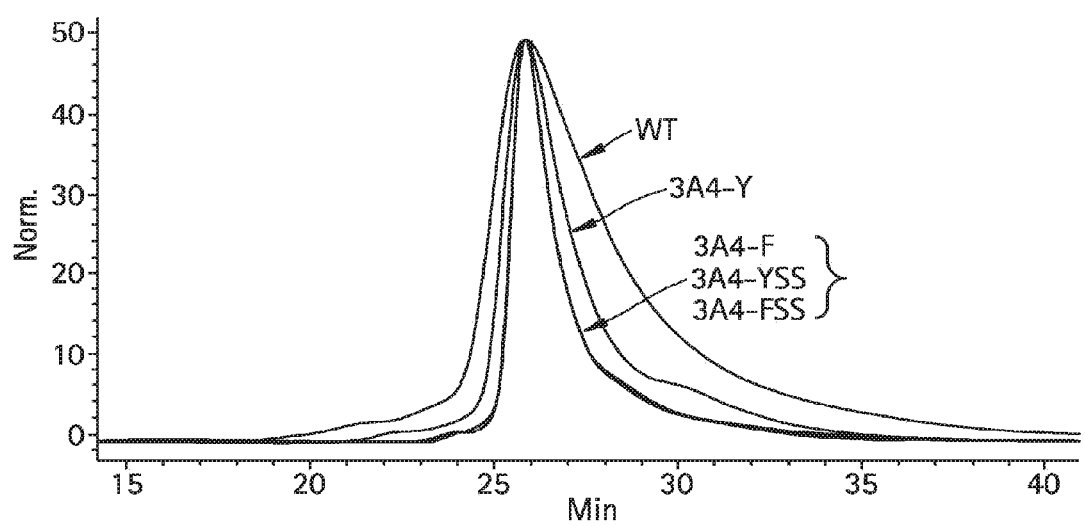

FIG. 18 shows ion exchange analysis of aDNP antibodies (aDNP-3A4, aDNP-3A4-Y, aDNP-3A4-F, aDNP-3A4-YSS and aDNP-3A4-FSS). They were analyzed for homogeneity using a Tosohaas SP-5PW column (10-µm particle, 7.5 mm ID×7.5 cm long) using Buffer A (10 mM sodium acetate, pH 5.0) and Buffer B (10 mM sodium acetate, 600 mM NaCl, pH 5.0) flowed at 1 ml/min with a programmed linear gradient (1 min 0% B, 10 min 35% B, 30 min 70% B, 3 min 90% B and 3 min 0% B).

Figure 19A:
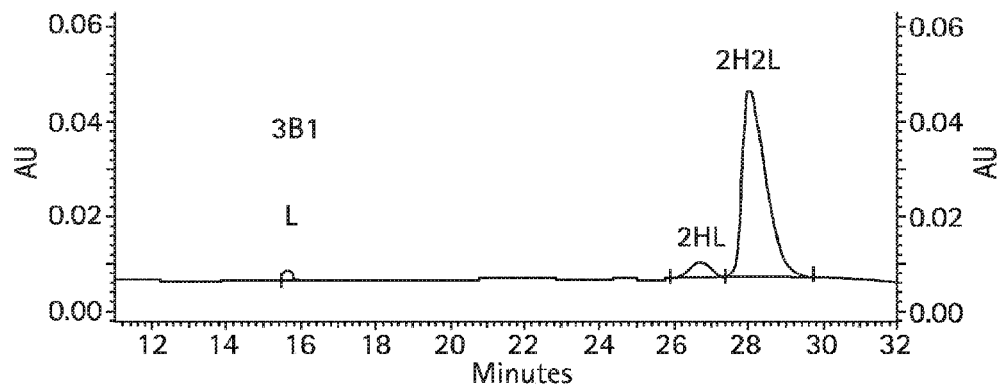
Figure 19B:
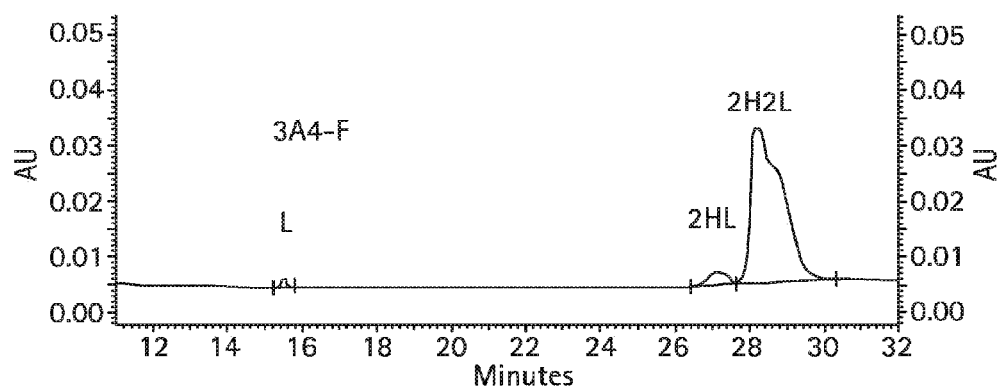
Figure 19C:
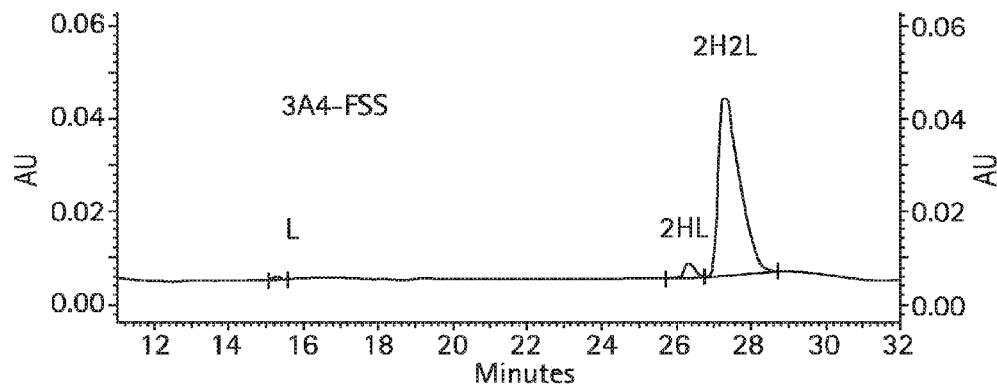

FIG. 19 shows an analysis of aDNP 3B1 (FIG. 19A), aDNP 3A4-F (FIG. 19B), and aDNP 3A4-FSS (FIG. 19C) antibodies by non-reducing CE-SDS with detection of absorbance at 220 nm. A bare-fused silica capillary 50 µm×30.2 cm was used for the separation analysis.

Figure 20A:
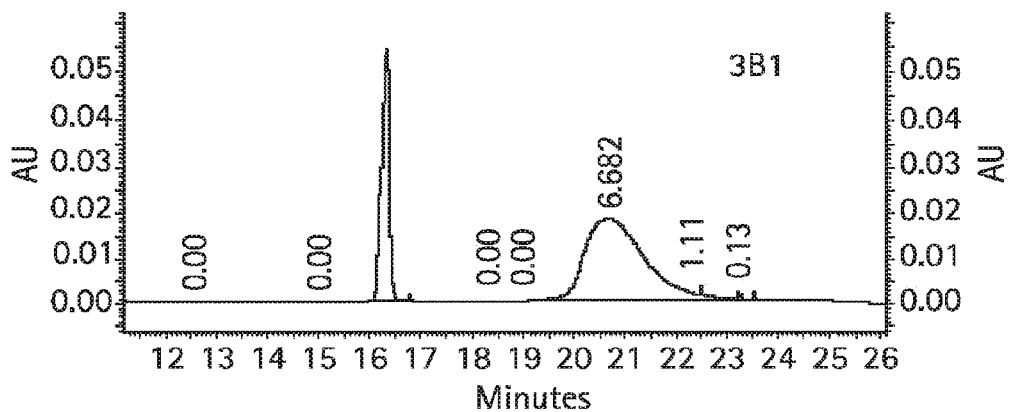
Figure 20B:
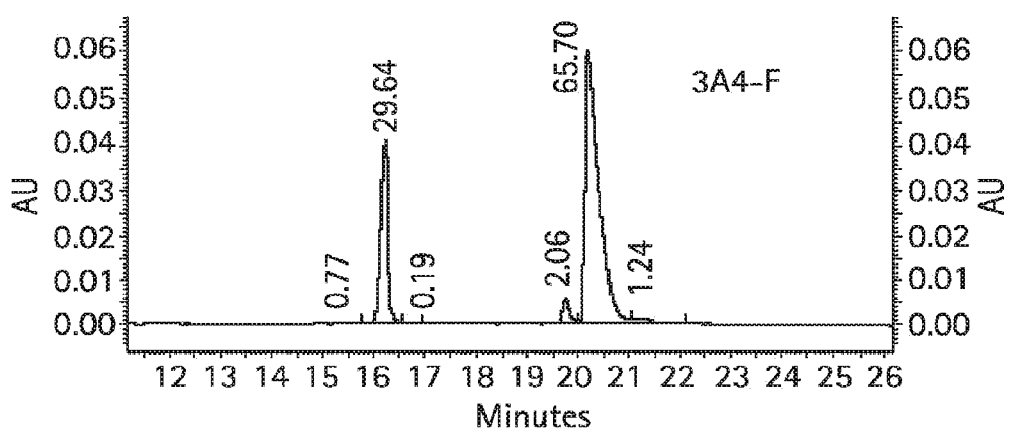
Figure 20C:
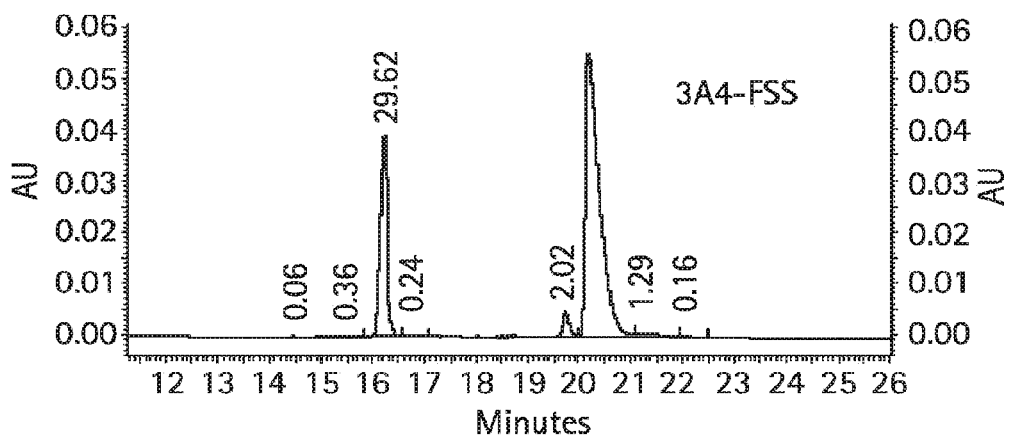

FIG. 20 shows an analysis of aDNP 3B1 (FIG. 20A), aDNP 3A4-F (FIG. 20B), and aDNP 3A4-FSS (FIG. 20C) antibodies by reducing CE-SDS with detection of absorbance at 220 nm. A bare-fused silica capillary 50 µm×30.2 cm was used for the separation analysis.

Figure 21:
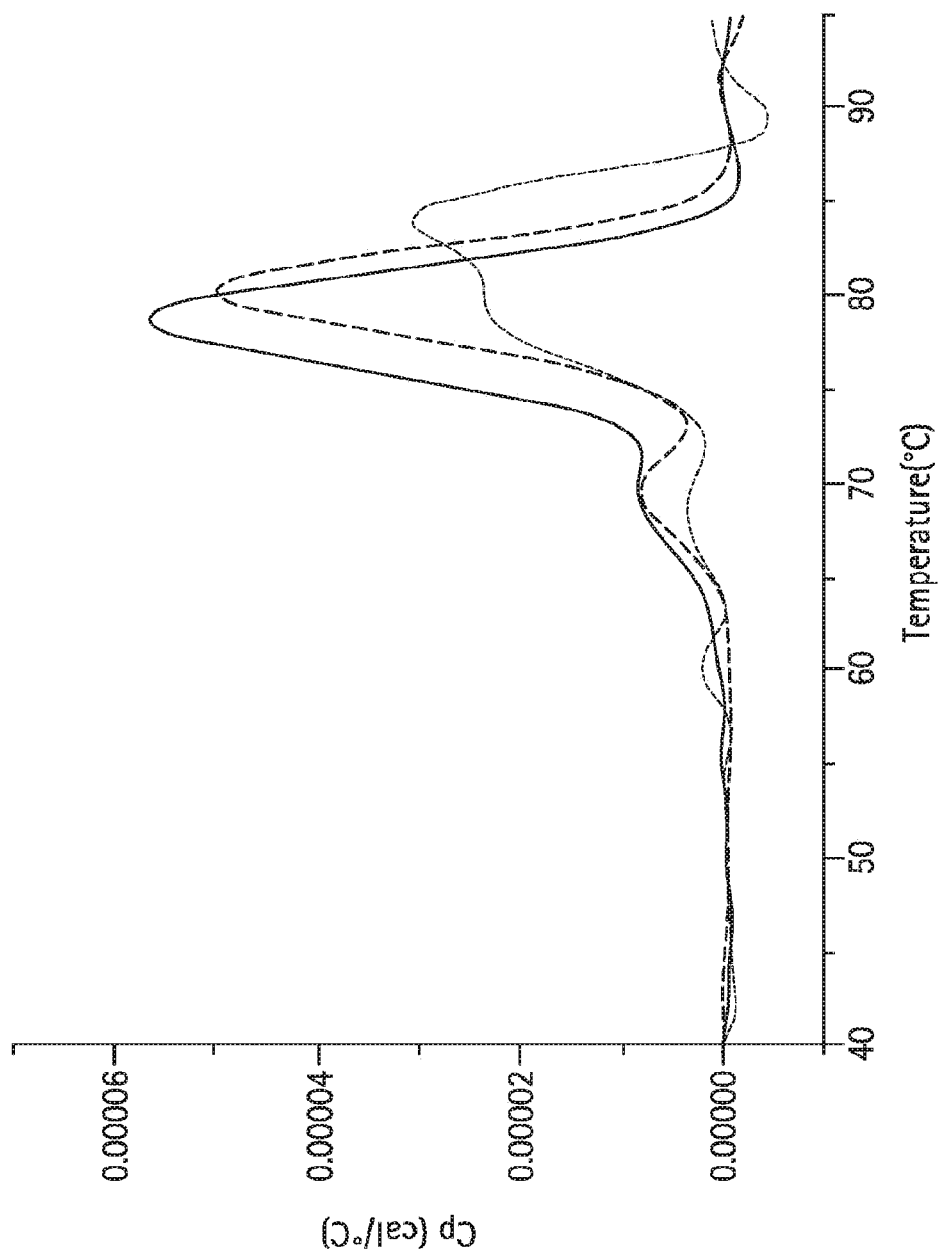

FIG. 21 shows an analysis of aDNP-3A4-F (dotted curve), aDNP-3A4-FSS (solid curve) and aDNP-3B1 (dashed curve) antibodies were analyzed by DSC using a MicrCal VP-DSC where the samples were heated from 20° C. to 95° C. at a rate of 1° C. per minute. The protein concentration was 0.5 mg/ml in 10 mM sodium acetate, 9% sucrose, pH 5.0.

Figure 22:
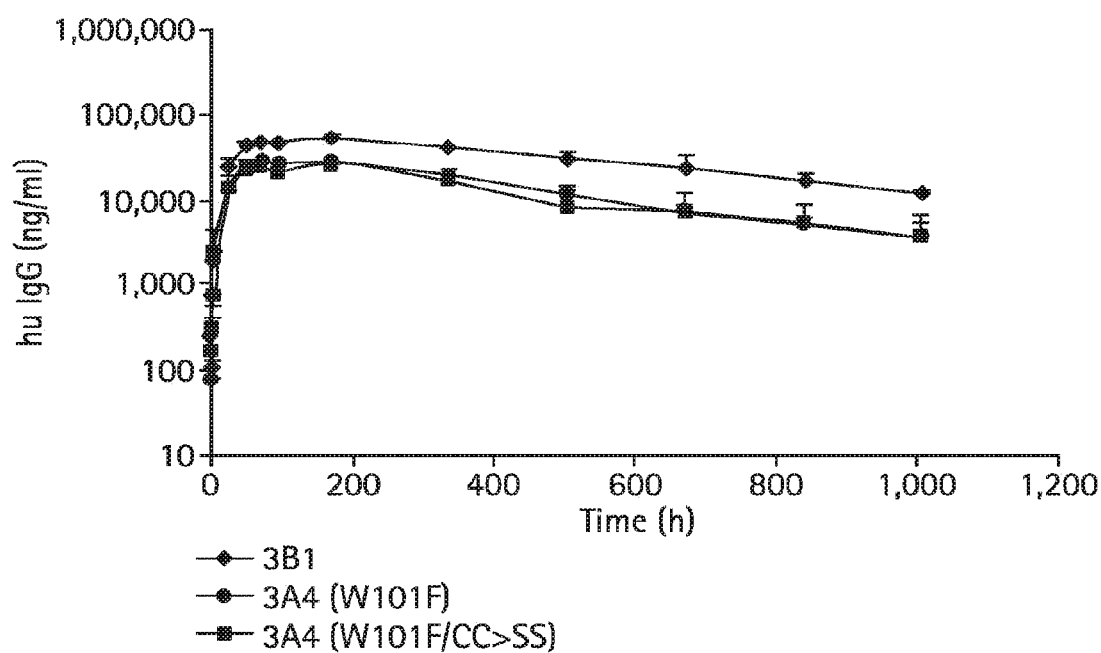

FIG. 22 shows serum concentrations of aDNP 3A4-F, aDNP 3A4-FSS, and aDNP 3B1 antibodies in rats receiving a single subcutaneous injection of 5 mg/kg, as determined by ELISA. Blood samples were collected at 0, 0.25, 1, 4, 24, 48, 72, 96, 168, 336, 504, 672, 840 and 1008 hours post-dose.

Figure 23:
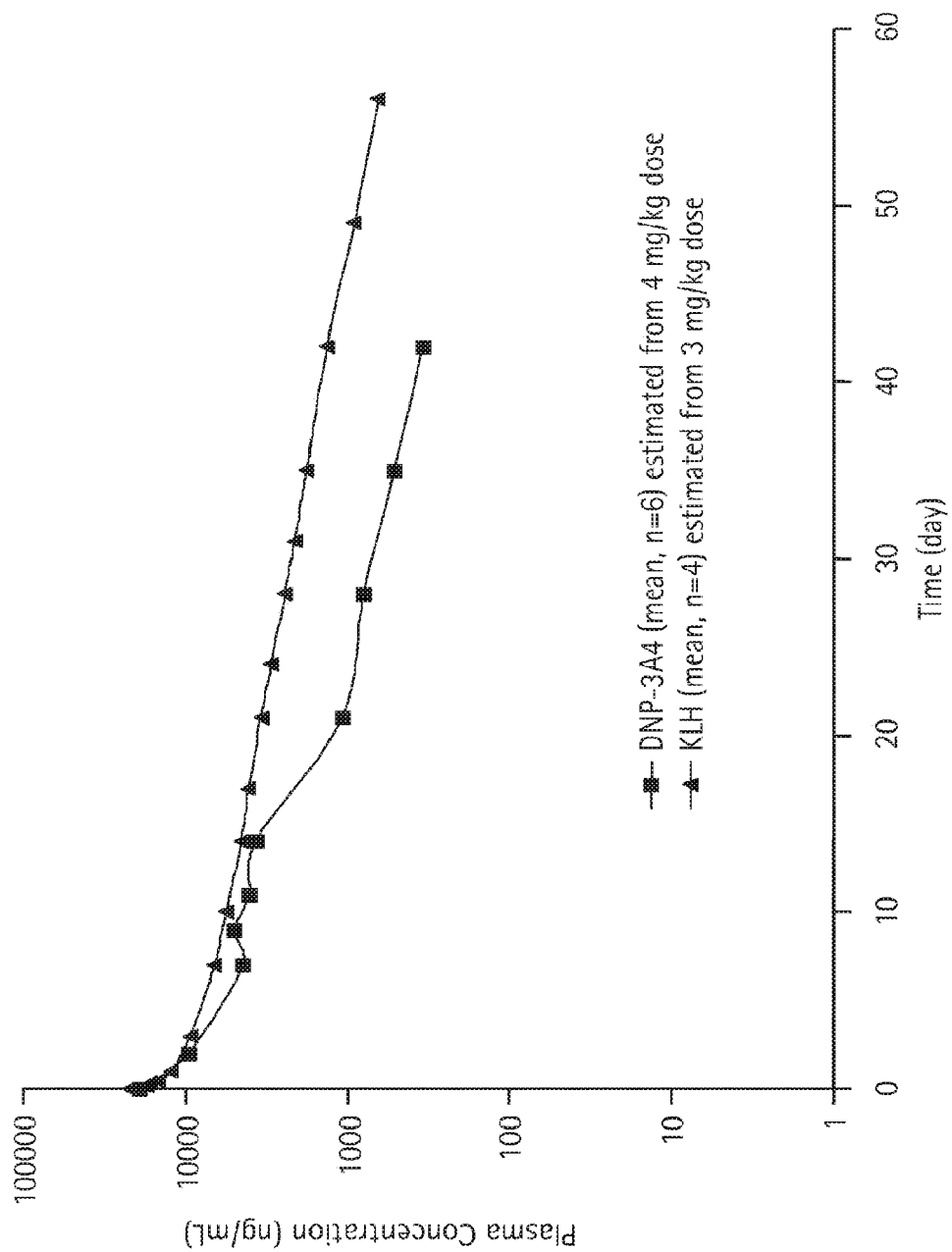

FIG. 23 shows plasma concentrations of aDNP 3A4 or aKLH 120.6 in male cynomolgus monkeys receiving a bolus intravenous injection aDNP 3A4 (4 mg/kg) or aKLH 120.6 (3 mg/kg) antibodies, respectively. Serum samples were taken periodically and plasma concentrations of the antibodies was determined by ELISA. The data for aDNP 3A4 was normalized to 3 mg/kg for comparison purposes.

Figure 24:
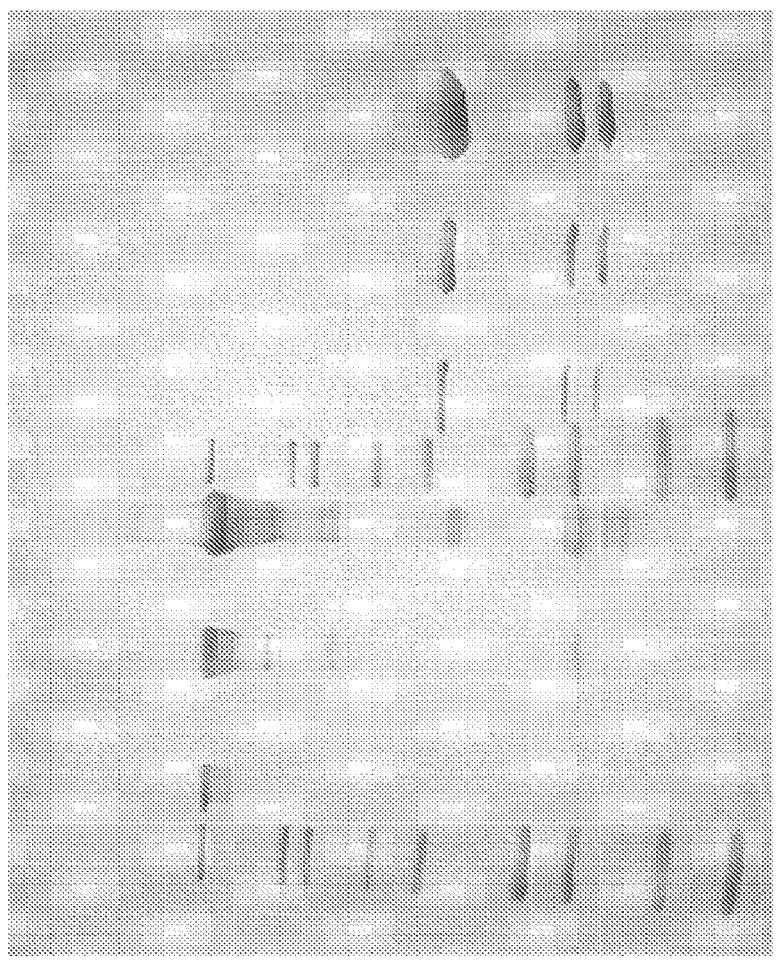

FIG. 24 shows a Coomassie brilliant blue stained Trisglycine 4-20% SDS-PAGE of the final monovalent aKLH 120.6 LC-ShK[1-35, Q16K] Ab product, described in Example 4. Lanes 1-12 were loaded as follows: lane 1: Novex Mark12 wide range protein standards (10 µl); lane 2: 0.5 µg product, non-reduced; lane 3: blank; lane 4: 2.0 µg product, non-reduced; lane 5: blank; lane 6: 10 µg product, non-reduced; lane 7: Novex Mark12 wide range protein standards (10 µl); lane 8: 0.5 µg product, reduced; lane 9: blank; lane 10: 2.0 µg product, reduced; lane 11: blank; lane 12: 10 µg product, reduced.

Figure 25:
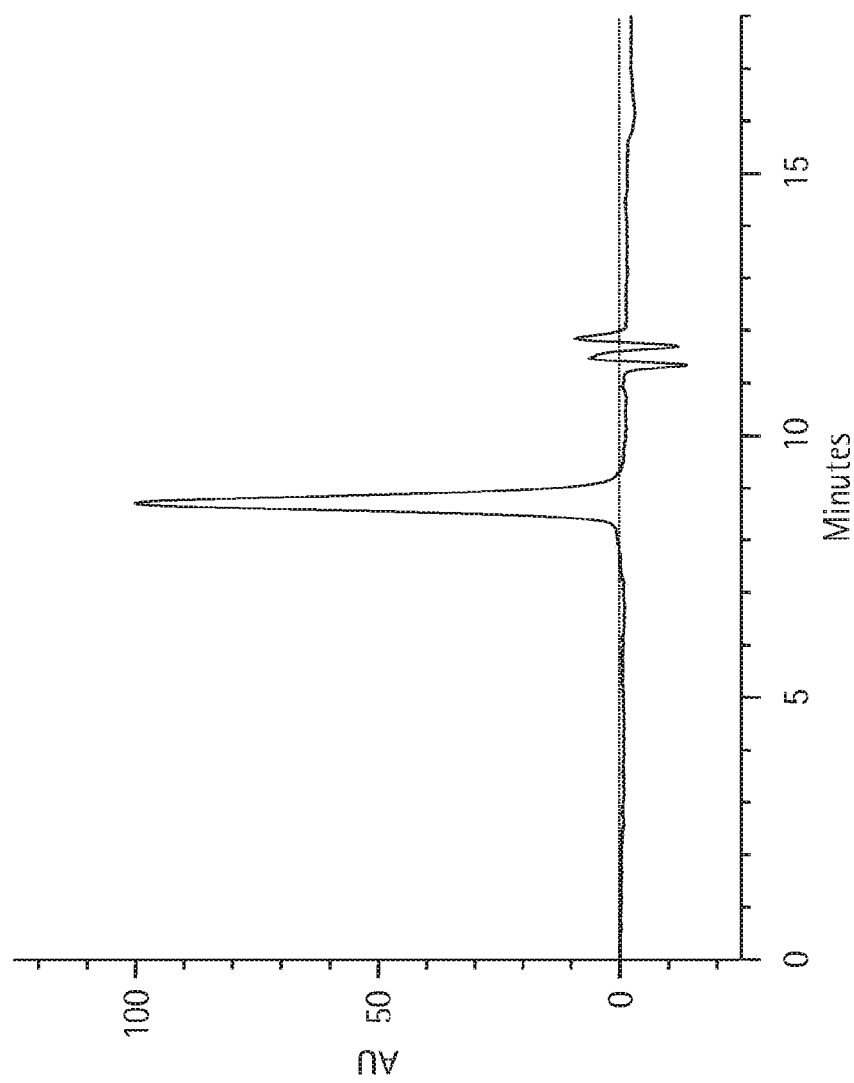

FIG. 25 shows size exclusion chromatography on 25 µg of the final monovalent aKLH 120.6 LC-ShK[1-35, Q16K] Ab product, described in Example 4, injected onto a Phenomenex BioSep SEC-3000 column (7.8×300 mm) in 50 mM $NaH_2PO_4$, 250 mM NaCl pH 6.9, at 1 mL/min detecting the absorbance at 280 nm.

Figure 26A:
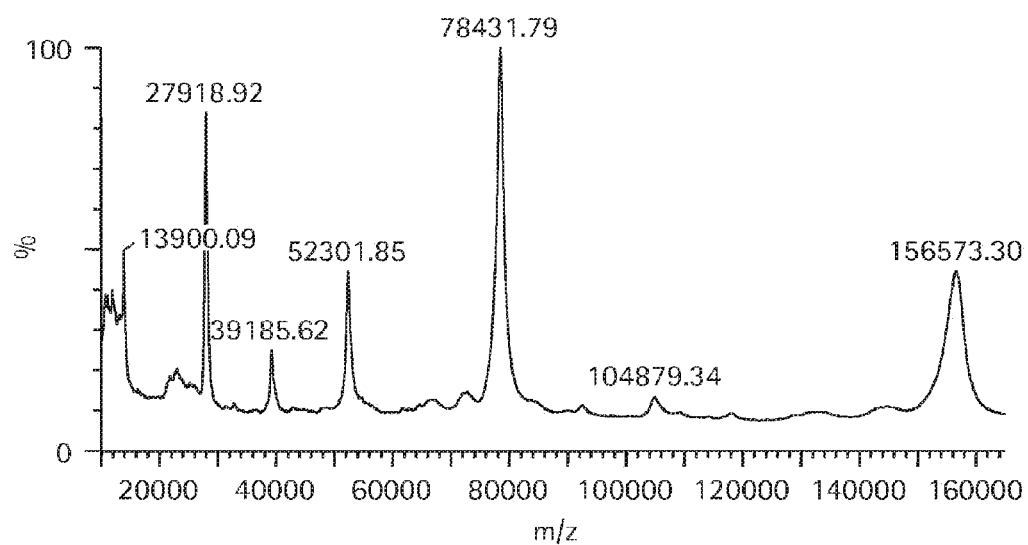
Figure 26B:
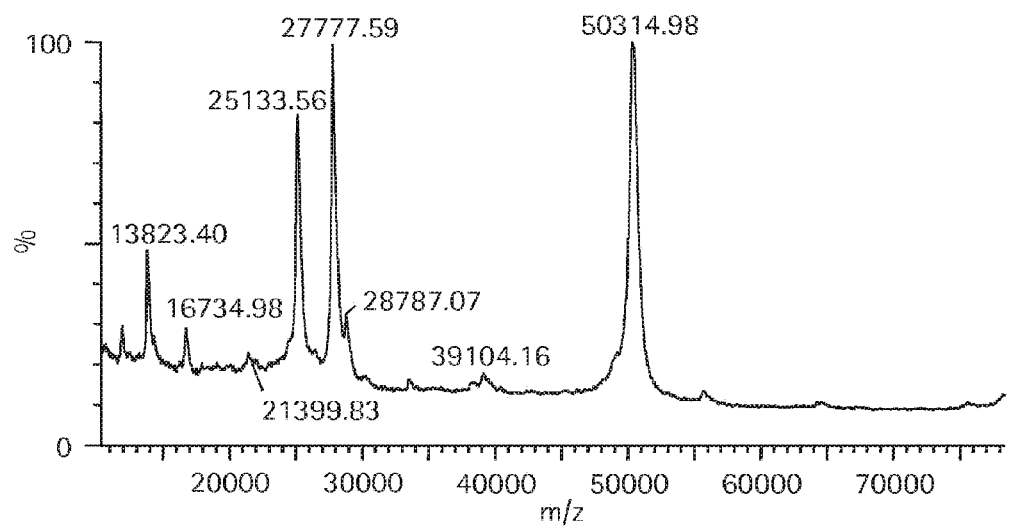

FIG. 26A-B shows non-reducing (FIG. 26A) and reducing (FIG. 26B) MALDI-MS mass spectral analysis of the final sample of monovalent aKLH 120.6 LC-ShK[1-35, Q16K] product, described in Example 4, using a Micromass MALDI micro MX mass spectrometer equipped with a nitrogen laser. The sample was run at positive linear mode. The instrument's voltage was set at 12 kV and the high mass detector was set at 5 kV. Each spectrum was produced by accumulating data from about 200 laser shots. External mass calibration was achieved using purified proteins of known molecular masses.

Figure 27:
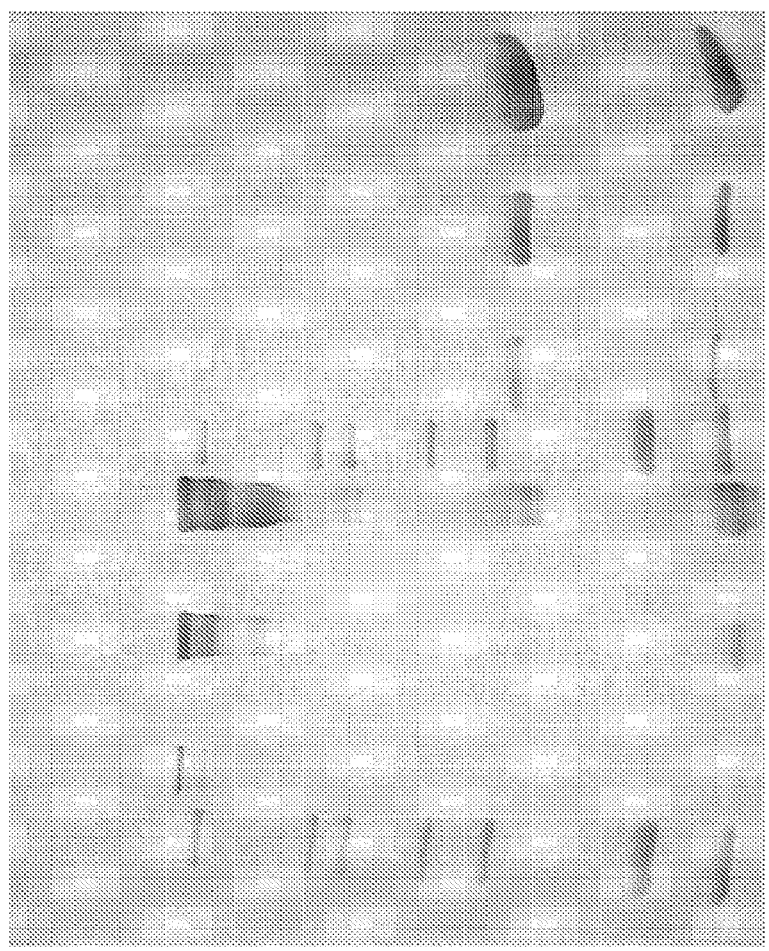

FIG. 27 shows a Coomassie brilliant blue stained Tris-glycine 4-20% SDS-PAGE of the final bivalent aKLH 120.6 LC-ShK[1-35, Q16K] Ab product, described in Example 4. Lanes 1-12 were loaded as follows: lane 1: Novex Mark12 wide range protein standards (10 μl); lane 2: 0.5 μg product, non-reduced; lane 3: blank; lane 4: 2.0 μg product, non-reduced; lane 5: blank; lane 6: 10 μg product, non-reduced; lane 7: Novex Mark12 wide range protein standards (10 μl); lane 8: 0.5 μg product, reduced; lane 9: blank; lane 10: 2.0 μg product, reduced; lane 11: blank; lane 12: 10 μg product, reduced.

Figure 28:
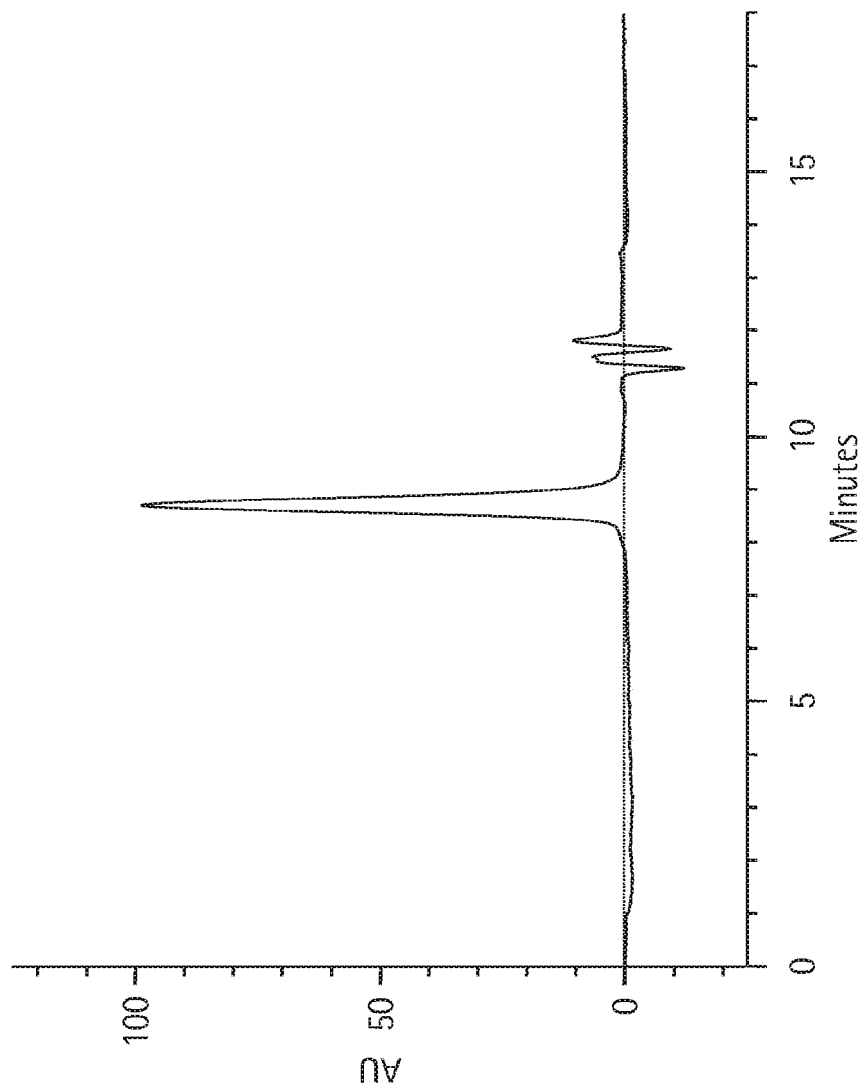

FIG. 28 shows size exclusion chromatography on 25 μg of the final bivalent aKLH 120.6 LC-ShK[1-35, Q16K] Ab product, described in Example 4, injected onto a Phenomenex BioSep SEC-3000 column (7.8×300 mm) in 50 mM $NaH_2PO_4$, 250 mM NaCl, pH 6.9, at 1 mL/min detecting the absorbance at 280 nm.

Figure 29A:
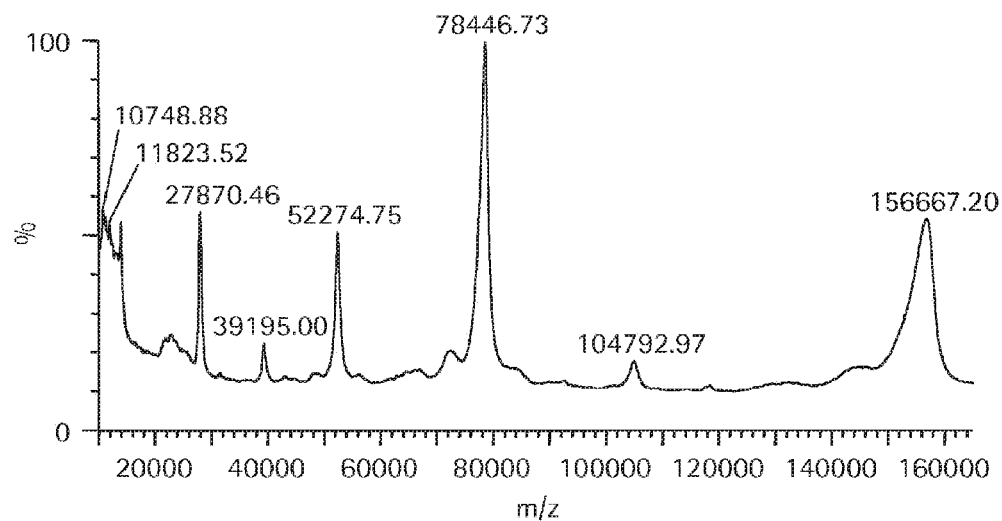
Figure 29B:
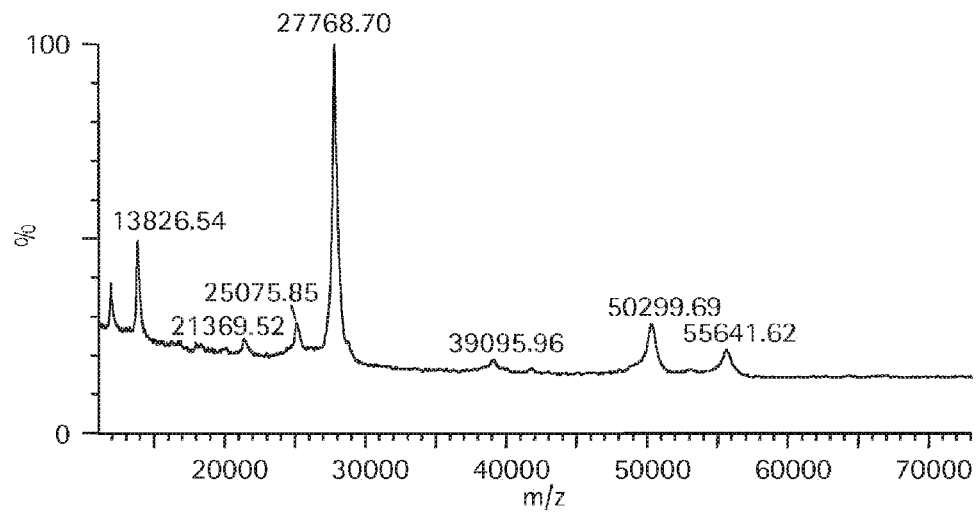

FIG. 29A-B shows non-reducing (FIG. 29A) and reducing (FIG. 29B) MALDI-MS mass spectral analysis of the final sample of bivalent aKLH 120.6 LC-ShK[1-35, Q16K] Ab product, described in Example 4, using a Micromass MALDI micro MX mass spectrometer equipped with a nitrogen laser. The sample was run at positive linear mode. The instrument's voltage was set at 12 kV and the high mass detector was set at 5 kV. Each spectrum was produced by accumulating data from about 200 laser shots. External mass calibration was achieved using purified proteins of known molecular masses.

Figure 30:
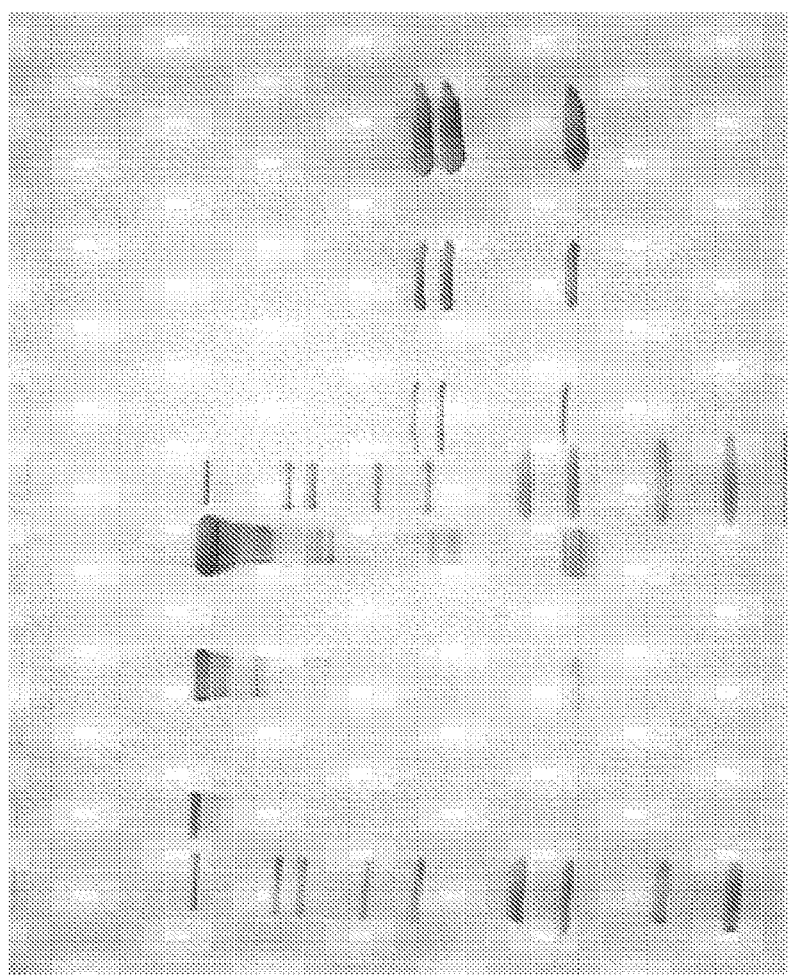

FIG. 30 shows a Coomassie brilliant blue stained Tris-glycine 4-20% SDS-PAGE of the final trivalent aKLH 120.6 LC-ShK[1-35, Q16K] Ab product, described in Example 4. Lanes 1-12 were loaded as follows: lane 1: Novex Mark12 wide range protein standards (10 μl); lane 2: 0.5 μg product, non-reduced; lane 3: blank; lane 4: 2.0 μg product, non-reduced; lane 5: blank; lane 6: 10 μg product, non-reduced; lane 7: Novex Mark12 wide range protein standards (10 μl); lane 8: 0.5 μg product, reduced; lane 9: blank; lane 10: 2.0 μg product, reduced; lane 11: blank; lane 12: 10 μg product, reduced.

Figure 31:
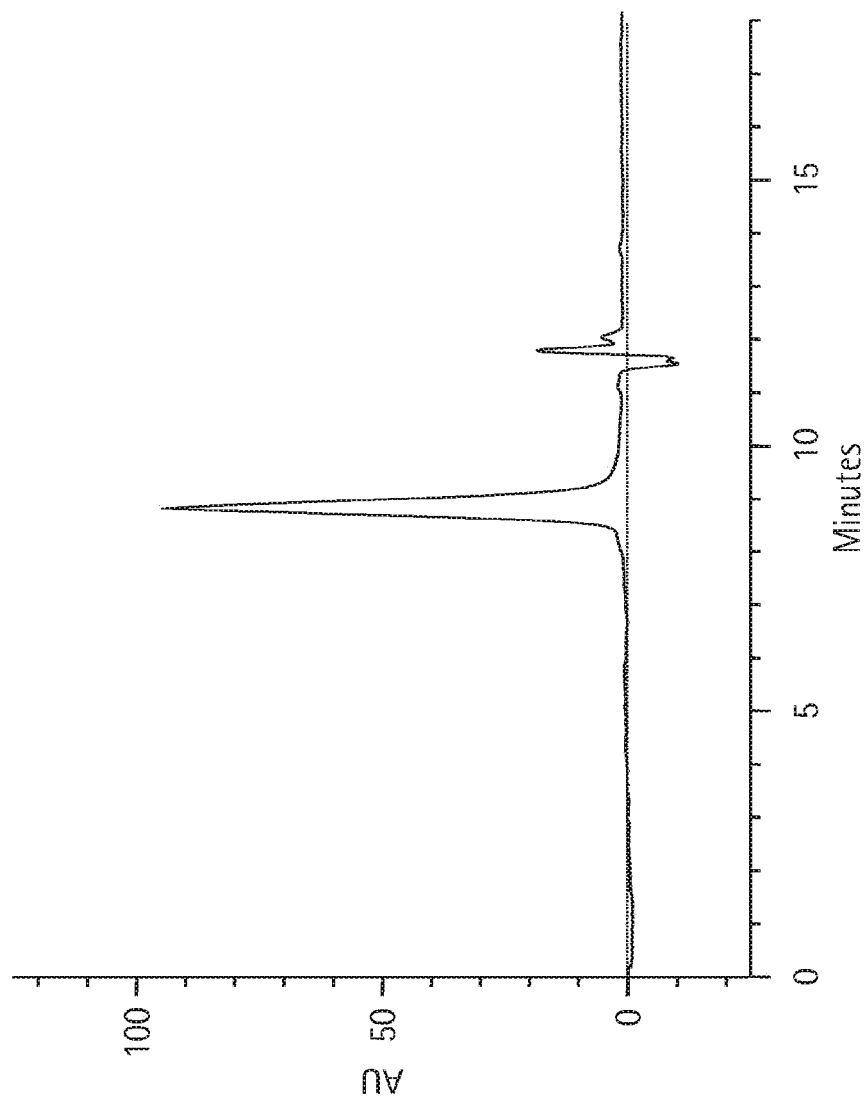

FIG. 31 shows size exclusion chromatography on 25 μg of the final trivalent aKLH 120.6 LC-ShK[1-35, Q16K] Ab product, described in Example 4, injected onto a Phenomenex BioSep SEC-3000 column (7.8×300 mm) in 50 mM $NaH_2PO_4$, 250 mM NaCl, pH 6.9, at 1 mL/min detecting the absorbance at 280 nm.

Figure 32A:
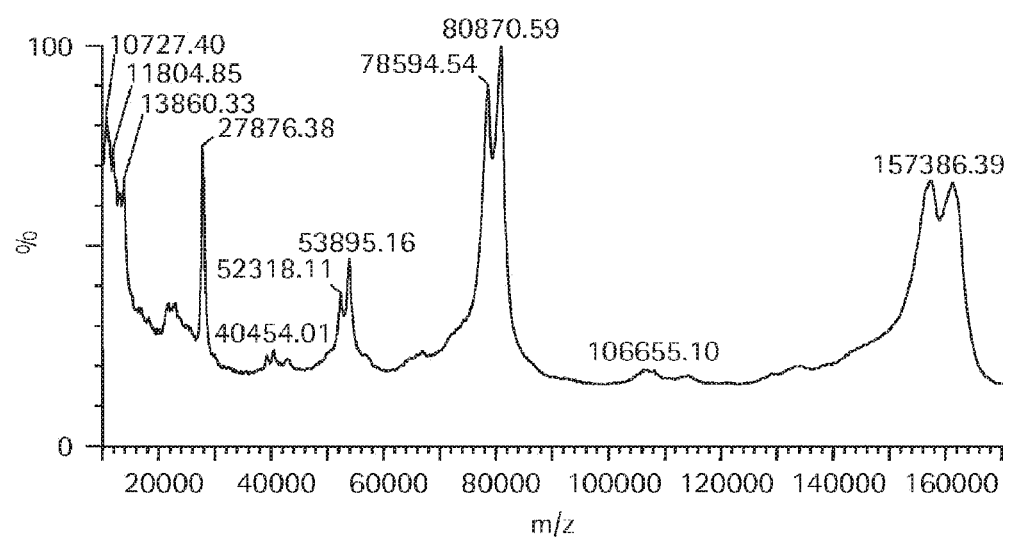
Figure 32B:
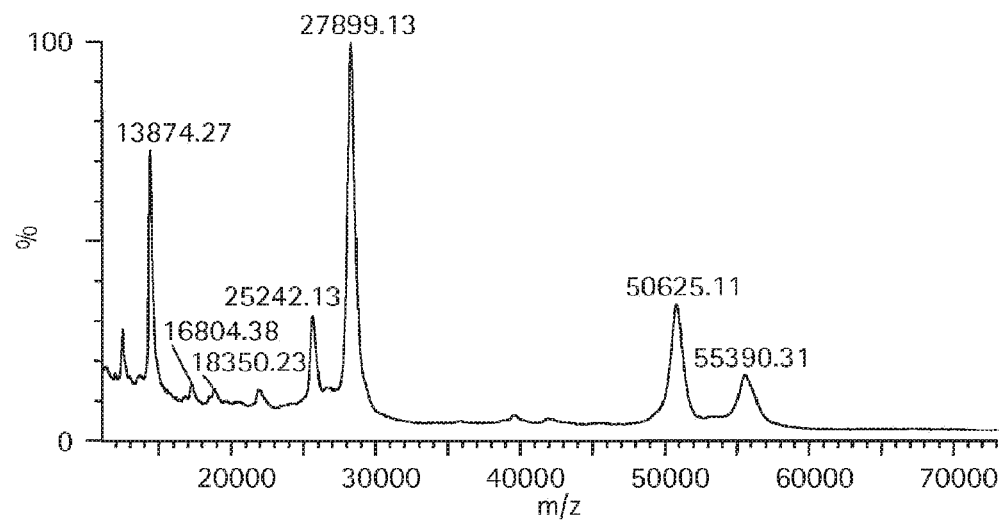

FIG. 32A-B shows non-reducing (FIG. 32A) and reducing (FIG. 32B) MALDI-MS mass spectral analysis of the final sample of trivalent aKLH 120.6 LC-ShK[1-35, Q16K] Ab product, described in Example 4, using a Micromass MALDI micro MX mass spectrometer equipped with a nitrogen laser. The sample was run at positive linear mode. The instrument's voltage was set at 12 kV and the high mass detector was set at 5 kV. Each spectrum was produced by accumulating data from about 200 laser shots. External mass calibration was achieved using purified proteins of known molecular masses.

Figure 33:
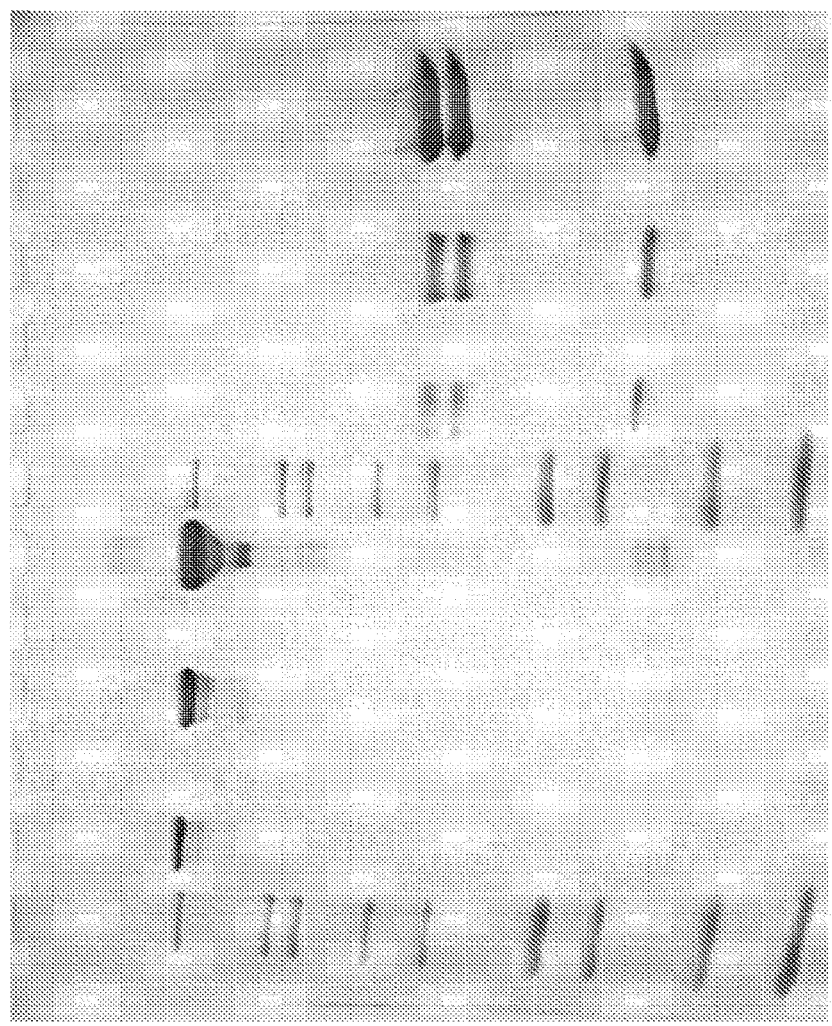

FIG. 33 shows a Coomassie brilliant blue stained Tris-glycine 4-20% SDS-PAGE of the final monovalent aKLH 120.6 IgG2 HC-Shk[1-35, R1A, I4A, Q16K] Ab product, described in Example 4. Lanes 1-12 were loaded as follows: lane 1: Novex Mark12 wide range protein standards (10 μl); lane 2: 0.5 μg product, non-reduced; lane 3: blank; lane 4: 2.0 μg product, non-reduced; lane 5: blank; lane 6: 10 μg product, non-reduced; lane 7: Novex Mark12 wide range protein standards (10 μl); lane 8: 0.5 μg product, reduced; lane 9: blank; lane 10: 2.0 μg product, reduced; lane 11: blank; lane 12: 10 μg product, reduced.

Figure 34:
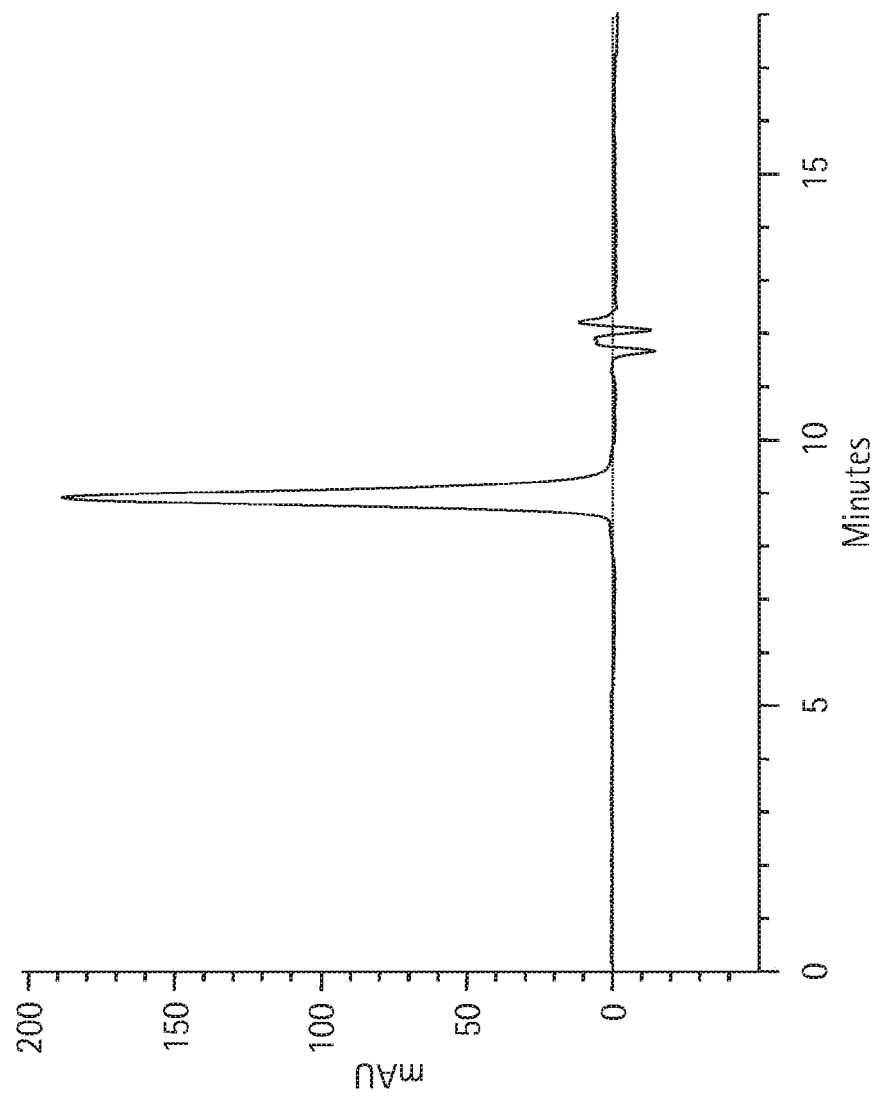

FIG. 34 shows size exclusion chromatography on 25 μg of the final monovalent aKLH 120.6 IgG2 HC-Shk[1-35, R1A, I4A, Q16K] Ab product, described in Example 4, injected onto a Phenomenex BioSep SEC-3000 column (7.8×300 mm) in 50 mM $NaH_2PO_4$, 250 mM NaCl, pH 6.9, at 1 mL/min detecting the absorbance at 280 nm.

Figure 35:
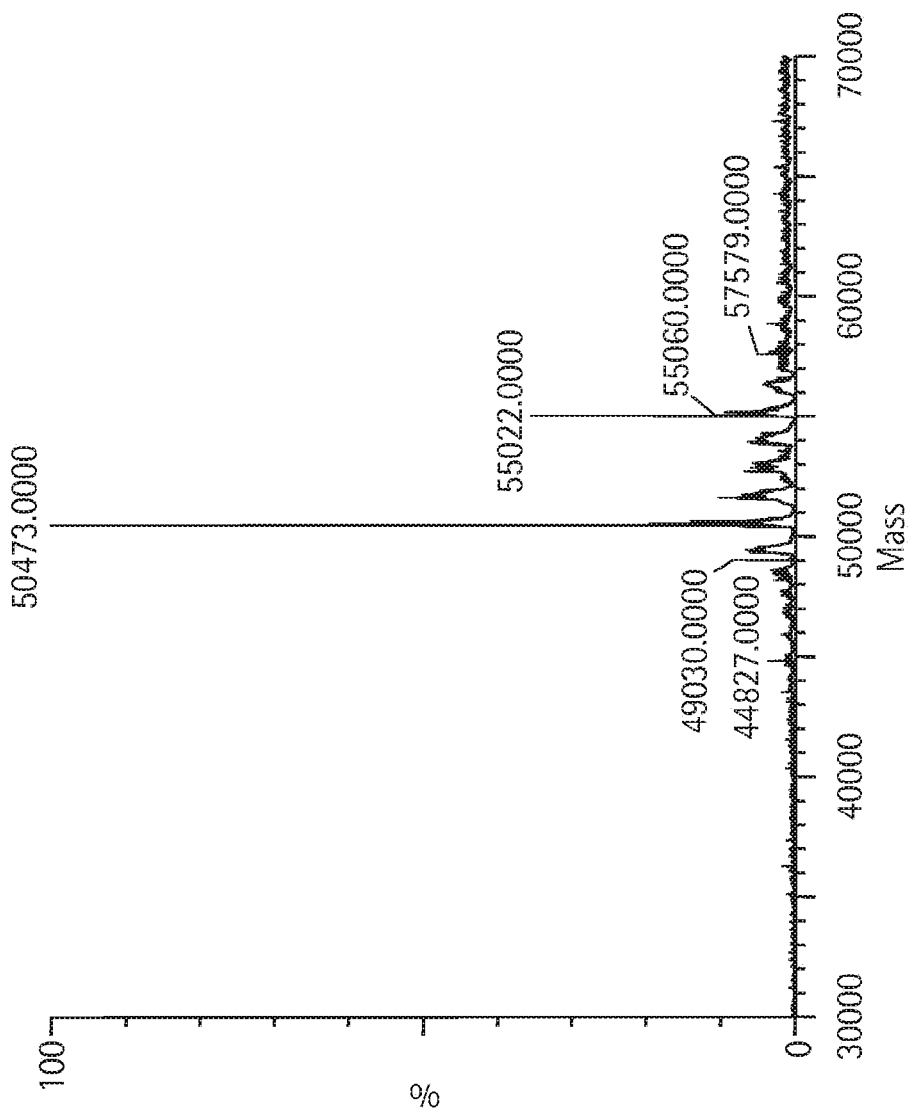

FIG. 35 shows reduced LC-MS mass spectral analysis of the heavy chain in the final sample of monovalent aKLH 120.6 IgG2 HC-ShK[1-35, R1A, I4A, Q16K] Ab product, described in Example 4. The product was chromatographed through a Waters MassPREP micro desalting column using a Waters ACQUITY UPLC system. The column was set at 80° C. and the protein eluted using a linear gradient of increasing acetonitrile concentration in 0.1% formic acid. Part of the column effluent was diverted into a Waters LCT Premier ESI-TOF mass spectrometer for mass analysis. The instrument was run in the positive V mode. The capillary voltage was set at 3,200 V and the cone voltage at 80 V. The mass spectrum was acquired from 800 to 3000 m/z and deconvoluted using the MaxEnt1 software provided by the instrument manufacturer.

Figure 36:
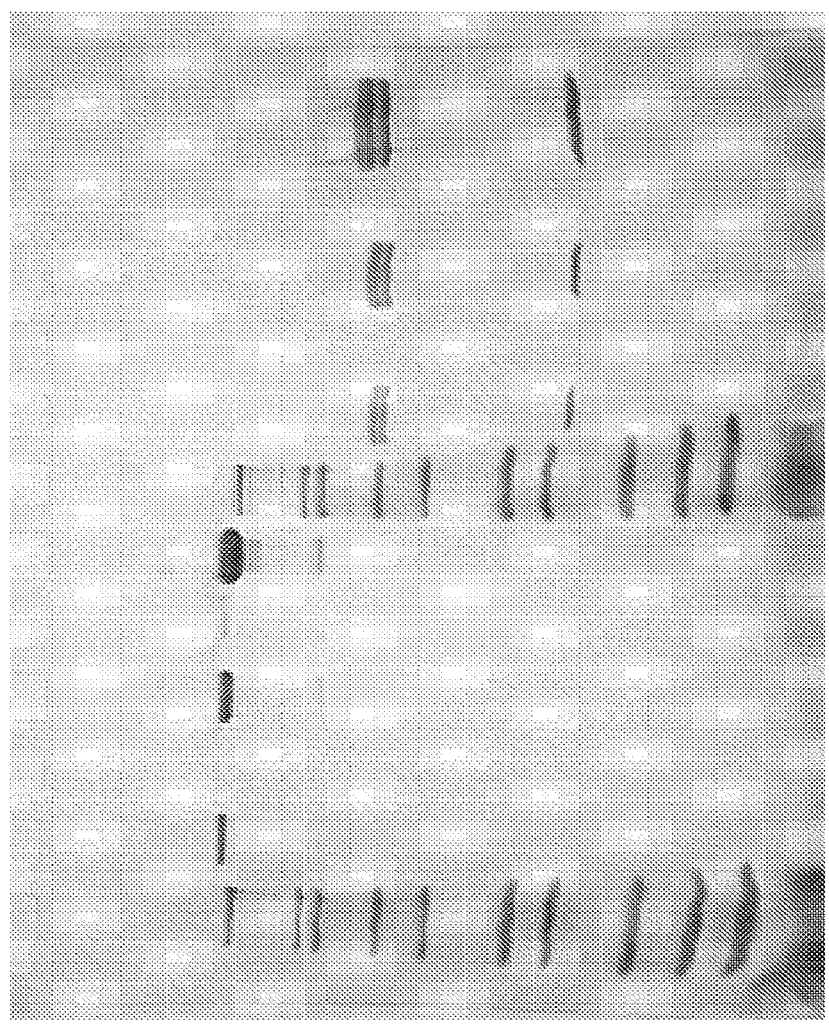

FIG. 36 shows a Coomassie brilliant blue stained Tris-glycine 4-20% SDS-PAGE of the final aKLH 120.6 IgG2 HC-C681 Ab product, described in Example 11. Lanes 1-12 were loaded as follows: lane 1: Novex Mark12 wide range protein standards (10 μl); lane 2: 0.5 μg product, non-reduced; lane 3: blank; lane 4: 2.0 μg product, non-reduced; lane 5: blank; lane 6: 10 μg product, non-reduced; lane 7: Novex Mark12 wide range protein standards (10 μl); lane 8: 0.5 μg product, reduced; lane 9: blank; lane 10: 2.0 μg product, reduced; lane 11: blank; lane 12: 10 μg product, reduced.

Figure 37:
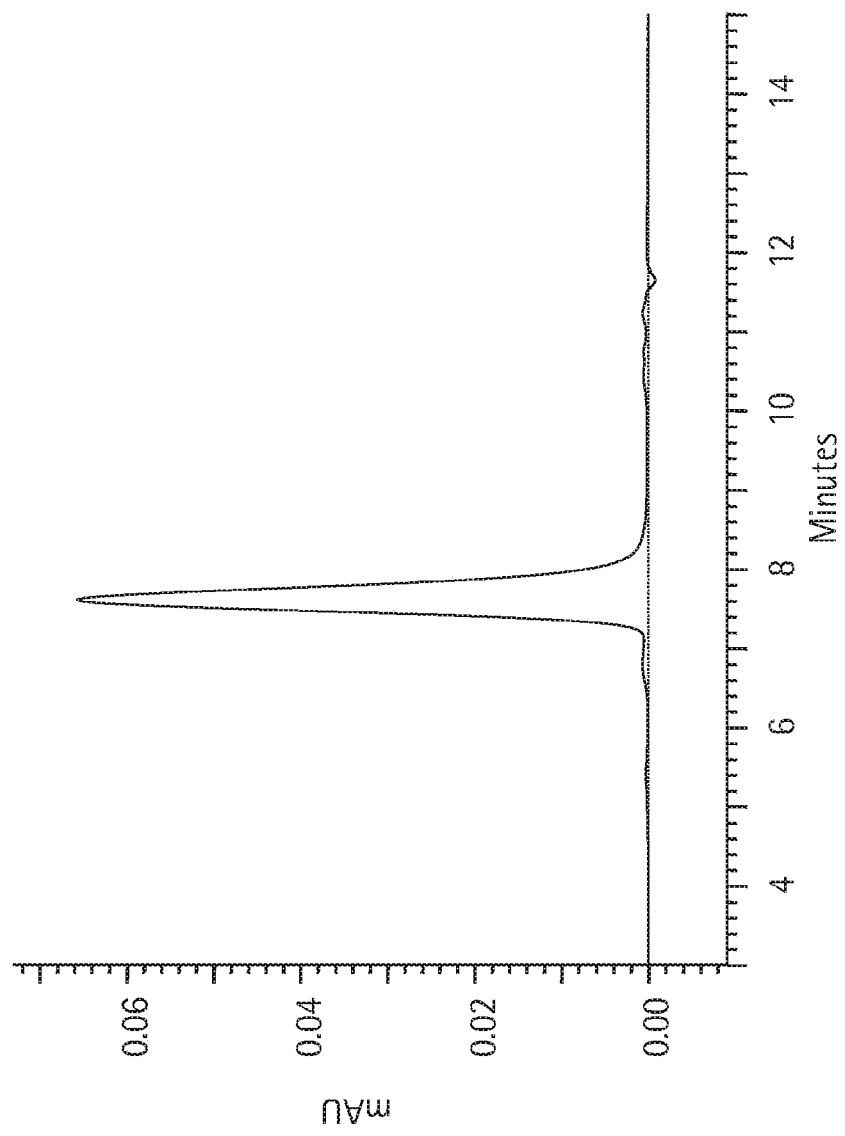

FIG. 37 shows size exclusion chromatography on 25 μg of the final aKLH 120.6 IgG2 HC-C681 Ab product, described in Example 11, injected onto a Phenomenex BioSep SEC-3000 column (7.8×300 mm) in 50 mM $NaH_2PO_4$, 250 mM NaCl, pH 6.9, at 1 mL/min detecting the absorbance at 280 nm.

Figure 38A:
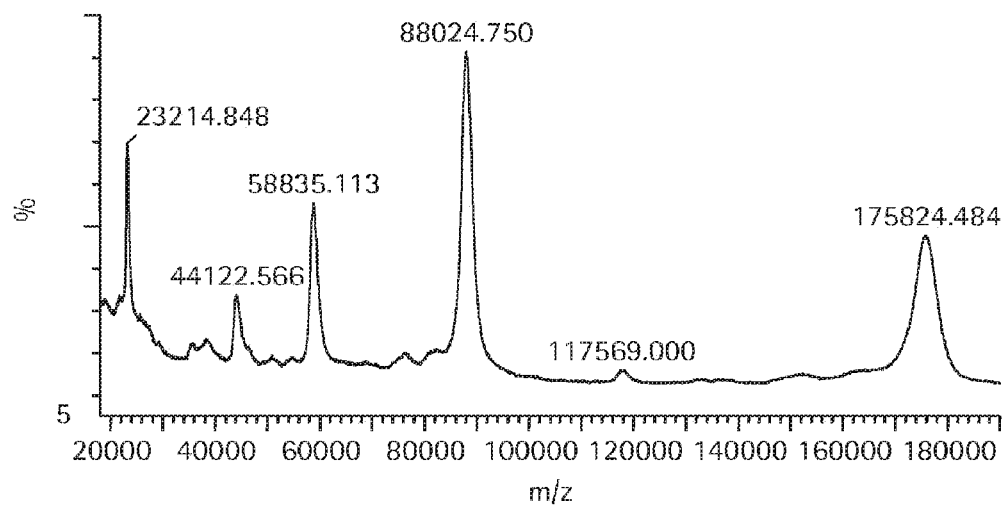
Figure 38B:
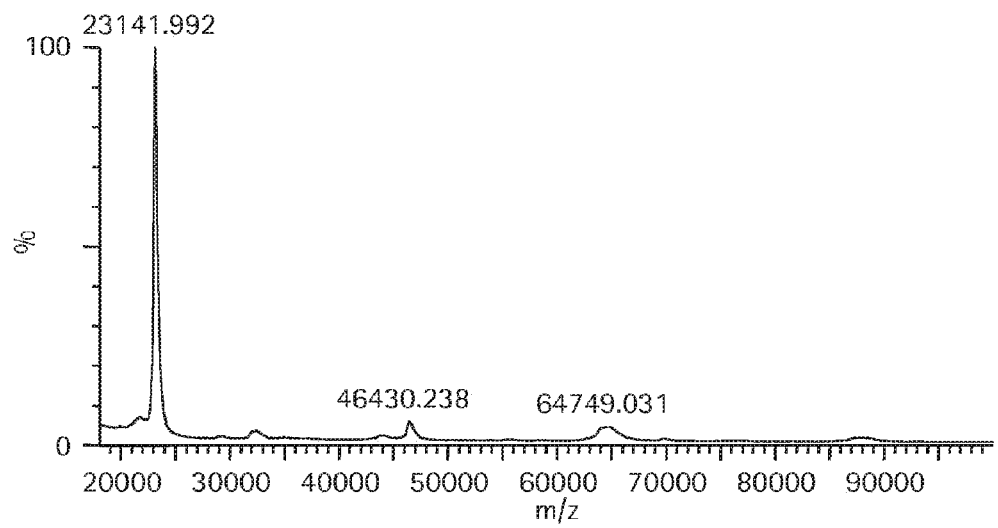

FIG. 38A-B shows non-reducing (FIG. 38A) and reducing (FIG. 38B) MALDI-MS mass spectral analysis of the final sample of aKLH 120.6 IgG2 HC-C681 product, described in Example 11, using a Micromass MALDI micro MX mass spectrometer equipped with a nitrogen laser. The sample was run at positive linear mode. The instrument's voltage was set at 12 kV and the high mass detector was set at 5 kV. Each spectrum was produced by accumulating data from about 200 laser shots. External mass calibration was achieved using purified proteins of known molecular masses.

Figure 39:
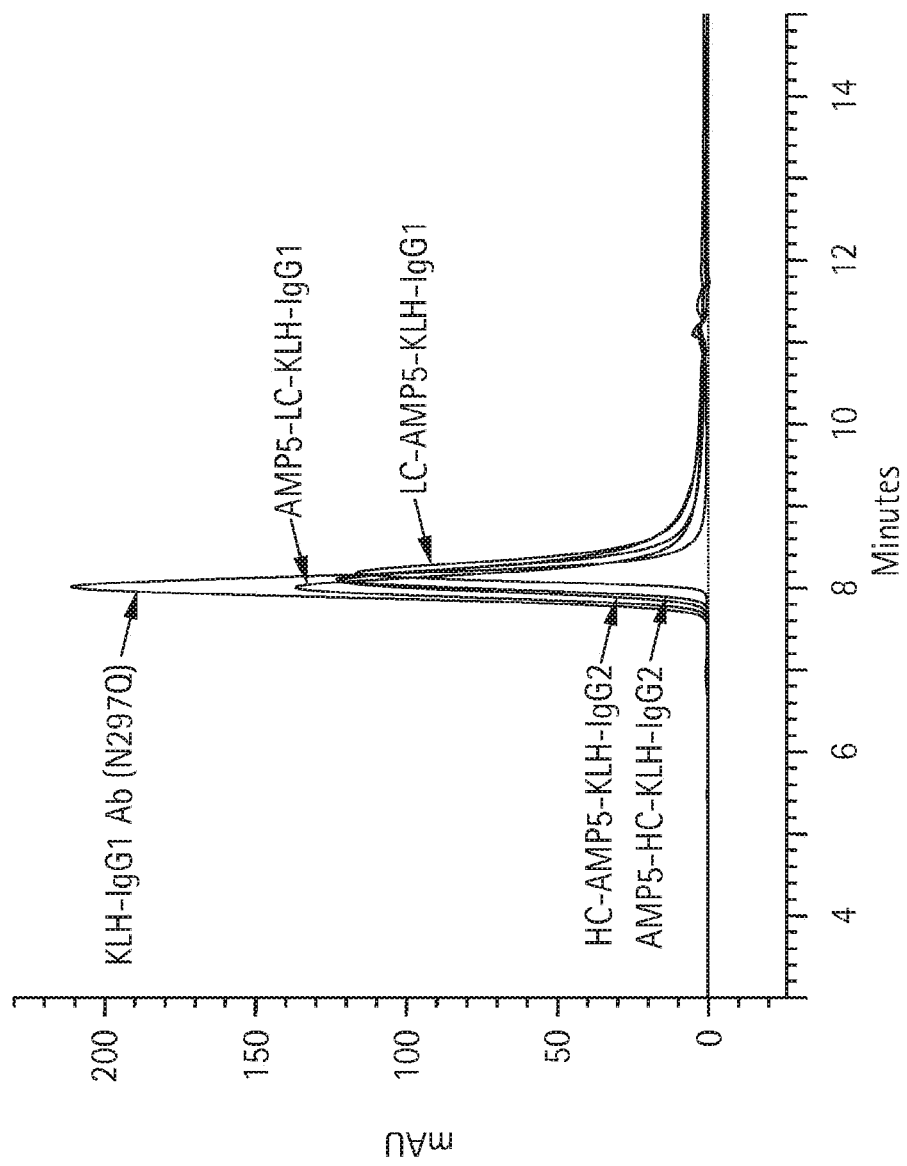
Figure 40B:
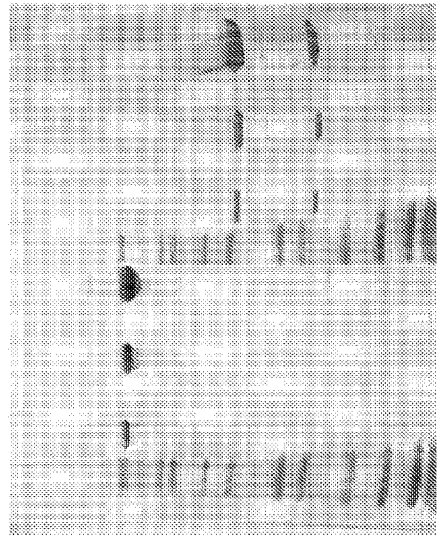
Figure 40A:
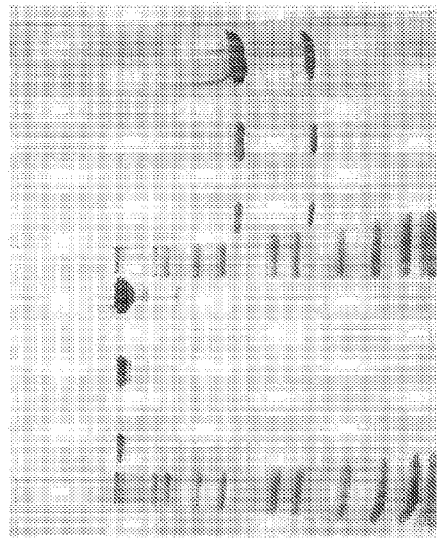
Figure 40C:
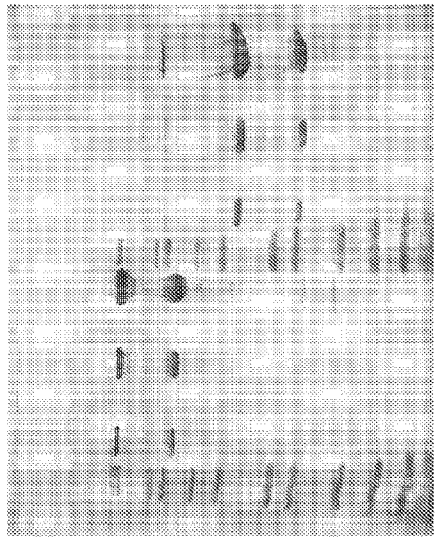
Figure 40E:
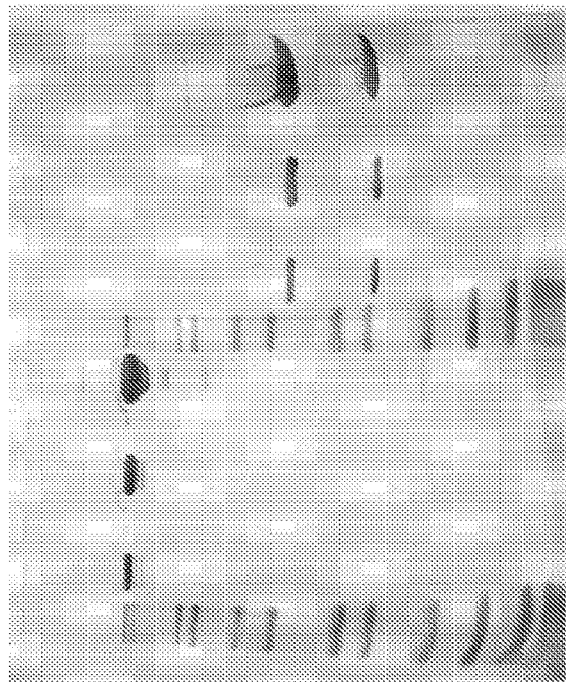
Figure 40D:
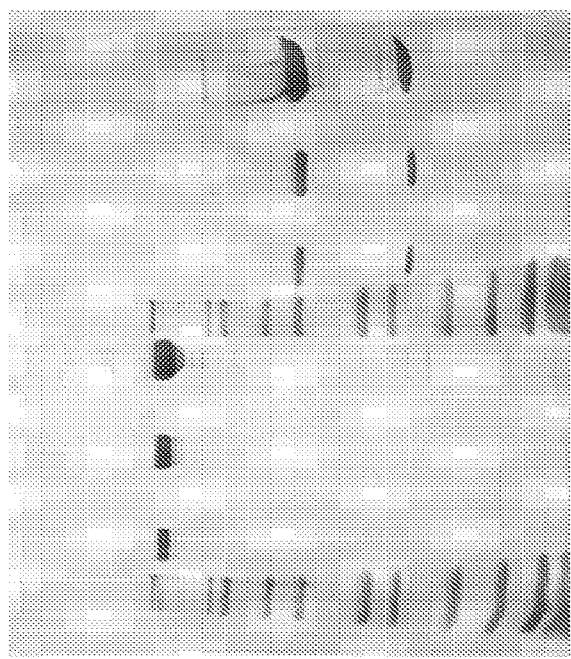

FIG. 39 shows size exclusion chromatography on 50 μg each of aKLH IgG1(N297Q), AMP5-HC aKLH IgG2, HC-AMP5 aKLH IgG2, AMP5-LC aKLH IgG1 and LC-AMP5 aKLH IgG1) products, described in Example 9, injected onto a Phenomenex BioSep SEC-3000 column (7.8×300 mm) in 50 mM $NaH_2PO_4$, 250 mM NaCl, pH 6.9, at 1 mL/min detecting the absorbance at 280 nm.

FIG. 40A-E shows analysis of antibodies (described in Example 9) aKLH IgG1 N297Q (FIG. 40A), AMP5-HC aKLH IgG2 (FIG. 40B), LC-AMP5 aKLH IgG2 (FIG. 40C), HC-AMP5 aKLH IgG2 (FIG. 40D), and AMP5-LC aKLH IgG1 (FIG. 40E) on a 1.0 mm Tris-glycine 4-20% SDS-PAGE (Novex) developed at 220V using non-reducing loading buffer and staining with QuickBlue (Boston Biologicals). Lanes 1-12 were loaded as follows: lane 1: Novex Mark12 wide range protein standards (10 µl); lane 2: 0.5 µg product, non-reduced; lane 3: blank; lane 4: 2.0 µg product, non-reduced; lane 5: blank; lane 6: 10 µg product, non-reduced; lane 7: Novex Mark12 wide range protein standards (10 µl); lane 8: 0.5 µg product, reduced; lane 9: blank; lane 10: 2.0 µg product, reduced; lane 11: blank; lane 12: 10 µg product, reduced.

FIG. 41A-D shows mass spectrographic analysis of reduced samples of LC-AMP5 aKLH IgG2 (FIG. 41A), AMP5-HC aKLH IgG2 (FIG. 41B), HC-AMP5 aKLH IgG2 (FIG. 41C), and AMP5-LC aKLH IgG1 (FIG. 41D), described in Example 9. Each sample was chromatographed through a Waters Massprep micro desalting column (2.1×5 mm) using an Acquity UPLC system then introduced into a Waters time-of-flight LCT premier mass spectrometer for mass measurement, and the mass spectrum was deconvoluted using the MaxEnt1 software.

Figure 42:
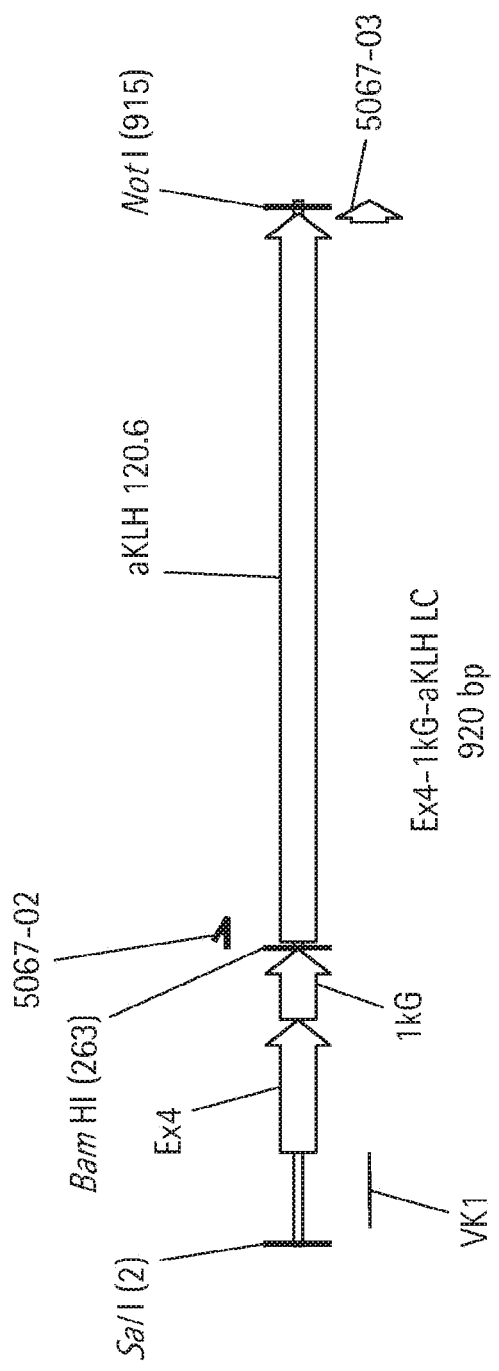

FIG. 42 is a schematic map of the Exendin-4 ("Ex4")-1kG-aKLH 120.6 LC fusion construct, described in Example 10.

Figure 43:
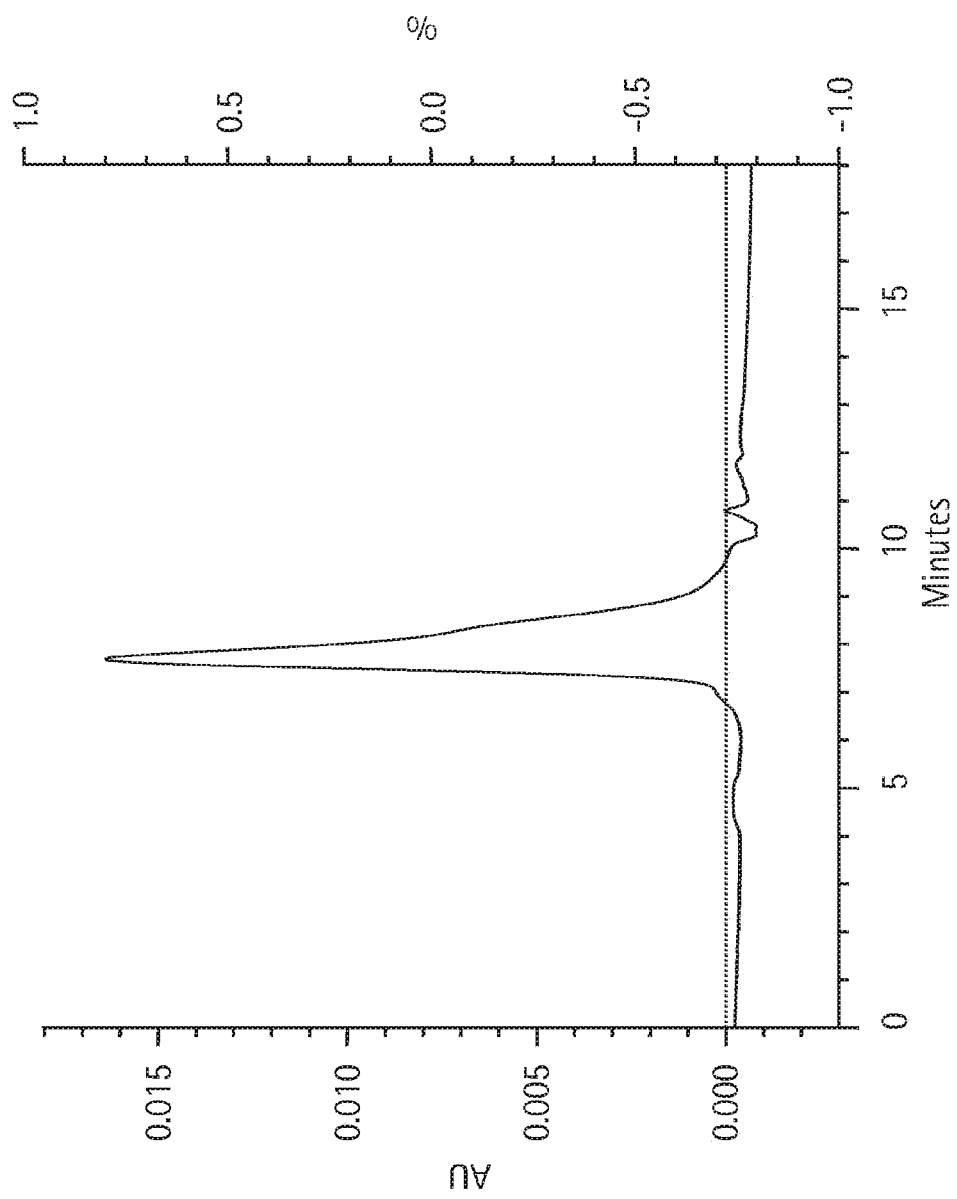

FIG. 43 shows size exclusion chromatography of 25 µg of the final Ex4-1kG-aKLH 120.6 LC antibody fusion, described in Example 10, injected onto a Phenomenex BioSep SEC-3000 column (7.8×300 mm) in 50 mM $NaH_2PO_4$, 250 mM NaCl, pH 6.9, at 1 mL/min detecting the absorbance at 280 nm.

Figure 44:
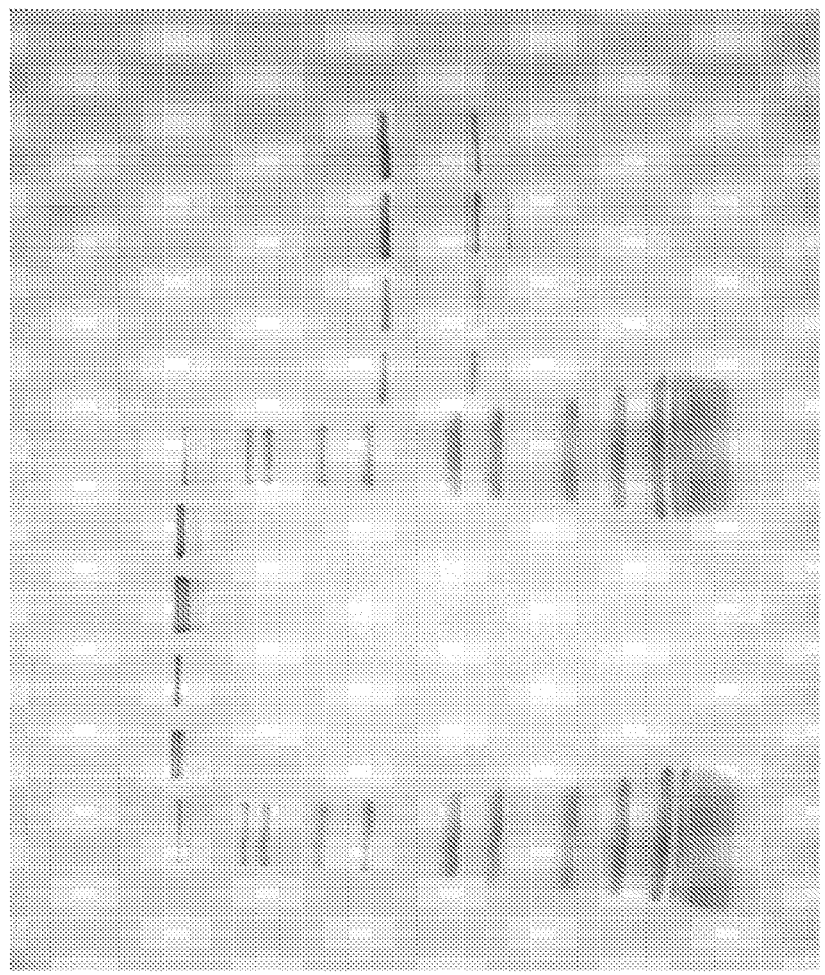

FIG. 44 shows analysis of on a 1.0 mm Tris-glycine 4-20% SDS-PAGE (Novex) developed at 220V using reducing and non-reducing loading buffers and staining with QuickBlue (Boston Biologicals). Lanes 1-10 were loaded as follows: lane 1: Novex Mark12 wide range protein standards (10 µl); lane 2: 0.5 µg other protein; lane 3: 0.5 µg Ex4-aKLH 120.6 Ab, non-reduced; lane 4: 2.0 µg other protein, lane 5: 2.0 µg Ex4-aKLH 120.6 Ab, non-reduced; lane 6: Novex Mark12 wide range protein standards (10 µl); lane 7: 0.5 µg other protein; lane 8: 0.5 µg Ex4-aKLH 120.6 Ab, reduced; lane 9: 2.0 µg other protein, lane 10: 2.0 µg Ex4-aKLH 120.6 Ab, reduced.

Figure 45:
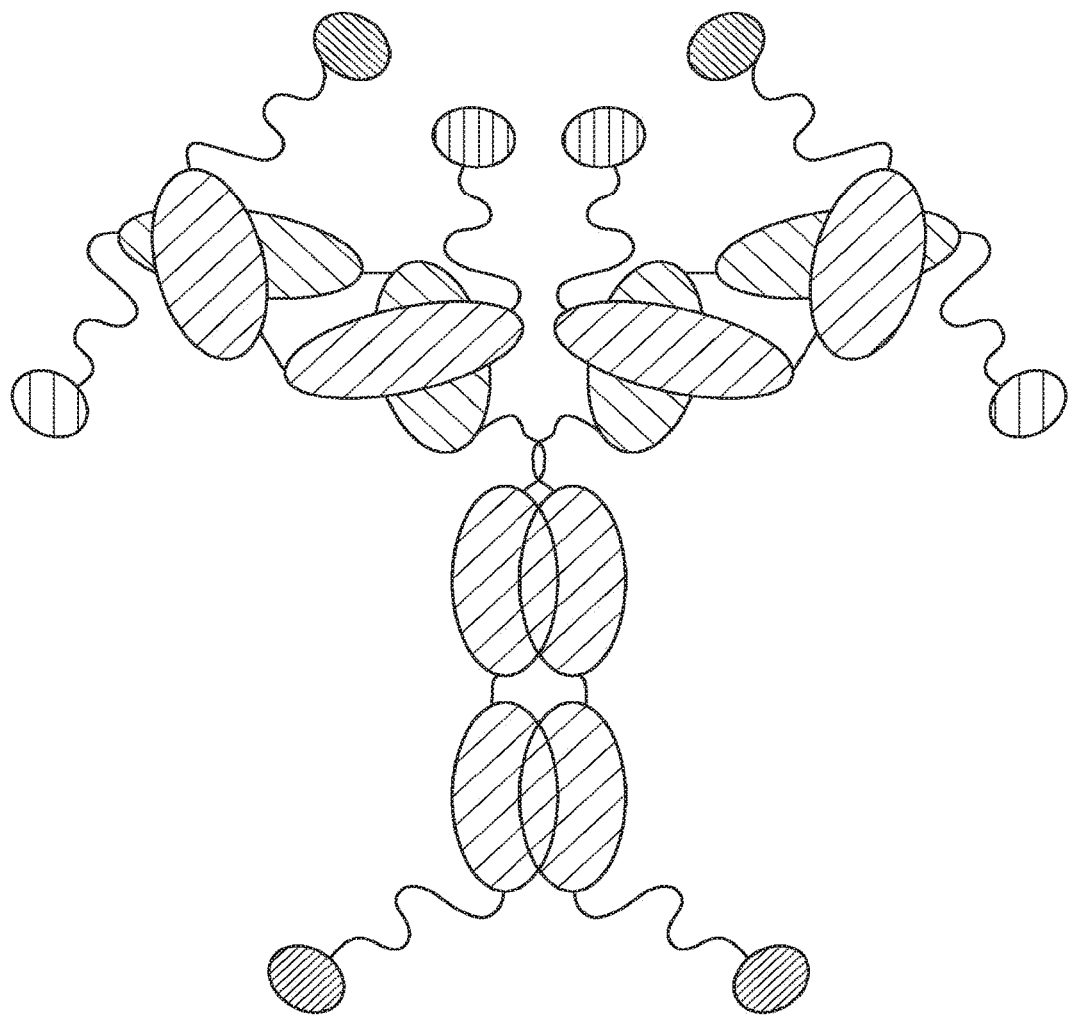

FIG. 45 shows a schematic representation of N-terminal and C-terminal fusions of pharmacologically active chemical moieties with the HC and LC monomers of an antibody of the invention, as further exemplified in Example 9.

DETAILED DESCRIPTION OF EMBODIMENTS

The section headings used herein are for organizational purposes only and are not to be construed as limiting the subject matter described.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. For example, reference to "a protein" includes a plurality of proteins; reference to "a cell" includes populations of a plurality of cells.

"Polypeptide" and "protein" are used interchangeably herein and include a molecular chain of two or more amino acids linked covalently through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be expressed recombinantly using known protein engineering techniques. In addition, fusion proteins can be derivatized as described herein by well-known organic chemistry techniques.

The term "isolated protein" referred means that a subject protein (1) is free of at least some other proteins with which it would normally be found in nature, (2) is essentially free of other proteins from the same source, e.g., from the same species, (3) is expressed recombinantly by a cell of a heterologous species or kind, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, and/or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

A "variant" of a polypeptide (e.g., an antigen binding protein, or an antibody) comprises an amino acid sequence wherein one or more amino acid residues are inserted into, deleted from and/or substituted into the amino acid sequence relative to another polypeptide sequence. Variants include fusion proteins.

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

A "secreted" protein refers to those proteins capable of being directed to the ER, secretory vesicles, or the extracellular space as a result of a secretory signal peptide sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage. In some other embodiments of the inventive composition, the toxin peptide analog can be synthesized by the host cell as a secreted protein, which can then be further purified from the extracellular space and/or medium.

As used herein "soluble" when in reference to a protein produced by recombinant DNA technology in a host cell is a protein that exists in aqueous solution; if the protein contains a twin-arginine signal amino acid sequence the soluble protein is exported to the periplasmic space in gram negative bacterial hosts, or is secreted into the culture medium by eukaryotic host cells capable of secretion, or by bacterial host possessing the appropriate genes (e.g., the kil gene). Thus, a soluble protein is a protein which is not found in an inclusion body inside the host cell. Alternatively, depending on the context, a soluble protein is a protein which is not found integrated in cellular membranes; in contrast, an insoluble protein is one which exists in denatured form inside cytoplasmic granules (called an inclusion body) in the host cell, or again depending on the context, an insoluble protein is one which is present in cell membranes, including but not limited to, cytoplasmic membranes, mitochondrial membranes, chloroplast membranes, endoplasmic reticulum membranes, etc.

The term "recombinant" indicates that the material (e.g., a nucleic acid or a polypeptide) has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well known molecular biological procedures. Examples of such molecular biological procedures are found in Maniatis et al., Molecular Cloning. A Laboratory Manual. Cold Spring Harbour Laboratory, Cold Spring Harbour, N.Y. (1982). A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid.

The term "polynucleotide" or "nucleic acid" includes both single-stranded and double-stranded nucleotide polymers containing two or more nucleotide residues. The nucleotide residues comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phosphoraniladate and phosphoroamidate.

The term "oligonucleotide" means a polynucleotide comprising 200 or fewer nucleotide residues. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays. Oligonucleotides may be used, for example, as PCR primers, cloning primers or hybridization probes.

A "polynucleotide sequence" or "nucleotide sequence" or "nucleic acid sequence," as used interchangeably herein, is the primary sequence of nucleotide residues in a polynucleotide, including of an oligonucleotide, a DNA, and RNA, a nucleic acid, or a character string representing the primary sequence of nucleotide residues, depending on context. From any specified polynucleotide sequence, either the given nucleic acid or the complementary polynucleotide sequence can be determined. Included are DNA or RNA of genomic or synthetic origin which may be single- or double-stranded, and represent the sense or antisense strand. Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

As used herein, an "isolated nucleic acid molecule" or "isolated nucleic acid sequence" is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the antigen binding protein (e.g., antibody) where, for example, the nucleic acid molecule is in a chromosomal location different from that of natural cells.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (protein) chain. The DNA sequence thus codes for the RNA sequence and for the amino acid sequence.

The term "gene" is used broadly to refer to any nucleic acid associated with a biological function. Genes typically include coding sequences and/or the regulatory sequences required for expression of such coding sequences. The term "gene" applies to a specific genomic or recombinant sequence, as well as to a cDNA or mRNA encoded by that sequence. A "fusion gene" contains a coding region that encodes a toxin peptide analog. Genes also include non-expressed nucleic acid segments that, for example, form recognition sequences for other proteins. Non-expressed regulatory sequences including transcriptional control elements to which regulatory proteins, such as transcription factors, bind, resulting in transcription of adjacent or nearby sequences.

"Expression of a gene" or "expression of a nucleic acid" means transcription of DNA into RNA (optionally including modification of the RNA, e.g., splicing), translation of RNA into a polypeptide (possibly including subsequent post-translational modification of the polypeptide), or both transcription and translation, as indicated by the context.

As used herein the term "coding region" or "coding sequence" when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

The term "control sequence" or "control signal" refers to a polynucleotide sequence that can, in a particular host cell, affect the expression and processing of coding sequences to which it is ligated. The nature of such control sequences may depend upon the host organism. In particular embodiments, control sequences for prokaryotes may include a promoter, a ribosomal binding site, and a transcription termination sequence. Control sequences for eukaryotes may include promoters comprising one or a plurality of recognition sites for transcription factors, transcription enhancer sequences or elements, polyadenylation sites, and transcription termination sequences. Control sequences can include leader sequences and/or fusion partner sequences. Promoters and enhancers consist of short arrays of DNA that interact specifically with cellular proteins involved in transcription (Maniatis, et al., Science 236:1237 (1987)). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 (1986) and Maniatis, et al., Science 236:1237 (1987)).

The term "vector" means any molecule or entity (e.g., nucleic acid, plasmid, bacteriophage or virus) used to transfer protein coding information into a host cell.

The term "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. Such techniques are well known in the art. (E.g., Goodey, Andrew R.; et al., Peptide and DNA sequences, U.S. Pat. No. 5,302,697; Weiner et al., Compositions and methods for protein secretion, U.S. Pat. No. 6,022,952 and U.S. Pat. No. 6,335,178; Uemura et al., Protein expression vector and utilization thereof, U.S. Pat. No. 7,029,909; Ruben et al., 27 human secreted proteins, US 2003/0104400 A1).

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed, or is capable of being transformed, with a nucleic acid and thereby expresses a gene of interest. The term includes the progeny of the parent cell, whether or not the progeny is identical in morphology or in genetic make-up to the original parent cell, so long as the gene of interest is present. Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial host cells in culture include bacteria (such as *Escherichia coli* sp.), yeast (such as *Saccharomyces* sp.) and other fungal cells, insect cells, plant cells, mammalian (including human) cells, e.g., CHO cells and HEK-293 cells. Modifications can be made at the DNA level, as well. The peptide-encoding DNA sequence may be changed to codons more compatible with the chosen host cell. For *E. coli*, optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired compounds are expressed. Such fermentation conditions are well known in the art.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al., 1981, Gene 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

By "physiologically acceptable salt" of a composition of matter, for example a salt of the antigen binding protein, such as an antibody, is meant any salt or salts that are known or later discovered to be pharmaceutically acceptable. Some non-limiting examples of pharmaceutically acceptable salts are: acetate; trifluoroacetate; hydrohalides, such as hydrochloride and hydrobromide; sulfate; citrate; maleate; tartrate; glycolate; gluconate; succinate; mesylate; besylate; salts of gallic acid esters (gallic acid is also known as 3,4,5 trihydroxybenzoic acid) such as PentaGalloylGlucose (PGG) and epigallocatechin gallate (EGCG), salts of cholesteryl sulfate, pamoate, tannate and oxalate salts.

A "domain" or "region" (used interchangeably herein) of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., a ligand binding domain, or a cytosolic, transmembrane or extracellular domain).

"Treatment" or "treating" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. "Treatment" includes any indicia of success in the amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, self-reporting by a patient, neuropsychiatric exams, and/or a psychiatric evaluation.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with migraine headache. In some embodiments, the effective amount is a therapeutically effective amount or a prophylactically effective amount. A "therapeutically effective amount" is an amount sufficient to remedy a disease state (e.g., transplant rejection or GVHD, inflammation, multiple sclerosis, cancer, diabetes, neuropathy, pain) or symptom(s), particularly a state or symptom(s) associated with the disease state, or otherwise prevent, hinder, retard or reverse the progression of the disease state or any other undesirable symptom associated with the disease in any way whatsoever (i.e. that provides "therapeutic efficacy"). A "prophylactically effective amount" is an amount of a pharmaceutical composition that, when administered to a subject, will have the intended prophylactic effect, e.g., preventing or delaying the onset (or reoccurrence) of migraine headache or multiple sclerosis symptoms, or reducing the likelihood of the onset (or reoccurrence) of migraine headache, migraine headache symptoms, or multiple sclerosis symptoms. The full therapeutic or prophylactic effect does not necessarily occur by administration of one dose, and may occur only after administration of a series of doses. Thus, a therapeutically or prophylactically effective amount may be administered in one or more administrations.

"Mammal" for purposes of treatment refers to any animal classified as a mammal, including humans, domestic and farm animals, and zoo, sports, or pet animals, such as dogs, horses, cats, cows, rats, mice, monkeys, etc. Preferably, the mammal is human.

The term "naturally occurring" as used throughout the specification in connection with biological materials such as polypeptides, nucleic acids, host cells, and the like, refers to materials which are found in nature.

The term "antibody", or interchangeably "Ab", is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab, Fab', F(ab')$_2$, Fv, single chain antibodies, diabodies), comprising complementarity determining regions (CDRs) of the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes have different effector functions; for example, IgG1 and IgG3 isotypes have antibody-dependent cellular cytotoxicity (ADCC) activity.

The term "antigen binding protein" (ABP) includes antibodies or antibody fragments, as defined above, and recombinant peptides or other compounds that contain sequences derived from CDRs having the desired antigen-binding properties.

In general, an antigen binding protein, e.g., an antibody or antibody fragment, "specifically binds" to an antigen (e.g., keyhole limpet hemocynin (KLH) or dinitrophenol (DNP)) when it has a significantly higher binding affinity for, and consequently is capable of distinguishing, that antigen, compared to its affinity for other unrelated proteins, under similar binding assay conditions. Typically, an antigen binding protein is said to "specifically bind" its target antigen when the dissociation constant ($K_D$) is $\leq 10^{-8}$ M. The antibody specifically binds antigen with "high affinity" when the $K_D$ is $\leq 5\times10^{-9}$ M, and with "very high affinity" when the $K_D$ is $\leq 5\times10^{-10}$ M. In one embodiment, the antibodies will bind to KLH or DNP with a $K_D$ of between about $10^{-8}$ M and $10^{-10}$ M, and in yet another embodiment the antibodies will bind with a $K_D \leq 5\times10^{-9}$.

"Antigen binding region" or "antigen binding site" means a portion of a protein, that specifically binds a specified antigen, e.g., keyhole limpet hemocynin (KLH) or dinitrophenol (DNP). For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs"). Certain antigen binding regions also include one or more "framework" regions ("FRs"). A "CDR" is an amino acid sequence that contributes to antigen binding specificity and affinity. "Framework" regions can aid in maintaining the proper conformation of the CDRs to promote binding between the antigen binding region and an antigen.

An "isolated" antibody is one that has been identified and separated from one or more components of its natural environment or of a culture medium in which it has been secreted by a producing cell. "Contaminant" components of its natural environment or medium are materials that would interfere with diagnostic or therapeutic uses for the antibody, and may include enzymes, hormones, and other proteinaceous or nonproteinaceous solutes. In some embodiments, the antibody will be purified (1) to greater than 95% by weight of antibody, and most preferably more than 99% by weight, or (2) to homogeneity by SDS-PAGE under reducing or nonreducing conditions, optionally using a stain, e.g., Coomassie blue or silver stain. Isolated naturally occurring antibody includes the antibody in situ within recombinant cells since at least one component of the antibody's natural environment will not be present. Typically, however, isolated antibody will be prepared by at least one purification step.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against an individual antigenic site or epitope, in contrast to polyclonal antibody preparations that typically include different antibodies directed against different epitopes. Nonlimiting examples of monoclonal antibodies include murine, rabbit, rat, chicken, chimeric, humanized, or human antibodies, fully assembled antibodies, multispecific antibodies (including bispecific antibodies), antibody fragments that can bind an antigen (including, Fab, Fab', F(ab')$_2$, Fv, single chain antibodies, diabodies), maxibodies, nanobodies, and recombinant peptides comprising CDRs of the foregoing as long as they exhibit the desired biological activity, or variants or derivatives thereof.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 [1975], or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 [1991] and Marks et al., J. Mol. Biol., 222:581-597 (1991), for example.

A "multispecific" binding agent or antigen binding protein or antibody is one that targets more than one antigen or epitope.

A "bispecific," "dual-specific" or "bifunctional" binding agent or antigen binding protein or antibody is a hybrid having two different antigen binding sites. Biantigen binding proteins, antigen binding proteins and antibodies are a species of multiantigen binding protein, antigen binding protein or multispecific antibody and may be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antigen binding protein or antibody will bind to two different epitopes, which may reside on the same or different protein targets.

The term "immunoglobulin" encompasses full antibodies comprising two dimerized heavy chains (HC), each covalently linked to a light chain (LC); a single undimerized immunoglobulin heavy chain and covalently linked light chain (HC+LC), or a chimeric immunoglobulin (light chain+heavy chain)-Fc heterotrimer (a so-called "hemibody").

An "antibody" is a tetrameric glycoprotein. In a naturally-occurring antibody, each tetramer is composed of two identical pairs of polypeptide chains, each pair having one "light" chain of about 220 amino acids (about 25 kDa) and one "heavy" chain of about 440 amino acids (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function. The variable region differs among different antibodies. The constant region is the same among different antibodies. Within the variable region of each heavy or light chain, there are three hypervariable subregions that help determine the antibody's specificity for antigen. The variable domain residues between the hypervariable regions are called the framework residues and generally are somewhat homologous among different antibodies. Immunoglobulins can be assigned to different classes depending on the amino acid sequence of the constant domain of their heavy chains. Human light chains are classified as kappa (κ) and lambda (λ) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)). Within the scope of the invention, an "antibody" also encompasses a recombinantly made antibody, and antibodies that are lacking glycosylation.

The term "light chain" or "immunoglobulin light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" or "immunoglobulin heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The $V_H$ domain is at the amino-terminus of the polypeptide, and the CH domains are at the carboxyl-terminus, with the $C_H3$ being closest to the carboxy-terminus of the polypeptide. Heavy chains are classified as mu (μ), delta (Δ), gamma (γ), alpha (α), and epsilon (ε), and define the antibody's isotype as IgM, IgD, IgG, IgA, and IgE, respectively. In separate embodiments of the invention, heavy chains may be of any isotype, including IgG (including IgG1, IgG2, IgG3 and IgG4 subtypes), IgA (including IgA1 and IgA2 subtypes), IgM and IgE. Several of these may be further divided into subclasses or isotypes, e.g. IgG1, IgG2, IgG3, IgG4, IgA1 and IgA2. Different IgG isotypes may have different effector functions (mediated by the Fc region), such as antibody-dependent cellular cytotoxicity (ADCC) and complement-dependent cytotoxicity (CDC). In ADCC, the Fc region of an antibody binds to Fc receptors (FcγRs) on the surface of immune effector cells such as natural killers and macrophages, leading to the phagocytosis or lysis of the targeted cells. In CDC, the antibodies kill the targeted cells by triggering the complement cascade at the cell surface.

An "Fc region", or used interchangeably herein, "Fc domain" or "immunoglobulin Fc domain", contains two heavy chain fragments, which in a full antibody comprise the $C_H1$ and $C_H2$ domains of the antibody. The two heavy chain fragments are held together by two or more disulfide bonds and by hydrophobic interactions of the $C_H3$ domains.

The term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

"Allotypes" are variations in antibody sequence, often in the constant region, that can be immunogenic and are encoded by specific alleles in humans. Allotypes have been identified for five of the human IGHC genes, the IGHG1, IGHG2, IGHG3, IGHA2 and IGHE genes, and are designated as G1m, G2m, G3m, A2m, and Em allotypes, respectively. At least 18 Gm allotypes are known: nG1m(1), nG1m(2), G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5). There are two A2m allotypes A2m(1) and A2m(2).

For a detailed description of the structure and generation of antibodies, see Roth, D. B., and Craig, N. L., *Cell*, 94:411-414 (1998), herein incorporated by reference in its entirety. Briefly, the process for generating DNA encoding the heavy and light chain immunoglobulin sequences occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged variable regions of the heavy and light immunoglobulin genes. This gene segment rearrangement process appears to be sequential. First, heavy chain D-to-J joints are made, followed by heavy chain V-to-DJ joints and light chain V-to-J joints. In addition to the rearrangement of V, D and J segments, further diversity is generated in the primary repertoire of immunoglobulin heavy and light chains by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity. The net effect of such rearrangements in the variable region gene segments and the variable recombination which may occur during such joining is the production of a primary antibody repertoire.

The term "hypervariable" region refers to the amino acid residues of an antibody which are responsible for antigen-binding. The hypervariable region comprises amino acid residues from a complementarity determining region or CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)]. Even a single CDR may recognize and bind antigen, although with a lower affinity than the entire antigen binding site containing all of the CDRs.

An alternative definition of residues from a hypervariable "loop" is described by Chothia et al., *J. Mol. Biol.* 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain.

"Framework" or "FR" residues are those variable region residues other than the hypervariable region residues.

"Antibody fragments" comprise a portion of an intact full length antibody, preferably the antigen binding or variable region of the intact antibody. Examples of antibody fragments include Fab, Fab', F(ab')$_2$, and Fv fragments; diabodies; linear antibodies (Zapata et al., Protein Eng., 8(10): 1057-1062 (1995)); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment which contains the constant region. The Fab fragment contains all of the variable domain, as well as the constant domain of the light chain and the first constant domain (CH1) of the heavy chain. The Fc fragment displays carbohydrates and is responsible for many antibody effector functions (such as binding complement and cell receptors), that distinguish one class of antibody from another.

Pepsin treatment yields an F(ab')$_2$ fragment that has two "Single-chain Fv" or "scFv" antibody fragments comprising the VH and VL domains of antibody, wherein these domains are present in a single polypeptide chain. Fab fragments differ from Fab' fragments by the inclusion of a few additional residues at the carboxy terminus of the heavy chain CH1 domain including one or more cysteines from the antibody hinge region. Preferably, the Fv polypeptide further comprises a polypeptide linker between the VH and VL domains that enables the Fv to form the desired structure for antigen binding. For a review of scFv see Pluckthun in The Pharmacology of Monoclonal Antibodies, vol. 1 13, Rosenburg and Moore eds., Springer-Verlag, New York, pp. 269-315 (1994).

A "Fab fragment" is comprised of one light chain and the $C_H1$ and variable regions of one heavy chain. The heavy chain of a Fab molecule cannot form a disulfide bond with another heavy chain molecule.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form an F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen binding site on the surface of the VH VL dimer. A single variable domain (or half of an Fv comprising only three CDRs specific for an antigen) has the ability to recognize and bind antigen, although at a lower affinity than the entire binding site.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. No. 4,946,778 and U.S. Pat. No. 5,260,203, the disclosures of which are incorporated by reference in their entireties.

"Single-chain Fv" or "scFv" antibody fragments comprise the $V_H$ and $V_L$ domains of antibody, wherein these domains are present in a single polypeptide chain, and optionally comprising a polypeptide linker between the $V_H$ and $V_L$ domains that enables the Fv to form the desired structure for antigen binding (Bird et al., Science 242:423-426, 1988, and Huston et al., Proc. Natl. Acad. Sci. USA 85:5879-5883, 1988). An "Fd" fragment consists of the $V_H$ and $C_H1$ domains.

The term "diabodies" refers to small antibody fragments with two antigen-binding sites, which fragments comprise a heavy-chain variable domain (VH) connected to a light-chain variable domain (VL) in the same polypeptide chain (VH VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

The term "compete" when used in the context of antigen binding proteins (e.g., neutralizing antigen binding proteins or neutralizing antibodies) that compete for the same epitope means competition between antigen binding proteins is determined by an assay in which the antigen binding protein (e.g., antibody or immunologically functional fragment thereof) under test prevents or inhibits specific binding of a reference antigen binding protein (e.g., a ligand, or a reference antibody) to a common antigen (e.g., KLH or a fragment thereof, or DNP). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176: 546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit specific binding of a reference antigen binding protein to a common antigen by at least 40%, 45%, 50%, 55%, 60%, 65%, 70% or 75%. In some instance, binding is inhibited by at least 80%, 85%, 90%, 95%, or 97% or more.

The term "antigen" refers to a molecule or a portion of a molecule capable of being bound by a selective binding agent, such as an antigen binding protein (including, e.g., an antibody or immunological functional fragment thereof), and additionally capable of being used in an animal to produce antibodies capable of binding to that antigen. An antigen may possess one or more epitopes that are capable of interacting with different antigen binding proteins, e.g., antibodies.

The terms "DNP" or "dinitrophenol" are used interchangeably herein and denote the antigen 2,4-dinitrophenol. "Anti-DNP" or "aDNP" or "aDNP" are used interchangeably herein to refer to an antigen binding protein, e.g., an antibody or antibody fragment, that specifically binds DNP.

The terms "KLH" or "keyhole limpet hemocyanin" are used interchangeably herein and denote the Imject® Mariculture Keyhole Limpet hemocyanin (mcKLH; Pierce Biotechnology, Rockford, Ill.). According to the manufacturer, mcKLH is harvested from select populations of the mollusk Megathura crenulata (keyhole limpet) that are grown in mariculture, rather than being extracted from wild populations; KLH has a high molecular mass ($4.5 \times 10^5$-$1.3 \times 10^7$ Daltons of mixed aggregates of 350 and 390 kDa subunits) and elicits a stronger immune response than BSA or ovalbumin. "Anti-KLH" or "aKLH" or "aKLH" are used interchangeably herein to refer to an antigen binding protein, e.g., an antibody or antibody fragment, that specifically binds KLH.

The term "epitope" is the portion of a molecule that is bound by an antigen binding protein (for example, an antibody). The term includes any determinant capable of specifically binding to an antigen binding protein, such as an antibody or to a T-cell receptor. An epitope can be contiguous or non-contiguous (e.g., in a single-chain polypeptide, amino acid residues that are not contiguous to one another in the polypeptide sequence but that within the context of the molecule are bound by the antigen binding protein). In certain embodiments, epitopes may be mimetic in that they comprise a three dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073. For example, sequence identity can be determined by standard methods that are commonly used to compare the similarity in position of the amino acids of two polypeptides. Using a computer program such as BLAST or FASTA, two polypeptide or two polynucleotide sequences are aligned for optimal matching of their respective residues (either along the full length of one or both sequences, or along a pre-determined portion of one or both sequences). The programs provide a default opening penalty and a default gap penalty, and a scoring matrix such as PAM 250 [a standard scoring matrix; see Dayhoff et al., in *Atlas of Protein Sequence and Structure*, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences. In calculating percent identity, the sequences being compared are aligned in a way that gives the largest match between the sequences.

The GCG program package is a computer program that can be used to determine percent identity, which package includes GAP (Devereux et al., 1984, Nucl. Acid Res. 12:387; Genetics Computer Group, University of Wisconsin, Madison, Wis.). The computer algorithm GAP is used to align the two polypeptides or two polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Recommended parameters for determining percent identity for polypeptides or nucleotide sequences using the GAP program include the following:
Algorithm: Needleman et al., 1970, J. Mol. Biol. 48:443-453;
Comparison matrix: BLOSUM 62 from Henikoff et al., 1992, supra;
Gap Penalty: 12 (but with no penalty for end gaps)
Gap Length Penalty: 4
Threshold of Similarity: 0
Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

The term "modification" when used in connection with antigen binding proteins, including antibodies and antibody fragments, of the invention, include, but are not limited to, one or more amino acid changes (including substitutions, insertions or deletions); chemical modifications; covalent modification by conjugation to therapeutic or diagnostic agents; labeling (e.g., with radionuclides or various enzymes); covalent polymer attachment such as PEGylation (derivatization with polyethylene glycol) and insertion or substitution by chemical synthesis of non-natural amino acids. Modified antigen binding proteins of the invention will retain the binding properties of unmodified molecules of the invention.

The term "derivative" when used in connection with antigen binding proteins (including antibodies and antibody fragments) of the invention refers to antigen binding proteins that are covalently modified by conjugation to therapeutic or diagnostic agents, labeling (e.g., with radionuclides or various enzymes), covalent polymer attachment such as PEGylation (derivatization with polyethylene glycol) and insertion or substitution by chemical synthesis of non-natural amino acids. Derivatives of the invention will retain the binding properties of underivatized molecules of the invention.

Immunoglobulin Embodiments of Antigen Binding Proteins

In full-length immunoglobulin light and heavy chains, the variable and constant regions are joined by a "J" region of about twelve or more amino acids, with the heavy chain also including a "D" region of about ten more amino acids. See, e.g., Fundamental Immunology, 2nd ed., Ch. 7 (Paul, W., ed.) 1989, New York: Raven Press (hereby incorporated by reference in its entirety for all purposes). The variable regions of each light/heavy chain pair typically form the antigen binding site.

One example of a human IgG2 heavy chain (HC) constant domain has the amino acid sequence:

```
                                          SEQ. ID NO: 86
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK//.
```

Constant region sequences of other IgG isotypes are known in the art for making recombinant versions of the inventive antigen binding protein having an IgG1, IgG2, IgG3, or IgG4 immunoglobulin isotype, if desired. In general, human IgG2 can be used for targets where effector functions are not desired, and human IgG1 in situations where such effector functions (e.g., antibody-dependent cytotoxicity (ADCC)) are desired. Human IgG3 has a relatively short half life and human IgG4 forms antibody "half-molecules." There are four known allotypes of human IgG1. The preferred allotype is referred to as "hIgG1z", also known as the "KEEM" allotype. Human IgG1 allotypes "hIgG1za" (KDEL), "hIgG1f" (REEM), and "hIgG1fa" are also useful; all appear to have ADCC effector function.

Human hIgG1z heavy chain (HC) constant domain has the amino acid sequence:

SEQ ID NO: 87
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRW
QQGNVFSCSVMHEALHNHYTQKSLSLSPGK//.

Human hIgG1za heavy chain (HC) constant domain has the amino acid sequence:

SEQ ID NO: 88
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK//.

Human hIgG1f heavy chain (HC) constant domain has the amino acid sequence:

SEQ ID NO: 89
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRW
QQGNVFSCSVMHEALHNHYTQKSLSLSPGK//.

Human hIgG1fa heavy chain (HC) constant domain has the amino acid sequence:

SEQ ID NO: 90
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK//.

One example of a human immunoglobulin light chain (LC) constant region sequence is the following (designated "CL-1"):

SEQ ID NO: 91
GQPKANPTVTLFPPSSEELQANKATLVCLISDFYPGAVTVAWKADGSPVK
AGVETTKPSKQSNNKYAASSYLSLTPEQWKSHRSYSCQVTHEGSTVEKTV
APTECS//.

CL-1 is useful to increase the pI of antibodies and is convenient. There are three other human immunoglobulin light chain constant regions, designated "CL-2", "CL-3" and "CL-7", which can also be used within the scope of the present invention. CL-2 and CL-3 are more common in the human population.

CL-2 human light chain (LC) constant domain has the amino acid sequence:

SEQ ID NO: 92
GQPKAAPSVTLFPPSSEELQANKATLVCLISDFYPGAVTVAWKADSSPVK
AGVETTTPSKQSNNKYAASSYLSLTPEQWKSHRSYSCQVTHEGSTVEKTV
APTECS//.

CL-3 human LC constant domain has the amino acid sequence:

SEQ ID NO: 93
GQPKAAPSVTLFPPSSEELQANKATLVCLISDFYPGAVTVAWKADSSPVK
AGVETTTPSKQSNNKYAASSYLSLTPEQWKSHKSYSCQVTHEGSTVEKTV
APTECS//.

CL-7 human LC constant domain has the amino acid sequence:

SEQ ID NO: 94
GQPKAAP SVTLFPPSSEELQANKATLVCLVSDFYPGAVTVAWKADGSPV
KVGVETTKPSKQSNNKYAASSYLSLTPEQWKSHRSYSCRVTHEGSTVEKT
VAPAECS//.

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope or domain on the target (e.g., KLH or DNP). From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, *J. Mol. Biol.* 196:901-917; Chothia et al., 1989, Nature 342: 878-883.

Specific examples of some of the full length light and heavy chains of the antibodies that are provided and their corresponding amino acid sequences are summarized in Table 1A and Table 1B below. Table 1A shows exemplary light chain sequences, all of which have a common constant region lambda constant region 1 (CL-1; SEQ ID NO:91) for all lambda light chains. Table 1B shows exemplary heavy chain sequences, all of which include constant region human IgG2 (SEQ ID NO:86). However, encompassed within the present invention are immunoglobulins with sequence changes in the constant or framework regions of those listed in Table 1A and/or Table 1B (e.g. IgG4 vs IgG2, CL2 vs CL1). Also, the signal peptide (SP) sequences for all of the sequence in Table 1A and Table 1B are the same, i.e., the VK-1 SP signal peptide: MDMRVPAQLLGLLLLWLRGARC (SEQ ID NO:103; single underlined) that is used in the high throughput cloning process, but any other suitable signal peptide sequence may be employed within the scope of the invention. Another example of a useful signal peptide sequence is VH21 SP MEWSWVFLFFLSVTTGVHS (SEQ ID NO:95). Other exemplary signal peptide sequences are shown in Table 1A-B.

TABLE 1A

Immunoglobulin Light Chain Sequences.

| SEQ ID NO: | Designation | Contained in Clone(s) | Sequence |
|---|---|---|---|
| Anti-DNP | | | |
| 105 | L1 | 3A1 | MDMRVPAQLLGLLLLWLRGARCDIQM TQSPSSVSASVGDRVTITCRASQGIS NWLAWYQRKPGKAPKLLIYAASSLQS GVPSRFSGSGSGTDFTLTISSLQPED FAAYYCQQASSFPWTFGQGTRVEIKR TVAAPSVFIFPPSDEQLKSGTASVVC LLNNFYPREAKVQWKVDNALQSGNSQ ESVTEQDSKDSTYSLSSTLTLSKADY EKHKVYACEVTHQGLSSPVTKSFNRG EC |
| 109 | L2 | 3A4 | MDMRVPAQLLGLLLLWLRGARCDIQM TQSPSSVSASVGDRVTITCRASQGIS RRLAWYQQKPGKAPKLLIYAASSLQS GVPSRFSGSGSGTDFTLTISSLQPED FATYYCQQANSFPFTFGQGTKVDIKR TVAAPSVFIFPPSDEQLKSGTASVVC LLNNFYPREAKVQWKVDNALQSGNSQ ESVTEQDSKDSTYSLSSTLTLSKADY EKHKVYACEVTHQGLSSPVTKSFNRG EC |
| 121 | L3 | 3B1 | MDMRVPAQLLGLLLLWLRGARCDIQM TQSPSSLSASEGDRVTITCRASQGIR NDLGWYQQKPGKAPKRLIYAASSLQS GVPLRFSGSGSGTEFTLTISSLQPED FATYYCLQYNSYPWTFGQGTKVEIKR TVAAPSVFIFPPSDEQLKSGTASVVC LLNNFYPREAKVQWKVDNALQSGNSQ ESVTEQDSKDSTYSLSSTLTLSKADY EKHKVYACEVTHQGLSSPVTKSFNRG EC |
| 125 | L4 | 3C2 | MDMRVPAQLLGLLLLWLRGARCDIQM TQSPSSLSASVGDRVTITCRASQGMS NYLAWYQQKPRKVPKLLIYAASTLQS GVPSRFSGSGSGTDFTLTISSLQPED VATYYCQKFNSAPFTFGPGTKVDIKR TVAAPSVFIFPPSDEQLKSGTASVVC LLNNFYPREAKVQWKVDNALQSGNSQ ESVTEQDSKDSTYSLSSTLTLSKADY EKHKVYACEVTHQGLSSPVTKSFNRG EC |

TABLE 1A-continued

Immunoglobulin Light Chain Sequences.

| SEQ ID NO: | Designation | Contained in Clone(s) | Sequence |
|---|---|---|---|
| 127 | L5 | 3H4 | MDMRVPAQLLGLLLLWLRGARCDIQM TLSPSSLSASVGDRVTITCRASQGIR NDLGWYQQKPGKAPKRLIYAASSLQS GVPSRFSGSGSGTEFTLTISSLQPED FATYYCLQYNSSPWTFGQGTEVEIKR TVAAPSVFIFPPSDEQLKSGTASVVC LLNNFYPREAKVQWKVDNALQSGNSQ ESVTEQDSKDSTYSLSSTLTLSKADY EKHKVYACEVTHQGLSSPVTKSFNRG EC |
| Anti-KLH | | | |
| 131 | L6 | 16.3.1 | MDMRVPAQLLGLLLLWLSGARCDIQM TQSPSSLSVSVGDRVTITCQAGQDIR NYLNWYQQKPGKAPKLLIYDASNLET GVPSRFSGSGSGTAFTFTISSLQPED IATYYCQQYDNLTFGQGTKLEIKRTV AAPSVFIFPPSDEQLKSGTASVVCLL NNFYPREAKVQWKVDNALQSGNSQES VTEQDSKDSTYSLSSTLTLSKADYEK HKVYACEVTHQGLSSPVTKSFNRGEC |
| 135 | L7 | 108.1.2 | METPAQLLFLLLLWLPDTTGEIVLTQ QSPGTLSLSPGERATLSCRASQ IST NYLAWGSGSGTDFTLTISRLEPEDFA VYYCQQFGRSPR SFGQGTKLEIKRT VAAPSVFIFPPSDEQLKSGTASVVCL LNNFYPREAKVQWKVDNALQSGNSQE SVTEQDSKDSTYSLSSTLTLSKADYE KHKVYACEVTHQGLSSPVTKSFNRGE C |
| 137 | L8 | 108.1.2 (N > Q, C > S) | METPAQLLFLLLLWLPDTTGEIVLTQ SPGTLSLSPGERATLSCRASQ ISTN YLAWYQQKPGQAPRFLIYGASSRATG IPDRFSGSGSGTDFTLTISRLEPEDF AVYYCQQFGRSPR SFGQGTKLEIKR TVAAPSVFIFPPSDEQLKSGTASVVC LLNNFYPREAKVQWKVDNALQSGNSQ ESVTEQDSKDSTYSLSSTLTLSKADY EKHKVYACEVTHQGLSSPVTKSFNRG EC |
| 141 | L9 | 120.6 | MDMRVPAQLLGLLLLWFPGARCDIQM TQSPSSLSASVGDRVTITCRASQGIR NDLGWYQQKPGKAPKRLIYAASSLQS GVPSRFSGSGSGTEFTLTISSLQPED FATYYCLQHNSYPLTFGGGTKVEIKR TVAAPSVFIFPPSDEQLKSGTASVVC LLNNFYPREAKVQWKVDNALQSGNSQ ESVTEQDSKDSTYSLSSTLTLSKADY EKHKVYACEVTHQGLSSPVTKSFNRG EC |
| 28 | L10 | 120.6 | MDMRVPAQLLGLLLLWLRGARCDIQM TQSPSSLSASVGDRVTITCRASQGIR NDLGWYQQKPGKAPKRLIYAASSLQS GVPSRFSGSGSGTEFTLTISSLQPED FATYYCLQHNSYPLTFGGGTKVEIKR TVAAPSVFIFPPSDEQLKSGTASVVC LLNNFYPREAKVQWKVDNALQSGNSQ ESVTEQDSKDSTYSLSSTLTLSKADY |

TABLE 1A-continued

Immunoglobulin Light Chain Sequences.

| SEQ ID NO: | Designation | Contained in Clone(s) | Sequence |
|---|---|---|---|
| | | | EKHKVYACEVTHQGLSSPVTKSFNRGEC |

Signal peptide sequences are indicated by a double underline, CDR regions are indicated by single underline, and framework and constant regions are not underlined.

TABLE 1B

Immunoglobulin Heavy Chain Sequences.

| SEQ ID NO: | Designation | Contained in Clone(s) | Sequence |
|---|---|---|---|
| Anti-DNP | | | |
| 107 | H1 | 3A1 | MDMRVPAQLLGLLLLWLRGARCQVQLQESGPGLVKPSETLSLTCTVSGGSISHYYWSWIRQPPGKGLGWIGYIYYSGSTNYNPSLKSRVTISVDTSKNQFSLKLTSVTAADTAVYYCARARGDGYNYPDAFDIWGQGTMVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 111 | H2 | 3A4 3C2 | MDMRVPAQLLGLLLLWLRGARCQVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARYNxNYGMDVWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKxxVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 113 | H3 | 3A4-F (W101F) | MDMRVPAQLLGLLLLWLRGARCQVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARYNxNYGMDVWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 115 | H4 | 3A4-Y (W101Y) | MDMRVPAQLLGLLLLWLRGARCQVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARYNxNYGMDVWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 117 | H5 | 3A4-FSS | MDMRVPAQLLGLLLLWLRGARCQVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARYNxNYGMDVWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKxxVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 119 | H6 | 3A4-YSS | MDMRVPAQLLGLLLLWLRGARCQVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARYNxNYGMDVWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKxxVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 123 | H7 | 3B1 | MDMRVPAQLLGLLLLWLRGARCQVQLQESGPGLVKPSETLSLTCTVSGGSISSYYWSWIRQPPGKGLEWIGYIYYSGNTNSNPSLKSRVTISVDTSKNQFSLKLSSVTAADTAVYYCARTYYDSSGYYYRAFDIWGQGTMVTVSSASTKGPSVFPLAPCSRSTSESTAALGCLVKDYFPEPV |

TABLE 1B-continued

Immunoglobulin Heavy Chain Sequences.

| SEQ ID NO: | Designation | Contained in Clone(s) | Sequence |
|---|---|---|---|
| | | | TVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 129 | H8 | 3H4 | MDMRVPAQLLGLLLLWLRGARCQVQLQESGPGLVKPLQTLSLTCTVSGGSISSGGYYWSWIRQHPGKGLEWIGYIYYSRSTYYNPSLKSRVTISVDTSKNQFSLKLSSVTAADTAVYYCARTGYSSGWYPFDYWGOGTLVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| 144 | H9 | 3A1 | MDMRVPAQLLGLLLLWLRGARCQVQLQESGPGLVKPSETLSLTCTVSGGSISHYYWSWIRQPPGKGLGWIGYIYYSGSTNYNPSLKSRVTISVDTSKNQFSLKLTSVTAADTAVYYCARARGDGYNYPDAFDIWGQGTMVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPG |
| 145 | H10 | 3A4 3C2 | MDMRVPAQLLGLLLLWLRGARCQVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARYN*NYGMDVWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERK**VECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPG |
| 77 | H11 | 3A4-F (W101F) | MDMRVPAQLLGLLLLWLRGARCQVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARYNFNYGMDVWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPG |
| 181 | H12 | 3A4-Y (W101Y) | MDMRVPAQLLGLLLLWLRGARCQVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARYN*NYGMDVWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPG |
| 182 | H13 | 3A4-FSS | MDMRVPAQLLGLLLLWLRGARCQVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARYN*NYGMDVWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERK**VECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPG |
| 183 | H14 | 3A4-YSS | MDMRVPAQLLGLLLLWLRGARCQVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARYN*NYGMDVWGQGTTVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERK**VECPPCPAPPVAGPSVFLFPPKPKDTLMISRTPEVTCVVVDVSHEDPEVQFNWYVDGVEVHNAKTKPRE |

TABLE 1B-continued

Immunoglobulin Heavy Chain Sequences.

| SEQ ID NO: | Desig- nation | Contained in Clone(s) | Sequence |
|---|---|---|---|
|  |  |  | EQFNSTFRVVSVLTVVHQDWLNGKEY KCKVSNKGLPAPIEKTISKTKGQPRE PQVYTLPPSREEMTKNQVSLTCLVKG FYPSDIAVEWESNGQPENNYKTTPPM LDSDGSFFLYSKLTVDKSRWQQGNVF SCSVMHEALHNHYTQKSLSLSPG |
| 184 | H15 | 3B1 | <u>MDMRVPAQLLGLLLLWLRGARC</u>QVQL QESGPGLVKPSETLSLTCTVSGGSIS <u>SYYWS</u>WIRQPPGKGLEWIG<u>YIYYSGN TNSNPSLKS</u>RVTISVDTSKNQFSLKL SSVTAADTAVYYCAR<u>TYYDSSGYYYR AFDI</u>WGQGTMVTVSSASTKGPSVFPL APCSRSTSESTAALGCLVKDYFPEPV TVSWNSGALTSGVHTFPAVLQSSGLY SLSSVVTVPSSNFGTQTYTCNVDHKP SNTKVDKTVERKCCVECPPCPAPPVA GPSVFLFPPKPKDTLMISRTPEVTCV VVDVSHEDPEVQFNWYVDGVEVHNAK TKPREEQFNSTFRVVSVLTVVHQDWL NGKEYKCKVSNKGLPAPIEKTISKTK GQPREPQVYTLPPSREEMTKNQVSLT CLVKGFYPSDIAVEWESNGQPENNYK TTPPMLDSDGSFFLYSKLTVDKSRWQ QGNVFSCSVMHEALHNHYTQKSLSLS PG |
| 185 | H16 | 3H4 | <u>MDMRVPAQLLGLLLLWLRGARC</u>QVQL QESGPGLVKPLQTLSLTCTVSGGSIS <u>SGGYYWS</u>WIRQHPGKGLEWIG<u>YIYYS RSTYYNPSLKS</u>RVTISVDTSKNQFSL KLSSVTAADTAVYYCAR<u>TGYSSGWYP FDY</u>WGQGTLVTVSSASTKGPSVFPLA PCSRSTSESTAALGCLVKDYFPEPVT VSWNSGALTSGVHTFPAVLQSSGLYS LSSVVTVPSSNFGTQTYTCNVDHKPS NTKVDKTVERKCCVECPPCPAPPVAG PSVFLFPPKPKDTLMISRTPEVTCVV VDVSHEDPEVQFNWYVDGVEVHNAKT KPREEQFNSTFRVVSVLTVVHQDWLN GKEYKCKVSNKGLPAPIEKTISKTKG QPREPQVYTLPPSREEMTKNQVSLTC LVKGFYPSDIAVEWESNGQPENNYKT TPPMLDSDGSFFLYSKLTVDKSRWQQ GNVFSCSVMHEALHNHYTQKSLSLSP G |
| Anti- KLH |  |  |  |
| 133 | H17 | 16.3.1 | <u>MELGLSWVFLFAILEGVQC</u>EVQLVES GGGLVQPGGSLRLSCAASGFTFS<u>NYD MYW</u>VRQTTGKGLEWVS<u>AIGTAGDTYY PGSVKG</u>RFTISRENAKNSLYLQMNSL RAGDTAVYYCAR<u>EKSSTSAFDY</u>WGQG TLVTVSSASTKGPSVFPLAPCSRSTS ESTAALGCLVKDYFPEPVTVSWNSGA LTSGVHTFPAVLQSSGLYSLSSVVTV PSSNFGTQTYTCNVDHKPSNTKVDKT VERKCCVECPPCPAPPVAGPSVFLFP PKPKDTLMISRTPEVTCVVVDVSHED PEVQFNWYVDGVEVHNAKTKPREEQF NSTFRVVSVLTVVHQDWLNGKEYKCK VSNKGLPAPIEKTISKTKGQPREPQV YTLPPSREEMTKNQVSLTCLVKGFYP SDIAVEWESNGQPENNYKTTPPMLDS DGSFFLYSKLTVDKSRWQQGNVFSCS VMHEALHNHYTQKSLSLSPGK |
| 139 | H18 | 108.1.2 | <u>MKHLWFFLLLVAAPRWVLS</u>QLQLQES GPGLMKPSETLSLTCTVSGGSIS<u>SSS YFW</u>GWIRQPPGKGLEWIG<u>SIYYSGNT FYNPSLKS</u>RVTISVDTSKNQFSLKLN SMTAADTAVYFCAR<u>QGGIAARTGYWY |

TABLE 1B-continued

Immunoglobulin Heavy Chain Sequences.

| SEQ ID NO: | Desig- nation | Contained in Clone(s) | Sequence |
|---|---|---|---|
|  |  |  | FDL</u>WGRGTTVTVSSASTKGPSVFPLA PCSRSTSESTAALGCLVKDYFPEPVT VSWNSGALTSGVHTFPAVLQSSGLYS LSSVVTVPSSNFGTQTYTCNVDHKPS NTKVDKTVERKCCVECPPCPAPPVAG PSVFLFPPKPKDTLMISRTPEVTCVV VDVSHEDPEVQFNWYVDGVEVHNAKT KPREEQFNSTFRVVSVLTVVHQDWLN GKEYKCKVSNKGLPAPIEKTISKTKG QPREPQVYTLPPSREEMTKNQVSLTC LVKGFYPSDIAVEWESNGQPENNYKT TPPMLDSDGSFFLYSKLTVDKSRWQQ GNVFSCSVMHEALHNHYTQKSLSLSP GK |
| 143 | H19 | 120.6 | <u>MDWTWRILFLVAAATGAHS</u>QVQLVQS GAEVKKPGASVKVSCKASGYTFT<u>GYH MHW</u>VRQAPGQGLEWMG<u>WINPNSGGTN YAQKFQG</u>RVTMTRDTSISTAYMELSR LRSDDTAVYYCAR<u>DRGSYYWFDP</u>WGQ GTLVTVSSASTKGPSVFPLAPCSRST SESTAALGCLVKDYFPEPVTVSWNSG ALTSGVHTFPAVLQSSGLYSLSSVVT VPSSNFGTQTYTCNVDHKPSNTKVDK TVERKCCVECPPCPAPPVAGPSVFLF PPKPKDTLMISRTPEVTCVVVDVSHE DPEVQFNWYVDGVEVHNAKTKPREEQ FNSTFRVVSVLTVVHQDWLNGKEYKC KVSNKGLPAPIEKTISKTKGQPREPQ VYTLPPSREEMTKNQVSLTCLVKGFY PSDIAVEWESNGQPENNYKTTPPMLD SDGSFFLYSKLTVDKSRWQQGNVFSC SVMHEALHNHYTQKSLSLSPGK |
| 46 | H20 | 120.6 | <u>MDMRVPAQLLGLLLLWLRGARC</u>QVQL VQSGAEVKKPGASVKVSCKASGYTFT <u>GYHMHW</u>VRQAPGQGLEWMG<u>WINPNSG GTNYAQKFQG</u>RVTMTRDTSISTAYME LSRLRSDDTAVYYCAR<u>DRGSYYWFDP</u> WGQGTLVTVSSASTKGPSVFPLAPCS RSTSESTAALGCLVKDYFPEPVTVSW NSGALTSGVHTFPAVLQSSGLYSLSS VVTVPSSNFGTQTYTCNVDHKPSNTK VDKTVERKCCVECPPCPAPPVAGPSV FLFPPKPKDTLMISRTPEVTCVVVDV SHEDPEVQFNWYVDGVEVHNAKTKPR EEQFNSTFRVVSVLTVVHQDWLNGKE YKCKVSNKGLPAPIEKTISKTKGQPR EPQVYTLPPSREEMTKNQVSLTCLVK GFYPSDIAVEWESNGQPENNYKTTPP MLDSDGSFFLYSKLTVDKSRWQQGNV FSCSVMHEALHNHYTQKSLSLSPG |
| 186 | H21 | 16.3.1 | <u>MELGLSWVFLFAILEGVQC</u>EVQLVES GGGLVQPGGSLRLSCAASGFTFS<u>NYD MYW</u>VRQTTGKGLEWVS<u>AIGTAGDTYY PGSVKG</u>RFTISRENAKNSLYLQMNSL RAGDTAVYYCAR<u>EKSSTSAFDY</u>WGQG TLVTVSSASTKGPSVFPLAPCSRSTS ESTAALGCLVKDYFPEPVTVSWNSGA LTSGVHTFPAVLQSSGLYSLSSVVTV PSSNFGTQTYTCNVDHKPSNTKVDKT EVRKCCVECPPCPAPPVAGPSVFLFP KPPKDTLMISRTPEVTCVVVDVSHED EPVQFNWYVDGVEVHNAKTKPREEQF NSTFRVVSVLTVVHQDWLNGKEYKCK VSNKGLPAPIEKTISKTKGQPREPQV YTLPPSREEMTKNQVSLTCLVKGFYP SDIAVEWESNGQPENNYKTTPPMLDS DGSFFLYSKLTVDKSRWQQGNVFSCS MVHEALHNHYTQKSLSLSPG |
| 187 | H22 | 108.1.2 | <u>MKHLWFFLLLVAAPRWVLS</u>QLQLQES GPGLMKPSETLSLTCTVSGGSIS<u>SSS |

TABLE 1B-continued

Immunoglobulin Heavy Chain Sequences.

| SEQ ID NO: | Designation | Contained in Clone(s) | Sequence |
|---|---|---|---|
| | | | YFWGWIRQPPGKGLEWIG<u>SIYYSGNT FYNPSLKS</u>RVTISVDTSKNQFSLKLN SMTAADTAVYFCAR<u>QGGIAARTGYWY FDL</u>WGRGTTVTVSSASTKGPSVFPLA PCSRSTSESTAALGCLVKDYFPEPVT VSWNSGALTSGVHTFPAVLQSSGLYS LSSVVTVPSSNFGTQTYTCNVDHKPS NTKVDKTVERKCCVECPPCPAPPVAG PSVFLFPPKPKDTLMISRTPEVTCVV VDVSHEDPEVQFNWYVDGVEVHNAKT KPREEQFNSTFRVVSVLTVVHQDWLN GKEYKCKVSNKGLPAPIEKTISKTKG QPREPQVYTLPPSREEMTKNQVSLTC LVKGFYPSDIAVEWESNGQPENNYKT TPPMLDSDGSFFLYSKLTVDKSRWQQ GNVFSCSVMHEALHNHYTQKSLSLSP G |
| 366 | H23 | 120.6 | <u>MDWTWRILFLVAAATGAHS</u>QVQLVQS GAEVKKPGASVKVSCKASGYTFT<u>GYH MHWVRQAPGQGLEWMGWINPNSGGTN YAQKFQG</u>RVTMTRDTSISTAYMELSR LRSDDTAVYYCAR<u>DRGSYYWFDPWGQ</u> GTLVTVSSASTKGPSVFPLAPCSRST SESTAALGCLVKDYFPEPVTVSWNSG ALTSGVHTFPAVLQSSGLYSLSSVVT VPSSNFGTQTYTCNVDHKPSNTKVDK TVERKCCVECPPCPAPPVAGPSVFLF PPKPKDTLMISRTPEVTCVVVDVSHE DPEVQFNWYVDGVEVHNAKTKPREEQ FNSTFRVVSVLTVVHQDWLNGKEYKC KVSNKGLPAPIEKTISKTKGQPREPQ VYTLPPSREEMTKNQVSLTCLVKGFY PSDIAVEWESNGQPENNYKTTPPMLD SDGSFFLYSKLTVDKSRWQQGNVFSC SVMHEALHNHYTQKSLSLSPG |
| 367 | H24 | 120.6 | <u>MDMRVPAQLLGLLLLWLRGAR</u>CQVQL VQSGAEVKKPGASVKVSCKASGYTFT <u>GYHMH</u>WVRQAPGQGLEWMG<u>WINPNSG GTNYAQKFQG</u>RVTMTRDTSISTAYME LSRLRSDDTAVYYCARD<u>RGSYYWFDP</u> WGQGTLVTVSSASTKGPSVFPLAPCS RSTSESTAALGCLVKDYFPEPVTVSW NSGALTSGVHTFPAVLQSSGLYSLSS VVTVPSSNFGTQTYTCNVDHKPSNTK VDKTVERKCCVECPPCPAPPVAGPSV FLFPPKPKDTLMISRTPEVTCVVVDV SHEDPEVQFNWYVDGVEVHNAKTKPR EEQFNSTFRVVSVLTVVHQDWLNGKE YKCKVSNKGLPAPIEKTISKTKGQPR EPQVYTLPPSREEMTKNQVSLTCLVK GFYPSDIAVEWESNGQPENNYKTTPP MLDSDGSFFLYSKLTVDKSRWQQGNV FSCSVMHEALHNHYTQKSLSLSPGK |

Signal peptide sequences are indicated by a double underline, CDR regions are indicated by single underline, and framework and constant regions are not underlined.

Some embodiments of the isolated anti-DNP antigen binding protein comprising an antibody or antibody fragment, comprise:

(a) an immunoglobulin heavy chain comprising the amino acid sequence of SEQ ID NO:77, SEQ ID NO:107, SEQ ID NO:111, SEQ ID NO:113, SEQ ID NO:115, SEQ ID NO:117, SEQ ID NO:119, SEQ ID NO:123, SEQ ID NO:129, SEQ ID NO:144, SEQ ID NO:145, SEQ ID NO:181, SEQ ID NO:182, SEQ ID NO:183, SEQ ID NO:184, or SEQ ID NO:185, or comprising any one of the foregoing sequences from which one, two, three, four or five amino acid residues are lacking from the N-terminal or C-terminal, or both;

(b) an immunoglobulin light chain comprising the amino acid sequence of SEQ ID NO:105, SEQ ID NO:109, SEQ ID NO:121; SEQ ID NO:125, or SEQ ID NO:127, or comprising any one of the foregoing sequences from which one, two, three, four or five amino acid residues are lacking from the N-terminal or C-terminal, or both; or (c) the immunoglobulin heavy chain of (a) and the immunoglobulin light chain of (b).

Some embodiments of the isolated anti-KLH antigen binding protein comprising an antibody or antibody fragment, comprise:

(a) an immunoglobulin heavy chain comprising the amino acid sequence of SEQ ID NO:46, SEQ ID NO:133, SEQ ID NO:139, SEQ ID NO:143, SEQ ID NO:186, or SEQ ID NO:187, SEQ ID NO:366, or SEQ ID NO:367, or comprising any one of the foregoing sequences from which one, two, three, four or five amino acid residues are lacking from the N-terminal or C-terminal, or both;

(b) an immunoglobulin light chain comprising the amino acid sequence of SEQ ID NO:28, SEQ ID NO:131, SEQ ID NO:135, SEQ ID NO:137; or SEQ ID NO:141, or comprising any one of the foregoing sequences from which one, two, three, four or five amino acid residues are lacking from the N-terminal or C-terminal, or both; or (c) the immunoglobulin heavy chain of (a) and the immunoglobulin light chain of (b).

Again, each of the exemplary anti-DNP heavy chains (H1, H2, H3, . . . etc.) listed in Table 1B can be combined with any of the exemplary anti-DNP light chains shown in Table 1A to form an antibody. Examples of such combinations include H1 combined with any of L1 through L5; H2 combined with any of L1 through L5; H3 combined with any of L1 through L5, H4 combined with any of L1 through L5, and so on. In some instances, the antibodies include at least one anti-DNP heavy chain and one anti-DNP light chain from those listed in Table 1A and 1B. In some instances, the antibodies comprise two different anti-DNP heavy chains and two different anti-DNP light chains listed in Table 1A and Table 1B. In other instances, the antibodies contain two identical light chains and two identical heavy chains. As an example, an antibody or immunologically functional fragment may include two H1 heavy chains and two L1 light chains, or two H2 heavy chains and two L2 light chains, or two H3 heavy chains and two L3 light chains and other similar combinations of pairs of anti-DNP light chains and pairs of anti-DNP heavy chains as listed in Table 1A and Table 1B.

Again, each of the exemplary anti-KLH heavy chains (H1, H2, H3, . . . etc.) listed in Table 1B can be combined with any of the exemplary anti-KLH light chains shown in Table 1A to form an antibody. Examples of such combinations include H1 combined with any of L1 through L5; H2 combined with any of L1 through L5; H3 combined with any of L1 through L5, H4 combined with any of L1 through L5, and so on. In some instances, the antibodies include at least one anti-KLH heavy chain and one anti-KLH light chain from those listed in Table 1A and 1B. In some instances, the antibodies comprise two different anti-KLH heavy chains and two different anti-KLH light chains listed in Table 1A and Table 1B. In other instances, the antibodies contain two identical light chains and two identical heavy chains. As an example, an antibody or immunologically functional fragment may include two H1 heavy chains and two L1 light chains, or two H2 heavy chains and two L2 light chains, or two H3 heavy chains and two L3 light chains and other similar combinations of pairs of anti-KLH light chains and pairs of anti-KLH heavy chains as listed in Table 1A and Table 1B.

Other antigen binding proteins that are provided are variants of antibodies formed by combination of the heavy and light chains shown in Tables 1A and Table 1B and comprise light and/or heavy chains that each have at least 70%, at least 75%, at least 80%, at least 85%, at least 90%, at least 95%, at least 97% or at least 99% identity to the amino acid sequences of these chains. In some instances, such antibodies include at least one heavy chain and one light chain, whereas in other instances the variant forms contain two identical light chains and two identical heavy chains. It is within the scope of the invention that the heavy chain(s) and/or light chain(s) may have one, two, three, four or five amino acid residues lacking from the N-terminal or C-terminal, or both, in relation to any one of the heavy and light chains set forth in Tables 1A and Table 1B, e.g., due to post-translational modifications. For example, CHO cells typically cleave off a C-terminal lysine.

Variable Domains of Antibodies

The various heavy chain and light chain variable regions provided herein are depicted in Table 2A-B. Each of these variable regions may be attached to the above heavy and light chain constant regions to form a complete antibody heavy and light chain, respectively. Further, each of the so generated heavy and light chain sequences may be combined to form a complete antibody structure. It should be understood that the heavy chain and light chain variable regions provided herein can also be attached to other constant domains having different sequences than the exemplary sequences listed above.

Also provided are antigen binding proteins, including antibodies or antibody fragments, that contain or include at least one immunoglobulin anti-DNP heavy chain variable region selected from $V_H1$, $V_H2$, $V_H3$, $V_H4$, $V_H5$, and $V_H6$ and/or at least one immunoglobulin anti-DNP light chain variable region selected from $V_L1$, $V_L2$, $V_L3$, $V_L4$, and $V_L5$, as shown in Table 2A below, and immunologically functional fragments, derivatives, muteins and variants of these light chain and heavy chain variable regions.

Also provided are antigen binding proteins, including antibodies or antibody fragments, that contain or include at least one immunoglobulin anti-KLH heavy chain variable region selected from $V_H7$, $V_H8$, and $V_H9$ and/or at least one immunoglobulin anti-KLH light chain variable region selected from $V_L6$, $V_L7$, $V_L8$, and $V_L9$, as shown in Table 2B below, and immunologically functional fragments, derivatives, muteins and variants of these light chain and heavy chain variable regions.

Antigen binding proteins of this type can generally be designated by the formula "$V_Hx/V_Ly$," where "x" corresponds to the number of heavy chain variable regions included in the antigen binding protein and "y" corresponds to the number of the light chain variable regions included in the antigen binding protein (in general, x and y are each 1 or 2).

TABLE 2A

Exemplary anti-DNP $V_H$ and $V_L$ Chains:

| Contained in Reference in Table 1A-B | Designation | SEQ ID NO | Amino Acid Sequence |
|---|---|---|---|
| L1 | VL1 | 232 | DIQMTQSPSSVSASVGDRVTITC<u>RAS QGISNWLA</u>WYQRKPGKAPKLLIY<u>AAS SLQS</u>GVPSRFSGSGSGTDFTLTISSL QPEDFAAYYC<u>QQASSFPWT</u>FGQGTRV EIK |
| L2 | VL2 | 234 | DIQMTQSPSSVSASVGDRVTITC<u>RAS QGISRRLA</u>WYQQKPGKAPKLLIY<u>AAS SLQS</u>GVPSRFSGSGSGTDFTLTISSL QPEDFATYYC<u>QQANSFPFT</u>FGPGTKV DIK |
| L3 | VL3 | 236 | DIQMTQSPSSLSASEGDRVTITC<u>RAS QGIRNDLG</u>WYQQKPGKAPKRLIY<u>AAS SLQS</u>GVPLRFSGSGSGTEFTLTISSL QPEDFATYYC<u>LQYNSYPWT</u>FGQGTKV EIK |
| L4 | VL4 | 238 | DIQMTQSPSSLSASVGDRVTITC<u>RAS QGMSNYLA</u>WYQQKPRKVPKLLIY<u>AAS TLQS</u>GVPSRFSGSGSGTDFTLTISSL QPEDVATYYC<u>QKFNSAPFT</u>FGPGTKV DIK |
| L5 | VL5 | 240 | DIQMTLSPSSLSASVGDRVTITC<u>RAS QGIRNDLG</u>WYQQKPGKAPKRLIY<u>AAS SLQS</u>GVPSRFSGSGSGTEFTLTISSL QPEDFATYYC<u>LQYNSSPWT</u>FGQGTEV EIK |
| H1, H9 | VH1 | 250 | QVQLQESGPGLVKPSETLSLTCTVSG GSIS<u>HYYWS</u>WIRQPPGKGLGWIG<u>YIY YSGSTNYNPSLKS</u>RVTISVDTSKNQF SLKLTSVTAADTAVYYCAR<u>ARGDGYN YPDAFDI</u>WGQGTMVTVSS |
| H2, H10 | VH2 | 252 | QVQLVESGGGVVQPGRSLRLSCAASG FTFS<u>SYGMH</u>WVRQAPGKGLEWVA<u>VIW YDGSNKYYADSVKG</u>RFTISRDNSKNT LYLQMNSLRAEDTAVYYCAR<u>YN*NYG MDV</u>WGQGTTVTVSS |
| H3, H5, H11, H13 | VH3 | 254 | QVQLVESGGGVVQPGRSLRLSCAASG FTFS<u>SYGMH</u>WVRQAPGKGLEWVA<u>VIW YDGSNKYYADSVKG</u>RFTISRDNSKNT LYLQMNSLRAEDTAVYYCAR<u>YN*NYG MDV</u>WGQGTTVTVSS |
| H4, H6, H12, H14 | VH4 | 256 | QVQLVESGGGVVQPGRSLRLSCAASG FTFS<u>SYGMH</u>WVRQAPGKGLEWVA<u>VIW YDGSNKYYADSVKG</u>RFTISRDNSKNT LYLQMNSLRAEDTAVYYCAR<u>YN NYG MDV</u>WGQGTTVTVSS |
| H7, H15 | VH5 | 258 | QVQLQESGPGLVKPSETLSLTCTVSG GSIS<u>SYYWS</u>WIRQPPGKGLEWIG<u>YIY YSGNTNSNPSLKS</u>RVTISVDTSKNQF SLKLSSVTAADTAVYYCAR<u>TYYDSSG YYYRAFDI</u>WGQGTMVTVSS |
| H8, H16 | VH6 | 260 | QVQLQESGPGLVKPLQTLSLTCTVSG GSIS<u>SGGYYWS</u>WIRQHPGKGLEWIG<u>Y IYYSRSTYYNPSLKS</u>RVTISVDTSKN QFSLKLSSVTAADTAVYYCAR<u>TGYSS GWYPFDY</u>WGQGTLVTVSS |

CDR regions are indicated by underline, and framework regions are not underlined. Optional N-terminal signal sequences are not shown (See, Table 1A-B).

TABLE 2B

Exemplary anti-KLH $V_H$ and $V_L$ Chains: CDR regions are indicated by underline, and framework regions are not underlined. Optional N-terminal signal sequences are not shown (See, Table 1A-B; see, e.g., SEQ ID NO: 95 and SEQ ID NO: 103).

| Contained in Reference in Table 1A-B | Designation | SEQ ID NO | Amino Acid Sequence |
|---|---|---|---|
| L6 | VL6 | 242 | DIQMTQSPSSLSVSVGDRVTITC<u>QAGQDIRNYLN</u>WYQQKPGKAPKLLIY<u>DASNLET</u>GVPSRFSGSGSGTAFTFTISSLQPEDIATYYC<u>QQYDNLT</u>FGQGTKLEIK |
| L7 | VL7 | 244 | EIVLTQSPGTLSLSPGERATLSC<u>RASQNISTNYLA</u>WYQQKPGQAPRFLIY<u>GASSRAT</u>GIPDRFSGSGSGTDFTLTISRLEPEDFAVYYC<u>QQFGRSPRCS</u>FGQGTKLEIK |
| L8 | VL8 | 246 | EIVLTQSPGTLSLSPGERATLSC<u>RASQQISTNYLA</u>WYQQKPGQAPRFLIY<u>GASSRAT</u>GIPDRFSGSGSGTDFTLTISRLEPEDFAVYYC<u>QQFGRSPRSS</u>FGQGTKLEIK |
| L9, L10 | VL9 | 248 | DIQMTQSPSSLSASVGDRVTITC<u>RASQGIRNDLG</u>WYQQKPGKAPKRLIY<u>AASSLQS</u>GVPSRFSGSGSTEFTLTISSLQPEDFATYYC<u>LQHNSYPLT</u>FGGGTKVEIK |
| H17, H21 | VH7 | 262 | EVQLVESGGGLVQPGGSLRLSCAASGFTFS<u>NYDMY</u>WVRQTTGKGLEWVS<u>AIGTAGDTYYPGSVKG</u>RFTISRENAKNSLYLQMNSLRAGDTAVYYCAR<u>EKSSTSAFDY</u>WGQGTLVTVSS |
| H18, H22 | VH8 | 264 | QLQLQESGPGLMKPSETLSLTCTVSGGSIS<u>SSSYFWG</u>WIRQPPGKGLEWIG<u>SIYYSGNTFYNPSLKSRV</u>TISVDTSKNQFSLKLNSMTAADTAVYFCAR<u>QGGIAARTGYWYFDL</u>WGRGTTVTVSS |
| H19, H20, H23, H24 | VH9 | 266 | QVQLVQSGAEVKKPGASVKVSCKASGYTFT<u>GYHMH</u>WVRQAPGQGLEWMG<u>WINPNSGGTNYAQKFQG</u>RVTMTRDTSISTAYMELSRLRSDDTAVYYCAR<u>DRGSYYWFDP</u>WGQGTLVTVSS |

Some embodiments of the isolated antigen binding protein that comprises an anti-DNP antibody or antibody fragment, comprising an immunoglobulin heavy chain variable region and an immunoglobulin light chain variable region:

(a) the heavy chain variable region comprises an amino acid sequence at least 95%, 96%, 97%, 98%, 99%, or 100% identical to the sequence of SEQ ID NO:250, SEQ ID NO:252, SEQ ID NO:254, SEQ ID NO:256, SEQ ID NO:258, or SEQ ID NO:260; or (b) the light chain variable region comprises an amino acid sequence at least 95%, 96%, 97%, 98%, 99%, or 100% identical to the sequence of SEQ ID NO:232, SEQ ID NO:234, SEQ ID NO:236, SEQ ID NO:238, or SEQ ID NO:240; or (c) the heavy chain variable region of (a) and the light chain variable region of (b).

Some embodiments of the isolated antigen binding protein that comprises an anti-DNP antibody or antibody fragment, comprising an immunoglobulin heavy chain variable region and an immunoglobulin light chain variable region:

(a) the heavy chain variable region comprises an amino acid sequence at least 95%, 96%, 97%, 98%, 99%, or 100% identical to the sequence of SEQ ID NO:262, SEQ ID NO:264, or SEQ ID NO:266; or (b) the light chain variable region comprises an amino acid sequence at least 95%, 96%, 97%, 98%, 99%, or 100% identical to the sequence of SEQ ID NO:242, SEQ ID NO:244, SEQ ID NO:246, or SEQ ID NO:248; or (c) the heavy chain variable region of (a) and the light chain variable region of (b).

Each of the heavy chain variable regions listed in Table 2A, whether or not it is included in a larger heavy chain, may be combined with any of the light chain variable regions shown in Table 2A to form an antigen binding protein. Examples of such combinations include $V_H1$ combined with any of $V_L1$, $V_L2$, $V_L3$, $V_L4$, or $V_L5$; $V_H2$ combined with any of $V_L1$, $V_L2$, $V_L3$, $V_L4$, or $V_L5$; $V_H3$ combined with any of $V_L1$, $V_L2$, $V_L3$, $V_L4$, or $V_L5$; $V_H4$ combined with any of $V_L1$, $V_L2$, $V_L3$, $V_L4$, or $V_L5$, and so on.

Each of the heavy chain variable regions listed in Table 2B, whether or not it is included in a larger heavy chain, may be combined with any of the light chain variable regions shown in Table 2B to form an antigen binding protein. Examples of such combinations include $V_H7$ combined with any of $V_L6$, $V_L7$, $V_L8$ or $V_L9$; $V_H8$ combined with any of $V_L6$, $V_L7$, $V_L8$ or $V_L9$; $V_H8$ combined with any of $V_L6$, $V_L7$, $V_L8$ or $V_L9$; $V_H9$ combined with any of $V_L6$, $V_L7$, $V_L8$ or $V_L9$.

In some instances, the antigen binding protein includes at least one heavy chain variable region and/or one light chain variable region from those listed in Table 2A. In some instances, the antigen binding protein includes at least two different heavy chain variable regions and/or light chain variable regions from those listed in Table 2A. An example of such an antigen binding protein comprises (a) one $V_H1$, and (b) one of $V_H2$, $V_H3$, or $V_H4$, etc. Another example comprises (a) one $V_H2$, and (b) one of $V_H1$, $V_H3$, or $V_H4$, etc. Again another example comprises (a) one $V_H3$, and (b) one of $V_H1$, $V_H2$, or $V_H4$, etc. Again another example comprises (a) one $V_H4$, and (b) one of $V_H1$, $V_H2$, or $V_H3$, etc. Again another example comprises (a) one $V_H5$, and (b) one of $V_H1$, $V_H2$, or $V_H3$, etc. Again another example comprises (a) one $V_H6$, and (b) one of $V_H1$, $V_H2$, or $V_H3$, etc.

Again another example of such an antigen binding protein comprises (a) one $V_L1$, and (b) one of $V_L2$ or $V_L3$, etc. Again another example of such an antigen binding protein comprises (a) one $V_L2$, and (b) one of $V_L1$ or $V_L3$, etc. Again another example of such an antigen binding protein comprises (a) one $V_L3$, and (b) one of $V_L1$ or $V_L2$, etc., and so on.

The various combinations of heavy chain variable regions set forth in Table 2A may be combined with any of the various combinations of light chain variable regions set forth in Table 2A.

In other instances, the antigen binding protein contains two identical light chain variable regions and/or two identical heavy chain variable regions. As an example, the antigen binding protein may be an antibody or immunologically functional fragment that includes two light chain variable regions and two heavy chain variable regions in combinations of pairs of light chain variable regions and pairs of heavy chain variable regions as listed in Table 2A.

In some instances, the antigen binding protein includes at least one heavy chain variable region and/or one light chain variable region from those listed in Table 2B. In some instances, the antigen binding protein includes at least two different heavy chain variable regions and/or light chain variable regions from those listed in Table 2B. An example of such an antigen binding protein comprises (a) one $V_H7$, and (b) one of $V_H7$, $V_H8$, or $V_H9$. Another example comprises (a) one $V_H8$, and (b) one of $V_H7$, $V_H8$, or $V_H9$. Again another example comprises (a) one $V_H9$, and (b) one of $V_H7$, $V_H8$, or $V_H9$.

Again another example of such an antigen binding protein comprises (a) one $V_L6$, and (b) one of $V_L6$, $V_L7$, $V_L8$ or $V_L9$. Again another example of such an antigen binding protein comprises (a) one $V_L7$, and (b) one of $V_L6$, $V_L7$, $V_L8$ or $V_L9$. Again another example of such an antigen binding protein comprises (a) one $V_L8$, and (b) one of $V_L6$, $V_L7$, $V_L8$ or $V_L9$. Again another example of such an antigen binding protein comprises (a) one $V_L9$, and (b) one of $V_L6$, $V_L7$, $V_L8$ or $V_L9$.

The various combinations of heavy chain variable regions set forth in Table 2B may be combined with any of the various combinations of light chain variable regions set forth in Table 2B.

In other instances, the antigen binding protein contains two identical light chain variable regions and/or two identical heavy chain variable regions. As an example, the antigen binding protein may be an antibody or immunologically functional fragment that includes two light chain variable regions and two heavy chain variable regions in combinations of pairs of light chain variable regions and pairs of heavy chain variable regions as listed in Table 2B.

Some antigen binding proteins that are provided comprise a heavy chain variable domain comprising a sequence of amino acids that differs from the sequence of a heavy chain variable domain selected from $V_H1$, $V_H2$, $V_H3$, $V_H4$, $V_H5$, $V_H6$, $V_H7$, $V_H8$, and $V_H9$, at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The heavy chain variable region in some antigen binding proteins comprises a sequence of amino acids that has at least 70%, at least 75%, at least 80%, at least 85%, at least 90%, at least 95%, at least 97% or at least 99% sequence identity to the amino acid sequences of the heavy chain variable region of $V_H1$, $V_H2$, $V_H3$, $V_H4$, $V_H5$, $V_H6$, $V_H7$, $V_H8$, or $V_H9$.

Certain antigen binding proteins comprise a light chain variable domain comprising a sequence of amino acids that differs from the sequence of a light chain variable domain selected from $V_L1$, $V_L2$, $V_L3$, $V_L4$, $V_L5$, $V_L6$, $V_L7$, $V_L8$, and $V_L9$ at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The light chain variable region in some antigen binding proteins comprises a sequence of amino acids that has at least 70%, at least 75%, at least 80%, at least 85%, at least 90%, at least 95%, at least 97% or at least 99% sequence identity to the amino acid sequences of the light chain variable region of $V_L1$, $V_L2$, $V_L3$, $V_L4$, $V_L5$, $V_L6$, $V_L7$, $V_L8$, or $V_L9$.

Still other antigen binding proteins, e.g., antibodies or immunologically functional fragments, include variant forms of a variant heavy chain and a variant light chain as described herein.

CDRs

The antigen binding proteins disclosed herein are polypeptides into which one or more CDRs are grafted, inserted and/or joined. An antigen binding protein can have 1, 2, 3, 4, 5 or 6 CDRs. An antigen binding protein thus can have, for example, one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/or one light chain CDR3 ("CDRL3"). Some antigen binding proteins include both a CDRH3 and a CDRL3. Specific heavy and light chain CDRs are identified in Table 3A-B (anti-DNP) and Table 3C-D (anti-KLH), respectively.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. Certain antibodies that are disclosed herein comprise one or more amino acid sequences that are identical or have substantial sequence identity to the amino acid sequences of one or more of the CDRs presented in Table 3A (anti-DNP CDRHs), Table 3B (anti-DNP CDRLs), Table 3C (anti-KLH CDRHs), and Table 3D (anti-KLH CDRLs).

TABLE 3A

Exemplary Anti-DNP CDRH Sequences

| Contained in HC | Designation | Sequence | SEQ ID NO: |
|---|---|---|---|
| H1, H9 | CDRH 1-1 | HYYWS | 188 |
| H2, H3, H4, H5, H6, | CDRH 1-2 | SYGMH | 189 |

TABLE 3A-continued

Exemplary Anti-DNP CDRH Sequences

| Contained in HC | Designation | Sequence | SEQ ID NO: |
|---|---|---|---|
| H10, H11, H12, H13, H14 | | | |
| H7, H15, | CDRH 1-3 | SYYWS | 190 |
| H8, H16 | CDRH 1-4 | SGGYYWS | 191 |
| H1, H9 | CDRH 2-1 | YIYYSGSTNYNPSLKS | 192 |
| H2, H3, H4, H5, H6, H10, H11, H12, H13, H14 | CDRH 2-2 | VIWYDGSNKYYADSVKG | 193 |
| H7, H15 | CDRH 2-3 | YIYYSGNTNSNPSLKS | 194 |
| H8, H16 | CDRH 2-4 | YIYYSRSTYYNPSLKS | 195 |
| H1, H9 | CDRH 3-1 | ARGDGYNYPDAFDI | 196 |
| H2, H10 | CDRH 3-2 | YNWNYGMDV | 197 |
| H3, H5, H11, H13 | CDRH 3-3 | YNFNYGMDV | 198 |
| H4, H6, H12, H14 | CDRH 3-4 | YNYNYGMDV | 199 |
| H7, H15 | CDRH 3-5 | TYYDSSGYYYRAFDI | 200 |
| H8, H16 | CDRH 3-6 | TGYSSGWYPFDY | 201 |

TABLE 3B

Exemplary Anti-DNP CDRL Sequences

| Contained in LC | Designation | Sequence | SEQ ID NO: |
|---|---|---|---|
| L1 | CDRL 1-1 | RASQGISNWLA | 202 |
| L2 | CDRL 1-2 | RASQGISRRLA | 203 |
| L3, L5 | CDRL 1-3 | RASQGIRNDLG | 204 |
| L4 | CDRL 1-4 | RASQGMSNYLA | 205 |
| L1, L2, L3, L5 | CDRL 2-1 | AASSLQS | 206 |
| L4 | CDRL 2-2 | AASTLQS | 207 |
| L1 | CDRL 3-1 | QQASSFPWT | 208 |
| L2 | CDRL 3-2 | QQANSFPFT | 209 |
| L3 | CDRL 3-3 | LQYNSYPWT | 210 |
| L4 | CDRL 3-4 | QKFNSAPFT | 211 |
| L5 | CDRL 3-5 | LQYNSSPWT | 212 |

TABLE 3C

Exemplary Anti-KLH CDRH Sequences

| Contained in HC | Designation | Sequence | SEQ ID NO: |
|---|---|---|---|
| H17, H21 | CDRH 1-5 | NYDMY | 213 |
| H18, H22 | CDRH 1-6 | SSSYFWG | 214 |
| H19, H20, H23, H24 | CDRH 1-7 | GYHMH | 215 |
| H17, H21 | CDRH 2-5 | AIGTAGDTYYPGSVKG | 216 |
| H18, H22 | CDRH 2-6 | SIYYSGNTFYNPSLKS | 217 |
| H19, H20, H23, H24 | CDRH 2-7 | WINPNSGGTNYAQKFQG | 218 |
| H17, H21 | CDRH 3-7 | EKSSTSAFDY | 219 |
| H18, H22 | CDRH 3-8 | QGGIAARTGYWYFDL | 220 |
| H19, H20, H23, H24 | CDRH 3-9 | DRGSYYWFDP | 221 |

TABLE 3D

Exemplary Anti-KLH CDRL Sequences

| Contained in LC | Designation | Sequence | SEQ ID NO: |
|---|---|---|---|
| L6 | CDRL 1-5 | QAGQDIRNYLN | 222 |
| L7 | CDRL 1-6 | RASQNISTNYLA | 223 |
| L8 | CDRL 1-7 | RASQQISTNYLA | 224 |
| L9, L10 | CDRL 1-8 | RASQGIRNDLG | 204 |
| L6 | CDRL 2-3 | DASNLET | 225 |
| L7, L8 | CDRL 2-4 | GASSRAT | 226 |
| L9, L10 | CDRL 2-5 | AASSLQS | 206 |
| L6 | CDRL 3-6 | QQYDNLT | 227 |
| L7 | CDRL 3-7 | QQFGRSPRCS | 228 |
| L8 | CDRL 3-8 | QQFGRSPRSS | 229 |
| L9, L10 | CDRL 3-9 | LQHNSYPLT | 230 |

The structure and properties of CDRs within a naturally occurring antibody have been described, supra. Briefly, in a traditional antibody, the CDRs are embedded within a framework in the heavy and light chain variable region where they constitute the regions responsible for antigen binding and recognition. A variable region comprises at least three heavy or light chain CDRs, see, supra (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991, supra; see also Chothia and Lesk, 1987, supra). The CDRs provided herein, however, may not only be used to define the antigen binding domain of a traditional antibody structure, but may be embedded in a variety of other polypeptide structures, as described herein.

Some embodiments of the isolated antigen binding protein comprise an anti-DNP antibody or antibody fragment, comprising an immunoglobulin heavy chain variable region and an immunoglobulin light chain variable region. The heavy chain variable region comprise three complementarity determining regions designated CDRH1, CDRH2 and CDRH3, and/or the light chain variable region comprises three CDRs designated CDRL1, CDRL2 and CDRL3, wherein:

(a) CDRH1 has the amino acid sequence of SEQ ID NO:188, SEQ ID NO:189, SEQ ID NO:190, or SEQ ID NO:191; and/or (b) CDRH2 has the amino acid sequence of SEQ ID NO:192, SEQ ID NO:193, SEQ ID NO:194, or SEQ ID NO:195; and/or (c) CDRH3 has the amino acid sequence of SEQ ID NO:196, SEQ ID NO:197, SEQ ID NO:198, SEQ ID NO:199, SEQ ID NO:200, or SEQ ID NO:201; and/or (d) CDRL1 has the amino acid sequence of SEQ ID NO:202, SEQ ID NO:203, SEQ ID NO:204, or SEQ ID NO:205; and/or (e) CDRL2 has the amino acid sequence of SEQ ID NO:206 or SEQ ID NO:207; and/or (f) CDRL3 has the amino acid sequence of SEQ ID NO:208, SEQ ID NO:209, SEQ ID NO:210, SEQ ID NO:211, or SEQ ID NO:212.

In other aspects, the CDRs provided are (A) a CDRH selected from (i) a CDRH1 selected from SEQ ID NO:188, SEQ ID NO:189, SEQ ID NO:190, and SEQ ID NO:191; (ii) a CDRH2 selected from SEQ ID NO:192, SEQ ID NO:193, SEQ ID NO:194, and SEQ ID NO:195; (iii) a CDRH3 selected from SEQ ID NO:196, SEQ ID NO:197, SEQ ID NO:198, SEQ ID NO:199, SEQ ID NO:200, and SEQ ID NO:201; and (iv) a CDRH of (i), (ii) and (iii) that contains one or more amino acid substitutions, deletions or insertions of no more than five, four, three, two, or one amino acids; (B) a CDRL selected from (i) a CDRL1 selected from SEQ ID NO:202, SEQ ID NO:203, SEQ ID NO:204, and SEQ ID NO:205; (ii) a CDRL2 selected from SEQ ID NO:206 and SEQ ID NO:207; (iii) a CDRL3 selected from SEQ ID NO:208, SEQ ID NO:209, SEQ ID NO:210, SEQ ID NO:211, and SEQ ID NO:212; and (iv) a CDRL of (i), (ii) and (iii) that contains one or more amino acid substitutions, deletions or insertions of no more than five, four, three, two, or one amino acids amino acids.

Some embodiments of the isolated antigen binding protein comprise an anti-KLH antibody or antibody fragment, comprising an immunoglobulin heavy chain variable region and an immunoglobulin light chain variable region. The heavy chain variable region comprise three complementarity determining regions designated CDRH1, CDRH2 and CDRH3, and/or the light chain variable region comprises three CDRs designated CDRL1, CDRL2 and CDRL3, wherein:

(a) CDRH1 has the amino acid sequence of SEQ ID NO:213, SEQ ID NO:214, or SEQ ID NO:215; and/or (b) CDRH2 has the amino acid sequence of SEQ ID NO:216, SEQ ID NO:217, or SEQ ID NO:218; and/or (c) CDRH3 has the amino acid sequence of SEQ ID NO:219, SEQ ID NO:220, or SEQ ID NO:221; and/or (d) CDRL1 has the amino acid sequence of SEQ ID NO:204, SEQ ID NO:222, SEQ ID NO:223, or SEQ ID NO:224; and/or (e) CDRL2 has the amino acid sequence of SEQ ID NO:206, SEQ ID NO:225, or SEQ ID NO:226; and/or (f) CDRL3 has the amino acid sequence of SEQ ID NO:227, SEQ ID NO:228, SEQ ID NO:229, or SEQ ID NO:230.

In other aspects, the CDRs provided are (A) a CDRH selected from (i) a CDRH1 selected from SEQ ID NO:213, SEQ ID NO:214, and SEQ ID NO:215; (ii) a CDRH2 selected from SEQ ID NO:216, SEQ ID NO:217, and SEQ ID NO:218; (iii) a CDRH3 selected from SEQ ID NO:219, SEQ ID NO:220, and SEQ ID NO:221; and (iv) a CDRH of (i), (ii) and (iii) that contains one or more amino acid substitutions, deletions or insertions of no more than five, four, three, two, or one amino acids; (B) a CDRL selected from (i) a CDRL1 selected from SEQ ID NO:204, SEQ ID NO:222, SEQ ID NO:223, and SEQ ID NO:224; (ii) a CDRL2 selected from SEQ ID NO:206, SEQ ID NO:225, and SEQ ID NO:226; (iii) a CDRL3 selected from SEQ ID NO:227, SEQ ID NO:228, SEQ ID NO:229, and SEQ ID NO:230; and (iv) a CDRL of (i), (ii) and (iii) that contains one or more amino acid substitutions, deletions or insertions of no more than five, four, three, two, or one amino acids amino acids.

In another aspect, an antigen binding protein includes 1, 2, 3, 4, 5, or 6 variant forms of the CDRs listed in Table 3A and Table 3B, each having at least 80%, at least 85%, at least 90% or at least 95% sequence identity to a CDR sequence listed in Table 3A and Table 3B. Some antigen binding proteins include 1, 2, 3, 4, 5, or 6 of the CDRs listed in Table 3A and Table 3B, each differing by no more than 1, 2, 3, 4 or 5 amino acids from the CDRs listed in these tables.

In another aspect, an antigen binding protein includes 1, 2, 3, 4, 5, or 6 variant forms of the CDRs listed in Table 3C and Table 3D, each having at least 80%, at least 85%, at least 90% or at least 95% sequence identity to a CDR sequence listed in Table 3C and Table 3D. Some antigen binding proteins include 1, 2, 3, 4, 5, or 6 of the CDRs listed in Table 3C and Table 3D, each differing by no more than 1, 2, 3, 4 or 5 amino acids from the CDRs listed in these tables.

In yet another aspect, the CDRs disclosed herein include consensus sequences derived from groups of related monoclonal antibodies. As described herein, a "consensus sequence" refers to amino acid sequences having conserved amino acids common among a number of sequences and variable amino acids that vary within a given amino acid sequences. The CDR consensus sequences provided include CDRs corresponding to each of CDRH1, CDRH2, CDRH3, CDRL1, CDRL2 and CDRL3.

Antibody-antigen interactions can be characterized by the association rate constant in $M^{-1}s^{-1}$ ($k_a$), or the dissociation rate constant in $s^{-1}$ ($k_d$), or alternatively the dissociation equilibrium constant in M ($K_D$).

The present invention provides a variety of antigen binding proteins, including but not limited to antibodies that specifically bind DNP or KLH, respectively, that exhibit desirable characteristics such as binding affinity as measured by $K_D$ (dissociation equilibrium constant) for DNP or KLH, respectively, in the range of $10^{-9}$ M or lower, ranging down to $10^{-12}$ M or lower, or avidity as measured by $k_d$ (dissociation rate constant) for DNP or KLH, respectively, in the range of $10^{-4}$ $s^{-1}$ or lower, or ranging down to $10^{-10}$ $s^{-1}$ or lower. (See, Example 12 herein).

In some embodiments, the antigen binding proteins (e.g., antibodies or antibody fragments) exhibit desirable characteristics such as binding avidity as measured by $k_d$ (dissociation rate constant) for DNP or KLH, respectively, of about $10^{-2}$, $10^{-3}$, $10^{-4}$, $10^{-5}$, $10^{-6}$, $10^{-7}$, $10^{-8}$, $10^{-9}$, $10^{-10}$ $s^{-1}$ or lower (lower values indicating higher binding avidity), and/or binding affinity as measured by $K_D$ (dissociation equilibrium constant) for DNP or KLH, respectively, of about $10^{-9}$, $10^{-10}$, $10^{-11}$, $10^{-12}$, $10^{-13}$, $10^{-14}$, $10^{-15}$, $10^{-16}$ M or lower (lower values indicating higher binding affinity). Association rate constants, dissociation rate constants, or dissociation equilibrium constants may be readily determined using kinetic analysis techniques such as surface plasmon resonance (BIAcore®; e.g., Fischer et al., A peptide-immunoglobulin-conjugate, WO 2007/045463 A1, Example 10, which is incorporated herein by reference in its entirety), or KinExA using general procedures outlined by the manufacturer or other methods known in the art. The kinetic data obtained by BIAcore® or KinExA may be analyzed by methods described by the manufacturer.

In some embodiments, the antibody comprises all three light chain CDRs, all three heavy chain CDRs, or all six CDRs. In some exemplary embodiments, two light chain CDRs from an antibody may be combined with a third light chain CDR from a different antibody. Alternatively, a CDRL1 from one antibody can be combined with a CDRL2 from a different antibody and a CDRL3 from yet another antibody, particularly where the CDRs are highly homologous. Similarly, two heavy chain CDRs from an antibody may be combined with a third heavy chain CDR from a different antibody; or a CDRH1 from one antibody can be combined with a CDRH2 from a different antibody and a CDRH3 from yet another antibody, particularly where the CDRs are highly homologous.

Thus, the invention provides a variety of compositions comprising one, two, and/or three CDRs of a heavy chain variable region and/or a light chain variable region of an antibody including modifications or derivatives thereof. Such compositions may be generated by techniques described herein or known in the art.

In some embodiments, the antigen binding protein (including antibodies and antibody fragments) can be useful as a therapeutic molecule which can be used singularly or in combination with other therapeutics to achieve the desired effects. In such embodiments, the inventive antigen binding protein (including antibodies and antibody fragments) further comprises one to twenty-four, one to sixteen, one to eight, or one to four, pharmacologically active chemical moieties conjugated thereto, whether a small molecule or a polypeptide. The pharmacologically active small molecule or polypeptide chemical moieties can be conjugated at or via the N-terminal or C-terminal residue of the antigen binding protein immunoglobulin monomers (e.g., LC or HC monomers), chemical reactions known in the art and further described herein. Alternatively encompassed by the invention, is conjugation of the pharmacologically active chemical moiety, or moieties, at or via functional groups on one or more side chains of the amino acid residue(s) within the primary chain of the inventive antigen binding protein. Useful methods and internal conjugation sites (e.g., particular cysteine residues) within immunoglobulin chains are known in the art (e.g., Gegg et al., Modified Fc Molecules, published in WO 2007/022070 and US 20070269369, which are incorporated herein by reference in their entireties).

In other embodiments of the invention, in which the pharmacologically active chemical moiety is a polypeptide, a recombinant fusion protein can be produced with the pharmacologically active polypeptide being inserted in the primary amino acid sequence of the of the immunoglobulin heavy chain within an internal loop of the Fc domain of the immunoglobulin heavy chain, instead of at the N- and/or C-terminus, as further described in the Examples herein and in the art (e.g., Gegg et al., U.S. Pat. No. 7,442,778; U.S. Pat. No. 7,655,765; U.S. Pat. No. 7,655,764; U.S. Pat. No. 7,662,931; U.S. Pat. No. 7,645,861; published U.S. Patent Applications US 2009/0281286; and US 2009/0286964, each of which are incorporated herein by reference in their entireties).

"Conjugated" means that the pharmacologically active chemical moieties are covalently linked, or bound, directly to an amino acid residue of the antigen binding protein, or optionally, to a peptidyl or non-peptidyl linker moiety that is covalently linked to the amino acid residue of the antigen binding protein.

As stated above, some embodiments of the inventive compositions involve at least one pharmacologically active polypeptide moiety conjugated to the pharmacologically inactive antigen binding protein of the invention, for example constituting a recombinant fusion protein of the pharmacologically active polypeptide moiety conjugated to the pharmacologically inactive antigen binding protein of the invention. The term "pharmacologically active" means that a substance so described is determined to have activity that affects a medical parameter (e.g., blood pressure, blood cell count, cholesterol level, pain perception) or disease state (e.g., cancer, autoimmune disorders, chronic pain). Conversely, the term "pharmacologically inactive" means that no activity affecting a medical parameter or disease state can be determined for that substance. Thus, pharmacologically active peptides or proteins comprise agonistic or mimetic and antagonistic peptides as defined below. The present invention encompasses the use of any pharmacologically active protein, which has an amino acid sequence ranging from about 5 to about 80 amino acid residues in length, and which is amenable to recombinant expression. In some useful embodiments of the invention, the pharmacologically active protein is modified in one or more ways relative to a native sequence of interest, including amino acid additions or insertions, amino acid deletions, peptide truncations, amino acid substitutions, or chemical derivatization of amino acid residues (accomplished by known chemical techniques), so long as the requisite bioactivity is maintained.

The terms "-mimetic peptide," "peptide mimetic," and "-agonist peptide" refer to a peptide or protein having biological activity comparable to a naturally occurring protein of interest, for example, but not limited to, a toxin peptide molecule, e.g., ShK or OSK1 toxin peptides, or peptide analogs thereof. These terms further include peptides that indirectly mimic the activity of a naturally occurring peptide molecule, such as by potentiating the effects of the naturally occurring molecule.

The term "-antagonist peptide," "peptide antagonist," and "inhibitor peptide" refer to a peptide that blocks or in some way interferes with the biological activity of a receptor of interest, or has biological activity comparable to a known antagonist or inhibitor of a receptor of interest (such as, but not limited to, an ion channel or a G-Protein Coupled Receptor (GPCR)).

Examples of pharmacologically active proteins that can be used within the present invention include, but are not limited to, a toxin peptide (e.g., OSK1 or an OSK1 peptide analog; ShK or an ShK peptide analog), an IL-6 binding peptide, a CGRP peptide antagonist, a bradykinin B1 receptor peptide antagonist, a parathyroid hormone (PTH) agonist peptide, a parathyroid hormone (PTH) antagonist peptide, an ang-1 binding peptide, an ang-2 binding peptide, a myostatin binding peptide, an erythropoietin-mimetic (EPO-mimetic) peptide, a thrombopoietin-mimetic (TPO-mimetic) peptide (e.g., AMP2 or AMP5), a nerve growth factor (NGF) binding peptide, a B cell activating factor (BAFF) binding peptide, and a glucagon-like peptide (GLP)-1 or a peptide mimetic thereof or GLP-2 or a peptide mimetic thereof.

Glucagon-like peptide 1 (GLP-1) and the related peptide glucagon are produced via differential processing of proglucagon and have opposing biological activities. Proglucagon itself is produced in α-cells of the pancreas and in the enteroendocrine L-cells, which are located primarily in the distal small intestine and colon. In the pancreas, glucagon is selectively cleaved from proglucagon. In the intestine, in contrast, proglucagon is processed to form GLP-1 and glucagon-like peptide 2 (GLP-2), which correspond to amino acid residues 78-107 and 126-158 of proglucagon, respectively (see, e.g., Irwin and Wong, 1995, *Mol. Endocrinol.* 9:267-277 and Bell et al., 1983, *Nature* 304:368-371). By convention, the numbering of the amino acids of GLP-1 is based on the GLP-1 (1-37) formed from cleavage of proglucagon. The biologically active forms are generated from further processing of this peptide, which, in one numbering convention, yields GLP-1 (7-37)-OH and GLP-1 (7-36)-$NH_2$. Both GLP-1 (7-37)-OH (or simply GLP-1 (7-37)) and GLP-1 (7-36)-$NH_2$ have the same activities. For convenience, the term "GLP-1", is used to refer to both of these forms. The first amino acid of these processed peptides is His7 in this numbering convention. Another numbering convention recognized in the art, however, assumes that the numbering of the processed peptide begins with His as position 1 rather than position 7. Thus, in this numbering scheme, GLP-1 (1-31) is the same as GLP-1(7-37), and GLP-1(1-30) is the same as GLP-1 (7-36). Examples of GLP-1 mimetic polypeptide sequences include:

HGEGTFTSDQSSYLEGQAAKEFIAWLVKGRG// ; (SEQ ID NO: 290)

HGEGTFTSDQSSYLEGQAAKEFIAWLQKGRG// ; (SEQ ID NO: 291)

HGEGTFTSDVSSYQEGQAAKEFIAWLVKGRG// ; (SEQ ID NO: 292)

HGEGTFTSDVSSYLEGQAAKEFIAQLVKGRG// ; (SEQ ID NO: 293)

HGEGTFTSDVSSYLEGQAAKEFIAQLQKGRG// ; (SEQ ID NO: 294)

HGEGTFTSDVSSYLEGQAAKEFIAWLQKGRG// ; (SEQ ID NO: 295)

HNETTFTSDVSSYLEGQAAKEFIAWLVKGRG// (SEQ ID NO: 296)

HGEGTFTSDVSSYLENQTAKEFIAWLVKGRG// ; (SEQ ID NO: 297)

HGEGTFTSDVSSYLEGNATKEFIAWLVKGRG// ; (SEQ ID NO: 298)

HGEGTFTSDVSSYLEGQAAKEFIAWLVNGTG// ; (SEQ ID NO: 299)

HGEGTFTSDVSSYLEGQAAKEFIAWLVKNRT// ; (SEQ ID NO: 300)

HGEGTFTSDVSSYLEGQAAKEFIAWLVKGRNGT// ; (SEQ ID NO: 301)

HGEGTFTSDVSSYLEGQAAKEFIAWLVKGRGGTGNGT// ; and (SEQ ID NO: 302)

HGEGTFTSDVSSYLEGQAAKEFIAWLVKGRGGSGNGT// . (SEQ ID NO: 303)

Human GLP-2 and GLP-2-mimetic analogs are also known in the art. (See, e.g., Prasad et al., Glucagonlike peptide-2 analogue enhances intestinal mucosal mass after ischemia and reperfusion, J. Pediatr. Surg. 2000 February; 35(2):357-59 (2000); Yusta et al., Glucagon-like peptide-2 receptor activation engages bad and glycogen synthase kinase-3 in a protein kinase A-dependent manner and prevents apoptosis following inhibition of phosphatidylinositol 3-kinase, J. Biol. Chem. 277(28):24896-906 (2002)).

"Toxin peptides" include peptides and polypeptides having the same amino acid sequence of a naturally occurring pharmacologically active peptide or polypeptide that can be isolated from a venom, and also include modified peptide analogs of such naturally occurring molecules. (See, e.g., Kalman et al., ShK-Dap22, a potent Kv1.3-specific immunosuppressive polypeptide, J. Biol. Chem. 273(49):32697-707 (1998); Kem et al., U.S. Pat. No. 6,077,680; Mouhat et al., OsK1 derivatives, WO 2006/002850 A2; Chandy et al., Analogs of SHK toxin and their uses in selective inhibition of Kv1.3 potassium channels, WO 2006/042151; Sullivan et al., Toxin Peptide therapeutic agents, WO 2006/116156 A2, all of which are incorporated herein by reference in their entirety). Snakes, scorpions, spiders, bees, snails and sea anemone are a few examples of organisms that produce venom that can serve as a rich source of small bioactive toxin peptides or "toxins" that potently and selectively target ion channels and receptors. An example of a toxin peptide is OSK1 (also known as OsK1), a toxin peptide isolated from *Orthochirus scrobiculosus* scorpion venom. (e.g., Mouhat et al., K+ channel types targeted by synthetic OSK1, a toxin from *Orthochirus scrobiculosus* scorpion venom, Biochem. J. 385:95-104 (2005); Mouhat et al., Pharmacological profiling of *Orthochirus scrobiculosus* toxin 1 analogs with a trimmed N-terminal domain, Molec. Pharmacol. 69:354-62 (2006); Mouhat et al., OsK1 derivatives, WO 2006/002850 A2). Another example is ShK, isolated from the venom of the sea anemone *Stichodactyla helianthus*. (E.g., Tudor et al., Ionisation behaviour and solution properties of the potassium-channel blocker ShK toxin, Eur. J. Biochem. 251(1-2):133-41 (1998); Pennington et al., Role of disulfide bonds in the structure and potassium channel blocking activity of ShK toxin, Biochem. 38(44): 14549-58 (1999); Kem et al., ShK toxin compositions and methods of use, U.S. Pat. No. 6,077,680; Lebrun et al., Neuropeptides originating in scorpion, U.S. Pat. No. 6,689,749; Beeton et al., Targeting effector memory T cells with a selective peptide inhibitor of Kv1.3 channels for therapy of autoimmune diseases, Molec. Pharmacol. 67(4):1369-81 (2005)).

The toxin peptides are usually between about 20 and about 80 amino acids in length, contain 2-5 disulfide linkages and form a very compact structure. Toxin peptides (e.g., from the venom of scorpions, sea anemones and cone snails) have been isolated and characterized for their impact on ion channels. Such peptides appear to have evolved from a relatively small number of structural frameworks that are particularly well suited to addressing the critical issues of potency and stability. The majority of scorpion and Conus toxin peptides, for example, contain 10-40 amino acids and up to five disulfide bonds, forming extremely compact and constrained structure (microproteins) often resistant to proteolysis. The conotoxin and scorpion toxin peptides can be divided into a number of superfamilies based on their disulfide connections and peptide folds. The solution structure of many of these has been determined by NMR spectroscopy, illustrating their compact structure and verifying conservation of their family fold. (E.g., Tudor et al., Ionisation behaviour and solution properties of the potassium-channel blocker ShK toxin, Eur. J. Biochem. 251(1-2):133-41 (1998); Pennington et al., Role of disulfide bonds in the structure and potassium channel blocking activity of ShK toxin, Biochem. 38(44): 14549-58 (1999); Jaravine et al., Three-dimensional structure of toxin OSK1 from *Orthochirus scrobiculosus* scorpion venom, Biochem. 36(6):1223-32 (1997); del Rio-Portillo et al.; NMR solution structure of Cn12, a novel peptide from the Mexican scorpion *Centruroides noxius* with a typical beta-toxin sequence but with alpha-like physiological activity, Eur. J. Biochem. 271(12): 2504-16 (2004); Prochnicka-Chalufour et al., Solution structure of discrepin, a new K+-channel blocking peptide from the alpha-KTx15 subfamily, Biochem. 45(6):1795-1804 (2006)). Examples of pharmacologically active toxin peptides for which the practice of the present invention can be useful include, but are not limited to ShK, OSK1, charybdotoxin (ChTx), kaliotoxin1 KTX1), or maurotoxin, or toxin peptide analogs of any of these, modified from the native sequences at one or more amino acid residues. Other examples are known in the art, or can be found in Sullivan et al., WO06116156 A2 or U.S. patent application Ser. No. 11/406,454 (titled: Toxin Peptide Therapeutic Agents, published as US 2007/0071764); Mouhat et al., OsK1 derivatives, WO 2006/002850 A2; Sullivan et al., U.S. patent application Ser. No. 11/978,076 (titled: Conjugated Toxin Peptide Therapeutic Agents, filed 25 Oct. 2007, and published as US20090291885 on Nov. 26, 2009), Sullivan et al., WO 2008/088422; Lebrun et al., U.S. Pat. No. 6,689,749, and Sullivan et al., Selective and Potent Peptide Inhibitors of Kv1.3, U.S. Provisional Application No. 61/210,594, filed Mar. 20, 2009, which are each incorporated by reference in their entireties.

The term "peptide analog" refers to a peptide having a sequence that differs from a peptide sequence existing in nature by at least one amino acid residue substitution, internal addition, or internal deletion of at least one amino acid, and/or amino- or carboxy-terminal end truncations, or additions). An "internal deletion" refers to absence of an amino acid from a sequence existing in nature at a position other than the N- or C-terminus. Likewise, an "internal addition" refers to presence of an amino acid in a sequence existing in nature at a position other than the N- or C-terminus. "Toxin peptide analogs", such as, but not limited to, an OSK1 peptide analog, ShK peptide analog, or ChTx peptide analog, contain modifications of a native toxin peptide sequence of interest (e.g., amino acid residue substitutions, internal additions or insertions, internal deletions, and/or amino- or carboxy-terminal end truncations, or additions as previously described above) relative to a native toxin peptide sequence of interest.

A "CGRP peptide antagonist" is a peptide that preferentially binds the $CGRP_1$ receptor, such as, but not limited to, a CGRP peptide analog, and that antagonizes, blocks, decreases, reduces, impedes, or inhibits $CGRP_1$ receptor activation by full length native human αCGRP or CGRP under physiological conditions of temperature, pH, and ionic strength. CGRP peptide antagonists include full and partial antagonists. Such antagonist activity can be detected by known in vitro methods or in vivo functional assay methods. (See, e.g., Smith et al., Modifications to the N-terminus but not the C-terminus of calcitonin gene-related peptide (8-37) produce antagonists with increased affinity, J. Med. Chem., 46:2427-2435 (2003)). Examples of useful CGRP peptide antagonists are disclosed in Gegg et al., CGRP peptide antagonists and conjugates, WO 2007/048026 A2 and U.S. Ser. No. 11/584,177, filed on Oct. 19, 2006, published as US 2008/0020978 A1, which is incorporated herein by reference in its entirety.

The terms "parathyroid hormone (PTH) agonist" and "PTH agonist" refer to a molecule that binds to PTH-1 or PTH-2 receptor and increases or decreases one or more PTH activity assay parameters as does full-length native human parathyroid hormone. Examples of useful PTH agonist peptides are disclosed in Table 1 of U.S. Pat. No. 6,756,480, titled Modulators of receptors for parathyroid hormone and parathyroid hormone-related protein, which is incorporated herein by reference in its entirety. An exemplary PTH activity assay is disclosed in Example 1 of U.S. Pat. No. 6,756,480.

The term "parathyroid hormone (PTH) antagonist" refers to a molecule that binds to PTH-1 or PTH-2 receptor and blocks or prevents the normal effect on those parameters by full length native human parathyroid hormone. Examples of useful PTH antagonist peptides are disclosed in Table 2 of U.S. Pat. No. 6,756,480, which is incorporated herein by reference in its entirety. An exemplary PTH activity assay is disclosed in Example 2 of U.S. Pat. No. 6,756,480.

The terms "bradykinin B1 receptor antagonist peptide" and "bradykinin B1 receptor peptide antagonist" mean a peptide with antagonist activity with respect to human bradykinin B1 receptor (hB1). Useful bradykinin B1 receptor antagonist peptides can be identified or derived as described in Ng et al., Antagonist of the bradykinin B1 receptor, US 2005/0215470 A1, published Sep. 29, 2005, which issued as U.S. Pat. No. 7,605,120; U.S. Pat. No. 5,834,431 or 5,849,863. An exemplary B1 receptor activity assays are disclosed in Examples 6-8 of US 2005/0215470 A1.

The terms "thrombopoietin (TPO)-mimetic peptide" and "TPO-mimetic peptide" refer to peptides that can be identified or derived as described in Cwirla et al. (1997), *Science* 276: 1696-9, U.S. Pat. Nos. 5,869,451 and 5,932,946, which are incorporated by reference in their entireties; U.S. Pat. App. No. 2003/0176352, published Sep. 18, 2003, which is incorporated by reference in its entirety; WO 03/031589, published Apr. 17, 2003; WO 00/24770, published May 4, 2000; and any peptides appearing in Table 5 of published application US 2006/0140934 (U.S. Ser. No. 11/234,731, filed Sep. 23, 2005, titled Modified Fc Molecules, which is incorporated herein by reference in its entirety). Those of ordinary skill in the art appreciate that each of these references enables one to select different peptides than actually disclosed therein by following the disclosed procedures with different peptide libraries.

The terms "EPO-mimetic peptide" and "erythropoietin-mimetic peptide" refers to peptides that can be identified or derived as described in Wrighton et al. (1996), *Science* 273: 458-63, and Naranda et al. (1999), Proc. Natl. Acad. Sci. USA 96: 7569-74, both of which are incorporated herein by reference in their entireties. Useful EPO-mimetic peptides include EPO-mimetic peptides listed in Table 5 of published U.S. patent application US 2007/0269369 A1 and in U.S. Pat. No. 6,660,843, which are both hereby incorporated by reference in their entireties.

The term "ang-2-binding peptide" comprises peptides that can be identified or derived as described in U.S. Pat. App. No. 2003/0229023, published Dec. 11, 2003; WO 03/057134, published Jul. 17, 2003; U.S. 2003/0236193, published Dec. 25, 2003 (each of which is incorporated herein by reference in its entirety); and any peptides appearing in Table 6 of published application US 2006/0140934 (U.S. Ser. No. 11/234,731, filed Sep. 23, 2005, titled Modified Fc Molecules, which is incorporated herein by reference in its entirety). Those of ordinary skill in the art appreciate that each of these references enables one to select different peptides than actually disclosed therein by following the disclosed procedures with different peptide libraries.

The terms "nerve growth factor (NGF) binding peptide" and "NGF-binding peptide" comprise peptides that can be identified or derived as described in WO 04/026329, published Apr. 1, 2004 and any peptides identified in Table 7 of published application US 2006/0140934 (U.S. Ser. No. 11/234,731, filed Sep. 23, 2005, titled Modified Fc Molecules, which is incorporated herein by reference in its entirety). Those of ordinary skill in the art appreciate that this reference enables one to select different peptides than actually disclosed therein by following the disclosed procedures with different peptide libraries.

The term "myostatin-binding peptide" comprises peptides that can be identified or derived as described in U.S. Ser. No. 10/742,379, filed Dec. 19, 2003, which is incorporated herein by reference in its entirety, and peptides appearing in Table 8 of published application US 2006/0140934 (U.S. Ser. No. 11/234,731, filed Sep. 23, 2005, titled Modified Fc Molecules, which is incorporated herein by reference in its entirety). Those of ordinary skill in the art appreciate that each of these references enables one to select different peptides than actually disclosed therein by following the disclosed procedures with different peptide libraries.

The terms "BAFF-antagonist peptide" and "BAFF binding peptide" comprise peptides that can be identified or derived as described in U.S. Pat. Appln. No. 2003/0195156 A1, which is incorporated herein by reference in its entirety and those peptides appearing in Table 9 of published application US 2006/0140934 (U.S. Ser. No. 11/234,731, filed Sep. 23, 2005, titled Modified Fc Molecules, which is incorporated herein by reference in its entirety). Those of ordinary skill in the art appreciate that the foregoing references enable one to select different peptides than actually disclosed therein by following the disclosed procedures with different peptide libraries.

The foregoing are intended merely as non-limiting examples of the pharmacologically active polypeptides that can be usefully conjugated or fused to the inventive antigen binding proteins (including antibodies and antibody fragments). Any include pharmacologically active polypeptide moiety can be used within the scope of the invention, including a polypeptide having a so-called avimer structure (see, e.g., Kolkman et al., Novel Proteins with Targeted Binding, US 2005/0089932; Baker et al., IL-6 Binding Proteins, US 2008/0281076; Stemmer et al., Protein Scaffolds and Uses Thereof, US 2006/0223114 and US 2006/0234299).

Useful preclinical animal models are known in the art for use in validating a drug in a therapeutic indication of interest (e.g., an adoptive-transfer model of periodontal disease by Valverde et al., J. Bone Mineral Res. 19:155 (2004); an ultrasonic perivascular Doppler flow meter-based animal model of arterial thrombosis in Gruner et al., Blood 105: 1492-99 (2005); pulmonary thromboembolism model, aorta occlusion model, and murine stroke model in Braun et al., WO 2009/115609 A1). For example, an adoptive transfer experimental autoimmune encephalomyelitis (AT-EAE) model of multiple sclerosis has been described for investigations concerning immune diseases, such as multiple sclerosis (Beeton et al., J. Immunol. 166:936 (2001); Beeton et al., PNAS 98:13942 (2001); Sullivan et al., Example 45 of WO 2008/088422 A2, incorporated herein by reference in its entirety). In the AT-EAE model, significantly reduced disease severity and increased survival are expected for animals treated with an effective amount of the inventive pharmaceutical composition, while untreated animals are expected to develop severe disease and/or mortality. For running the AT-EAE model, the encephalomyelogenic CD4+ rat T cell line, PAS, specific for myelin-basic protein (MBP) originated from Dr. Evelyne Beraud. The maintenance of these cells in vitro and their use in the AT-EAE model has been described earlier [Beeton et al. (2001) PNAS 98, 13942].

PAS T cells are maintained in vitro by alternating rounds of antigen stimulation or activation with MBP and irradiated thymocytes (2 days), and propagation with T cell growth factors (5 days). Activation of PAS T cells ($3 \times 10^5$/ml) involves incubating the cells for 2 days with 10 μg/ml MBP and $15 \times 10^6$/ml syngeneic irradiated (3500 rad) thymocytes. On day 2 after in vitro activation, $10\text{-}15 \times 10^6$ viable PAS T cells are injected into 6-12 week old female Lewis rats (Charles River Laboratories) by tail IV. Daily subcutaneous injections of vehicle (2% Lewis rat serum in PBS) or test pharmaceutical composition are given from days −1 to 3, where day −1 represent 1 day prior to injection of PAS T cells (day 0). In vehicle treated rats, acute EAE is expected to develop 4 to 5 days after injection of PAS T cells. Typically, serum is collected by tail vein bleeding at day 4 and by cardiac puncture at day 8 (end of the study) for analysis of levels of inhibitor. Rats are typically weighed on days −1, 4, 6, and 8. Animals may be scored blinded once a day from the day of cell transfer (day 0) to day 3, and twice a day from day 4 to day 8. Clinical signs are evaluated as the total score of the degree of paresis of each limb and tail. Clinical scoring: 0=No signs, 0.5=distal limp tail, 1.0=limp tail, 2.0=mild paraparesis, ataxia, 3.0=moderate paraparesis, 3.5=one hind leg paralysis, 4.0=complete hind leg paralysis, 5.0=complete hind leg paralysis and incontinence, 5.5=tetraplegia, 6.0=moribund state or death. Rats reaching a score of 5.0 are typically euthanized.

Production of Antibody Embodiments of the Antigen Binding Proteins

Polyclonal Antibodies.

Polyclonal antibodies are preferably raised in animals by multiple subcutaneous (sc) or intraperitoneal (ip) injections of the relevant antigen and an adjuvant. Alternatively, antigen may be injected directly into the animal's lymph node (see Kilpatrick et al., Hybridoma, 16:381-389, 1997). An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates, or derivatives by combining, e.g., 100 μg of the protein or conjugate (for mice) with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies.

The inventive antigen binding proteins or antigen binding proteins that are provided include monoclonal antibodies that bind to DNP or KLH, respectively. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. For example, monoclonal antibodies may be made using the hybridoma method first described by Kohler et al., Nature, 256:495 (1975), or may be made by recombinant DNA methods (e.g., Cabilly et al., Methods of producing immunoglobulins, vectors and transformed host cells for use therein, U.S. Pat. No. 6,331,415), including methods, such as the "split DHFR" method, that facilitate the generally equimolar production of light and heavy chains, optionally using mammalian cell lines (e.g., CHO cells) that can glycosylate the antibody (See, e.g., Page, Antibody production, EP0481790 A2 and U.S. Pat. No. 5,545,403).

In the hybridoma method, a mouse or other appropriate host mammal, such as rats, hamster or macaque monkey, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

In some instances, a hybridoma cell line is produced by immunizing a transgenic animal having human immunoglobulin sequences with a DNP or KLH immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds DNP or KLH, respectively. Such hybridoma cell lines, and monoclonal antibodies produced by them, are aspects of the present invention.

The present invention also encompasses a hybridoma that produces the inventive antigen binding protein that is a monoclonal antibody. Accordingly, the present invention is also directed to a method, comprising:

(a) culturing the hybridoma in a culture medium under conditions permitting expression of the antigen binding protein by the hybridoma; and (b) recovering the antigen binding protein from the culture medium, which can be accomplished by known antibody purification techniques, such as but not limited to, monoclonal antibody purification techniques disclosed in Example 1 herein.

The hybridoma cells, once prepared, are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)). Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by BIAcore® or Scatchard analysis (Munson et al., Anal. Biochem., 107:220 (1980); Fischer et al., A peptide-immunoglobulin-conjugate, WO 2007/045463 A1, Example 10, which is incorporated herein by reference in its entirety).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

Hybridomas or mAbs may be further screened to identify mAbs with particular properties, such as the ability to inhibit $K^{1+}$ flux though Kv1.x channels. Examples of such screens are provided in the examples below. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, affinity chromatography, or any other suitable purification technique known in the art.

Recombinant Production of Antibodies.

The invention provides isolated nucleic acids encoding any of the antibodies (polyclonal and monoclonal), including antibody fragments, of the invention described herein, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium. Similar materials and methods apply to production of polypeptide-based antigen binding proteins.

Relevant amino acid sequences from an immunoglobulin or polypeptide of interest may be determined by direct protein sequencing, and suitable encoding nucleotide sequences can be designed according to a universal codon table. Alternatively, genomic or cDNA encoding the monoclonal antibodies may be isolated and sequenced from cells producing such antibodies using conventional procedures (e.g., by using oligonucleotide probes that are capable of binding specifically to genes encoding the heavy and light chains of the monoclonal antibodies).

Cloning of DNA is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+mRNA, preferably membrane-associated mRNA, and the library screened using probes specific for human immunoglobulin polypeptide gene sequences. In one embodiment, however, the polymerase chain reaction (PCR) is used to amplify cDNAs (or portions of full-length cDNAs) encoding an immunoglobulin gene segment of interest (e.g., a light or heavy chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

One source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal. Yet another source of nucleic acids encoding antibodies is a library of such nucleic acids generated, for example, through phage display technology. Polynucleotides encoding peptides of interest, e.g., variable region peptides with desired binding characteristics, can be identified by standard techniques such as panning.

The sequence encoding an entire variable region of the immunoglobulin polypeptide may be determined; however, it will sometimes be adequate to sequence only a portion of a variable region, for example, the CDR-encoding portion. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Isolated DNA can be operably linked to control sequences or placed into expression vectors, which are then transfected into host cells that do not otherwise produce immunoglobulin protein, to direct the synthesis of monoclonal antibodies in the recombinant host cells. Recombinant production of antibodies is well known in the art.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Many vectors are known in the art. Vector components may include one or more of the following: a signal sequence (that may, for example, direct secretion of the antibody; e.g., ATGGACATGAGGGTGCCCGCTCAGCTC-CTGGGGCTCCTGCTGCTGTGGCT GAGAGGT-GCGCGCTGT// SEQ ID NO:102, which encodes the VK-1 signal peptide sequence MDMRVPAQLLGLLLLWLR-GARC// SEQ ID NO:103), an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Exemplary host cells include prokaryote, yeast, or higher eukaryote cells. Prokaryotic host cells include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacillus* such as *B. subtilis* and *B. licheniformis, Pseudomonas*, and *Streptomyces*. Eukaryotic microbes such as filamentous fungi or yeast are suitable cloning or expression hosts for recombinant polypeptides or antibodies. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris, Schizosaccharomyces pombe; Kluyveromyces, Yarrowia; Candida; Trichoderma reesia; Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Host cells for the expression of glycosylated antigen binding protein, including antibody, can be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-1 variant of *Autographa californica* NPV and the Bm-5 strain of *Bombyx mori* NPV.

Vertebrate host cells are also suitable hosts, and recombinant production of antigen binding protein (including antibody) from such cells has become routine procedure. Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., J. Gen Virol. 36: 59

(1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y Acad. Sci. 383: 44-68 (1982)); MRC 5 cells or FS4 cells; or mammalian myeloma cells.

Host cells are transformed or transfected with the above-described nucleic acids or vectors for production antigen binding proteins and are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of antigen binding proteins.

The host cells used to produce the antigen binding proteins of the invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Patent Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Upon culturing the host cells, the antigen binding protein can be produced intracellularly, in the periplasmic space, or directly secreted into the medium. If the antigen binding protein is produced intracellularly, as a first step, the particulate debris, either host cells or lysed fragments, is removed, for example, by centrifugation or ultrafiltration.

The antigen binding protein (e.g., an antibody or antibody fragment) can be purified using, for example, hydroxylapatite chromatography, cation or anion exchange chromatography, or preferably affinity chromatography, using the antigen of interest or protein A or protein G as an affinity ligand. Protein A can be used to purify proteins that include polypeptides are based on human γ1, γ2, or γ4 heavy chains (Lindmark et al., J. Immunol. Meth. 62: 1-13 (1983)). Protein G is recommended for all mouse isotypes and for human γ3 (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the protein comprises a $C_H3$ domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the antibody to be recovered.

Chimeric, Humanized and Human Engineered™ Monoclonal Antibodies.

Chimeric monoclonal antibodies, in which the variable Ig domains of a rodent monoclonal antibody are fused to human constant Ig domains, can be generated using standard procedures known in the art (See Morrison, S. L., et al. (1984) Chimeric Human Antibody Molecules; Mouse Antigen Binding Domains with Human Constant Region Domains, Proc. Natl. Acad. Sci. USA 81, 6841-6855; and, Boulianne, G. L., et al, Nature 312, 643-646. (1984)). A number of techniques have been described for humanizing or modifying antibody sequence to be more human-like, for example, by (1) grafting the non-human complementarity determining regions (CDRs) onto a human framework and constant region (a process referred to in the art as humanizing through "CDR grafting") or (2) transplanting the entire non-human variable domains, but "cloaking" them with a human-like surface by replacement of surface residues (a process referred to in the art as "veneering") or (3) modifying selected non-human amino acid residues to be more human, based on each residue's likelihood of participating in antigen-binding or antibody structure and its likelihood for immunogenicity. See, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991); Co, M. S., et al. (1994), J. Immunol. 152, 2968-2976); Studnicka et al. Protein Engineering 7: 805-814 (1994); each of which is incorporated herein by reference in its entirety.

A number of techniques have been described for humanizing or modifying antibody sequence to be more human-like, for example, by (1) grafting the non-human complementarity determining regions (CDRs) onto a human framework and constant region (a process referred to in the art as humanizing through "CDR grafting") or (2) transplanting the entire non-human variable domains, but "cloaking" them with a human-like surface by replacement of surface residues (a process referred to in the art as "veneering") or (3) modifying selected non-human amino acid residues to be more human, based on each residue's likelihood of participating in antigen-binding or antibody structure and its likelihood for immunogenicity. See, e.g., Jones et al., Nature 321:522 525 (1986); Morrison et al., Proc. Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun. 28:489 498 (1991); Padlan, Molec. Immunol. 31(3):169 217 (1994); and Kettleborough, C. A. et al., Protein Eng. 4(7): 773 83 (1991); Co, M. S., et al. (1994), J. Immunol. 152, 2968-2976); Studnicka et al. Protein Engineering 7: 805-814 (1994); each of which is incorporated herein by reference in its entirety.

In one aspect, the CDRs of the light and heavy chain variable regions of the antibodies provided herein (see, Table 2A-B) are grafted to framework regions (FRs) from antibodies from the same, or a different, phylogenetic species. For example, the CDRs of the heavy chain variable regions (e.g., $V_H1$, $V_H2$, $V_H3$, $V_H4$, $V_H5$, $V_H6$, $V_H7$, $V_H8$, or $V_H9$) and/or light chain variable regions (e.g., $V_L1$, $V_L2$, $V_L3$, $V_L4$, $V_L5$, $V_L6$, $V_L7$, $V_L8$, or $V_L9$) can be grafted to consensus human FRs. To create consensus human FRs, FRs from several human heavy chain or light chain amino acid sequences may be aligned to identify a consensus amino acid sequence. In other embodiments, the FRs of a heavy chain or light chain disclosed herein are replaced with the FRs from a different heavy chain or light chain. In one aspect, rare amino acids in the FRs of the heavy and light chains of the antibody are not replaced, while the rest of the FR amino acids are replaced. A "rare amino acid" is a specific amino acid that is in a position in which this particular amino acid is not usually found in an FR. Alternatively, the grafted variable regions from the one heavy or light chain may be used with a constant region that is different from the constant region of that particular heavy or light chain as disclosed herein. In other embodiments, the grafted variable regions are part of a single chain Fv antibody.

Antibodies can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody producing cells can be removed from the animal and used to produce hybridomas that secrete human-derived monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein. See also Jakobovits et al., Proc. Natl. Acad. Sci. USA, 90:2551 (1993); Jakobovits et al., Nature, 362:255-258 (1993); Bruggermann et al., Year in Immuno., 7:33 (1993); Mendez et al., Nat. Genet. 15:146-156 (1997); and U.S. Pat. No. 5,591,669, U.S. Pat. No. 5,589,369, U.S. Pat. No. 5,545,807; and U.S Patent Application No. 20020199213. U.S. Patent Application No. 20030092125 describes methods for biasing the immune response of an animal to the desired epitope. Human antibodies may also be generated by in vitro activated B cells (see U.S. Pat. Nos. 5,567,610 and 5,229,275).

Antibody Production by Phage Display Techniques

The development of technologies for making repertoires of recombinant human antibody genes, and the display of the encoded antibody fragments on the surface of filamentous bacteriophage, has provided another means for generating human-derived antibodies. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference in its entirety. The antibodies produced by phage technology are usually produced as antigen binding fragments, e.g. Fv or Fab fragments, in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Typically, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning. Antibody fragments specific for the antigen are enriched and finally isolated.

Phage display techniques can also be used in an approach for the humanization of rodent monoclonal antibodies, called "guided selection" (see Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., J. Mol. Biol., 227:381 (1991); Marks et al., J. Mol. Biol, 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); and, Winter, G., et al., Annu. Rev. Immunol. 12, 433-455 (1994); U.S. patent application no. 20020004215 and WO92/01047; U.S. patent application no. 20030190317 published Oct. 9, 2003 and U.S. Pat. No. 6,054,287; U.S. Pat. No. 5,877,293.

Watkins, "Screening of Phage-Expressed Antibody Libraries by Capture Lift," Methods in Molecular Biology, Antibody Phage Display: Methods and Protocols 178: 187-193, and U.S. Patent Application Publication No. 20030044772 published Mar. 6, 2003 describes methods for screening phage-expressed antibody libraries or other binding molecules by capture lift, a method involving immobilization of the candidate binding molecules on a solid support.

Other Embodiments of Antigen Binding Proteins: Antibody Fragments

As noted above, antibody fragments comprise a portion of an intact full length antibody, preferably an antigen binding or variable region of the intact antibody, and include linear antibodies and multispecific antibodies formed from antibody fragments. Nonlimiting examples of antibody fragments include Fab, Fab', F(ab')2, Fv, Fd, domain antibody (dAb), complementarity determining region (CDR) fragments, single-chain antibodies (scFv), single chain antibody fragments, maxibodies, diabodies, triabodies, tetrabodies, minibodies, linear antibodies, chelating recombinant antibodies, tribodies or bibodies, intrabodies, nanobodies, small modular immunopharmaceuticals (SMIPs), an antigen-binding-domain immunoglobulin fusion protein, a camelized antibody, a VHH containing antibody, or muteins or derivatives thereof, and polypeptides that contain at least a portion of an immunoglobulin that is sufficient to confer specific antigen binding to the polypeptide, such as a CDR sequence, as long as the antibody retains the desired biological activity. Such antigen fragments may be produced by the modification of whole antibodies or synthesized de novo using recombinant DNA technologies or peptide synthesis.

Additional antibody fragments include a domain antibody (dAb) fragment (Ward et al., *Nature* 341:544-546, 1989) which consists of a $V_H$ domain.

"Linear antibodies" comprise a pair of tandem Fd segments ($V_H$-$C_H$1-$V_H$-$C_H$1) which form a pair of antigen binding regions. Linear antibodies can be bispecific or monospecific (Zapata et al. Protein Eng. 8:1057-62 (1995)).

A "minibody" consisting of scFv fused to $C_H$3 via a peptide linker (hingeless) or via an IgG hinge has been described in Olafsen, et al., Protein Eng Des Sel. 2004 April; 17(4):315-23.

The term "maxibody" refers to bivalent scFvs covalently attached to the Fc region of an immunoglobulin, see, for example, Fredericks et al, Protein Engineering, Design & Selection, 17:95-106 (2004) and Powers et al., Journal of Immunological Methods, 251:123-135 (2001).

Functional heavy-chain antibodies devoid of light chains are naturally occurring in certain species of animals, such as nurse sharks, wobbegong sharks and Camelidae, such as camels, dromedaries, alpacas and llamas. The antigen-binding site is reduced to a single domain, the $VH_H$ domain, in these animals. These antibodies form antigen-binding regions using only heavy chain variable region, i.e., these functional antibodies are homodimers of heavy chains only having the structure $H_2L_2$ (referred to as "heavy-chain antibodies" or "HCAbs"). Camelized $V_{HH}$ reportedly recombines with IgG2 and IgG3 constant regions that contain hinge, CH2, and CH3 domains and lack a CH1 domain. Classical $V_H$-only fragments are difficult to produce in soluble form, but improvements in solubility and specific binding can be obtained when framework residues are altered to be more $V_H$-like. (See, e.g., Reichman, et al., J Immunol Methods 1999, 231:25-38.) Camelized domains have been found to bind to antigen with high affinity (Desmyter et al., *J Biol. Chem.* 276:26285-90, 2001) and possess high stability in solution (Ewert et al., *Biochemistry* 41:3628-36, 2002). Methods for generating antibodies having camelized heavy chains are described in, for example, in U.S. Patent Publication Nos. 2005/0136049 and 2005/0037421. Alternative scaffolds can be made from human variable-like domains that more closely match the shark V-NAR scaffold and may provide a framework for a long penetrating loop structure.

Because the variable domain of the heavy-chain antibodies is the smallest fully functional antigen-binding fragment with a molecular mass of only 15 kDa, this entity is referred to as a nanobody (Cortez-Retamozo et al., *Cancer Research* 64:2853-57, 2004). A nanobody library may be generated from an immunized dromedary as described in Conrath et al., (*Antimicrob Agents Chemother* 45: 2807-12, 2001).

Intrabodies are single chain antibodies which demonstrate intracellular expression and can manipulate intracellular protein function (Biocca, et al., EMBO 9:101-108, 1990; Colby et al., *Proc Natl Acad Sci USA.* 101:17616-21, 2004). Intrabodies, which comprise cell signal sequences which retain the antibody contruct in intracellular regions, may be produced as described in Mhashilkar et al (*EMBO J* 14:1542-51, 1995) and Wheeler et al. (*FASEB J.* 17:1733-5. 2003). Transbodies are cell-permeable antibodies in which a protein transduction domains (PTD) is fused with single chain variable fragment (scFv) antibodies Heng et al., (*Med Hypotheses.* 64:1105-8, 2005).

Further encompassed by the invention are antibodies that are SMIPs or binding domain immunoglobulin fusion proteins specific for target protein. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

Various techniques have been developed for the production of antibody fragments. Traditionally, these fragments were derived via proteolytic digestion of intact antibodies, but can also be produced directly by recombinant host cells. See, for example, Better et al., Science 240: 1041-1043 (1988); Skerra et al. Science 240: 1038-1041 (1988); Carter et al., Bio/Technology 10:163-167 (1992).

Other Embodiments of Antigen Binding Proteins: Multivalent Antibodies

In some embodiments, it may be desirable to generate multivalent or even a multispecific (e.g. bispecific, trispecific, etc.) monoclonal antibody. Such antibody may have binding specificities for at least two different epitopes of the target antigen, or alternatively it may bind to two different molecules, e.g. to the target antigen and to a cell surface protein or receptor. For example, a bispecific antibody may include an arm that binds to the target and another arm that binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the target-expressing cell. As another example, bispecific antibodies may be used to localize cytotoxic agents to cells which express target antigen. These antibodies possess a target-binding arm and an arm which binds the cytotoxic agent (e.g., saporin, anti-interferon-60, vinca alkaloid, ricin A chain, methotrexate or radioactive isotope hapten). Multispecific antibodies can be prepared as full length antibodies or antibody fragments.

Additionally, the anti-DNP or anti-KLH antibodies of the present invention can also be constructed to fold into multivalent forms, which may improve binding affinity, specificity and/or increased half-life in blood. Multivalent forms of anti-DNP or anti-KLH can be prepared by techniques known in the art.

Bispecific or multispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques. Another method is designed to make tetramers by adding a streptavidin-coding sequence at the C-terminus of the scFv. Streptavidin is composed of four subunits, so when the scFv-streptavidin is folded, four subunits associate to form a tetramer (Kipriyanov et al., Hum Antibodies Hybridomas 6(3): 93-101 (1995), the disclosure of which is incorporated herein by reference in its entirety).

According to another approach for making bispecific antibodies, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO 96/27011 published Sep. 6, 1996.

Techniques for generating bispecific or multispecific antibodies from antibody fragments have also been described in the literature. For example, bispecific or trispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes. Better et al., Science 240: 1041-1043 (1988) disclose secretion of functional antibody fragments from bacteria (see, e.g., Better et al., Skerra et al. Science 240: 1038-1041 (1988)). For example, Fab'-SH fragments can be directly recovered from *E. coli* and chemically coupled to form bispecific antibodies (Carter et al., Bio/Technology 10:163-167 (1992); Shalaby et al., J. Exp. Med. 175:217-225 (1992)).

Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecfic antibody.

Various techniques for making and isolating bispecific or multispecific antibody fragments directly from recombinant cell culture have also been described. For example, bispecific antibodies have been produced using leucine zippers, e.g. GCN4. (See generally Kostelny et al., J. Immunol. 148(5):1547-1553 (1992).) The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

Diabodies, described above, are one example of a bispecific antibody. See, for example, Hollinger et al., Proc. Natl. Acad. Sci. USA, 90:6444-6448 (1993). Bivalent diabodies can be stabilized by disulfide linkage.

Stable monospecific or bispecific Fv tetramers can also be generated by noncovalent association in (scFv$_2$)$_2$ configuration or as bis-tetrabodies. Alternatively, two different scFvs can be joined in tandem to form a bis-scFv.

Another strategy for making bispecific antibody fragments by the use of single-chain Fv (sFv) dimers has also been reported. See Gruber et al., J. Immunol. 152: 5368 (1994). One approach has been to link two scFv antibodies with linkers or disulfide bonds (Mallender and Voss, J. Biol. Chem. 269:199-2061994, WO 94/13806, and U.S. Pat. No. 5,989,830, the disclosures of which are incorporated herein by reference in their entireties).

Alternatively, the bispecific antibody may be a "linear antibody" produced as described in Zapata et al. Protein Eng. 8(10):1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are also contemplated. For example, trispecific antibodies can be prepared. (Tutt et al., J. Immunol. 147:60 (1991)).

A "chelating recombinant antibody" is a bispecific antibody that recognizes adjacent and non-overlapping epitopes of the target antigen, and is flexible enough to bind to both epitopes simultaneously (Neri et al., *J Mol Biol*. 246:367-73, 1995).

Production of bispecific Fab-scFv ("bibody") and trispecific Fab-(scFv)(2) ("tribody") are described in Schoonjans et al. (*J Immunol*. 165:7050-57, 2000) and Willems et al. (*J Chromatogr B Analyt Technol Biomed Life Sci*. 786:161-76, 2003). For bibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab.

In yet another method, dimers, trimers, and tetramers are produced after a free cysteine is introduced in the parental protein. A peptide-based cross linker with variable numbers (two to four) of maleimide groups was used to cross link the protein of interest to the free cysteines (Cochran et al., Immunity 12(3): 241-50 (2000), the disclosure of which is incorporated herein in its entirety).

Other Embodiments of Antigen Binding Proteins

Inventive antigen binding proteins also include peptibodies. The term "peptibody" refers to a molecule comprising an antibody Fc domain attached to at least one peptide. The production of peptibodies is generally described in PCT publication WO 00/24782, published May 4, 2000. Any of these peptides may be linked in tandem (i.e., sequentially), with or without linkers. Peptides containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized, for example the carboxyl terminus may be capped with an amino group, cysteines may be cappe, or amino acid residues may substituted by moieties other than amino acid residues (see, e.g., Bhatnagar et al., J. Med. Chem. 39: 3814-9 (1996), and Cuthbertson et al., J. Med. Chem. 40: 2876-82 (1997), which are incorporated by reference herein in their entirety). The peptide sequences may be optimized, analogous to affinity maturation for antibodies, or otherwise altered by alanine scanning or random or directed mutagenesis followed by screening to identify the best binders. Lowman, Ann. Rev. Biophys. Biomol. Struct. 26: 401-24 (1997). Various molecules can be inserted into the antigen binding protein structure, e.g., within the peptide portion itself or between the peptide and vehicle portions of the antigen binding proteins, while retaining the desired activity of antigen binding protein. One can readily insert, for example, molecules such as an Fc domain or fragment thereof, polyethylene glycol or other related molecules such as dextran, a fatty acid, a lipid, a cholesterol group, a small carbohydrate, a peptide, a detectable moiety as described herein (including fluorescent agents, radiolabels such as radioisotopes), an oligosaccharide, oligonucleotide, a polynucleotide, interference (or other) RNA, enzymes, hormones, or the like. Other molecules suitable for insertion in this fashion will be appreciated by those skilled in the art, and are encompassed within the scope of the invention. This includes insertion of, for example, a desired molecule in between two consecutive amino acids, optionally joined by a suitable linker.

Linkers.

A "linker" or "linker moiety", as used interchangeably herein, refers to a biologically acceptable peptidyl or non-peptidyl organic group that is covalently bound to an amino acid residue of a polypeptide chain (e.g., an immunoglobulin HC or immunoglobulin LC or immunoglobulin Fc domain) contained in the inventive composition, which linker moiety covalently joins or conjugates the polypeptide chain to another peptide or polypeptide chain in the molecule, or to a therapeutic moiety, such as a biologically active small molecule or oligopeptide, or to a half-life extending moiety, e.g., see, Sullivan et al., Toxin Peptide Therapeutic Agents, US2007/0071764; Sullivan et al., Toxin Peptide Therapeutic Agents, PCT/US2007/022831, published as WO 2008/088422; and U.S. Provisional Application Ser. No. 61/210, 594, filed Mar. 20, 2009, which are all incorporated herein by reference in their entireties.

The presence of any linker moiety in the antigen binding proteins of the present invention is optional. When present, the linker's chemical structure is not critical, since it serves primarily as a spacer to position, join, connect, or optimize presentation or position of one functional moiety in relation to one or more other functional moieties of a molecule of the inventive antigen binding protein. The presence of a linker moiety can be useful in optimizing pharmacological activity of some embodiments of the inventive antigen binding protein (including antibodies and antibody fragments). The linker is preferably made up of amino acids linked together by peptide bonds. The linker moiety, if present, can be independently the same or different from any other linker, or linkers, that may be present in the inventive antigen binding protein.

As stated above, the linker moiety, if present (whether within the primary amino acid sequence of the antigen binding protein, or as a linker for attaching a therapeutic moiety or half-life extending moiety to the inventive antigen binding protein), can be "peptidyl" in nature (i.e., made up of amino acids linked together by peptide bonds) and made up in length, preferably, of from 1 up to about 40 amino acid residues, more preferably, of from 1 up to about 20 amino acid residues, and most preferably of from 1 to about 10 amino acid residues. Preferably, but not necessarily, the amino acid residues in the linker are from among the twenty canonical amino acids, more preferably, cysteine, glycine, alanine, proline, asparagine, glutamine, and/or serine. Even more preferably, a peptidyl linker is made up of a majority of amino acids that are sterically unhindered, such as glycine, serine, and alanine linked by a peptide bond. It is also desirable that, if present, a peptidyl linker be selected that avoids rapid proteolytic turnover in circulation in vivo. Some of these amino acids may be glycosylated, as is well understood by those in the art. For example, a useful linker sequence constituting a sialylation site is $X_1X_2NX_4X_5G$ (SEQ ID NO:148), wherein $X_1$, $X_2$, $X_4$ and $X_5$ are each independently any amino acid residue.

In other embodiments, the 1 to 40 amino acids of the peptidyl linker moiety are selected from glycine, alanine, proline, asparagine, glutamine, and lysine. Preferably, a linker is made up of a majority of amino acids that are sterically unhindered, such as glycine and alanine. Thus, preferred linkers include polyglycines, polyserines, and polyalanines, or combinations of any of these. Some exemplary peptidyl linkers are poly(Gly)$_{1-8}$, particularly (Gly)$_3$, (Gly)$_4$ (SEQ ID NO:149), (Gly)$_5$ (SEQ ID NO:150) and (Gly)$_7$ (SEQ ID NO:151), as well as, poly(Gly)$_4$Ser (SEQ ID NO:152), poly(Gly-Ala)$_{2-4}$ and poly(Ala)$_{1-8}$. Other specific examples of peptidyl linkers include (Gly)$_5$Lys (SEQ ID NO:154), and (Gly)$_5$LysArg (SEQ ID NO:155). Other examples of useful peptidyl linkers are: Other examples of useful peptidyl linkers are:

```
                                           (SEQ ID NO: 159)
    (Gly)3Lys(Gly)4;

(SEQ ID NO: 156)
    (Gly)3AsnGlySer(Gly)2;

(SEQ ID NO: 157)
    (Gly)3Cys(Gly)4;
    and (SEQ ID NO: 158)
    GlyProAsnGlyGly.
```

To explain the above nomenclature, for example, (Gly)$_3$Lys(Gly)$_4$ means Gly-Gly-Gly-Lys-Gly-Gly-Gly-Gly (SEQ ID NO:159). Other combinations of Gly and Ala are also useful.

Commonly used linkers include those which may be identified herein as "L5" (GGGGS; or "G$_4$S"; SEQ ID NO:152), "L10" (GGGGSGGGGS; SEQ ID NO:153), "L25" (GGGGSGGGGSGGGGSGGGGSGGGGS; SEQ ID NO:146) and any linkers used in the working examples hereinafter.

In some embodiments of the compositions of this invention, which comprise a peptide linker moiety, acidic residues, for example, glutamate or aspartate residues, are placed in the amino acid sequence of the linker moiety. Examples include the following peptide linker sequences:

```
                                           (SEQ ID NO: 160)
    GGEGGG;

(SEQ ID NO: 161)
    GGEEEGGG;

(SEQ ID NO: 162)
    GEEEG;

(SEQ ID NO: 163)
    GEEE;

(SEQ ID NO: 164)
    GGDGGG;

(SEQ ID NO: 165)
    GGDDDGG;

(SEQ ID NO: 166)
    GDDDG;

(SEQ ID NO: 167)
    GDDD;

(SEQ ID NO: 168)
    GGGGSDDSDEGSDGEDGGGGS;

(SEQ ID NO: 169)
    WEWEW;
```

FEFEF; (SEQ ID NO: 170)

EEEWWW; (SEQ ID NO: 171)

EEEFFF; (SEQ ID NO: 172)

WWEEEWW; (SEQ ID NO: 173)
or

FFEEEFF. (SEQ ID NO: 174)

In other embodiments, the linker constitutes a phosphorylation site, e.g., $X_1X_2YX_4X_5G$ (SEQ ID NO:175), wherein $X_1$, $X_2$, $X_4$, and $X_5$ are each independently any amino acid residue; $X_1X_2SX_4X_5G$ (SEQ ID NO:176), wherein $X_1$, $X_2$, $X_4$ and $X_5$ are each independently any amino acid residue; or $X_1X_2TX_4X_5G$ (SEQ ID NO:177), wherein $X_1$, $X_2$, $X_4$ and $X_5$ are each independently any amino acid residue.

The linkers shown here are exemplary; peptidyl linkers within the scope of this invention may be much longer and may include other residues. A peptidyl linker can contain, e.g., a cysteine, another thiol, or nucleophile for conjugation with a half-life extending moiety. In another embodiment, the linker contains a cysteine or homocysteine residue, or other 2-amino-ethanethiol or 3-amino-propanethiol moiety for conjugation to maleimide, iodoacetaamide or thioester, functionalized half-life extending moiety.

Another useful peptidyl linker is a large, flexible linker comprising a random Gly/Ser/Thr sequence, for example: GSGSATGGSGSTASSGSGSATH (SEQ ID NO:178) or HGSGSATGGSGSTASSGSGSAT (SEQ ID NO:179), that is estimated to be about the size of a 1 kDa PEG molecule. Alternatively, a useful peptidyl linker may be comprised of amino acid sequences known in the art to form rigid helical structures (e.g., Rigid linker: -AEAAAKEAAAKEAAAK-AGG-) (SEQ ID NO:180). Additionally, a peptidyl linker can also comprise a non-peptidyl segment such as a 6 carbon aliphatic molecule of the formula —$CH_2$—$CH_2$—$CH_2$—$CH_2$—$CH_2$—$CH_2$—. The peptidyl linkers can be altered to form derivatives as described herein.

Optionally, a non-peptidyl linker moiety is also useful for conjugating the half-life extending moiety to the peptide portion of the half-life extending moiety-conjugated toxin peptide analog. For example, alkyl linkers such as —NH—$(CH_2)_s$—C(O)—, wherein s=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. Exemplary non-peptidyl linkers are polyethylene glycol (PEG) linkers (e.g., shown below):

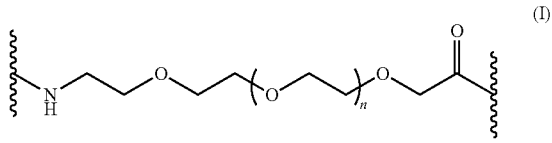

(I)

wherein n is such that the linker has a molecular weight of about 100 to about 5000 Daltons (Da), preferably about 100 to about 500 Da.

In one embodiment, the non-peptidyl linker is aryl. The linkers may be altered to form derivatives in the same manner as described in the art, e.g., in Sullivan et al., Toxin Peptide Therapeutic Agents, US2007/0071764; Sullivan et al., Toxin Peptide Therapeutic Agents, PCT/US2007/022831, published as WO 2008/088422; and U.S. Provisional Application Ser. No. 61/210,594, filed Mar. 20, 2009, which are all incorporated herein by reference in their entireties.

In addition, PEG moieties may be attached to the N-terminal amine or selected side chain amines by either reductive alkylation using PEG aldehydes or acylation using hydroxysuccinimido or carbonate esters of PEG, or by thiol conjugation.

"Aryl" is phenyl or phenyl vicinally-fused with a saturated, partially-saturated, or unsaturated 3-, 4-, or 5 membered carbon bridge, the phenyl or bridge being substituted by 0, 1, 2 or 3 substituents selected from $C_{1-8}$ alkyl, $C_{1-4}$ haloalkyl or halo.

"Heteroaryl" is an unsaturated 5, 6 or 7 membered monocyclic or partially-saturated or unsaturated 6-, 7-, 8-, 9-, 10- or 11 membered bicyclic ring, wherein at least one ring is unsaturated, the monocyclic and the bicyclic rings containing 1, 2, 3 or 4 atoms selected from N, O and S, wherein the ring is substituted by 0, 1, 2 or 3 substituents selected from $C_{1-8}$ alkyl, $C_{1-4}$ haloalkyl and halo.

Non-peptide portions of the inventive composition of matter, such as non-peptidyl linkers or non-peptide half-life extending moieties can be synthesized by conventional organic chemistry reactions.

The above is merely illustrative and not an exhaustive treatment of the kinds of linkers that can optionally be employed in accordance with the present invention.

Production of Antigen Binding Protein Variants.

As noted above, recombinant DNA- and/or RNA-mediated protein expression and protein engineering techniques, or any other methods of preparing peptides, are applicable to the making of the inventive compositions. For example, polypeptides can be made in transformed host cells. Briefly, a recombinant DNA molecule, or construct, coding for the peptide is prepared. Methods of preparing such DNA molecules are well known in the art. For instance, sequences encoding the peptides can be excised from DNA using suitable restriction enzymes. Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial host cells in culture include bacteria (such as *Escherichia coli* sp.), yeast (such as *Saccharomyces* sp.) and other fungal cells, insect cells, plant cells, mammalian (including human) cells, e.g., CHO cells and HEK-293 cells, and others noted herein or otherwise known in the art. Modifications can be made at the DNA level, as well. The peptide-encoding DNA sequence may be changed to codons more compatible with the chosen host cell. For *E. coli*, optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired compounds are expressed. Such fermentation conditions are well known in the art. In addition, the DNA optionally further encodes, 5' to the coding region of a fusion protein, a signal peptide sequence (e.g., a secretory signal peptide) operably linked to the expressed specific binding agent or antigen binding protein, e.g., an immunoglobulin protein. For further examples of appropriate recombinant methods and exemplary DNA constructs useful for recombinant expression of the inventive compositions by mammalian cells, including dimeric Fc fusion proteins ("peptibodies") or chimeric immunoglobulin (light chain+heavy chain)-Fc heterotrimers ("hemibodies"), conjugated to specific binding agents of the invention, see, e.g., Sullivan et al., Toxin Peptide Therapeutic Agents, US2007/0071764; Sullivan et al., Toxin Peptide Therapeutic Agents, PCT/US2007/022831, published as WO 2008/088422; and U.S. Provisional Application Ser. No. 61/210,594, filed Mar. 20, 2009, which are all incorporated herein by reference in their entireties.

Amino acid sequence variants of the desired antigen binding protein may be prepared by introducing appropriate nucleotide changes into the encoding DNA, or by peptide synthesis. Such variants include, for example, deletions and/or insertions and/or substitutions of residues within the amino acid sequences of the antigen binding proteins or antibodies. Any combination of deletion, insertion, and substitution is made to arrive at the final construct, provided that the final construct possesses the desired characteristics. The amino acid changes also may alter post-translational processes of the antigen binding protein, such as changing the number or position of glycosylation sites. In certain instances, antigen binding protein variants are prepared with the intent to modify those amino acid residues which are directly involved in epitope binding. In other embodiments, modification of residues which are not directly involved in epitope binding or residues not involved in epitope binding in any way, is desirable, for purposes discussed herein. Mutagenesis within any of the CDR regions and/or framework regions is contemplated. Covariance analysis techniques can be employed by the skilled artisan to design useful modifications in the amino acid sequence of the antigen binding protein, including an antibody or antibody fragment. (E.g., Choulier, et al., Covariance Analysis of Protein Families: The Case of the Variable Domains of Antibodies, Proteins: Structure, Function, and Genetics 41:475-484 (2000); Demarest et al., Optimization of the Antibody $C_H3$ Domain by Residue Frequency Analysis of IgG Sequences, J. Mol. Biol. 335:41-48 (2004); Hugo et al., VL position 34 is a key determinant for the engineering of stable antibodies with fast dissociation rates, Protein Engineering 16(5):381-86 (2003); Aurora et al., Sequence covariance networks, methods and uses thereof, US 2008/0318207 A1; Glaser et al., Stabilized polypeptide compositions, US 2009/0048122 A1; Urech et al., Sequence based engineering and optimization of single chain antibodies, WO 2008/110348 A1; Borras et al., Methods of modifying antibodies, and modified antibodies with improved functional properties, WO 2009/000099 A2). Such modifications determined by covariance analysis can improve potency, pharmacokinetic, pharmacodynamic, and/or manufacturability characteristics of an antigen binding protein.

Nucleic acid molecules encoding amino acid sequence variants of the antigen binding protein or antibody are prepared by a variety of methods known in the art. Such methods include oligonucleotide-mediated (or site-directed) mutagenesis, PCR mutagenesis, and cassette mutagenesis of an earlier prepared variant or a non-variant version of the antigen binding protein.

Substitutional mutagenesis within any of the hypervariable or CDR regions or framework regions is contemplated. A useful method for identification of certain residues or regions of the antigen binding protein that are preferred locations for mutagenesis is called "alanine scanning mutagenesis," as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed variants are screened for the desired activity.

Some embodiments of the antigen binding proteins of the present invention can also be made by synthetic methods. Solid phase synthesis is the preferred technique of making individual peptides since it is the most cost-effective method of making small peptides. For example, well known solid phase synthesis techniques include the use of protecting groups, linkers, and solid phase supports, as well as specific protection and deprotection reaction conditions, linker cleavage conditions, use of scavengers, and other aspects of solid phase peptide synthesis. Suitable techniques are well known in the art. (E.g., Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527; "Protecting Groups in Organic Synthesis," 3rd Edition, T. W. Greene and P. G. M. Wuts, Eds., John Wiley & Sons, Inc., 1999; NovaBiochem Catalog, 2000; "Synthetic Peptides, A User's Guide," G. A. Grant, Ed., W.H. Freeman & Company, New York, N.Y., 1992; "Advanced Chemtech Handbook of Combinatorial & Solid Phase Organic Chemistry," W. D. Bennet, J. W. Christensen, L. K. Hamaker, M. L. Peterson, M. R. Rhodes, and H. H. Saneii, Eds., Advanced Chemtech, 1998; "Principles of Peptide Synthesis, 2nd ed.," M. Bodanszky, Ed., Springer-Verlag, 1993; "The Practice of Peptide Synthesis, 2nd ed.," M. Bodanszky and A. Bodanszky, Eds., Springer-Verlag, 1994; "Protecting Groups," P. J. Kocienski, Ed., Georg Thieme Verlag, Stuttgart, Germany, 1994; "Fmoc Solid Phase Peptide Synthesis, A Practical Approach," W. C. Chan and P. D. White, Eds., Oxford Press, 2000, G. B. Fields et al., Synthetic Peptides: A User's Guide, 1990, 77-183). For further examples of synthetic and purification methods known in the art, which are applicable to making the inventive compositions of matter, see, e.g., Sullivan et al., Toxin Peptide Therapeutic Agents, US2007/0071764 and Sullivan et al., Toxin Peptide Therapeutic Agents, PCT/US2007/022831, published as WO 2008/088422 A2, which are both incorporated herein by reference in their entireties.

In further describing any of the antigen binding proteins herein, as well as variants, a one-letter abbreviation system is frequently applied to designate the identities of the twenty "canonical" amino acid residues generally incorporated into naturally occurring peptides and proteins (Table 4). Such one-letter abbreviations are entirely interchangeable in meaning with three-letter abbreviations, or non-abbreviated amino acid names. Within the one-letter abbreviation system used herein, an upper case letter indicates a L-amino acid, and a lower case letter indicates a D-amino acid. For example, the abbreviation "R" designates L-arginine and the abbreviation "r" designates D-arginine.

TABLE 4

One-letter abbreviations for the canonical amino acids.
Three-letter abbreviations are in parentheses.

| Amino Acid | Abbreviation |
|---|---|
| Alanine (Ala) | A |
| Glutamine (Gln) | Q |
| Leucine (Leu) | L |
| Serine (Ser) | S |
| Arginine (Arg) | R |
| Glutamic Acid (Glu) | E |
| Ly sine (Lys) | K |
| Threonine (Thr) | T |
| Asparagine (Asn) | N |
| Glycine (Gly) | G |
| Methionine (Met) | M |
| Tryptophan (Trp) | W |
| Aspartic Acid (Asp) | D |
| Histidine (His) | H |
| Phenylalanine (Phe) | F |
| Tyrosine (Tyr) | Y |
| Cysteine (Cys) | C |
| Isoleucine (Ile) | I |
| Proline (Pro) | P |
| Valine (Val) | V |

An amino acid substitution in an amino acid sequence is typically designated herein with a one-letter abbreviation for the amino acid residue in a particular position, followed by the numerical amino acid position relative to an original sequence of interest, which is then followed by the one-letter symbol for the amino acid residue substituted in. For example, "T30D" symbolizes a substitution of a threonine residue by an aspartate residue at amino acid position 30, relative to the original sequence of interest. Another example, "W101F" symbolizes a substitution of a tryptophan residue by a phenylalanine residue at amino acid position 101, relative to the original sequence of interest.

Non-canonical amino acid residues can be incorporated into a polypeptide within the scope of the invention by employing known techniques of protein engineering that use recombinantly expressing cells. (See, e.g., Link et al., Non-canonical amino acids in protein engineering, Current Opinion in Biotechnology, 14(6):603-609 (2003)). The term "non-canonical amino acid residue" refers to amino acid residues in D- or L-form that are not among the 20 canonical amino acids generally incorporated into naturally occurring proteins, for example, β-amino acids, homoamino acids, cyclic amino acids and amino acids with derivatized side chains. Examples include (in the L-form or D-form) β-alanine, β-aminopropionic acid, piperidinic acid, aminocaprioic acid, aminoheptanoic acid, aminopimelic acid, desmosine, diaminopimelic acid, $N^\alpha$-ethylglycine, $N^\alpha$-ethylaspargine, hydroxylysine, allo-hydroxylysine, isodesmosine, allo-isoleucine, ω-methylarginine, $N^\alpha$-methylglycine, $N^\alpha$-methylisoleucine, $N^\alpha$-methylvaline, γ-carboxyglutamate, ε-N,N,N-trimethylly sine, ε-N-acetyllysine, O-phosphoserine, $N^\alpha$-acetylserine, $N^\alpha$-formylmethionine, 3-methylhistidine, 5-hydroxylysine, and other similar amino acids, and those listed in Table 5 below, and derivatized forms of any of these as described herein. Table 5 contains some exemplary non-canonical amino acid residues that are useful in accordance with the present invention and associated abbreviations as typically used herein, although the skilled practitioner will understand that different abbreviations and nomenclatures may be applicable to the same substance and appear interchangeably herein.

TABLE 5

Useful non-canonical amino acids for amino acid addition, insertion, or substitution into peptide sequences in accordance with the present invention. In the event an abbreviation listed in Table 5 differs from another abbreviation for the same substance disclosed elsewhere herein, both abbreviations are understood to be applicable. The amino acids listed in Table 5 can be in the L-form or D-form.

| Amino Acid | Abbreviation(s) |
|---|---|
| Acetamidomethyl | Acm |
| Acetylarginine | acetylarg |
| α-aminoadipic acid | Aad |
| aminobutyric acid | Abu |
| 6-aminohexanoic acid | Ahx; εAhx |
| 3-amino-6-hydroxy-2-piperidone | Ahp |
| 2-aminoindane-2-carboxylic acid | Aic |
| α-amino-isobutyric acid | Aib |
| 3-amino-2-naphthoic acid | Anc |
| 2-aminotetraline-2-carboxylic acid | Atc |
| Aminophenylalanine | Aminophe; Amino-Phe |
| 4-amino-phenylalanine | 4AmP |
| 4-amidino-phenylalanine | 4AmPhe |
| 2-amino-2-(1-carbamimidoylpiperidin-4-yl)acetic acid | 4AmPig |
| Arg ψ($CH_2NH$)-reduced amide bond | rArg |
| β-homoarginine | bhArg |
| β-homolysine | bhomoK |
| β-homo Tic | BhTic |
| β-homophenylalanine | BhPhe |
| β-homoproline | BhPro |
| β-homotryptophan | BhTrp |
| 4,4'-biphenylalanine | Bip |
| β, β-diphenyl-alanine | BiPhA |
| β-phenylalanine | BPhe |
| p-carboxyl-phenylalanine | Cpa |
| Citrulline | Cit |
| Cyclohexylalanine | Cha |
| Cyclohexylglycine | Chg |
| Cyclopentylglycine | Cpg |
| 2-amino-3-guanidinopropanoic acid | 3G-Dpr |
| α, γ-diaminobutyric acid | Dab |
| 2,4-diaminobutyric acid | Dbu |
| diaminopropionic acid | Dap |
| α, β-diaminopropionoic acid (or 2,3-diaminopropionic acid | Dpr |
| 3,3-diphenylalanine | Dip |
| 4-guanidino phenylalanine | Guf |
| 4-guanidino proline | 4GuaPr |
| Homoarginine | hArg; hR |
| Homocitrulline | hCit |
| Homoglutamine | hQ |
| Homolysine | hLys; hK; homoLys |
| Homophenylalanine | hPhe; homoPhe |
| 4-hydroxyproline (or hydroxyproline) | Hyp |
| 2-indanylglycine (or indanylglycine) | IgI |
| indoline-2-carboxylic acid | Idc |
| Iodotyrosine | I-Tyr |
| Lys ψ($CH_2NH$)-reduced amide bond | rLys |
| methinine oxide | Met[O] |
| methionine sulfone | Met[O]$_2$ |
| $N^\alpha$-methylarginine | NMeR |
| Nα-[$(CH_2)_3$NHCH(NH)$NH_2$] substituted glycine | N-Arg |
| $N^\alpha$-methylcitrulline | NMeCit |
| $N^\alpha$-methylglutamine | NMeQ |
| $N^\alpha$-methylhomocitrulline | $N^\alpha$-MeHoCit |
| $N^\alpha$-methylhomolysine | NMeHoK |
| $N^\alpha$-methylleucine | $N^\alpha$-MeL; NMeL; NMeLeu; NMe-Leu |
| $N^\alpha$-methyllysine | NMe-Lys |
| Nε-methyl-lysine | N-eMe-K |

TABLE 5-continued

Useful non-canonical amino acids for amino acid addition, insertion, or substitution into peptide sequences in accordance with the present invention. In the event an abbreviation listed in Table 5 differs from another abbreviation for the same substance disclosed elsewhere herein, both abbreviations are understood to be applicable. The amino acids listed in Table 5 can be in the L-form or D-form.

| Amino Acid | Abbreviation(s) |
|---|---|
| Nε-ethyl-lysine | N-eEt-K |
| Nε-isopropyl-lysine | N-eIPr-K |
| $N^\alpha$-methylnorleucine | NMeNle; NMe-Nle |
| $N^\alpha$-methylornithine | $N^\alpha$-MeOrn; NMeOrn |
| $N^\alpha$-methylphenylalanine | NMe-Phe |
| 4-methyl-phenylalanine | MePhe |
| α-methylphenylalanine | AMeF |
| $N^\alpha$-methylthreonine | NMe-Thr; NMeThr |
| $N^\alpha$-methylvaline | NMeVal; NMe-Val |
| Nε-(O-(aminoethyl)-O'-(2-propanoyl)-undecaethyleneglycol)-Lysine | K(NPeg11) |
| Nε-(O-(aminoethyl)-O'-(2-propanoyl)-(ethyleneglycol)27-Lysine | K(NPeg27) |
| 3-(1-naphthyl)alanine | 1-Nal; 1Nal |
| 3-(2-naphthyl)alanine | 2-Nal; 2Nal |
| nipecotic acid | Nip |
| Nitrophenylalanine | nitrophe |
| norleucine | Nle |
| norvaline | Nva or Nvl |
| O-methyltyrosine | Ome-Tyr |
| octahydroindole-2-carboxylic acid | Oic |
| Ornithine | Orn |
| Orn ψ(CH2NH)-reduced amide bond | rOrn |
| 4-piperidinylalanine | 4PipA |
| 4-pyridinylalanine | 4Pal |
| 3-pyridinylalanine | 3Pal |
| 2-pyridinylalanine | 2Pal |
| para-aminophenylalanine | 4AmP; 4-Amino-Phe |
| para-iodophenylalanine (or 4-iodophenylalanine) | pI-Phe |
| Phenylglycine | Phg |
| 4-phenyl-phenylalanine (or biphenylalanine) | 4Bip |
| 4,4-biphenyl alanine | Bip |
| pipecolic acid | Pip |
| 4-amino-1-piperidine-4-carboxylic acid | 4Pip |
| Sarcosine | Sar |
| 1,2,3,4-tetrahydroisoquinoline | Tic |
| 1,2,3,4-tetrahydroisoquinoline-1-carboxylic acid | Tiq |
| 1,2,3,4-tetrahydroisoquinoline-7-hydroxy-3-carboxylic acid | Hydroxyl-Tic |
| 1,2,3,4-tetrahydronorharman-3-carboxylic acid | Tpi |
| thiazolidine-4-carboxylic acid | Thz |
| 3-thienylalanine | Thi |

Nomenclature and Symbolism for Amino Acids and Peptides by the UPAC-IUB Joint Commission on Biochemical Nomenclature (JCBN) have been published in the following documents: Biochem. J., 1984, 219, 345-373; Eur. J. Biochem., 1984, 138, 9-37; 1985, 152, 1; 1993, 213, 2; Internat. J. Pept. Prot. Res., 1984, 24, following p 84; J. Biol. Chem., 1985, 260, 14-42; Pure Appl. Chem., 1984, 56, 595-624; Amino Acids and Peptides, 1985, 16, 387-410; Biochemical Nomenclature and Related Documents, 2nd edition, Portland Press, 1992, pages 39-69.

The one or more useful modifications to peptide domains of the inventive antigen binding protein can include amino acid additions or insertions, amino acid deletions, peptide truncations, amino acid substitutions, and/or chemical derivatization of amino acid residues, accomplished by known chemical techniques. For example, the thusly modified amino acid sequence includes at least one amino acid residue inserted or substituted therein, relative to the amino acid sequence of the native sequence of interest, in which the inserted or substituted amino acid residue has a side chain comprising a nucleophilic or electrophilic reactive functional group by which the peptide is conjugated to a linker and/or half-life extending moiety. In accordance with the invention, useful examples of such a nucleophilic or electrophilic reactive functional group include, but are not limited to, a thiol, a primary amine, a seleno, a hydrazide, an aldehyde, a carboxylic acid, a ketone, an aminooxy, a masked (protected) aldehyde, or a masked (protected) keto functional group. Examples of amino acid residues having a side chain comprising a nucleophilic reactive functional group include, but are not limited to, a lysine residue, a homolysine, an α,β-diaminopropionic acid residue, an α,γ-diaminobutyric acid residue, an ornithine residue, a cysteine, a homocysteine, a glutamic acid residue, an aspartic acid residue, or a selenocysteine residue.

Amino acid residues are commonly categorized according to different chemical and/or physical characteristics. The term "acidic amino acid residue" refers to amino acid residues in D- or L-form having side chains comprising acidic groups. Exemplary acidic residues include aspartatic acid and glutamatic acid residues. The term "alkyl amino acid residue" refers to amino acid residues in D- or L-form having $C_{1-6}$alkyl side chains which may be linear, branched, or cyclized, including to the amino acid amine as in proline, wherein the $C_{1-6}$alkyl is substituted by 0, 1, 2 or 3 substituents selected from $C_{1-4}$haloalkyl, halo, cyano, nitro, $-C(=O)R^b$, $-C(=O)OR^a$, $-C(=O)NR^aR^a$, $-C(=NR^a)NR^aR^a$, $-NR^aC(=NR^a)NR^aR^a$, $-OR^a$, $-OC(=O)R^b$, $-OC(=O)NR^aR^a$, $-OC_{2-6}$alkyl$NR^aR^a$, $-OC_{2-6}$alkyl$OR^a$, $-SR^a$, $-S(=O)R^b$, $-S(=O)_2R^b$, $-S(=O)_2NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}$ alkyl$NR^aR^a$ and $-NR^aC_{2-6}$alkyl$OR^a$; wherein $R^a$ is independently, at each instance, H or $R^b$; and $R^b$ is independently, at each instance $C_{1-6}$alkyl substituted by 0, 1, 2 or 3 substituents selected from halo, $C_{1-4}$alk, $C_{1-3}$haloalk, $-OC_{1-4}$alk, $-NH_2$, $-NHC_{1-4}$alk, and $-N(C_{1-4}$alk$)C_{1-4}$alk; or any protonated form thereof, including alanine, valine, leucine, isoleucine, proline, serine, threonine, lysine, arginine, histidine, aspartate, glutamate, asparagine, glutamine, cysteine, methionine, hydroxyproline, but which residues do not contain an aryl or aromatic group. The term "aromatic amino acid residue" refers to amino acid residues in D- or L-form having side chains comprising aromatic groups. Exemplary aromatic residues include tryptophan, tyrosine, 3-(1-naphthyl)alanine, or phenylalanine residues. The term "basic amino acid residue" refers to amino acid residues in D- or L-form having side chains comprising basic groups. Exemplary basic amino acid residues include histidine, lysine, homolysine, ornithine, arginine, N-methyl-arginine, ω-aminoarginine, ω-methyl-arginine, 1-methyl-histidine, 3-methyl-histidine, and homoarginine (hR) residues. The term "hydrophilic amino acid residue" refers to amino acid residues in D- or L-form having side chains comprising polar groups. Exemplary hydrophilic residues include cysteine, serine, threonine, histidine, lysine, asparagine, aspartate, glutamate, glutamine, and citrulline (Cit) residues. The terms "lipophilic amino acid residue" refers to amino acid residues in D- or L-form having sidechains comprising uncharged, aliphatic or aromatic groups. Exemplary lipophilic sidechains include phenylalanine, isoleucine, leucine, methionine, valine, tryptophan, and tyrosine. Alanine (A) is amphiphilic—it is capable of acting as a hydrophilic or lipophilic residue. Alanine, therefore, is included within the definition of both "lipophilic residue"

and "hydrophilic residue." The term "nonfunctional amino acid residue" refers to amino acid residues in D- or L-form having side chains that lack acidic, basic, or aromatic groups. Exemplary neutral amino acid residues include methionine, glycine, alanine, valine, isoleucine, leucine, and norleucine (Nle) residues.

Additional useful embodiments of can result from conservative modifications of the amino acid sequences of the polypeptides disclosed herein. Conservative modifications will produce half-life extending moiety-conjugated peptides having functional, physical, and chemical characteristics similar to those of the conjugated (e.g., PEG-conjugated) peptide from which such modifications are made. Such conservatively modified forms of the conjugated polypeptides disclosed herein are also contemplated as being an embodiment of the present invention.

In contrast, substantial modifications in the functional and/or chemical characteristics of peptides may be accomplished by selecting substitutions in the amino acid sequence that differ significantly in their effect on maintaining (a) the structure of the molecular backbone in the region of the substitution, for example, as an α-helical conformation, (b) the charge or hydrophobicity of the molecule at the target site, or (c) the size of the molecule.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., Acta Physiol. Scand. Suppl., 643:55-67 (1998); Sasaki et al., 1998, Adv. Biophys. 35:1-24 (1998), which discuss alanine scanning mutagenesis).

Desired amino acid substitutions (whether conservative or non-conservative) can be determined by those skilled in the art at the time such substitutions are desired. For example, amino acid substitutions can be used to identify important residues of the peptide sequence, or to increase or decrease the affinity of the peptide or vehicle-conjugated peptide molecules described herein.

Naturally occurring residues may be divided into classes based on common side chain properties:

1) hydrophobic: norleucine (Nor or Nle), Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced into regions of the toxin peptide analog.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. One may also identify epitopes from primary amino acid sequences on the basis of hydrophilicity. These regions are also referred to as "epitopic core regions."

Examples of conservative substitutions include the substitution of one non-polar (hydrophobic) amino acid residue such as isoleucine, valine, leucine norleucine, alanine, or methionine for another, the substitution of one polar (hydrophilic) amino acid residue for another such as between arginine and lysine, between glutamine and asparagine, between glycine and serine, the substitution of one basic amino acid residue such as lysine, arginine or histidine for another, or the substitution of one acidic residue, such as aspartic acid or glutamic acid for another. The phrase "conservative amino acid substitution" also includes the use of a chemically derivatized residue in place of a non-derivatized residue, provided that such polypeptide displays the requisite bioactivity. Other exemplary amino acid substitutions that can be useful in accordance with the present invention are set forth in Table 6 below.

TABLE 6

Some Useful Amino Acid Substitutions.

| Original Residues | Exemplary Substitutions |
|---|---|
| Ala | Val, Leu, Ile |
| Arg | Lys, Gln, Asn |

TABLE 6-continued

Some Useful Amino Acid Substitutions.

| Original Residues | Exemplary Substitutions |
|---|---|
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, 1,4-Diamino-butyric Acid, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

Ordinarily, amino acid sequence variants of the antigen binding protein will have an amino acid sequence having at least 60% amino acid sequence identity with the original antigen binding protein or antibody amino acid sequences of either the heavy or the light chain variable region, or at least 65%, or at least 70%, or at least 75% or at least 80% identity, more preferably at least 85% identity, even more preferably at least 90% identity, and most preferably at least 95% identity, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to this sequence is defined herein as the percentage of amino acid residues in the candidate sequence that are identical with the original sequence, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antigen binding protein or antibody sequence shall be construed as affecting sequence identity or homology.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antigen binding protein with an N-terminal methionyl residue or the antigen binding protein (including antibody or antibody fragment) fused to an epitope tag or a salvage receptor binding epitope. Other insertional variants of the antigen binding protein or antibody molecule include the fusion to a polypeptide which increases the serum half-life of the antigen binding protein, e.g. at the N-terminus or C-terminus.

Examples of epitope tags include the flu HA tag polypeptide and its antibody 12CA5 [Field et al., Mol. Cell. Biol. 8: 2159-2165 (1988)]; the c-myc tag and the 8F9, 3C7, 6E10, G4, B7 and 9E10 antibodies thereto [Evan et al., Mol. Cell. Biol. 5(12): 3610-3616 (1985)]; and the Herpes Simplex virus glycoprotein D (gD) tag and its antibody [Paborsky et al., Protein Engineering 3(6): 547-553 (1990)]. Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.) are well known and routinely used in the art.

Some particular, non-limiting, embodiments of amino acid substitution variants of the inventive antigen binding proteins, including antibodies and antibody fragments are exemplified below.

Any cysteine residue not involved in maintaining the proper conformation of the antigen binding protein also may be substituted, generally with serine, to improve the oxidative stability of the molecule and prevent aberrant crosslinking. Conversely, cysteine bond(s) may be added to the antigen binding protein to improve its stability (particularly where the antigen binding protein is an antibody fragment such as an Fv fragment).

In certain instances, antigen binding protein variants are prepared with the intent to modify those amino acid residues which are directly involved in epitope binding. In other embodiments, modification of residues which are not directly involved in epitope binding or residues not involved in epitope binding in any way, is desirable, for purposes discussed herein. Mutagenesis within any of the CDR regions and/or framework regions is contemplated.

In order to determine which antigen binding protein amino acid residues are important for epitope recognition and binding, alanine scanning mutagenesis can be performed to produce substitution variants. See, for example, Cunningham et al., Science, 244:1081-1085 (1989), the disclosure of which is incorporated herein by reference in its entirety. In this method, individual amino acid residues are replaced one-at-a-time with an alanine residue and the resulting anti-DNP or anti-KLH antigen binding protein is screened for its ability to bind its specific epitope relative to the unmodified polypeptide. Modified antigen binding proteins with reduced binding capacity are sequenced to determine which residue was changed, indicating its significance in binding or biological properties.

Substitution variants of antigen binding proteins can be prepared by affinity maturation wherein random amino acid changes are introduced into the parent polypeptide sequence. See, for example, Ouwehand et al., Vox Sang 74 (Suppl 2):223-232, 1998; Rader et al., Proc. Natl. Acad. Sci. USA 95:8910-8915, 1998; Dall'Acqua et al., Curr. Opin. Struct. Biol. 8:443-450, 1998, the disclosures of which are incorporated herein by reference in their entireties. Affinity maturation involves preparing and screening the anti-DNP or anti-KLH antigen binding proteins, or variants thereof and selecting from the resulting variants those that have modified biological properties, such as increased binding affinity relative to the parent anti-DNP or anti-KLH antigen binding protein. A convenient way for generating substitutional variants is affinity maturation using phage display. Briefly, several hypervariable region sites are mutated to generate all possible amino substitutions at each site. The variants thus generated are expressed in a monovalent fashion on the surface of filamentous phage particles as fusions to the gene III product of M13 packaged within each particle. The phage-displayed variants are then screened for their biological activity (e.g., binding affinity). See e.g., WO 92/01047, WO 93/112366, WO 95/15388 and WO 93/19172.

Current antibody affinity maturation methods belong to two mutagenesis categories: stochastic and nonstochastic. Error prone PCR, mutator bacterial strains (Low et al., J.

*Mol. Biol.* 260, 359-68, 1996), and saturation mutagenesis (Nishimiya et al., *J. Biol. Chem.* 275:12813-20, 2000; Chowdhury, P. S. *Methods Mol. Biol.* 178, 269-85, 2002) are typical examples of stochastic mutagenesis methods (Rajpal et al., *Proc Natl Acad Sci USA*. 102:8466-71, 2005). Non-stochastic techniques often use alanine-scanning or site-directed mutagenesis to generate limited collections of specific muteins. Some methods are described in further detail below.

Affinity Maturation Via Panning Methods—

Affinity maturation of recombinant antibodies is commonly performed through several rounds of panning of candidate antibodies in the presence of decreasing amounts of antigen. Decreasing the amount of antigen per round selects the antibodies with the highest affinity to the antigen thereby yielding antibodies of high affinity from a large pool of starting material. Affinity maturation via panning is well known in the art and is described, for example, in Huls et al. (*Cancer Immunol Immunother.* 50:163-71, 2001). Methods of affinity maturation using phage display technologies are described elsewhere herein and known in the art (see e.g., Daugherty et al., *Proc Natl Acad Sci USA*. 97:2029-34, 2000).

Look-through mutagenesis—Look-through mutagenesis (LTM) (Rajpal et al., Proc Natl Acad Sci USA. 102:8466-71, 2005) provides a method for rapidly mapping the antibody-binding site. For LTM, nine amino acids, representative of the major side-chain chemistries provided by the 20 natural amino acids, are selected to dissect the functional side-chain contributions to binding at every position in all six CDRs of an antibody. LTM generates a positional series of single mutations within a CDR where each "wild type" residue is systematically substituted by one of nine selected amino acids. Mutated CDRs are combined to generate combinatorial single-chain variable fragment (scFv) libraries of increasing complexity and size without becoming prohibitive to the quantitative display of all muteins. After positive selection, clones with improved binding are sequenced, and beneficial mutations are mapped.

Error-prone PCR—Error-prone PCR involves the randomization of nucleic acids between different selection rounds. The randomization occurs at a low rate by the intrinsic error rate of the polymerase used but can be enhanced by error-prone PCR (Zaccolo et al., J. Mol. Biol. 285:775-783, 1999) using a polymerase having a high intrinsic error rate during transcription (Hawkins et al., J Mol Biol. 226:889-96, 1992). After the mutation cycles, clones with improved affinity for the antigen are selected using routine methods in the art.

Techniques utilizing gene shuffling and directed evolution may also be used to prepare and screen anti-DNP or anti-KLH antigen binding proteins, or variants thereof, for desired activity. For example, Jermutus et al., Proc Natl Acad Sci USA., 98(1):75-80 (2001) showed that tailored in vitro selection strategies based on ribosome display were combined with in vitro diversification by DNA shuffling to evolve either the off-rate or thermodynamic stability of scFvs; Fermer et al., Tumour Biol. 2004 January-April; 25(1-2):7-13 reported that use of phage display in combination with DNA shuffling raised affinity by almost three orders of magnitude. Dougherty et al., Proc Natl Acad Sci USA. 2000 Feb. 29; 97(5):2029-2034 reported that (i) functional clones occur at an unexpectedly high frequency in hypermutated libraries, (ii) gain-of-function mutants are well represented in such libraries, and (iii) the majority of the scFv mutations leading to higher affinity correspond to residues distant from the binding site.

Alternatively, or in addition, it may be beneficial to analyze a crystal structure of the antigen-antibody complex to identify contact points between the antibody and antigen, or to use computer software to model such contact points. Such contact residues and neighboring residues are candidates for substitution according to the techniques elaborated herein. Once such variants are generated, they are subjected to screening as described herein and antibodies with superior properties in one or more relevant assays may be selected for further development.

Antigen Binding Proteins with Modified Carbohydrate

Antigen binding protein variants can also be produced that have a modified glycosylation pattern relative to the parent polypeptide, for example, adding or deleting one or more of the carbohydrate moieties bound to the antigen binding protein, and/or adding or deleting one or more glycosylation sites in the antigen binding protein.

Glycosylation of polypeptides, including antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to a antigen binding protein by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to a antigen binding protein by inserting or substituting one or more serine or threonine residues to the sequence of the original antigen binding protein or antibody.

Altered Effector Function

Cysteine residue(s) may be removed or introduced in the Fc region of an antibody or Fc-containing polypeptide, thereby eliminating or increasing interchain disulfide bond formation in this region. A homodimeric antigen binding protein thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148: 2918-2922 (1992). Homodimeric antigen binding proteins or antibodies may also be prepared using heterobifunctional cross-linkers as described in Wolff et al., Cancer Research 53: 2560-2565 (1993). Alternatively, a antigen binding protein can be engineered which has dual Fc regions and may thereby have enhanced complement lysis and ADCC capabilities. See Stevenson et al., Anti-CancerDrug Design 3: 219-230 (1989).

It has been shown that sequences within the CDR can cause an antibody to bind to MHC Class II and trigger an unwanted helper T-cell response. A conservative substitution can allow the antigen binding protein to retain binding activity yet reduce its ability to trigger an unwanted T-cell response. It is also contemplated that one or more of the N-terminal 20 amino acids of the heavy or light chain are removed.

Modifications to increase serum half-life also may desirable, for example, by incorporation of or addition of a salvage receptor binding epitope (e.g., by mutation of the appropriate region or by incorporating the epitope into a peptide tag that is then fused to the antigen binding protein at either end or in the middle, e.g., by DNA or peptide synthesis) (see, e.g., WO96/32478) or adding molecules such as PEG or other water soluble polymers, including polysaccharide polymers.

The salvage receptor binding epitope preferably constitutes a region wherein any one or more amino acid residues from one or two loops of a Fc domain are transferred to an analogous position of the antigen binding protein or fragment. Even more preferably, three or more residues from one or two loops of the Fc domain are transferred. Still more preferred, the epitope is taken from the CH2 domain of the Fc region (e.g., of an IgG) and transferred to the CH1 CH3, or VH region, or more than one such region, of the antigen binding protein or antibody. Alternatively, the epitope is taken from the CH2 domain of the Fc region and transferred to the $C_L$ region or $V_L$ region, or both, of the antigen binding protein fragment. See also International applications WO 97/34631 and WO 96/32478 which describe Fc variants and their interaction with the salvage receptor.

Other sites and amino acid residue(s) of the constant region have been identified that are responsible for complement dependent cytotoxicity (CDC), such as the C1q binding site, and/or the antibody-dependent cellular cytotoxicity (ADCC) [see, e.g., Molec. Immunol. 29 (5): 633-9 (1992); Shields et al., J. Biol. Chem., 276(9):6591-6604 (2001); Lazar et al., Proc. Nat'l. Acad. Sci. 103(11): 4005 (2006) which describe the effect of mutations at specific positions, each of which is incorporated by reference herein in its entirety]. Mutation of residues within Fc receptor binding sites can result in altered (i.e. increased or decreased) effector function, such as altered affinity for Fc receptors, altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different subclass (e.g. replacing an IgG1 residue with a corresponding IgG2 residue at that position).

The invention also encompasses production of antigen binding protein molecules, including antibodies and antibody fragments, with altered carbohydrate structure resulting in altered effector activity, including antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., Biotechnol Bioeng. 2004 Sep. 5; 87(5):614-22). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., Mol Immunol. 1989 December; 26(12): 1113-23). Some host cell strains, e.g. Lec13 or rat hybridoma YB2/0 cell line naturally produce antibodies with lower fucosylation levels. Shields et al., J Biol Chem. 2002 Jul. 26; 277(30):26733-40; Shinkawa et al., J Biol Chem. 2003 Jan. 31; 278(5):3466-73. An increase in the level of bisected carbohydrate, e.g. through recombinantly producing antibody in cells that overexpress GnTIII enzyme, has also been determined to increase ADCC activity. Umana et al., Nat Biotechnol. 1999 February; 17(2):176-80. It has been predicted that the absence of only one of the two fucose residues may be sufficient to increase ADCC activity. (Ferrara et al., J Biol Chem. 2005 Dec. 5).

Other Covalent Modifications of Antigen Binding Proteins

Other particular covalent modifications of the anti-DNP or anti-KLH antigen binding protein, are also included within the scope of this invention. They may be made by chemical synthesis or by enzymatic or chemical cleavage of the antigen binding protein or antibody, if applicable. Other types of covalent modifications can be introduced by reacting targeted amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, .alpha.-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R—N.dbd.C.dbd.N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antigen binding protein (e.g., antibody or antibody fragment). These procedures are advantageous in that they do not require production of the antigen binding protein in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Removal of any carbohydrate moieties present on the antigen binding protein may be accomplished chemically or enzymatically. Chemical deglycosylation requires exposure of the antigen binding protein to the compound trifluoromethanesulfonic acid, or an equivalent compound. This treatment results in the cleavage of most or all sugars except the linking sugar (N-acetylglucosamine or N-acetylgalactosamine), while leaving the antigen binding protein intact. Chemical deglycosylation is described by Hakimuddin, et al. Arch. Biochem. Biophys. 259: 52 (1987) and by Edge et al. Anal. Biochem., 118: 131 (1981). Enzymatic cleavage of carbohydrate moieties on a antigen binding protein can be achieved by the use of a variety of endo- and exo-glycosidases as described by Thotakura et al. Meth. Enzymol. 138: 350 (1987).

Another type of covalent modification of the antigen binding proteins of the invention (including antibodies and antibody fragments) comprises linking the antigen binding protein to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art, see, e.g. U.S. Pat. Nos. 4,640,835; 4,496,689; 4,301,144; 4,670,417; 4,791,192, 4,179,337, 4,766,106, 4,179,337, 4,495,285, 4,609,546 or EP 315 456.

Isolated Nucleic Acids

Another aspect of the present invention is an isolated nucleic acid that encodes an antigen binding protein of the invention, such as, but not limited to, an isolated nucleic acid that encodes an antibody or antibody fragment of the invention. Such nucleic acids are made by recombinant techniques known in the art and/or disclosed herein.

For example, the isolated nucleic acid encodes an antigen binding protein comprising an immunoglobulin heavy chain variable region comprising an amino acid sequence at least 95% identical to SEQ ID NO:250, SEQ ID NO:252, SEQ ID NO:254, SEQ ID NO:256, SEQ ID NO:258, or SEQ ID NO:260.

In other embodiments, the isolated nucleic acid encodes an antigen binding protein comprising an immunoglobulin light chain variable region comprising an amino acid sequence at least 95% identical to SEQ ID NO:232, SEQ ID NO:234, SEQ ID NO:236, SEQ ID NO:238, or SEQ ID NO:240.

Other examples of the isolated nucleic acid include such that encodes an immunoglobulin heavy chain variable region, wherein the isolated nucleic acid comprises coding sequences for three complementarity determining regions, designated CDRH1, CDRH2 and CDRH3, and wherein:

(a) CDRH1 comprises the amino acid sequence of SEQ ID NO:188, SEQ ID NO:189, SEQ ID NO:190, or SEQ ID NO:191;

(b) CDRH2 comprises the amino acid sequence of SEQ ID NO:192, SEQ ID NO:193, SEQ ID NO:194, or SEQ ID NO:195; and (c) CDRH3 comprises the amino acid sequence of SEQ ID NO:196, SEQ ID NO:197, SEQ ID NO:198, SEQ ID NO:199, SEQ ID NO:200, or SEQ ID NO:201.

Still other examples of the isolated nucleic acid include such that encodes an immunoglobulin light chain variable region, wherein the isolated nucleic acid comprises coding sequences for three complementarity determining regions, designated CDRL1, CDRL2 and CDRL3, and wherein:

(a) CDRL1 comprises the amino acid sequence of SEQ ID NO:202, SEQ ID NO:203, SEQ ID NO:204, or SEQ ID NO:205;

(b) CDRL2 comprises the amino acid sequence of SEQ ID NO:206 or SEQ ID NO:207; and (c) CDRL3 comprises the amino acid sequence of SEQ ID NO:208, SEQ ID NO:209, SEQ ID NO:210, SEQ ID NO:211, or SEQ ID NO:212.

In other embodiments the isolated nucleic acid encodes an antigen binding protein comprising an immunoglobulin heavy chain comprising the amino acid sequence of SEQ ID NO:77, SEQ ID NO:107, SEQ ID NO:111, SEQ ID NO:113, SEQ ID NO:115, SEQ ID NO:117, SEQ ID NO:119, SEQ ID NO:123, SEQ ID NO:129, SEQ ID NO:144, SEQ ID NO:145, SEQ ID NO:181, SEQ ID NO:182, SEQ ID NO:183, SEQ ID NO:184, or SEQ ID NO:185, or comprising any one of the foregoing sequences from which one, two, three, four or five amino acid residues are lacking from the N-terminal or C-terminal, or both.

And in some embodiments the isolated nucleic acid encodes an antigen binding protein comprising an immunoglobulin light chain comprising the amino acid sequence of SEQ ID NO:105, SEQ ID NO:109, SEQ ID NO:121; SEQ ID NO:125, or SEQ ID NO:127, or comprising any one of the foregoing sequences from which one, two, three, four or five amino acid residues are lacking from the N-terminal or C-terminal, or both.

For another example, the isolated nucleic acid encodes an antigen binding protein comprising an immunoglobulin heavy chain variable region comprising an amino acid sequence at least 95% identical to the sequence of SEQ ID NO:262, SEQ ID NO:264, or SEQ ID NO:266.

In other embodiments, the isolated nucleic acid encodes an antigen binding protein comprising an immunoglobulin light chain variable region comprising an amino acid sequence at least 95% identical to SEQ ID NO:242, SEQ ID NO:244, SEQ ID NO:246, or SEQ ID NO:248.

Other examples of the isolated nucleic acid include such that encodes an immunoglobulin heavy chain variable region, wherein the isolated nucleic acid comprises coding sequences for three complementarity determining regions, designated CDRH1, CDRH2 and CDRH3, and wherein:

(a) CDRH1 comprises the amino acid sequence of SEQ ID NO:213, SEQ ID NO:214, or SEQ ID NO:215;

(b) CDRH2 comprises the amino acid sequence of SEQ ID NO:216, SEQ ID NO:217, or SEQ ID NO:218; and (c) CDRH3 comprises the amino acid sequence of SEQ ID NO:219, SEQ ID NO:220, or SEQ ID NO:221.

Still other examples of the isolated nucleic acid include such that encodes an immunoglobulin light chain variable region, wherein the isolated nucleic acid comprises coding sequences for three complementarity determining regions, designated CDRL1, CDRL2 and CDRL3, and wherein:

(a) CDRL1 comprises the amino acid sequence of SEQ ID NO:204, SEQ ID NO:222, SEQ ID NO:223, or SEQ ID NO:224;

(b) CDRL2 comprises the amino acid sequence of SEQ ID NO:206, SEQ ID NO:225, or SEQ ID NO:226; and (c) CDRL3 comprises the amino acid sequence of SEQ ID NO:227, SEQ ID NO:228, SEQ ID NO:229, or SEQ ID NO:230.

In other embodiments the isolated nucleic acid encodes an antigen binding protein comprising an immunoglobulin heavy chain comprising the amino acid sequence of SEQ ID NO:46, SEQ ID NO:133, SEQ ID NO:139, SEQ ID NO:143, SEQ ID NO:186, or comprising any one of the foregoing sequences from which one, two, three, four or five amino acid residues are lacking from the N-terminal or C-terminal, or both.

And in some embodiments the isolated nucleic acid encodes an antigen binding protein comprising an immunoglobulin light chain comprising the amino acid sequence of SEQ ID NO:28, SEQ ID NO:131, SEQ ID NO:135, SEQ ID NO:137; or SEQ ID NO:141, or comprising any one of the foregoing sequences from which one, two, three, four or five amino acid residues are lacking from the N-terminal or C-terminal, or both.

The present invention is also directed to vectors, including expression vectors, that comprise any of the inventive isolated nucleic acids. An isolated host cell that comprises the expression vector is also encompassed by the present invention, which is made by molecular biological techniques known in the art and/or disclosed herein. The invention is also directed to a method involving:

(a) culturing the host cell in a culture medium under conditions permitting expression of the antigen binding protein encoded by the expression vector; and (b) recovering the antigen binding protein from the culture medium.

Recovering the antigen binding protein is accomplished by known methods of antibody purification, such as but not limited to, antibody purification techniques disclosed in Example 1 and elsewhere herein.

Gene Therapy

Delivery of a therapeutic antigen binding protein to appropriate cells can be effected via gene therapy ex vivo, in situ, or in vivo by use of any suitable approach known in the art. For example, for in vivo therapy, a nucleic acid encoding the desired antigen binding protein or antibody, either alone or in conjunction with a vector, liposome, or precipitate may be injected directly into the subject, and in some embodiments, may be injected at the site where the expression of the antigen binding protein compound is desired. For ex vivo treatment, the subject's cells are removed, the nucleic acid is introduced into these cells, and the modified cells are returned to the subject either directly or, for example, encapsulated within porous membranes which are implanted into the patient. See, e.g. U.S. Pat. Nos. 4,892,538 and 5,283,187.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, chemical treatments, DEAE-dextran, and calcium phosphate precipitation. Other in vivo nucleic acid transfer techniques include transfection with viral vectors (such as adenovirus, Herpes simplex I virus, adeno-associated virus or retrovirus) and lipid-based systems. The nucleic acid and transfection agent are optionally associated with a microparticle. Exemplary transfection agents include calcium phosphate or calcium chloride co-precipitation, DEAE-dextran-mediated transfection, quaternary ammonium amphiphile DOTMA ((dioleoyloxypropyl) trimethylammonium bromide, commercialized as Lipofectin by GIBCO-BRL)) (Felgner et al, (1987) Proc. Natl. Acad. Sci. USA 84, 7413-7417; Malone et al. (1989) Proc. Natl Acad. Sci. USA 86 6077-6081); lipophilic glutamate diesters with pendent trimethylammonium heads (Ito et al. (1990) Biochem. Biophys. Acta 1023, 124-132); the metabolizable parent lipids such as the cationic lipid dioctadecylamido glycylspermine (DOGS, Transfectam, Promega) and dipalmitoylphosphatidyl ethanolamylspermine (DPPES) (J. P. Behr (1986) Tetrahedron Lett. 27, 5861-5864; J. P. Behr et al. (1989) Proc. Natl. Acad. Sci. USA 86, 6982-6986); metabolizable quaternary ammonium salts (DOTB, N-(1-[2,3-dioleoyloxy]propyl)-N,N,N-trimethylammonium methylsulfate (DOTAP) (Boehringer Mannheim), polyethyleneimine (PEI), dioleoyl esters, ChoTB, ChoSC, DOSC) (Leventis et al. (1990) Biochim. Inter. 22, 235-241); 3beta[N—(N',N'-dimethylaminoethane)-carbamoyl] cholesterol (DC-Chol), dioleoylphosphatidyl ethanolamine (DOPE)/3beta[N—(N',N'-dimethylaminoethane)-carbamoyl]cholesterolDC-Chol in one to one mixtures (Gao et al., (1991) Biochim. Biophys. Acta 1065, 8-14), spermine, spermidine, lipopolyamines (Behr et al., Bioconjugate Chem, 1994, 5: 382-389), lipophilic polylysines (LPLL) (Zhou et al., (1991) Biochim. Biophys. Acta 939, 8-18), [[(1,1,3,3-tetramethylbutyl)cre-soxy]ethoxy]ethyl]dimethylbenzylammonium hydroxide (DEBDA hydroxide) with excess phosphatidylcholine/cholesterol (Ballas et al., (1988) Biochim. Biophys. Acta 939, 8-18), cetyltrimethylammonium bromide (CTAB)/DOPE mixtures (Pinnaduwage et al, (1989) Biochim. Biophys. Acta 985, 33-37), lipophilic diester of glutamic acid (TMAG) with DOPE, CTAB, DEBDA, didodecylammonium bromide (DDAB), and stearylamine in admixture with phosphatidylethanolamine (Rose et al., (1991) Biotechnique 10, 520-525), DDAB/DOPE (TransfectACE, GIBCO BRL), and oligogalactose bearing lipids. Exemplary transfection enhancer agents that increase the efficiency of transfer include, for example, DEAE-dextran, polybrene, lysosome-disruptive peptide (Ohmori N I et al, Biochem Biophys Res Commun Jun. 27, 1997; 235(3):726-9), chondroitan-based proteoglycans, sulfated proteoglycans, polyethylenimine, polylysine (Pollard H et al. J Biol Chem, 1998 273 (13):7507-11), integrin-binding peptide CYGGRGDTP (SEQ ID NO:235), linear dextran nonasaccharide, glycerol, cholesteryl groups tethered at the 3'-terminal internucleoside link of an oligonucleotide (Letsinger, R. L. 1989 Proc Natl Acad Sci USA 86: (17):6553-6), lysophosphatide, lysophosphatidylcholine, lysophosphatidylethanolamine, and 1-oleoyl lysophosphatidylcholine.

In some situations it may be desirable to deliver the nucleic acid with an agent that directs the nucleic acid-containing vector to target cells. Such "targeting" molecules include antigen binding proteins specific for a cell-surface membrane protein on the target cell, or a ligand for a receptor on the target cell. Where liposomes are employed, proteins which bind to a cell-surface membrane protein associated with endocytosis may be used for targeting and/or to facilitate uptake. Examples of such proteins include capsid proteins and fragments thereof tropic for a particular cell type, antigen binding proteins for proteins which undergo internalization in cycling, and proteins that target intracellular localization and enhance intracellular half-life. In other embodiments, receptor-mediated endocytosis can be used. Such methods are described, for example, in Wu et al., 1987 or Wagner et al., 1990. For review of the currently known gene marking and gene therapy protocols, see Anderson 1992. See also WO 93/25673 and the references cited therein. For additional reviews of gene therapy technology, see Friedmann, Science, 244: 1275-1281 (1989); Anderson, Nature, supplement to vol. 392, no 6679, pp. 25-30 (1998); Verma, Scientific American: 68-84 (1990); and Miller, Nature, 357: 455460 (1992).

Administration and Preparation of Pharmaceutical Formulations

The anti-DNP or anti-KLH antigen binding proteins or antibodies used in the practice of a method of the invention may be formulated into pharmaceutical compositions and medicaments comprising a carrier suitable for the desired delivery method. Suitable carriers include any material which, when combined with the anti-DNP or anti-KLH antigen binding protein or antibody, retains the high-affinity binding of DNP or KLH, respectively, and is nonreactive with the subject's immune systems. Examples include, but are not limited to, any of a number of standard pharmaceutical carriers such as sterile phosphate buffered saline solutions, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Exemplary antigen binding protein concentrations in the formulation may range from about 0.1 mg/ml to about 180 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the antigen binding protein may be prepared in a pH-buffered solution, for example, at pH ranging from about 4.5 to about 6.5, or from about 4.8 to about 5.5, or alternatively about 5.0. Examples of buffers that are suitable for a pH within this range include acetate (e.g. sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

A tonicity agent, which may also stabilize the antigen binding protein, may be included in the formulation. Exemplary tonicity agents include polyols, such as mannitol, sucrose or trehalose. Preferably the aqueous formulation is isotonic, although hypertonic or hypotonic solutions may be suitable. Exemplary concentrations of the polyol in the formulation may range from about 1% to about 15% w/v.

A surfactant may also be added to the antigen binding protein formulation to reduce aggregation of the formulated antigen binding protein and/or minimize the formation of particulates in the formulation and/or reduce adsorption. Exemplary surfactants include nonionic surfactants such as polysorbates (e.g. polysorbate 20, or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

In one embodiment, the formulation contains the above-identified agents (i.e. antigen binding protein, buffer, polyol and surfactant) and is essentially free of one or more preservatives, such as benzyl alcohol, phenol, m-cresol, chlorobutanol and benzethonium Cl. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antoxidants including ascorbic acid and methionine; chelating agents such as EDTA; metal complexes (e.g. Zn-protein complexes); biodegradable polymers such as polyesters; and/or salt-forming counterions such as sodium.

Therapeutic formulations of the antigen binding protein are prepared for storage by mixing the antigen binding protein having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In one embodiment, a suitable formulation of the claimed invention contains an isotonic buffer such as a phosphate, acetate, or Tris buffer in combination with a tonicity agent such as a polyol, Sorbitol, sucrose or sodium chloride which tonicifies and stabilizes. One example of such a tonicity agent is 5% Sorbitol or sucrose. In addition, the formulation could optionally include a surfactant such as to prevent aggregation and for stabilization at 0.01 to 0.02% wt/vol. The pH of the formulation may range from 4.5-6.5 or 4.5 to 5.5. Other exemplary descriptions of pharmaceutical formulations for antibodies may be found in US 2003/0113316 and U.S. Pat. No. 6,171,586, each incorporated herein by reference in its entirety.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Suspensions and crystal forms of antigen binding proteins are also contemplated. Methods to make suspensions and crystal forms are known to one of skill in the art.

The formulations to be used for in vivo administration must be sterile. The compositions of the invention may be sterilized by conventional, well known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration.

The process of freeze-drying is often employed to stabilize polypeptides for long-term storage, particularly when the polypeptide is relatively unstable in liquid compositions. A lyophilization cycle is usually composed of three steps: freezing, primary drying, and secondary drying; Williams and Polli, Journal of Parenteral Science and Technology, Volume 38, Number 2, pages 48-59 (1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration; Chen, Drug Development and Industrial Pharmacy, Volume 18, Numbers 11 and 12, pages 1311-1354 (1992).

Excipients have been noted in some cases to act as stabilizers for freeze-dried products; Carpenter et al., Developments in Biological Standardization, Volume 74, pages 225-239 (1991). For example, known excipients include polyols (including mannitol, sorbitol and glycerol); sugars (including glucose and sucrose); and amino acids (including alanine, glycine and glutamic acid).

In addition, polyols and sugars are also often used to protect polypeptides from freezing and drying-induced damage and to enhance the stability during storage in the dried state. In general, sugars, in particular disaccharides, are effective in both the freeze-drying process and during storage. Other classes of molecules, including mono- and disaccharides and polymers such as PVP, have also been reported as stabilizers of lyophilized products.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antigen binding protein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention may be designed to be short-acting, fast-releasing, long-acting, or sustained-releasing as described herein. Thus, the pharmaceutical formulations may also be formulated for controlled release or for slow release.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The antigen binding protein is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. In addition, the antigen binding protein is suitably administered by pulse infusion, particularly with declining doses of the antigen binding protein or antibody. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. Most preferably, the antigen binding protein of the invention is administered intravenously in a physiological solution at a dose ranging between 0.01 mg/kg to 100 mg/kg at a frequency ranging from daily to weekly to monthly (e.g. every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of 2 or 3 times per week, or up to 45 mg/kg once a month.

The invention is illustrated by the following examples, which are not intended to be limiting in any way.

EXAMPLES

Example 1

Generation of Antibodies to DNP or KLH and Screening

Immunizations.

Anti-DNP antibodies were generated by immunizing XenoMouse® mice with DNP-KLH, over a period of 4 weeks, and by screening for those antibodies that bind to DNP-lysine. More particularly, XenoMouse® XMG2 strain of mice were generated generally as described previously (Mendez et al., *Nat. Genet.* 15:146-156 (1997); published International Patent Application Nos. WO 98/24893, and WO 00/76310, the disclosures of which are hereby incorporated by reference) and immunized with 2,4-Dinitrophenyl-Keyhole Limpet Hemocyanin (DNP-KLH conjugate; BioSearch Technologies, Novato, Calif.), using a range of 10-30 µg/mouse of immunogen emulsified in TiterMax Gold adjuvant (Sigma-Aldrich, Oakville, Ontario) for the initial immunization of the XMG2 strain of XenoMouse™ according to the methods disclosed in International Patent Application Nos. WO 98/24893, and WO 00/76310, the disclosures of all of which are hereby incorporated by reference. Following the initial immunization, subsequent boost of immunogen (5-20 µg/mouse) were administered on a schedule and for the duration necessary to induce a suitable anti-DNP titer in the mice. Titers were determined by enzyme immunoassay using immobilized DNP-BSA (BioSearch Technologies, Novato, Calif.), this conjugate was prepared such that the final DNP:BSA molar ratio was 30:1.

Immunizations to raise anti-KLH antibodies were conducted, over a period of 4 weeks, using Imject® Mariculture Keyhole Limpet hemocyanin (mcKLH; Pierce Biotechnology, Rockford, Ill.; cat #77600, lot #B144095B). Immunizations were conducted using 10 µg of KLH per mouse in Aluminium Phosphate Gel Adjuvant (HCI Biosector, Frederikssund, Denmark; Catalog #1452-250); delivered via footpad injection. The initial immunization of the XMG1K strain of XenoMouse® was according to methods previously disclosed (Mendez et al., *Nat. Genet.* 15:146-156 (1997); published International Patent Application Nos. WO 98/24893, and WO 00/76310, the disclosures of which are hereby incorporated by reference, which are all hereby incorporated by reference). Following the initial immunization, subsequent boosts of immunogen (5-10 µg/mouse) were administered on a schedule and for the duration necessary to induce a suitable anti-KLH titer in the mice. Titers were determined by enzyme immunoassay using immobilized KLH (Pierce Biotechnology, Rockford, Ill.).

Preparation of Monoclonal Antibodies.

Mice exhibiting suitable titers were identified, and lymphocytes and splenocytes were obtained from draining lymph nodes and spleen, then were pooled for each cohort. B cells were dissociated from the tissue by grinding in a suitable medium (for example, Dulbecco's Modified Eagle Medium; DMEM; Invitrogen, Carlsbad, Calif.) to release the cells from the tissues, and were suspended in DMEM. B cells were selected and/or expanded using standard methods, and fused with suitable fusion partner, for example, nonsecretory myeloma P3X63Ag8.653 cells (American Type Culture Collection CRL 1580; Kearney et al, *J. Immunol.* 123:1548-1550 (1979)), using techniques known in the art.

B cells were mixed with fusion partner cells at a ratio of 1:4. The cell mixture was gently pelleted by centrifugation at 400×g for 4 minutes, the supernatant was decanted, and the cell mixture was gently mixed by using a 1 ml pipette. Fusion was induced with PEG/DMSO (polyethylene glycol/dimethyl sulfoxide; obtained from Sigma-Aldrich, St. Louis Mo.; 1 ml per million of lymphocytes). PEG/DMSO was slowly added with gentle agitation over one minute followed, by one minute of mixing. IDMEM (DMEM without glutamine; 2 ml per million of B cells), was then added over 2 minutes with gentle agitation, followed by additional IDMEM (8 ml per million B-cells) which was added over 3 minutes.

The fused cells were gently pelleted (400×g 6 minutes) and resuspended in 20 ml Selection medium (for example, DMEM containing Azaserine and Hypoxanthine [HA] and other supplemental materials as necessary) per million B-cells. Cells were incubated for 20-30 minutes at 37° C. and then were resuspended in 200 ml Selection medium and cultured for three to four days in T175 flasks prior to 96-well plating.

Cells were distributed into 96-well plates using standard techniques to maximize clonality of the resulting colonies. After several days of culture, the hybridoma supernatants were collected and subjected to screening assays as detailed in the examples below, including confirmation of binding to KLH or DNP, respectively. Positive cells were further selected and subjected to standard cloning and subcloning techniques. Clonal lines were expanded in vitro, and the secreted human antibodies obtained for analysis. Several cell lines secreting DNP-specific antibodies were obtained, and the antibodies were further characterized. The sequences thereof are presented herein and in the Sequence Listing, and results of various tests using these antibodies are provided.

Cloning and Engineering of Carrier Antibodies Anti-KLH and Anti-DNP.

The sequences for the Xenomouse derived human anti-KLH antibodies were obtained by the polymerase chain reaction (PCR) amplification technique known as 5' RACE (rapid amplification of cDNA ends). Total RNA was isolated from three hybridomas expressing KLH binding monoclonal antibodies; 16.3.1, 108.1.2 and 120.6, using TRIzol reagent (Invitrogen) followed by a further purification using the RNeasy Mini Kit (Qiagen). Mixed random and oligo-dT primed first strand, RACE ready cDNAs were prepared using the GeneRacer Kit (Invitrogen). PCR amplifications of the cDNAs were performed with Advantage HF2 DNA polymerase (Clontech) with the forward primer, GeneRacer™ nested primer:

5'-GGA CAC TGA CAT GGA CTG AAG AGT A-3'// (SEQ ID NO:271); and the reverse primers:

5'-CTC CTG GGA GTT ACC CGA TTG-3'// (SEQ ID NO:272, for the light chain, and 5'-GAT GGG CCC TTG GTG GAG GCT GAG GAG ACG GTG ACC GTG G-3'// (SEQ ID NO:273), for the heavy chain. The PCR reaction cycles consisted of a 30 second denaturation of the cDNA at 94° C., followed by three cycles of amplification with each cycles consisting of 20 seconds at 94° C.; 30 seconds at 55° C.; and 90 seconds at 72° C. plus an additional 27 cycles consisting of 20 seconds at 94° C.; 30 seconds at 65° C.; and 90 seconds at 72° C. The reactions were then incubated for 7 minutes at 72° C. following the last PCR cycle to insure complete elongation. The RACE PCR products were cloned into pCR4-TOPO (Invitrogen) and their sequences determined using ABI DNA sequencing instruments (Perkin Elmer). Consensus sequences were determined using Vector NTI 8.0 software (Invitrogen) and used to design primers for full-length antibody chain PCR amplification.

To obtain the complete coding region sequences for the expression of anti-KLH antibodies, using 16.3.1 as an example, PCR was again used. The light chain 5' PCR primer encoded the amino terminus of the signal sequence, a SalI restriction enzyme site, and an optimized Kozak sequence was:

5'-AAG CTC GAG GTC GAC TAG ACC ACC ATG GAC ATG AGG-3'// (SEQ ID NO:274), and the 3' primer that encoded the carboxyl terminus and termination codon, as well as a NotI restriction site was:

```
                                       (SEQ ID NO: 275)
5'-AAC CGT TTA AAC GCG GCC GCT CAA CAC TCT CCC CTG

TTG AA-3'//.
```

The heavy chain 5' PCR primer encoded the amino terminus of the signal sequence, a SalI restriction enzyme site, and an optimized Kozak sequence was:

5'-AAG CTC GAG GTC GAC TAG ACC ACC ATG GAA TTG GGA CTG AG-3'// (SEQ ID NO:276), and the 3' primer encoded the carboxyl terminus and termination codon, as well as a NotI restriction site was:

```
                                       (SEQ ID NO: 277)
5'-AAC CGT TTA AAC GCG GCC GCT CAT TTA CCC GGA GAC

AGG GA-3'//.
```

The PCRs were performed using Advantage HF2 DNA polymerase and the reaction cycles consisted of a 30 second denaturation of the cDNA at 94° C., followed by 30 cycles consisting of 20 seconds at 94° C.; 30 seconds at 65° C.; and 90 seconds at 72° C. The reactions were then incubated for 7 minutes at 72° C. following the last PCR cycle to insure complete elongation. The resulting PCR products were gel isolated, purified using QIAquick spin columns (Qiagen), digested with SalI (NEBL) and NotI (NEBL), gel isolated and purified using QIAquick spin columns, and then ligated into the mammalian expression vector pTT5.

The sequences for the XenoMouse®-derived human anti-DNP antibody variable regions were obtained by sequencing reverse transcription PCR products. PCR was then used to adapt the variable region sequence ends to make them compatible with the ends of pTT5 vectors containing a VK1 signal peptide and the appropriate antibody constant region. As example, anti-DNP 3A4 light chain was cloned into pTT5 using the unique BssHII site at the end of a Vk1 signal peptide and the unique BsiW1 site at the beginning of the human kappa constant region. To add the BssHII and the BsiWI sites to the ends of the 3A4 variable region was amplified by PCR using 5' primer:

```
                                       (SEQ ID NO: 278)
5' TTT TTT TTG CGC GCT GTG ACA TCC AGA TGA CCC AGT

C 3'//,
and
```

```
                                       (SEQ ID NO: 279)
3' primer 5' AAA AAA CGT ACG TTT GAT ATC CAC TTT

GGT CC 37//.
```

The anti-DNP 3A4 contained a tryptophan in the variable region of the heavy chain. The tryptophan codon was mutated to a phenylalanine by PCR using (+) strand primer:

```
                                       (SEQ ID NO: 280)
5' CTG TGT ATT ACT GTG CGA GGT ATA ACT TCA ACT ACG

GTA TGG ACG TCT GG 3'// and (-) strand primer:

(SEQ ID NO: 281)
5' CCA GAC GTC CAT ACC GTA GTT GAA GTT ATA CCT CGC

ACA GTA ATA CAC AG 3'// and to a tyrosine by PCR using (+) strand primer:

(SEQ ID NO: 282)
5' CTG TGT ATT ACT GTG CGA GGT ATA ACT ACA ACT ACG

GTA TGG ACG TCT GG 3'// and (-) strand primer:

(SEQ ID NO: 283)
5' CCA GAC GTC CAT ACC GTA GTT GTA GTT ATA CCT CGC

ACA GTA ATA CAC AG 3'// in conjunction with the heavy chain 5' end primer:

(SEQ ID NO: 284)
5' AAG CTC GAG GTC GAC TAG ACC ACC ATG GAC ATG AGG

GTG CCC GCT CAG CTC CTG GGG CT 3'// and the heavy chain 3' primer:
```

5' AAC CGT TTA AAC GCG GCC GCT CAT TTA CCC GGA GAC AGG GA 3'// (SEQ ID NO:285). Also, to reduce disulfide scrambling in the hinge region of the 3A4 IgG2 heavy chain, as example, the hinge cysteines 219 and 220 (EU numbering) were mutated by PCR using (+) strand primer:

```
                                       (SEQ ID NO: 286)
5' GGA CAA GAC AGT TGA GCG CAA ATC TTC TGT CGA GTG

CCC ACC GTG CCC AG 3'// and (-) strand primer:

(SEQ ID NO: 287)
5' CTG GGC ACG GTG GGC ACT CGA CAG AAG ATT TGC GCT

CAA CTG TCT TGT CC 3'// in conjunction with the heavy chain 5' end primer:

(SEQ ID NO: 288)
5' AAG CTC GAG GTC GAC TAG ACC ACC ATG GAC ATG AGG

GTG CCC GCT CAG CTC CTG GGG CT 3'// and the heavy chain 3' primer:

(SEQ ID NO: 289)
5' AAC CGT TTA AAC GCG GCC GCT CAT TTA CCC GGA GAC

AGG GA 3'//.
```

Transient Expression to Generate Recombinant Monoclonal Antibodies.

Transient transfections were carried out in HEK 293-6E cells as follows. The human embryonic kidney 293 cell line stably expressing Epstein Barr virus Nuclear Antigen-1

(293-6E cells) was obtained from the National Research Council (Montreal, Canada). Cells were maintained as serum-free suspension cultures using F17 medium (Invitrogen, Carlsbad, Calif.) supplemented with 6 mM L-glutamine (Invitrogen, Carlsbad, Calif.), 1.1% F-68 Pluronic (Invitrogen, Carlsbad, Calif.) and 250 µg/ul Geneticin (Invitrigen, Carlsbad, Calif.). The suspension cell cultures were maintained in Erlenmeyer shake flask cultures. The culture flasks were shaken at 65 rpm at 37° C. in a humidified, 5% $CO_2$ atmosphere. A stock solution (1 mg/ml) of 25-kDa linear PEI (Polysciences, Warrington, Pa.) was prepared in water, acidified with HCl to pH 2.0 until dissolved, then neutralized with NaOH, sterilized by filtration (0.2 µm), aliquoted, and stored at −20° C. until used. Tryptone N1 was obtained from OrganoTechni S.A. (TekniScience, QC, Canada). A stock solution (20%, w/v) was prepared in Freestyle medium (Invitrogem, Carlsbad, Calif.), sterilized by filtration through 0.2 µm filters, and stored at 4° C. until use. Typically, transfections were performed at the 1 L scale. Cells (293-6E) were grown too a viable cell density of $1.1 \times 10^6$ cells/ml then transfection complexes were prepared in 1/10th volume of the final culture volume. For a 1-L transfection culture, transfection complexes were prepared in 100 ml F17 basal medium, and 500 µg plasmid DNA (heavy chain and light chain DNA, 1:1 ratio) was first diluted in 100 ml F17 medium. After a 5-minute incubation at room temperature, 1.5 ml of PEI solution was added. The complexes were vortexed mildly, then incubated for 15 minutes at room temperature. The cells were transfected by adding the transfection complex mix to the cells in the shale flask culture. 24 hours post-transfection, Tryptone N1 was added to the transfected culture to a final concentration of 0.5%, and the transfected cultures were maintained on a shaker at 65 rpm at 37° C. in a humidified, 5% $CO_2$ atmosphere for another 5 days after which they were harvested. The conditioned medium was harvested by centrifugation at 4000 rpm, and then sterile filtered through 0.2 µm filter (Corning Inc.).

The stably expressed aKLH 120.6 control antibody pool was created by transfecting CHO d-host cells with expression plasmids pDC323 anti-KLH 120.6 kappa LC and pDC324 anti-KLH 120.6-IgG2 HC using a standard electroporation procedure. After transfection, the cells were grown as a pool in a serum free -GHT selective growth media to allow for selection and recovery of the plasmid containing cells. Cell pools grown in -GHT selective media were cultured until they reached >85% viability. The selected cell pools were amplified with 150 nm and 300 nM methotrexate (MTX). Upon reaching >85% viability the 150 nM pools were then further re amplified in 500 nm MTX. When the viability of the MTX amplified pools reached >85% viability, the pools were screened using an abbreviated six day batch production assay with an enriched production media to assess expression. The expression of the amplified pools ranged from 120-400 µg/mL. The best pool was chosen based on the six-day assay and scaled-up using a ten-day fed batch process. The conditioned media was harvested and purified to provide protein for analysis.

The stably expressed aKLH 120.6 antibody pool was created by transfecting CHO d-host cells with expression plasmids pDC323 anti-KLH 120.6 kappa LC and pDC324 anti-KLH 120.6-IgG2 HC using a standard electroporation procedure. After transfection, the cells were grown as a pool in a serum free -GHT selective growth media to allow for selection and recovery of the plasmid containing cells. Cell pools grown in -GHT selective media were cultured until they reached >85% viability. The selected cell pools were amplified with 150 nm and 300 nM MTX. Upon reaching >85% viability the 150 nM pools were then further re amplified in 500 nm MTX. When the viability of the MTX amplified pools reached >85% viability, the pools were screened using an abbreviated six day batch production assay with an enriched production media to assess expression. The expression of the amplified pools ranged from 120-400 µg/mL. The best pool was chosen based on the six day assay and scaled up using a ten day fed batch process. The conditioned media was harvested and purified to provide protein for analysis.

The aDNP 3A4-F and aDNP 3B1 antibody stable expression pools were created by transfecting CHO DHFR(−) host cells with corresponding heavy chain and light chain expression plasmid sets using a standard electroporation procedure. Per each antibody molecule, 3-4 different transfections were performed to generate multiple pools. After transfection the cells were grown as a pool in a serum free -GHT selective growth media to allow for selection and recovery of the plasmid containing cells. Cell pools grown in -GHT selective media were cultured until they reached >85% viability. The selected cell pools were amplified with 150 nm methotrexate. When the viability of the methotrexate amplified pools reached >85% viability, the pools were screened using an abbreviated six day batch production assay with an enriched production media to assess expression. The best pool was chosen based on the six day assay titer and correct mass confirmation.

Antibody Purification and Selections.

The antibodies were purified by Mab Select Sure chromatography (GE Life Sciences) using 8 column volumes of Dulbecco's PBS without divalent cations as the wash buffer and 100 mM acetic acid, pH 3.5, as the elution buffer at 7° C. The elution peak was pooled based on the chromatogram and the pH was raised to about 5.0 using 2 M Tris base. The pool was then diluted with at least 3 volumes of water, filtered through a 0.22-µm cellulose acetate filter and then loaded on to an SP-HP sepharose column (GE Life Sciences) and washed with 10 column volumes of S-Buffer A (20 mM acetic acid, pH 5.0) followed by elution using a 20 column volume gradient to 50% S-Buffer B (20 mM acetic acid, 1 M NaCl, pH 5.0) at 7° C. A pool was made based on the chromatogram and SDS-PAGE analysis, then the material was concentrated about 7-fold and diafiltered against about 5 volumes of 10 mM acetic acid, 9% sucrose, pH 5.0 using a VivaFlow TFF cassette with a 30 kDa membrane. The dialyzed material was then filtered through a 0.22-µm cellulose acetate filter and the concentration was determined by the absorbance at 280 nm.

The lead candidates were then selected based on the product behavior by SDS-PAGE. The aDNP 3B1, 3H4, 3C2, 3A1 and 3A4 antibodies from both transient and stable expression mammalian cell lines were analyzed for product quality on a 1.0-mm Tris-glycine 4-20% SDS-PAGE (Novex) using reducing loading buffer (FIG. 11). Using these data, the aDNP 3H4 antibody produced a heterogenous product from the stable cell line, which indicated that it was not a good candidate as a carrier antibody, since a homogenous product is desirable. The aDNP 3A1, 3A4, 3C2, and 3B1 and aKLH 120.6 antibodies were analyzed for product quality on a 1.0-mm Tris-glycine 4-20% SDS-PAGE (Novex) using non-reducing loading buffer (FIG. 12A-B). The aDNP 3C2 antibody produced a heterogenous product with exceptional high molecular mass material, indicating it was not an ideal candidate as a carrier antibody, since a product containing high molecular mass material is not desirable. In addition, the aDNP 3B1 antibody showed a doublet under these conditions. The aDNP 3B1 and aDNP 3A1 antibodies were then compared using both Tris-glycine SDS-PAGE as well as bis-Tris NuPAGE systems under non-reducing conditions (FIG. 13A-B). It was found that the aDNP 3B1 antibody clearly produces a doublet not observed with aDNP 3A1 on the Tris-glycine SDS-PAGE; however, the aDNP 3B1 antibody appeared more homogenous than the aDNP 3A1 antibody when analyzed by bis-Tris NuPAGE, indicating that the doublet may be an artifact of the method of analysis. When the aDNP 3B1 antibody was analyzed by Tris-glycine SDS-PAGE after treatment with non-reducing sample buffer at room temperature, 85° C., or 100° C., the doublet was not eliminated (FIG. 14A). However, when the aDNP 3B1 antibody was examined by Tris-glycine SDS-PAGE using 0.4% SDS in the gel running buffer rather than the usual 0.1%, the doublet was greatly reduced (FIG. 14B), offering additional evidence that the doublet was an artifact of the system of analysis.

Antibodies were further analyzed for homogeneity using two size exclusion columns (TSK-GEL G3000SWXL, 5 mm particle size, 7.8×300 mm, TosohBioscience, 08541) in series with a 100 mM sodium phosphate, 250 mM NaCl, pH 6.8, mobile phase flowed at 0.5 mL/min (FIG. 15). The aDNP 3C2 antibody displayed a substantial post-peak shoulder, which was deemed undesirable, so this antibody was demoted as a candidate carrier antibody. In addition, it was observed that the aDNP 3C2 and aDNP 3A4 antibodies eluted later than expected indicating a potential interactions with the stationary phase of the chromatography column.

Antibodies (aDNP 3A1, aDNP 3C2 and aDNP 3A4) were tested for resistance to photodegradation. The antibodies were either exposed to fluorescent light at 4° C. for 3 weeks or were protected from light by covering samples of each with aluminum foil. The antibody samples were then analyzed using two size exclusion columns (TSK-GEL G3000SWXL, 5 mm particle size, 7.8×300 mm, TosohBioscience, 08541) in series with a 100 mM sodium phosphate, 250 mM NaCl, pH 6.8, mobile phase flowed at 0.5 mL/min (FIG. 16). The aDNP 3C2 and aDNP 3A4 antibodies showed substantial peak broadening after light exposure, which is consistent with oxidation of a susceptible tryptophan. To reduce the oxidation susceptibility of the aDNP 3A4 antibody, several variants with the CDR3 tryptophan mutated to either tyrosine or phenylalanine were constructed (aDNP 3A4, aDNP 3A4-Y, aDNP 3A4-F, aDNP 3A4-YSS and aDNP 3A4-FSS). These antibodies were then evaluated by SEC for resistance to photodegradation after two days of light exposure (336 W/m2 UV light and 331 k-lux for fluorescent light) at 6° C., by analysis using two size exclusion columns (TSK-GEL G3000SWXL, 5 mm particle size, 7.8×300 mm, TosohBioscience, 08541) in series with a 100 mM sodium phosphate, 250 mM NaCl at pH 6.8 mobile phase flowed at 0.5 mL/min (FIG. 17A-B).

All four of the aDNP 3A4 variants showed substantially less peak broadening than the wild type molecule, indicating that the CDR3 tryptophan was responsible for this undesirable phenomenon. Furthermore, the retention time extension on SEC was also greatly reduced with the variants indicating less interaction with the stationary phase of the column. Anti-DNP 3A4 antibodies with various mutations (aDNP 3A4, aDNP 3A4-Y, aDNP 3A4-F, aDNP 3A4-YSS and aDNP 3A4-FSS) were analyzed for homogeneity using a Tosohaas SP-5PW column (10-µm particle, 7.5 mm ID×7.5 cm long) using Buffer A (10 mM sodium acetate, pH 5.0) and Buffer B (10 mM sodium acetate, 600 mM NaCl, pH 5.0) flowed at 1 ml/min with a programmed linear gradient (1 min 0% B, 10 min 35% B, 30 min 70% B, 3 min 90% B and 3 min 0% B) (FIG. 18). The aDNP 3A4 antibody with the CDR3 tryptophan converted to phenylalanine produced a more desirable narrower elution peak than the wild type or tyrosine variant; therefore, the aDNP 3A4-F variant was deemed to be the superior molecule. The aDNP 3B1, aDNP 3A4-F, and aDNP 3A4-FSS antibodies were analyzed by non-reducing CE-SDS (FIG. 19A-C). All CE SDS experiments were performed using Beckman PA800 CE system (Fullerton, Calif.) equipped with UV diode detector. 221 nm and 220 nm wavelength were employed. A bare-fused silica capillary 50 µm×30.2 cm was used for the separation analysis. Buffer vial preparation and loading as well as Install Capillary Cartridge were described in the Beckman Coulter manual for IgG Purity/Heterogeneity. The running conditions for reduced and non-reduced CE-SDS were similar to those described in Beckman Coulter manual for IgG Purity/Heterogeneity with some modifications which are briefly described below. For non-reducing conditions, the antibody sample (150 µg) was added 20 µl of SDS reaction buffer and 5 µl of 70 mM N-ethylmaleimide. Water was then added to make final volume 35 µl and the protein concentration was brought to 4.3 mg/ml. The SDS reaction buffer was made of 4% SDS, 0.01 M citrate phosphate buffer (Sigma) and 0.036 M sodium phosphate dibasic. The preparation was vortexed thoroughly, and heated at 45° C. for 5 min. The preparation was then added additional 115 µl of 4% SDS. After being vortexed and centrifuged, the preparation was placed in a 200 µl PCR vial and then loaded onto the PA800 instrument. The sample was injected at the anode with reverse polarity using −10 kV for 30 sec, and was then separated at −15 kV with 20 psi pressure at both ends of capillary during 35 min separation. The aDNP 3B1 antibody produced the most desirable profile with the highest level of uniformity under non-reducing conditions. The aDNP 3B1, aDNP 3A4-F, and aDNP 3A4-FSS antibodies were analyzed by reducing CE-SDS (FIG. 20A-C herein). For reducing conditions, the antibody sample was diluted to 2.1 mg/ml by adding purified $H_2O$, and 95 µl of the antibody was added 105 µl of SDS sample buffer (Beckman) with 5.6% beta mercaptoethanol. The preparation was then vortexed thoroughly and then heated at 70° C. for 10 min. After being centrifuged, the supernatant was placed in a 200 µl PCR vial and then loaded onto the PA800 instrument. The sample was injected at the anode with reverse polarity using −5 kV for 20 sec, and was then separated at −15 kV with 20 psi pressure at both ends of capillary during 30 min separation. The aDNP 3A4-F produced the most desirable uniform peaks under reducing conditions.

The aDNP 3A4-F, aDNP 3A4-FSS and aDNP 3B1 antibodies were analyzed for thermoresistance by DSC using a MicrCal VP-DSC where the samples were heated from 20° C. to 95° C. at a rate of 1° C. per minute. The proteins were at 0.5 mg/ml in 10 mM sodium acetate, 9% sucrose, pH 5.0 (FIG. 21). The aDNP 3B1 and aDNP 3A4-F antibodies produced the most desirable melting profiles, with a higher temperature for the initial transition. The aDNP 3B1 and aDNP 3A4-F antibodies were differentiated by the presence of a single melting transition for the aDNP 3B1 antibody and a double transition for the aDNP 3A4-F antibody.

ELISA Assays.

ELISA assays were conducted as follows. Costar 3072 medium binding 384 well plates (Corning Life Sciences) were coated with DNP-BSA (BioSearch Technologies, Novato, Calif.) at 5 µg/ml in 1×PBS/0.05% Azide, (40 µl/well). The plates were incubated at 4° C. overnight. The plates were then washed using 3-cycle wash on a Titertek M384 plate washer (Titertek, Huntsville, Ala.). The plates were blocked with 90 µl of 1×PBS/1% milk and incubated approximately 30 minutes at room temperature. The plates were then washed using a 3-cycle wash on a Titertek plate washer. 10 ul antibody samples were added to 40 ul 1×PBS/1% milk. The plates were then incubated for 1 hour at room temperature. Next, plates were then washed using 3-cycle wash on a Titertek M384 plate washer (Titertek, Huntsville, Ala.). Goat anti Human IgG Fc HRP was then added at 100 ng/ml (1:4000) in 1×PBS/1% milk/10 mM $Ca^{2+}$ (50 µl/well) was added to the plate and was incubated 1 hour at room temperature. The plates were washed once again, using a 3-cycle wash. The plates were then patted dry with paper towel. Finally, 1 step TMB (Neogen, Lexington, Ky.) (50 µl/well) was added to the plate and was quenched with 1N hydrochloric acid (50 µl/well) after 30 minutes at room temperature. OD's were read immediately at 450 nm using a Titertek plate reader.

Example 2

Pharmacokinetic (PK) & Pharmacodynamic (PD) Studies of Anti-DNP Antibody Embodiments of the Invention The pharmacokinetic profile of the aDNP 3A4-F, aDNP 3A4-FSS and aDNP 3B1 antibodies was determined in adult Sprague-Dawley rats (8-12 weeks old) by injecting 5 mg/kg subcutaneously and collecting approximately 250 µL of blood in Microtainer® serum separator tubes at 0, 0.25, 1, 4, 24, 48, 72, 96, 168, 336, 504, 672, 840 and 1008 hours post-dose from the lateral tail vein (FIG. 22). Each sample was maintained at room temperature following collection, and following a 30-40 minute clotting period, samples were centrifuged at 2-8° C. at 11,500 rpm for about 10 minutes using a calibrated Eppendorf 5417R Centrifuge System (Brinkmann Instruments, Inc., Westbury, N.Y.). The collected serum was then transferred into a pre-labeled (for each rat), cryogenic storage tube and stored at −60° C. to −80° C. for analysis. To measure the serum sample concentrations from the PK study samples, the following method was used: ½ area black plate (Corning 3694) was coated with 2 µg/ml of Anti-hu FC, Ab 1.35.1 in 1×PBS and then incubated overnight at 4° C. The plate was washed and blocked with I-Block™ (Applied Biosystems) overnight at 4° C. If samples needed to be diluted, then they were diluted in Rat SD serum. The standards and samples were diluted 1:20 in I-Block™+5% BSA into 380 µl of diluting buffer. The plate was washed and 50-µl samples of pretreated standards and samples were transferred into an Ab 1.35.1 coated plate and incubated for 1.5 h at room temperature. The plate was washed, then 50 µl of 100 ng/ml of anti-hu FC Ab 21.1-HRP conjugate in I-Block™+5% BSA were added and incubated for 1.5 h. The plate was washed, then 50 µl of Pico substrate were added, after which the plate was immediately analyzed with a luminometer. The pharmacokentic profile was good for all antibodies, but the aDNP 3B1 showed the best overall profile.

The pharmacokinetic profile of the aDNP 3A4-F antibody was determined in 6 male cynomologous monkeys (3-7 kg) by injecting 6 mg/kg bolus dose intravenously and taking blood samples at 0 and 30 minutes and 2, 7, 9, 11, 14, 21, 28, 35, 42, 49, 56 and 63 days (FIG. 23). The pharmacokinetic profile of the aKLH 120.6 antibody was determined in 4 male cynomologous monkeys (2-4 kg) by injecting 3 mg/kg bolus dose intravenously and taking blood samples at 0, 0.25, 1, 4, 8, 12, 24, 72, 168, 240, 336, 408, 504, 576, 672, 744, 840, 1008, 1176 and 1344 hours (FIG. 23). To measure the serum sample concentrations from the PK study samples, the same method as mentioned above for the rat pharmacokinetic study was employed. The pharmacokinetic profile for both antibodies in cynomologous monkeys was good, but the dose normalized profile for the aKLH 120.6 was marginally better than that of the aDNP 3A4-F.

Example 3

Human Tissue Cross-Reactivity Assessment

In general accordance with the guidance laid out in *Points to Consider in the Manufacture and Testing of Monoclonal Antibody Products for Human Use* (U.S. Department of Health and Human Services, Food and Drug Administraton, Center for Biologics Evaluation and Research (1997)), a preliminary non-GLP study was carried out to determine cross-reactivity of inventive antibodies with a variety of human tissues. If an antibody is intended for drug development, a more extensive testing under GLP conditions is required. The tissue cross-reactivity of antibodies aDNP 3A4-F and aKLH 120.6 was evaluated (Charles River Laboratories, Preclinical Services, Reno, Nev.) with cryosections of selected human tissues using Alexa Fluor 488 labeled forms of the test articles. Normal human tissues from two unique individuals (unless otherwise indicated) were obtained from the Special Pathology Services Human Tissue Bank collected by the National Disease Research Interchange (NDRI, Philadelphia, Pa.), Cureline, Inc. (Burlingame, Calif.), Cybrdi (Rockville, Md.), or Rocky Mountain Lions Eye Bank (Aurora, Colo.). Tissues tested included human cerebellum, lung, cerebral cortex, ovary (from mature female), eye, placenta, gastrointestinal tract (small intestine), skin (1 individual), heart, spleen, kidney (1 individual), thyroid, liver, testis. Sections of fresh-frozen human tissues and control bead blocks (DNP[31]-bovine serum albumin [BSA] beads [positive], and human serum albumin [HSA] beads [negative]) were cut on the cryostat and thaw mounted onto capillary gap slides. The tissue and control bead slides were fixed in cold acetone for approximately 10 minutes at −10° C. to −25° C. The fixed slides were allowed to dry for at least one hour (to overnight). If stored frozen, fixed slides were removed from the freezer on the day prior to an experiment and allowed to thaw overnight prior to use. All the following steps were performed at room temperature unless otherwise specified. The slides were incubated with 1× Morphosave™ for approximately 15 minutes to preserve tissue morphology then washed two times for approximately 5 minutes each in 1× phosphate-buffered saline (PBS). To block endogenous peroxidase, the slides were incubated in a glucose oxidase solution for approximately 1 hour at approximately 37° C. The slides were washed two times in 1×PBS for approximately 5 minutes each. Endogenous biotin was blocked by sequential incubation (approximately 15 minutes each) in avidin and biotin solutions. Following the incubation in biotin, the tissue sections were blocked with a blocking antibody solution for approximately 25 minutes. Alexa Fluor 488-Ab 3A4 W101F (anti-DNP), and Alexa Fluor 488 anti-KLH (anti-KLH Ab) were applied to sections at the optimal concentration (2.0 µg/mL) or 5 times the optimal concentration (10.0 µg/mL) for approximately 25 minutes. Slides were washed 3 times with wash buffer and then incubated with the secondary antibody (rabbit anti-Alexa Fluor 488) for approximately 25 minutes. Following incubation with the secondary antibody, slides were washed 4 times with wash buffer then incubated with the tertiary antibody (horseradish peroxidase conjugated goat anti-rabbit IgG antibody) for approximately 25 minutes and binding visualized with a diaminobenzidine (DAB) chromogen substrate. DNP(31)-BSA beads were used as a positive control in all experiments. HSA beads were used as a negative control. Tissues were qualified as adequate for immunohistochemistry via staining with an antibody against CD31 (anti-CD31) i.e., platelet endothelial cell adhesion molecule (PECAM-1). There was no specific staining in any human tissue examined at either 2.0 or 10.0 µg/mL concentration for any of the tested antibodies.

Example 4

Expression and Purification of Monovalent or Multivalent Immunoglobulin- and/or Fc Domain-Toxin Peptide Analog Fusions An assortment of monovalent, bivalent and trivalent structures were expressed and purified for comparison, including exemplary embodiments of the invention. Those included aKLH IgG2/Fc-ShK variants (see schematic representation of FIG. 1E: "hemibody" configuration), and anti-KLH IgG2-ShK variants (see FIG. 1F-L). For example, bivalent Fc-L10-ShK[1-35], monovalent anti-Keyhole Limpet Hemocyanin (KLH) immunoglobulin heavy chain-[Lys16]ShK fusion antibody (designated "aKLH HC-[Lys16]ShK Ab"; see FIG. 1F), and monovalent anti-KLH immunoglobulin light chain-[Lys16]ShK antibody (designated "aKLH LC-[Lys16]ShK Ab"; see FIG. 1J). IgG2 Fc/Fc-ShK variants (see FIG. 1A), bivalent Fc-L10-ShK[2-35], monovalent Fc/Fc-L10-ShK[2-35] were made for comparison, by recombinant methods as described in Sullivan et al., WO 2008/088422 A2, and in particular Examples 1, 2, and 56 therein, incorporated by reference in its entirety, or as modified herein.

Transient expression system used to generate toxin peptide analog-Fc fusions ("peptibodies") or other immunoglobulin fusion embodiments. HEK 293-6E cells were maintained in 3 L Fernbach Erlenmeyer Flasks between 2e5 and 1.2e6 cells/ml in F17 medium supplemented with L-Glutamine (6 mM) and Geneticin (25 µg/ml) at 37° C., 5% $CO_2$, and shaken at 65 RPM. At the time of transfection, cells were diluted to $1.1 \times 10^6$ cells/mL in the F17 medium mentioned above at 90% of the final culture volume. DNA complex was prepared in Freestyle293 medium at 10% of the final culture volume. DNA complex includes 500 ug total DNA per liter of culture and 1.5 ml PEImax per liter of culture. DNA complex is briefly shaken once ingredients are added and incubated at room temperature for 10 to 20 minutes before being added to the cell culture and placed back in the incubator. The day after transfection, Tryptone N1 (5 g/L) was added to the culture from liquid 20% stock. Six days after transfection, culture was centrifuged at 4,000 RPM for 40 minutes to pellet the cells and the cultured medium was harvested through a 0.45 um filter.

In preparing the DNA complex, the ratio of plasmids was proportional to the desired molar ratio of the peptides needed to generate the intended product. The components of the IgG2 Fc/Fc-ShK include IgG2 Fc and IgG2 Fc-ShK at a 1:1 ratio. During expression these assemble into IgG2 Fc homodimers, IgG2 Fc/Fc-ShK heterodimers, and IgG2 Fc-ShK homodimers. The IgG2 Fc/Fc-ShK heterodimer (monovalent form) was isolated during purification using cation exchange chromatography.

IgG2 Fc-ShK[2-35]; IgG2 Fc Shk[2-35, Q16K]; IgG2 Fc-Shk[1-35], IgG2 Fc-ShK[1-35, Q16K] Mammalian Expression.

DNA sequences coding for the immunoglobulin Fc domain of human IgG2:

```
                                      (SEQ ID NO: 1)
MEWSWVFLFFLSVTTGVHSERKVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPGK//,
``` fused in-frame to a monomer of the Kv1.3 inhibitor peptide ShK[2-35] or a mutated ShK[2-35, Q16K] were constructed using standard PCR technology. The ShK[2-35] or ShK[2-35, Q16K] and the 10 amino acid linker portion of the molecule were generated in a PCR reaction using the original Fc-2xL-ShK[2-35] in pcDNA3.1(+)CMVi as a template (see Sullivan et al., WO 2008/088422 A2, Example 2, FIG. 15A-B therein). The ShK[1-35] was generated in a PCR reaction using the original Fc-2xL-ShK[1-35] in pcDNA3.1(+)CMVi as a template (Sullivan et al., WO 2008/088422 A2, Example 1, FIG. 14A-B therein). These ShK constructs have the following modified VH21 Signal peptide amino acid sequence of MEWSWVFLFFLSVTT-GVHSERKVECPPCP// SEQ ID NO:2 generated from a pSelexis-Vh21-hIgG2-Fc template with the following oligos:

```
                                      (SEQ ID NO: 3)
5'-CAT GAA TTC CCC ACC ATG GAA TGG AGC TGG-3';
and (SEQ ID NO: 4)
5'-CA CGG TGG GCA CTC GAC TTT GCG CTC GGA GTG GAC

ACC-3'.
```

Wild Type ShK[2-35] with N-terminal linker extension (amino acid sequence GGGGSGGGGSSCIDTIPK-SRCTAFQCKHSMKYRLSFCRKTCGTC// SEQ ID NO:6) was encoded by the DNA sequence below:

```
                                      (SEQ ID NO: 5)
GGAGGAGGAGGATCCGGAGGAGGAGGAAGCAGCTGCATCGACACCATCCC

CAAGAGCCGCTGCACCGCCTTCCAGTGCAAGCACAGCATGAAGTACCGCC

TGAGCTTCTGCCGCAAGACCTGCGGCACCTGC//.
```

A fragment containing this coding sequence (SEQ ID NO:5) was generated using the oligos below (SEQ ID NO:7 and SEQ ID NO:8)- and the original Fc-L10-ShK[2-35] in pcDNA3.1(+)CMVi as a template (Sullivan et al., WO 2008/088422 A2, Example 2, FIG. 15A-B therein, incorporated by reference):

```
                                      (SEQ ID NO: 7)
5'-GTC CAC TCC GAG CGC AAA GTC GAG TGC CCA CCG

TGC C-3';
and (SEQ ID NO: 8)
5'-TCC TCC TCC TTT ACC GGA GAC AGG GGA GAG-3'//.
```

Mutant ShK[2-35, Q16K] was generated using site directed mutagenesis with Stratagene's QuikChange Multi site-Directed Mutagenesis kit cat #200531 per the manufacturer's instruction. Oligos used to generate the mutagenesis were:
5'-GCT GCA CCG CCT TCA AGT GCA AGC ACA GC 3' (SEQ ID NO:9); and 5'-GCT GTG CTT GCA CTT GAA GGC GGT GCA GC-3' (SEQ ID NO:10); and using the original Fc-L10-ShK[2-35] in pcDNA3.1(+)CMVi as a template (Sullivan et al., WO 2008/088422 A2, Example 2, FIG. 15A-B therein) resulting in the DNA coding sequence

```
                                         (SEQ ID NO: 11)
GGAGGAGGAGGATCCGGAGGAGGAGGAAGCAGCTGCATCGACACCATC

CCCAAGAGCCGCTGCACCGCCTTCAAGTGCAAGCACAGCATGAAGTACC

GCCTGAGCTTCTGCCGCAAGACCTGCGGCACCTGC//,
``` which encodes the amino acid sequence Shk(2-35, K16) with a N-terminal linker extension: GGGGSGGGGSSCID-TIPKSRCTAFKCKHSMKYRLSFCRKTCGTC// SEQ ID NO:12).

ShK[1-35]WT fragment was generated using the original Fc-2xL-ShK[1-35] in pcDNA3.1(+)CMVi as a template (Sullivan et al., WO 2008/088422 A2, Example 1, FIG. 14A-B therein) and oligos:

```
                                         (SEQ ID NO: 7)
5'-GTC CAC TCC GAG CGC AAA GTC GAG TGC CCA CCG

TGC C-3';
and (SEQ ID NO: 8)
5'-TCC TCC TCC TTT ACC CGG AGA CAG GGA GAG -3'.
```

The IgG2Fc region was generated using oligos:
5'-CCG GGT AAA GGA GGA GGA GGA TCC GGA G-3' (SEQ ID NO:13); and 5'-CAT GCG GCC GCT CAT TAG CAG GTG-3' (SEQ ID NO:14), and the pSelexis Vh21-hIgG2-Fc template resulting in a fragment containing the following DNA coding sequence:

```
                                         SEQ ID NO: 15
GCACCACCTGTGGCAGGACCGTCAGTCTTCCTCTTCCCCCCAAAACCCAA

GGACACCCTCATGATCTCCCGGACCCCTGAGGTCACGTGCGTGGTGGTGG

ACGTGAGCCACGAAGACCCCGAGGTCCAGTTCAACTGGTACGTGGACGG

CGTGGAGGTGCATAATGCCAAGACAAAGCCACGGGAGGAGCAGTTCAAC

AGCACGTTCCGTGTGGTCAGCGTCCTCACCGTTGTGCACCAGGACTGGCT

GAACGGCAAGGAGTACAAGTGCAAGGTCTCCAACAAAGGCCTCCCAGCC

CCCATCGAGAAAACCATCTCCAAAACCAAAGGGCAGCCCCGAGAACCAC

AGGTGTACACCCTGCCCCCATCCCGGGAGGAGATGACCAAGAACCAGGT

CAGCCTGACCTGCCTGGTCAAAGGCTTCTACCCCAGCGACATCGCCGTGG

AGTGGGAGAGCAATGGGCAGCCGGAGAACAACTACAAGACCACACCTCC

CATGCTGGACTCCGACGGCTCCTTCTTCCTCTACAGCAAGCTCACCGTGG

ACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGG

GTAAA //, which encodes the amino acid sequence
```

```
                                         (SEQ ID NO: 16)
APPVAGPSVFLFPPKPKDTLMISRTPEVTCVVVDVSHEDPEVQFNWYVDG

VEVHNAKTKPREEQFNSTFRVVSVLTVVHQDWLNGKEYKCKVSNKGLPAP

IEKTISKTKGQPREPQVYTLPPSREEMTKNQVSLTCLVKGFYPSDIAVEW

ESNGQPENNYKTTPPMLDSDGSFFLYSKLTVDKSRWQQGNVFSCSVMHEA

LHNHYTQKSLSLSPGK.
```

The PCR fragments were generated and the products were run out on a gel. After gel purification, the DNA fragments were put together in a PCR tube and sewn together with outside primers:

```
                                         (SEQ ID NO: 3)
5'-CAT GAA TTC CCC ACC ATG GAA TGG AGC TGG-3';
and (SEQ ID NO: 14)
5'-CAT GCG GCC GCT CAT TAG CAG GTG-3'.
```

The PCR products were digested with EcoRI and NotI (Roche) restriction enzymes and agarose gel purified by Gel Purification Kit. At the same time, the pTT14 vector (an Amgen vector containing a CMV promoter, Poly A tail and a Puromycin resistance gene) was digested with EcoRI and NotI restriction enzymes and the large fragment was purified by Gel Purification Kit. Each purified PCR product was ligated to the large fragment and transformed into OneShot Top10 bacteria. DNAs from transformed bacterial colonies were isolated and subjected to EcoRI and NotI restriction enzyme digestions and resolved on a one percent agarose gel. DNAs resulting in an expected pattern were submitted for sequencing. Although, analysis of several sequences of clones yielded a 100% percent match with the above sequence, only one clone of each construct was selected for large scaled plasmid purification. The final pTT14-VH1SP-IgG2-Fc construct encoded IgG2-Fc-L10-ShK(2-35) fusion polypeptide having the following sequence:

```
                                         (SEQ ID NO: 17)
MEWSWVFLFFLSVTTGVHSERKVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPGKGGGGS

GGGGSSCIDTIPKSRCTAFQCKHSMKYRLSFCRKTCGTC//.
```

The pTT14-VH21SP-IgG2-Fc-L10-ShK(2-35,Q16K) construct encoded a IgG2-Fc L10-ShK(2-35, Q16K) fusion polypeptide sequence:

```
                                         SEQ ID NO: 18
MEWSWVFLFFLSVTTGVHSERKVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP
```

-continued

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPGKGGGGS

GGGGSSCIDTIPKSRCTAFKCKHSMKYRLSFCRKTCGTC//;

and pTT14-VH21SP-IgG2-Fc ShK1-35 construct contained a coding sequence for IgG2 Fc-L10-ShK(1-35) fusion polypeptide having the following sequence:

(SEQ ID NO: 19)
MEWSWVFLFFLSVTTGVHSERKVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPGKGGGGS

GGGGSRSCIDTIPKSRCTAFQCKHSMKYRLSFCRKTCGTC//.

Generating the VH21SP-IgG2-Fc-only construct in pYD16 (an Amgen vector containing a CMV promoter, Poly A tail and a Hygromycin resistance gene) occurred as follows: The VH21 signal peptide was generated using the following oligos:
5'-CAT AAG CTT CCC ACC ATG GAA TGG AGC TGG-3' (SEQ ID NO:20); and 5'-CA CGG TGG GCA CTC GAC TTT GCG CTC GGA GTG GAC ACC-3' (SEQ ID NO:4), and using the pSelexis template as noted above.

The Fc region was generated using the pSelexis template described above and following oligos:

(SEQ ID NO: 7)
5'-GTC CAC TCC GAG CGC AAA GTC GAG TGC CCA CCG

TGC C-3';
and (SEQ ID NO: 21)
5'-CAT GGA TCC TCA TTT ACC CGG AGA CAG GGA G-3'.

The PCR fragments were gel purified and sewn together in single PCR reaction using outside primers SEQ ID NO:335 and SEQ ID NO:336. The resulting PCR fragment was gel purified, and digested by HindIII and BamHI. Concurrently, pYD16 vector (an Amgen vector containing a CMV promoter, Poly A tail and a Hygromycin resistance gene) was also cut by HindIII and BamHI and the large vector fragment was purified by Qiagen's Gel Purification Kit. The purified PCR product was ligated to the large fragment and transformed into OneShot Top10 bacteria. DNA from transformed bacterial colonies were isolated and subjected to HindIII and BamHI restriction enzyme digestions and resolved on a one percent agarose gel. DNAs resulting in an expected pattern were submitted for sequencing. Although, analysis of several sequences of clones yielded a 100% percent match with the above sequence, only one clone was selected for large scaled plasmid purification. The final pYD16-VH21SP-IgG2-Fc construct encoded human IgG2-Fc (SEQ ID NO:1 above).

Anti-KLH IgG2-Fc ShK[1-35, Q16K] Mammalian Expression.

Using the DNA pTT5-aKLH120.6-VK1SP-IgG2-HC-L10-ShK[1-35, Q16K] construct, the fragment containing the DNA coding sequence (SEQ ID NO: 22)
GGATCCGGAGGAGGAGGAAGCCGCAGCTGCATCGACACCATCCCCAAGAG

CCGCTGCACCGCCTTCAAGTGCAAGCACAGCATGAAGTACCGCCTGAGCT

TCTGCCGCAAGACCTGCGGCACCTGCTAATGAGCGGCCGCTCGAGGCCGG

CAAGGCCGGATCC// was cut out using BamHI/BamHI. This coding sequence (SEQ ID NO:23) encodes ShK(1-35, Q16K) with an N-terminal linker sequence:

(SEQ ID NO: 23)
GSGGGGGSRSCIDTIPKSRCTAFKCKHSMKYRLSFCRKTCGTC//.

At the same time, pTT14-hIgG2-Fc-ShK[1-35]WT construct, was also digested by BamHI/BamHI, thereby removing the Shk[1-35] coding region to yield the coding sequence (SEQ ID NO: 24)
ATGGAATGGAGCTGGGTCTTTCTCTTCTTCCTGTCAGTAACGACTGGTGT

CCACTCCGAGCGCAAAGTCGAGTGCCCACCGTGCCCAGCACCACCTGTGG

CAGGACCGTCAGTCTTCCTCTTCCCCCCAAAACCCAAGGACACCCTCATG

ATCTCCCGGACCCCTGAGGTCACGTGCGTGGTGGTGGACGTGAGCCACGA

AGACCCCGAGGTCCAGTTCAACTGGTACGTGGACGGCGTGGAGGTGCATA

ATGCCAAGACAAAGCCACGGGAGGAGCAGTTCAACAGCACGTTCCGTGTG

GTCAGCGTCCTCACCGTTGTGCACCAGGACTGGCTGAACGGCAAGGAGTA

CAAGTGCAAGGTCTCCAACAAAGGCCTCCCAGCCCCCATCGAGAAAACCA

TCTCCAAAACCAAAGGGCAGCCCCGAGAACCACAGGTGTACACCCTGCCC

CCATCCCGGGAGGAGATGACCAAGAACCAGGTCAGCCTGACCTGCCTGGT

CAAAGGCTTCTACCCCAGCGACATCGCCGTGGAGTGGGAGAGCAATGGGC

AGCCGGAGAACAACTACAAGACCACACCTCCCATGCTGGACTCCGACGGC

TCCTTCTTCCTCTACAGCAAGCTCACCGTGGACAAGAGCAGGTGGCAGCA

GGGGAACGTCTTCTCATGCTCCGTGATGCATGAGGCTCTGCACAACCACT

ACACGCAGAAGAGCCTCTCCCTGTCTCCGGGTAAAGGAGGAGGA //, encoding the amino acid sequence (SEQ ID NO: 25)
MEWSWVFLFFLSVTTGVHSERKVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPGKGG

G//.

The pTT14-hIgG2-Fc vector with the ShK removed was treated with Calf Intestine Phosphatase (CIP) to remove the 5' Phosphate group and Phenol/Chloroform extracted to prevent religation of the vector upon itself. The insert ShK[1-35, Q16K] fragment was gel purified away from its vector and cleaned up with Qiagen Gel Purification Kit. The purified insert was ligated to the large vector fragment and transformed into OneShot Top10 bacteria. DNAs from transformed bacterial colonies were isolated and subjected to BamHI restriction enzyme digestion and resolved on a one percent agarose gel. DNAs resulting in an expected pattern were submitted for sequencing. Although, analysis of several sequences of clones yielded a 100% percent match with the above sequence, only one clone was selected for large scaled plasmid purification. The final pTT14-IgG2-Fc-ShK [1-35, Q16K] construct encoded the following IgG2 Fc-L10-ShK(1-35, Q16K) fusion protein sequence:

(SEQ ID NO: 26)
MEWSWVFLFFLSVTTGVHSERKVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPGKGGGGS

GGGGSRSCIDTIPKSRCTAFKCKHSMKYRLSFCRKTCGTC//.

Mammalian Expression of Anti-KLH Immunoglobulin Heavy Chain (HC) and Light Chain (LC) Toxin Peptide (and Toxin Peptide Analog) Fusions.

Figure 1A:
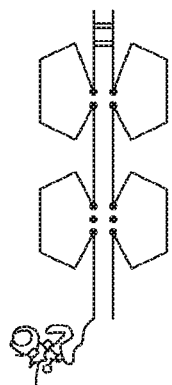
FIG. 1A-N shows schematic structures of some embodiments of a composition of the invention that include one or more units of a pharmacologically active toxin peptide analog (squiggle) fused, via an optional peptidyl linker moiety such as but not limited to L5 or L10 described herein, with one or more domains of an immunoglobulin. These schematics show a more typical IgG1, although they are intended to apply as well to IgG2s, which will have 4 disulfide bonds in the hinge and a different arrangement of the disulfide bond linking the heavy and light chain, and IgG3s and IgG4s.
Figure 1B:
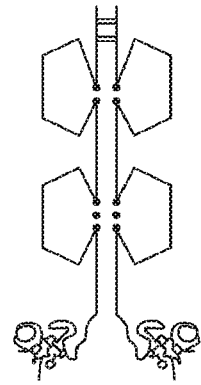
FIG. 1B represents a bivalent homodimeric Fc-toxin peptide analog fusion, with toxin peptide analogs fused to the C-terminal ends of both of the immunoglobulin Fc domain monomers.
Figure 1C:
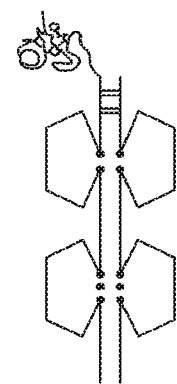
FIG. 1C represents a monovalent heterodimeric toxin peptide analog-Fc fusion with the toxin peptide analog fused to the N-terminal end of one of the immunoglobulin Fc domain monomers.
Figure 1D:
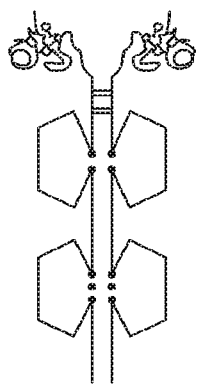
FIG. 1D represents a bivalent homodimeric toxin peptide analog-Fc fusion, with toxin peptide analogs fused to the N-terminal ends of both of the immunoglobulin Fc domain monomers.
Figure 1E:
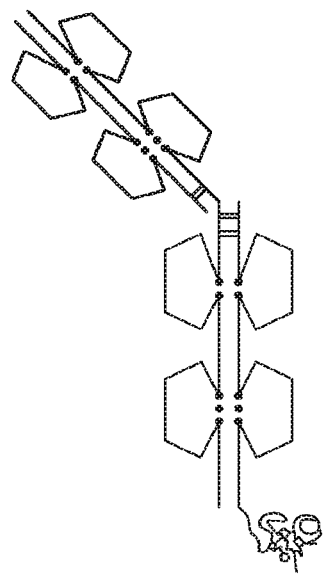
FIG. 1E represents a monovalent heterotrimeric Fc-toxin peptide analog/Ab comprising an immunoglobulin heavy chain (HC)+immunoglobulin light chain (LC)+an immunoglobulin Fc monomer with a toxin peptide analog fused to its C-terminal end.

The components of the aKLH IgG2/Fc-ShK (schematically represented by FIG. 1E) included:

(a) aKLH 120.6 kappa LC (SEQ ID NO:28, below), which incorporates a N-terminal VK-1 SP signal peptide sequence (SEQ ID NO:103):

(SEQ ID NO: 28)
MDMRVPAQLLGLLLLWLRGARCDIQMTQSPSSLSASVGDRVTITCRASQG

IRNDLGWYQQKPGKAPKRLIYAASSLQSGVPSRFSGSGSGTEFTLTISSL

QPEDFATYYCLQHNSYPLTFGGGTKVEIKRTVAAPSVFIFPPSDEQLKSG

TASVVCLLNNFYPREAKVQWKVDNALQSGNSQESVTEQDSKDSTYSLSST

LTLSKADYEKHKVYACEVTHQGLSSPVTKSFNRGEC//;

(b) aKLH 120.6 IgG2 HC (SEQ ID NO:29, below), which incorporates a N-terminal VK-1 SP signal peptide sequence (SEQ ID NO:103):

(SEQ ID NO: 29)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGK//;

and (c) IgG2 Fc-L10-ShK(1-35):

(SEQ ID NO: 30)
MEWSWVFLFFLSVTTGVHSERKVECPPCPAPPVAGPSVFLFPPKPKDTLM

-continued

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPGKGGGGS

GGGGSRSCIDTIPKSRCTAFQCKHSMKYRLSFCRKTCGTC//.

The desired aKLH IgG2/Fc-ShK product contained one copy of each of components (a)-(c), immediately above, configured as in FIG. 1E. Because of this, the ratio was 1:1:1. This product can be described as half antibody and half Fc fusion ("hemibody"), coupled together at the Fc domain. Additional peptide assemblies that had to be removed from the culture were the aKLH Ab and the Fc-ShK homodimer.

Monovalent aKLH 120.6 IgG2-ShK and ShK Peptide Analog Fusions.

The components of the aKLH 120.6 IgG2-ShK fusion antibody (schematically represented in FIG. 1F) included monomers:

(a) aKLH 120.6 kappa LC (SEQ ID NO:28, above);

(b) aKLH 120.6 IgG2 HC (SEQ ID NO:29, above); and (c) aKLH 120.6 IgG2-ShK fusion having the following HC sequence:

(SEQ ID NO: 31)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGSGGGGSRSCIDTIPKSRCTAFQCKHSMKYR

LSFCRKTCGTC//.

The components of a monovalent aKLH 120.6 IgG2-ShK [1-35, Q16K] fusion antibody (schematically represented in FIG. 1F) included monomers:

(a) aKLH 120.6 kappa LC (SEQ ID NO:28, above);

(b) aKLH 120.6 IgG2 HC (SEQ ID NO:29, above); and (c) aKLH 120.6 IgG2-ShK[1-35, Q16K] fusion having the following sequence:

(SEQ ID NO: 32)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGSGGGGSRSCIDTIPKSRCTAFKCKHSMKYR

LSFCRKTCGTC//.

The components of the monovalent aKLH 120.6 HC-ShK [1-35, R1A, I4A, Q16K] fusion antibody (schematically represented in FIG. 1F) included the following monomers:
(a) aKLH 120.6 kappa LC (SEQ ID NO:28);

(b) aKLH 120.6 IgG2 HC (SEQ ID NO:29); and (c) aKLH 120.6 IgG2 HC-ShK[1-35, R1A, I4A, Q16K] fusion having the following amino acid sequence:

```
                                         (SEQ ID NO: 304)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGSGGGGSASCADTIPKSRCTAFKCKHSMKYR

LSFCRKTCGTC//.
```

The desired monovalent aKLH 120.6 IgG2 HC-ShK analogue product was a full antibody with the ShK peptide fused to the C-terminus of one heavy chain. With two different heavy chains sharing one variety of light chain, the ratio of heavy chain:chain:light chain:heavychain-ShK was 1:2:1. The expected expression products are aKLH 120.6 IgG2 antibody, monovalent aKLH 120.6 IgG2 HC-ShK peptide analog, and bivalent aKLH 120.6 IgG2 HC-ShK peptide analog. The monovalent aKLH 120.6 IgG2 HC-toxin peptide fusion-containing antibody was isolated from the mix using cation exchange chromatography, as described herein.

The components of the monovalent aKLH 120.6 HC-ShK [1-35, R1A, Q16K, K30E] fusion antibody (schematically represented in FIG. 1F) included the following monomers:

(a) aKLH 120.6 kappa LC (SEQ ID NO:28);

(b) aKLH 120.6 IgG2 HC (SEQ ID NO:29); and (c) aKLH 120.6 IgG2-ShK[1-35, R1A, Q16K, K30E] fusion having the following sequence:

```
                                         (SEQ ID NO: 305)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC
```

-continued

```
PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGSGGGGSASCIDTIPKSRCTAFKCKHSMKYR

LSFCRETCGTC//.
```

The desired monovalent aKLH 120.6 IgG2 HC-ShK analogue product was a full antibody with the ShK peptide fused to the C-terminus of one heavy chain. With two different heavy chains sharing one variety of light chain, the ratio of heavy chain:chain:light chain:heavychain-ShK was 1:2:1. The expected expression products are aKLH 120.6 IgG2 antibody, monovalent aKLH 120.6 IgG2 HC-ShK peptide analog, and bivalent aKLH 120.6 IgG2 HC-ShK peptide analog. The monovalent aKLH 120.6 IgG2 HC-toxin peptide fusion-containing antibody was isolated from the mix using cation exchange chromatography, as described herein.

The components of the monovalent aKLH 120.6 HC (IgG2)-ShK[1-35, R1H, I4A, Q16K] fusion antibody (schematically represented in FIG. 1F) included monomers:

(a) aKLH 120.6 kappa LC (SEQ ID NO:28);

(b) aKLH 120.6 IgG2 HC (SEQ ID NO:29); and (c) aKLH 120.6 HC IgG2-ShK[1-35, R1H, I4A, Q16K] fusion having the following amino acid sequence:

```
                                         (SEQ ID NO: 306)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGSGGGGSHSCADTIPKSRCTAFKCKHSMKYR

LSFCRKTCGTC//.
```

The desired monovalent aKLH 120.6 IgG2 HC-ShK analogue product was a full antibody with the ShK peptide fused to the C-terminus of one heavy chain. With two different heavy chains sharing one variety of light chain, the ratio of heavy chain:chain:light chain:heavychain-ShK was 1:2:1. The expected expression products are aKLH 120.6 IgG2 antibody, monovalent aKLH 120.6 IgG2 HC-ShK peptide analog, and bivalent aKLH 120.6 IgG2 HC-ShK peptide analog. The monovalent aKLH 120.6 IgG2 HC-toxin peptide fusion-containing antibody was isolated from the mix using cation exchange chromatography, as described herein.

The components of the monovalent aKLH 120.6 HC-ShK [1-35, R1H, Q16K, K30E] fusion antibody (schematically represented in FIG. 1F) included the monomers:

(a) aKLH 120.6 kappa LC (SEQ ID NO:28);

(b) aKLH 120.6 IgG2 HC (SEQ ID NO:29); and (c) aKLH 120.6 IgG2-ShK[1-35, R1H, Q16K, K30E] fusion having the following sequence:

(SEQ ID NO: 307)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGSGGGGSHSCIDTIPKSRCTAFKCKHSMKYR

LSFCRETCGTC//.

The desired monovalent aKLH 120.6 IgG2 HC-ShK analogue product was a full antibody with the ShK peptide fused to the C-terminus of one heavy chain. With two different heavy chains sharing one variety of light chain, the ratio of heavy chain:chain:light chain:heavychain-ShK was 1:2:1. The expected expression products are aKLH 120.6 IgG2 antibody, monovalent aKLH 120.6 IgG2 HC-ShK peptide analog, and bivalent aKLH 120.6 IgG2 HC-ShK peptide analog. The monovalent aKLH 120.6 IgG2 HC-toxin peptide fusion-containing antibody was isolated from the mix using cation exchange chromatography, as described herein.

The components of the monovalent aKLH 120.6 HC-ShK [1-35, R1K, I4A, Q16K] fusion antibody (schematically represented in FIG. 1F) included the monomers:

(a) aKLH 120.6 kappa LC (SEQ ID NO:28);

(b) aKLH 120.6 IgG2 HC (SEQ ID NO:29); and (c) aKLH 120.6 HC (IgG2)-ShK[1-35, R1K, I4A, Q16K] fusion having the following sequence:

(SEQ ID NO: 308)

MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGSGGGGSKSCADTIPKSRCTAFKCKHSMKYR

LSFCRKTCGTC//.

The desired monovalent aKLH 120.6 IgG2 HC-ShK analogue product was a full antibody with the ShK peptide fused to the C-terminus of one heavy chain. With two different heavy chains sharing one variety of light chain, the ratio of heavy chain:chain:light chain:heavychain-ShK was 1:2:1. The expected expression products are aKLH 120.6 IgG2 antibody, monovalent aKLH 120.6 IgG2 HC-ShK peptide analog, and bivalent aKLH 120.6 IgG2 HC-ShK peptide analog. The monovalent aKLH 120.6 IgG2 HC-toxin peptide fusion-containing antibody was isolated from the mix using cation exchange chromatography, as described herein.

The components of the monovalent aKLH 120.6 HC-ShK [1-35, R1K, Q16K, K30E] fusion antibody (schematically represented in FIG. 1F) included the monomers:

(a) aKLH 120.6 kappa LC (SEQ ID NO:28);

(b) aKLH 120.6 IgG2 HC (SEQ ID NO:29); and (c) aKLH 120.6 IgG2-ShK[1-35, R1K, Q16K, K30E] fusion having the following amino acid sequence:

(SEQ ID NO: 309)

MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGSGGGGSKSCIDTIPKSRCTAFKCKHSMKYR

LSFCRETCGTC//.

The desired monovalent aKLH 120.6 IgG2 HC-ShK analogue product was a full antibody with the ShK peptide fused to the C-terminus of one heavy chain. With two different heavy chains sharing one variety of light chain, the ratio of heavy chain:chain:light chain:heavychain-ShK was 1:2:1. The expected expression products are aKLH 120.6 IgG2 antibody, monovalent aKLH 120.6 IgG2 HC-ShK peptide analog, and bivalent aKLH 120.6 IgG2 HC-ShK peptide analog. The monovalent aKLH 120.6 IgG2 HC-toxin peptide fusion-containing antibody was isolated from the mix using cation exchange chromatography, as described herein.

The components of a monovalent aKLH 120.6 IgG2-ShK [2-35, Q16K] fusion antibody (schematically represented in FIG. 1F) included monomers:

(a) aKLH 120.6 kappa LC (SEQ ID NO:28, above);

(b) aKLH 120.6 IgG2 HC (SEQ ID NO:29, above); and (c) aKLH 120.6 IgG2-ShK[2-35, Q16K] fusion having the following HC sequence:

(SEQ ID NO: 33)

MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGSGGGGSSCIDTIPKSRCTAFKCKHSMKYRL

SFCRKTCGTC//.

Figure 1F:
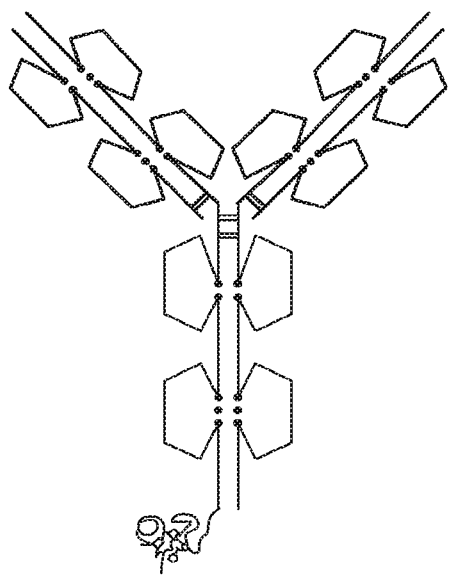
FIG. 1F represents a monovalent heterotetrameric (HT) antibody HC-toxin peptide analog fusion, with a toxin peptide analog fused to the C-terminal end of one of the HC monomers.

The desired aKLH 120.6 IgG2-ShK analog product was a full antibody with the ShK peptide fused to the C-terminus of one heavy chain, configured as in FIG. 1F. With two different heavy chains sharing one variety of light chain, the ratio of heavy chain:light chain:heavy chain-ShK was 1:2:1. The expected expression products are aKLH 120.6 IgG2, monovalent aKLH 120.6 IgG2-ShK, and bivalent aKLH 120.6 IgG2-ShK. The monovalent aKLH 120.6 IgG2-toxin peptide (or toxin peptide analog) fusion antibody was isolated from the mix using cation exchange chromatography, as described herein.

Anti-KLH IgG1-loop-ShK.

The aKLH IgG1-loop-ShK also had a single copy of the ShK peptide sequence inserted into one of the heavy chains, but in this case it was inserted into an internal conjugation in the Fc domain instead of at the C-terminus. (See, e.g., Gegg et al., U.S. Pat. No. 7,442,778; U.S. Pat. No. 7,655,765; U.S. Pat. No. 7,655,764; U.S. Pat. No. 7,662,931; U.S. Pat. No. 7,645,861; published U.S. Patent Applications US 2009/0281286; and US 2009/0286964, each of which are incorporated herein by reference in their entireties). The components of the aKLH IgG1-loop-ShK antibody include (a) aKLH 120.6 kappa LC (SEQ ID NO:28, above);

(b) aKLH 120.6 IgG1 HC:

(SEQ ID NO: 34)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKRVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCS

VMHEALHNHYTQKSLSLSPGK//;

and
(c) aKLH 120.6 IgG1-loop-ShK:

(SEQ ID NO: 35)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKRVEPKSCDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELGGRSCIDTIPKSRCTAFK

CKHSMKYRLSFCRKTCGTCGGTKNQVSLTCLVKGFYPSDIAVEWESNGQP

ENNYKTTPPVLDSDGSFFLYSKLTVDKSRWQQGNVFSCSVMHEALHNHYT

QKSLSLSPGK//.

Figure 1G:
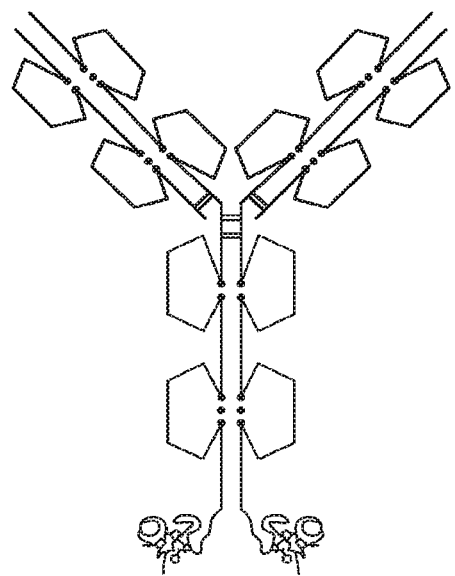
FIG. 1G represents a bivalent HT antibody Ab HC-toxin peptide analog fusion having toxin peptide analogs on the C-terminal ends of both HC monomers.
Figure 1H:
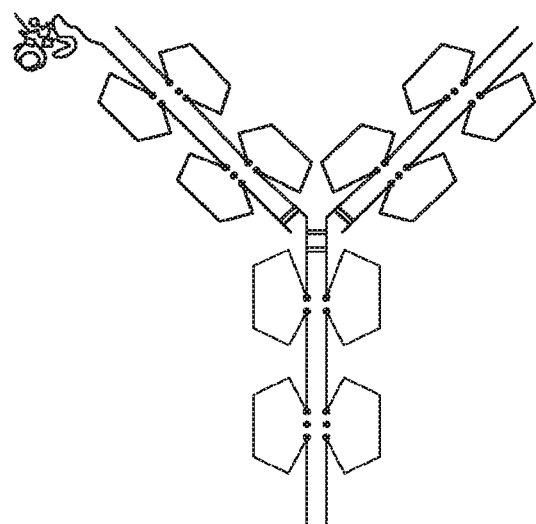
FIG. 1H represents a monovalent HT toxin peptide analog-LC Ab, with the toxin peptide analog fused to the N-terminal end of one of the LC monomers.
Figure 1I:
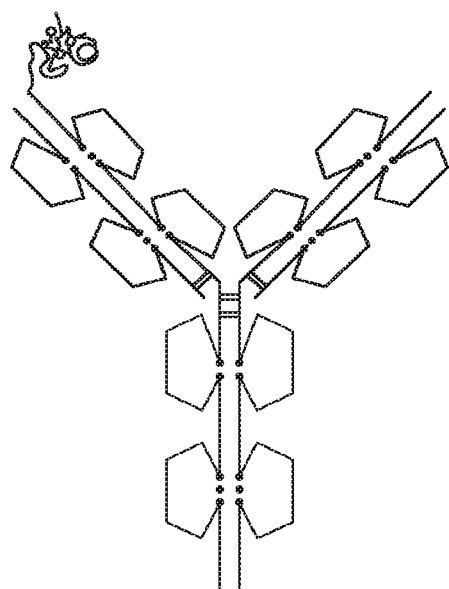
FIG. 1I represents a monovalent HT toxin peptide analog-HC Ab, with the toxin peptide analog fused to the N-terminal end of one of the HC monomers.

With two different heavy chains sharing one light chain, the ratio of heavy chain:light chain:heavy chain-ShK is 1:2:1. The expected expression products are aKLH 120.6 IgG1, monovalent aKLH 120.6 IgG1-loop-ShK, and bivalent aKLH 120.6 IgG1-loop-ShK. The monovalent aKLH 120.6 IgG1-loop-ShK fusion antibody (represented schematically by FIG. 1N) was isolated from the mix using cation exchange chromatography as described herein.

Monovalent aKLH 120.6 kappa LC-ShK[1-35, Q16K] Fusion.

The components of the monovalent aKLH 120.6 kappa LC-ShK[1-35, Q16K] fusion antibody (schematically represented in FIG. 1J) included the monomers:

(a) aKLH 120.6 IgG2 HC (SEQ ID NO:29);

(b) aKLH 120.6 kappa LC (SEQ ID NO:28); and (c) aKLH 120.6 kappa LC-ShK[1-35, Q16K] fusion having the following sequence:

(SEQ ID NO: 267)
MDMRVPAQLLGLLLLWLRGARCDIQMTQSPSSLSASVGDRVTITCRASQG

IRNDLGWYQQKPGKAPKRLIYAASSLQSGVPSRFSGSGSGTEFTLTISSL

QPEDFATYYCLQHNSYPLTFGGGTKVEIKRTVAAPSVFIFPPSDEQLKSG

TASVVCLLNNFYPREAKVQWKVDNALQSGNSQESVTEQDSKDSTYSLSST

LTLSKADYEKHKVYACEVTHQGLSSPVTKSFNRGECGGGGSGGGGSRSCI

DTIPKSRCTAFKCKHSMKYRLSFCRKTCGTC//.

Figure 1J:
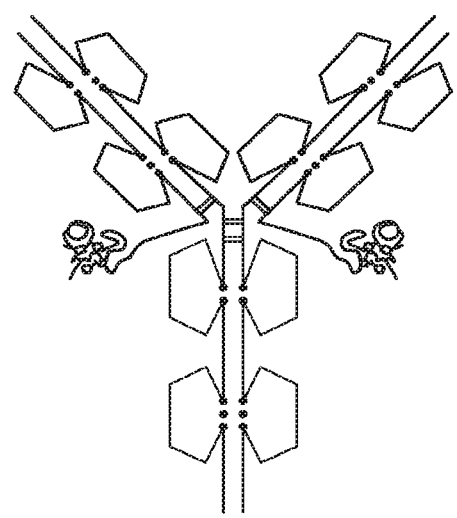
FIG. 1J represents a monovalent HT Ab LC-toxin peptide analog fusion (i.e., LC-toxin peptide analog fusion+LC+2(HC)), with the toxin peptide analog fused to the C-terminal end of one of the LC monomers.

This embodiment of monovalent aKLH 120.6 IgG2 LC-ShK [1-35, Q16K] product was a full antibody with the ShK peptide fused to the C-terminus of one light chain as shown in FIG. 1J. With two different light chains sharing one variety of heavy chain, the ratio of light chain:heavy chain: light chain-ShK[1-35, Q16K] was 1:2:1. The expected expression products are aKLH 120.6 IgG2, monovalent aKLH 120.6 IgG2 LC-ShK[1-35, Q16K], and bivalent aKLH 120.6 IgG2 LC-ShK[1-35, Q16K]. The monovalent aKLH 120.6 IgG2 LC-toxin peptide fusion-containing antibody was isolated from the mix using cation exchange chromatography, as described herein.

Monovalent aKLH 120.6 kappa LC-ShK[2-35, Q16K] Fusion.

The components of the monovalent aKLH 120.6 kappa LC-ShK[2-35, Q16K] fusion antibodies (schematically represented in FIG. 1J) included the monomers:

(a) aKLH 120.6 IgG2 HC (SEQ ID NO:29);

(b) aKLH 120.6 kappa LC (SEQ ID NO:28); and (c) aKLH 120.6 kappa LC-ShK[2-35, Q16K] fusion having the following sequence:

(SEQ ID NO: 268)
MDMRVPAQLLGLLLLWLRGARCDIQMTQSPSSLSASVGDRVTITCRASQG

IRNDLGWYQQKPGKAPKRLIYAASSLQSGVPSRFSGSGSGTEFTLTISSL

-continued

```
QPEDFATYYCLQHNSYPLTFGGGTKVEIKRTVAAPSVFIFPPSDEQLKSG

TASVVCLLNNFYPREAKVQWKVDNALQSGNSQESVTEQDSKDSTYSLSST

LTLSKADYEKHKVYACEVTHQGLSSPVTKSFNRGECGGGGSGGGGSSCID

TIPKSRCTAFKCKHSMKYRLSFCRKTCGTC//.
```

This embodiment of monovalent aKLH 120.6 IgG2 LC-ShK [2-35, Q16K] product was a full antibody with the ShK peptide fused to the C-terminus of one light chain as shown in FIG. 1J. With two different light chains sharing one variety of heavy chain, the ratio of light chain:heavy chain: light chain-ShK[2-35, Q16K] was 1:2:1. The expected expression products are aKLH 120.6 IgG2, monovalent aKLH 120.6 IgG2 LC-ShK[2-35, Q16K], and bivalent aKLH 120.6 IgG2 LC-ShK[2-35, Q16K]. The monovalent aKLH 120.6 IgG2 LC-toxin peptide fusion-containing antibody was isolated from the mix using cation exchange chromatography, as described herein.

Bivalent aKLH 120.6 kappa LC-ShK[1-35, Q16K] Fusion.

The components of the bivalent aKLH 120.6 kappa LC-ShK[1-35, Q16K] fusion antibodies (schematically represented in FIG. 1K) included the monomers:
  (a) aKLH 120.6 IgG2 HC (SEQ ID NO:29); and
  (b) aKLH 120.6 kappa LC-ShK[1-35, Q16K] fusion (SEQ ID NO:267), above.

Figure 1K:
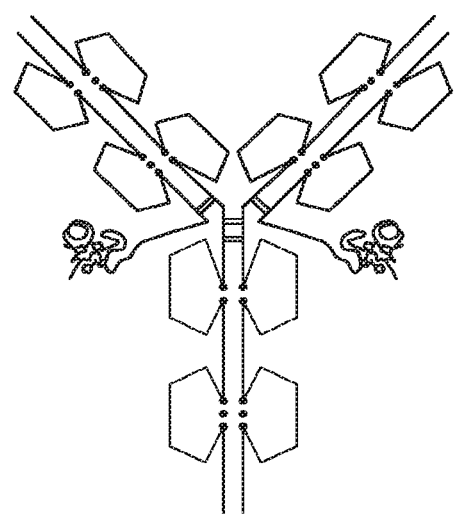
FIG. 1K represents a bivalent HT Ab LC-toxin peptide analog fusion (i.e., 2(LC-toxin peptide analog fusion)+2 (HC)), with toxin peptide analogs fused to the C-terminal end of both of the LC monomers.

This embodiment of bivalent aKLH 120.6 IgG2 LC-ShK[1-35, Q16K] antibody product was a full antibody with the ShK peptide fused to the C-terminus of both light chains as shown in FIG. 1K. The ratio of heavy chain:light chain-ShK[1-35, Q16K] was 1:1. The expected expression product is bivalent aKLH 120.6 IgG2 LC-ShK[1-35, Q16K]. The bivalent aKLH 120.6 IgG2 LC-ShK[1-35, Q16K] peptide fusion-containing antibody molecule was isolated from the mix using cation exchange chromatography, as described herein.

Bivalent aKLH 120.6 kappa LC-ShK[2-35, Q16K] Fusion.

The components of the bivalent aKLH 120.6 kappa LC-ShK[2-35, Q16K] fusion antibodies (schematically represented in FIG. 1K) included the monomers:
  (a) aKLH 120.6 IgG2 HC (SEQ ID NO:29); and
  (b) aKLH 120.6 kappa LC-ShK[2-35, Q16K] fusion (SEQ ID NO:268), above.

This embodiment of bivalent aKLH 120.6 IgG2 LC-ShK[2-35, Q16K] product was a full antibody with the ShK peptide fused to the C-terminus of both light chains as shown in FIG. 1K. The ratio of heavy chain:light chain-ShK[2-35, Q16K] was 1:1. The expected expression product is bivalent aKLH 120.6 IgG2 LC-ShK[2-35, Q16K] antibody. The bivalent aKLH 120.6 IgG2 LC-ShK[2-35, Q16K] toxin fusion-containing antibody was isolated from the mix using cation exchange chromatography, as described herein.

Trivalent aKLH 120.6 kappa LC-ShK[1-35, Q16K] Fusion.

The components of the trivalent aKLH 120.6 kappa LC-ShK[1-35, Q16K] fusion antibodies (schematically represented in FIG. 1L) included the monomers:
  a) aKLH 120.6 IgG2 HC (SEQ ID NO:29, above);
  (b) aKLH 120.6 IgG2 HC-Shk[1-35, Q16K] fusion having the amino acid of SEQ ID NO:32, above; and
  (c) aKLH 120.6 kappa LC-ShK[1-35, Q16K] fusion having the amino acid sequence of SEQ ID NO:267, above.

Figure 1L:
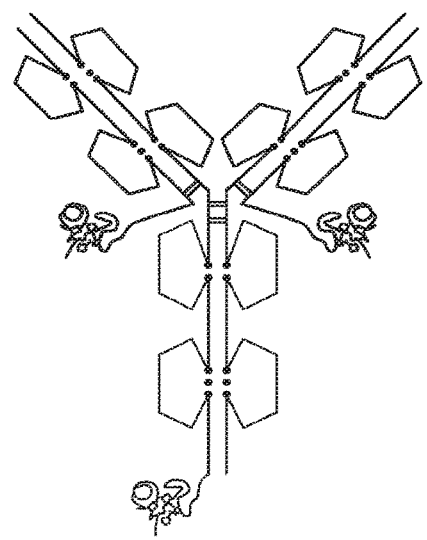
FIG. 1L represents a trivalent HT Ab LC-toxin peptide analog/HC-toxin peptide analog (i.e., 2(LC-toxin peptide analog fusion)+HC-toxin peptide analog fusion+HC), with the toxin peptide analogs fused to the C-terminal ends of both of the LC monomers and one of the HC monomers.

This embodiment of trivalent aKLH 120.6 IgG2 LC-ShK product was a full antibody with the ShK[1-35, Q16K] peptide fused to the C-terminus of both light chains and one heavy chain as shown in FIG. 1L. With two different heavy chains sharing one variety of light chain, the ratio of heavy chain:light chain-ShK[1-35, Q16K]:heavy chain-ShK[1-35, Q16K] was 1:2:1. The expected expression products were a bivalent aKLH 120.6 IgG2 LC-ShK[1-35, Q16K] antibody, trivalent aKLH 120.6 IgG2 LC-ShK[1-35, Q16K] antibody, and tetravalent aKLH 120.6 IgG2 LC-ShK[1-35, Q16K] antibody. The trivalent aKLH 120.6 IgG2 LC-toxin peptide fusion-containing antibody molecule was isolated from the mix using cation exchange chromatography, as described herein.

Trivalent aKLH 120.6 kappa LC-ShK[2-35, Q16K] Fusion.

The components of the trivalent aKLH 120.6 kappa LC-ShK[2-35, Q16K] fusion antibody (schematically represented in FIG. 1L) included the monomers:
  a) aKLH 120.6 IgG2 HC (SEQ ID NO:29);
  (b) aKLH 120.6 IgG2 HC-Shk[2-35, Q16K] fusion (SEQ ID NO:33), above; and
  (c) aKLH 120.6 kappa LC-ShK[2-35, Q16K] fusion (SEQ ID NO:268), above.

This embodiment of trivalent aKLH 120.6 IgG2 LC-ShK[2-35, Q16K] antibody product was a full antibody with the ShK[2-35, Q16K] peptide fused to the C-terminus of both light chains and one heavy chain as shown in FIG. 1L. With two different heavy chains sharing one variety of light chain, the ratio of heavy chain:light chain-ShK[2-35, Q16K]:heavy chain-ShK[2-35, Q16K] was 1:2:1. The expected expression products were a bivalent aKLH 120.6 IgG2 LC-ShK[2-35, Q16K] antibody, trivalent aKLH 120.6 IgG2 LC-ShK[2-35, Q16K] antibody, and tetravalent aKLH 120.6 IgG2 LC-ShK[2-35, Q16K] antibody. The trivalent aKLH 120.6 IgG2 LC-toxin peptide fusion-containing antibody molecule was isolated from the mix using cation exchange chromatography, as described herein.

Anti-KLH 120.6 Antibody Light Chain Mammalian Expression.

The XenoMouse® hybridoma expressing KLH monoclonal antibody 120.6 was used as a source to isolate total RNA using TRIzol® reagent (Invitrogen). First strand cDNA was synthesized using a random primer with an extension adapter 5'-GGC CGG ATA GGC CTC CAN NNN NNT-3' (SEQ ID NO:36) and a 5' RACE (rapid amplification of cDNA ends) was performed using the GeneRacer™ Kit (Invitrogen). For the light chain sequence determination, the forward primer was 5'-GTG GTT GAG AGG TGC CAG ATG TGA CAT TGT GAT GAC TCA GTC TCC-3' (SEQ ID NO:37) and the reverse primer was 5'-AAC CGT TTA AAC GCG GCC GCT CAA CAC TCT CCC CTG TTG AA-3' (SEQ ID NO:38). The RACE product was cloned into pCR4-TOPO (Invitrogen) and the sequences determined. Consensus sequences were used to determine probable framework and signal peptide sequence and design primers for full-length antibody chain PCR amplification.

The expression clone for the anti-KLH 120.6 kappa light chain was prepared by PCR. The 5' PCR primer encoded the amino terminus of the signal sequence, an SalI restriction enzyme site, and an optimized Kozak sequence 5'-AAG CTC GAG GTC GAC TAG ACC ACC ATG GAC ATG AGG GTC CCC G-3' (SEQ ID NO:39). The 3' primer encoded the carboxyl terminus and termination codon, as well as a Nod restriction site 5'-AAC CGT TTA AAC GCG GCC GCT CAA CAC TCT CCC CTG TTG AA-3' (SEQ ID NO:38). The resulting product was cloned into pCR4-TOPO (Invitrogen) and the sequences determined. After the insert was confirmed, the pCR4-TOPO product was cut with SalI and NoI, the insert gel isolated and Qiagen purified, and then ligated into the mammalian expression vector pTT5.

A PCR was done to change the signal peptide from the native peptide derived from the hybridoma to the VK1/O12 peptide. The primers used for the VK1/O12 fragment were 5' AAG CTC GAG GTC GAC TAG ACC ACC ATG GAC ATG AGG GTG CCC GCT 3' (SEQ ID NO:40) and 5'-TCA TCT GGA TGT CAC ATC TGG CAC C-3' (SEQ ID NO:41). The primers used for the mature light chain peptide were 5'-GGT GCC AGA TGT GAC ATC CAG ATG A-3' (SEQ ID NO:42) and (SEQ ID NO:38). The resulting fragments were joined by overlap PCR using primers (SEQ ID NO:40) and (SEQ ID NO:38). The sequence of the resulting clone encodes the following immunoglobulin kappa LC sequence:

(SEQ ID NO: 28)
MDMRVPAQLLGLLLLWLRGARCDIQMTQSPSSLSASVGDRVTITCRASQG

IRNDLGWYQQKPGKAPKRLIYAASSLQSGVPSRFSGSGSGTEFTLTISSL

QPEDFATYYCLQHNSYPLTFGGGTKVEIKRTVAAPSVFIFPPSDEQLKSG

TASVVCLLNNFYPREAKVQWKVDNALQSGNSQESVTEQDSKDSTYSLSST

LTLSKADYEKHKVYACEVTHQGLSSPVTKSFNRGEC//.

Anti-KLH 120.6 Antibody Light Chain-ShK Peptide Analog Mammalian Expression.

The Shk[1-35, Q16K] fragment was generated by PCR using the pTT14-huIgG2-Fc ShK[1-35, Q16K] encoding (SEQ ID NO:26), described above, as a template and the oligos:

(SEQ ID NO: 269)
5'-AAC AGG GGA GAG TGT GGA GGA GGA GGA TCC GGA G-3';
and (SEQ ID NO: 270)
5'-CAT GCG GCC GCT CAT TAG CAG G-3'.

The light chain fragment and ShK PCR product were then amplified by PCR using the outside primers CAT TCT AGA ACC ACC ATG GAC ATG AGG GTG// (SEQ ID NO:343) and SEQ ID NO:270. The PCR product was then digested by XbaI and NotI and PCR clean up kit (Qiagen) purified. At the same time, pYD16 was cut by XbaI and NotI. The pYD16 vector was run out on a 1% agarose gel and the larger fragment was cut out and gel purified by Qiagen's Gel Purification Kit. The purified PCR product was ligated to the large vector fragment and transformed into OneShot Top10 bacteria. DNAs from transformed bacterial colonies were isolated and subjected to XbaI and NotI restriction enzyme digestions and resolved on a one percent agarose gel. DNAs resulting in an expected pattern were submitted for sequencing. Although, analysis of several sequences of clones yielded a 100% percent match with the above sequence, only one clone was selected for large scaled plasmid purification. The final pYD16-aKLH120.6-VK1SP-LC-L10-ShK[1-35, Q16K] construct encoded an aKLH 120.6 LC-L10-ShK[1-35, Q16K] fusion polypeptide (SEQ ID NO:267).

The Shk[2-35, Q16K] fragment was generated as described above using pTT5-aKLH120.6 HC-ShK[2-35, Q16K] as a template and the oligonucleotide primers SEQ ID NO:269 and SEQ ID NO:270.

The light chain and ShK PCR products were amplified by PCR using the outside primers SEQ ID NO:343 and SEQ ID NO:270. The PCR product was then digested by XbaI and NotI and PCR clean up kit (Qiagen) purified. At the same time, pYD16 was cut by XbaI and NotI. The pYD16 vector was run out on a 1% agarose gel and the larger fragment was cut out and gel purified by Qiagen's Gel Purification Kit. The purified PCR product was ligated to the large vector fragment and transformed into OneShot Top10 bacteria. DNAs from transformed bacterial colonies were isolated and subjected to XbaI and NotI restriction enzyme digestions and resolved on a one percent agarose gel. DNAs resulting in an expected pattern were submitted for sequencing. Although, analysis of several sequences of clones yielded a 100% percent match with the above sequence, only one clone was selected for large scaled plasmid purification. The final pYD16-aKLH 120.6-VK1SP-LC-L10-ShK[2-35, Q16K] construct encoded an IgG2-LC-L10-ShK[2-35, Q16K] fusion polypeptide monomer (SEQ ID NO:268).

aKLH-IgG2 Heavy Chain-L10-ShK[1-35] and aKLH-IgG2 Heavy Chain-L10-ShK Peptide Analogs in Mammalian Expression.

Using Oligos (SEQ ID NO: 43)
5'-CAT TCT AGA CCC ACC ATG GAC ATG AGG GTG-3';
and (SEQ ID NO: 44)
5'-GGA TCC TCC TCC TCC ACC CGG AGA CAG GGA GAG G-3', the aKLH-IgG2-Heavy Chain region was amplified by PCR from a pTT5-aKLH 120.6-VK1SP-IgG2 Heavy Chain (HC) construct containing the coding sequence (SEQ ID NO:45; below), encoding aKLH 120.6-VK1SP-IgG2 Heavy Chain (SEQ ID NO:46; below):

(SEQ ID NO: 45)
ATGGACATGAGGGTGCCCGCTCAGCTCCTGGGGCTCCTGCTGCTGTGGCT

GAGAGGTGCCAGATGTCAGGTGCAGCTGGTGCAGTCTGGGGCTGAGGTGA

AGAAGCCTGGGGCCTCAGTGAAGGTCTCCTGCAAGGCTTCTGGATACACC

TTCACCGGCTACCACATGCACTGGGTGCGACAGGCCCCTGGACAAGGGCT

TGAGTGGATGGGATGGATCAACCCTAACAGTGGTGGCACAAACTATGCAC

AGAAGTTTCAGGGCAGGGTCACCATGACCAGGGACACGTCCATCAGCACA

GCCTACATGGAGCTGAGCAGGCTGAGATCTGACGACACGGCCGTGTATTA

CTGTGCGAGAGATCGTGGGAGCTACTACTGGTTCGACCCCTGGGGCCAGG

GAACCCTGGTCACCGTCTCCTCAGCCTCCACCAAGGGCCCATCGGTCTTC

CCCCTGGCGCCCTGCTCCAGGAGCACCTCCGAGAGCACAGCGGCCCTGGG

CTGCCTGGTCAAGGACTACTTCCCCGAACCGGTGACGGTGTCGTGGAACT

CAGGCGCTCTGACCAGCGGCGTGCACACCTTCCCAGCTGTCCTACAGTCC

TCAGGACTCTACTCCCTCAGCAGCGTGGTGACCGTGCCCTCCAGCAACTT

CGGCACCCAGACCTACACCTGCAACGTAGATCACAAGCCCAGCAACACCA

AGGTGGACAAGACAGTTGAGCGCAAATGTTGTGTCGAGTGCCCACCGTGC

CCAGCACCACCTGTGGCAGGACCGTCAGTCTTCCTCTTCCCCCCAAAACC

CAAGGACACCCTCATGATCTCCCGGACCCCTGAGGTCACGTGCGTGGTGG

TGGACGTGAGCCACGAAGACCCCGAGGTCCAGTTCAACTGGTACGTGGAC

```
GGCGTGGAGGTGCATAATGCCAAGACAAAGCCACGGGAGGAGCAGTTCAA

CAGCACGTTCCGTGTGGTCAGCGTCCTCACCGTTGTGCACCAGGACTGGC

TGAACGGCAAGGAGTACAAGTGCAAGGTCTCCAACAAAGGCCTCCCAGCC

CCCATCGAGAAAACCATCTCCAAAACCAAAGGGCAGCCCCGAGAACCACA

GGTGTACACCCTGCCCCCATCCCGGGAGGAGATGACCAAGAACCAGGTCA

GCCTGACCTGCCTGGTCAAAGGCTTCTACCCCAGCGACATCGCCGTGGAG

TGGGAGAGCAATGGGCAGCCGGAGAACAACTACAAGACCACACCTCCCAT

GCTGGACTCCGACGGCTCCTTCTTCCTCTACAGCAAGCTCACCGTGGACA

AGAGCAGGTGGCAGCAGGGGAACGTCTTCTCATGCTCCGTGATGCATGAG

GCTCTGCACAACCACTACACGCAGAAGAGCCTCTCCCTGTCTCCGGG

T//,
``` encoding the amino acid sequence

```
                                         (SEQ ID NO: 46)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPG//.
```

The ShK[1-35]WT fragment was generated using the original Fc-L10-ShK[1-35] in pcDNA3.1(+)CMVi as a template (described in Example 1, FIG. 14A-14B in Sullivan et al., Toxin Peptide Therapeutic Agents, PCT/US2007/022831, published as WO 2008/088422, which is incorporated herein by reference in its entirety) and the oligos:

```
                                          (SEQ ID NO: 47)
5'-TCC CTG TCT CCG GGT GGA GGA GGA GGA TCC GGA

G-3';
and (SEQ ID NO: 14)
5'-CAT GCG GCC GCT CAT TAG CAG GTG-3'
```

The PCR products were run on a 1% agarose gel. The bands were punched for an agarose plug and the plugs were placed in a fresh PCR reaction tube. The agarose plugs were then amplified by PCR using the outside primers SEQ ID NO:357 and SEQ ID NO:330. The PCR product was then digested by XbaI and NotI and PCR clean up kit (Qiagen) purified. At the same time, pTT5 Vector (an Amgen vector containing a CMV promoter and Poly A tail) was cut by XbaI and NotI. The pTT5 vector was run out on a 1% agarose gel and the larger fragment was cut out and gel purified by Qiagen's Gel Purification Kit. The purified PCR product was ligated to the large vector fragment and transformed into OneShot Top10 bacteria. DNAs from transformed bacterial colonies were isolated and subjected to XbaI and NotI restriction enzyme digestions and resolved on a one percent agarose gel. DNAs resulting in an expected pattern were submitted for sequencing. Although, analysis of several sequences of clones yielded a 100% percent match with the above sequence, only one clone was selected for large scaled plasmid purification. The final pTT5-aKLH 120.6-VK1SP-IgG2-HC-L10-ShK[1-35] construct encoded an IgG2-HC-L10-ShK[1-35] fusion polypeptide with the amino acid sequence:

```
                                          (SEQ ID NO: 48)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGSGGGGSRSCIDTIPKSRCTAFQCKHSMKYR

LSFCRKTCGTC//.
```

To generate the ShK[1-35, Q16K] mutant version of this construct, site-directed mutagenesis was performed using the Stratagene Quikchange Multi site Directed Mutagenesis Kit (Cat #200531), per manufacturer's instructions, and oligos:

```
                                           (SEQ ID NO: 9)
5'-GCT GCA CCG CCT TCA AGT GCA AGC ACA GC 3';
and (SEQ ID NO: 10)
5'-GCT GTG CTT GCA CTT GAA GGC GGT GCA GC-3',.
```

The final construct pTT5-aKLH120.6-VK1SP-IgG2-HC-L10-ShK[1-35, Q16K] encoded IgG2-HC-L10-ShK[1-35, Q16K] fusion polypeptide with the following amino acid sequence:

```
                                          (SEQ ID NO: 49)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGSGGGGSRSCIDTIPKSRCTAFKCKHSMKYR

LSFCRKTCGTC//.
``` aKLH-IgG2 Heavy Chain-L10-ShK[2-35, Q16K] Mammalian Expression.

Using DNA construct pTT5-aKLH 120.6-VK1SP-IgG2-HC-L10-ShK[1-35] as the vector, the ShK[1-35] was cut out using BamHI/BamHI. The vector fragment from pTT5-aKLH 120.6-VK1SP-IgG2-HC without ShK[1-35] contained the coding sequence:

(SEQ ID NO: 50)

```
ATGGACATGAGGGTGCCCGCTCAGCTCCTGGGGCTCCTGCTGCTGTGGCT
GAGAGGTGCCAGATGTCAGGTGCAGCTGGTGCAGTCTGGGGCTGAGGTGA
AGAAGCCTGGGGCCTCAGTGAAGGTCTCCTGCAAGGCTTCTGGATACACC
TTCACCGGCTACCACATGCACTGGGTGCGACAGGCCCCTGGACAAGGGCT
TGAGTGGATGGGATGGATCAACCCTAACAGTGGTGGCACAAACTATGCAC
AGAAGTTTCAGGGCAGGGTCACCATGACCAGGGACACGTCCATCAGCACA
GCCTACATGGAGCTGAGCAGGCTGAGATCTGACGACACGGCCGTGTATTA
CTGTGCGAGAGATCGTGGGAGCTACTACTGGTTCGACCCCTGGGGCCAGG
GAACCCTGGTCACCGTCTCCTCAGCCTCCACCAAGGGCCCATCGGTCTTC
CCCCTGGCGCCCTGCTCCAGGAGCACCTCCGAGAGCACAGCGGCCCTGGG
CTGCCTGGTCAAGGACTACTTCCCCGAACCGGTGACGGTGTCGTGGAACT
CAGGCGCTCTGACCAGCGGCGTGCACACCTTCCCAGCTGTCCTACAGTCC
TCAGGACTCTACTCCCTCAGCAGCGTGGTGACCGTGCCCTCCAGCAACTT
CGGCACCCAGACCTACACCTGCAACGTAGATCACAAGCCCAGCAACACCA
AGGTGGACAAGACAGTTGAGCGCAAATGTTGTGTCGAGTGCCCACCGTGC
CCAGCACCACCTGTGGCAGGACCGTCAGTCTTCCTCTTCCCCCCAAAACC
CAAGGACACCCTCATGATCTCCCGGACCCCTGAGGTCACGTGCGTGGTGG
TGGACGTGAGCCACGAAGACCCCGAGGTCCAGTTCAACTGGTACGTGGAC
GGCGTGGAGGTGCATAATGCCAAGACAAAGCCACGGGAGGAGCAGTTCAA
CAGCACGTTCCGTGTGGTCAGCGTCCTCACCGTTGTGCACCAGGACTGGC
TGAACGGCAAGGAGTACAAGTGCAAGGTCTCCAACAAAGGCCTCCCAGCC
CCCATCGAGAAAACCATCTCCAAAACCAAAGGGCAGCCCCGAGAACCACA
GGTGTACACCCTGCCCCCATCCCGGGAGGAGATGACCAAGAACCAGGTCA
GCCTGACCTGCCTGGTCAAAGGCTTCTACCCCAGCGACATCGCCGTGGAG
TGGGAGAGCAATGGGCAGCCGGAGAACAACTACAAGACCACACCTCCCAT
GCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAG
GCTCTGCACAACCACTACACGCAGAAGAGCCTCTCCCTGTCTCCGGGTGG
AGGAGGA//,
``` encoding the amino acid sequence (SEQ ID NO: 51)

```
MDMRVPAQLLGLLLLWLRGARCQVQLVQSGAEVKKPGASVKVSCKASGYT
FTGYHMHWVRQAPGQGLEWMGWINPNSGGTNYAQKFQGRVTMTRDTSIST
AYMELSRLRSDDTAVYYCARDRGSYYWFDPWGQGTLVTVSSASTKGPSVF
PLAPCSRSTSESTAALGCLVKDYFPEPVTVSWNSGALTSGVHTFPAVLQS
```

-continued

```
SGLYSLSSVVTVPSSNFGTQTYTCNVDHKPSNTKVDKTVERKCCVECPPC
PAPPVAGPSVFLFPPKPKDTLMISRTPEVTCVVVDVSHEDPEVQFNWYVD
GVEVHNAKTKPREEQFNSTFRVVSVLTVVHQDWLNGKEYKCKVSNKGLPA
PIEKTISKTKGQPREPQVYTLPPSREEMTKNQVSLTCLVKGFYPSDIAVE
WESNGQPENNYKTTPPMLDSDGSFFLYSKLTVDKSRWQQGNVFSCSVMHE
ALHNHYTQKSLSLSPGGGG//.
```

The vector fragment was then treated with Calf Intestine Phosphatase (CIP) to remove the 5' Phosphate group and Phenol/Chloroform extracted to prevent religation of the vector upon itself. The insert came from pTT14-VH21SP-IgG2-Fc-ShK[2-35, Q16K] encoding IgG2 Fc-L10-ShK(2-35, Q16K):

(SEQ ID NO: 18)

```
MEWSWVFLFFLSVTTGVHSERKVECPPCPAPPVAGPSVFLFPPKPKDTLM
ISRTPEVTCVVVDVSHEDPEVQFNWYVDGVEVHNAKTKPREEQFNSTFRV
VSVLTVVHQDWLNGKEYKCKVSNKGLPAPIEKTISKTKGQPREPQVYTLP
PSREEMTKNQVSLTCLVKGFYPSDIAVEWESNGQPENNYKTTPPMLDSDG
SFFLYSKLTVDKSRWQQGNVFSCSVMHEALHNHYTQKSLSLSPGKGGGGS
GGGGSSCIDTIPKSRCTAFKCKHSMKYRLSFCRKTCGTC//,
``` and the insert was also digested out using BamHI/BamHI. The insert ShK[2-35, Q16K] fragment was gel purified away from its vector and cleaned up with Qiagen Gel Purification Kit. A purified DNA insert containing the coding sequence (SEQ ID NO: 52)

```
GGA TCC GGA GGA GGA GGA AGC AGC TGC ATC GAC ACC
ATC CCC AAG AGC CGC TGC ACC GCC TTC AAG TGC AAG
CAC AGC ATG AAG TAC CGC CTG AGC TTC TGC CGC AAG
ACC TGC GGC ACC TGC TAA TGA//,
``` encoding the amino acid sequence (SEQ ID NO: 53)

```
GSGGGGSSCIDTIPKSRCTAFKCKHSMKYRLSFCRKTCGTC,
``` was ligated to the large vector fragment and transformed into OneShot Top10 bacteria. DNAs from transformed bacterial colonies were isolated and subjected to BamHI restriction enzyme digestion and resolved on a one percent agarose gel. DNAs resulting in an expected pattern were submitted for sequencing. Although, analysis of several sequences of clones yielded a 100% percent match with the above sequence, only one clone was selected for large scaled plasmid purification. The final construct pTT5-aKLH-IgG2 HC-L10-ShK[2-35,Q16K] encoded an IgG2 HC-L10-ShK [2-35,Q16K] fusion polypeptide:

(SEQ ID NO: 54)

```
MDMRVPAQLLGLLLLWLRGARCQVQLVQSGAEVKKPGASVKVSCKASGYT
FTGYHMHWVRQAPGQGLEWMGWINPNSGGTNYAQKFQGRVTMTRDTSIST
AYMELSRLRSDDTAVYYCARDRGSYYWFDPWGQGTLVTVSSASTKGPSVF
```

-continued
PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGSGGGGSSCIDTIPKSRCTAFKCKHSMKYRL

SFCRKTCGTC//.

The Shk[1-35, R1A, I4A, Q16K] fragment was generated using pTT5-aKLH 120.6-VK1SP-IgG2-HC-L10-ShK[1-35 Q16K] as a template and the oligos:

```
                                    (SEQ ID NO: 310)
5'-AGG AGG AGG AAG CGC CAG CTG CGC CGA CAC CAT

CCCC-3'//;
and
                                    (SEQ ID NO: 311)
5'-GGG GAT GGT GTC GGC GCA GCT GGC GCT TCC TCC

TCC T-3'//.
```

Site-directed mutagenesis was performed using the Stratagene Quikchange Multi site Directed Mutagenesis Kit, per manufacturer's instructions. The final pTT5-aKLH120.6-VK1SP-IgG2-HC-L10-ShK[1-35 R1A, I4A, Q16K] construct encoded an IgG2-HC-L10-ShK[1-35, R1A, I4A, Q16K] fusion polypeptide (SEQ ID NO:304).

The Shk[1-35, R1A, Q16K, K30E] fragment was generated as described above using the following four oligos:

```
                                    (SEQ ID NO: 312)
5'-GAG GAG GAG GAA GCG CCA GCT GCA TCG ACA-3'//;

(SEQ ID NO: 313)
5'-GAG CTT CTG CCG CGA GAC CTG CGG CAC-3'//;

(SEQ ID NO: 314)
5'-CGA TGC AGC TGG CGC TTC CTC CTC CTC-3'//;
and
                                    (SEQ ID NO: 315)
5'-GTG CCG CAG GTC TCG CGG CAG AAG CTC-3'//.
```

The final pTT5-aKLH 120.6-VK1SP-IgG2-HC-L10-ShK[1-35 R1A, Q16K, K30E] construct encoded an IgG2-HC-L10-ShK[1-35, R1A, Q16K, K30E] fusion polypeptide (SEQ ID NO:305).

The ShK[1-35, R1H, I4A, Q16K] fragment was generated using pTT5-aKLH120.6-VK1SP-IgG2-HC-L10-ShK[1-35 Q16K] as a template and the oligos:

```
                                    (SEQ ID NO: 316)
5'-GGA GGA GGA AGC CAC AGC TGC GCC GAC ACC ATC

CCC-3'//;
and
                                    (SEQ ID NO: 317)
5'-GGG GAT GGT GTC GGC GCA GCT GTG GCT TCC TCC

TCC-3'//.
```

Site-directed mutagenesis was performed using the Stratagene Quikchange Multi site Directed Mutagenesis Kit (Cat #200531), per manufacturer's instructions. The final pTT5-aKLH 120.6-VK1SP-IgG2-HC-L10-ShK[1-35 R1H, I4A, Q16K] construct encoded an IgG2-HC-L10-ShK[1-35, R1H, I4A, Q16K] fusion polypeptide (SEQ ID NO:306).

The Shk[1-35, R1H, Q16K, K30E] fragment was generated as described above using the following four oligos:

```
                       (SEQ ID NO: 318) and SEQ ID NO: 313
5'-GGA GGA GGA AGC CAC AGC TGC ATC GAC-3'//;

(SEQ ID NO: 319) and SEQ ID NO: 315
5'-GTC GAT GCA GCT GTG GCT TCC TCC TCC-3'//.
```

The final pTT5-aKLH 120.6-VK1SP-IgG2-HC-L10-ShK[1-35 R1H, Q16K, K30E] construct encoded an IgG2-HC-L10-ShK[1-35, R1H, Q16K, K30E] fusion polypeptide (SEQ ID NO:307).

The Shk[1-35, R1K, I4A, Q16K] fragment was generated using pTT5-aKLH 120.6-VK1SP-IgG2-HC-L10-ShK[1-35 Q16K] as a template and the oligos:

```
                                    (SEQ ID NO: 320)
5'-CCG GAG GAG GAG GAA GCA AGA GCT GCG CCG ACA CCA

TCC CCA AGA-3'//;
and
                                    (SEQ ID NO: 321)
5'-TCT TGG GGA TGG TGT CGG CGC AGC TCT TGC TTC CTC

CTC CTC CGG-3'//.
```

Site-directed mutagenesis was performed using the Stratagene Quikchange Multi site Directed Mutagenesis Kit (Cat #200531), per manufacturer's instructions. The final pTT5-aKLH 120.6-VK1SP-IgG2-HC-L10-ShK[1-35 R1K, I4A, Q16K] construct encoded an IgG2-HC-L10-ShK[1-35, R1K, I4A, Q16K] fusion polypeptide (SEQ ID NO:308).

The Shk[1-35, R1K, Q16K, K30E] fragment was generated as described above using the following four oligos:

```
                       (SEQ ID NO: 322) and SEQ ID NO: 313
5'-CGG AGG AGG AGG AAG CAA GAG CTG CAT CGA CAC CA-3'//;
                       (SEQ ID NO: 323) and SEQ ID NO: 315
5'-TGG TGT CGA TGC AGC TCT TGC TTC CTC CTC CTC

CG-3'//.
```

The final pTT5-aKLH 120.6-VK1SP-IgG2-HC-L10-ShK[1-35 R1K, Q16K, K30E] construct encoded an IgG2-HC-L10-ShK[1-35, R1K, Q16K, K30E] fusion polypeptide (SEQ ID NO:309).

Method for Isolating Monovalent Ab HC- and Monovalent, Bivalent and Trivalent Ab LC-Toxin Peptide Analog Fusions.

Initial purification of the conditioned media was done by affinity fast protein liquid chromatography (FPLC) capture of the Fc region using Protein A Sepharose (GE Healthcare) followed by a column wash with Dulbecco's PBS without divalent cations (Invitrogen) and step elution with 100 mM acetic acid, pH 3.5 at a flow rate of 2.5 cm/min. Protein containing fractions were pooled, and the pH was adjusted to 5.0 using 10 N NaOH and further diluted with 5 volumes of water. The material was filtered through a 0.45 µm cellulose acetate filter (Corning) and further purified by cation exchange FPLC (SP Sepharose High Performance; GE Healthcare). Samples were loaded onto a column equilibrated with 100% buffer A (50 mM acetic acid, pH 5.0) and eluted with a gradient of 0 to 80% buffer B (50 mM acetic acid, 1 M NaCl, pH 5.0) over 30 column volumes at a flowrate of 1.5 cm/min. Peaks containing target species were pooled and formulated into 10 mM sodium acetate, 9% sucrose, pH 5.0. Exemplary purifications of monovalent, bivalent and trivalent immunoglobulin-toxin peptide analog fusion proteins are shown in FIGS. 24-26A-B, 27-29A-B, 30-32A-B, and 33-35. The non-reducing SDS-PAGE analysis (FIGS. 24, 28, 30 and 33) demonstrate that the fully assembled antibody can be formed, and the reducing SDS-PAGE analysis demonstrates that the desired components are present. The size exclusion chromatograms (FIGS. 25, 28, 31 and 34) show that the majority of the purified product is in the desired non-aggregated state. Finally, the mass spectral analysis (FIGS. 26A-B, 29A-B, 32A-B and 35) demonstrates that the desired fusion products are present. Taken together these examples demonstrate that the aKLH 120.6 antibody can accept fusions in a wide variety of configurations including species containing an even- or odd-numbered valence of at least one to eight pharmacologically active polypeptide moieties.

VH21SP-N-Terminus ShK[1-35] Wild Type-IgG1-Fc Mammalian Expression.

A DNA sequence coding for a monomer of the Kv1.3 inhibitor peptide ShK[1-35] fused in-frame to the N-terminal Fc region of human IgG1 was constructed as described below.

For construction of VH21 SP-ShK(1-35)-L10-IgG1 Fc expression vector, a PCR strategy was employed to generate the VH21 signal peptide ShK(1-35) gene linked to a four glycine and one serine amino acid flanked by HindIII and BamHI restriction sites and a four glycine and one serine amino acid linked to IgG1 Fc fragment flanked by BamHI and NotI restriction sites was generated in a PCR reaction using the Fc-L10-OSK1 in pcDNA3.1(+)CMVi as a template (described in Example 41 and FIG. 42A-B of Sullivan et al., WO 2008/088422A2, incorporated by reference).

To generate VH21 SP-ShK(1-35)-G4S, two oligos with the sequence as depicted below were used in a PCR reaction with PfuTurbo HotStart DNA polymerase (Stratagene) at 95° C.-30 sec, 55° C.-30 sec, 75° C.-45 sec for 35 cycles; HindIII (aagctt) and BamHI (ggatcc) restriction sites are underlined:

```
Forward primer:
                                    (SEQ ID NO: 55)
TGCAGAAGCTTCTAGACCACCATGGAATGGAGCTGGGTCTTTCTCTTCTT

CCTGTCAGTAACGACTGGTGTCCACTCCCGCAGCTGCATCGACACCATCC

CCAAGAGCCGCTGCACCGCCTTCCAGT//;
and

Reverse primer:
                                    (SEQ ID NO: 56)
CTCCGGATCCTCCTCCTCCGCAGGTGCCGCAGGTCTTGCGGCAGAAGCTC

AGGCGGTACTTCATGCTGTGCTTGCACTGGAAGGCGGTGCAGCGGCTCTT

GGGGATGGTGTCGAT//.
```

The resulting PCR products were resolved as the 202 bp bands on a two percent agarose gel. The 202 bp PCR product was purified using PCR Purification Kit (Qiagen), then digested with HindIII and BamHI (Roche) restriction enzymes, and agarose gel was purified by Gel Extraction Kit (Qiagen).

To generate G4S-IgG1 Fc, two oligos with the sequence as depicted below were used in a PCR reaction with Pfu-Turbo HotStart DNA polymerase (Stratagene) at 95° C.-30 sec, 55° C.-30 sec, 75° C.-1 min for 30 cycles; BamHI (ggatcc) and NotI (gcggccgc) restriction sites are underlined:

```
Forward primer:
                                    (SEQ ID NO: 57)
GTAGGATCCGGAGGAGGAGGAAGCGACAAAACTCACAC//;
and Reverse primer:
                                    (SEQ ID NO: 58)
CGAGCGGCCGCTTACTATTTACCCGGAGACAGGGA//.
```

The resulting PCR products were resolved as the 721-bp bands on a one percent agarose gel. The 721-bp PCR product was purified using PCR Purification Kit (Qiagen), then digested with BamHI and NotI (Roche) restriction enzymes, and agarose gel was purified by Gel Extraction Kit (Qiagen).

The pcDNA3.1(+)CMVi-Fc-L10-OSK1 vector was digested with BamHI and NotI restriction enzymes and the large fragment was purified by Gel Extraction Kit. The gel purified 4GS-IgG1 Fc fragment was ligated to the purified large fragment and transformed into One Shot® Top10 (Invitrogen) to create a pCMVi-Fc-L10-IgG1 Fc vector. Subsequently, pCMVi-Fc-L10-IgG1 Fc vector was digested with HindIII and BamHI restriction enzymes and the large fragment was purified by Gel Extraction Kit. The gel purified VH21 SP-ShK(1-35)-4GS fragment was ligated to the purified large fragment and transformed into One Shot® Top10 (Invitrogen) resulting in a pCMVi-VH21 SP-ShK(1-35)-L10-IgG1 Fc construct. DNAs from transformed bacterial colonies were isolated and digested with BamHI and NotI restriction enzymes and resolved on a one percent agarose gel. DNAs resulting in an expected pattern were submitted for sequencing. Although, analysis of several sequences of clones yielded a 100% percent match with the above sequences, only one clone from each gene was selected for large scaled plasmid purification. The DNA from VH21 SP-ShK(1-35)-L10-IgG1 Fc in pCMVi vector was resequenced to confirm the Fc and linker regions and the sequence was 100% identical to the above sequence. Fragment VH21 SP-ShK(1-35)-L10-IgG1 Fc contained the coding sequence

```
                                    (SEQ ID NO: 59)
ATGGAATGGAGCTGGGTCTTTCTCTTCTTCCTGTCAGTAACGACTGGTGT

CCACTCCCGCAGCTGCATCGACACCATCCCCAAGAGCCGCTGCACCGCCT

TCCAGTGCAAGCACAGCATGAAGTACCGCCTGAGCTTCTGCCGCAAGACC

TGCGGCACCTGCGGAGGAGGAGGATCCGGAGGAGGAGGAAGCGACAAAAC

TCACACATGCCCACCGTGCCCAGCACCTGAACTCCTGGGGGACCGTCAG

TCTTCCTCTTCCCCCCAAAACCCAAGGACACCCTCATGATCTCCCGGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACAACAGCACGTACCGTGTGGTCAGCGTCCTC

ACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAT

GAGCTGACCAAGAACCAGGTCAGCCTGACCTGCCTGGTCAAAGGCTTCTA
```

```
TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTAAATAGTAA//,
``` encoding VH21 SP-ShK(1-35)-L10-IgG1 Fc amino acid sequence

```
                                                (SEQ ID NO: 60)
MEWSWVFLFFLSVTTGVHSRSCIDTIPKSRCTAFQCKHSMKYRLSFCRKT

CGTCGGGGSGGGGSDKTHTCPPCPAPELLGGPSVFLFPPKPKDTLMISRT

PEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFL

YSKLTVDKSRWQQGNVFSCSVMHEALHNHYTQKSLSLSPGK//.
```

Mammalian Expression of N-Terminus ShK[1-35, Q16K]-aKLH HC, and N-Terminus ShK[1-35Q16K]-aKLH LC.

Using a construct encoding N-terminus ShK[1-35]Wild Type-L10-IgG1-Fc, site directed mutagenesis was performed using the following oligos to produce a Q16K mutation in the ShK region:

```
                                       (SEQ ID NO: 9)
5'-GCT GCA CCG CCT TCA AGT GCA AGC ACA GC-3'//;
and
                                      (SEQ ID NO: 10)
5'-GCT GTG CTT GCA CTT GAA GGC GGT GCA GC-3'.
```

The Stratagene QuikChange Multi Site Directed Mutagenesis Kit was used according to the manufacturer's instructions. The final construct for pCMVi-N-terminus-ShK[1-35Q16K]-L10-IgG1-Fc encoded the following Signal peptide (VH21 SP)-ShK[1-35, Q16K]-L10-IgG1-Fc fusion polypeptide:

```
                                      (SEQ ID NO: 61)
MEWSWVFLFFLSVTTGVHSRSCIDTIPKSRCTAFKCKHSMKYRLSFCRKT

CGTCGGGGSGGGGSDKTHTCPPCPAPELLGGPSVFLFPPKPKDTLMISRT

PEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFL

YSKLTVDKSRWQQGNVFSCSVMHEALHNHYTQKSLSLSPGK//.
```

To generate the N-terminus ShK[1-35, Q16K]-aKLH HC construct, a PCR product containing the Signal peptide-ShK [1-35Q16K]-L10 linker was produced using the following oligos:

```
                                      (SEQ ID NO: 62)
5'-CAT TCT AGA CCA CCA TGG AAT GG-3';

(SEQ ID NO: 63)
5'-CAG CTG CAC CTG GCT TCC TCC TCC TCC GG-3';
``` and template pCMVi-N-terminus-ShK[1-35, Q16K]-L10-IgG1-Fc, resulted in a fragment containing the coding sequence

```
                                      (SEQ ID NO: 64)
ATGGAATGGAGCTGGGTCTTTCTCTTCTTCCTGTCAGTAACGACTGGTGT

CCACTCCCGCAGCTGCATCGACACCATCCCCAAGAGCCGCTGCACCGCCT

TCAAGTGCAAGCACAGCATGAAGTACCGCCTGAGCTTCTGCCGCAAGACC

TGCGGCACCTGCGGAGGAGGAGGATCCGGAGGAGGAGGAAGC//,
``` encoding the VH21 SP-ShK(1-35, Q16K)-L10 amino acid sequence

```
                                      (SEQ ID NO: 65)
MEWSWVFLFFLSVTTGVHSRSCIDTIPKSRCTAFKCKHSMKYRLSFCRKT

CGTCGGGGSGGGGS//.
```

To generate the aKLH-HC fragment, a PCR product was created using oligos:

```
                                      (SEQ ID NO: 66)
5'-GGA GGA GGA AGC CAG GTG CAG CTG GTG CAG-3';

(SEQ ID NO: 67)
5'-CAT GCG GCC GCT CAT TTA CCC-3';
``` and template pTT5-aKLH 120.6-HC, resulting in a DNA fragment containing the coding sequence

```
                                      (SEQ ID NO: 68)
CAGGTGCAGCTGGTGCAGTCTGGGGCTGAGGTGAAGAAGCCTGGGGCCTC

AGTGAAGGTCTCCTGCAAGGCTTCTGGATACACCTTCACCGGCTACCACA

TGCACTGGGTGCGACAGGCCCCTGGACAAGGGCTTGAGTGGATGGGATGG

ATCAACCCTAACAGTGGTGGCACAAACTATGCACAGAAGTTTCAGGGCAG

GGTCACCATGACCAGGGACACGTCCATCAGCACAGCCTACATGGAGCTGA

GCAGGCTGAGATCTGACGACACGGCCGTGTATTACTGTGCGAGAGATCGT

GGGAGCTACTACTGGTTCGACCCCTGGGGCCAGGGAACCCTGGTCACCGT

CTCCTCAGCCTCCACCAAGGGCCCATCGGTCTTCCCCCTGGCGCCCTGCT

CCAGGAGCACCTCCGAGAGCACAGCGGCCCTGGGCTGCCTGGTCAAGGAC

TACTTCCCCGAACCGGTGACGGTGTCGTGGAACTCAGGCGCTCTGACCAG

CGGCGTGCACACCTTCCCAGCTGTCCTACAGTCCTCAGGACTCTACTCCC

TCAGCAGCGTGGTGACCGTGCCCTCCAGCAACTTCGGCACCCAGACCTAC

ACCTGCAACGTAGATCACAAGCCCAGCAACACCAAGGTGGACAAGACAGT

TGAGCGCAAATGTTGTGTCGAGTGCCCACCGTGCCCAGCACCACCTGTGG

CAGGACCGTCAGTCTTCCTCTTCCCCCCAAAACCCAAGGACACCCTCATG

ATCTCCCGGACCCCTGAGGTCACGTGCGTGGTGGTGGACGTGAGCCACGA

AGACCCCGAGGTCCAGTTCAACTGGTACGTGGACGGCGTGGAGGTGCATA

ATGCCAAGACAAAGCCACGGGAGGAGCAGTTCAACAGCACGTTCCGTGTG

GTCAGCGTCCTCACCGTTGTGCACCAGGACTGGCTGAACGGCAAGGAGTA

CAAGTGCAAGGTCTCCAACAAAGGCCTCCCAGCCCCCATCGAGAAAACCA

TCTCCAAAACCAAAGGGCAGCCCCGAGAACCACAGGTGTACACCCTGCCC
```

CCATCCCGGGAGGAGATGACCAAGAACCAGGTCAGCCTGACCTGCCTGGT

CAAAGGCTTCTACCCCAGCGACATCGCCGTGGAGTGGGAGAGCAATGGGC

AGCCGGAGAACAACTACAAGACCACACCTCCCATGCTGGACTCCGACGGC

TCCTTCTTCCTCTACAGCAAGCTCACCGTGGACAAGAGCAGGTGGCAGCA

GGGGAACGTCTTCTCATGCTCCGTGATGCATGAGGCTCTGCACAACCACT

ACACGCAGAAGAGCCTCTCCCTGTCTCCGGGTAAATGA//, encoding amino acid sequence (SEQ ID NO: 69)
QVQLVQSGAEVKKPGASVKVSCKASGYTFTGYHMHWVRQAPGQGLEWMGW

INPNSGGTNYAQKFQGRVTMTRDTSISTAYMELSRLRSDDTAVYYCARDR

GSYYWFDPWGQGTLVTVSSASTKGPSVFPLAPCSRSTSESTAALGCLVKD

YFPEPVTVSWNSGALTSGVHTFPAVLQSSGLYSLSSVVTVPSSNFGTQTY

TCNVDHKPSNTKVDKTVERKCCVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTOKSLSLSPGK//.

The two PCR products were run out on a gel and the appropriate sized band was punched for an agarose plug. The agarose plugs were placed in a single new PCR reaction, and the fragments were sewn together using outer most primers (SEQ ID NO:62) and (SEQ ID NO:67). The PCR fragment was cut using XbaI and NotI and cleaned with Qiagen PCR Cleanup Kit. At the same time, pTT5 vector was also cut by XbaI and NotI and gel purified. The purified insert was ligated to the large vector fragment and transformed into OneShot Top10 bacteria. DNAs from transformed bacterial colonies were isolated and subjected to XbaI and NotI restriction enzyme digestions and resolved on a one percent agarose gel. DNAs resulting in an expected pattern were submitted for sequencing. Although, analysis of several sequences of clones yielded a 100% percent match with the above sequence, only one clone was selected for large scaled plasmid purification. The final construct pTT5-N-terminus ShK[1-35Q16K]-L10-aKLH120.6-HC encoded a VH21 SP-ShK[1-35, Q16K]-L10-aKLH120.6-HC fusion polypeptide:

(SEQ ID NO: 70)
MEWSWVFLFFLSVTTGVHSRSCIDTIPKSRCTAFKCKHSMKYRLSFCRKT

CGTCGGGSGGGGSQVQLVQSGAEVKKPGASVKVSCKASGYTFTGYHMHW

VRQAPGQGLEWMGWINPNSGGTNYAQKFQGRVTMTRDTSISTAYMELSRL

RSDDTAVYYCARDRGSYYWFDPWGQGTLVTVSSASTKGPSVFPLAPCSRS

TSESTAALGCLVKDYFPEPVTVSWNSGALTSGVHTFPAVLQSSGLYSLSS

VVTVPSSNFGTQTYTCNVDHKPSNTKVDKTVERKCCVECPPCPAPPVAGP

SVFLFPPKPKDTLMISRTPEVTCVVVDVSHEDPEVQFNWYVDGVEVHNAK

TKPREEQFNSTFRVVSVLTVVHQDWLNGKEYKCKVSNKGLPAPIEKTISK

TKGQPREPQVYTLPPSREEMTKNQVSLTCLVKGFYPSDIAVEWESNGQPE

NNYKTTPPMLDSDGSFFLYSKLTVDKSRWQQGNVFSCSVMHEALHNHYTQ

KSLSLSPGK//.

Lastly, the N-terminus-ShK[1-35, Q16K]-L10-aKLH120.6 Light Chain (LC) was generated in the same manner as above. A PCR product containing the signal peptide-ShK[1-35, Q16K]-L10 was created using oligos:

(SEQ ID NO: 62)
5'-CAT TCT AGA CCA CCA TGG AAT GG-3';
and (SEQ ID NO: 71)
5'-CAT CTG GAT GTC GCT TCC TCC TCC TCC GG-3';

and template pCMVi-N-terminus-ShK[1-35Q16K]-L10-IgG1-Fc, resulting in a DNA fragment containing the coding sequence (SEQ ID NO: 64)
ATGGAATGGAGCTGGGTCTTTCTCTTCTTCCTGTCAGTAACGACTGGTGT

CCACTCCCGCAGCTGCATCGACACCATCCCCAAGAGCCGCTGCACCGCCT

TCAAGTGCAAGCACAGCATGAAGTACCGCCTGAGCTTCTGCCGCAAGACC

TGCGGCACCTGCGGAGGAGGAGGATCCGGAGGAGGAGGAAGC//, encoding the amino acid sequence for a signal peptide (VH21 SP)-ShK(1-35, Q16K)-L10 linker:

(SEQ ID NO: 65)
MEWSWVFLFFLSVTTGVHSRSCIDTIPKSRCTAFKCKHSMKYRLSFCRKT

CGTCGGGGSGGGGS//.

Using template and oligos:

(SEQ ID NO: 72)
5'-GGA GGA GGA AGC GAC ATC CAG ATG ACC CAG TC-3';
and (SEQ ID NO: 73)
5'-CAT CTC GAG CGG CCG CTC AAC-3'.

The resulting cloned PCR fragment contained the coding sequence (SEQ ID NO: 74)
ATGGAATGGAGCTGGGTCTTTCTCTTCTTCCTGTCAGTAACGACTGGTGT

CCACTCCCGCAGCTGCATCGACACCATCCCCAAGAGCCGCTGCACCGCCT

TCAAGTGCAAGCACAGCATGAAGTACCGCCTGAGCTTCTGCCGCAAGAC

CTGCGGCACCTGCGGAGGAGGAGGATCCGGAGGAGGAGGAAGCGACAT

CCAGATGACCCAGTCTCCATCCTCCCTGTCTGCATCTGTAGGAGACAGAG

TCACCATCACTTGCCGGGCAAGTCAGGGCATTAGAAATGATTTAGGCTGG

TATCAGCAGAAACCAGGGAAAGCCCCTAAACGCCTGATCTATGCTGCAT

CCAGTTTGCAAAGTGGGGTCCCATCAAGGTTCAGCGGCAGTGGATCTGG

GACAGAATTCACTCTCACAATCAGCAGCCTGCAGCCTGAAGATTTTGCAA

CTTATTACTGTCTACAGCATAATAGTTACCCGCTCACTTTCGGCGGAGGG

ACCAAGGTGGAGATCAAACGAACTGTGGCTGCACCATCTGTCTTCATCTT

```
CCCGCCATCTGATGAGCAGTTGAAATCTGGAACTGCCTCTGTTGTGTGCC

TGCTGAATAACTTCTATCCCAGAGAGGCCAAAGTACAGTGGAAGGTGGA

TAACGCCCTCCAATCGGGTAACTCCCAGGAGAGTGTCACAGAGCAGGAC

AGCAAGGACAGCACCTACAGCCTCAGCAGCACCCTGACGCTGAGCAAAG

CAGACTACGAGAAACACAAAGTCTACGCCTGCGAAGTCACCCATCAGGG

CCTGAGCTCGCCCGTCACAAAGAGCTTCAACAGGGGAGAGTGTTGA//
``` was generated, encoding the amino acid sequence for N-terminus VH21 SP-ShK[1-35, Q16K]-L10-aKLH120.6 Light Chain (LC) with an N-terminal signal peptide:

```
                                       (SEQ ID NO: 75)
MEWSWVFLFFLSVTTGVHSRSCIDTIPKSRCTAFKCKHSMKYRLSFCRKT

CGTCGGGGSGGGGSDIQMTQSPSSLSASVGDRVTITCRASQGIRNDLGWY

QQKPGKAPKRLIYAASSLQSGVPSRFSGSGSGTEFTLTISSLQPEDFATY

YCLQHNSYPLTFGGGTKVEIKRTVAAPSVFIFPPSDEQLKSGTASVVCLL

NNFYPREAKVQWKVDNALQSGNSQESVTEQDSKDSTYSLSSTLTLSKADY

EKHKVYACEVTHQGLSSPVTKSFNRGEC//.
```

Both PCR fragments (DNA fragment containing the coding sequence (SEQ ID NO:64) and aKLH 120.6 Light Chain LC fragment containing the coding sequence (SEQ ID NO:74) were run out on a gel, and the appropriate sized band was punched for an agarose plug. The agarose plugs were placed in a single new PCR reaction, and the fragments were sewn together using outer most primers (SEQ ID NO:62) and (SEQ ID NO:73). The resulting PCR fragment was cut using XbaI and NotI and cleaned with Qiagen PCR Cleanup Kit.

At the same time, pTT14 vector (an Amgen vector containing a CMV promoter, Poly A tail and a Puromycin resistance gene) was also cut by XbaI and NotI and gel purified. The purified insert was ligated to the large vector fragment and transformed into OneShot Top10 bacteria. DNAs from transformed bacterial colonies were isolated and subjected to XbaI and NotI restriction enzyme digestions and resolved on a one percent agarose gel. DNAs resulting in an expected pattern were submitted for sequencing. The final construct pTT14-N-terminus ShK[1-35Q16K]-L10-aKLH120.6-LC encoding a Signal Peptide-ShK[1-35, Q16K]-L10-aKLH120.6-LC fusion polypeptide sequence (i.e., SEQ ID NO:75).

Mammalian Expression of aDNP 3A4 (W101F) IgG2-Shk[1-35].

Making of Plasmid pTT5-aDNP 3A4 (W101F) IgG2-Shk[1-35Q16K]:

DNA sequences coding for the heavy chain of human anti-2,4-dinitrophenyl (DNP) antibody fused in frame to a monomer of the Kv1.3 inhibitor toxin peptide analog ShK[1-35, Q16K] (SEQ ID NO:76) were constructed using standard cloning technology. Plasid pTT5-aDNP 3A4 (W101F) IgG2-Shk[1-35, Q16K] was generated by 3 way ligation of the pTT5 vector with a portion of an anti-DNP 3A4 (W101F) IgG2 Heavy Chain (pDC324:aDNP 3A4 HC (W101F) having the amino acid sequence:

```
                                       (SEQ ID NO: 77)
MDMRVPAQLLGLLLLWLRGARCQVQLVESGGGVVQPGRSLRLSCAASGFT

FSSYGMHWVRQAPGKGLEWVAVIWYDGSNKYYADSVKGRFTISRDNSKNT

LYLQMNSLRAEDTAVYYCARYNFNYGMDVWGQGTTVTVSSASTKGPSVFP

LAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCP

APPVAGPSVFLFPPKPKDTLMISRTPEVTCVVVDVSHEDPEVQFNWYVDG

VEVHNAKTKPREEQFNSTFRVVSVLTVVHQDWLNGKEYKCKVSNKGLPAP

IEKTISKTKGQPREPQVYTLPPSREEMTKNQVSLTCLVKGFYPSDIAVEW

ESNGQPENNYKTTPPMLDSDGSFFLYSKLTVDKSRWQQGNVFSCSVMHEA

LHNHYTQKSLSLSPG//;
``` and a portion from IgG2Fc-Shk[1-35, Q16K]. The pTT5 vector was cut with SalI/NotI releasing the multiple cloning site. The vector was then treated with Calf Intestine Phosphatase (CIP) to reduce background. The first insert came from pDC324:aDNP 3A4 HC (W101F) by cutting with SalI/StuI, resulting in the a DNA fragment containing the coding sequence

```
                                       (SEQ ID NO: 78)
ATGGACATGAGGGTGCCCGCTCAGCTCCTGGGGCTCCTGCTGCTGTGGCT

GAGAGGTGCGCGCTGTCAGGTGCAGCTGGTGGAGTCTGGGGGAGGCGTG

GTCCAGCCTGGGAGGTCCCTGAGACTCTCCTGTGCAGCGTCTGGATTCAC

CTTCAGTAGCTATGGCATGCACTGGGTCCGCCAGGCTCCAGGCAAGGGG

CTGGAGTGGGTGGCAGTTATATGGTATGATGGAAGTAATAAATACTATG

CAGACTCCGTGAAGGGCCGATTCACTATCTCCAGAGACAATTCCAAGAA

CACGCTGTATCTGCAAATGAACAGCCTGAGAGCCGAGGACACGGCTGTG

TATTACTGTGCGAGGTATAACTTCAACTACGGTATGGACGTCTGGGGCCA

AGGGACCACGGTCACCGTCTCTAGTGCCTCCACCAAGGGCCCATCGGTCT

TCCCCCTGGCGCCCTGCTCCAGGAGCACCTCCGAGAGCACAGCGGCCCTG

GGCTGCCTGGTCAAGGACTACTTCCCCGAACCGGTGACGGTGTCGTGGA

ACTCAGGCGCTCTGACCAGCGGCGTGCACACCTTCCCAGCTGTCCTACAG

TCCTCAGGACTCTACTCCCTCAGCAGCGTGGTGACCGTGCCCTCCAGCAA

CTTCGGCACCCAGACCTACACCTGCAACGTAGATCACAAGCCCAGCAAC

ACCAAGGTGGACAAGACAGTTGAGCGCAAATGTTGTGTCGAGTGCCCAC

CGTGCCCAGCACCACCTGTGGCAGGACCGTCAGTCTTCCTCTTCCCCCCA

AAACCCAAGGACACCCTCATGATCTCCCGGACCCCTGAGGTCACGTGCGT

GGTGGTGGACGTGAGCCACGAAGACCCCGAGGTCCAGTTCAACTGGTAC

GTGGACGGCGTGGAGGTGCATAATGCCAAGACAAAGCCACGGGAGGAG

CAGTTCAACAGCACGTTCCGTGTGGTCAGCGTCCTCACCGTTGTGCACCA

GGACTGGCTGAACGGCAAGGAGTACAAGTGCAAGGTCTCCAACAAAG

GC//, encoding amino acid sequence (SEQ ID NO: 79)
MDMRVPAQLLGLLLLWLRGARCQVQLVESGGGVVQPGRSLRLSCAASGFT

FSSYGMHWVRQAPGKGLEWVAVIWYDGSNKYYADSVKGRFTISRDNSKNT
```

-continued

LYLQMNSLRAEDTAVYYCARYNFNYGMDVWGQGTTVTVSSASTKGPSVFP

LAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCP

APPVAGPSVFLFPPKPKDTLMISRTPEVTCVVVDVSHEDPEVQFNWYVDG

VEVHNAKTKPREEQFNSTFRVVSVLTVVHQDWLNGKEYKCKVSNKG//.

The second insert was digested out using StuI/NotI and contained the coding sequence (SEQ ID NO: 80)
CTCCCAGCCCCCATCGAGAAAACCATCTCCAAAACCAAAGGGCAGCCCC

GAGAACCACAGGTGTACACCCTGCCCCCATCCCGGGAGGAGATGACCAA

GAACCAGGTCAGCCTGACCTGCCTGGTCAAAGGCTTCTACCCCAGCGAC

ATCGCCGTGGAGTGGGAGAGCAATGGGCAGCCGGAGAACAACTACAAG

ACCACACCTCCCATGCTGGACTCCGACGGCTCCTTCTTCCTCTACAGCAA

GCTCACCGTGGACAAGAGCAGGTGGCAGCAGGGGAACGTCTTCTCATGC

TCCGTGATGCATGAGGCTCTGCACAACCACTACACGCAGAAGAGCCTCTC

CCTGTCTCCGGGTAAAGGAGGAGGAGGATCCGGAGGAGGAGGAAGCCG

CAGCTGCATCGACACCATCCCCAAGAGCCGCTGCACCGCCTTCAAGTGCA

AGCACAGCATGAAGTACCGCCTGAGCTTCTGCCGCAAGACCTGCGGCAC

CTGCTAATGA//, encoding the following truncated IgG2 Fc-L10-ShK(1-35, Q16K) amino acid sequence (SEQ ID NO: 81)
LPAPIEKTISKTKGQPREPQVYTLPPSREEMTKNQVSLTCLVKGFYPSDI

AVEWESNGQPENNYKTTPPMLDSDGSFFLYSKLTVDKSRWQQGNVFSCSV

MHEALHNHYTQKSLSLSPGKGGGGSGGGGSRSCIDTIPKSRCTAFKCKHS

MKYRLSFCRKTCGTC//.

The vector and insert fragments were gel purified and cleaned up with Qiagen Gel Purification Kit. The purified inserts were ligated to the large vector fragment and transformed into OneShot Top10 bacteria. DNAs from transformed bacterial colonies were isolated and subjected to SalI/NotI restriction enzyme digestion and resolved on a one percent agarose gel. DNAs resulting in an expected pattern were submitted for sequencing. A clone yielding a 100% percent match with the above sequence was selected for large scale plasmid purification. The final pTT5-aDNP 3A4 (W101F) IgG2-Shk[1-35, Q16K] construct encoded a aDNP 3A4 (W101F) IgG2 HC-L10-Shk[1-35, Q16K] having the following amino acid sequence:

(SEQ ID NO: 82)
MDMRVPAQLLGLLLLWLRGARCQVQLVESGGGVVQPGRSLRLSCAASGFT

FSSYGMHWVRQAPGKGLEWVAVIWYDGSNKYYADSVKGRFTISRDNSKNT

LYLQMNSLRAEDTAVYYCARYNFNYGMDVWGQGTTVTVSSASTKGPSVFP

LAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCP

APPVAGPSVFLFPPKPKDTLMISRTPEVTCVVVDVSHEDPEVQFNWYVDG

VEVHNAKTKPREEQFNSTFRVVSVLTVVHQDWLNGKEYKCKVSNKGLPAP

IEKTISKTKGQPREPQVYTLPPSREEMTKNQVSLTCLVKGFYPSDIAVEW

ESNGQPENNYKTTPPMLDSDGSFFLYSKLTVDKSRWQQGNVFSCSVMHEA

LHNHYTQKSLSLSPGGGGSGGGGSRSCIDTIPKSRCTAFKCKHSMKYRL

SFCRKTCGTC//.

Mammalian Expression of Anti-DNP 3A4 Antibody Light Chain.

The XenoMouse® hybridoma expressing aDNP monoclonal antibody 3A4 was used as a source to isolate total RNA. One step RT-PCR with multiplex gene-specific primers was done to obtain a variable region product. This product was reamplified with a forward primer to add a 5' BssHII restriction site 5'-TTT TTT TTG CGC GCT GTG ACA TCC AGA TGA CCC AGT C-3' (SEQ ID NO:83) and a reverse primer to add a 3' BsiWI restriction site 5'-AAA AAA CGT ACG TTT GAT ATC CAC TTT GGT CC-3' (SEQ ID NO:84). The resulting PCR product was cleaned by Qiagen PCR clean-up, digested with BssHII and BsiWI restriction enzymes, cleaned by Qiagen nucleotide removal, and ligated into a mammalian expression vector pTT5 containing a 5' VK1/O12 signal peptide and a 3' human kappa constant region. The amino acid sequence of the resulting anti-DNP 3A4 Antibody Light Chain is the following:

(SEQ ID NO: 109)
MDMRVPAQLLGLLLLWLRGARCDIQMTQSPSSVSASVGDRVTITCRASQG

ISRRLAWYQQKPGKAPKLLIYAASSLQSGVPSRFSGSGSGTDFTLTISSL

QPEDFATYYCQQANSFPFTFGPGTKVDIKRTVAAPSVFIFPPSDEQLKSG

TASVVCLLNNFYPREAKVQWKVDNALQSGNSQESVTEQDSKDSTYSLSST

LTLSKADYEKHKVYACEVTHQGLSSPVTKSFNRGEC//.

Method for Isolating Monovalent Fc-Toxin Peptide Analog and Ab HC- or Ab LC-Toxin Peptide Analog Fusions.

Initial purification of the conditioned media was done by affinity fast protein liquid chromatography (FPLC) capture of the Fc region using Protein A Sepharose (GE Healthcare) followed by a column wash with Dulbecco's PBS without divalent cations (Invitrogen) and step elution with 100 mM acetic acid, pH 3.5 at a flow rate of 2.5 cm/min. Protein containing fractions were pooled, and the pH was adjusted to 5.0 using 10 N NaOH and further diluted with 5 volumes of water. The material was filtered through a 0.45 µm cellulose acetate filter (Corning) and further purified by cation exchange FPLC (SP Sepharose High Performance; GE Healthcare). Samples were loaded onto a column equilibrated with 100% buffer A (50 mM acetic acid, pH 5.0) and eluted with a gradient of 0 to 80% buffer B (50 mM acetic acid, 1 M NaCl, pH 5.0) over 30 column volumes at a flowrate of 1.5 cm/min. Peaks containing monovalent species were pooled and formulated into 10 mM sodium acetate, 9% sucrose, pH 5.0. Exemplary purifications of immunoglobulin-toxin peptide analog fusion proteins are shown in FIG. 3A-C, FIG. 4A-C, FIG. 5A-C, FIG. 6A-C and FIGS. 24-35.

Method for Isolating Monovalent Ab HC- and Monovalent, Bivalent and Trivalent Ab LC-Toxin Peptide Analog Fusions.

Initial purification of the conditioned media was done by affinity fast protein liquid chromatography (FPLC) capture of the Fc region using Protein A Sepharose (GE Healthcare) followed by a column wash with Dulbecco's PBS without divalent cations (Invitrogen) and step elution with 100 mM acetic acid, pH 3.5 at a flow rate of 2.5 cm/min. Protein containing fractions were pooled, and the pH was adjusted to 5.0 using 10 N NaOH and further diluted with 5 volumes of water. The material was filtered through a 0.45 µm cellulose acetate filter (Corning) and further purified by cation exchange FPLC (SP Sepharose High Performance; GE Healthcare). Samples were loaded onto a column equilibrated with 100% buffer A (50 mM acetic acid, pH 5.0) and eluted with a gradient of 0 to 80% buffer B (50 mM acetic acid, 1 M NaCl, pH 5.0) over 30 column volumes at a flowrate of 1.5 cm/min. Peaks containing target species were pooled and formulated into 10 mM sodium acetate, 9% sucrose, pH 5.0. Reducing and non-reducing (+iodoacetamide) analysis was done on 4-12% or 4-20% SDS-PAGE Tris-glycine gels (Invitrogen) with 0.5 µg, 2 µg, and 10 µg of protein, stained with QuickBlue (Boston Biologicals). Analytical SEC was done using a Biosep SEC-53000 column (Phenomenex) and an isocratic elution of 50 mM sodium phosphate, 250 mM NaCl, pH 6.9, over 18 min. Exemplary purifications of immunoglobulin-toxin peptide analog fusion proteins are shown in FIGS. 24-26A-B, 27-29A-B, 30-32A-B, and 33-35.

Example 5

Pharmacokinetic/Pharmacodynamic Evaluation of Monovalent Fc/Fc-L10-ShK[2-35] Heterodimers and Monovalent or Bivalent Fc/Fc-ShK(1-35 Q16K)(IgG2) Heterodimers and Immunoglobulin Fusion Proteins of the Invention Embodiments of the antigen binding proteins of the present invention, used as immunoglobulin carriers for pharmacologically active polypeptides were demonstrated to provide favorable pharmacokinetic and pharmacodynamic properties. Monovalent or bivalent Fc-L10-ShK[2-35], monovalent or bivalent Fc-L10-ShK[1-35], monovalent or bivalent Fc-L10-ShK(1-35, Q16K), monovalent or bivalent anti-KLH HC-ShK(1-35, Q16K) Ab, monovalent or bivalent anti-KLH AbLoop-[Lys16]ShK fusion proteins, monovalent Fc-ShK(1-35 Q16K)/KLH Ab heterotrimer, and other exemplary embodiments listed in Table 7H, were expressed, isolated and purified by methods described in Example 4. PEGylated and un-PEGylated toxin peptide comparators in Table 7H were prepared synthetically as follows:

Peptide Synthesis.

N$^\alpha$-Fmoc, side-chain protected amino acids and H-Cys (Trt)-2Cl-Trt resin were purchased from Novabiochem, Bachem, or Sigma Aldrich. The following side-chain protection strategy was employed: Asp(OtBu), Arg(Pbf), Cys (Trt), Glu(OtBu), His(Trt), Lys(Nε-Boc), Ser(OtBu), Thr (OtBu) and Tyr(OtBu). ShK (RSCIDTIPKSRCTAFQCKHSMKYRLSFCRKTCGTC// SEQ ID NO:361), [Lys16]ShK (RSCIDTIPK-SRCTAFKCKHSMKYRLSFCRKTCGTC//SEQ ID NO:76), or other toxin peptide analog amino acid sequences, were synthesized in a stepwise manner on an CS Bio peptide synthesizer by SPPS using DIC/HOBt coupling chemistry at 0.2 mmol equivalent scale using H-Cys(Trt)-2Cl-Trt resin (0.2 mmol, 0.32 mmol/g loading). For each coupling cycle, 1 mmol N$^\alpha$-Fmoc-amino acid was dissolved in 2.5 mL of 0.4 M 1-hydroxybenzotriazole (HOBt) in N,N-dimethylformamide (DMF). To the solution was added 1.0 mL of 1.0 M N,N'-diisopropylcarbodiimide (DIC) in DMF. The solution was agitated with nitrogen bubbling for 15 min to accomplish pre-activation and then added to the resin. The mixture was shaken for 2 h. The resin was filtered and washed three times with DMF, twice with dichloromethane (DCM), and three times with DMF. Fmoc deprotections were carried out by treatment with 20% piperdine in DMF (5 mL, 2×15 min). The first 23 residues were single coupled through repetition of the Fmoc-amino acid coupling and Fmoc removal steps described above. The remaining residues were double coupled by performing the coupling step twice before proceeding with Fmoc-removal.

Following synthesis, the resin was then drained, and washed sequentially with DCM, DMF, DCM, and then dried in vacuo. The peptide-resin was transferred to a 250-mL plastic round bottom flask. The peptide was deprotected and released from the resin by treatment with triisopropylsilane (1.5 mL), 3,6-dioxa-1,8-octane-dithiol (DODT, 1.5 mL), water (1.5 mL), trifluoroacetic acid (TFA, 20 mL), and a stir bar, and the mixture was stirred for 3 h. The mixture was filtered through a 150-mL sintered glass funnel into a 250-mL plastic round bottom flask. The mixture was filtered through a 150-mL sintered glass funnel into a 250-mL plastic round bottom flask, and the filtrate was concentrated in vacuo. The crude peptide was precipitated with the addition of cold diethyl ether, collected by centrifugation, and dried under vacuum.

Peptide Folding.

The dry crude linear peptide (about 600 mg), for example [Lys16]ShK peptide (SEQ ID NO:76) or [Lys16]ShK-Ala (also known as [Lys16, Ala36]-ShK; SEQ ID NO:362) peptide, was dissolved in 16 mL acetic acid, 64 mL water, and 40 mL acetonitrile. The mixture was stirred rapidly for 15 min to complete dissolution. The peptide solution was added to a 2-L plastic bottle that contained 1700 mL of water and a large stir bar. To the thus diluted solution was added 20 mL of concentrated ammonium hydroxide to raise the pH of the solution to 9.5. The pH was adjusted with small amounts of acetic acid or NH$_4$OH as necessary. The solution was stirred at 80 rpm overnight and monitored by LC-MS. Folding was usually judged to be complete in 24 to 48 h, and the solution was quenched by the addition of acetic acid and TFA (pH=2.5). The aqueous solution was filtered (0.45 µm cellulose membrane).

Reversed-Phase HPLC Purification.

Reversed-phase high-performance liquid chromatography was performed on an analytical (C18, 5 µm, 0.46 cm×25 cm) or a preparative (C18, 10 µm, 2.2 cm×25 cm) column. Chromatographic separations were achieved using linear gradients of buffer B in A (A=0.1% aqueous TFA; B=90% aq. ACN containing 0.09% TFA) typically 5-95% over 35 min at a flow rate of 1 mL/min for analytical analysis and 5-65% over 90 min at 20 mL/min for preparative separations. Analytical and preparative HPLC fractions were characterized by ESMS and photodiode array (PDA) HPLC, combined and lyophilized.

Mass Spectrometry.

Mass spectra were acquired on a single quadrupole mass spectrometer equipped with an Ionspray atmospheric pressure ionization source. Samples (25 µL) were injected into a moving solvent (10 µL/min; 30:50:20 ACN/MeOH containing 0.05% TFA) coupled directly to the ionization source via a fused silica capillary interface (50 µm i.d.). Sample droplets were ionized at a positive potential of 5 kV and entered the analyzer through an interface plate and subsequently through an orifice (100-120 μm diameter) at a potential of 60 V. Full scan mass spectra were acquired over the mass range 400-2200 Da with a scan step size of 0.1 Da. Molecular masses were derived from the observed m/z values.

PEGylation, Purification and Analysis.

Peptide, e.g., [Lys16]ShK (SEQ ID NO:76) or [Lys16] ShK-Ala (SEQ ID NO:362), was selectively PEGylated by reductive alkylation at its N-terminus, using activated linear or branched PEG. Conjugation was performed at 2 mg/ml in 50 mM NaH$_2$PO$_4$, pH 4.5 reaction buffer containing 20 mM sodium cyanoborohydride and a 2 molar excess of 20 kDa monomethoxy-PEG-aldehyde (NOF, Japan). Conjugation reactions were stirred for approximately 5 hrs at room temperature, and their progress was monitored by RP-HPLC. Completed reactions were quenched by 4-fold dilution with 20 mM NaOAc, pH 4 and chilled to 4° C. The PEG-peptides were then purified chromatographically at 40C; using SP Sepharose HP columns (GE Healthcare, Piscataway, N.J.) eluted with linear 0-1M NaCl gradients in 20 mM NaOAc, pH 4.0. Eluted peak fractions were analyzed by SDS-PAGE and RP-HPLC and pooling determined by purity>97%. Principle contaminants observed were di-PEGylated toxin peptide analog. Selected pools were concentrated to 2-5 mg/ml by centrifugal filtration against 3 kDa MWCO membranes and dialyzed into 10 mM NaOAc, pH 4 with 5% sorbitol. Dialyzed pools were then sterile filtered through 0.2 micron filters and purity determined to be >97% by SDS-PAGE (data not shown). Reverse-phase HPLC was performed on an Agilent 1100 model HPLC running a Zorbax® 5 μm 300SB-C8 4.6×50 mm column (Agilent) in 0.1% TFA/H$_2$O at 1 ml/min and column temperature maintained at 40° C. Samples of PEG-peptide (20 μg) were injected and eluted in a linear 6-60% gradient while monitoring wavelength 215 nm.

Fusion Proteins.

Generally, FIG. 1A and FIG. 1B show a schematic representation of monovalent and bivalent Fc-toxin peptide (or toxin peptide analog) fusion proteins (or "peptibodies"), respectively. The bivalent Fc-ShK molecule is a homodimer containing two Fc-ShK chains. The monovalent Fc-ShK toxin peptide (or toxin peptide analog) molecule is a heterodimer containing one Fc chain and one Fc-ShK (or analog) chain. Since the monovalent Fc-ShK molecule contains just a single ShK peptide per dimer, it is considered monovalent. Constructs or chains referred to as Fc-(toxin peptide analog), contain an N-terminal Fc region and an optional flexible linker sequence (e.g., L10 peptidyl linker GGGGSGGGGS; SEQ ID NO:153) covalently attached to the toxin peptide or toxin peptide analog, such that the orientation from N- to C-terminus would be: Fc-linker-toxin peptide or toxin peptide analog.

In Examples 1 and 2 of Sullivan et al., WO 2008/088422A2, were described the activity of bivalent Fc-ShK peptibodies, Fc-L10-ShK(1-35) and Fc-L10-ShK(2-35) expressed from mammalian cells. In Example 1 of WO 2008/088422A2, was also described isolation of a monovalent Fc-L10-ShK(1-35) molecule, formed as a small by-product during expression. The bivalent Fc-L10-ShK(1-35) and Fc-L10-ShK(2-35) conjugates provided potent blockade of Kv1.3 and T cell cytokine secretion in human whole blood (see, Table 7H). By whole cell patch clamp electrophysiology, the bivalent Fc-L10-ShK(1-35) molecule had about 8-fold greater Kv1.3 activity compared to the bivalent Fc-L10-ShK(2-35) molecule that is devoid of Arg1 of ShK. Like N-terminal PEG conjugates of native ShK (see, Examples 4), both bivalent Fc-ShK conjugates showed little selectivity for Kv1.3 versus Kv1.1. Thus, N-terminal conjugation of native ShK alone (with either PEG or Fc-linker) does not significantly improve its Kv1.3 versus Kv1.1 selectivity. Pharmacokinetic (PK) studies in rats were performed on bivalent Fc-L10-ShK(1-35) and Fc-L10-ShK(2-35) peptibodies to examine their stability and half-life in vivo. As a control, PK was also performed on CHO-derived recombinant human Fc (IgG1). All molecules were delivered as a single, intravenous bolus dose.

PK Assays

Antibodies to ShK. Rabbit polyclonal and mouse monoclonal antibodies to ShK (SEQ ID NO:361) were generated by immunization of animals with the Fc-ShK peptibody conjugate. Anti-ShK specific polyclonal antibodies were affinity purified from antisera to isolate only those antibodies specific for the ShK portion of the conjugate. Following fusion and screening, hybridomas specific for ShK were selected and isolated. Mouse anti-ShK specific monoclonal antibodies were purified from the conditioned media of the clones. By ELISA analysis, purified anti-ShK polyclonal and monoclonal antibodies reacted only to the ShK peptide alone and did not cross-react with Fc.

Pharmacokinetic (PK) studies on 20 kDa-PEG-ShK (SEQ ID NO:363) and 20 kDa-PEG-[Lys16]ShK (SEQ ID NO:364) peptide conjugates in rats and monkeys. Single subcutaneous doses were delivered to animals and serum was collected at various time points after injection. Studies in rats involved two to three animals per dose group, with blood and serum collection occurring at various time points over the course of the study. Male Sprague-Dawley (SD) rats (about 0.3 kg) and male cynomolgus monkeys (about 4 kg) were used in the studies described herein (n=3 animals per dose group). Approximately 5 male CD-1 mice were used per dose and time point in our mouse pharmacokinetic studies. Serum samples were stored frozen at −80° C., until analysis in an enzyme-linked immunosorbent assay (ELISA).

A brief description of the ELISA protocol for detecting serum levels of PEG-ShK and PEG-[Lys16]ShK is provided below:

(1) Protocol 1, (a)-(g) below, detects PEG-ShK and PEG-[Lys16]ShK, as well as the ShK and [Lys16]ShK peptides alone:

(a) Streptavidin microtiter plates were coated with 250 ng/ml biotinylated-anti-ShK mouse monoclonal antibody (mAb2.10, Amgen) in I block buffer [per liter: 1000 mL 1×PBS without CaCl$_2$, MgCl$_2$, 5 ml Tween 20 (Thermo Scientific), 2 g I block reagent (Tropix)] at 4° C., incubated overnight without shaking.

(b) Plates were washed three times with KPL wash buffer (Kirkegaard & Perry Laboratories).

(c) Standards (STD), quality controls (QC) and sample dilutions were prepared with 100% pooled sera, then diluted 1/5 (pretreatment) in I block buffer. Pretreated STDs, QCs and samples were added to the washed plate and incubated at room temperature for 2 hours. (Serial dilutions of STDs, QCs were prepared in 100% pooled sera. Samples needing dilution were also prepared with 100% pooled sera. The pretreatment was done to both stds, QCs and samples to minimize the matrix effect.)

(d) Plates were washed three times with KPL wash buffer.

(e) A HRP-labeled rabbit anti-ShK polyclonal Ab at 250 ng/ml in I block buffer was added and plates were incubated at room temperature for 1 hour with shaking.

(f) Plates were again washed three times with KPL wash buffer and the Femto [Thermo Scientific] substrate was added.

(g) The plate was read with a Lmax II 384 (Molecular Devices) luminometer.

Pharmacokinetic (PK) studies on Fc-, Ig-, or Ab conjugates of ShK and [Lys16]ShK were performed in male SD rats. Single subcutaneous doses were delivered to animals and serum was collected at various time points after injection. Three animals were used per dose group, with blood and serum collection occurring at various time points over the course of the study. Serum samples were stored frozen at −80° C., until analysis in an enzyme-linked immunosorbent assay (ELISA). A brief description of the ELISA protocol for detecting serum levels of Fc-, Ig-, or Ab-conjugates of ShK and [Lys16]ShK is provided below. Protocol 2, below detects both the human Ig, Fc or Ab portion of the molecule, as well as the ShK peptide portion. Protocol 3, below is an early assay that detects the human Fc region alone and was used for early assessment of serum levels of Fc-ShK peptibodies in rodent pharmacokinetic studies. A brief description of these ELISA protocols is provided:

(2) Protocol 2, (a)-(g) below, detects both the human Ig, Fc or Ab portion of the molecule, as well as the ShK peptide portion:

(a) Streptavidin microtiter plates were coated with 250 ng/ml biotinylated-anti-ShK mouse monoclonal antibody (mab 2.10, Amgen) in I block buffer [per liter: 1000 ml 1×PBS without $CaCl_2$, $MgCl_2$, 5 ml Tween 20 (Thermo Scientific), 2 g I block reagent (Tropix)] at 4° C., overnight without shaking;

(b) Plates were washed three times with KPL wash buffer (Kirkegaard & Perry Laboratories)

(c) Standards (STD), quality controls (QC) and sample dilutions with 100% pooled sera were prepared, then were diluted 1/5 (pretreatment) in I block buffer. Pretreated STDs, QCs and samples were added to the washed plate. Incubation was at room temperature for 2 hours. (Serial dilutions of STDs, QCs were prepared in 100% pooled sera. Samples needing dilution were also prepared with 100% pooled sera. The pretreatment was done to both stds, QCs and samples to minimize the matrix effect.);

(d) Plates were washed three times with KPL wash buffer;

(e) A HRP-labeled Ab35 (against human IgG Fc) at 150 ng/ml in I block buffer was added and plates were incubated at room temperature for 1 hour with shaking.

(f) Plates were washed three times with KPL wash buffer and the Femto [Thermo Scientific] substrate was added;

(g) The plate was read with a Lmax II 384 [Molecular Devices] luminometer.

(3) Protocol 3, (a)-(h) below, is an early assay that detects the human Fc region alone and was used for early assessment of serum levels of Fc-ShK peptibodies in rodent pharmacokinetic studies:

(a) Costar 3590 96-well EIA/RIA plates were coated with 0.1 mL/well of 2 μg/mL Goat anti-HuFc, Fab2, (Sigma 1-3391) diluted in 1× Coating Buffer (10× Coating Buffer: 1.59 g $Na_2CO_3$, 2.93 g $NaHCO_3$ in 100 ml $H_2O$). Plates were sealed and incubated at 4° C. overnight;

(b) Plates were washed three times with PBST (PBS+ 0.1% Tween-20) and blocked by addition of 0.3 ml of blotto (PBS, 0.1% Tween-20, 5% non-fat dry milk) to each well and incubated for 1 h at room temperature (RT) with shaking;

(c) Plates were washed with a KP Wash Solution (Cat #50-63-00, KPL, Gaithersburg, Md.);

(d) Diluted serum samples and controls/standards in Dilution Buffer (PBS, 0.1% BSA, 0.1% Tween-20) plus rat serum, if needed, were brought to 10% rat serum final and 0.1 ml sample was added per well. Plates were incubated at room temperature with shaking for 1 hour;

(e) Plates were washed with a KP Wash Solution (Cat #50-63-00, KPL, Gaithersburg, Md.);

(f) A HRP labeled secondary antibody (Pierce #31416-HRP Goat α-Hu IgG Fc) was diluted 1:5000 in PBST and then 100 μl/well is added and incubated at RT with shaking for 1 hour;

(g) Plates were washed with a KP Wash Solution (Cat #50-63-00, KPL, Gaithersburg, Md.) and 100 μl/well of ABTS substrate (ABTS Microwell Substrate 1-Component, Cat #50-66-018, KPL) was added;

(h) At appropriate times after substrate addition and shaking, the plate was read with a SpectraMax340 [Molecular Devices] plate reader.

Whereas, the original monovalent Fc-L10-ShK(1-35) molecule was isolated as a small by-product during mammalian expression of the bivalent molecule, Example 4 herein also describes cloning and mammalian expression of the monovalent Fc-L10-ShK[2-35] heterodimer. Briefly, to produce recombinant monovalent Fc-L10-ShK[2-35], two recombinant polypeptides are co-expressed in the same cell, those being a human Fc (IgG1) chain and a Fc-L10-ShK[2-35] chain (also with human IgG1 Fc region). Under these conditions it is possible to form three distinct dimers, which include an Fc/Fc homodimer, a Fc-L10-ShK(2-35)/Fc-L10-ShK(2-35) homodimer and a Fc/Fc-L10-ShK(2-35) heterodimer. By optimizing expression conditions, the monovalent Fc/Fc-L10-ShK(2-35) heterodimer (also referred to as just monovalent Fc-L10-ShK(2-35)) was produced efficiently and was readily purified to homogeneity (Example 4 herein). The monovalent Fc-L10-ShK(2-35) molecule had an IC50 of 2.1 nM (Table 7H) in blocking IL-2 secretion from human whole blood. The monovalent Fc-ShK/Fc heterodimer had an extended half-life in vivo and exhibited significantly greater exposure than the bivalent homodimers ShK-Fc/ShK-Fc (FIG. 10) and Fc-ShK/Fc-ShK. Since the potency of this construct was about 10-fold less than the PEG-ShK conjugate and conjugates of native ShK had poor Kv1.3/Kv1.1 selectivity, we developed additional monovalent peptibodies and formed conjugates of ShK toxin peptide analogs that were identified to have improved Kv1.3 versus Kv1.1 selectivity. The examples that follow provide additional details of monovalent peptibodies with improved selectivity and in vivo pharmacology. The results from these studies indicated that monovalent ShK toxin peptide analog molecules exhibited greater serum levels and exposure in rats when compared to the bivalent forms of the same molecule, yet retain the slow elimination rate observed in the original bivalent peptibodies.

Monovalent Fc/Fc-ShK(1-35 Q16K) Heterodimer (IgG2).

ShK[Lys16] toxin peptide analog (SEQ ID NO:76) shows significant Kv1.3 selectivity over neuronal Kv1.1 (Table 7H). To increase the stability of this toxin peptide analog in vivo, we generated a monovalent Fc fusion construct that from N- to C-terminus contained: human Fc(IgG2)-L10 linker-[Lys16]ShK molecule, that was co-expressed with the human Fc(IgG2) chain alone to generate a monovalent heterodimer (see, Example 4). A schematic representation of this monovalent construct is provided in FIG. 1A. The monovalent Fc/Fc-L10-ShK(1-35 Q16K) heterodimer [also referred to as monovalent Fc/Fc-ShK(1-35, Q16K)] potently blocked T cell inflammation in whole blood, suppressing IL-2 secretion with an IC50 of 0.16 nM (Table 7H). Unexpectedly, studies to examine the Kv1.3 versus Kv1.1 selectivity of the molecule, revealed that the monovalent Fc-L10-ShK(1-35 Q16K) conjugate had significantly better Kv1.3 selectivity than the [Lys16]ShK peptide alone. Whereas the [Lys16]ShK (SEQ ID NO:76) peptide alone showed about 18-fold selectivity for Kv1.3 versus Kv1.1 (Table 7H), the monovalent Fc/Fc-L10-ShK(1-35 Q16K) heterodimer was about 1225-fold more active in blocking Kv1.3 versus Kv1.1. Therefore, the [Lys16]ShK peptide when conjugated shows a unique pharmacology of enhanced selectivity. Since the Nα-20 kDa-PEG-[Lys16]ShK conjugate (SEQ ID NO:364) also showed enhanced Kv1.3 selectivity (Table 7H) relative to the peptide alone, the combined data suggests that the [Lys16]-ShK (SEQ ID NO:76) peptide when fused at its N-terminus with either PEG or Fc-linker exhibits a distinct pharmacology of improved Kv1.3 versus Kv1.1 selectivity.

To assess the pharmacokinetics and stability of the molecule in vivo, as a basis of comparison for the inventive molecules, single-dose PK studies were performed in rats. After a single 6 mg/kg subcutaneous dose, the monovalent Fc/Fc-L10-ShK(1-35, Q16K) heterodimer (of monomers SEQ ID NOS:1 and 26) exhibited an extended half-life in vivo (FIG. 7). Since the sandwich ELISA used to measure serum levels of the molecule ("protocol 2") requires binding of two antibodies, one an antibody specific to human Fc region and the other an antibody recognizing [Lys16]ShK (SEQ ID NO:76), the data here indicate that the conjugate had prolonged half-life and remained intact in vivo as a Fc-L10-ShK(1-35 Q16K) fusion protein (FIG. 7, open squares; Table 71 below). The monovalent Fc/Fc-L10-ShK (1-35 Q16K) molecule exhibited an extended half-life of about 56 hours, that was about 112 times longer than the ShK (SEQ ID NO:361) peptide alone that was reported to have a half-life of 20-30 min (C. Beeton et al., PNAS 98:13942 (2001)).

Bivalent Fc-ShK(1-35 Q16K) Homodimer (IgG2).

The bivalent Fc-ShK(1-35, Q16K) homodimer contains from N- to C-terminus: human Fc (IgG2)-L10 linker-[Lys16]ShK (SEQ ID NO:26). A schematic representation of this bivalent construct is provided in FIG. 1B. The molecule (homodimer of SEQ ID NO:26) was cloned, expressed and purified as described in Example 4 herein. The purified molecule was tested for activity in the human whole blood assay of inflammation and found to have an IC50 of 1.850 nM in blocking IL-2 secretion (Table 7H). The activity of this bivalent form was about 12 times less than the monovalent form (above) which had an IC50 of 0.16 nM in this same assay. The reason why the bivalent form was less active than the monovalent is unknown. It is possible that the bivalent molecule containing two positively charged [Lys16]ShK (SEQ ID NO:76) peptides at its end, is less stable and/or interferes with Kv1.3 channel binding to some extent.

Monovalent and Bivalent aKLH HC-ShK(1-35, Q16K) Ab.

Figure 2A:
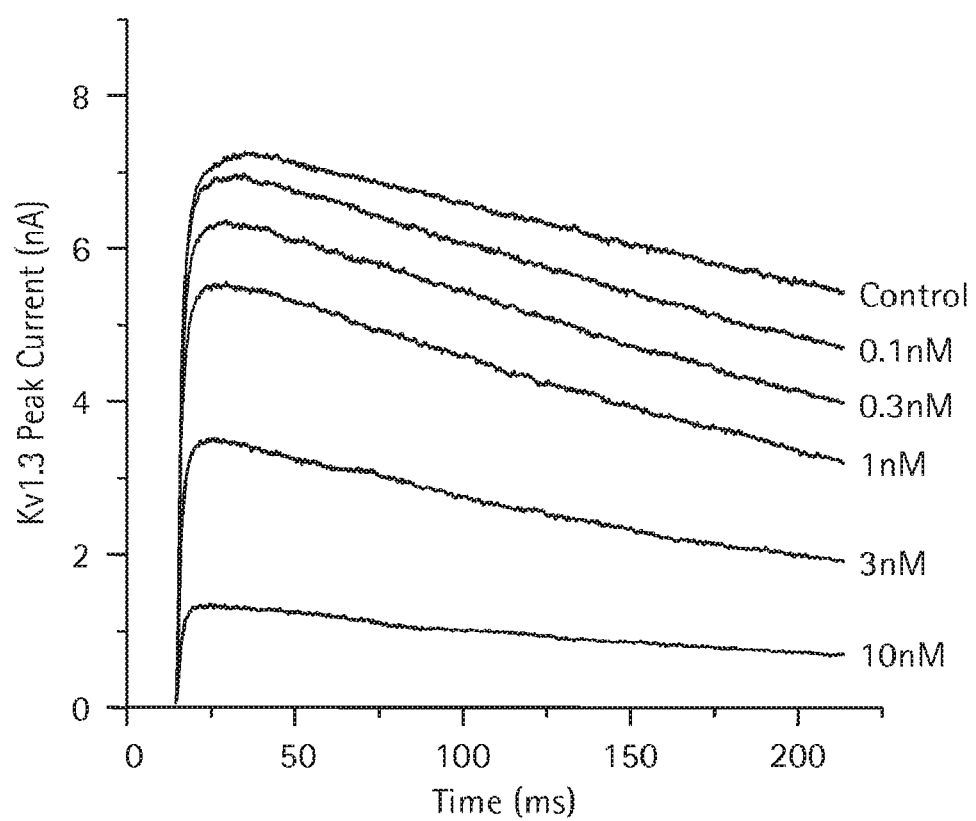
FIG. 2A-B demonstrates by PatchXpress® electrophysiology that the monovalent aKLH HC-ShK(1-35 Q16K) Ab (SEQ ID NO:28, 29, 32), as described in Examples 4 and 5, is more potent in blocking human Kv1.3 current (FIG. 2A) than human Kv1.1 current (FIG. 2B).
Figure 2B:
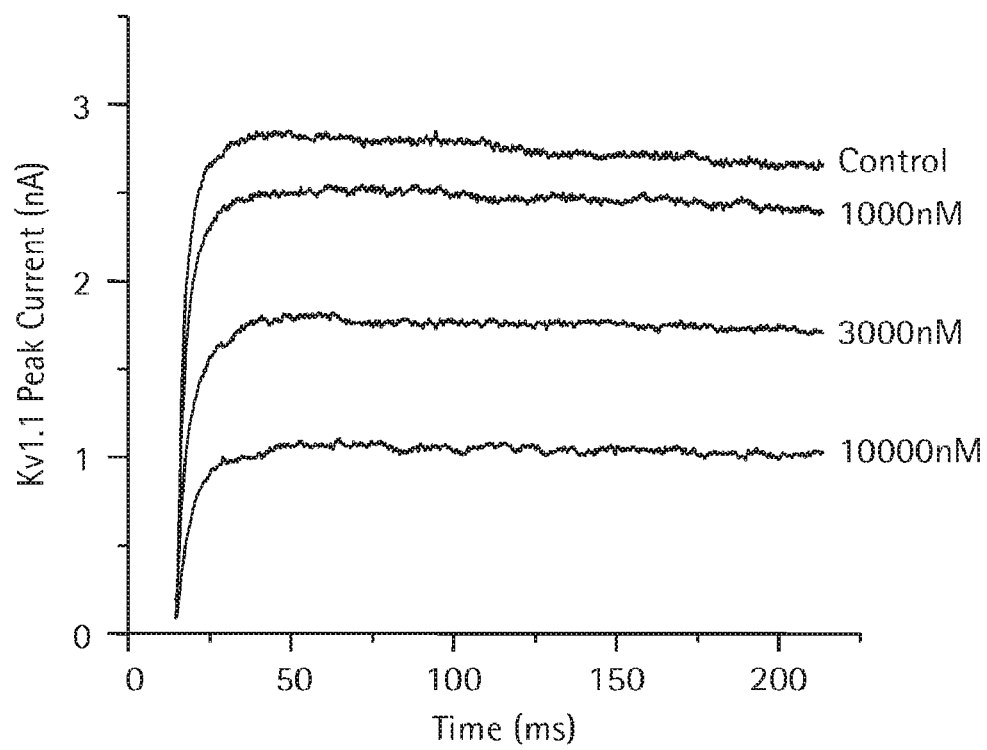
Figure 3A:
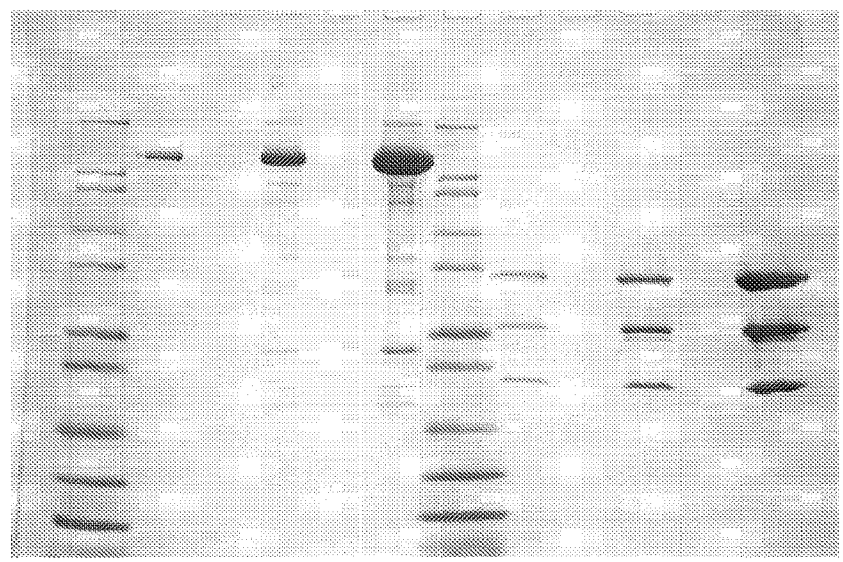
FIG. 3A shows a Coomassie brilliant blue stained Trisglycine 4-20% SDS-PAGE of the final monovalent Fc-L10-Shk[1-35, Q16K]/anti-KLH Ab product, described in Example 4 herein. Lanes 1-12 were loaded as follows: lane 1: Novex Mark12 wide range protein standards (10 μl); lane 2: 0.5 μg product, non-reduced; lane 3: blank; lane 4: 2.0 μg product, non-reduced; lane 5: blank; lane 6: 10 μg product, non-reduced; lane 7: Novex Mark12 wide range protein standards (10 μl); lane 8: 0.5 μg product, reduced; lane 9: blank; lane 10: 2.0 μg product, reduced; lane 11: blank; lane 12: 10 μg product, reduced.
Figure 3B:
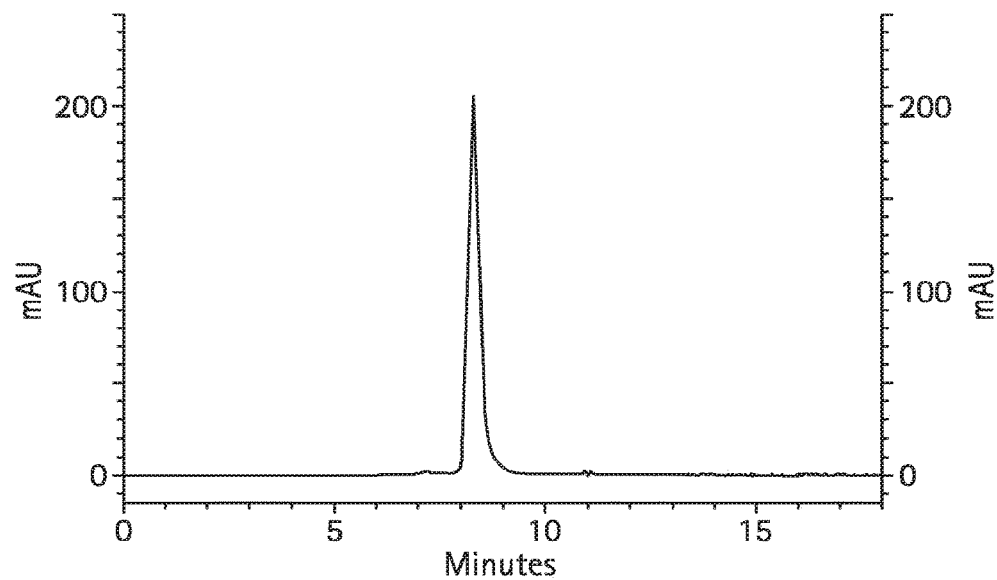
FIG. 3B shows size exclusion chromatography on 50 μg of the final monovalent Fc-L10-ShK[1-35, Q16K]/anti-KLH Ab product, described in Example 4, injected onto a Phenomenex BioSep SEC-3000 column (7.8×300 mm) in 50 mM $NaH_2PO_4$, 250 mM NaCl, and pH 6.9 at 1 mL/min observing the absorbance at 280 nm.
Figure 3C:
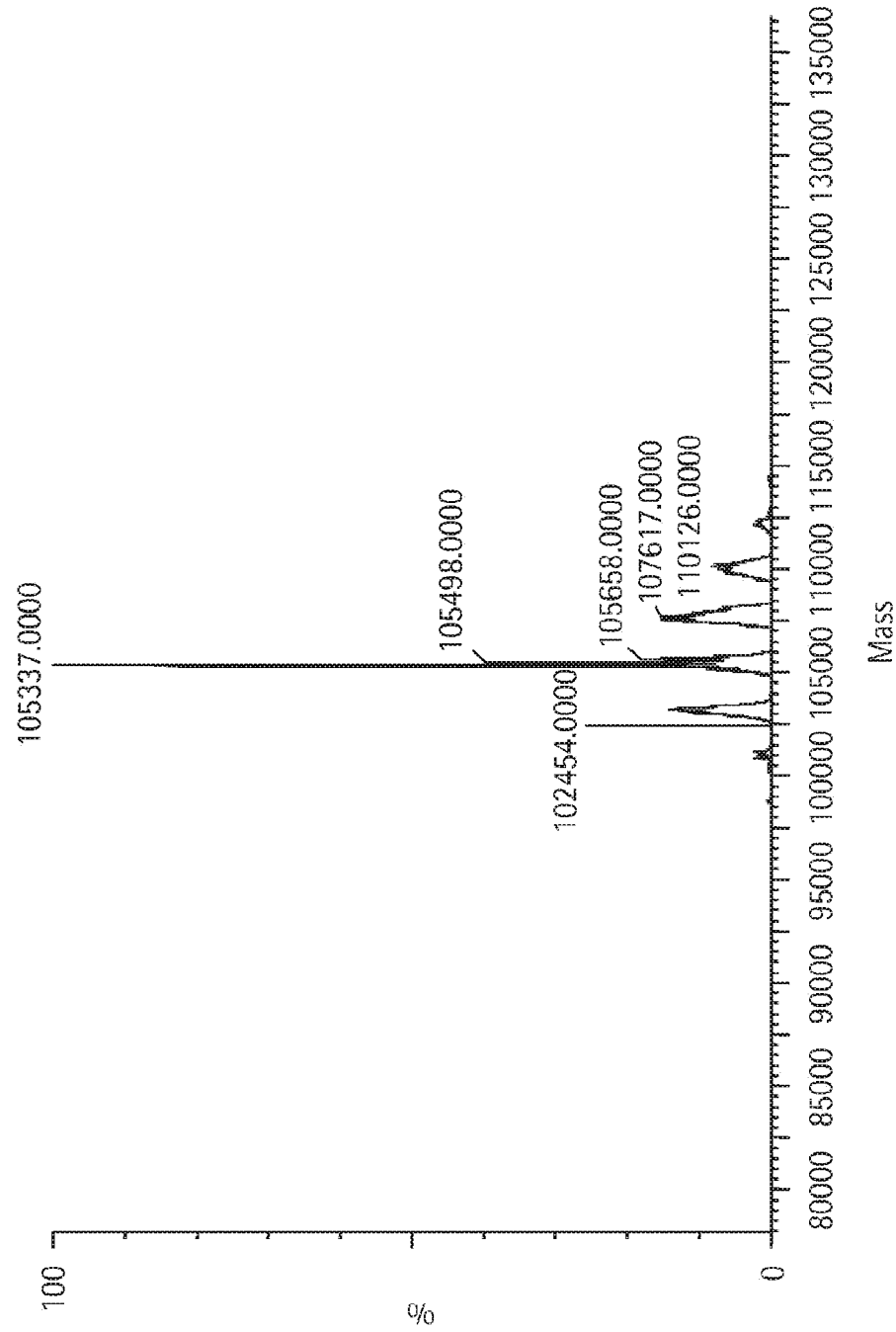
FIG. 3C shows an LC-MS analysis of the final sample of monovalent Fc-L10-ShK[1-35, Q16K]/anti-KLH Ab described in Example 4. The product was chromatographed through a Waters MassPREP micro desalting column using a Waters ACQUITY UPLC system. The column was set at 80° C. and the protein eluted using a linear gradient of increasing acetonitrile concentration in 0.1% formic acid.

The monovalent anti-KLH Heavy Chain (HC) fusion antibody (Ab) construct embodiment of the present invention contained, from N- to C-terminus: human anti-KLH Ab Heavy Chain-peptidyl linker-[Lys16]ShK molecule (SEQ ID NO:32), that was co-expressed with the human aKLH Heavy Chain alone (SEQ ID NO:29) and the human aKLH light chain (SEQ ID NO:28) to form a monovalent aKLH Ab-[Lys16]ShK molecule (heterotetramer of SEQ ID NO:28; SEQ ID NO:29; SEQ ID NO:28; and SEQ ID NO:32). A schematic representation of this monovalent construct is provided in FIG. 1F. The monovalent aKLH HC-ShK(1-35, Q16K) Ab potently blocked T cell inflammation in whole blood, suppressing IL-2 secretion with an IC50 of 0.274 nM (Table 7H). Unexpectedly, studies to examine the Kv1.3 versus Kv1.1 selectivity of the molecule, revealed that the monovalent aKLH HC-ShK(1-35, Q16K) Ab (heterotetramer of SEQ ID NO:28; SEQ ID NO:29; SEQ ID NO:28; and SEQ ID NO:32) had significantly better Kv1.3 selectivity than the [Lys16]ShK (SEQ ID NO:76) peptide alone. This monovalent Ab-ShK conjugate was about 1458-fold more active in blocking Kv1.3 versus Kv1.1 (Table 7H and FIG. 2A-B).

To assess the pharmacokinetics and stability of the molecule in vivo, single-dose PK studies were performed in rats. After a single 6 mg/kg subcutaneous dose, the monovalent aKLH HC-ShK(1-35 Q16K) Ab conjugate exhibited an extended half-life in vivo (FIG. 7, closed circles). Since the sandwich ELISA used to measure serum levels of the molecule ("protocol 2") requires binding of two antibodies, one an antibody specific to human Ig region and the other an antibody recognizing [Lys16]ShK (SEQ ID NO:76), the data here indicates that conjugate has prolonged half-life and remains intact in vivo as a monovalent aKLH HC-ShK(1-35 Q16K) Ab fusion protein (FIG. 7, FIG. 8, and Table 7J). The bivalent aKLH HC-ShK(1-35, Q16K) Ab molecule (schematically represented by FIG. 1G) given at the same 6 mg/kg dose, showed a similarly slow elimination rate (FIG. 8), but provided about 37 times less exposure (as measured by $AUC_{0-t}$, Table 7J) relative to the monovalent molecule (FIG. 8). The potent and selective monovalent anti-KLH-Ab-[Lys16]ShK molecule exhibited very slow clearance in rats (CL/F=10.9 mL $h^{-1}$ kg') (Table 7J).

Monovalent aKLH HC-ShK(2-35 Q16K) Ab.

This monovalent aKLH Heavy Chain (HC) fusion antibody (Ab) construct embodiment of the present invention contained from N- to C-terminus: human anti-KLH Ab Heavy Chain-linker-[desArg1, Lys16]ShK molecule (SEQ ID NO:33), that was co-expressed with the human aKLH Heavy Chain (SEQ ID NO:29) and the human aKLH light chain (SEQ ID NO:28) to form a monovalent aKLH Ab-[desArg1, Lys16]ShK molecule. A schematic representation of this monovalent construct is provided in FIG. 1F. The monovalent aKLH HC-ShK(2-35, Q16K) Ab (heterotramer of SEQ ID NO:28; SEQ ID NO:29; SEQ ID NO:28; and SEQ ID NO:33) potently blocked T cell inflammation in whole blood, suppressing IL-2 secretion with an IC50 of 0.570 nM (Table 7H) and unexpectedly was about 1576 fold more potent in blocking the T-cell potassium channel Kv1.3 than the neuronal channel Kv1.1.

Monovalent Fc-ShK(1-35 Q16K)/KLH Ab Heterotrimer.

The monovalent Fc-ShK(1-35, Q16K)/KLH Ab heterotrimer or hemibody embodiment of the present invention contained from N- to C-terminus: human Fc (IgG2)-L10 linker-[Lys16]ShK molecule (SEQ ID NO:26), that was co-expressed with the human aKLH Heavy Chain (IgG2) (SEQ ID NO:29) and the human aKLH light chain (SEQ ID NO:28). A schematic representation of this monovalent construct is provided in FIG. 1E. The monovalent Fc-ShK (1-35, Q16K)/KLH Ab heterotrimer (SEQ ID NO:28; SEQ ID NO:29; SEQ ID NO:26) potently blocked T cell inflammation in human whole blood, suppressing IL-2 secretion with an IC50 of 0.245 nM (Table 7H). Surprisingly, studies examining the Kv1.3 versus Kv1.1 selectivity of the molecule revealed that the monovalent Fc-ShK(1-35, Q16K)/ KLH Ab heterotrimer had significantly better Kv1.3 selectivity than the [Lys16]ShK peptide alone (SEQ ID NO:76). This monovalent heterotrimer was about 1935 fold more active in blocking Kv1.3 versus Kv1.1 (Table 7H).

Although we have not examined the pharmacokinetics (PK) of the Kv1.3 selective monovalent Fc-ShK(1-35, Q16K)/KLH Ab heterotrimer or hemibody, we have examined the PK profile of a similar hemibody, that being the Fc-ShK(2-35)/KLH Ab heterotrimer. A schematic of the structure of this molecule is provided in FIG. 1E, and the molecule from N- to C-terminus contains: human Fc (IgG2)-ShK(2-35), which is coexpressed with the human aKLH heavy chain and light chains. After a single 2 mg/kg subcutaneous dose, the monovalent Fc-ShK(2-35)/KLH Ab heterotrimer (also referred to as monovalent Fc-ShK/KLH Ab heterotrimer) exhibited an extended half-life in rats (FIG. 10). Since the sandwich ELISA used to measure serum levels of the molecule ("protocol 2") requires binding of two antibodies, one an antibody specific to human Ig region and the other an antibody recognizing ShK(2-35), the data here indicates that conjugate has prolonged half-life and remains intact in vivo (FIG. 10, Table 7K). The large, about 103 kDa monovalent Fc-ShK(2-35)KLH Ab heterotrimer or hemibody showed greater exposure and about 2-fold less clearance than the about 56 kDa monovalent Fc/Fc-ShK heterodimer (FIG. 10, Table 7K). The very small, about 4 kDa ShK-L5 peptide was cleared much more quickly, having a clearance value in rats (CL/F=2052 mL $h^{-1}$ $kg^{-1}$, Example 5) that was about 91 times faster than the large monovalent Fc-ShK(2-35)/KLH Ab heterotrimer (CL/F=22.6 mL $h^{-1}$ $kg^{-1}$) molecule.

Monovalent and Bivalent Anti-KLH AbLoop-[Lys16] ShK Fusion Proteins.

Recombinant monovalent and bivalent anti-KLH AbLoop-[Lys16]ShK fusion proteins embodiments of the present invention were constructed as described in Example 4 and U.S. Pat. No. 7,442,778 B2 to produce full antibodies with [Lys16]ShK toxin peptide analog inserted into loop regions of the Fc domain in one (monovalent) or both (bivalent) HC monomers. The monovalent aKLH HC-loop-ShK(1-35, Q16K) Ab contained three chains: a human aKLH Ab heavy chain, a human aKLH Ab light chain and a human aKLH Ab heavy chain where the [Lys16]ShK peptide was inserted into a loop within the Fc region of the heavy chain. The [Lys16]ShK peptide within the Fc loop contained a flexible linker sequence attached to its N- and C-terminus to allow for independent folding and extension from the loop. A schematic representation of this molecule is provided in provided in FIG. 1N. Linker sequences of differing amino acid composition and length were examined. The monovalent anti-KLH AbLoop-[Lys16]ShK fusion protein was a selective inhibitor of Kv1.3 activity (over Kv1.1; >121-fold more selective for Kv1.3; Table 7H and FIG. 2A-B). The monovalent KLH-AbLoop-[Lys16]ShK molecule exhibited the slowest clearance in rats of all the novel toxin-conjugates that we have examined (FIG. 7 and FIG. 9 and Table 7L).

The bivalent aKLH HC-loop-ShK(1-35, Q16K) Ab contained two chains: a human aKLH Ab light chain and a human aKLH Ab heavy chain where the [Lys16]ShK peptide was inserted into a loop within the Fc region of the heavy chain. A schematic representation of this molecule is provided in provided in FIG. 1M. To compare the pharmacokinetics and stability in vivo of this bivalent molecule to the monovalent form, single 6 mg/kg subcutaneous doses of each molecule were delivered to rats. Despite showing a slow elimination rate, the bivalent aKLH HC-loop-ShK(1-35, Q16K) Ab gave profoundly less exposure in rats than the monovalent form of the same molecule (monovalent aKLH HC-loop-ShK(1-35, Q16) Ab) (see FIG. 9). Exposure as measured by $AUC_{0-t}$, was about 161 times less for the bivalent aKLH HC-loop-ShK(1-35, Q16K) Ab molecule compared to the monovalent aKLH HC-loop-ShK(1-35Q16K) Ab molecule (Table 7L). Therefore, our novel monovalent forms show an unexpected and vastly better pharmacokinetic profile in vivo compared to typical bivalent forms of the same molecule.

Monovalent ShK(1-35, Q16K)-Fc/Fc Heterodimer.

The monovalent ShK(1-35, Q16K)-Fc/Fc heterodimer contains two chains, one being a human Fc(IgG2) chain and the other being ShK(1-35, Q16K) peptide fused to Fc that contains from N- to C-terminus: [Lys16]ShK-L10 linker-human Fc (IgG2). This peptide-fusion protein contained from N- to C-terminus: the 35 amino acid [Lys16]ShK peptide, a ten amino acid GGGGSGGGGS (SEQ ID NO:153) L10 linker sequence and the human Fc (IgG2) sequence. Therefore, the linker-Fc region was attached to the C-terminus of [Lys16]ShK following Cys35. This molecule is also referred to as monovalent ShK(1-35, Q16K)-Fc heterodimer. A schematic representation of this monovalent construct is provided in FIG. 1C. The molecule was cloned, expressed and purified as described Example 4 herein. The purified molecule was highly potent having an IC50 of 0.11 nM in blocking IL-2 secretion in the human whole blood assay of inflammation (Table 7H). Despite its excellent potency, the monovalent ShK(1-35, Q16K)-Fc/Fc heterodimer showed only a modest ~10 fold selectivity for Kv1.3 versus Kv1.1 (Table 7H). Therefore, it would appear that this linker-Fc fusion partner attached the C-terminus of [Lys16]ShK does not result in a further enhancement of Kv1.3 selectivity. This contrasts with N-terminal fusions to [Lys16]ShK, such as the monovalent Fc/Fc-ShK(1-35, Q16K) heterodimer (Table 7H) which showed ~1225 fold selectivity and had the Fc-linker sequence attached to the N-terminal Arg1 residue of [Lys16]ShK. An important and notable exception, however, is the [Lys16]ShK-Ala peptide (SEQ ID NO:362) which contains a single C-terminal Ala residue adding following Cys35 of [Lys16]ShK. This molecule exhibited an enhanced 262 fold improved selectivity for Kv1.3 versus Kv1.1 (Table 7H). Therefore, we envision that the specific amino acid residue added after Cys35 at the C-terminus of [Lys16]ShK, can alter the selectivity profile of the fusion protein. For example, the monovalent ShK(1-35, Q16K)-L10-Fc molecule described in this example contains the linker Gly residue added after Cys35 of [Lys16] ShK. If an Ala residue was added instead following Cys35, an enhanced Kv1.3 selectivity might be observed. Indeed, we do see 262 fold improved Kv1.3 selectivity by the [Lys16]ShK-Ala peptide. Thus, we anticipate that specific amino acid residue at the fusion junction would alter the selectivity profile. These residue can be readily incorporated into the linker sequence between the [Lys16]ShK peptide and the human Fc domain or immunoglobulin light chain or heavy chain to improve the conjugates Kv1.3 selectivity.

Monovalent ShK(1-35, Q16K)-HC aKLH Ab.

The monovalent ShK(1-35, Q16K)-HC aKLH Ab embodiment of the present invention contains three chains, one being the human aKLH Ab light chain, another being the human aKLH Ab heavy chain and the third being a peptide-aKLH Ab heavy chain fusion that contained from N- to C-terminus: [Lys16]ShK-L10 linker-human aKLH heavy chain. Therefore, this fusion contained the linker-heavy chain region attached to the C-terminus of [Lys16]ShK following Cys35. A schematic representation of the monovalent ShK(1-35, Q16K)-HC aKLH Ab molecule is provided in Figure H. The purified molecule was highly potent having an IC50 of 0.214 nM in blocking IL-2 secretion in the human whole blood assay of inflammation (Table 7H). Despite being very large in size and fused to a human Ig heavy chain, the monovalent [Lys16]-aKLH Ab molecule retained high potency in blocking T cell responses.

Monovalent aDNP HC-ShK(1-35, Q16K) Ab.

The monovalent aDNP Heavy Chain (HC) fusion antibody (Ab) construct embodiment of the present invention contained from N- to C-terminus: human anti-DNP Ab Heavy Chain-linker-[Lys16]ShK molecule, that was co-expressed with the human aDNP Heavy Chain and the human aDNP light chain to form a monovalent aDNP Ab-[Lys16]ShK molecule. A schematic representation of this monovalent construct is provided in FIG. 1F. The monovalent aDNP HC-ShK(1-35, Q16K) Ab potently blocked T cell inflammation in human whole blood, suppressing IL-2 secretion with an IC50 of 0.278 nM (Table 7H). Studies to examine the Kv1.3 versus Kv1.1 selectivity of the molecule, unexpectedly revealed that the monovalent aDNP HC-ShK(1-35, Q16K) Ab conjugate had significantly better Kv1.3 selectivity than the [Lys16]ShK peptide alone. This monovalent Ab-ShK conjugate was >5806 fold more active in blocking Kv1.3 versus Kv1.1 (Table 7H).

Table 7H. Data demonstrating various conjugates of [Lys16] ShK having improved Kv1.3 selectivity. Toxin peptides and toxin peptide analogs were PEGylated as described in Example 4 herein. Immunoglobulin-containing compounds were recombinantly expressed and purified as described in Example 4. Electrophysiology was by PatchXpress® (PX), except asterisks indicate data from whole cell patch clamp (see, Examples 6 and 8 herein). Human whole blood ("WB") assays of IL-2 and interferon-gamma ("IFNg") were conducted as described in Example 7 herein).

TABLE 7H

| SEQ ID NO or citation | Conjugate Type | Designation | Kv1.3 (PX) IC50 (nM) | Kv1.1 (PX) IC50 (nM) | Kv1.1/ Kv1.3 Selectivity Ratio by PX | WB (IL-2) IC50 (nM) | WB (IFNg) IC50 (nM) | Potency Relative to ShK (WB, IL2) |
|---|---|---|---|---|---|---|---|---|
| 361 | none | ShK(1-35) | 0.062 | 0.087 | 1.40 | 0.067 | 0.078 | 1.00 |
| 76 | none | [Lys 16]ShK | 0.207 | 3.677 | 17.76 | 0.110 | 0.158 | 1.64 |
| 362 | none | [Lys 16]ShK-Ala | 0.06 | 15.726 | 262.10 | 0.138 | 0.266 | 2.06 |
| 363 | PEG | 20kDa-PEG-ShK | 0.299* | 1.628* | 5.44 | 0.380 | 0.840 | 5.67 |
| 364 | PEG | 20kDa-PEG-+Lys16+ShK | 0.94 | 997 | 1060.64 | 0.092 | 0.160 | 1.37 |
| 365 | PEG | 20kDa-PEG-+Lys16+ShK-Ala | 0.596 | 2156 | 3617.45 | 0.754 | 1.187 | 11.25 |
| Example 1, W02008/088422A2 | IgG1 | Bivalent Fc-L10-ShK[1-35] homodimer | 0.015* | 0.067* | 4.47 | 0.386 | 0.320 | 5.76 |
| Example 2, W02008/088422A2 | IgG1 | Bivalent Fc-L10-ShK[2-35] homodimer | 0.116* | 0.411* | 3.54 | 0.585 | 2.285 | 8.73 |
| Example 2, W02008/088422A2 | IgG1 | Monovalent Fc/Fc-L10-ShK[2-35] heterodimer | ND | ND | ND | 2.149 | 5.199 | 32.07 |
| 1; 26 | IgG2 | Monovalent Fc/Fc-ShK(1-35 Q16K) heterodimer | 2.73 | 3344 | 1224.91 | 0.160 | 0.499 | 2.39 |
| 26; 26 | IgG2 | Bivalent Fc-ShK(1-35 Q16K) homodimer | ND | ND | ND | 1.850 | 3.140 | 27.61 |
| 28; 29; 26 | IgG2 | Monovalent Fc-ShK(1-35 016K)/KLH Ab Heterotrimer | 0.98 | 1896 | 1934.69 | 0.245 | 0.665 | 3.66 |
| 109; 82; 109; 77 | IgG2 | Monovalent aDNP HC-ShK(1-35 016K) Ab | 0.574 | >3333 | >5806.62 | 0.278 | 0.660 | 4.15 |
| 28; 29; 28; 32 | IgG2 | Monovalent aKLH HC-ShK(1-35 016K) Ab | 3.96 | 5774 | 1458.08 | 0.274 | 0.657 | 4.09 |
| 28; 32; 28; 32 | IgG2 | Bivalent aKLH HC-ShK(1-35 016K) Ab | ND | ND | ND | 1.392 | 3.568 | 20.78 |
| 28; 29; 28; 33 | IgG2 | Monovalent aKLH HC-ShK(2-35 016K) Ab | 1.66 | 2617 | 1576.51 | 0.570 | 0.820 | 8.51 |
| 28; 29; 28; 70 | IgG2 | Monovalent ShK(1-35 016K)-HC aKLH Ab | ND | ND | ND | 0.214 | 0.332 | 3.19 |

TABLE 7H-continued

| SEQ ID NO or citation | Conjugate Type | Designation | Kv1.3 (PX) IC50 (nM) | Kv1.1 (PX) IC50 (nM) | Kv1.1/Kv1.3 Selectivity Ratio by PX | WB (IL-2) IC50 (nM) | WB (IFNg) IC50 (nM) | Potency Relative to ShK (WB, IL2) |
|---|---|---|---|---|---|---|---|---|
| 28; 35; 28; 34 | IgG1 | Monovalent aKLH HC-loop-ShK(1-35016K) Ab | 8.264 | >1000 | >121.01 | 1.604 | 5.386 | 23.94 |
| 28; 35; 28; 35 | IgG1 | Bivalent aKLH HC-loop-ShK(1-35 016K) Ab | ND | ND | ND | 3.910 | 55.235 | 58.36 |

TABLE 7I

Pharmacokinetics of monovalent Fc/Fc-[Lys16]ShK in Sprague-Dawley rats (n = 3).

| CMPD | Tmax (h) | Cmax (ng/ml) | AUC0-t (ng · hr · mL$^{-1}$) | AUC0-inf (ng · hr · mL$^{-1}$) | CL/F (mL · hr$^{-1}$ · kg$^{-1}$) | HL (h) |
|---|---|---|---|---|---|---|
| Monovalent Fc/Fc-[Lys16]ShK | 4 ± 3.46 | 1530 ± 1230 | 39600 ± 13900 | 43900 ± 14600 | 146 ± 47.1 | 56.3 ± 19.3 |

TABLE 7J

Pharmacokinetic data for recombinant monovalent and bivalent anti-KLH Ab-[Lys16]ShK fusion proteins administered by subcutaneous injection (dose = 6 mg/kg) to Sprague-Dawley rats (n = 3).

| CMPD | Tmax (h) | Cmax (ng/ml) | AUC0-t (ng · hr · mL$^{-1}$) | AUC0-inf (ng · hr · mL$^{-1}$) | CL/F (mL · hr$^{-1}$ · kg$^{-1}$) | HL (h) |
|---|---|---|---|---|---|---|
| Monovalent | 32 ± 13.9 | 5890 ± 1770 | 481000 ± 157000 | 594000 ± 182000 | 10.9 ± 3.47 | 32 ± 13.9 |
| Bivalent | 60 ± 50.5 | 126 ± 83.4 | 12900 ± 9750 | 17800 ± 17100 | 655 ± 551 | 60 ± 50.5 |

TABLE 7K

Pharmacokinetic data for recombinant monovalent Fc/Fc-ShK heterodimer, monovalent Fc-ShK/KLH Ab heterotrimer and bivalent ShK-Fc/ShK-Fc homodimer fusion proteins administered by subcutaneous injection (dose = 2 mg/kg) to Sprague-Dawley rats (n = 3).

| CMPD | Tmax (h) | Cmax (ng/ml) | AUC0-t (ng · hr · mL$^{-1}$) | AUC0-inf (ng · hr · mL$^{-1}$) | CL/F (mL · hr$^{-1}$ · kg$^{-1}$) | MRT (h) |
|---|---|---|---|---|---|---|
| Monovalent Fc/Fc-ShK (heterodimer) | 18.7 ± 9.2 | 728 ± 64.6 | 42469 ± 6566 | 44012 ± 7484 | 46.4 ± 8.6 | 46.8 ± 6.6 |
| Monovalent Fc-ShK/KLH Ab (heterotrimer) | 32.0 ± 13.9 | 1107 ± 26.2 | 83355.2 ± 5673 | 89158.6 ± 7915 | 22.6 ± 1.9 | 63.0 ± 8.7 |
| Bivalent ShK-Fc/ShK-Fc (homodimer) | 18.7 ± 9.2 | 27.0 ± 4.7 | 1418.8 ± 232 | 1460.7 ± 238 | 1395.0 ± 239 | 43.6 ± 2.3 |

TABLE 7L

Pharmacokinetic data for recombinant monovalent and bivalent anti-KLH AbLoop-[Lys16]ShK fusion proteins administered by subcutaneous injection (dose = 6 mg/kg) to Sprague-Dawley rats (n = 3).

| CMPD | Tmax (h) | Cmax (ng/ml) | AUC0-t (ng · hr · mL$^{-1}$) | AUC0-inf (ng · hr · mL$^{-1}$) | CL/F (mL · hr$^{-1}$ · kg$^{-1}$) | HL (h) |
|---|---|---|---|---|---|---|
| monovalent | 40.7 ± 35.6 | 7870 ± 605 | 878000 ± 259000 | 2730000 ± 2060000 | 3.11 ± 2.28 | 245 ± 151 |
| bivalent | 3.33 ± 1.15 | 102 ± 41.3 | 5460 ± 3930 | 6070 ± 4510 | 1440 ± 985 | 49.5 ± 13.1 |

Example 6

Kv1.3 and Kv1.1 Electrophysiology

Cell Lines Expressing Kv1.1 Through Kv1.7.

CHO-K1 cells were stably transfected with human Kv1.3, or for counterscreens (see, Example 8 herein), with hKv1.4, hKv1.6, or hKv1.7; HEK293 cells were stably expressing human Kv1.3 or with human Kv1.1. Cell lines were from Amgen or BioFocus DPI (A Galapagos Company). CHO K1 cells stably expressing hKv1.2, for counterscreens, were purchased from Millipore (Cat #.CYL3015).

Whole Cell Patch Clamp Electrophysiology.

Whole-cell currents were recorded at room temperature using MultiClamp 700B amplifier from Molecular Devices Corp. (Sunnyvale, Calif.), with 3-5 MΩ pipettes pulled from borosilicate glass (World Precision Instruments, Inc). During data acquisition, capacitive currents were canceled by analogue subtraction, no series resistance compensation was used, and all currents were filtered at 2 kHz. The cells were bathed in an extracellular solution containing 1.8 mM $CaCl_2$, 5 mM KCl, 135 mM NaCl, 5 mM Glucose, 10 mM HEPES, pH 7.4, 290-300 mOsm. The internal solution containing 90 mM KCl, 40 mM KF, 10 mM NaCl, 1 mM $MgCl_2$, 10 mM EGTA, 10 mM HEPES, pH 7.2, 290-300 mOsm. The currents were evoked by applying depolarizing voltage steps from −80 mV to +30 mV every 30 s (Kv1.3) or 10 s (Kv1.1) for 200 ms intervals at holding potential of −80 mV. To determine IC50, 5-6 peptide or peptide conjugate concentration at 1:3 dilutions were made in extracellular solution with 0.1% BSA and delivered locally to cells with Rapid Solution Changer RSc-160 (BioLogic Science Instruments). Currents were achieved to steady state for each concentration. Data analysis was performed using pCLAMP (version 9.2) and OriginPro (version 7), and peak currents before and after each test article application were used to calculate the percentage of current inhibition at each concentration.

PatchXpress®, Planar Patch-Clamp Electrophysiology.

Cells were bathed in an extracellular solution containing 1.8 mM $CaCl_2$, 5 mM KCl, 135 mM NaCl, 5 mM Glucose, 10 mM HEPES, pH 7.4, 290-300 mOsm. The internal solution contained 90 mM KCl, 40 mM KF, 10 mM NaCl, 1 mM $MgCl_2$, 10 mM EGTA, 10 mM HEPES, pH 7.2, 290-300 mOsm. Usually 5 peptide or peptide conjugate concentrations at 1:3 dilutions are made to determine the IC50s. The peptide or peptide conjugates are prepared in extracellular solution containing 0.1% BSA. Dendrotoxin-k and Margatoxin were purchased from Alomone Labs Ltd. (Jerusalem, Israel); ShK toxin was purchased from Bachem Bioscience, Inc. (King of Prussia, Pa.); 4-AP was purchased from Sigma-Aldrich Corp. (St. Louis, Mo.). Currents were recorded at room temperature using a PatchXpress® 7000A electrophysiology system from Molecular Devices Corp. (Sunnyvale, Calif.). The voltage protocols for hKv1.3 and hKv1.1 are shown in Table 7M in Example 8 herein. An extracellular solution with 0.1% BSA was applied first to obtain 100% percent of control (POC), then followed by 5 different concentrations of 1:3 peptide or peptide conjugate dilutions for every 400 ms incubation time. At the end, excess of a specific benchmark ion channel inhibitor (Table 7M in Example 8) was added to define full or 100% blockage. The residual current present after addition of benchmark inhibitor, was used in some cases for calculation of zero percent of control. The benchmark inhibitors for Kv1.3 and Kv1.1 are described in Table 7M in Example 8.

Each individual set of traces or trial were visually inspected and either accepted or rejected. The general criteria for acceptance were:

1. Baseline current must be stable
2. Initial peak current must be >300 pA
3. Intitial Rm and final Rm must >300 Ohm
4. Peak current must achieve a steady-state prior to first compound addition.

The POC was calculated from the average peak current of the last 5 sweeps before the next concentration compound addition and exported to Excel for IC50 calculation.

IonWorks, High-Throughput, Planar Patch-Clamp Electrophysiology.

Electrophysiology was performed on CHO cells stably expressing hKv1.3 and HEK293 cells stably expressing hKv1.1. The procedure for preparation of the "Assay Plate" containing ShK analogues and conjugates for IWQ electrophysiology was as follows: all analogues were dissolved in extracellular buffer (PBS, with 0.9 mM $Ca^{2+}$ and 0.5 mM $Mg^{2+}$) with 0.3% BSA and dispensed in the row H of 96-well polypropylene plates at the concentration of 100 nM from column 1 to column 10. Column 11 and 12 were reserved for negative and positive controls, then serial diluted at 1:3 ratio to row A. IonWorks Quattro (IWQ) electrophysiology and data analysis were accomplished as follows: re-suspended cells (in extracellular buffer), the Assay Plate, a Population Patch Clamp (PPC) PatchPlate as well as appropriate intracellular (90 mM potassium gluconate, 20 mM KF, 2 mM NaCl, 1 mM $MgCl_2$, 10 mM EGTA, 10 mM HEPES, pH 7.35) and extracellular buffers were positioned on IonWorks Quattro. When the analogues were added to patch plates, they were further diluted 3-fold from the assay plate to achieve a final test concentration range from 33.3 nM to 15 pM with 0.1% BSA. Electrophysiology recordings were made from the CHO-Kv1.3 and HEK-Kv1.1 cells using an amphotericin-based perforated patch-clamp method. Using the voltage-clamp circuitry of the IonWorks Quattro, cells were held at a membrane potential of −80 mV and voltage-activated K+ currents were evoked by stepping the membrane potential to +30 mV for 400 ms. K+ currents were evoked under control conditions i.e., in the absence of inhibitor at the beginning of the experiment and after 10-minute incubation in the presence of the analogues and controls. The mean K+ current amplitude was measured between 430 and 440 ms and the data were exported to a Microsoft Excel spreadsheet. The amplitude of the K+ current in the presence of each concentration of the analogues and controls was expressed as a percentage of the K+ current of the pre-compound current amplitude in the same well. When these % of control values were plotted as a function of concentration, the IC50 value for each compound could be calculated using the dose-response fit model 201 in Excel fit program which utilizes the following equation:

$$\% \text{ of control} = y_{min} + \left( \frac{y_{max} - y_{min}}{1 + \left(\frac{conc.}{IC_{50}}\right)^n} \right)$$

where ymin is the minimum y-value of the curve, ymax is the maximum y-value of the curve, conc. is the test concentration and n is the Hill slope of the curve.

Example 7

Measuring Bioactivity in Human Whole Blood

Ex Vivo Assay to Examine Impact of Toxin Peptide Analog Kv1.3 Inhibitors on Secretion of IL-2 and IFN-g.

The potency of ShK analogs and conjugates in blocking T cell inflammation in human whole blood was examined using an ex vivo assay that has been described earlier (see Example 46 of WO 2008/088422 A2, incorporated herein by reference in its entirety). In brief, 50% human whole blood is stimulated with thapsigargin to induce store depletion, calcium mobilization and cytokine secretion. To assess the potency of molecules in blocking T cell cytokine secretion, various concentrations of Kv1.3 blocking peptides and peptide-conjugates were pre-incubated with the human whole blood sample for 30-60 min prior to addition of the thapsigargin stimulus. After 48 hours at 37° C., 5% $CO_2$, conditioned medium was collected and the level of cytokine secretion was determined using a 4-spot electrochemiluminescent immunoassay from MesoScale Discovery. Using the thapsigargin stimulus, the cytokines IL-2 and IFN-g were secreted robustly from blood isolated from multiple donors. The IL-2 and IFN-g produced in human whole blood following thapsigargin stimulation were produced from T cells, as revealed by intracellular cytokine staining and fluorescence-activated cell sorting (FACS) analysis.

Kv1.3 is the major voltage-gated potassium channel present on T cells. Allowing for $K^+$ efflux, Kv1.3 provides the driving force for continued $Ca^{2+}$ influx which is necessary for the sustained elevation in intracellular calcium needed for efficient T cell activation and cytokine secretion. Kv1.3 inhibitors have been shown earlier to suppress this calcium flux induced by TCR ligation (G. C. Koo et al., 1999, Cell. Immunol. 197, 99-107). Thapsigargin-induced store-depletion and TCR ligation elicits similar patterns of $Ca^{2+}$ mobilization in isolated T cells (E. Donnadieu et al., 1991, J. Biol. Chem. 267, 25864-25872), but we have found thapsigargin gives a more robust response in whole blood. Therefore, we developed a bioassay whereby the bioactivity of Kv1.3 inhibitors is assessed by examining their ability to block thapsigargin-induced cytokine secretion from T cells in human whole blood. Since whole blood is a complex fluid containing high protein levels, the activity of peptides and peptide conjugates in this whole blood assay has an additional advantage in assessing the molecules stability over 48 hours in a biologically relevant fluid. The whole blood assay provides important confirmation of the Kv1.3 potency of molecules determined by electrophysiology (ePhys), since ePhys assays are generally of short duration (<1-2 hours) and use physiological saline containing no protein. The longer duration of the whole blood assay may allow for more effective determination of equilibrium binding kinetics relative to ePhys studies which are of short duration.

Example 8

Ion Channel Counterscreens

Kv1.1, Kv1.2, Kv1.3, Kv1.4, Kv1.6 and Kv1.7, PatchXpress®, planar patch-clamp electrophysiology. Ion channel currents can be recorded at room temperature using PatchXpress® 7000A electrophysiology system from MDC using methods and cells described in Example 6 above. The voltage protocols for each channel are shown in Table 7M, below.

TABLE 7

MVoltage protocols and recording conditions.

| Ion Channel | Voltage Step | Pulse Duration | Time between pulses | Holding Potential | Benchmark Inhibitor |
|---|---|---|---|---|---|
| hKv1.1 | From −80 mV to +30 mV | 200 ms | 10 s | −80 mV | 10 nM DTX-k |
| hKv1.2 | From −80 mV to +60 mV | 400 ms | 10 s | −80 mV | 1 nM MgTx |
| hKv1.3 | From −80 mV to +30 mV | 200 ms | 30 s | −80 mV | 1 nM ShK |
| hKv1.4 | From −80 mV to +30 mV | 200 ms | 30 s | −80 mV | 1 mM 4-AP |
| hKv1.6 | From −80 mV to +60 mV | 500 ms | 15 s | −80 mV | 1 mM 4-AP |
| hKv1.7 | From −80 mV to +30 mV | 1000 ms | 15 s | −80 mV | 1 mM 4-AP |

Cardiac ion channel counterscreens (hERG, hKvLQt1/hminK, hNav1.5, hKv1.5, hCav1.2, hKv4.3).

Cell Lines.

HEK293 cells stably transfected with hKvLQT1/hminK and hERG were from Amgen or Cytomyx, Inc. HEK293 cells stable transfected with human hNav1.5 were purchased from Cytomyx, Inc. HEK293 cells stably expressing hKv4.3 and CHO cells stably expressing hKv1.5 were from ChanTest. CHO cells stably expressing the human L-type calcium channel Cav1.2 were from ChanTest and contained the human CACNA1C gene encoding hCav1.2 and coexpressed the beta 2 subunit encoded by human CACNB2 and alpha2delta1 encoded by the CACNA2D1 gene.

FASTPatch® studies were performed at ChanTest to examine the impact of peptides and conjugates on the cloned human L-type calcium channel hCav1.2, cloned hKv4.3 and cloned hKv1.5 involved PatchXpress (Model 7000A, Molecular Devices, Union City, Calif.) electrophysiology at room temperature. The extracellular recording solution (HB-PS) contained 137 mM NaCl, 4 mM KCl, 1.8 mM $CaCl_2$, 1 mM $MgCl_2$, 10 mM HEPES and 10 mM Glucose adjusted to pH 7.40 with NaOH. The intracellular recording solution for hKv4.3 and hKv1.5 contained 130 mM potassium aspartate, 5 mM MgCl2, 5 mM EGTA, 4 mM ATP and 10 mM HEPES adjusted to pH 7.2 with KOH. The intracellular solution for hCav1.2 contained 130 mM cesium aspartate, 5 mM $MgCl_2$, 5 mM EGTA, 4 mM ATP, 2 mM EDTA, 1 mM $CaCl_2$, 0.1 mM GTP and 10 mM HEPES adjusted to pH 7.2 with N-methyl-D-glucamine. In preparation for recording, intracellular solution is loaded into the intracellular compartments of the Sealchip$_{16}$ planar electrode. Cell suspensions are pipetted into the extracellular compartments of the Sealchip$_{16}$ planar electrode. After establishing a whole-cell configuration, membrane currents are recorded using dual-channel patch clamp amplifiers in the PatchXpress® system. Before digitization, the currents were low-pass filtered at one-fifth of the sampling frequency. Three concentrations of peptide conjugates (test article) diluted into HB-PS with 1% BSA are applied at five minute intervals to naïve cells. Solution exchange were performed in quadruplicate and the duration of exposure to each test article concentration was five minutes. Vehicle controls were also applied to naïve cells and after a solution exchange positive controls are applied to verify sensitivity to ion channel blockade. All positive controls were diluted into HB-PS with 0.3% DMSO. Positive controls for blockade of channels included: nifedipine (0.01 μM) which produced about 75% hCav1.2 current block, flecainide (0.1 mM) which produced about 75% inhibition of the hKv4.3 current and 4-aminopyridine (2 mM) which blocked about 80% of the hKv1.5 current. Valid whole-cell recordings must meet the following criteria: (1) membrane resistance (Rm) ≥200 MΩ, (2) leak current≤25% channel current. The test procedures for hCav1.2, hKv4.3 and hKv1.5 were as follows:

a.) hCav1.2 Test Procedure.

Onset and steady state block of hCav1.2/β2/α2δ channels were measured using a stimulus voltage pattern consisting of a depolarizing test pulse (duration, 200 ms; amplitude, 10 mV) at 10-s intervals from a −40 mV holding potential. Test article concentrations may be applied cumulatively in ascending order without washout between applications. Peak current was measured during the step to 10 mV. Saturating concentration of nifedipine (10 µM) is added at the end of each experiment to block hCav1.2 current. Leak current was digitally subtracted from the total membrane current record.

b.) hKv4.3 Test Procedure.

Onset and steady state block of hKv4.3 current were measured using a pulse pattern with fixed amplitudes (depolarization: 0 mV for 300 ms) repeated at 10-s intervals from a holding potential of −80 mV. Peak and sustained test pulse current amplitudes were measured during the step to zero mV.

c.) hKv1.5 Test Procedure.

Onset and steady state block of hKv1.5 current were measured using a pulse pattern with fixed amplitudes (depolarization: +20 mV amplitude, 300 ms duration) repeated at 10-s intervals from a holding potential of −80 mV. Current amplitude was measured at the end of the step to +20 mV.

Counterscreens Against the Cloned Human Nav1.5 Sodium Channel Using the PatchXpress® System.

The extracellular (HB-PS2) recording solution contained 70 mM NaCl, 67 mM N-methyl-D-glucamine, 4 mM KCl, 1.8 mM $CaCl_2$, 1 mM $MgCl_2$, 10 mM HEPES, 10 mM Glucose adjusted to pH 7.4 with HCl. The internal recording solution contained 130 mM CsF, 10 mM NaCl, 10 mM EGTA, 2 mM $MgCl_2$, 10 mM HEPES adjusted to pH 7.20 with CsOH. Stock solutions of reference standard or test articles were diluted into HB-PS2 prior to application. Test articles included either peptides or peptide conjugates described herein. Lidocaine (1-30 µM) was the reference standard. A standardized step protocol is used to elicit ionic current through the hNav1.5 sodium channel. Cells are held at −80 mV. Onset and steady state block of hNav1.5 sodium current due to Test Article was measured using a pulse pattern with fixed amplitudes (conditioning prepulse: −120 mV for 50 ms; depolarizing test step to −30 mV for 20 ms) repeated at 10-s intervals. Currents are filtered at 3 kHz and acquired at 10 kHz, in episodic mode. When a good recording was established, cells were washed for 2 minutes, following by applying control vehicle for 5 minutes. Then control and each concentration of test article was applied for 5 minutes. There were 3 additions for each concentration with 1-minute interval. Dispense speed was 40 µL/s with suction on. To determine $IC_{50}$, Test Article at 1 µM, 3 µM, 10 µM and 30 µM was applied to cells (n=3 cells) cumulatively (without washout between test article concentrations) in ascending order, to each cell (n=3 where n=number of cells). Each concentration of test article was applied for 5 minutes. There were 3 additions for each concentration with a 1-minute interval. Electrophysiological data acquisition was performed using PatchXpress Commander v1.4 (Axon Instruments, Union City, Calif.) and analyses was performed using DataXpress v1.4 (Axon Instruments, Union City, Calif.). The 5 peak currents before and after test article application were used to calculate the percentage of current inhibition at each concentration. Acceptance criteria for a good recording include: (1) seal resistance>200 MΩ, (2) access resistance<10 MΩ, (3) peak tail current>200 pA, (4) leakage current<25% of the peak tail current, (5) rundown<2.5%/minute in control vehicle.

Counterscreens Against the Human IKs (hKvLQT1+hminK) Potassium Channel Using the PatchXpress® System.

The extracellular recording solution was HB-PS. The internal recording solution contained 20 mM KF, 90 mM KCl, 10 mM NaCl, 10 mM EGTA, 5 mM $K_2ATP$, 1 mM $MgCl_2$, 10 mM HEPES adjusted to pH 7.20 with KOH. Stock solutions of reference standard or test articles were diluted into HB-PS prior to application. Test articles included either peptides or peptide conjugates described herein. Chromanol 293B (0.3-10 µM) was the reference standard. A standardized step protocol was used to elicit ionic current through the IKs potassium channel. Cells were held at −80 mV. Onset and steady state block of IKs potassium current due to Test Article was measured using a pulse pattern with fixed amplitudes (depolarizing test step to +50 mV for 5 s) repeated at 10-s intervals. Currents is filtered at 3 kHz and acquired at 10 kHz, in episodic mode. When a good recording was established, cells were washed for 2 minutes, following by applying control vehicle for 5 minutes. Then control and each concentration of test article were applied for 5 minutes. There were 3 additions for each concentration with 1 minute interval. Dispense speed was 40 µL/s with suction on. Test article at 1 µM, 3 µM, 10 µM and 30 µM were applied to cells (n=3 cells) cumulatively (without washout between test article concentrations) in ascending order, to each cell (n=3 where n=number of cells). Each concentration of test article was applied for 5 minutes. There were 3 additions for each concentration with a 1 minute interval. Electrophysiological data acquisition was performed using PatchXpress® Commander v1.4 (Axon Instruments, Union City, Calif.) and analyses is performed using DataXpress v1.4 (Axon Instruments, Union City, Calif.). The 5 peak currents before and after test article application were used to calculate the percentage of current inhibition at each concentration. Acceptance criteria for a good recording includes: (1) seal resistance>200 MΩ, (2) access resistance<10 MΩ, (3) peak tail current>200 pA, (4) leakage current<25% of the peak current, (5) rundown<2.5%/minute in control vehicle.

Counterscreens against the human IKr (hERG or hKv11.1) potassium channel by conventional whole cell patch clamp electrophysiology. One to 2 drops of the cell suspension is added to a 35 mm poly-d-lysine coated cover slip for overnight incubation before electrophysiology experiments. Whole-cell currents were recorded from single cells by using tight GΩ seal configuration of the patch-clamp technique. A 35 mm cover slip was transferred to the recording stage after rinsing and replacing the culture medium with extracellular recording buffer containing 135 mM NaCl, 5 mM KCl, 1.8 mM $CaCl_2$, 10 mM HEPES, and 5 mM Glucose (pH was adjusted to 7.40 with NaOH and osmolarity was set at 300 mOsm). Cells were continuously perfused with the extracellular recording buffer via one of the glass capillaries arranged in parallel and attached to a motorized rod, which places the glass capillary directly on top of the cell being recorded. For hERG profiling, the recording pipette solution contained 130 mM KF, 2 mM $MgCl_2$, 10 mM EGTA, and 10 mM HEPES adjusted to pH 7.40 with KOH and osmolarity set at 280 mOsm). Experiments were performed at room temperature and recorded using Multiclamp 700A amplifier (Molecular Devices Inc.).

Pipette resistances were typically 2-3 MΩ. Cells were held at a potential of −80 mV. To achieve a baseline or reference point for the peak outward tail current, a step to −50 mV for 500 ms was used. This was followed by a depolarizing step to +20 mV for 2 s to drive the channels to the inactivated state. A step back to −50 mV for 2 s allowed the inactivation to be relieved and peak hERG current to be measured. Pulses were repeated once every 10 s. Total hERG current was measured as the difference between the peak current at the repolarizing −50 mV step and the baseline current at −50 mV. Test articles (up to 10 µM), which included the peptides and peptide conjugates described herein, were mixed into the extracellular recording buffer containing 0.1% bovine serum albumin (BSA) and subsequently transferred to glass perfusion reservoirs. Electronic pinch valves controlled the flow of the test articles from the reservoirs onto the cell being recorded. IC50 values and curve fits were estimated using the four parameter logistic fit of XLfit software. The hERG channel inhibitor, cisapride, was used to validate the assay.

Counterscreens against calcium-activated potassium channels human IKCa1 and BKCa by conventional whole cell patch clamp electrophysiology. CHO IKCa and BKCa cell lines were obtained from BioFocus DPI (A Galapagos Company). One to 2 drops of the hIKCa1 or BKCa cell suspension is added to a 35 mm poly-d-lysine coated cover slip for overnight incubation before electrophysiology experiments. Whole-cell currents were recorded from single cells by using tight GΩ seal configuration of the patch-clamp technique. A 35 mm cover slip was transferred to the recording stage after rinsing and replacing the culture medium with the extracellular recording buffer containing 135 mM NaCl, 5 mM KCl, 1.8 mM $CaCl_2$, 10 mM HEPES, and 5 mM Glucose (pH was adjusted to 7.40 with NaOH and osmolarity was set at 300 mOsm). Cells were continuously perfused with the extracellular recording buffer via one of the glass capillaries arranged in parallel and attached to a motorized rod, which places the glass capillary directly on top of the cell being recorded. The recording pipette solution contained 130 mM potassium aspartate, 1 mM $MgCl_2$, 1.26 mM $CaCl_2$, 2 mM EGTA, 2 mM Mg-ATP and 10 mM HEPES adjusted to pH 7.40 with KOH and osmolarity set at 280 mOsm. Experiments were performed at room temperature and recorded using Multiclamp 700A amplifier (Molecular Devices Inc.). Cells were held at potential of −80 mV. Both BK and IK currents were activated as calcium ion diffused into the cell from recording pipette solution. Activation of the calcium dependent outward potassium current by calcium diffusion generally takes 3 to 5 min for full activation. Outward currents were continuously monitored at holding potential of +50 mV before and during drug exposure. Alternatively, 400 ms voltage ramps from −120 to +60 mV were repeated once every 10 s to characterize the current voltage relation for both channels before and during drug exposure. Test articles (up to 10 µM), which included the peptides and peptide conjugates described herein, were mixed into the extracellular recording buffer containing 0.1% bovine serum albumin (BSA) and subsequently transferred to glass perfusion reservoirs. Electronic pinch valves controlled the flow of the test articles from the reservoirs onto the cell being recorded. Pipette resistances were typically 2-3 MΩ. IC50 values and curve fits were estimated using the four parameter logistic fit of XLfit software. A IKCa and BK peptide inhibitor, charybdotoxin (100 nM), was applied at the conclusion of the assay procedures for pharmacological validation of the assay.

Example 9

AMP5-aKLH Fusions

The AMP5 TPO-mimetic peptide was genetically fused to anti-KLH antibodies of the invention in all four possible terminal fusion configurations (represented schematically in FIG. 1F-1K; FIG. 45), i.e., N-terminally fused and C-terminally fused to both immunoglobulin light chain monomers and to both immunoglobulin heavy chain monomers, and was expressed in mammalian (CHO) cells. The fusions were then purified by protein A chromatography (GE Life Sciences) using 10 column volumes of Dulbecco's PBS without divalent cations as the wash buffer and 100 mM acetic acid as the elution buffer at 7° C. The elution peak was pooled based on the chromatogram and the pH was raised to ~5.0 using 2 M Tris base. The pool was then diluted with at least 4 volumes of water and then loaded on to an SP-HP sepharose column (GE Life Sciences) and washed with 10 column volumes of S-Buffer A (20 mM acetic acid, pH 5.0, followed by elution using a 20 column volume gradient to 60% S-Buffer B (20 mM acetic acid, 1 M NaCl, pH 5.0) at 7° C. A pool was made based on the chromatogram and the material was dialyzed against >20 volumes of 10 mM acetic acid, 9% sucrose, pH 5.0 using 10 kDa Slide-A-Lyzers (Pierce) at 4° C. The dialyzed material was then filtered through a 0.22 µm cellulose acetate filter and concentration was determined by the absorbance at 280 nm. Injected 50 µg of each antibody along with an unfused control on to a Phenomenex SEC 3000 column (7.8×300 mm) in 50 mM $NaH_2PO_4$ pH 6.5, 250 mM NaCl at developed at 1 ml/min observing the absorbance at 280 nm (FIG. 39). Each antibody was analyzed using a 1.0 mm Tris-glycine 4-20% SDS-PAGE (Novex) developed at 220V using reducing and non-reducing loading buffers and staining with QuickBlue (Boston Biologicals) (FIG. 40A-E), and the masses were determined by LC-MS (FIG. 41A-D).

The components of the various aKLH 120.6 IgG2-AMP5, AMP5-aKLH 120.6 IgG2, aKLH 120.6 hIgG1 (N297Q)-AMP5-Fc($C_H3$) Loop fusion, and AMP5-aKLH 120.6 Kappa embodiments include the following polypeptide monomers:

(a) aKLH 120.6 kappa LC (SEQ ID NO:28, above);
(b) aKLH 120.6 IgG2 HC (SEQ ID NO:29, above);
(c) aKLH 120.6 IgG1 HC (SEQ ID NO:34, above);
(c) aKLH 120.6 IgG2 HC-Amp5 having the following amino acid sequence:

```
                                              (SEQ ID. NO: 324)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECWYV

DGVEVHNAKTKPREEQFNSTFRVVSVLTVVHQDWLNGKEYKCKVSPPCPA

PPVAGPSVFLFPPKPKDTLMISRTPEVTCVVVDVSHEDPEVQFNNKGLPA

PIEKTISKTKGQPREPQVYTLPPSREEMTKNQVSLTCLVKGFYPSDIAVE
```

WESNGQPENNYKTTPPMLDSDGSFFLYSKLTVDKSRWQQGNVFSCSVMHE

ALHNHYTQKSLSLSPGGGGGGQGCSSGGPTLREWQQCRRAQHS//;

(d) Amp5-aKLH 120.6 IgG2 HC (SEQ ID NO:332) having the following amino acid sequence:

(SEQ ID NO: 332)
MDMRVPAQLLGLLLLWLRGARCQGCSSGGPTLREWQQCRRAQHSGGGGGQ

VQLVQSGAEVKKPGASVKVSCKASGYTFTGYHMHWVRQAPGQGLEWMGWI

NPNSGGTNYAQKFQGRVTMTRDTSISTAYMELSRLRSDDTAVYYCARDRG

SYYWFDPWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKRVEPKSCDKTHTCPPCPAPELLGGPSVFLFPPKPKD

TLMISRTPEVTCVVVDVSHEDPEVKFNWYVDGVEVHNAKTKPREEQYQST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG//.

(e) aKLH 120.6 hIgG1 N297Q-Amp5 Fc(CH3) Loop having the following amino acid sequence:

(SEQ ID NO: 341)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKRVEPKSCDKTHTC

PPCPAPELLGGPSVFLFPPKPKDTLMISRTPEVTCVVVDVSHEDPEVKFN

WYVDGVEVHNAKTKPREEQYQSTYRVVSVLTVLHQDWLNGKEYKCKVSNK

ALPAPIEKTISKAKGQPREPQVYTLPPSREEMGGQGCSSGGPTLREWQQC

RRAQHSGGTKNQVSLTCLVKGFYPSDIAVEWESNGQPENNYKTTPPVLDS

DGSFFLYSKLTVDKSRWQQGNVFSCSVMHEALHNHYTQKSLSLSPG//;

(f): Amp5-aKLH 120.6 kappa LC polypeptide fusion having the following amino acid sequence:

(SEQ ID NO: 342)
MDMRVPAQLLGLLLLWLRGARCQGCSSGGPTLREWQQCRRAQHSGGGGGD

IQMTQSPSSLSASVGDRVTITCRASQGIRNDLGWYQQKPGKAPKRLIYAA

SSLQSGVPSRFSGSGSGTEFTLTISSLQPEDFATYYCLQHNSYPLTFGGG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC//.

aKLH 120.6-IgG2 Heavy Chain (HC)-AMP5 Mammalian Expression.

The desired aKLH 120.6 IgG2 DesK-AMP5 product is a full antibody with the AMP5 peptide fused to the C-terminus of one heavy chain, configured as in the schematic representation of FIG. 1F, and was assembled by two separate rounds of Polymerase Chain Reaction (PCR) using PFU High Fidelity Ultra, by Stratagene. The first round of PCR generated two fragments: VK1sp-aKLH 120.6 IgG2 HC DesK-G5 and G5-AMP5 fragment. The oligo's and PCR templates that were used to generate these fragments were SEQ ID NO:325 and 326, below. Polymerase Chain Reaction 1(PCR1) generated the VK1sp-aKLH 120.6 IgG2 HC DesK-G5 fragment and existing DNA that coded for the VK1sp-aKLH 120.6 IgG2 DesK HC peptide was used as template.

Forward primer sequence was:
(SEQ ID NO: 325)
AAG CTC GAG GTC GAC TAG ACC ACC ATG GAC ATG AGG GTG CCC GCT CAG CTC CTG GGG CT//;
and Reverse Primer sequence was:
(SEQ ID NO: 326)
GCC GCT GCT GCA GCC CTG ACC ACC ACC TCC ACC ACC

CGG AGA CAG GGA GAG//.

The amino acid sequence encoded by the VK1sp-aKLH120.6 IgG2 HC DesK-G5 fragment, generated from PCR1 was:

(SEQ ID NO: 327)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGGQGC//.

Polymerase Chain Reaction 2 (PCR2) generated the G5-AMP5 fragment (SEQ ID NO:330), and existing DNA that coded for the AMP5 polypeptide was used as template with the following primers sequence:

Forward primer sequence was
(SEQ ID NO: 328)
CTC TCC CTG TCT CCG GGT GGT GGA GGT GGT GGT CAG GGC TGC AGC AGCGGC//;
and Reverse primer sequence was:
(SEQ ID NO: 329)
CTA CTA GCG GCC GCT CAG CTA TGC TGA GCG CGG CG//.

The amino acid sequence encoded by the fragment generated from PCR2 was:

(SEQ ID NO: 330)
LSLSPGGGGGGQGCSSGGPTLREWQQCRRAQHS//.

The products were run on a 1% agarose gel. The bands were punched for an agarose plug and the plugs were placed in a fresh PCR reaction tube. The agarose plugs were then amplified in PCR3 using the outside primers SEQ ID NO:325 and SEQ ID NO:329. The final PCR product was run on a 1% agarose gel. The correct size product was cut out, then gel purified by Qiagen's Gel Purification Kit. The purified gel fragment of VK1sp-aKLH 120.6 IgG2 DesK HC-G5-AMP5 was digested with restriction enzymes SalI and NotI, and then the digested product was purified by Qiagen's PCR Purification Kit. At the same time, pTT5 Vector (an Amgen vector containing a CMV promoter and Poly A tail) was cut by SalI and NotI. The pTT5 vector was run out on a 1% agarose gel and the larger fragment was cut out and gel purified by Qiagen's Gel Purification Kit. The VK1sp-aKLH 120.6 IgG2 DesK HC-G5-AMP5 product was ligated to the large vector fragment and transformed into OneShot® Top10 bacterial cells. The DNAs from transformed bacterial colonies were isolated and submitted for sequence analysis. One correct clone was selected for large scale plasmid purification.

The final pTT5:VK1sp-aKLH 120.6-IgG2 DesK HC-G5-AMP5 construct encoded the following IgG2 DesK HC-AMP5 polypeptide:

(SEQ ID NO: 331)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGQGCSSGGPTLREWQQCRRAQHS//.

AMP5-aKLH120.6-IgG2 Heavy Chain (HC) Mammalian Expression.

The desired AMP5-aKLH 120.6 IgG2 DesK HC product (SEQ ID NO:332, above) including the monomer is a full antibody with the AMP5 peptide fused to the N-terminus of one heavy chain, configured as in schematic representation FIG. 1I, and was assembled by two separate rounds of PCR using PFU High Fidelity Ultra, by Stratagene. The first round of PCR generated three fragments: VK1sp-AMP5, AMP5-G5, and G5-aKLH 120.6 IgG2 DesK HC fragment. The oligo's and PCR templates that were used to generate these fragments are listed below. Polymerase Chain Reaction 1 (PCR1) generated the VK1sp-AMP5 and existing DNA which coded for the VK1sp was used as template. Note this fragment was also used in construction of the VK1sp-AMP5-G5-aKLH 120.6 Kappa LC.

The forward primer sequence was:

(SEQ ID NO: 325)
AAG CTC GAG GTC GAC TAG ACC ACC ATG GAC ATG AGG

GTG CCCGCT CAG CTC CTG GGG CT//;
and

The reverse primer sequence was:
(SEQ ID NO: 333)
GCC GCT GCT GCA GCC CTG ACA TCT GGC ACC TCT CAA

CC//.

NO:333). The amino acid sequence encoded by the fragment generated from PCR1 was:

(SEQ ID NO: 334)
MDMRVPAQLLGLLLLWLRGARCQGCSSG//.

PCR2 generated the AMP5-G5 and existing DNA which coded for the AMP5 peptide was used as template.

Forward Primer sequence was:
(SEQ ID NO: 335)
GGT TGA GAG GTG CCA GAT GTC AGG GCT GCA GCA GCG GC//;
and The reverse primer sequence was:
(SEQ ID NO: 336)
CAG CTG CAC CTG ACC ACC ACC TCC ACC GCT ATG CTG

AGC GCG//.

The amino acid sequence encoded by the fragment generated from PCR2 was:

(SEQ ID NO: 337)
WLRGARCQGCSSGGPTLREWQQCRRAQHSGGGGGQVQLV//.

PCR3 generated G5-aKLH 120.6 IgG2 DesK HC, and existing DNA which coded for the aKLH 120.6 IgG2 HC (SEQ ID NO:29) monomer was used as template.

The forward primer sequence was:
(SEQ ID NO: 338)
CGC GCT CAG CAT AGC GGT GGA GGT GGT GGT CAG GTG CAG CTG//;
and The reverse primer sequence was:
(SEQ ID NO: 339)
CTA CTA GCG GCC GCT CAA CCC GGA GAC AGG GAG A//.

The amino acid sequence encoded by the fragment generated from PCR3 was:

(SEQ ID NO: 340)
RAQHSGGGGGQVQLVQSGAEVKKPGASVKVSCKASGYTFTGYHMHWVRQA

PGQGLEWMGWINPNSGGTNYAQKFQGRVTMTRDTSISTAYMELSRLRSDD

TAVYYCARDRGSYYWFDPWGQGTLVTVSSASTKGPSVFPLAPSSKSTSGG

TAALGCLVKDYFPEPVTVSWNSGALTSGVHTFPAVLQSSGLYSLSSVVTV

PSSSLGTQTYICNVNHKPSNTKVDKRVEPKSCDKTHTCPPCPAPELLGGP

SVFLFPPKPKDTLMISRTPEVTCVVVDVSHEDPEVKFNWYVDGVEVHNAK

TKPREEQYQSTYRVVSVLTVLHQDWLNGKEYKCKVSNKALPAPIEKTISK

AKGQPREPQVYTLPPSREEMTKNQVSLTCLVKGFYPSDIAVEWESNGQPE

-continued

NNYKTTPPVLDSDGSFFLYSKLTVDKSRWQQGNVFSCSVMHEALHNHYTQ

KSLSLSPG//.

The products were run on a 1% agarose gel. The bands were punched for an agarose plug and the plugs were placed in a fresh PCR reaction tube. The agarose plugs were then amplified by PCR4 using the outside primers SEQ ID NO:325 and SEQ ID NO:339. The final PCR product was run on a 1% agarose gel. The correct size product was cut out, then gel purified by Qiagen's Gel Purification Kit. The purified gel fragment of VK1sp-AMP5-G5-aKLH 120.6 IgG2 DesK HC was digested with restriction enzymes SalI and NotI, and then the digested product was purified by Qiagen's PCR Purification Kit. At the same time, pTT5 Vector (an Amgen vector containing a CMV promoter and Poly A tail) was cut by SalI and NotI. The pTT5 vector was run out on a 1% agarose gel and the larger fragment was cut out and gel purified by Qiagen's Gel Purification Kit. The VK1sp-AMP5-G5-aKLH 120.6 IgG2 DesK HC product was ligated to the large vector fragment and transformed into OneShot® Top10 bacterial cells. The DNA's from transformed bacterial colonies were isolated and submitted for sequence analysis. One correct clone was selected for large scale plasmid purification. The final pTT5:VK1sp-AMP5-G5-aKLH 120.6-IgG2 DesK HC construct encoded the AMP5-IgG2 DesK HC polypeptide (SEQ ID NO:332, above).

aKLH 120.6 aglycosylated hIgG1-AMP5 Fc(CH3) Loop Heavy Chain (HC) Mammalian Expression.

Figure 1M:
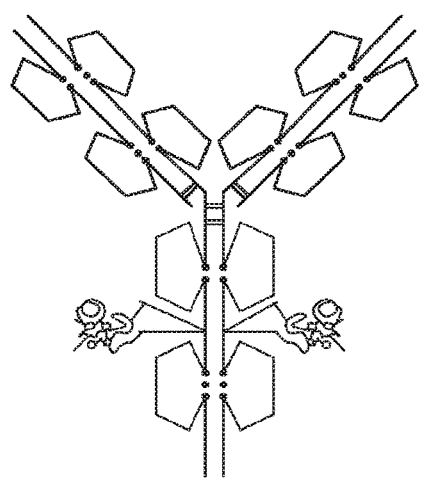
FIG. 1M represents a bivalent antibody with a toxin peptide analog moiety inserted into an internal loop of the immunoglobulin Fc domain of each HC monomer.
Figure 1N:
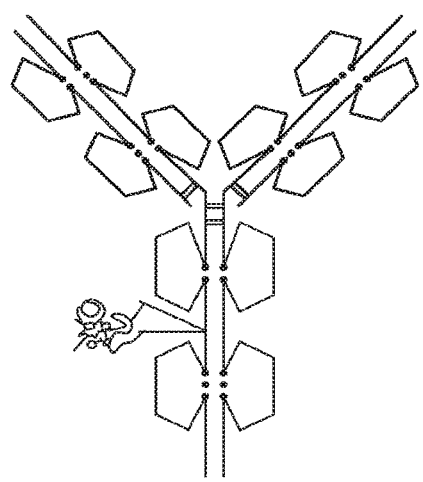

The desired aKLH 120.6 IgG1 aglycosylated (N297Q)-AMP5-Fc HC product comprising HC fusion monomer SEQ ID NO:341 (above) is a full antibody with the Amp5 peptide inserted into the CH3 domain of the IgG1 (N297Q) Fc DesK heavy chain, configured as schematically represented in FIG. 1M. The VK1sp-aKLH 120.6 IgG1 (N297Q)-AMP5-Fc DesK HC product was ordered by the synthetic gene company, Blue Heron. The final product was generated by digesting the VK1sp-aKLH 120.6 IgG1(N297Q)-AMP5-Fc DesK HC with its corresponding restriction enzymes, SalI and NotI. The digested product was run on a 1% agarose gel. The fragment was cut out, gel purified by Qiagen's Gel Purification Kit. At the same time, pTT5 Vector (an Amgen vector containing a CMV promoter and Poly A tail) was cut by SalI and NotI. The pTT5 vector was run out on a 1% agarose gel and the larger fragment was cut out and gel purified by Qiagen's Gel Purification Kit. The purified gel fragment of aKLH 120.6 IgG1 (N297Q)-AMP5-Fc DesK HC was ligated to the large vector fragment and transformed into OneShot® Top10 bacterial cells. The DNA's from transformed bacterial colonies were isolated and submitted for sequence analysis. One correct clone was selected for large scale plasmid purification. The final pTT5:VK1sp-aKLH 120.6 IgG1(N297Q)-AMP5-Fc DesK HC construct encodes for the aKLH 120.6 IgG1 (N297Q)-AMP5-DesK polypeptide fusion monomer (SEQ ID NO:341, above).

AMP5-G5-aKLH 120.6-Kappa Light Chain (LC) Mammalian Expression.

The desired AMP5-aKLH 120.6 Kappa LC product is a full antibody with AMP5 peptide fused to the N-terminus of one light chain fusion monomer (SEQ ID NO:342, above), configured as schematically represented in FIG. 1H, and was assembled by two separate rounds of Polymerase Chain Reaction (PCR) using PFU High Fidelity Ultra, by Stratagene. The first round of PCR generated three fragments which included, VK1sp-AMP5, AMP5-G5, and G5-aKLH 120.6 Kappa LC. The oligo's and templates used for PCR reactions to generate the fragments are listed below. The fragment that generated the VK1sp-AMP5 is the same fragment that was used in construction of the AMP5-aKLH 120.6 IgG2 DesK HC, and is described in that section. Polymerase Chain Reaction 2(PCR2) generated the AMP5-G5 fragment and existing DNA that coded for the AMP5 peptide was used as template. Forward primer sequence was (SEQ ID NO:335, above) and reverse primer sequence was CTG GGT CAT CTG GAT GTC ACC ACC ACC TCC ACC GCT ATG CTG AGC GCG// (SEQ ID NO:344). The amino acid sequence encoded by the fragment generated from PCR2 was:

(SEQ ID NO: 345)
WLRGARCQGCSSGGPTLREWQQCRRAQHSGGGGGDIQMTQ//.

PCR3 generated the G5-aKLH 120.6-Kappa LC fragment and existing DNA that coded for the aKLH 120.6 Kappa LC (SEQ ID NO:28) was used as template.

The forward primer sequence was:
(SEQ ID NO: 346)
CGC GCT CAG CAT AGC GGT GGA GGT GGT GGT GAC ATC CAG ATG ACC CAG//;
and the reverse primer sequence was:
(SEQ ID NO: 347)
AAC CGT TTA AAC GCG GCC GCT CAA CAC TCT CCC CTG

TTG AA//.

NO:347). The peptide sequence of the fragment generated from PCR3 was:

(SEQ ID NO: 348)
RAQHSGGGGGDIQMTQSPSSLSASVGDRVTITCRASQGIRNDLGWYQQKP

GKAPKRLIYAASSLQSGVPSRFSGSGSGTEFTLTISSLQPEDFATYYCLQ

HNSYPLTFGGGTKVEIKRTVAAPSVFIFPPSDEQLKSGTASVVCLLNNFY

PREAKVQWKVDNALQSGNSQESVTEQDSKDSTYSLSSTLTLSKADYEKHK

VYACEVTHQGLSSPVTKSFNRGEC//.

The products were run on a 1% agarose gel. The bands were punched for an agarose plug and the plugs were placed in a fresh PCR reaction tube. The agarose plugs were then amplified by PCR4 using the outside primers SEQ ID NO: 325 and SEQ ID NO:347. The final PCR product was run on a 1% agarose gel. The correct size product was cut out, then gel purified by Qiagen's Gel Purification Kit. The purified gel fragment of VK1sp-AMP5-G5-aKLH 120.6 Kappa LC was digested with restriction enzymes SalI and NotI, and then the digested product was purified by Qiagen's PCR Purification Kit. At the same time, pTT5 Vector (an Amgen vector containing a CMV promoter and Poly A tail) was cut by SalI and NotI. The pTT5 vector was run out on a 1% agarose gel and the larger fragment was cut out and gel purified by Qiagen's Gel Purification Kit. The VK1sp-AMP5-G5-aKLH 120.6 Kappa LC product was ligated to the large vector fragment and transformed into OneShot® Top10 bacteria. DNAs from transformed bacterial colonies were isolated and submitted for sequence analysis. One correct clone was selected for large scaled plasmid purification. The final pTT5:VK1sp-AMP5-G5-aKLH 120.6-

Kappa LC construct encoded an AMP5-Kappa LC polypeptide fusion monomer (SEQ ID NO:342, above).

Transient transfection was carried out in 293-6E cells (NRCC) using PEI (Polyethylenimine, linear, 25 kDa, 1 mg/ml sterile stock solution, pH 7.0, Polysciences). The 293-6E cell density was 1.1×10⁶ before transfection, then using 500 micrograms of DNA (heavy chain and light chain DNA, 1:1 ratio) per liter of cells transfected. The DNA was added to 50 ml 293 FreeStyle media (Invitrogen) and combined with 1.5 ml of PEI solution, vortexed mildly and then incubated 15 minutes at room temperature. The cells were transfected by adding the whole PEI-DNA mixture to the culture. Cells were then incubated on a shaker (120 rpm) at 37° C. containing 5% $CO_2$ for 24 hours. Tryptone N1 (TekniScience Inc, 20% in FreeStyle media) was then added to a final concentration of 0.5% and the incubation was continued for 5 days. The condition medium was harvested at day 5 by centrifuge at 4000 rpm followed by filtration through a 0.45 µm filter (Corning Inc.).

The fusions were then purified by protein A chromatography (GE Life Sciences) using 10 column volumes of Dulbecco's PBS without divalent cations as the wash buffer and 100 mM acetic acid as the elution buffer at 7° C. The elution peak was pooled based on the chromatogram and the pH was raised to about 5.0 using 2 M Tris base. The pool was then diluted with at least 4 volumes of water and then loaded on to an SP-HP sepharose column (GE Life Sciences) and washed with 10 column volumes of S-Buffer A (20 mM acetic acid, pH 5.0, followed by elution using a 20 column volume gradient to 60% S-Buffer B (20 mM acetic acid, 1 M NaCl, pH 5.0) at 7° C. A pool was made based on the chromatogram and the material was dialyzed against >20 volumes of 10 mM acetic acid, 9% sucrose, pH 5.0, using 10 kDa Slide-A-Lyzers (Pierce) at 4° C. The dialyzed material was then filtered through a 0.22 um cellulose acetate filter and concentration was determined by the absorbance at 280 nm. Injected 50 µg of each antibody along with an unfused control on to a Phenomenex SEC 3000 column (7.8×300 mm) in 50 mM $NaH_2PO_4$, pH 6.5, 250 mM NaCl, developed at 1 ml/min, detecting the absorbance at 280 nm (FIG. 39). All five antibodies showed the expected retention time for molecules of their size showing that very little aggregate was present. Each antibody was analyzed using a 1.0 mm Tris-glycine 4-20% SDS-PAGE (Novex) developed at 220V using reducing and non-reducing loading buffers and staining with QuickBlue (Boston Biologicals; FIG. 40A-E), and the masses were determined by LC-MS (FIG. 41A-D). In a typical experiment, 10 µg of the sample was reduced in 25 µl of 8 M GdHCl 50 mM Tris (pH 8.5) for 30 min at 55° C., then the reduced material was chromatographed through a Waters Massprep micro desalting column (2.1×5 mm) using an Acquity UPLC system (solvent A was 0.1% formic acid in water and solvent B was 0.1% formic acid in acetonitrile). The column was equilibrated with 5% solvent B at a flow rate 0.2 ml per min at 80° C., and upon sample introduction, the column was washed with 5% B for 1 min before the protein was eluted using a linear gradient from 5 to 40% B over 10 min. The column effluent was introduced into a Waters time-of-flight LCT premier mass spectrometer for mass measurement. CsI ions (3 mg CsI per ml in 50% isopropanol) was used as lock mass. The mass spectrum was deconvoluted using the MaxEnt1 software supplied with the instrument. The SDS-PAGE analysis demonstrated that all the expected quaternary structures were formed, and the mass spectral analysis demonstrates that the expected fusions were present in the purified molecules. Taken together these data indicate that fusions can be made with any of the four possible N-terminal or C-terminal fusion configurations of the monomers of aKLH 120.6 antibody, as well as Fc domain internal loop inserts (see, FIG. 1F-1N and FIG. 45 schematic representations).

Example 10

Ex4-aKLH Ab Fusions

The Exendin-4 peptide (HGEGTFTSDL SKQMEEEAVR LFIEWLKNGG PSSGAPPPS// SEQ ID NO:349) was genetically fused to N-terminus of the light chain of the anti-KLH 120.6 antibody through the 1kG linker (designated "Ex-4-1kG-aKLH 120.6-Ab" and expressed in mammalian cells. FIG. 42 is a schematic map of the Exendin-4 ("Ex4")-1kG-aKLH 120.6 LC fusion construct.

The components of the Ex-4-1kG-aKLH 120.6-Ab fusion included the following monomers:

(a) Ex-4-1kG-aKLH 120.6 kappa LC having the following amino acid sequence:

```
                                        (SEQ ID NO: 355)
MDMRVPAQLLGLLLLWLRGARCHGEGTFTSDL SKQMEEEAVR

LFIEWLKNGG PSSGAPPPSG SGSATGGSGSGASSGSGSAT

GSDIQMTQSP SSLSASVGDR VTITCRASQG IRNDLGWYQQ

KPGKAPKRLI YAASSLQSGV PSRFSGSGSG TEFTLTISSL

QPEDFATYYCLQHNSYPLTF GGGTKVEIKR TVAAPSVFIF

PPSDEQLKSG TASVVCLLNNFYPREAKVQW KVDNALQSGN

SQESVTEQDS KDSTYSLSST LTLSKADYEKHKVYACEVTH

QGLSSPVTKS FNRGEC//;
``` and (b) aKLH 120.6 IgG2 HC (SEQ ID NO:29, above).

The desired Ex-4-1kG-aKLH 120.6-Ab product was a full antibody configured with the Ex-4 peptide fused to the N-termini of both light chains (see, schematic representation in FIG. 1K). The ratio of Ex-4-light chain:heavy chain was 1:1. The isolation and cloning of the genes encoding Xeno-Mouse® hybridoma expressing aKLH 120.6 monoclonal antibody 120.6 heavy and light chains have been described in Example 1 and Example 4, above. Its native signal peptides have been replaced by the VK1/O12 peptide (MD-MRVPAQLLGLLLLWLRGARC// SEQ ID NO:103) as described above. DNA fragments encoding aKLH 120.6 LC (SEQ ID NO:28) and aKLH 120.6 HC IgG2 (SEQ ID NO:29) monomers were individually cloned into mammalian expression vector pTT5 (An Amgen vector containing a CMV promoter and Poly A tail.) to generate pTT5:aKLH120.6-VK1SP-kappa Light Chain (LC) construct and pTT5:aKLH120.6-VK1SP-IgG2 Heavy Chain (HC) construct, respectively.

A DNA fragment (SEQ ID NO:351, below) flanked by SalI (5') and BamHI (3') that comprises the Kozak sequence and the first part of an ORF that encompasses the VK1/O12 signal peptide (SEQ ID NO:103), the Ex-4 (1-39) peptide (SEQ ID NO:349), and the 1kG linker peptide was synthesized and cloned by GenScript (Piscataway, N.J.) according to standard gene synthesis techniques.

SalI
~~~~~~
(SEQ ID NO: 351)
GTCGACTAGACCACCATGGACATGAGGGTCCCCGCTCAGCTCCTGGGGCT

CCTGCTATTGTGGTTGAGAGGTGCCAGATGTCATGGGGAGGGAACATTTA

CAAGCGATCTGAGCAAACAAATGGAGGAAGAGGCAGTTAGACTGTTCATT

GAATGGCTCAAGAACGGCGGACCGAGTAGTGGTGCTCCGCCTCCCAGCGG

ATCTGGCAGCGCTACTGGTGGATCTGGATCGGGTGCATCCTCTGGATCTG

GAAGCGCTACCGGATCC//
~~~~~~
BamHI

The BamHI (5') to NotI (3') fragment (SEQ ID NO:368, below) that covers the latter part of an ORF that consists of the mature aKLH 120.6-Ab LC was amplified from the aKLH 120.6-Ab LC DNA template described above (pTT5-aKLH 120.6-VK1SP-kappa Light Chain (LC) construct) with a pair of oligo primers:
AAT GGA TCC GAC ATC CAG ATG ACC CAG TC/(SEQ ID NO:352); and AAT GCG GCC GCT CAA CAC TCT CC// (SEQ ID NO:353), according to standard PCR techniques.

BamHI
~~~~~~
(SEQ ID NO: 368)
GGATCCGACATCCAGATGACCCAGTCTCCATCCTCCCTGTCTGCATCTGT

AGGAGACAGAGTCACCATCACTTGCCGGGCAAGTCAGGGCATTAGAAATG

ATTTAGGCTGGTATCAGCAGAAACCAGGGAAAGCCCCTAAACGCCTGATC

TATGCTGCATCCAGTTTGCAAAGTGGGGTCCCATCAAGGTTCAGCGGCAG

TGGATCTGGGACAGAATTCACTCTCACAATCAGCAGCCTGCAGCCTGAAG

ATTTTGCAACTTATTACTGTCTACAGCATAATAGTTACCCGCTCACTTTC

GGCGGAGGGACCAAGGTGGAGATCAAACGAACTGTGGCTGCACCATCTGT

CTTCATCTTCCCGCCATCTGATGAGCAGTTGAAATCTGGAACTGCCTCTG

TTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGA

GCAGGACAGCAAGGACAGCACCTACAGCCTCAGCAGCACCCTGACGCTGA

GCAAAGCAGACTACGAGAAACACAAAGTCTACGCCTGCGAAGTCACCCAT

CAGGGCCTGAGCTCGCCCGTCACAAAGAGCTTCAACAGGGGAGAGTGTTG

AGCGGCCGC//
~~~~~~~~
NotI

The synthetic SalI-BamHI fragment and the PCR-amplified BamHI-NotI fragment were digested by corresponding restriction enzymes, isolated from an agarose gel and ligated into the SalI and NotI cloning sites of the pTT5 mammalian transient expression vector according to standard molecular cloning techniques (and described above in Example 4 re aKLH 120.6-HC-[Lys16]ShK Ab) resulting in the expression vector pTT5:Ex-4-1kG-aKLH 120.6 LC containing a clone (SEQ ID NO:354) that encodes the amino acid sequence of the Ex-4-1kG-aKLH 120.6 LC monomer (with N-terminal VK1/O12 signal peptide) (SEQ ID NO:355).

SalI
~~~~~
(SEQ ID NO: 354)
GTCGACTAGACCACCATGGACATGAGGGTCCCCGCTCAGCTCCTGGGGCT

CCTGCTATTGTGGTTGAGAGGTGCCAGATGTCATGGGGAGGGAACATTTA

CAAGCGATCTGAGCAAACAAATGGAGGAAGAGGCAGTTAGACTGTTCATT

GAATGGCTCAAGAACGGCGGACCGAGTAGTGGTGCTCCGCCTCCCAGCGG

ATCTGGCAGCGCTACTGGTGGATCTGGATCGGGTGCATCCTCTGGATCTG

GAAGCGCTACCGGATCCGACATCCAGATGACCCAGTCTCCATCCTCCCTG

TCTGCATCTGTAGGAGACAGAGTCACCATCACTTGCCGGGCAAGTCAGGG

CATTAGAAATGATTTAGGCTGGTATCAGCAGAAACCAGGGAAAGCCCCTA

AACGCCTGATCTATGCTGCATCCAGTTTGCAAAGTGGGGTCCCATCAAGG

TTCAGCGGCAGTGGATCTGGGACAGAATTCACTCTCACAATCAGCAGCCT

GCAGCCTGAAGATTTTGCAACTTATTACTGTCTACAGCATAATAGTTACC

CGCTCACTTTCGGCGGAGGGACCAAGGTGGAGATCAAACGAACTGTGGCT

GCACCATCTGTCTTCATCTTCCCGCCATCTGATGAGCAGTTGAAATCTGG

AACTGCCTCTGTTGTGTGCCTGCTGAATAACTTCTATCCCAGAGAGGCCA

AAGTACAGTGGAAGGTGGATAACGCCCTCCAATCGGGTAACTCCCAGGAG

AGTGTCACAGAGCAGGACAGCAAGGACAGCACCTACAGCCTCAGCAGCAC

CCTGACGCTGAGCAAAGCAGACTACGAGAAACACAAAGTCTACGCCTGCG

AAGTCACCCATCAGGGCCTGAGCTCGCCCGTCACAAAGAGCTTCAACAGG

GGAGAGTGTTGAGCGGCCGC//
~~~~~~~~~
NotI

Transient expression was conducted with these pair of expression vectors (pTT5:Ex-4-1kG-aKLH 120.6 LC and pTT5: aKLH 120.6 HC) to generate conditioned medium for the purification of Ex4-1kG-aKLH 120.6-Ab fusion. The human embryonic kidney 293 cell line stably expressing Epstein Barr virus Nuclear Antigen-1 (293-6E cells) was obtained from the National Research Council (Montreal, Canada). Cells were maintained as serum-free suspension cultures using F17 medium (Invitrogen, Carlsbad, Calif.) supplemented with 6 mM L-glutamine (Invitrogen, Carlsbad, Calif.), 1.1% F-68 Pluronic (Invitrogen, Carlsbad, Calif.) and 250 ug/ul Geneticin (Invitrigen, Carlsbad, Calif.). The suspension cell cultures were maintained in Erlenmeyer shake flask cultures. The culture flasks were shaken at 65 rpm at 37° C. in a humidified, 5% $CO_2$ atmosphere. A stock solution (1 mg/ml) of 25-kDa linear PEI (Polysciences, Warrington, Pa.) was prepared in water, acidified with HCl to pH 2.0 until dissolved, then neutralized with NaOH, sterilized by filtration (0.2 µm), aliquoted, and stored at −20° C. until used. Tryptone N1 was obtained from OrganoTechni S.A. (TekniScience, QC, Canada). A stock solution (20%, w/v) was prepared in Freestyle medium (Invitrogem, Carlsbad, Calif.), sterilized by filtration through 0.2 µm filters, and stored at 4° C. until use. Typically, transfections were performed at the 1 L scale. Cells (293-6E) were grown too a viable cell density of $1.1 \times 10^6$ cells/ml then transfection complexes were prepared in $1/10^{th}$ volume of the final culture volume. For a 1-L transfection culture, transfection complexes were prepared in 100 ml F17 basal medium, and 500 µg plasmid DNA (heavy chain and light chain DNA, 1:1 ratio) was first diluted in 100 ml F17 medium. After a 5 minute incubation at room temperature, 1.5 ml of PEI solution was added. The complexes were vortexed mildly, then incubated for 15 minutes at room temperature. The cells were transfected by adding the transfection complex mix to the cells in the shake flask culture. Twenty-four hours post-transfection, Tryptone N1 was added to the transfected culture to a final concentration of 0.5%, and the transfected cultures were maintained on a shaker at 65 rpm at 37° C. in a humidified, 5% $CO_2$ atmosphere for another 5 days after which they were harvested. The conditioned medium was harvested by centrifugation at 4000 rpm, and then sterile filtered through 0.2 µm filter (Corning Inc.).

The fusions were then purified by protein A chromatography (GE Life Sciences) using 10 column volumes of Dulbecco's PBS without divalent cations as the wash buffer and 100 mM acetic acid, pH 3.5, as the elution buffer at 7° C. The pH of the fractions were increased by leaving 0.025 volumes of 2 M Tris base in the fraction collector tubes. The elution peak was pooled based on the chromatogram and then dialyzed against >20 volumes of 10 mM acetic acid, 9% sucrose, pH 5.0, using 10 kDa Slide-A-Lyzers (Pierce) at room temperature for 3 hours. The dialyzed material was then filtered through a 0.22 µm cellulose acetate filter and concentration was determined by the absorbance at 280 nm. Samples of 25 µg of the antibody fusion were injected on to a Phenomenex SEC 3000 column (7.8×300 mm) in 50 mM $NaH_2PO_4$ pH 6.5, 250 mM NaCl at developed at 1 ml/min observing the absorbance at 280 nm (FIG. 43). Since the fusion protein eluted with the expected retention time for a protein of its expected size, this indicates that the protein was able to form the expected complex without excessive aggregation. The Ex4-aKLH 120.6 antibody was analyzed using a 1.0 mm Tris-glycine 4-20% SDS-PAGE (Novex) developed at 220V using reducing and non-reducing loading buffers and staining with QuickBlue (Boston Biologicals) (FIG. 44). The non-reducing SDS-PAGE indicates that the expected quaternary complex of the fusion protein was formed and fusion of the exendin-4 peptide to the aKLH 120.6 antibody results in a product with the expected structure.

Example 11

Avimer-aKLH Fusions

The C681 polypeptide is an IL-6 binding polypeptide with a so-called avimer structure. (See, e.g., Kolkman et al., Novel Proteins with Targeted Binding, US 2005/0089932; Baker et al., IL-6 Binding Proteins, US 2008/0281076; Stemmer et al., Protein Scaffolds and Uses Thereof, US 2006/0223114 and US 2006/0234299).

The components of the C681-aKLH 120.6 IgG2 HC fusion included the monomers:
(a) aKLH 120.6 kappa LC (SEQ ID NO:28); and
(b) (VK-1 SP)-C681-(G5)-aKLH 120.6 IgG2 HC fusion having the following amino acid sequence:

(SEQ ID NO: 356)
MDMRVPAQLLGLLLLWLRGARCSGGSCLPDQFRCGNGQCIPLDWVCDGVN

DCPDDSDEEGCPPRTCAPSQFQCGSGYCISQRWVCDGENDCEDGSDEANC

AGSVPTCPSDEFRCRNGRCIPRAWRCDGVNDCADNSDEEDCTEHTGGGGG

QVQLVQSGAEVKKPGASVKVSCKASGYTFTGYHMHWVRQAPGQGLEWMGW

INPNSGGTNYAQKFQGRVTMTRDTSISTAYMELSRLRSDDTAVYYCARDR

GSYYWFDPWGQGTLVTVSSASTKGPSVFPLAPCSRSTSESTAALGCLVKD

YFPEPVTVSWNSGALTSGVHTFPAVLQSSGLYSLSSVVTVPSSNFGTQTY

TCNVDHKPSNTKVDKTVERKCCVECPPCPAPPVAGPSVFLFPPKPKDTLM

ISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPG//.

The desired C681-aKLH 120.6 IgG2 HC product was a full antibody with the Avimer fused to the N-terminus of both heavy chains. The ratio of C681-heavy chain:light chain was 1:1. The expected C681-aKLH 120.6 IgG2 HC fusion protein was isolated using ion exchange chromatography, as described herein.

The C681-aKLH 120.6 IgG2 variable HC fusion was ordered from Blue Heron as a synthetic gene encoding the following amino acid sequence:

(SEQ ID NO: 350)
MDMRVPAQLLGLLLLWLRGARCSGGSCLPDQFRCGNGQCIPLDWVCDGVN

DCPDDSDEEGCPPRTCAPSQFQCGSGYCISQRWVCDGENDCEDGSDEANC

AGSVPTCPSDEFRCRNGRCIPRAWRCDGVNDCADNSDEEDCTEHTGGGGG

QVQLVQSGAEVKKPGASVKVSCKASGYTFTGYHMHWVRQAPGQGLEWMGW

INPNSGGTNYAQKFQGRVTMTRDTSISTAYMELSRLRSDDTAVYYCARDR

GSYYWFDPWGQGTLVTVSSASTK//.

The fragment was digested with SalI and BsmbI, run out on a 1% agarose gel and the corresponding fragment cut out and purified by Qiagen's Gel Purification Kit. At the same time, a pTT5-VK1SP-aKLH 120.6 IgG2 HC DNA template was digested and purified similarly, yielding a pTT5 vector backbone with the constant HC region. The Avimer fragment was ligated to the pTT5-IgG2 HC constant region and transformed into OneShot® Top10 bacteria. DNAs were submitted for sequencing. Although, analysis of several sequences of clones yielded a 100% percent match with the above sequence, only one clone was selected for large-scaled plasmid purification. The final pTT5-VK1SP-C681-aKLH 120.6 IgG2 HC construct encoded a C681-(G5)-aKLH 120.6 IgG2 HC fusion polypeptide (SEQ ID NO:356).

The components of the aKLH 120.6 IgG2 HC-C681 fusion included the monomers:
(a) aKLH 120.6 kappa LC (SEQ ID NO:28); and
(b) aKLH 120.6 IgG2 HC-C681 fusion having the following amino acid sequence:

(SEQ ID NO: 357)
MDMRVPAQLLGLLLLWLRGARCQVQLVQSGAEVKKPGASVKVSCKASGYT

FTGYHMHWVRQAPGQGLEWMGWINPNSGGTNYAQKFQGRVTMTRDTSIST

AYMELSRLRSDDTAVYYCARDRGSYYWFDPWGQGTLVTVSSASTKGPSVF

PLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPC

-continued

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVMHE

ALHNHYTQKSLSLSPGGGGGGSGGSCLPDQFRCGNGQCIPLDWVCDGVND

CPDDSDEEGCPPRTCAPSQFQCGSGYCISQRWVCDGENDCEDGSDEANCA

GSVPTCPSDEFRCRNGRCIPRAWRCDGVNDCADNSDEEDCTEHT//.

The desired aKLH 120.6 IgG2 HC-C681 product was a full antibody with the Avimer fused to the C-terminus of both heavy chains (schematically represented in FIG. 1G). The ratio of heavy chain-C681:light chain was 1:1. The expected aKLH 120.6 IgG2 HC-C681 fusion protein was isolated using ion exchange chromatography, as described herein.

The C681 fragment with flanking SexAI and NotI restriction sites was ordered from Blue Heron as a synthetic gene encoding the following amino acid sequence:

(SEQ ID NO: 358)
MTKNQVSLTCLVKGFYPSDIAVEWESNGQPENNYKTTPPMLDSDGSFFLY

SKLTVDKSRWQQGNVFSCSVMHEALHNHYTQKSLSLSPGGGGGGSGGSCL

PDQFRCGNGQCIPLDWVCDGVNDCPDDSDEEGCPPRTCAPSQFQCGSGYC

ISQRWVCDGENDCEDGSDEANCAGSVPTCPSDEFRCRNGRCIPRAWRCDG

VNDCADNSDEEDCTEHT//.

The fragment was digested with SexAI and NotI, run out on a 1% agarose gel and the corresponding fragment cut out and purified by Qiagen's Gel Purification Kit. At the same time, a pTT5-VK1SP-aKLH 120.6 IgG2 HC DNA template was digested with SalI and SexAI and purified similarly to generate the DNA coding sequence for aKLH 120.6 IgG2 HC monomer (SEQ ID NO:29). A pTT5 vector was cut with SalI and NotI, run out on a 1% agarose gel and the larger fragment cut out and gel purified by Qiagen's Gel Purification Kit. The Avimer and aKLH 120.6 IgG2 HC fragments were ligated to the pTT5 fragment and transformed into OneShot Top10 bacteria. DNAs were submitted for sequencing. Although, analysis of several sequences of clones yielded a 100% percent match with the above sequence, only one clone was selected for large scaled plasmid purification. The final pTT5-VK1SP-aKLH 120.6 IgG2 HC-C681 construct encoded aKLH 120.6 IgG2 HC-(G5)-C681 fusion polypeptide (SEQ ID NO:357).

The components of the C681-aKLH 120.6 kappa LC fusion included the monomers:
(a) aKLH 120.6 IgG2 HC (SEQ ID NO:29); and
(b) C681-aKLH 120.6 kappa LC fusion having the following amino acid sequence:

(SEQ ID NO: 359)
MDMRVPAQLLGLLLLWLRGARCSGGSCLPDQFRCGNGQCIPLDWVCDGVN

DCPDDSDEEGCPPRTCAPSQFQCGSGYCISQRWVCDGENDCEDGSDEANC

AGSVPTCPSDEFRCRNGRCIPRAWRCDGVNDCADNSDEEDCTEHTGGGGG

DIQMTQSPSSLSASVGDRVTITCRASQGIRNDLGWYQQKPGKAPKRLIYA

ASSLQSGVPSRFSGSGSGTEFTLTISSLQPEDFATYYCLQHNSYPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC//.

The desired C681-aKLH 120.6 kappa LC product was a full antibody with the Avimer fused to the N-terminus of both light chains. The ratio of C681-light chain:heavy chain was 1:1. The expected C681-aKLH 120.6 kappa LC fusion protein was isolated using ion exchange chromatography, as described herein.

The (VK-1 SP)-C681-(G5)-aKLH 120.6 kappa variable LC fusion was ordered from Blue Heron with flanking SalI BsiWI restriction sites as a synthetic gene encoding the following amino acid sequence:

(SEQ ID NO: 360)
MDMRVPAQLLGLLLLWLRGARCSGGSCLPDQFRCGNGQCIPLDWVCDGVN

DCPDDSDEEGCPPRTCAPSQFQCGSGYCISQRWVCDGENDCEDGSDEANC

AGSVPTCPSDEFRCRNGRCIPRAWRCDGVNDCADNSDEEDCTEHTGGGGG

DIQMTQSPSSLSASVGDRVTITCRASQGIRNDLGWYQQKPGKAPKRLIYA

ASSLQSGVPSRFSGSGSGTEFTLTISSLQPEDFATYYCLQHNSYPLTFGG

GTKVEIKRTVA//

The fragment was digested with SalI and BsiWI, run out on a 1% agarose gel and the corresponding fragment cut out and purified by Qiagen's Gel Purification Kit. At the same time, a pTT5-VK1SP-aKLH 120.6 kappa LC DNA template was digested and purified similarly, yielding a pTT5 vector backbone with the constant LC region. The Avimer fragment was ligated to the pTT5-kappa LC constant region and transformed into OneShot Top10 bacteria. DNAs were submitted for sequencing. Although, analysis of several sequences of clones yielded a 100% percent match with the above sequence, only one clone was selected for large scaled plasmid purification. The final pTT5-VK1SP-C681-aKLH 120.6 kappa LC construct encoded a C681-(G5)-aKLH 120.6 kappa LC fusion polypeptide (SEQ ID NO:359).

Method for Isolating Avimer-immunoglobin fusions. Initial purification of the conditioned media was done by affinity fast protein liquid chromatography (FPLC) capture of the Fc region using Protein A Sepharose (GE Healthcare) followed by a column wash with Tris-buffered saline, 1 mM $CaCl_2$ (Teknova) and step elution with 100 mM acetic acid, 1 mM $CaCl_2$, pH 3.5 at a flow rate of 2.5 cm/min. Protein containing fractions were pooled, and the pH was adjusted to 8.0 using 10 N NaOH and further diluted with 5 volumes of water. The material was filtered through a 0.45 µm cellulose acetate filter (Corning) and further purified by anion exchange FPLC (Q Sepharose High Performance; GE Healthcare). Samples were loaded onto a column equilibrated with 100% buffer A (20 mM Tris, 1 mM, pH 8.0) and eluted with a gradient of 0 to 80% buffer B (20 mM Tris, 1 M NaCl, 1 mM $CaCl_2$, pH 8.0) over 30 column volumes at a flowrate of 1.5 cm/min. Peaks containing target species were pooled and formulated into 10 mM Tris, 150 mM NaCl, 1 mM $CaCl_2$, pH 8.0. Exemplary purifications of N-terminal HC and LC and C-terminal HC fusion proteins are shown in FIGS. 36-38. The non-reducing SDS-PAGE analysis (FIG. 36) demonstrates that the fully assembled antibody can be formed and the reducing SDS-PAGE analysis demonstrates that the desired components are present. The size exclusion chromatogram (FIG. 37) shows that the majority of the purified product is in the desired non-aggregated state. Finally, the mass spectral analysis (FIG. 38) demonstrates that the desired fusion products are present. Taken together these examples demonstrate that the aKLH 120.6 antibody can accept fusions to Avimers forming the desired product.

Example 12

BIAcore® Binding Assays of aDNP and aKLH Antibodies

Materials.

Purified anti-DNP antibodies from either hybridoma (3A1, 3C2, 3A4 and 3B1) or recombinant CHO (3A4-F-G2 and 3B1-G2) expression were tested. Anti-human IgG, Fcγ-specific antibody was from Jackson ImmunoResearch Laboratories, Inc. (West Grove, Pa.). DNP-BSA (2,4-dinitrophenol conjugated to bovine serum albumin) was from Biosearch Technologies, Inc. (Novato, Calif.). BIACore 2000, research grade sensor chip CM5, surfactant P-20 (polyoxyethylenesorbitan), HBS-EP (10 mM HEPES, 0.15M NaCl, 3.4 mM EDTA, 0.005% P-20, pH 7.4), amine coupling reagents, 10 mM acetate pH 4.0 and 10 mM glycine, pH 1.5 were from BIACore, Inc. (Piscataway, N.J.). Phosphate-buffered saline (PBS, 1×, no calcium chloride, no magnesium chloride) was from Invitrogen (Carlsbad, Calif.). Bovine serum albumin (BSA, fraction V, IgG free) was from Sigma (St. Louis, Mo.).

Purified anti-KLH antibody (human IgG1, clone 120.6.1) expressed from hybridoma was tested. Multimeric high molecular weight keyhole limpet hemocyanin (KLH) was from Pierce (Rockford, Ill.). Anti-human IgG, Fcγ-specific antibody was from Jackson ImmunoResearch Laboratories, Inc. (West Grove, Pa.). BIACore 2000, research grade sensor chip CM5, surfactant P-20 (polyoxyethylenesorbitan), HBS-EP (10 mM HEPES, 0.15M NaCl, 3.4 mM EDTA, 0.005% P-20, pH 7.4), amine coupling reagents, 10 mM acetate, pH 4.5, and 10 mM glycine, pH 1.5 were from BIACore, Inc. (Piscataway, N.J.). Phosphate-buffered saline (PBS, 1×, no calcium chloride, no magnesium chloride) was from Invitrogen (Carlsbad, Calif.). Bovine serum albumin (BSA, fraction V, IgG free) was from Sigma (St. Louis, Mo.).

Methods. BIAcore® analyses were carried out as follows. Immobilization of anti-human IgG, Fcγ-specific antibody to the CM5 sensor chip surface was performed according to manufacturer's instructions, using a continuous flow of 10 mM HEPES, 0.15M NaCl, 3.4 mM EDTA, 0.005% P-20, pH 7.4 (HBS-EP buffer). Briefly, carboxyl groups on the sensor chip surfaces were activated by injecting 60 μL of a mixture containing 0.2 M 1-ethyl-3-[3-dimethylaminopropyl] carbodiimide hydrochloride (EDC) and 0.05 M N-hydroxysuccinimide (NHS). Specific surfaces were obtained by injecting 180 μL of anti-human IgG, Fcγ-specific antibody diluted in 10 mM acetate buffer (for assay of aKLH antibodies: pH 4.5 at a concentration of 30 μg/mL; for assay of aDNP antibodies: pH 4.0 at a concentration of 60 μg/mL). Excess reactive groups on the surfaces were deactivated by injecting 60 μL of 1 M ethanolamine. Final immobilized levels were about 9,000 (for assay of aKLH antibodies) or about 10,000 (for assay of aDNP antibodies) resonance units (RU). A blank, mock-coupled reference surface was also prepared on the sensor chip. Antibodies and antigen were diluted in sample buffer consisting of PBS+0.005% P-20+0.1 mg/mL BSA.

Anti-DNP antibodies were captured on individual flow cells, followed by injection of either sample buffer or DNP-BSA, ranging in concentration from 0.78-100 nM. Two different DNP-BSA samples were tested for affinity to the anti-DNP antibodies. The DNP-BSA samples differed in the number of DNP moieties coupled to each molecule of BSA, with one sample containing 3 DNP moieties per BSA and the other containing 31 DNP moieties per BSA. Only the DNP(31)-BSA (at concentrations from 0.39-50 nM) was tested for affinity to the recombinant anti-DNP antibodies. In each cycle, three individual antibodies were captured on flow cells 2, 3 and 4, with flow cell 1 left blank to serve as a reference surface. Following sample buffer or antigen injection, each surface was regenerated by two injections of 10 mM glycine, pH 1.5 to dissociate captured antibody from the immobilized anti-human Fc surfaces. BIAevaluation software was used to determine apparent kinetic parameters for binding of DNP-BSA to captured anti-DNP antibodies.

Anti-KLH antibody was captured on individual flow cells, followed by injection of either sample buffer or KLH, ranging in concentration from 0.19-100 nM. To prepare dilutions of the multimeric high molecular weight KLH, an average molecular weight of 5,000,000 daltons was used. Following sample buffer or antigen injection, each surface was regenerated by two injections of 10 mM glycine, pH 1.5 to dissociate captured antibody from the immobilized anti-human Fc surfaces. BIAevaluation software was used to determine apparent kinetic parameters for binding of KLH to captured anti-KLH antibodies.

BIAcore® Binding Assay Results.

Table 8A below summarizes the apparent association ($k_a$) and dissociation ($k_d$) rate constants, as well as equilibrium dissociation constants ($K_D$) obtained for the binding analysis of anti-DNP antibodies binding to DNP-BSA. The data in Table 8A demonstrate that the anti-DNP antibodies bind specifically to DNP, and that they bind more tightly to the higher density DNP(31)-BSA than to the lower density DNP(3)-BSA, as would be expected. Apparent binding affinities for DNP(31)-BSA are all single digit nanomolar or higher.

Table 8B below summarizes the apparent association ($k_a$) and dissociation ($k_d$) rate constants, as well as equilibrium dissociation constants ($K_D$) obtained for the binding analysis of anti-KLH 120.6.1 antibody binding to KLH. The data in Table 8B demonstrate that this hybridoma-produced anti-KLH antibody binds specifically to multimeric KLH, with an apparent sub-nanomolar binding affinity.

TABLE 8A

BIAcore ® binding assays for aDNP antibodies. ND = not determined; ne(y) = n × 10^(y)

| Antibody | Binding to DNP(3)-BSA | | | Binding to DNP(31)-BSA | | |
|---|---|---|---|---|---|---|
| | $k_a$ ($M^{-1}s^{-1}$) | $k_d$ ($s^{-1}$) | $K_D$ (nM) | $k_a$ ($M^{-1}s^{-1}$) | $k_d$ ($s^{-1}$) | $K_D$ (nM) |
| 3A1 | 1.2e3 | 6.5e−4 | 526 | 3.4e4 | 3.1e−4 | 9 |
| 3C2 | 9.2e4 | 5.5e−4 | 6 | 1.3e5 | 2.8e−4 | 2 |
| 3A4 | 2.0e5 | 4e−4 | 2 | 5.9e5 | 4.8e−4 | 0.8 |
| 3B1 | 1.4e5 | 3.6e−4 | 3 | 3.7e5 | 5.8e−5 | 0.2 |
| 3A4-F-G2 (recombinant) | ND | ND | ND | 2.6e5 | 5.5e−4 | 2 |
| 3B1-G2 (recombinant) | ND | ND | ND | 4.2e5 | 3.1e−4 | 0.7 |

TABLE 8B

BIAcore ® binding assays for aKLH antibodies. ne(y) = n × 10^(y)

| Antibody | Binding to Multimeric KLH | | |
|---|---|---|---|
| | $k_a$ ($M^{-1}s^{-1}$) | $k_d$ ($s^{-1}$) | $K_D$ (nM) |
| IgG1 (120.6.1) | 1.2e5 | 2.5e−5 | 0.2 |

ABBREVIATIONS

Abbreviations used throughout this specification are as defined below, unless otherwise defined in specific circumstances.

Ac acetyl (used to refer to acetylated residues)
AcBpa acetylated p-benzoyl-L-phenylalanine
ACN acetonitrile
AcOH acetic acid
ADCC antibody-dependent cellular cytotoxicity
Aib aminoisobutyric acid
bA beta-alanine
Bpa p-benzoyl-L-phenylalanine
BrAc bromoacetyl (BrCH$_2$C(O))
BSA Bovine serum albumin
Bzl Benzyl
Cap Caproic acid
CBC complete blood count
COPD Chronic obstructive pulmonary disease
CTL Cytotoxic T lymphocytes
DCC Dicylcohexylcarbodiimide
Dde 1-(4,4-dimethyl-2,6-dioxo-cyclohexylidene)ethyl
DNP 2,4-dinitrophenol
DOPC 1,2-Dioleoyl-sn-Glycero-3-phosphocholine
DOPE 1,2-Dioleoyl-sn-Glycero-3-phosphoethanolamine
DPPC 1,2-Dipalmitoyl-sn-Glycero-3-phosphocholine
DSPC 1,2-Distearoyl-sn-Glycero-3-phosphocholine
DTT Dithiothreitol
EAE experimental autoimmune encephalomyelitis
ECL enhanced chemiluminescence
ESI-MS Electron spray ionization mass spectrometry
FACS fluorescence-activated cell sorting
Fmoc fluorenylmethoxycarbonyl
HOBt 1-Hydroxybenzotriazole
HPLC high performance liquid chromatography
HSL homoserine lactone
IB inclusion bodies
KCa calcium-activated potassium channel (including IKCa, BKCa, SKCa)
KLH Keyhole Limpet Hemocyanin
Kv voltage-gated potassium channel
Lau Lauric acid
LPS lipopolysaccharide
LYMPH lymphocytes
MALDI-MS Matrix-assisted laser desorption ionization mass spectrometry
Me methyl
MeO methoxy
MeOH methanol
MHC major histocompatibility complex
MMP matrix metalloproteinase
MW Molecular Weight
MWCO Molecular Weight Cut Off
1-Nap 1-napthylalanine
NEUT neutrophils
Nle norleucine
NMP N-methyl-2-pyrrolidinone
OAc acetate
PAGE polyacrylamide gel electrophoresis
PBMC peripheral blood mononuclear cell
PBS Phosphate-buffered saline
Pbf 2,2,4,6,7-pendamethyldihydrobenzofuran-5-sulfonyl
PCR polymerase chain reaction
PD pharmacodynamic
Pec pipecolic acid
PEG Poly(ethylene glycol)
pGlu pyroglutamic acid
Pic picolinic acid
PK pharmacokinetic
pY phosphotyrosine
RBS ribosome binding site
RT room temperature (about 25° C.)
Sar sarcosine
SDS sodium dodecyl sulfate
STK serine-threonine kinases
t-Boc tert-Butoxycarbonyl
tBu tert-Butyl
TCR T cell receptor
TFA trifluoroacetic acid
THF thymic humoral factor
Trt trityl

What is claimed is:

1. An isolated antigen binding protein comprising an immunoglobulin heavy chain variable region and an immunoglobulin light chain variable region, wherein the heavy chain variable region comprises three complementarity determining regions (CDRs) designated CDRH1, CDRH2 and CDRH3, and the light chain variable region comprises three CDRs designated CDRL1, CDRL2 and CDRL3, wherein:
   (a) CDRH1 comprises the amino acid sequence of SEQ ID NO: 190;
   (b) CDRH2 comprises the amino acid sequence of SEQ ID NO: 194;
   (c) CDRH3 comprises the amino acid sequence of SEQ ID NO: 200;
   (d) CDRL1 comprises the amino acid sequence of SEQ ID NO:204;
   (e) CDRL2 comprises the amino acid sequence of SEQ ID NO:206; and
   (f) CDRL3 comprises the amino acid sequence of SEQ ID NO:210.

2. The isolated antigen binding protein of claim 1, wherein the isolated antigen binding protein comprises an antibody or antibody fragment.

3. The isolated antigen binding protein of claim 2, comprising an IgG1, IgG2, IgG3 or IgG4.

4. The isolated antigen binding protein of claim 2, comprising a monoclonal antibody.

5. The isolated antigen binding protein of claim 4, comprising a chimeric or humanized antibody.

6. The isolated antigen binding protein of claim 4, comprising a human antibody.

7. The isolated antigen binding protein of claim 2, comprising:
   (a) an immunoglobulin heavy chain comprising the amino acid sequence of the mature polypeptide set forth in SEQ ID NO: 123 or SEQ ID NO: 184, or comprising the amino acid sequence of the mature polypeptide set forth in either of the foregoing sequences from which one, two, three, four or five amino acid residues are lacking from the N-terminus or C-terminus, or both;
   (b) an immunoglobulin light chain comprising the amino acid sequence of the mature polypeptide set forth in SEQ ID NO:121, or comprising the amino acid sequence of the mature polypeptide set forth in of the foregoing sequences from which one, two, three, four or five amino acid residues are lacking from the N-terminus or C-terminus, or both; or
   (c) the immunoglobulin heavy chain of (a) and the immunoglobulin light chain of (b).

8. The isolated antigen binding protein of claim 1, further comprising at least one pharmacologically active chemical moiety conjugated thereto.

9. The isolated antigen binding protein of claim 8, wherein the pharmacologically active chemical moiety is a pharmacologically active polypeptide.

10. The isolated antigen binding protein of claim 9, wherein the antigen binding protein is recombinantly produced.

11. The isolated antigen binding protein of claim 10, wherein the antigen binding protein comprises at least one immunoglobulin heavy chain and at least one immunoglobulin light chain, and wherein the pharmacologically active polypeptide is inserted in the primary amino acid sequence of the immunoglobulin heavy chain within an internal loop of the Fc domain of the immunoglobulin heavy chain.

12. The isolated antigen binding protein of claim 9, wherein the antigen binding protein comprises at least one immunoglobulin heavy chain and at least one immunoglobulin light chain, and wherein the pharmacologically active polypeptide is conjugated at the N-terminus or C-terminus of the immunoglobulin heavy chain.

13. The isolated antigen binding protein of claim 9, wherein the antigen binding protein comprises at least one immunoglobulin heavy chain and at least one immunoglobulin light chain, and wherein the pharmacologically active polypeptide is conjugated at the N-terminus or C-terminus of the immunoglobulin light chain.

14. The isolated antigen binding protein of claim 9, wherein the pharmacologically active polypeptide is a toxin peptide or peptide analog, an IL-6 binding peptide, a CGRP peptide antagonist, a bradykinin B1 receptor peptide antagonist, a PTH agonist peptide, a PTH antagonist peptide, an ang-1 binding peptide, an ang-2 binding peptide, a myostatin binding peptide, an EPO-mimetic peptide, a TPO-mimetic peptide, a NGF binding peptide, a BAFF antagonist peptide, a GLP-1 or peptide mimetic thereof, or a GLP-2 or peptide mimetic thereof.

15. The isolated antigen binding protein of claim 14, wherein the toxin peptide or peptide analog is ShK or a ShK peptide analog.

16. A pharmaceutical composition comprising the antigen binding protein of claim 1; and a pharmaceutically acceptable diluent, excipient or carrier.

17. A hybridoma, wherein the hybridoma produces the antigen binding protein of claim 1.

18. A method, comprising:
(a) culturing the hybridoma of claim 17 in a culture medium under conditions permitting expression of the antigen binding protein by the hybridoma; and
(b) recovering the antigen binding protein from the culture medium.

19. The isolated antigen binding protein of claim 1, wherein the heavy chain variable region comprises an amino acid sequence at least 95% identical to the sequence of SEQ ID NO: 258.

20. The isolated antigen binding protein of claim 1, wherein the light chain variable region comprises an amino acid sequence at least 95% identical to the sequence of SEQ ID NO:236.

21. The isolated antigen binding protein of claim 1, wherein the heavy chain variable region comprises the amino acid sequence of SEQ ID NO: 258 and the light chain variable region comprises the amino acid sequence of SEQ ID NO:236.

22. The isolated antigen binding protein of claim 9, wherein the pharmacologically active polypeptide is conjugated to the antigen binding protein via a non-peptidyl or peptidyl linker.

23. The isolated antigen binding protein of claim 22, wherein the peptidyl linker comprises glycine, serine, alanine, or combinations thereof.

24. The isolated antigen binding protein of claim 22, wherein the non-peptidyl linker is a polyethylene glycol linker.

* * * * *

UNITED STATES PATENT AND TRADEMARK OFFICE
CERTIFICATE OF CORRECTION

Page 1 of 1

PATENT NO. : 10,189,912 B2
APPLICATION NO. : 15/405233
DATED : January 29, 2019
INVENTOR(S) : Walker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 54 days.

Signed and Sealed this
Twenty-ninth Day of October, 2019

Andrei Iancu
*Director of the United States Patent and Trademark Office*

SEQUENCE LISTING

<160> NUMBER OF SEQ ID NOS: 368

<210> SEQ ID NO 1
<211> LENGTH: 245
<212> TYPE: PRT
<213> ORGANISM: Homo sapiens
<220> FEATURE:
<221> NAME/KEY: MISC_FEATURE
<223> OTHER INFORMATION: Immunoglobulin Fc domain of human IgG2

<400> SEQUENCE: 1

Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30

Val Ala Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Phe Arg Val Val Ser Val Leu Thr Val Val His Gln Asp Trp Leu
            100                 105                 110

Asn Gly Lys Glu Tyr Lys Cys Lys Val Ser Asn Lys Gly Leu Pro Ala
        115                 120                 125

Pro Ile Glu Lys Thr Ile Ser Lys Thr Lys Gly Gln Pro Arg Glu Pro
    130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys
                245

<210> SEQ ID NO 2
<211> LENGTH: 19
<212> TYPE: PRT
<213> ORGANISM: ARTIFICIAL SEQUENCE
<220> FEATURE:
<223> OTHER INFORMATION: Modifed VH21signal peptide

<400> SEQUENCE: 2

Met Glu Trp Ser Trp Val Phe Leu Phe Phe Leu Ser Val Thr Thr Gly
1               5                   10                  15

Val His Ser

<210> SEQ ID NO 3
<211> LENGTH: 30

-continued

<212> TYPE: DNA
<213> ORGANISM: ARTIFICIAL SEQUENCE
<220> FEATURE:
<223> OTHER INFORMATION: Primer sequence

<400> SEQUENCE: 3
catgaattcc ccaccatgga atggagctgg                                          30

<210> SEQ ID NO 4
<211> LENGTH: 38
<212> TYPE: DNA
<213> ORGANISM: ARTIFICIAL SEQUENCE
<220> FEATURE:
<223> OTHER INFORMATION: Primer sequence

<400> SEQUENCE: 4
cacggtgggc actcgactttt gcgctcggag tggacacc                                38

<210> SEQ ID NO 5
<211> LENGTH: 132
<212> TYPE: DNA
<213> ORGANISM: ARTIFICIAL SEQUENCE
<220> FEATURE:
<223> OTHER INFORMATION: ShK[2-35] with N-terminal linker extension

<400> SEQUENCE: 5
ggaggaggag gatccggagg aggaggaagc agctgcatcg acaccatccc caagagccgc         60
tgcaccgcct tccagtgcaa gcacagcatg aagtaccgcc tgagcttctg ccgcaagacc        120
tgcggcacct gc                                                            132

<210> SEQ ID NO 6
<211> LENGTH: 44
<212> TYPE: PRT
<213> ORGANISM: ARTIFICIAL SEQUENCE
<220> FEATURE:
<223> OTHER INFORMATION: ShK[2-35] with N-terminal linker extension

<400> SEQUENCE: 6

Gly Gly Gly Gly Ser Gly Gly Gly Gly Ser Ser Cys Ile Asp Thr Ile
1               5                   10                  15

Pro Lys Ser Arg Cys Thr Ala Phe Gln Cys Lys His Ser Met Lys Tyr
            20                  25                  30

Arg Leu Ser Phe Cys Arg Lys Thr Cys Gly Thr Cys
        35                  40

<210> SEQ ID NO 7
<211> LENGTH: 37
<212> TYPE: DNA
<213> ORGANISM: ARTIFICIAL SEQUENCE
<220> FEATURE:
<223> OTHER INFORMATION: Primer sequence

<400> SEQUENCE: 7
gtccactccg agcgcaaaagt cgagtgccca ccgtgcc                                 37

<210> SEQ ID NO 8
<211> LENGTH: 30
<212> TYPE: DNA
<213> ORGANISM: ARTIFICIAL SEQUENCE
<220> FEATURE:
<223> OTHER INFORMATION: Primer sequence

<400> SEQUENCE: 8
tcctcctcct ttacccggag acagggagag                                          30

<210> SEQ ID NO 9
<211> LENGTH: 29
<212> TYPE: DNA
<213> ORGANISM: ARTIFICIAL SEQUENCE
<220> FEATURE:
<223> OTHER INFORMATION: Primer sequence

<400> SEQUENCE: 9
gctgcaccgc cttcaagtgc aagcacagc                                    29

<210> SEQ ID NO 10
<211> LENGTH: 29
<212> TYPE: DNA
<213> ORGANISM: ARTIFICIAL SEQUENCE
<220> FEATURE:
<223> OTHER INFORMATION: Primer sequence

<400> SEQUENCE: 10
gctgtgcttg cacttgaagg cggtgcagc                                    29

<210> SEQ ID NO 11
<211> LENGTH: 132
<212> TYPE: DNA
<213> ORGANISM: ARTIFICIAL SEQUENCE
<220> FEATURE:
<223> OTHER INFORMATION: ShK[2-35, K16] with N-terminal linker extension

<400> SEQUENCE: 11
ggaggaggag gatccggagg aggaggaagc agctgcatcg acaccatccc caagagccgc    60
tgcaccgcct tcaagtgcaa gcacagcatg aagtaccgcc tgagcttctg ccgcaagacc   120
tgcggcacct gc                                                      132

<210> SEQ ID NO 12
<211> LENGTH: 44
<212> TYPE: PRT
<213> ORGANISM: ARTIFICIAL SEQUENCE
<220> FEATURE:
<223> OTHER INFORMATION: ShK[2-35, Q16K] with N-terminal linker
      extension

<400> SEQUENCE: 12

Gly Gly Gly Gly Ser Gly Gly Gly Gly Ser Ser Cys Ile Asp Thr Ile
1               5                  10                  15

Pro Lys Ser Arg Cys Thr Ala Phe Lys Cys Lys His Ser Met Lys Tyr
            20                  25                  30

Arg Leu Ser Phe Cys Arg Lys Thr Cys Gly Thr Cys
        35                  40

<210> SEQ ID NO 13
<211> LENGTH: 28
<212> TYPE: DNA
<213> ORGANISM: ARTIFICIAL SEQUENCE
<220> FEATURE:
<223> OTHER INFORMATION: Primer sequence

<400> SEQUENCE: 13
ccgggtaaag gaggaggagg atccggag                                     28

<210> SEQ ID NO 14
<211> LENGTH: 24
<212> TYPE: DNA
<213> ORGANISM: ARTIFICIAL SEQUENCE
<220> FEATURE:

<223> OTHER INFORMATION: Primer sequence

<400> SEQUENCE: 14
catgcggccg ctcattagca ggtg                                              24

<210> SEQ ID NO 15
<211> LENGTH: 648
<212> TYPE: DNA
<213> ORGANISM: Homo sapiens
<220> FEATURE:
<221> NAME/KEY: misc_feature
<223> OTHER INFORMATION: Coding sequence of fragment of immunoglobulin
      Fc domain of human IgG2

<400> SEQUENCE: 15
gcaccacctg tggcaggacc gtcagtcttc ctcttccccc caaaacccaa ggacaccctc          60
atgatctccc ggacccctga ggtcacgtgc gtggtggtgg acgtgagcca cgaagacccc         120
gaggtccagt tcaactggta cgtggacggc gtggaggtgc ataatgccaa gacaaagcca         180
cgggaggagc agttcaacag cacgttccgt gtggtcagcg tcctcaccgt tgtgcaccag         240
gactggctga acggcaagga gtacaagtgc aaggtctcca acaaaggcct cccagccccc         300
atcgagaaaa ccatctccaa aaccaaaggg cagccccgag aaccacaggt gtacaccctg         360
cccccatccc gggaggagat gaccaagaac caggtcagcc tgacctgcct ggtcaaaggc         420
ttctacccca gcgacatcgc cgtggagtgg gagagcaatg ggcagccgga gaacaactac         480
aagaccacac ctcccatgct ggactccgac ggctccttct tcctctacag caagctcacc         540
gtggacaaga gcaggtggca gcaggggaac gtcttctcat gctccgtgat gcatgaggct         600
ctgcacaacc actacacgca gaagagcctc tccctgtctc cgggtaaa                     648

<210> SEQ ID NO 16
<211> LENGTH: 216
<212> TYPE: PRT
<213> ORGANISM: Homo sapiens
<220> FEATURE:
<221> NAME/KEY: MISC_FEATURE
<223> OTHER INFORMATION: Fragment of immunoglobulin Fc domain of human
      IgG2

<400> SEQUENCE: 16

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

```
Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
            165                 170                 175

Ser Lys Leu Thr Val Asp Lys Ser Arg Trp Gln Gln Gly Asn Val Phe
        180                 185                 190

Ser Cys Ser Val Met His Glu Ala Leu His Asn His Tyr Thr Gln Lys
    195                 200                 205

Ser Leu Ser Leu Ser Pro Gly Lys
    210                 215

<210> SEQ ID NO 17
<211> LENGTH: 289
<212> TYPE: PRT
<213> ORGANISM: ARTIFICIAL SEQUENCE
<220> FEATURE:
<223> OTHER INFORMATION: VH21SP-IgG2-Fc-L10-ShK(1-35, Q16K) Fusion
      polypeptide

<400> SEQUENCE: 17

Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30

Val Ala Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
50                  55                  60

Ser His Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Phe Arg Val Val Ser Val Leu Thr Val Val His Gln Asp Trp Leu
            100                 105                 110

Asn Gly Lys Glu Tyr Lys Cys Lys Val Ser Asn Lys Gly Leu Pro Ala
        115                 120                 125

Pro Ile Glu Lys Thr Ile Ser Lys Thr Lys Gly Gln Pro Arg Glu Pro
130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys Gly Gly Gly Ser Gly Gly Gly Gly Ser
                245                 250                 255

Cys Ile Asp Thr Ile Pro Lys Ser Arg Cys Thr Ala Phe Gln Cys Lys
            260                 265                 270

His Ser Met Lys Tyr Arg Leu Ser Phe Cys Arg Lys Thr Cys Gly Thr
        275                 280                 285
```

<210> SEQ ID NO 18
<211> LENGTH: 289
<212> TYPE: PRT
<213> ORGANISM: ARTIFICIAL SEQUENCE
<220> FEATURE:
<223> OTHER INFORMATION: VH21SP-IgG2-Fc-L10-ShK(1-35, Q16K) Fusion polypeptide

<400> SEQUENCE: 18

```
Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30

Val Ala Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Phe Arg Val Val Ser Val Leu Thr Val Val His Gln Asp Trp Leu
            100                 105                 110

Asn Gly Lys Glu Tyr Lys Cys Lys Val Ser Asn Lys Gly Leu Pro Ala
        115                 120                 125

Pro Ile Glu Lys Thr Ile Ser Lys Thr Lys Gly Gln Pro Arg Glu Pro
    130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys Gly Gly Gly Ser Gly Gly Gly Gly Ser Ser
                245                 250                 255

Cys Ile Asp Thr Ile Pro Lys Ser Arg Cys Thr Ala Phe Lys Cys Lys
            260                 265                 270

His Ser Met Lys Tyr Arg Leu Ser Phe Cys Arg Lys Thr Cys Gly Thr
        275                 280                 285

Cys
```

<210> SEQ ID NO 19
<211> LENGTH: 290
<212> TYPE: PRT
<213> ORGANISM: ARTIFICIAL SEQUENCE
<220> FEATURE:
<223> OTHER INFORMATION: VH21SP-IgG2-Fc-L10-ShK(1-35, Q16K) Fusion polypeptide

<400> SEQUENCE: 19

```
Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30

Val Ala Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
50                  55                  60

Ser His Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Phe Arg Val Val Ser Val Leu Thr Val Val His Gln Asp Trp Leu
            100                 105                 110

Asn Gly Lys Glu Tyr Lys Cys Lys Val Ser Asn Lys Gly Leu Pro Ala
        115                 120                 125

Pro Ile Glu Lys Thr Ile Ser Lys Thr Lys Gly Gln Pro Arg Glu Pro
130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
210                 215                 220

Val Met His Glu Ala Leu His Asn His Tyr Thr Gln Lys Ser Leu Ser
225                 230                 235                 240

Leu Ser Pro Gly Lys Gly Gly Gly Ser Gly Gly Gly Ser Arg
                245                 250                 255

Ser Cys Ile Asp Thr Ile Pro Lys Ser Arg Cys Thr Ala Phe Gln Cys
            260                 265                 270

Lys His Ser Met Lys Tyr Arg Leu Ser Phe Cys Arg Lys Thr Cys Gly
            275                 280                 285

Thr Cys
    290
```

<210> SEQ ID NO 20
<211> LENGTH: 30
<212> TYPE: DNA
<213> ORGANISM: ARTIFICIAL SEQUENCE
<220> FEATURE:
<223> OTHER INFORMATION: Primer sequence

<400> SEQUENCE: 20
cataagcttc ccaccatgga atggagctgg     30

<210> SEQ ID NO 21
<211> LENGTH: 31
<212> TYPE: DNA
<213> ORGANISM: ARTIFICIAL SEQUENCE
<220> FEATURE:
<223> OTHER INFORMATION: Primer sequence

<400> SEQUENCE: 21
catggatcct catttacccg gagacaggga g                              31

<210> SEQ ID NO 22
<211> LENGTH: 163
<212> TYPE: DNA
<213> ORGANISM: ARTIFICIAL SEQUENCE
<220> FEATURE:
<223> OTHER INFORMATION: Coding sequence ShK{1-35, Q16K) with an
      N-terminal linker

<400> SEQUENCE: 22
ggatccggag gaggaggaag ccgcagctgc atcgacacca tccccaagag ccgctgcacc    60
gccttcaagt gcaagcacag catgaagtac cgcctgagct tctgccgcaa gacctgcggc   120
acctgctaat gagcggccgc tcgaggccgg caaggccgga tcc                     163

<210> SEQ ID NO 23
<211> LENGTH: 42
<212> TYPE: PRT
<213> ORGANISM: ARTIFICIAL SEQUENCE
<220> FEATURE:
<223> OTHER INFORMATION: ShK{1-35, Q16K) with an N-terminal linker

<400> SEQUENCE: 23

Gly Ser Gly Gly Gly Gly Ser Arg Ser Cys Ile Asp Thr Ile Pro Lys
1               5                   10                  15

Ser Arg Cys Thr Ala Phe Lys Cys Lys His Ser Met Lys Tyr Arg Leu
            20                  25                  30

Ser Phe Cys Arg Lys Thr Cys Gly Thr Cys
        35                  40

<210> SEQ ID NO 24
<211> LENGTH: 744
<212> TYPE: DNA
<213> ORGANISM: ARTIFICIAL SEQUENCE
<220> FEATURE:
<223> OTHER INFORMATION: Coding sequence - IgG2 fragment

<400> SEQUENCE: 24
atggaatgga gctgggtctt tctcttcttc ctgtcagtaa cgactggtgt ccactccgag    60
cgcaaagtcg agtgcccacc gtgcccagca ccacctgtgg caggaccgtc agtcttcctc   120
ttccccccaa acccaagga caccctcatg atctcccgga cccctgaggt cacgtgcgtg   180
gtggtggacg tgagccacga agaccccgag gtccagttca actggtacgt ggacggcgtg   240
gaggtgcata atgccaagac aaagccacgg gaggagcagt tcaacagcac gttccgtgtg   300
gtcagcgtcc tcaccgttgt gcaccaggac tggctgaacg gcaaggagta caagtgcaag   360
gtctccaaca aaggcctccc agcccccatc gagaaaacca tctccaaaac caagggcag   420 ccccgagaac cacaggtgta caccctgccc ccatcccggg aggagatgac caagaaccag   480
gtcagcctga cctgcctggt caaaggcttc taccccagcg acatcgccgt ggagtgggag   540
agcaatgggc agccggagaa caactacaag accacacctc ccatgctgga ctccgacggc   600
tccttcttcc tctacagcaa gctcaccgtg gacaagagca ggtggcagca ggggaacgtc   660
ttctcatgct ccgtgatgca tgaggctctg cacaaccact acacgcagaa gagcctctcc   720
ctgtctccgg gtaaaggagg agga                                           744

<210> SEQ ID NO 25
<211> LENGTH: 248

-continued

```
<212> TYPE: PRT
<213> ORGANISM: ARTIFICIAL SEQUENCE
<220> FEATURE:
<223> OTHER INFORMATION: IgG2 fragment

<400> SEQUENCE: 25

Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30

Val Ala Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Phe Arg Val Val Ser Val Leu Thr Val Val His Gln Asp Trp Leu
            100                 105                 110

Asn Gly Lys Glu Tyr Lys Cys Lys Val Ser Asn Lys Gly Leu Pro Ala
        115                 120                 125

Pro Ile Glu Lys Thr Ile Ser Lys Thr Lys Gly Gln Pro Arg Glu Pro
    130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys Gly Gly Gly
                245

<210> SEQ ID NO 26
<211> LENGTH: 290
<212> TYPE: PRT
<213> ORGANISM: ARTIFICIAL SEQUENCE
<220> FEATURE:
<223> OTHER INFORMATION: IgG2 Fc-L10-ShK(1-35, Q16K) fusion protein

<400> SEQUENCE: 26

Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30

Val Ala Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Gln Phe Asn Trp Tyr Val Asp Gly Val
65                  70                  75                  80
```

-continued

```
Glu Val His Asn Ala Lys Thr Lys Pro Arg Glu Glu Gln Phe Asn Ser
                85                  90                  95

Thr Phe Arg Val Val Ser Val Leu Thr Val Val His Gln Asp Trp Leu
            100                 105                 110

Asn Gly Lys Glu Tyr Lys Cys Lys Val Ser Asn Lys Gly Leu Pro Ala
        115                 120                 125

Pro Ile Glu Lys Thr Ile Ser Lys Thr Lys Gly Gln Pro Arg Glu Pro
    130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Met Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys Gly Gly Gly Ser Gly Gly Gly Ser Arg
                245                 250                 255

Ser Cys Ile Asp Thr Ile Pro Lys Ser Arg Cys Thr Ala Phe Lys Cys
                260                 265                 270

Lys His Ser Met Lys Tyr Arg Leu Ser Phe Cys Arg Lys Thr Cys Gly
                275                 280                 285

Thr Cys
    290

<210> SEQ ID NO 27
<211> LENGTH: 35
<212> TYPE: PRT
<213> ORGANISM: Stichodactyla helianthus
<220> FEATURE:
<221> NAME/KEY: MISC_FEATURE
<223> OTHER INFORMATION: ShK

<400> SEQUENCE: 27

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 28
<211> LENGTH: 236
<212> TYPE: PRT
<213> ORGANISM: ARTIFICIAL SEQUENCE
<220> FEATURE:
<223> OTHER INFORMATION: aKLH 120.6 kappa LC

<400> SEQUENCE: 28

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30
```

```
Leu Ser Ala Ser Val Gly Asp Arg Val Thr Ile Thr Cys Arg Ala Ser
         35                  40                  45

Gln Gly Ile Arg Asn Asp Leu Gly Trp Tyr Gln Lys Pro Gly Lys
 50                  55                  60

Ala Pro Lys Arg Leu Ile Tyr Ala Ala Ser Ser Leu Gln Ser Gly Val
 65                  70                  75                  80

Pro Ser Arg Phe Ser Gly Ser Gly Ser Gly Thr Glu Phe Thr Leu Thr
                 85                  90                  95

Ile Ser Ser Leu Gln Pro Glu Asp Phe Ala Thr Tyr Tyr Cys Leu Gln
                100                 105                 110

His Asn Ser Tyr Pro Leu Thr Phe Gly Gly Gly Thr Lys Val Glu Ile
                115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
                210                 215                 220

Ser Pro Val Thr Lys Ser Phe Asn Arg Gly Glu Cys
225                 230                 235

<210> SEQ ID NO 29
<211> LENGTH: 467
<212> TYPE: PRT
<213> ORGANISM: ARTIFICIAL SEQUENCE
<220> FEATURE:
<223> OTHER INFORMATION: aKLH 120.6 IgG2 HC

<400> SEQUENCE: 29

Met Asp Met Arg Val Pro Ala Gln Leu Leu Gly Leu Leu Leu Leu Trp
  1               5                  10                  15

Leu Arg Gly Ala Arg Cys Gln Val Gln Leu Val Gln Ser Gly Ala Glu
                 20                  25                  30

Val Lys Lys Pro Gly Ala Ser Val Lys Val Ser Cys Lys Ala Ser Gly
                 35                  40                  45

Tyr Thr Phe Thr Gly Tyr His Met His Trp Val Arg Gln Ala Pro Gly
 50                  55                  60

Gln Gly Leu Glu Trp Met Gly Trp Ile Asn Pro Asn Ser Gly Gly Thr
 65                  70                  75                  80

Asn Tyr Ala Gln Lys Phe Gln Gly Arg Val Thr Met Thr Arg Asp Thr
                 85                  90                  95

Ser Ile Ser Thr Ala Tyr Met Glu Leu Ser Arg Leu Arg Ser Asp Asp
                100                 105                 110

Thr Ala Val Tyr Tyr Cys Ala Arg Asp Arg Gly Ser Tyr Tyr Trp Phe
                115                 120                 125

Asp Pro Trp Gly Gln Gly Thr Leu Val Thr Val Ser Ser Ala Ser Thr
                130                 135                 140

Lys Gly Pro Ser Val Phe Pro Leu Ala Pro Cys Ser Arg Ser Thr Ser
145                 150                 155                 160
```

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 30
<211> LENGTH: 290
<212> TYPE: PRT
<213> ORGANISM: ARTIFICIAL SEQUENCE
<220> FEATURE:
<223> OTHER INFORMATION: IgG2 Fc-L10-ShK(1-35)

<400> SEQUENCE: 30

Met Glu Trp Ser Trp Val Phe Leu Phe Phe Leu Ser Val Thr Thr Gly
1               5                   10                  15

Val His Ser Glu Arg Lys Val Glu Cys Pro Pro Cys Pro Ala Pro Pro
            20                  25                  30

Val Ala Gly Pro Ser Val Phe Leu Phe Pro Pro Lys Pro Lys Asp Thr
        35                  40                  45

```
Leu Met Ile Ser Arg Thr Pro Glu Val Thr Cys Val Val Asp Val
 50                 55                  60

Ser His Glu Asp Pro Glu Val Gln Phe Asn Trp Tyr Val Asp Gly Val
 65                 70                  75                  80

Glu Val His Asn Ala Lys Thr Lys Pro Arg Glu Glu Gln Phe Asn Ser
                 85                  90                  95

Thr Phe Arg Val Val Ser Val Leu Thr Val Val His Gln Asp Trp Leu
            100                 105                 110

Asn Gly Lys Glu Tyr Lys Cys Lys Val Ser Asn Lys Gly Leu Pro Ala
                115                 120                 125

Pro Ile Glu Lys Thr Ile Ser Lys Thr Lys Gly Gln Pro Arg Glu Pro
130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
                180                 185                 190

Pro Pro Met Leu Asp Ser Asp Gly Ser Phe Phe Leu Tyr Ser Lys Leu
            195                 200                 205

Thr Val Asp Lys Ser Arg Trp Gln Gln Gly Asn Val Phe Ser Cys Ser
210                 215                 220

Val Met His Glu Ala Leu His Asn His Tyr Thr Gln Lys Ser Leu Ser
225                 230                 235                 240

Leu Ser Pro Gly Lys Gly Gly Gly Gly Ser Gly Gly Gly Gly Ser Arg
                245                 250                 255

Ser Cys Ile Asp Thr Ile Pro Lys Ser Arg Cys Thr Ala Phe Gln Cys
                260                 265                 270

Lys His Ser Met Lys Tyr Arg Leu Ser Phe Cys Arg Lys Thr Cys Gly
            275                 280                 285

Thr Cys
    290

<210> SEQ ID NO 31
<211> LENGTH: 511
<212> TYPE: PRT
<213> ORGANISM: ARTIFICIAL SEQUENCE
<220> FEATURE:
<223> OTHER INFORMATION: aKLH 120.6 IgG2-ShK fusion

<400> SEQUENCE: 31

Met Asp Met Arg Val Pro Ala Gln Leu Leu Gly Leu Leu Leu Leu Trp
 1                  5                  10                  15

Leu Arg Gly Ala Arg Cys Gln Val Gln Leu Val Gln Ser Gly Ala Glu
                 20                  25                  30

Val Lys Lys Pro Gly Ala Ser Val Lys Val Ser Cys Lys Ala Ser Gly
             35                  40                  45

Tyr Thr Phe Thr Gly Tyr His Met His Trp Val Arg Gln Ala Pro Gly
         50                  55                  60

Gln Gly Leu Glu Trp Met Gly Trp Ile Asn Pro Asn Ser Gly Gly Thr
 65                 70                  75                  80

Asn Tyr Ala Gln Lys Phe Gln Gly Arg Val Thr Met Thr Arg Asp Thr
                 85                  90                  95

Ser Ile Ser Thr Ala Tyr Met Glu Leu Ser Arg Leu Arg Ser Asp Asp
            100                 105                 110
```

Thr Ala Val Tyr Tyr Cys Ala Arg Asp Arg Gly Ser Tyr Tyr Trp Phe
            115                 120                 125

Asp Pro Trp Gly Gln Gly Thr Leu Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
            165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Asn Phe Gly Thr Gln Thr Tyr Thr Cys
            210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Gln Phe Asn Trp Tyr Val Asp Gly Val Glu Val
            290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
            325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
            355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Gly Gly Gly Ser Gly Gly Gly Ser Arg Ser Cys
465                 470                 475                 480

Asp Thr Ile Pro Lys Ser Arg Cys Thr Ala Phe Gln Cys Lys His Ser
            485                 490                 495

Met Lys Tyr Arg Leu Ser Phe Cys Arg Lys Thr Cys Gly Thr Cys
            500                 505                 510

<210> SEQ ID NO 32
<211> LENGTH: 511
<212> TYPE: PRT

```
<213> ORGANISM: ARTIFICIAL SEQUENCE
<220> FEATURE:
<223> OTHER INFORMATION: aKLH 120.6 IgG2-ShK[1-35, Q16K] fusion

<400> SEQUENCE: 32
```

| | | | | | | | | | | | | | | |
|---|---|---|---|---|---|---|---|---|---|---|---|---|---|---|
| Met | Asp | Met | Arg | Val | Pro | Ala | Gln | Leu | Leu | Gly | Leu | Leu | Leu | Trp |
| 1 | | | | 5 | | | | | 10 | | | | | 15 |

Leu Arg Gly Ala Arg Cys Gln Val Gln Leu Val Gln Ser Gly Ala Glu
             20                  25                  30

Val Lys Lys Pro Gly Ala Ser Val Lys Val Ser Cys Lys Ala Ser Gly
         35                  40                  45

Tyr Thr Phe Thr Gly Tyr His Met His Trp Val Arg Gln Ala Pro Gly
     50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
             85                  90                  95

Ser Ile Ser Thr Ala Tyr Met Glu Leu Ser Arg Leu Arg Ser Asp Asp
         100                 105                 110

Thr Ala Val Tyr Tyr Cys Ala Arg Asp Arg Gly Ser Tyr Tyr Trp Phe
     115                 120                 125

Asp Pro Trp Gly Gln Gly Thr Leu Val Thr Val Ser Ser Ala Ser Thr
     130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
             165                 170                 175

Pro Val Thr Val Ser Trp Asn Ser Gly Ala Leu Thr Ser Gly Val His
         180                 185                 190

Thr Phe Pro Ala Val Leu Gln Ser Ser Gly Leu Tyr Ser Leu Ser Ser
     195                 200                 205

Val Val Thr Val Pro Ser Ser Asn Phe Gly Thr Gln Thr Tyr Thr Cys
     210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
             245                 250                 255

Gly Pro Ser Val Phe Leu Phe Pro Pro Lys Pro Lys Asp Thr Leu Met
         260                 265                 270

Ile Ser Arg Thr Pro Glu Val Thr Cys Val Val Val Asp Val Ser His
     275                 280                 285

Glu Asp Pro Glu Val Gln Phe Asn Trp Tyr Val Asp Gly Val Glu Val
     290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
             325                 330                 335

Lys Glu Tyr Lys Cys Lys Val Ser Asn Lys Gly Leu Pro Ala Pro Ile
         340                 345                 350

Glu Lys Thr Ile Ser Lys Thr Lys Gly Gln Pro Arg Glu Pro Gln Val
     355                 360                 365

Tyr Thr Leu Pro Pro Ser Arg Glu Glu Met Thr Lys Asn Gln Val Ser
     370                 375                 380

Leu Thr Cys Leu Val Lys Gly Phe Tyr Pro Ser Asp Ile Ala Val Glu

```
                385             390             395             400
Trp Glu Ser Asn Gly Gln Pro Glu Asn Tyr Lys Thr Thr Pro Pro
                    405             410             415

Met Leu Asp Ser Asp Gly Ser Phe Phe Leu Tyr Ser Lys Leu Thr Val
                420             425             430

Asp Lys Ser Arg Trp Gln Gln Gly Asn Val Phe Ser Cys Ser Val Met
                435             440             445

His Glu Ala Leu His Asn His Tyr Thr Gln Lys Ser Leu Ser Leu Ser
            450             455             460

Pro Gly Gly Gly Gly Ser Gly Gly Gly Gly Ser Arg Ser Cys Ile
465             470             475             480

Asp Thr Ile Pro Lys Ser Arg Cys Thr Ala Phe Lys Cys Lys His Ser
                485             490             495

Met Lys Tyr Arg Leu Ser Phe Cys Arg Lys Thr Cys Gly Thr Cys
                500             505             510

<210> SEQ ID NO 33
<211> LENGTH: 510
<212> TYPE: PRT
<213> ORGANISM: ARTIFICIAL SEQUENCE
<220> FEATURE:
<223> OTHER INFORMATION: aKLH 120.6 IgG2-ShK[2-35, Q16K] fusion

<400> SEQUENCE: 33

Met Asp Met Arg Val Pro Ala Gln Leu Leu Gly Leu Leu Leu Trp
1               5               10              15

Leu Arg Gly Ala Arg Cys Gln Val Gln Leu Val Gln Ser Gly Ala Glu
                20              25              30

Val Lys Lys Pro Gly Ala Ser Val Lys Val Ser Cys Lys Ala Ser Gly
            35              40              45

Tyr Thr Phe Thr Gly Tyr His Met His Trp Val Arg Gln Ala Pro Gly
    50              55              60

Gln Gly Leu Glu Trp Met Gly Trp Ile Asn Pro Asn Ser Gly Gly Thr
65              70              75              80

Asn Tyr Ala Gln Lys Phe Gln Gly Arg Val Thr Met Thr Arg Asp Thr
                85              90              95

Ser Ile Ser Thr Ala Tyr Met Glu Leu Ser Arg Leu Arg Ser Asp Asp
            100             105             110

Thr Ala Val Tyr Tyr Cys Ala Arg Asp Arg Gly Ser Tyr Tyr Trp Phe
        115             120             125

Asp Pro Trp Gly Gln Gly Thr Leu Val Thr Val Ser Ser Ala Ser Thr
130             135             140

Lys Gly Pro Ser Val Phe Pro Leu Ala Pro Cys Ser Arg Ser Thr Ser
145             150             155             160

Glu Ser Thr Ala Ala Leu Gly Cys Leu Val Lys Asp Tyr Phe Pro Glu
                165             170             175

Pro Val Thr Val Ser Trp Asn Ser Gly Ala Leu Thr Ser Gly Val His
            180             185             190

Thr Phe Pro Ala Val Leu Gln Ser Ser Gly Leu Tyr Ser Leu Ser Ser
        195             200             205

Val Val Thr Val Pro Ser Ser Asn Phe Gly Thr Gln Thr Tyr Thr Cys
        210             215             220

Asn Val Asp His Lys Pro Ser Asn Thr Lys Val Asp Lys Thr Val Glu
225             230             235             240

Arg Lys Cys Cys Val Glu Cys Pro Pro Cys Pro Ala Pro Pro Val Ala
```

```
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
            275                 280                 285
Glu Asp Pro Glu Val Gln Phe Asn Trp Tyr Val Asp Gly Val Glu Val
            290                 295                 300
His Asn Ala Lys Thr Lys Pro Arg Glu Gln Phe Asn Ser Thr Phe
305                 310                 315                 320
Arg Val Val Ser Val Leu Thr Val Val His Gln Asp Trp Leu Asn Gly
                325                 330                 335
Lys Glu Tyr Lys Cys Lys Val Ser Asn Lys Gly Leu Pro Ala Pro Ile
                340                 345                 350
Glu Lys Thr Ile Ser Lys Thr Lys Gly Gln Pro Arg Glu Pro Gln Val
                355                 360                 365
Tyr Thr Leu Pro Pro Ser Arg Glu Glu Met Thr Lys Asn Gln Val Ser
            370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Met Leu Asp Ser Asp Gly Ser Phe Phe Leu Tyr Ser Lys Leu Thr Val
                420                 425                 430
Asp Lys Ser Arg Trp Gln Gln Gly Asn Val Phe Ser Cys Ser Val Met
                435                 440                 445
His Glu Ala Leu His Asn His Tyr Thr Gln Lys Ser Leu Ser Leu Ser
            450                 455                 460
Pro Gly Gly Gly Gly Ser Gly Gly Gly Ser Ser Cys Ile Asp
465                 470                 475                 480
Thr Ile Pro Lys Ser Arg Cys Thr Ala Phe Lys Cys Lys His Ser Met
                485                 490                 495
Lys Tyr Arg Leu Ser Phe Cys Arg Lys Thr Cys Gly Thr Cys
            500                 505                 510

<210> SEQ ID NO 34
<211> LENGTH: 471
<212> TYPE: PRT
<213> ORGANISM: ARTIFICIAL SEQUENCE
<220> FEATURE:
<223> OTHER INFORMATION: aKLH 120.6 IgG1 HC

<400> SEQUENCE: 34

Met Asp Met Arg Val Pro Ala Gln Leu Leu Gly Leu Leu Leu Leu Trp
1               5                   10                  15
Leu Arg Gly Ala Arg Cys Gln Val Gln Leu Val Gln Ser Gly Ala Glu
                20                  25                  30
Val Lys Lys Pro Gly Ala Ser Val Lys Val Ser Cys Lys Ala Ser Gly
                35                  40                  45
Tyr Thr Phe Thr Gly Tyr His Met His Trp Val Arg Gln Ala Pro Gly
            50                  55                  60
Gln Gly Leu Glu Trp Met Gly Trp Ile Asn Pro Asn Ser Gly Gly Thr
65                  70                  75                  80
Asn Tyr Ala Gln Lys Phe Gln Gly Arg Val Thr Met Thr Arg Asp Thr
                85                  90                  95
Ser Ile Ser Thr Ala Tyr Met Glu Leu Ser Arg Leu Arg Ser Asp Asp
```

```
               100                 105                 110
Thr Ala Val Tyr Tyr Cys Ala Arg Asp Arg Gly Ser Tyr Tyr Trp Phe
            115                 120                 125

Asp Pro Trp Gly Gln Gly Thr Leu Val Thr Val Ser Ser Ala Ser Thr
            130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Leu Gly Thr Gln Thr Tyr Ile Cys
            210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 35
<211> LENGTH: 510
<212> TYPE: PRT
<213> ORGANISM: ARTIFICIAL SEQUENCE
<220> FEATURE:
<223> OTHER INFORMATION: aKLH 120.6 IgG1-loop-ShK
```

<400> SEQUENCE: 35

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Gly Gly
    370                 375                 380

Arg Ser Cys Ile Asp Thr Ile Pro Lys Ser Arg Cys Thr Ala Phe Lys
385                 390                 395                 400

Cys Lys His Ser Met Lys Tyr Arg Leu Ser Phe Cys Arg Lys Thr Cys
                405                 410                 415
```

-continued

```
Gly Thr Cys Gly Gly Thr Lys Asn Gln Val Ser Leu Thr Cys Leu Val
                420                 425                 430

Lys Gly Phe Tyr Pro Ser Asp Ile Ala Val Glu Trp Glu Ser Asn Gly
            435                 440                 445

Gln Pro Glu Asn Asn Tyr Lys Thr Thr Pro Pro Val Leu Asp Ser Asp
    450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495

Asn His Tyr Thr Gln Lys Ser Leu Ser Leu Ser Pro Gly Lys
                500                 505                 510

<210> SEQ ID NO 36
<211> LENGTH: 24
<212> TYPE: DNA
<213> ORGANISM: ARTIFICIAL SEQUENCE
<220> FEATURE:
<223> OTHER INFORMATION: Random primer with an extension adapter
<220> FEATURE:
<221> NAME/KEY: misc_feature
<222> LOCATION: (18)..(23)
<223> OTHER INFORMATION: Any deoxriboneucleotide

<400> SEQUENCE: 36
ggccggatag gcctccannn nnnt                                              24

<210> SEQ ID NO 37
<211> LENGTH: 45
<212> TYPE: DNA
<213> ORGANISM: ARTIFICIAL SEQUENCE
<220> FEATURE:
<223> OTHER INFORMATION: Forward primer

<400> SEQUENCE: 37
gtggttgaga ggtgccagat gtgacattgt gatgactcag tctcc                       45

<210> SEQ ID NO 38
<211> LENGTH: 41
<212> TYPE: DNA
<213> ORGANISM: ARTIFICIAL SEQUENCE
<220> FEATURE:
<223> OTHER INFORMATION: Reverse primer

<400> SEQUENCE: 38
aaccgtttaa acgcggccgc tcaacactct cccctgttga a                           41

<210> SEQ ID NO 39
<211> LENGTH: 43
<212> TYPE: DNA
<213> ORGANISM: ARTIFICIAL SEQUENCE
<220> FEATURE:
<223> OTHER INFORMATION: Optimized Kozak seqence

<400> SEQUENCE: 39
aagctcgagg tcgactagac caccatggac atgagggtcc ccg                         43

<210> SEQ ID NO 40
<211> LENGTH: 45
<212> TYPE: DNA
<213> ORGANISM: ARTIFICIAL SEQUENCE
<220> FEATURE:
<223> OTHER INFORMATION: Primer sequence
```

<400> SEQUENCE: 40
aagctcgagg tcgactagac caccatggac atgagggtgc ccgct          45

<210> SEQ ID NO 41
<211> LENGTH: 25
<212> TYPE: DNA
<213> ORGANISM: ARTIFICIAL SEQUENCE
<220> FEATURE:
<223> OTHER INFORMATION: Primer sequence

<400> SEQUENCE: 41
tcatctggat gtcacatctg gcacc          25

<210> SEQ ID NO 42
<211> LENGTH: 25
<212> TYPE: DNA
<213> ORGANISM: ARTIFICIAL SEQUENCE
<220> FEATURE:
<223> OTHER INFORMATION: Primer sequence

<400> SEQUENCE: 42
ggtgccagat gtgacatcca gatga          25

<210> SEQ ID NO 43
<211> LENGTH: 30
<212> TYPE: DNA
<213> ORGANISM: ARTIFICIAL SEQUENCE
<220> FEATURE:
<223> OTHER INFORMATION: Primer sequence

<400> SEQUENCE: 43
cattctagac ccaccatgga catgagggtg          30

<210> SEQ ID NO 44
<211> LENGTH: 34
<212> TYPE: DNA
<213> ORGANISM: ARTIFICIAL SEQUENCE
<220> FEATURE:
<223> OTHER INFORMATION: Primer sequence

<400> SEQUENCE: 44
ggatcctcct cctccacccg agacaggga gagg          34

<210> SEQ ID NO 45
<211> LENGTH: 1398
<212> TYPE: DNA
<213> ORGANISM: ARTIFICIAL SEQUENCE
<220> FEATURE:
<223> OTHER INFORMATION: aKLH 120.6-VK1SP-IgG2 Heavy Chain coding
      sequence

<400> SEQUENCE: 45
atggacatga gggtgcccgc tcagctcctg gggctcctgc tgctgtggct gagaggtgcc     60
agatgtcagg tgcagctggt gcagtctggg gctgaggtga agaagcctgg ggcctcagtg    120
aaggtctcct gcaaggcttc tggatacacc ttcaccggct accacatgca ctgggtgcga    180
caggcccctg gacaagggct tgagtggatg ggatggatca accctaacag tggtggcaca    240
aactatgcac agaagtttca gggcagggtc accatgacca gggacacgtc catcagcaca    300
gcctacatgg agctgagcag gctgagatct gacgacacgg ccgtgtatta ctgtgcgaga    360
gatcgtggga gctactactg gttcgacccc tggggccagg gaaccctggt caccgtctcc    420
tcagcctcca ccaagggccc atcggtcttc cccctggcgc cctgctccag gagcacctcc    480

```
gagagcacag cggccctggg ctgcctggtc aaggactact tccccgaacc ggtgacggtg    540
tcgtggaact caggcgctct gaccagcggc gtgcacacct tcccagctgt cctacagtcc    600
tcaggactct actccctcag cagcgtggtg accgtgccct ccagcaactt cggcacccag    660
acctacacct gcaacgtaga tcacaagccc agcaacacca aggtggacaa gacagttgag    720
cgcaaatgtt gtgtcgagtg cccaccgtgc ccagcaccac ctgtggcagg accgtcagtc    780
ttcctcttcc ccccaaaacc caaggacacc ctcatgatct cccggacccc tgaggtcacg    840
tgcgtggtgg tggacgtgag ccacgaagac cccgaggtcc agttcaactg gtacgtggac    900
ggcgtggagg tgcataatgc caagacaaag ccacgggagg agcagttcaa cagcacgttc    960
cgtgtggtca gcgtcctcac cgttgtgcac caggactggc tgaacggcaa ggagtacaag   1020
tgcaaggtct ccaacaaagg cctcccagcc cccatcgaga aaaccatctc caaaaccaaa   1080
gggcagcccc gagaaccaca ggtgtacacc ctgcccccat cccgggagga gatgaccaag   1140
aaccaggtca gcctgacctg cctggtcaaa ggcttctacc ccagcgacat cgccgtggag   1200
tgggagagca atgggcagcc ggagaacaac tacaagacca cacctcccat gctggactcc   1260
gacggctcct tcttcctcta cagcaagctc accgtggaca gagcaggtg gcagcagggg     1320 aacgtcttct catgctccgt gatgcatgag gctctgcaca accactacac gcagaagagc   1380 ctctcccctgt ctccgggt                                                 1398
```

<210> SEQ ID NO 46
<211> LENGTH: 466
<212> TYPE: PRT
<213> ORGANISM: ARTIFICIAL SEQUENCE
<220> FEATURE:
<223> OTHER INFORMATION: aKLH 120.6-VK1SP-IgG2 Heavy Chain

<400> SEQUENCE: 46

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
```

```
                195                 200                 205
Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
                275                 280                 285

Glu Asp Pro Glu Val Gln Phe Asn Trp Tyr Val Asp Gly Val Glu Val
                290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
                340                 345                 350

Glu Lys Thr Ile Ser Lys Thr Lys Gly Gln Pro Arg Glu Pro Gln Val
                355                 360                 365

Tyr Thr Leu Pro Pro Ser Arg Glu Glu Met Thr Lys Asn Gln Val Ser
                370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
    450                 455                 460

Pro Gly
465

<210> SEQ ID NO 47
<211> LENGTH: 34
<212> TYPE: DNA
<213> ORGANISM: ARTIFICIAL SEQUENCE
<220> FEATURE:
<223> OTHER INFORMATION: Primer sequence

<400> SEQUENCE: 47
tccctgtctc cgggtggagg aggaggatcc ggag                           34

<210> SEQ ID NO 48
<211> LENGTH: 511
<212> TYPE: PRT
<213> ORGANISM: ARTIFICIAL SEQUENCE
<220> FEATURE:
<223> OTHER INFORMATION: IgG2-HC-L10-ShK[1-35] fusion polypeptide

<400> SEQUENCE: 48

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
```

```
            20                  25                  30
Val Lys Lys Pro Gly Ala Ser Val Lys Val Ser Cys Lys Ala Ser Gly
            35                  40                  45
Tyr Thr Phe Thr Gly Tyr His Met His Trp Val Arg Gln Ala Pro Gly
            50                  55                  60
Gln Gly Leu Glu Trp Met Gly Trp Ile Asn Pro Asn Ser Gly Gly Thr
 65                  70                  75                  80
Asn Tyr Ala Gln Lys Phe Gln Gly Arg Val Thr Met Thr Arg Asp Thr
                 85                  90                  95
Ser Ile Ser Thr Ala Tyr Met Glu Leu Ser Arg Leu Arg Ser Asp Asp
                100                 105                 110
Thr Ala Val Tyr Tyr Cys Ala Arg Asp Arg Gly Ser Tyr Tyr Trp Phe
            115                 120                 125
Asp Pro Trp Gly Gln Gly Thr Leu Val Thr Val Ser Ser Ala Ser Thr
            130                 135                 140
Lys Gly Pro Ser Val Phe Pro Leu Ala Pro Cys Ser Arg Ser Thr Ser
145                 150                 155                 160
Glu Ser Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
            195                 200                 205
Val Val Thr Val Pro Ser Ser Asn Phe Gly Thr Gln Thr Tyr Thr Cys
            210                 215                 220
Asn Val Asp His Lys Pro Ser Asn Thr Lys Val Asp Lys Thr Val Glu
225                 230                 235                 240
Arg Lys Cys Cys Val Glu Cys Pro Pro Cys Pro Ala Pro Pro Val Ala
                245                 250                 255
Gly Pro Ser Val Phe Leu Phe Pro Pro Lys Pro Lys Asp Thr Leu Met
                260                 265                 270
Ile Ser Arg Thr Pro Glu Val Thr Cys Val Val Val Asp Val Ser His
            275                 280                 285
Glu Asp Pro Glu Val Gln Phe Asn Trp Tyr Val Asp Gly Val Glu Val
            290                 295                 300
His Asn Ala Lys Thr Lys Pro Arg Glu Glu Gln Phe Asn Ser Thr Phe
305                 310                 315                 320
Arg Val Val Ser Val Leu Thr Val Val His Gln Asp Trp Leu Asn Gly
                325                 330                 335
Lys Glu Tyr Lys Cys Lys Val Ser Asn Lys Gly Leu Pro Ala Pro Ile
                340                 345                 350
Glu Lys Thr Ile Ser Lys Thr Lys Gly Gln Pro Arg Glu Pro Gln Val
            355                 360                 365
Tyr Thr Leu Pro Pro Ser Arg Glu Glu Met Thr Lys Asn Gln Val Ser
            370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Met Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
            435                 440                 445
```

His Glu Ala Leu His Asn His Tyr Thr Gln Lys Ser Leu Ser Leu Ser
                450                 455                 460

Pro Gly Gly Gly Gly Ser Gly Gly Gly Gly Ser Arg Ser Cys Ile
465                 470                 475                 480

Asp Thr Ile Pro Lys Ser Arg Cys Thr Ala Phe Gln Cys Lys His Ser
                485                 490                 495

Met Lys Tyr Arg Leu Ser Phe Cys Arg Lys Thr Cys Gly Thr Cys
                500                 505                 510

<210> SEQ ID NO 49
<211> LENGTH: 511
<212> TYPE: PRT
<213> ORGANISM: ARTIFICIAL SEQUENCE
<220> FEATURE:
<223> OTHER INFORMATION: IgG2-HC-L10-ShK[1-35, Q16K] fusion polypeptide

<400> SEQUENCE: 49

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
                20                  25                  30

Val Lys Lys Pro Gly Ala Ser Val Lys Val Ser Cys Lys Ala Ser Gly
                35                  40                  45

Tyr Thr Phe Thr Gly Tyr His Met His Trp Val Arg Gln Ala Pro Gly
                50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
                100                 105                 110

Thr Ala Val Tyr Tyr Cys Ala Arg Asp Arg Gly Ser Tyr Tyr Trp Phe
                115                 120                 125

Asp Pro Trp Gly Gln Gly Thr Leu Val Thr Val Ser Ser Ala Ser Thr
                130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
                195                 200                 205

Val Val Thr Val Pro Ser Ser Asn Phe Gly Thr Gln Thr Tyr Thr Cys
                210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
                275                 280                 285

Glu Asp Pro Glu Val Gln Phe Asn Trp Tyr Val Asp Gly Val Glu Val
                290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
            325                 330                 335

Lys Glu Tyr Lys Cys Lys Val Ser Asn Lys Gly Leu Pro Ala Pro Ile
        340                 345                 350

Glu Lys Thr Ile Ser Lys Thr Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Met Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Gly Gly Gly Ser Gly Gly Gly Ser Arg Ser Cys Ile
465                 470                 475                 480

Asp Thr Ile Pro Lys Ser Arg Cys Thr Ala Phe Lys Cys Lys His Ser
            485                 490                 495

Met Lys Tyr Arg Leu Ser Phe Cys Arg Lys Thr Cys Gly Thr Cys
        500                 505                 510

<210> SEQ ID NO 50
<211> LENGTH: 1407
<212> TYPE: DNA
<213> ORGANISM: ARTIFICIAL SEQUENCE
<220> FEATURE:
<223> OTHER INFORMATION: Coding sequence

<400> SEQUENCE: 50
atggacatga gggtgcccgc tcagctcctg gggctcctgc tgctgtggct gagaggtgcc      60
agatgtcagg tgcagctggt gcagtctggg gctgaggtga agaagcctgg ggcctcagtg     120
aaggtctcct gcaaggcttc tggatacacc ttcaccggct accacatgca ctgggtgcga     180
caggcccctg gacaagggct tgagtggatg ggatggatca ccctaacagt ggtggcaca     240 aactatgcac agaagtttca gggcagggtc accatgacca gggacacgtc catcagcaca     300
gcctacatgg agctgagcag gctgagatct gacgacacgg ccgtgtatta ctgtgcgaga     360
gatcgtggga gctactactg gttcgacccc tggggccagg gaaccctggt caccgtctcc     420
tcagcctcca ccaagggccc atcggtcttc cccctggcgc cctgctccag gagcacctcc     480
gagagcacag cggccctggg ctgcctggtc aaggactact cccccgaacc ggtgacggtg     540
tcgtggaact caggcgctct gaccagcggc gtgcacacct tcccagctgt cctacagtcc     600
tcaggactct actccctcag cagcgtggtg accgtgccct ccagcaactt cggcacccag     660
acctacacct gcaacgtaga tcacaagccc agcaacacca aggtggacaa gacagttgag     720
cgcaaatgtt gtgtcgagtg cccaccgtgc ccagcaccac ctgtggcagg accgtcagtc     780
ttcctcttcc cccaaaaacc caaggacacc ctcatgatct cccggacccc tgaggtcacg     840
tgcgtggtgg tggacgtgag ccacgaagac cccgaggtcc agttcaactg gtacgtggac     900

```
ggcgtggagg tgcataatgc aagacaaag ccacgggagg agcagttcaa cagcacgttc    960
cgtgtggtca gcgtcctcac cgttgtgcac caggactggc tgaacggcaa ggagtacaag   1020
tgcaaggtct ccaacaaagg cctcccagcc cccatcgaga aaccatctc caaaccaaa    1080 gggcagcccc gagaaccaca ggtgtacacc ctgccccat cccgggagga gatgaccaag   1140
aaccaggtca gcctgacctg cctggtcaaa ggcttctacc ccagcgacat cgccgtggag   1200
tgggagagca atgggcagcc ggagaacaac tacaagacca cacctcccat gctggactcc   1260
gacggctcct tcttcctcta cagcaagctc accgtggaca gagcaggtg gcagcagggg    1320 aacgtcttct catgctccgt gatgcatgag gctctgcaca accactacac gcagaagagc   1380
ctctccctgt ctccgggtgg aggagga                                     1407
```

```
<210> SEQ ID NO 51
<211> LENGTH: 469
<212> TYPE: PRT
<213> ORGANISM: ARTIFICIAL SEQUENCE
<220> FEATURE:
<223> OTHER INFORMATION: Polypeptide sequence

<400> SEQUENCE: 51

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270
```

```
Ile Ser Arg Thr Pro Glu Val Thr Cys Val Val Val Asp Val Ser His
    275                 280                 285
Glu Asp Pro Glu Val Gln Phe Asn Trp Tyr Val Asp Gly Val Glu Val
290                 295                 300
His Asn Ala Lys Thr Lys Pro Arg Glu Glu Gln Phe Asn Ser Thr Phe
305                 310                 315                 320
Arg Val Val Ser Val Leu Thr Val Val His Gln Asp Trp Leu Asn Gly
                325                 330                 335
Lys Glu Tyr Lys Cys Lys Val Ser Asn Lys Gly Leu Pro Ala Pro Ile
            340                 345                 350
Glu Lys Thr Ile Ser Lys Thr Lys Gly Gln Pro Arg Glu Pro Gln Val
        355                 360                 365
Tyr Thr Leu Pro Pro Ser Arg Glu Glu Met Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Met Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Gly Gly Gly
465

<210> SEQ ID NO 52
<211> LENGTH: 129
<212> TYPE: DNA
<213> ORGANISM: ARTIFICIAL SEQUENCE
<220> FEATURE:
<223> OTHER INFORMATION: Coding sequence

<400> SEQUENCE: 52
ggatccggag gaggaggaag cagctgcatc gacaccatcc ccaagagccg ctgcaccgcc      60
ttcaagtgca agcacagcat gaagtaccgc ctgagcttct gccgcaagac ctgcggcacc     120
tgctaatga                                                              129

<210> SEQ ID NO 53
<211> LENGTH: 41
<212> TYPE: PRT
<213> ORGANISM: ARTIFICIAL SEQUENCE
<220> FEATURE:
<223> OTHER INFORMATION: Polypeptide sequence

<400> SEQUENCE: 53

Gly Ser Gly Gly Gly Gly Ser Ser Cys Ile Asp Thr Ile Pro Lys Ser
1               5                   10                  15
Arg Cys Thr Ala Phe Lys Cys Lys His Ser Met Lys Tyr Arg Leu Ser
            20                  25                  30
Phe Cys Arg Lys Thr Cys Gly Thr Cys
        35                  40

<210> SEQ ID NO 54
<211> LENGTH: 510
<212> TYPE: PRT
```

<213> ORGANISM: ARTIFICIAL SEQUENCE
<220> FEATURE:
<223> OTHER INFORMATION: IgG2-HC-L10-ShK[2-35] fusion polypeptide

<400> SEQUENCE: 54

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
```

|     |     |     |     | 385 |     |     |     |     | 390 |     |     |     |     | 395 |     |     |     |     | 400 |
| --- | --- | --- | --- | --- | --- | --- | --- | --- | --- | --- | --- | --- | --- | --- | --- | --- | --- | --- | --- |
| Trp | Glu | Ser | Asn | Gly | Gln | Pro | Glu | Asn | Tyr | Lys | Thr | Thr | Pro | Pro |
|     |     |     |     | 405 |     |     |     |     | 410 |     |     |     |     | 415 |

Met Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Gly Gly Gly Ser Gly Gly Gly Ser Ser Cys Ile Asp
465                 470                 475                 480

Thr Ile Pro Lys Ser Arg Cys Thr Ala Phe Lys Cys Lys His Ser Met
                485                 490                 495

Lys Tyr Arg Leu Ser Phe Cys Arg Lys Thr Cys Gly Thr Cys
                500                 505                 510

<210> SEQ ID NO 55
<211> LENGTH: 127
<212> TYPE: DNA
<213> ORGANISM: ARTIFICIAL SEQUENCE
<220> FEATURE:
<223> OTHER INFORMATION: Forward primer
<220> FEATURE:
<221> NAME/KEY: misc_feature
<222> LOCATION: (6)..(11)
<223> OTHER INFORMATION: HINDIII Site

<400> SEQUENCE: 55
tgcagaagct tctagaccac catggaatgg agctgggtct ttctcttctt cctgtcagta    60
acgactggtg tccactcccg cagctgcatc gacaccatcc ccaagagccg ctgcaccgcc   120
ttccagt                                                            127

<210> SEQ ID NO 56
<211> LENGTH: 115
<212> TYPE: DNA
<213> ORGANISM: ARTIFICIAL SEQUENCE
<220> FEATURE:
<223> OTHER INFORMATION: Reverse primer
<220> FEATURE:
<221> NAME/KEY: misc_feature
<222> LOCATION: (5)..(10)
<223> OTHER INFORMATION: BAMHI Site

<400> SEQUENCE: 56
ctccggatcc tcctcctccg caggtgccgc aggtcttgcg gcagaagctc aggcggtact    60
tcatgctgtg cttgcactgg aaggcggtgc agcggctctt ggggatggtg tcgat        115

<210> SEQ ID NO 57
<211> LENGTH: 38
<212> TYPE: DNA
<213> ORGANISM: ARTIFICIAL SEQUENCE
<220> FEATURE:
<223> OTHER INFORMATION: Forward primer
<220> FEATURE:
<221> NAME/KEY: misc_feature
<222> LOCATION: (4)..(9)
<223> OTHER INFORMATION: BAMHI Site

<400> SEQUENCE: 57
gtaggatccg gaggaggagg aagcgacaaa actcacac                            38

<210> SEQ ID NO 58

<211> LENGTH: 35
<212> TYPE: DNA
<213> ORGANISM: ARTIFICIAL SEQUENCE
<220> FEATURE:
<223> OTHER INFORMATION: Reverse primer
<220> FEATURE:
<221> NAME/KEY: misc_feature
<222> LOCATION: (4)..(11)
<223> OTHER INFORMATION: NOTI Site

<400> SEQUENCE: 58
cgagcggccg cttactattt acccggagac aggga                          35

<210> SEQ ID NO 59
<211> LENGTH: 879
<212> TYPE: DNA
<213> ORGANISM: ARTIFICIAL SEQUENCE
<220> FEATURE:
<223> OTHER INFORMATION: VH21 SP-ShK(1-35)-L10-IgG1 Fc coding sequence

<400> SEQUENCE: 59
atggaatgga gctgggtctt tctcttcttc ctgtcagtaa cgactggtgt ccactccgc      60 agctgcatcg acaccatccc aagagccgc tgcaccgcct ccagtgcaa gcacagcatg     120 aagtaccgcc tgagcttctg ccgcaagacc tgcggcacct gcggaggagg aggatccgga    180
ggaggaggaa gcgacaaaac tcacacatgc ccaccgtgcc cagcacctga actcctgggg    240
ggaccgtcag tcttcctctt ccccccaaaa cccaaggaca cctcatgat ctcccggacc     300 cctgaggtca catgcgtggt ggtggacgtg agccacgaag accctgaggt caagttcaac    360
tggtacgtgg acggcgtgga ggtgcataat gccaagacaa agccgcggga ggagcagtac    420
aacagcacgt accgtgtggt cagcgtcctc accgtcctgc accaggactg gctgaatggc    480
aaggagtaca agtgcaaggt ctccaacaaa gccctcccag cccccatcga gaaaaccatc    540
tccaaagcca aagggcagcc ccgagaacca caggtgtaca ccctgccccc atcccgggat    600
gagctgacca gaaccaggt cagcctgacc tgcctggtca aaggcttcta tcccagcgac    660
atcgccgtgg agtgggagag caatgggcag ccggagaaca actacaagac cacgcctccc    720
gtgctggact ccgacggctc cttcttcctc tacagcaagc tcaccgtgga caagagcagg    780
tggcagcagg ggaacgtctt ctcatgctcc gtgatgcatg aggctctgca caaccactac    840
acgcagaaga gcctctccct gtctccgggt aaatagtaa                            879

<210> SEQ ID NO 60
<211> LENGTH: 291
<212> TYPE: PRT
<213> ORGANISM: ARTIFICIAL SEQUENCE
<220> FEATURE:
<223> OTHER INFORMATION: VH21 SP-ShK(1-35)-L10-IgG1 Fc

<400> SEQUENCE: 60

Met Glu Trp Ser Trp Val Phe Leu Phe Phe Leu Ser Val Thr Thr Gly
1               5                   10                  15

Val His Ser Arg Ser Cys Ile Asp Thr Ile Pro Lys Ser Arg Cys Thr
            20                  25                  30

Ala Phe Gln Cys Lys His Ser Met Lys Tyr Arg Leu Ser Phe Cys Arg
        35                  40                  45

Lys Thr Cys Gly Thr Cys Gly Gly Gly Gly Ser Gly Gly Gly Gly Ser
    50                  55                  60

Asp Lys Thr His Thr Cys Pro Pro Cys Pro Ala Pro Glu Leu Leu Gly
65                  70                  75                  80

Gly Pro Ser Val Phe Leu Phe Pro Pro Lys Pro Lys Asp Thr Leu Met
            85                  90                  95

Ile Ser Arg Thr Pro Glu Val Thr Cys Val Val Val Asp Val Ser His
            100                 105                 110

Glu Asp Pro Glu Val Lys Phe Asn Trp Tyr Val Asp Gly Val Glu Val
            115                 120                 125

His Asn Ala Lys Thr Lys Pro Arg Glu Glu Gln Tyr Asn Ser Thr Tyr
            130                 135                 140

Arg Val Val Ser Val Leu Thr Val Leu His Gln Asp Trp Leu Asn Gly
145                 150                 155                 160

Lys Glu Tyr Lys Cys Lys Val Ser Asn Lys Ala Leu Pro Ala Pro Ile
            165                 170                 175

Glu Lys Thr Ile Ser Lys Ala Lys Gly Gln Pro Arg Glu Pro Gln Val
            180                 185                 190

Tyr Thr Leu Pro Pro Ser Arg Asp Glu Leu Thr Lys Asn Gln Val Ser
            195                 200                 205

Leu Thr Cys Leu Val Lys Gly Phe Tyr Pro Ser Asp Ile Ala Val Glu
            210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Lys Leu Thr Val
            245                 250                 255

Asp Lys Ser Arg Trp Gln Gln Gly Asn Val Phe Ser Cys Ser Val Met
            260                 265                 270

His Glu Ala Leu His Asn His Tyr Thr Gln Lys Ser Leu Ser Leu Ser
            275                 280                 285

Pro Gly Lys
    290

<210> SEQ ID NO 61
<211> LENGTH: 291
<212> TYPE: PRT
<213> ORGANISM: ARTIFICIAL SEQUENCE
<220> FEATURE:
<223> OTHER INFORMATION: VH21 SP-ShK(1-35, Q16K)-L10-IgG1 Fc

<400> SEQUENCE: 61

Met Glu Trp Ser Trp Val Phe Leu Phe Leu Ser Val Thr Thr Gly
1               5                   10                  15

Val His Ser Arg Ser Cys Ile Asp Thr Ile Pro Lys Ser Arg Cys Thr
            20                  25                  30

Ala Phe Lys Cys Lys His Ser Met Lys Tyr Arg Leu Ser Phe Cys Arg
            35                  40                  45

Lys Thr Cys Gly Thr Cys Gly Gly Gly Ser Gly Gly Gly Gly Ser
            50                  55                  60

Asp Lys Thr His Thr Cys Pro Pro Cys Pro Ala Pro Glu Leu Leu Gly
65                  70                  75                  80

Gly Pro Ser Val Phe Leu Phe Pro Pro Lys Pro Lys Asp Thr Leu Met
            85                  90                  95

Ile Ser Arg Thr Pro Glu Val Thr Cys Val Val Val Asp Val Ser His
            100                 105                 110

Glu Asp Pro Glu Val Lys Phe Asn Trp Tyr Val Asp Gly Val Glu Val
            115                 120                 125

His Asn Ala Lys Thr Lys Pro Arg Glu Glu Gln Tyr Asn Ser Thr Tyr
            130                 135                 140

```
Arg Val Val Ser Val Leu Thr Val Leu His Gln Asp Trp Leu Asn Gly
145                 150                 155                 160

Lys Glu Tyr Lys Cys Lys Val Ser Asn Lys Ala Leu Pro Ala Pro Ile
            165                 170                 175

Glu Lys Thr Ile Ser Lys Ala Lys Gly Gln Pro Arg Glu Pro Gln Val
        180                 185                 190

Tyr Thr Leu Pro Pro Ser Arg Asp Glu Leu Thr Lys Asn Gln Val Ser
    195                 200                 205

Leu Thr Cys Leu Val Lys Gly Phe Tyr Pro Ser Asp Ile Ala Val Glu
    210                 215                 220

Trp Glu Ser Asn Gly Gln Pro Glu Asn Asn Tyr Lys Thr Thr Pro Pro
225                 230                 235                 240

Val Leu Asp Ser Asp Gly Ser Phe Phe Leu Tyr Ser Lys Leu Thr Val
            245                 250                 255

Asp Lys Ser Arg Trp Gln Gln Gly Asn Val Phe Ser Cys Ser Val Met
        260                 265                 270

His Glu Ala Leu His Asn His Tyr Thr Gln Lys Ser Leu Ser Leu Ser
    275                 280                 285

Pro Gly Lys
    290

<210> SEQ ID NO 62
<211> LENGTH: 23
<212> TYPE: DNA
<213> ORGANISM: ARTIFICIAL SEQUENCE
<220> FEATURE:
<223> OTHER INFORMATION: Primer sequence

<400> SEQUENCE: 62
cattctagac caccatggaa tgg                                          23

<210> SEQ ID NO 63
<211> LENGTH: 29
<212> TYPE: DNA
<213> ORGANISM: ARTIFICIAL SEQUENCE
<220> FEATURE:
<223> OTHER INFORMATION: Primer sequence

<400> SEQUENCE: 63
cagctgcacc tggcttcctc ctcctccgg                                    29

<210> SEQ ID NO 64
<211> LENGTH: 192
<212> TYPE: DNA
<213> ORGANISM: ARTIFICIAL SEQUENCE
<220> FEATURE:
<223> OTHER INFORMATION: VH21 SP-ShK(1-35, Q16K)-L10 coding sequence

<400> SEQUENCE: 64
atggaatgga gctgggtctt tctcttcttc ctgtcagtaa cgactggtgt ccactcccgc    60
agctgcatcg acaccatccc caagagccgc tgcaccgcct tcaagtgcaa gcacagcatg   120
aagtaccgcc tgagcttctg ccgcaagacc tgcggcacct gcggaggagg aggatccgga   180
ggaggaggaa gc                                                      192

<210> SEQ ID NO 65
<211> LENGTH: 64
<212> TYPE: PRT
<213> ORGANISM: ARTIFICIAL SEQUENCE
<220> FEATURE:
<223> OTHER INFORMATION: VH21 SP-ShK(1-35, Q16K)-L10
```

<400> SEQUENCE: 65

| Met | Glu | Trp | Ser | Trp | Val | Phe | Leu | Phe | Leu | Ser | Val | Thr | Thr | Gly |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Val | His | Ser | Arg | Ser | Cys | Ile | Asp | Thr | Ile | Pro | Lys | Ser | Arg | Cys | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Phe | Lys | Cys | Lys | His | Ser | Met | Lys | Tyr | Arg | Leu | Ser | Phe | Cys | Arg |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Lys | Thr | Cys | Gly | Thr | Cys | Gly | Gly | Gly | Ser | Gly | Gly | Gly | Gly | Ser |
|-----|-----|-----|-----|-----|-----|-----|-----|-----|-----|-----|-----|-----|-----|-----|
|     | 50  |     |     |     | 55  |     |     |     | 60  |     |     |     |     |     |

<210> SEQ ID NO 66
<211> LENGTH: 30
<212> TYPE: DNA
<213> ORGANISM: ARTIFICIAL SEQUENCE
<220> FEATURE:
<223> OTHER INFORMATION: Primer sequence

<400> SEQUENCE: 66
ggaggaggaa gccaggtgca gctggtgcag                                    30

<210> SEQ ID NO 67
<211> LENGTH: 21
<212> TYPE: DNA
<213> ORGANISM: ARTIFICIAL SEQUENCE
<220> FEATURE:
<223> OTHER INFORMATION: Primer sequence

<400> SEQUENCE: 67
catgcggccg ctcatttacc c                                             21

<210> SEQ ID NO 68
<211> LENGTH: 1338
<212> TYPE: DNA
<213> ORGANISM: ARTIFICIAL SEQUENCE
<220> FEATURE:
<223> OTHER INFORMATION: aKLH 120.6-HC coding sequence

<400> SEQUENCE: 68
caggtgcagc tggtgcagtc tggggctgag gtgaagaagc ctggggcctc agtgaaggtc      60
tcctgcaagg cttctggata caccttcacc ggctaccaca tgcactgggt gcgacaggcc     120
cctggacaag gcttgagtg gatgggatgg atcaaccta cagtggtgg cacaaactat       180
gcacagaagt ttcagggcag ggtcaccatg accagggaca cgtccatcag cacagcctac    240
atggagctga gcaggctgag atctgacgac acggccgtgt attactgtgc gagagatcgt    300
gggagctact actggttcga ccctggggc cagggaaccc tggtcaccgt ctcctcagcc     360
tccaccaagg gcccatcggt cttccccctg gcgccctgct ccaggagcac ctccgagagc    420
acagcggccc tgggctgcct ggtcaaggac tacttccccg aaccggtgac ggtgtcgtgg    480
aactcaggcg ctctgaccag cggcgtgcac accttcccag ctgtcctaca gtcctcagga    540
ctctactccc tcagcagcgt ggtgaccgtg ccctccagca cttcggcac ccagacctac     600
acctgcaacg tagatcacaa gcccagcaac accaaggtgg acaagacagt tgagcgcaaa    660
tgttgtgtcg agtgcccacc gtgcccagca ccacctgtgg caggaccgtc agtcttcctc    720
ttccccccaa aacccaagga caccctcatg atctcccgga cccctgaggt cacgtgcgtg    780
gtggtggacg tgagccacga agaccccgag gtccagttca actggtacgt ggacggcgtg    840
gaggtgcata atgccaagac aaagccacgg gaggagcagt tcaacagcac gttccgtgtg    900

-continued

```
gtcagcgtcc tcaccgttgt gcaccaggac tggctgaacg gcaaggagta caagtgcaag    960
gtctccaaca aaggcctccc agcccccatc gagaaaacca tctccaaaac caaagggcag   1020
ccccgagaac cacaggtgta caccctgccc ccatcccggg aggagatgac caagaaccag   1080
gtcagcctga cctgcctggt caaaggcttc taccccagcg acatcgccgt ggagtgggag   1140
agcaatgggc agccggagaa caactacaag accacacctc ccatgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaatga                                                 1338
```

<210> SEQ ID NO 69
<211> LENGTH: 445
<212> TYPE: PRT
<213> ORGANISM: ARTIFICIAL SEQUENCE
<220> FEATURE:
<223> OTHER INFORMATION: aKLH 120.6-HC polypeptide sequence

<400> SEQUENCE: 69

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Arg Gly Ser Tyr Tyr Trp Phe Asp Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285
```

Pro Arg Glu Glu Gln Phe Asn Ser Thr Phe Arg Val Val Ser Val Leu
            290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 70
<211> LENGTH: 509
<212> TYPE: PRT
<213> ORGANISM: ARTIFICIAL SEQUENCE
<220> FEATURE:
<223> OTHER INFORMATION: VH21 SP-ShK[1-35, Q16K]-L10-aKLH120.6-HC
      fusion polypeptide

<400> SEQUENCE: 70

Met Glu Trp Ser Trp Val Phe Leu Phe Phe Leu Ser Val Thr Thr Gly
1               5                   10                  15

Val His Ser Arg Ser Cys Ile Asp Thr Ile Pro Lys Ser Arg Cys Thr
            20                  25                  30

Ala Phe Lys Cys Lys His Ser Met Lys Tyr Arg Leu Ser Phe Cys Arg
        35                  40                  45

Lys Thr Cys Gly Thr Cys Gly Gly Gly Ser Gly Gly Gly Gly Ser
    50                  55                  60

Gln Val Gln Leu Val Gln Ser Gly Ala Glu Val Lys Lys Pro Gly Ala
65                  70                  75                  80

Ser Val Lys Val Ser Cys Lys Ala Ser Gly Tyr Thr Phe Thr Gly Tyr
            85                  90                  95

His Met His Trp Val Arg Gln Ala Pro Gly Gln Gly Leu Glu Trp Met
            100                 105                 110

Gly Trp Ile Asn Pro Asn Ser Gly Gly Thr Asn Tyr Ala Gln Lys Phe
        115                 120                 125

Gln Gly Arg Val Thr Met Thr Arg Asp Thr Ser Ile Ser Thr Ala Tyr
    130                 135                 140

Met Glu Leu Ser Arg Leu Arg Ser Asp Asp Thr Ala Val Tyr Tyr Cys
145                 150                 155                 160

Ala Arg Asp Arg Gly Ser Tyr Tyr Trp Phe Asp Pro Trp Gly Gln Gly
            165                 170                 175

Thr Leu Val Thr Val Ser Ser Ala Ser Thr Lys Gly Pro Ser Val Phe
            180                 185                 190

Pro Leu Ala Pro Cys Ser Arg Ser Thr Ser Glu Ser Thr Ala Ala Leu

```
            195                 200                 205
Gly Cys Leu Val Lys Asp Tyr Phe Pro Glu Pro Val Thr Val Ser Trp
210                 215                 220

Asn Ser Gly Ala Leu Thr Ser Gly Val His Thr Phe Pro Ala Val Leu
225                 230                 235                 240

Gln Ser Ser Gly Leu Tyr Ser Leu Ser Ser Val Val Thr Val Pro Ser
            245                 250                 255

Ser Asn Phe Gly Thr Gln Thr Tyr Thr Cys Asn Val Asp His Lys Pro
            260                 265                 270

Ser Asn Thr Lys Val Asp Lys Thr Val Glu Arg Lys Cys Cys Val Glu
        275                 280                 285

Cys Pro Pro Cys Pro Ala Pro Pro Val Ala Gly Pro Ser Val Phe Leu
    290                 295                 300

Phe Pro Pro Lys Pro Lys Asp Thr Leu Met Ile Ser Arg Thr Pro Glu
305                 310                 315                 320

Val Thr Cys Val Val Val Asp Val Ser His Glu Asp Pro Glu Val Gln
            325                 330                 335

Phe Asn Trp Tyr Val Asp Gly Val Glu Val His Asn Ala Lys Thr Lys
            340                 345                 350

Pro Arg Glu Glu Gln Phe Asn Ser Thr Phe Arg Val Val Ser Val Leu
        355                 360                 365

Thr Val Val His Gln Asp Trp Leu Asn Gly Lys Glu Tyr Lys Cys Lys
    370                 375                 380

Val Ser Asn Lys Gly Leu Pro Ala Pro Ile Glu Lys Thr Ile Ser Lys
385                 390                 395                 400

Thr Lys Gly Gln Pro Arg Glu Pro Gln Val Tyr Thr Leu Pro Pro Ser
            405                 410                 415

Arg Glu Glu Met Thr Lys Asn Gln Val Ser Leu Thr Cys Leu Val Lys
            420                 425                 430

Gly Phe Tyr Pro Ser Asp Ile Ala Val Glu Trp Glu Ser Asn Gly Gln
        435                 440                 445

Pro Glu Asn Asn Tyr Lys Thr Thr Pro Pro Met Leu Asp Ser Asp Gly
    450                 455                 460

Ser Phe Phe Leu Tyr Ser Lys Leu Thr Val Asp Lys Ser Arg Trp Gln
465                 470                 475                 480

Gln Gly Asn Val Phe Ser Cys Ser Val Met His Glu Ala Leu His Asn
            485                 490                 495

His Tyr Thr Gln Lys Ser Leu Ser Leu Ser Pro Gly Lys
            500                 505

<210> SEQ ID NO 71
<211> LENGTH: 29
<212> TYPE: DNA
<213> ORGANISM: ARTIFICIAL SEQUENCE
<220> FEATURE:
<223> OTHER INFORMATION: Primer sequence

<400> SEQUENCE: 71
catctggatg tcgcttcctc ctcctccgg                                    29

<210> SEQ ID NO 72
<211> LENGTH: 32
<212> TYPE: DNA
<213> ORGANISM: ARTIFICIAL SEQUENCE
<220> FEATURE:
<223> OTHER INFORMATION: Primer sequence
```

<400> SEQUENCE: 72
ggaggaggaa gcgacatcca gatgacccag tc                                    32

<210> SEQ ID NO 73
<211> LENGTH: 21
<212> TYPE: DNA
<213> ORGANISM: ARTIFICIAL SEQUENCE
<220> FEATURE:
<223> OTHER INFORMATION: Primer sequence

<400> SEQUENCE: 73
catctcgagc ggccgctcaa c                                                21

<210> SEQ ID NO 74
<211> LENGTH: 837
<212> TYPE: DNA
<213> ORGANISM: ARTIFICIAL SEQUENCE
<220> FEATURE:
<223> OTHER INFORMATION: VH21 SP-ShK[1-35, Q16K]-L10-aKLH120.6 Light
      Chain coding sequence

<400> SEQUENCE: 74
atggaatgga gctgggtctt tctcttcttc ctgtcagtaa cgactggtgt ccactcccgc      60
agctgcatcg acaccatccc aagagccgc tgcaccgcct tcaagtgcaa gcacagcatg      120
aagtaccgcc tgagcttctg ccgcaagacc tgcggcacct gcggaggagg aggatccgga    180
ggaggaggaa gcgacatcca gatgacccag tctccatcct ccctgtctgc atctgtagga    240
gacagagtca ccatcacttg ccgggcaagt cagggcatta gaaatgattt aggctggtat    300
cagcagaaac cagggaaagc ccctaaacgc ctgatctatg ctgcatccag tttgcaaagt    360
ggggtcccat caaggttcag cggcagtgga tctgggacag aattcactct cacaatcagc    420
agcctgcagc ctgaagattt tgcaacttat tactgtctac agcataatag ttacccgctc    480
actttcggcg agggaccaa ggtggagatc aaacgaactg tggctgcacc atctgtcttc     540
atcttcccgc catctgatga gcagttgaaa tctggaactg cctctgttgt gtgcctgctg    600
aataacttct atcccagaga ggccaaagta cagtggaagg tggataacgc cctccaatcg    660
ggtaactccc aggagagtgt cacagagcag gacagcaagg acagcaccta cagcctcagc    720
agcaccctga cgctgagcaa agcagactac gagaaacaca agtctacgc ctgcgaagtc     780
acccatcagg gcctgagctc gcccgtcaca aagagcttca cagggggaga gtgttga        837

<210> SEQ ID NO 75
<211> LENGTH: 278
<212> TYPE: PRT
<213> ORGANISM: ARTIFICIAL SEQUENCE
<220> FEATURE:
<223> OTHER INFORMATION: VH21 SP-ShK[1-35, Q16K]-L10-aKLH120.6 Light
      Chain

<400> SEQUENCE: 75

Met Glu Trp Ser Trp Val Phe Leu Phe Phe Leu Ser Val Thr Thr Gly
1               5                   10                  15

Val His Ser Arg Ser Cys Ile Asp Thr Ile Pro Lys Ser Arg Cys Thr
            20                  25                  30

Ala Phe Lys Cys Lys His Ser Met Lys Tyr Arg Leu Ser Phe Cys Arg
        35                  40                  45

Lys Thr Cys Gly Thr Cys Gly Gly Gly Ser Gly Gly Gly Gly Ser
    50                  55                  60

Asp Ile Gln Met Thr Gln Ser Pro Ser Ser Leu Ser Ala Ser Val Gly

```
                65                  70                  75                  80
Asp Arg Val Thr Ile Thr Cys Arg Ala Ser Gln Gly Ile Arg Asn Asp
                    85                  90                  95

Leu Gly Trp Tyr Gln Gln Lys Pro Gly Lys Ala Pro Lys Arg Leu Ile
                100                 105                 110

Tyr Ala Ala Ser Ser Leu Gln Ser Gly Val Pro Ser Arg Phe Ser Gly
                115                 120                 125

Ser Gly Ser Gly Thr Glu Phe Thr Leu Thr Ile Ser Ser Leu Gln Pro
            130                 135                 140

Glu Asp Phe Ala Thr Tyr Tyr Cys Leu Gln His Asn Ser Tyr Pro Leu
145                 150                 155                 160

Thr Phe Gly Gly Gly Thr Lys Val Glu Ile Lys Arg Thr Val Ala Ala
                    165                 170                 175

Pro Ser Val Phe Ile Phe Pro Pro Ser Asp Glu Gln Leu Lys Ser Gly
                180                 185                 190

Thr Ala Ser Val Val Cys Leu Leu Asn Asn Phe Tyr Pro Arg Glu Ala
                195                 200                 205

Lys Val Gln Trp Lys Val Asp Asn Ala Leu Gln Ser Gly Asn Ser Gln
            210                 215                 220

Glu Ser Val Thr Glu Gln Asp Ser Lys Asp Ser Thr Tyr Ser Leu Ser
225                 230                 235                 240

Ser Thr Leu Thr Leu Ser Lys Ala Asp Tyr Glu Lys His Lys Val Tyr
                    245                 250                 255

Ala Cys Glu Val Thr His Gln Gly Leu Ser Ser Pro Val Thr Lys Ser
                260                 265                 270

Phe Asn Arg Gly Glu Cys
            275

<210> SEQ ID NO 76
<211> LENGTH: 35
<212> TYPE: PRT
<213> ORGANISM: ARTIFICIAL SEQUENCE
<220> FEATURE:
<223> OTHER INFORMATION: ShK[1-35, Q16K] polypeptide

<400> SEQUENCE: 76

Arg Ser Cys Ile Asp Thr Ile Pro Lys Ser Arg Cys Thr Ala Phe Lys
1               5                   10                  15

Cys Lys His Ser Met Lys Tyr Arg Leu Ser Phe Cys Arg Lys Thr Cys
                20                  25                  30

Gly Thr Cys
        35

<210> SEQ ID NO 77
<211> LENGTH: 465
<212> TYPE: PRT
<213> ORGANISM: ARTIFICIAL SEQUENCE
<220> FEATURE:
<223> OTHER INFORMATION: anti-DNP 3A4 (W101F) IgG2 Heavy Chain

<400> SEQUENCE: 77

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
                20                  25                  30

Val Val Gln Pro Gly Arg Ser Leu Arg Leu Ser Cys Ala Ala Ser Gly
            35                  40                  45
```

```
Phe Thr Phe Ser Ser Tyr Gly Met His Trp Val Arg Gln Ala Pro Gly
 50                  55                  60
Lys Gly Leu Glu Trp Val Ala Val Ile Trp Tyr Asp Gly Ser Asn Lys
 65                  70                  75                  80
Tyr Tyr Ala Asp Ser Val Lys Gly Arg Phe Thr Ile Ser Arg Asp Asn
                 85                  90                  95
Ser Lys Asn Thr Leu Tyr Leu Gln Met Asn Ser Leu Arg Ala Glu Asp
            100                 105                 110
Thr Ala Val Tyr Tyr Cys Ala Arg Tyr Asn Phe Asn Tyr Gly Met Asp
            115                 120                 125
Val Trp Gly Gln Gly Thr Thr Val Thr Val Ser Ser Ala Ser Thr Lys
130                 135                 140
Gly Pro Ser Val Phe Pro Leu Ala Pro Cys Ser Arg Ser Thr Ser Glu
145                 150                 155                 160
Ser Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
            195                 200                 205
Val Thr Val Pro Ser Ser Asn Phe Gly Thr Gln Thr Tyr Thr Cys Asn
210                 215                 220
Val Asp His Lys Pro Ser Asn Thr Lys Val Asp Lys Thr Val Glu Arg
225                 230                 235                 240
Lys Cys Cys Val Glu Cys Pro Pro Cys Pro Ala Pro Pro Val Ala Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
            275                 280                 285
Asp Pro Glu Val Gln Phe Asn Trp Tyr Val Asp Gly Val Glu Val His
            290                 295                 300
Asn Ala Lys Thr Lys Pro Arg Glu Glu Gln Phe Asn Ser Thr Phe Arg
305                 310                 315                 320
Val Val Ser Val Leu Thr Val Val His Gln Asp Trp Leu Asn Gly Lys
                325                 330                 335
Glu Tyr Lys Cys Lys Val Ser Asn Lys Gly Leu Pro Ala Pro Ile Glu
            340                 345                 350
Lys Thr Ile Ser Lys Thr Lys Gly Gln Pro Arg Glu Pro Gln Val Tyr
            355                 360                 365
Thr Leu Pro Pro Ser Arg Glu Glu Met Thr Lys Asn Gln Val Ser Leu
370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Met
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
            435                 440                 445
Glu Ala Leu His Asn His Tyr Thr Gln Lys Ser Leu Ser Leu Ser Pro
450                 455                 460

Gly
```

<210> SEQ ID NO 78
<211> LENGTH: 1038
<212> TYPE: DNA
<213> ORGANISM: ARTIFICIAL SEQUENCE
<220> FEATURE:
<223> OTHER INFORMATION: Coding sequence - IgG2 fragment

<400> SEQUENCE: 78

```
atggacatga gggtgcccgc tcagctcctg gggctcctgc tgctgtggct gagaggtgcg      60
cgctgtcagg tgcagctggt ggagtctggg ggaggcgtgg tccagcctgg gaggtccctg     120
agactctcct gtgcagcgtc tggattcacc ttcagtagct atggcatgca ctgggtccgc     180
caggctccag gcaaggggct ggagtgggtg gcagttatat ggtatgatgg aagtaataaa     240
tactatgcag actccgtgaa ggccgattc actatctcca gagacaattc caagaacacg      300
ctgtatctgc aaatgaacag cctgagagcc gaggacacgg ctgtgtatta ctgtgcgagg     360
tataacttca actacggtat ggacgtctgg ggccaaggga ccacggtcac cgtctctagt     420
gcctccacca agggcccatc ggtcttcccc ctggcgccct gctccaggag cacctccgag     480
agcacagcgg ccctgggctg cctggtcaag gactacttcc ccgaaccggt gacggtgtcg     540
tggaactcag gcgctctgac cagcggcgtg cacaccttcc cagctgtcct acagtcctca     600
ggactctact ccctcagcag cgtggtgacc gtgcccctca gcaacttcgg cacccagacc     660
tacacctgca acgtagatca caagcccagc aacaccaagg tggacaagac agttgagcgc     720
aaatgttgtg tcgagtgccc accgtgccca gcaccacctg tggcaggacc gtcagtcttc     780
ctcttccccc caaaacccaa ggacaccctc atgatctccc ggaccctga ggtcacgtgc      840
gtggtggtgg acgtgagcca cgaagacccc gaggtccagt tcaactggta cgtggacggc     900
gtggaggtgc ataatgccaa gacaaagcca cgggaggagc agttcaacag cacgttccgt     960
gtggtcagcg tcctcaccgt tgtgcaccag gactggctga acggcaagga gtacaagtgc    1020
aaggtctcca acaaaggc                                                  1038
```

<210> SEQ ID NO 79
<211> LENGTH: 346
<212> TYPE: PRT
<213> ORGANISM: ARTIFICIAL SEQUENCE
<220> FEATURE:
<223> OTHER INFORMATION: IgG2 fragment

<400> SEQUENCE: 79

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110
```

Thr Ala Val Tyr Tyr Cys Ala Arg Tyr Asn Phe Asn Tyr Gly Met Asp
            115                 120                 125

Val Trp Gly Gln Gly Thr Thr Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly
            340                 345

<210> SEQ ID NO 80
<211> LENGTH: 501
<212> TYPE: DNA
<213> ORGANISM: ARTIFICIAL SEQUENCE
<220> FEATURE:
<223> OTHER INFORMATION: truncated IgG2 Fc-L10-ShK(1-35, Q16K) coding
      sequence

<400> SEQUENCE: 80
ctcccagccc ccatcgagaa aaccatctcc aaaaccaaag gcagccccg agaaccacag      60 gtgtacaccc tgcccccatc ccgggaggag atgaccaaga accaggtcag cctgacctgc    120
ctggtcaaag gcttctaccc cagcgacatc gccgtggagt gggagagcaa tgggcagccg    180
gagaacaact acaagaccac acctcccatg ctggactccg acggctcctt cttcctctac    240
agcaagctca ccgtggacaa gagcaggtgg cagcagggga acgtcttctc atgctccgtg    300
atgcatgagg ctctgcacaa ccactacacg cagaagagcc tctccctgtc tccgggtaaa    360
ggaggaggag gatccggagg aggaggaagc cgcagctgca tcgacaccat ccccaagagc    420
cgctgcaccg ccttcaagtg caagcacagc atgaagtacc gcctgagctt ctgccgcaag    480
acctgcggca cctgctaatg a                                              501

<210> SEQ ID NO 81
<211> LENGTH: 165
<212> TYPE: PRT
<213> ORGANISM: ARTIFICIAL SEQUENCE

-continued

```
<220> FEATURE:
<223> OTHER INFORMATION: truncated IgG2 Fc-L10-ShK(1-35, Q16K) amino
      acid sequence

<400> SEQUENCE: 81

Leu Pro Ala Pro Ile Glu Lys Thr Ile Ser Lys Thr Lys Gly Gln Pro
1               5                   10                  15

Arg Glu Pro Gln Val Tyr Thr Leu Pro Pro Ser Arg Glu Glu Met Thr
            20                  25                  30

Lys Asn Gln Val Ser Leu Thr Cys Leu Val Lys Gly Phe Tyr Pro Ser
        35                  40                  45

Asp Ile Ala Val Glu Trp Glu Ser Asn Gly Gln Pro Glu Asn Asn Tyr
    50                  55                  60

Lys Thr Thr Pro Pro Met Leu Asp Ser Asp Gly Ser Phe Phe Leu Tyr
65                  70                  75                  80

Ser Lys Leu Thr Val Asp Lys Ser Arg Trp Gln Gln Gly Asn Val Phe
                85                  90                  95

Ser Cys Ser Val Met His Glu Ala Leu His Asn His Tyr Thr Gln Lys
            100                 105                 110

Ser Leu Ser Leu Ser Pro Gly Lys Gly Gly Gly Gly Ser Gly Gly Gly
        115                 120                 125

Gly Ser Arg Ser Cys Ile Asp Thr Ile Pro Lys Ser Arg Cys Thr Ala
    130                 135                 140

Phe Lys Cys Lys His Ser Met Lys Tyr Arg Leu Ser Phe Cys Arg Lys
145                 150                 155                 160

Thr Cys Gly Thr Cys
                165

<210> SEQ ID NO 82
<211> LENGTH: 510
<212> TYPE: PRT
<213> ORGANISM: ARTIFICIAL SEQUENCE
<220> FEATURE:
<223> OTHER INFORMATION: aDNP 3A4 (W101F) IgG2 HC-L10-ShK[1-35, Q16K]
      fusion protein

<400> SEQUENCE: 82

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Tyr Asn Phe Asn Tyr Gly Met Asp
        115                 120                 125

Val Trp Gly Gln Gly Thr Thr Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160
```

```
Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Gly Gly Gly Ser Gly Gly Gly Ser Arg Ser Cys Ile Asp
465                 470                 475                 480

Thr Ile Pro Lys Ser Arg Cys Thr Ala Phe Lys Cys Lys His Ser Met
                485                 490                 495

Lys Tyr Arg Leu Ser Phe Cys Arg Lys Thr Cys Gly Thr Cys
            500                 505                 510

<210> SEQ ID NO 83
<211> LENGTH: 37
<212> TYPE: DNA
<213> ORGANISM: ARTIFICIAL SEQUENCE
<220> FEATURE:
<223> OTHER INFORMATION: Forward primer

<400> SEQUENCE: 83 tttttttgc gcgctgtgac atccagatga cccagtc                    37
```

<210> SEQ ID NO 84

<400> SEQUENCE: 84

000

<210> SEQ ID NO 85
<211> LENGTH: 236
<212> TYPE: PRT
<213> ORGANISM: ARTIFICIAL SEQUENCE
<220> FEATURE:
<223> OTHER INFORMATION: anti-DNP 3A4 Antibody Light Chain

<400> SEQUENCE: 85

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Arg Arg Leu Ala Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asn Ser Phe Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 86
<211> LENGTH: 326
<212> TYPE: PRT
<213> ORGANISM: Homo sapiens
<220> FEATURE:
<221> NAME/KEY: MISC_FEATURE
<223> OTHER INFORMATION: IgG2 heavy chain (HC) constant domain

<400> SEQUENCE: 86

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 87
<211> LENGTH: 330
<212> TYPE: PRT
<213> ORGANISM: Homo sapiens
<220> FEATURE:
<221> NAME/KEY: MISC_FEATURE
<223> OTHER INFORMATION: hIgG1z heavy chain (HC) constant domain

<400> SEQUENCE: 87

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60
```

```
Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 88
<211> LENGTH: 330
<212> TYPE: PRT
<213> ORGANISM: Homo sapiens
<220> FEATURE:
<221> NAME/KEY: MISC_FEATURE
<223> OTHER INFORMATION: hIgG1za heavy chain (HC) constant domain

<400> SEQUENCE: 88

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
```

-continued

```
                    85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
        130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 89
<211> LENGTH: 330
<212> TYPE: PRT
<213> ORGANISM: Homo sapiens
<220> FEATURE:
<221> NAME/KEY: MISC_FEATURE
<223> OTHER INFORMATION: hIgG1f heavy chain (HC) constant domain

<400> SEQUENCE: 89

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 90
<211> LENGTH: 330
<212> TYPE: PRT
<213> ORGANISM: Homo sapiens
<220> FEATURE:
<221> NAME/KEY: MISC_FEATURE
<223> OTHER INFORMATION: hIgG1fa heavy chain (HC) constant domain

<400> SEQUENCE: 90

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140
```

-continued

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 91
<211> LENGTH: 106
<212> TYPE: PRT
<213> ORGANISM: Homo sapiens
<220> FEATURE:
<221> NAME/KEY: MISC_FEATURE
<223> OTHER INFORMATION: CL-1 human immunoglobulin light chain (LC)
      constant region

<400> SEQUENCE: 91

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
                100                 105

<210> SEQ ID NO 92
<211> LENGTH: 106
<212> TYPE: PRT
<213> ORGANISM: Homo sapiens
<220> FEATURE:
<221> NAME/KEY: MISC_FEATURE
<223> OTHER INFORMATION: CL-2 human immunoglobulin light chain (LC)
      constant region

<400> SEQUENCE: 92

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 93
<211> LENGTH: 106
<212> TYPE: PRT
<213> ORGANISM: Homo sapiens
<220> FEATURE:
<221> NAME/KEY: MISC_FEATURE
<223> OTHER INFORMATION: CL-3 human immunoglobulin light chain (LC)
      constant region

<400> SEQUENCE: 93

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 94
<211> LENGTH: 106
<212> TYPE: PRT
<213> ORGANISM: Homo sapiens
<220> FEATURE:
<221> NAME/KEY: MISC_FEATURE
<223> OTHER INFORMATION: CL-7 human immunoglobulin light chain (LC)
      constant region

<400> SEQUENCE: 94

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn

```
              50                  55                  60
Lys Tyr Ala Ala Ser Ser Tyr Leu Ser Leu Thr Pro Glu Gln Trp Lys
 65                  70                  75                  80

Ser His Arg Ser Tyr Ser Cys Arg Val Thr His Glu Gly Ser Thr Val
                 85                  90                  95

Glu Lys Thr Val Ala Pro Ala Glu Cys Ser
            100                 105

<210> SEQ ID NO 95
<211> LENGTH: 19
<212> TYPE: PRT
<213> ORGANISM: ARTIFICIAL SEQUENCE
<220> FEATURE:
<223> OTHER INFORMATION: VH21 SP

<400> SEQUENCE: 95

Met Glu Trp Ser Trp Val Phe Leu Phe Phe Leu Ser Val Thr Thr Gly
 1               5                  10                  15

Val His Ser

<210> SEQ ID NO 96
<211> LENGTH: 448
<212> TYPE: PRT
<213> ORGANISM: ARTIFICIAL SEQUENCE
<220> FEATURE:
<223> OTHER INFORMATION: Anti-KLH heavy chain (IgG1)

<400> SEQUENCE: 96

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

His Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                85                  90                  95

Ala Arg Asp Arg Gly Ser Tyr Tyr Trp Phe Asp Pro Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
```

```
                225                 230                 235                 240
Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                    260                 265                 270

Pro Glu Val Lys Phe Asn Trp Tyr Val Asp Gly Val Glu Val His Asn
                    275                 280                 285

Ala Lys Thr Lys Pro Arg Glu Glu Gln Tyr Gln Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                    340                 345                 350

Leu Pro Pro Ser Arg Glu Glu Met Thr Lys Asn Gln Val Ser Leu Thr
                    355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Asn His Tyr Thr Gln Lys Ser Leu Ser Leu Ser Pro Gly
                435                 440                 445

<210> SEQ ID NO 97
<211> LENGTH: 241
<212> TYPE: PRT
<213> ORGANISM: ARTIFICIAL SEQUENCE
<220> FEATURE:
<223> OTHER INFORMATION: Anti-KLH light chain-AMP5

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys Gly Gly Gly Gly Gln Gly Cys Ser Ser
210                 215                 220

Gly Gly Pro Thr Leu Arg Glu Trp Gln Gln Cys Arg Arg Ala Gln His
225                 230                 235                 240

Ser

<210> SEQ ID NO 98
<211> LENGTH: 471
<212> TYPE: PRT
<213> ORGANISM: ARTIFICIAL SEQUENCE
<220> FEATURE:
<223> OTHER INFORMATION: AMP5-Anti-KLH HC (IgG2)

<400> SEQUENCE: 98

Gln Gly Cys Ser Ser Gly Gly Pro Thr Leu Arg Glu Trp Gln Gln Cys
1               5                   10                  15

Arg Arg Ala Gln His Ser Gly Gly Gly Gly Gln Val Gln Leu Val
                20                  25                  30

Gln Ser Gly Ala Glu Val Lys Lys Pro Gly Ala Ser Val Lys Val Ser
            35                  40                  45

Cys Lys Ala Ser Gly Tyr Thr Phe Thr Gly Tyr His Met His Trp Val
        50                  55                  60

Arg Gln Ala Pro Gly Gln Gly Leu Glu Trp Met Gly Trp Ile Asn Pro
65                  70                  75                  80

Asn Ser Gly Gly Thr Asn Tyr Ala Gln Lys Phe Gln Gly Arg Val Thr
                85                  90                  95

Met Thr Arg Asp Thr Ser Ile Ser Thr Ala Tyr Met Glu Leu Ser Arg
                100                 105                 110

Leu Arg Ser Asp Asp Thr Ala Val Tyr Tyr Cys Ala Arg Asp Arg Gly
            115                 120                 125

Ser Tyr Tyr Trp Phe Asp Pro Trp Gly Gln Gly Thr Leu Val Thr Val
        130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
                180                 185                 190

Thr Ser Gly Val His Thr Phe Pro Ala Val Leu Gln Ser Ser Gly Leu
            195                 200                 205

Tyr Ser Leu Ser Ser Val Val Thr Val Pro Ser Ser Asn Phe Gly Thr
        210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
                260                 265                 270
```

```
Lys Asp Thr Leu Met Ile Ser Arg Thr Pro Glu Val Thr Cys Val Val
            275                 280                 285

Val Val Asp Val Ser His Glu Asp Pro Glu Val Gln Phe Asn Trp Tyr Val
        290                 295                 300

Asp Gly Val Glu Val His Asn Ala Lys Thr Lys Pro Arg Glu Glu Gln
305                 310                 315                 320

Phe Asn Ser Thr Phe Arg Val Val Ser Val Leu Thr Val Val His Gln
                325                 330                 335

Asp Trp Leu Asn Gly Lys Glu Tyr Lys Cys Lys Val Ser Asn Lys Gly
                340                 345                 350

Leu Pro Ala Pro Ile Glu Lys Thr Ile Ser Lys Thr Lys Gly Gln Pro
                355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Met Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
                450                 455                 460

Ser Leu Ser Leu Ser Pro Gly
465                 470

<210> SEQ ID NO 99
<211> LENGTH: 214
<212> TYPE: PRT
<213> ORGANISM: ARTIFICIAL SEQUENCE
<220> FEATURE:
<223> OTHER INFORMATION: Anti-KLH LC

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 100
<211> LENGTH: 471
<212> TYPE: PRT
<213> ORGANISM: ARTIFICIAL SEQUENCE
<220> FEATURE:
<223> OTHER INFORMATION: Anti-KLH HC-AMP5 (IgG2)

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Arg Gly Ser Tyr Tyr Trp Phe Asp Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

```
Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Gly Gln Gly Cys Ser Ser Gly Gly Pro Thr Leu Arg Glu Trp Gln Gln
    450                 455                 460

Cys Arg Arg Ala Gln His Ser
465                 470

<210> SEQ ID NO 101
<211> LENGTH: 241
<212> TYPE: PRT
<213> ORGANISM: ARTIFICIAL SEQUENCE
<220> FEATURE:
<223> OTHER INFORMATION: AMP5-Anti-KLH LC

<400> SEQUENCE: 101

Gln Gly Cys Ser Ser Gly Gly Pro Thr Leu Arg Glu Trp Gln Gln Cys
1               5                   10                  15

Arg Arg Ala Gln His Ser Gly Gly Gly Gly Asp Ile Gln Met Thr
            20                  25                  30

Gln Ser Pro Ser Ser Leu Ser Ala Ser Val Gly Asp Arg Val Thr Ile
        35                  40                  45

Thr Cys Arg Ala Ser Gln Gly Ile Arg Asn Asp Leu Gly Trp Tyr Gln
    50                  55                  60

Gln Lys Pro Gly Lys Ala Pro Lys Arg Leu Ile Tyr Ala Ala Ser Ser
65                  70                  75                  80

Leu Gln Ser Gly Val Pro Ser Arg Phe Ser Gly Ser Gly Ser Gly Thr
                85                  90                  95

Glu Phe Thr Leu Thr Ile Ser Ser Leu Gln Pro Glu Asp Phe Ala Thr
            100                 105                 110

Tyr Tyr Cys Leu Gln His Asn Ser Tyr Pro Leu Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190
```

```
Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
        210                 215                 220

His Gln Gly Leu Ser Ser Pro Val Thr Lys Ser Phe Asn Arg Gly Glu
225                 230                 235                 240

Cys

<210> SEQ ID NO 102
<211> LENGTH: 66
<212> TYPE: DNA
<213> ORGANISM: ARTIFICIAL SEQUENCE
<220> FEATURE:
<223> OTHER INFORMATION: VK-1 SP signal peptide coding sequence

<400> SEQUENCE: 102
atggacatga gggtgcccgc tcagctcctg ggctcctgc tgctgtggct gagaggtgcg    60
cgctgt                                                             66

<210> SEQ ID NO 103
<211> LENGTH: 22
<212> TYPE: PRT
<213> ORGANISM: ARTIFICIAL SEQUENCE
<220> FEATURE:
<223> OTHER INFORMATION: VK-1 SP signal peptide

<400> SEQUENCE: 103

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 104
<211> LENGTH: 708
<212> TYPE: DNA
<213> ORGANISM: ARTIFICIAL SEQUENCE
<220> FEATURE:
<223> OTHER INFORMATION: aDNP 3A1 LC sequence
<220> FEATURE:
<221> NAME/KEY: CDS
<222> LOCATION: (1)..(708)

<400> SEQUENCE: 104 atg gac atg agg gtg ccc gct cag ctc ctg ggg ctc ctg ctg ctg tgg    48
Met Asp Met Arg Val Pro Ala Gln Leu Leu Gly Leu Leu Leu Leu Trp
1               5                   10                  15 ctg aga ggt gcg cgc tgt gac atc cag atg acc cag tct cca tct tcc    96
Leu Arg Gly Ala Arg Cys Asp Ile Gln Met Thr Gln Ser Pro Ser Ser
            20                  25                  30 gtg tct gca tct gta ggt gac aga gtc acc atc act tgt cgg gcg agt   144
Val Ser Ala Ser Val Gly Asp Arg Val Thr Ile Thr Cys Arg Ala Ser
        35                  40                  45 cag ggt att agc aac tgg tta gcc tgg tat cag cgg aaa cca ggg aaa   192
Gln Gly Ile Ser Asn Trp Leu Ala Trp Tyr Gln Arg Lys Pro Gly Lys
    50                  55                  60 gcc cct aag ctc ctg atc tat gct gca tcc agt ttg caa agt ggg gtc   240
Ala Pro Lys Leu Leu Ile Tyr Ala Ala Ser Ser Leu Gln Ser Gly Val
65                  70                  75                  80 cca tca agg ttc agc ggc agt gga tct ggg aca gat ttc act ctc acc   288
Pro Ser Arg Phe Ser Gly Ser Gly Ser Gly Thr Asp Phe Thr Leu Thr
                85                  90                  95
```

| | | |
|---|---|---|
| atc agc agc ctg cag cct gaa gat ttt gca gct tac tat tgt caa cag<br>Ile Ser Ser Leu Gln Pro Glu Asp Phe Ala Ala Tyr Tyr Cys Gln Gln<br>    100                 105                 110 | | 336 |
| gct agc agt ttc ccg tgg acg ttc ggc caa ggg acc agg gtg gaa atc<br>Ala Ser Ser Phe Pro Trp Thr Phe Gly Gln Gly Thr Arg Val Glu Ile<br>115                 120                 125 | | 384 |
| aaa cgt acg gtg gct gca cca tct gtc ttc atc ttc ccg cca tct gat<br>Lys Arg Thr Val Ala Ala Pro Ser Val Phe Ile Phe Pro Pro Ser Asp<br>130                 135                 140 | | 432 |
| gag cag ttg aaa tct gga act gcc tct gtt gtg tgc ctg ctg aat aac<br>Glu Gln Leu Lys Ser Gly Thr Ala Ser Val Val Cys Leu Leu Asn Asn<br>145                 150                 155                 160 | | 480 |
| ttc tat ccc aga gag gcc aaa gta cag tgg aag gtg gat aac gcc ctc<br>Phe Tyr Pro Arg Glu Ala Lys Val Gln Trp Lys Val Asp Asn Ala Leu<br>                165                 170                 175 | | 528 |
| caa tcg ggt aac tcc cag gag agt gtc aca gag cag gac agc aag gac<br>Gln Ser Gly Asn Ser Gln Glu Ser Val Thr Glu Gln Asp Ser Lys Asp<br>            180                 185                 190 | | 576 |
| agc acc tac agc ctc agc agc acc ctg acg ctg agc aaa gca gac tac<br>Ser Thr Tyr Ser Leu Ser Ser Thr Leu Thr Leu Ser Lys Ala Asp Tyr<br>        195                 200                 205 | | 624 |
| gag aaa cac aaa gtc tac gcc tgc gaa gtc acc cat cag ggc ctg agc<br>Glu Lys His Lys Val Tyr Ala Cys Glu Val Thr His Gln Gly Leu Ser<br>    210                 215                 220 | | 672 |
| tcg ccc gtc aca aag agc ttc aac agg gga gag tgt<br>Ser Pro Val Thr Lys Ser Phe Asn Arg Gly Glu Cys<br>225                 230                 235 | | 708 |

<210> SEQ ID NO 105
<211> LENGTH: 236
<212> TYPE: PRT
<213> ORGANISM: ARTIFICIAL SEQUENCE
<220> FEATURE:
<223> OTHER INFORMATION: Synthetic Construct

<400> SEQUENCE: 105

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Asn Trp Leu Ala Trp Tyr Gln Arg Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Ala Tyr Tyr Cys Gln Gln
            100                 105                 110

Ala Ser Ser Phe Pro Trp Thr Phe Gly Gln Gly Thr Arg Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

```
Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 106
<211> LENGTH: 1410
<212> TYPE: DNA
<213> ORGANISM: ARTIFICIAL SEQUENCE
<220> FEATURE:
<223> OTHER INFORMATION: aDNP 3A1 HC sequence
<220> FEATURE:
<221> NAME/KEY: CDS
<222> LOCATION: (1)..(1410)

<400> SEQUENCE: 106
```

| | | | | | | | | | | | | | | | | |
|---|---|---|---|---|---|---|---|---|---|---|---|---|---|---|---|---|
| atg | gac | atg | agg | gtg | ccc | gct | cag | ctc | ctg | ggg | ctc | ctg | ctg | ctg | tgg | 48 |
| Met | Asp | Met | Arg | Val | Pro | Ala | Gln | Leu | Leu | Gly | Leu | Leu | Leu | Leu | Trp | |
| 1 | | | | 5 | | | | | 10 | | | | | 15 | | |
| ctg | aga | ggt | gcg | cgc | tgt | cag | gtg | cag | ctg | cag | gag | tcg | ggc | cca | gga | 96 |
| Leu | Arg | Gly | Ala | Arg | Cys | Gln | Val | Gln | Leu | Gln | Glu | Ser | Gly | Pro | Gly | |
| | | | 20 | | | | | 25 | | | | | 30 | | | |
| ctg | gtg | aag | cct | tcg | gag | acc | ctg | tcc | ctc | acc | tgc | act | gtc | tct | ggt | 144 |
| Leu | Val | Lys | Pro | Ser | Glu | Thr | Leu | Ser | Leu | Thr | Cys | Thr | Val | Ser | Gly | |
| | | 35 | | | | | 40 | | | | | 45 | | | | |
| ggc | tcc | atc | agt | cat | tac | tac | tgg | agc | tgg | atc | cgg | cag | ccc | cca | ggg | 192 |
| Gly | Ser | Ile | Ser | His | Tyr | Tyr | Trp | Ser | Trp | Ile | Arg | Gln | Pro | Pro | Gly | |
| | | | 50 | | | | | 55 | | | | | 60 | | | |
| aag | gga | ctg | ggg | tgg | att | ggg | tat | atc | tat | tac | agt | ggg | agc | acc | aac | 240 |
| Lys | Gly | Leu | Gly | Trp | Ile | Gly | Tyr | Ile | Tyr | Tyr | Ser | Gly | Ser | Thr | Asn | |
| 65 | | | | | 70 | | | | | 75 | | | | | 80 | |
| tac | aac | ccc | tcc | ctc | aag | agt | cga | gtc | acc | ata | tca | gta | gac | acg | tcc | 288 |
| Tyr | Asn | Pro | Ser | Leu | Lys | Ser | Arg | Val | Thr | Ile | Ser | Val | Asp | Thr | Ser | |
| | | | | 85 | | | | | 90 | | | | | 95 | | |
| aag | aac | cag | ttc | tcc | ctg | aag | ctg | acc | tct | gtg | acc | gct | gcg | gac | acg | 336 |
| Lys | Asn | Gln | Phe | Ser | Leu | Lys | Leu | Thr | Ser | Val | Thr | Ala | Ala | Asp | Thr | |
| | | | 100 | | | | | 105 | | | | | 110 | | | |
| gcc | gtg | tat | tac | tgt | gcg | agg | gcc | cgg | gga | gat | ggc | tac | aat | tac | cct | 384 |
| Ala | Val | Tyr | Tyr | Cys | Ala | Arg | Ala | Arg | Gly | Asp | Gly | Tyr | Asn | Tyr | Pro | |
| | | 115 | | | | | 120 | | | | | 125 | | | | |
| gat | gct | ttt | gat | atc | tgg | ggc | caa | ggg | aca | atg | gtc | acc | gtc | tct | agt | 432 |
| Asp | Ala | Phe | Asp | Ile | Trp | Gly | Gln | Gly | Thr | Met | Val | Thr | Val | Ser | Ser | |
| | 130 | | | | | 135 | | | | | 140 | | | | | |
| gcc | tcc | acc | aag | ggc | cca | tcg | gtc | ttc | ccc | ctg | gcg | ccc | tgc | tcc | agg | 480 |
| Ala | Ser | Thr | Lys | Gly | Pro | Ser | Val | Phe | Pro | Leu | Ala | Pro | Cys | Ser | Arg | |
| 145 | | | | | 150 | | | | | 155 | | | | | 160 | |
| agc | acc | tcc | gag | agc | aca | gcg | gcc | ctg | ggc | tgc | ctg | gtc | aag | gac | tac | 528 |
| Ser | Thr | Ser | Glu | Ser | Thr | Ala | Ala | Leu | Gly | Cys | Leu | Val | Lys | Asp | Tyr | |
| | | | | 165 | | | | | 170 | | | | | 175 | | |
| ttc | ccc | gaa | ccg | gtg | acg | gtg | tcg | tgg | aac | tca | ggc | gct | ctg | acc | agc | 576 |
| Phe | Pro | Glu | Pro | Val | Thr | Val | Ser | Trp | Asn | Ser | Gly | Ala | Leu | Thr | Ser | |
| | | | 180 | | | | | 185 | | | | | 190 | | | |
| ggc | gtg | cac | acc | ttc | cca | gct | gtc | cta | cag | tcc | tca | gga | ctc | tac | tcc | 624 |
| Gly | Val | His | Thr | Phe | Pro | Ala | Val | Leu | Gln | Ser | Ser | Gly | Leu | Tyr | Ser | |
| | | 195 | | | | | 200 | | | | | 205 | | | | |
| ctc | agc | agc | gtg | gtg | acc | gtg | ccc | tcc | agc | aac | ttc | ggc | acc | cag | acc | 672 |
| Leu | Ser | Ser | Val | Val | Thr | Val | Pro | Ser | Ser | Asn | Phe | Gly | Thr | Gln | Thr | |

| | | | | | | | | | | | | | | | | |
|---|---|---|---|---|---|---|---|---|---|---|---|---|---|---|---|---|
| | | 210 | | | | 215 | | | | | 220 | | | | | |
| tac | acc | tgc | aac | gta | gat | cac | aag | ccc | agc | aac | acc | aag | gtg | gac | aag | 720 |
| Tyr | Thr | Cys | Asn | Val | Asp | His | Lys | Pro | Ser | Asn | Thr | Lys | Val | Asp | Lys | |
| 225 | | | | | 230 | | | | | 235 | | | | | 240 | |
| aca | gtt | gag | cgc | aaa | tgt | tgt | gtc | gag | tgc | cca | ccg | tgc | cca | gca | cca | 768 |
| Thr | Val | Glu | Arg | Lys | Cys | Cys | Val | Glu | Cys | Pro | Pro | Cys | Pro | Ala | Pro | |
| | | | | 245 | | | | | 250 | | | | | 255 | | |
| cct | gtg | gca | gga | ccg | tca | gtc | ttc | ctc | ttc | ccc | cca | aaa | ccc | aag | gac | 816 |
| Pro | Val | Ala | Gly | Pro | Ser | Val | Phe | Leu | Phe | Pro | Pro | Lys | Pro | Lys | Asp | |
| | | | 260 | | | | | 265 | | | | | 270 | | | |
| acc | ctc | atg | atc | tcc | cgg | acc | cct | gag | gtc | acg | tgc | gtg | gtg | gtg | gac | 864 |
| Thr | Leu | Met | Ile | Ser | Arg | Thr | Pro | Glu | Val | Thr | Cys | Val | Val | Val | Asp | |
| | | | 275 | | | | | 280 | | | | | 285 | | | |
| gtg | agc | cac | gaa | gac | ccc | gag | gtc | cag | ttc | aac | tgg | tac | gtg | gac | ggc | 912 |
| Val | Ser | His | Glu | Asp | Pro | Glu | Val | Gln | Phe | Asn | Trp | Tyr | Val | Asp | Gly | |
| | 290 | | | | | 295 | | | | | 300 | | | | | |
| gtg | gag | gtg | cat | aat | gcc | aag | aca | aag | cca | cgg | gag | gag | cag | ttc | aac | 960 |
| Val | Glu | Val | His | Asn | Ala | Lys | Thr | Lys | Pro | Arg | Glu | Glu | Gln | Phe | Asn | |
| 305 | | | | | 310 | | | | | 315 | | | | | 320 | |
| agc | acg | ttc | cgt | gtg | gtc | agc | gtc | ctc | acc | gtt | gtg | cac | cag | gac | tgg | 1008 |
| Ser | Thr | Phe | Arg | Val | Val | Ser | Val | Leu | Thr | Val | Val | His | Gln | Asp | Trp | |
| | | | | 325 | | | | | 330 | | | | | 335 | | |
| ctg | aac | ggc | aag | gag | tac | aag | tgc | aag | gtc | tcc | aac | aaa | ggc | ctc | cca | 1056 |
| Leu | Asn | Gly | Lys | Glu | Tyr | Lys | Cys | Lys | Val | Ser | Asn | Lys | Gly | Leu | Pro | |
| | | | 340 | | | | | 345 | | | | | 350 | | | |
| gcc | ccc | atc | gag | aaa | acc | atc | tcc | aaa | acc | aaa | ggg | cag | ccc | cga | gaa | 1104 |
| Ala | Pro | Ile | Glu | Lys | Thr | Ile | Ser | Lys | Thr | Lys | Gly | Gln | Pro | Arg | Glu | |
| | | | 355 | | | | | 360 | | | | | 365 | | | |
| cca | cag | gtg | tac | acc | ctg | ccc | cca | tcc | cgg | gag | gag | atg | acc | aag | aac | 1152 |
| Pro | Gln | Val | Tyr | Thr | Leu | Pro | Pro | Ser | Arg | Glu | Glu | Met | Thr | Lys | Asn | |
| 370 | | | | | 375 | | | | | 380 | | | | | | |
| cag | gtc | agc | ctg | acc | tgc | ctg | gtc | aaa | ggc | ttc | tac | ccc | agc | gac | atc | 1200 |
| Gln | Val | Ser | Leu | Thr | Cys | Leu | Val | Lys | Gly | Phe | Tyr | Pro | Ser | Asp | Ile | |
| 385 | | | | | 390 | | | | | 395 | | | | | 400 | |
| gcc | gtg | gag | tgg | gag | agc | aat | ggg | cag | ccg | gag | aac | aac | tac | aag | acc | 1248 |
| Ala | Val | Glu | Trp | Glu | Ser | Asn | Gly | Gln | Pro | Glu | Asn | Asn | Tyr | Lys | Thr | |
| | | | | 405 | | | | | 410 | | | | | 415 | | |
| aca | cct | ccc | atg | ctg | gac | tcc | gac | ggc | tcc | ttc | ttc | ctc | tac | agc | aag | 1296 |
| Thr | Pro | Pro | Met | Leu | Asp | Ser | Asp | Gly | Ser | Phe | Phe | Leu | Tyr | Ser | Lys | |
| | | | 420 | | | | | 425 | | | | | 430 | | | |
| ctc | acc | gtg | gac | aag | agc | agg | tgg | cag | cag | ggg | aac | gtc | ttc | tca | tgc | 1344 |
| Leu | Thr | Val | Asp | Lys | Ser | Arg | Trp | Gln | Gln | Gly | Asn | Val | Phe | Ser | Cys | |
| | | | 435 | | | | | 440 | | | | | 445 | | | |
| tcc | gtg | atg | cat | gag | gct | ctg | cac | aac | cac | tac | acg | cag | aag | agc | ctc | 1392 |
| Ser | Val | Met | His | Glu | Ala | Leu | His | Asn | His | Tyr | Thr | Gln | Lys | Ser | Leu | |
| 450 | | | | | 455 | | | | | 460 | | | | | | |
| tcc | ctg | tct | ccg | ggt | aaa | | | | | | | | | | | 1410 |
| Ser | Leu | Ser | Pro | Gly | Lys | | | | | | | | | | | |
| 465 | | | | | 470 | | | | | | | | | | | |

<210> SEQ ID NO 107
<211> LENGTH: 470
<212> TYPE: PRT
<213> ORGANISM: ARTIFICIAL SEQUENCE
<220> FEATURE:
<223> OTHER INFORMATION: Synthetic Construct

<400> SEQUENCE: 107

| | | | | | | | | | | | | | | | |
|---|---|---|---|---|---|---|---|---|---|---|---|---|---|---|---|
| Met | Asp | Met | Arg | Val | Pro | Ala | Gln | Leu | Leu | Gly | Leu | Leu | Leu | Leu | Trp |
| 1 | | | | 5 | | | | | 10 | | | | | 15 | |

```
Leu Arg Gly Ala Arg Cys Gln Val Gln Leu Gln Glu Ser Gly Pro Gly
                20                  25                  30
Leu Val Lys Pro Ser Glu Thr Leu Ser Leu Thr Cys Thr Val Ser Gly
            35                  40                  45
Gly Ser Ile Ser His Tyr Tyr Trp Ser Trp Ile Arg Gln Pro Pro Gly
        50                  55                  60
Lys Gly Leu Gly Trp Ile Gly Tyr Ile Tyr Tyr Ser Gly Ser Thr Asn
65                  70                  75                  80
Tyr Asn Pro Ser Leu Lys Ser Arg Val Thr Ile Ser Val Asp Thr Ser
                85                  90                  95
Lys Asn Gln Phe Ser Leu Lys Leu Thr Ser Val Thr Ala Ala Asp Thr
            100                 105                 110
Ala Val Tyr Tyr Cys Ala Arg Ala Arg Gly Asp Gly Tyr Asn Tyr Pro
        115                 120                 125
Asp Ala Phe Asp Ile Trp Gly Gln Gly Thr Met Val Thr Val Ser Ser
130                 135                 140
Ala Ser Thr Lys Gly Pro Ser Val Phe Pro Leu Ala Pro Cys Ser Arg
145                 150                 155                 160
Ser Thr Ser Glu Ser Thr Ala Ala Leu Gly Cys Leu Val Lys Asp Tyr
                165                 170                 175
Phe Pro Glu Pro Val Thr Val Ser Trp Asn Ser Gly Ala Leu Thr Ser
            180                 185                 190
Gly Val His Thr Phe Pro Ala Val Leu Gln Ser Ser Gly Leu Tyr Ser
        195                 200                 205
Leu Ser Ser Val Val Thr Val Pro Ser Ser Asn Phe Gly Thr Gln Thr
        210                 215                 220
Tyr Thr Cys Asn Val Asp His Lys Pro Ser Asn Thr Lys Val Asp Lys
225                 230                 235                 240
Thr Val Glu Arg Lys Cys Cys Val Glu Cys Pro Pro Cys Pro Ala Pro
                245                 250                 255
Pro Val Ala Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
        275                 280                 285
Val Ser His Glu Asp Pro Glu Val Gln Phe Asn Trp Tyr Val Asp Gly
        290                 295                 300
Val Glu Val His Asn Ala Lys Thr Lys Pro Arg Glu Glu Gln Phe Asn
305                 310                 315                 320
Ser Thr Phe Arg Val Val Ser Val Leu Thr Val Val His Gln Asp Trp
                325                 330                 335
Leu Asn Gly Lys Glu Tyr Lys Cys Lys Val Ser Asn Lys Gly Leu Pro
            340                 345                 350
Ala Pro Ile Glu Lys Thr Ile Ser Lys Thr Lys Gly Gln Pro Arg Glu
        355                 360                 365
Pro Gln Val Tyr Thr Leu Pro Pro Ser Arg Glu Glu Met Thr Lys Asn
        370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Met Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
```

```
                    435                 440                 445
Ser Val Met His Glu Ala Leu His Asn His Tyr Thr Gln Lys Ser Leu
    450                 455                 460

Ser Leu Ser Pro Gly Lys
465             470

<210> SEQ ID NO 108
<211> LENGTH: 708
<212> TYPE: DNA
<213> ORGANISM: ARTIFICIAL SEQUENCE
<220> FEATURE:
<223> OTHER INFORMATION: aDNP 3A4 LC sequence
<220> FEATURE:
<221> NAME/KEY: CDS
<222> LOCATION: (1)..(708)

<400> SEQUENCE: 108 atg gac atg agg gtg ccc gct cag ctc ctg ggg ctc ctg ctg ctg tgg      48
Met Asp Met Arg Val Pro Ala Gln Leu Leu Gly Leu Leu Leu Leu Trp
1               5                   10                  15 ctg aga ggt gcg cgc tgt gac atc cag atg acc cag tct cca tct tcc      96
Leu Arg Gly Ala Arg Cys Asp Ile Gln Met Thr Gln Ser Pro Ser Ser
                20                  25                  30 gtg tct gca tct gta gga gac aga gtc acc atc act tgt cgg gcg agt     144
Val Ser Ala Ser Val Gly Asp Arg Val Thr Ile Thr Cys Arg Ala Ser
            35                  40                  45 cag ggt att agt agg agg tta gcc tgg tat cag cag aaa cca ggg aaa     192
Gln Gly Ile Ser Arg Arg Leu Ala Trp Tyr Gln Gln Lys Pro Gly Lys
        50                  55                  60 gcc cct aag ctc ctg atc tat gct gca tcc agt ttg caa agt ggg gtc     240
Ala Pro Lys Leu Leu Ile Tyr Ala Ala Ser Ser Leu Gln Ser Gly Val
65                  70                  75                  80 cca tca agg ttc agc ggc agt gga tct ggg aca gat ttc act ctc acc     288
Pro Ser Arg Phe Ser Gly Ser Gly Ser Gly Thr Asp Phe Thr Leu Thr
                85                  90                  95 atc agc agc ctg cag cct gaa gat ttt gca act tac tat tgt caa cag     336
Ile Ser Ser Leu Gln Pro Glu Asp Phe Ala Thr Tyr Tyr Cys Gln Gln
            100                 105                 110 gct aac agt ttc cct ttc act ttc ggc cct ggg acc aaa gtg gat atc     384
Ala Asn Ser Phe Pro Phe Thr Phe Gly Pro Gly Thr Lys Val Asp Ile
        115                 120                 125 aaa cgt acg gtg gct gca cca tct gtc ttc atc ttc ccg cca tct gat     432
Lys Arg Thr Val Ala Ala Pro Ser Val Phe Ile Phe Pro Pro Ser Asp
    130                 135                 140 gag cag ttg aaa tct gga act gcc tct gtt gtg tgc ctg ctg aat aac     480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc     528
Phe Tyr Pro Arg Glu Ala Lys Val Gln Trp Lys Val Asp Asn Ala Leu
                165                 170                 175 caa tcg ggt aac tcc cag gag agt gtc aca gag cag gac agc aag gac     576
Gln Ser Gly Asn Ser Gln Glu Ser Val Thr Glu Gln Asp Ser Lys Asp
            180                 185                 190 agc acc tac agc ctc agc agc acc ctg acg ctg agc aaa gca gac tac     624
Ser Thr Tyr Ser Leu Ser Ser Thr Leu Thr Leu Ser Lys Ala Asp Tyr
        195                 200                 205 gag aaa cac aaa gtc tac gcc tgc gaa gtc acc cat cag ggc ctg agc     672
Glu Lys His Lys Val Tyr Ala Cys Glu Val Thr His Gln Gly Leu Ser
    210                 215                 220 tcg ccc gtc aca aag agc ttc aac agg gga gag tgt                     708
Ser Pro Val Thr Lys Ser Phe Asn Arg Gly Glu Cys
```

<210> SEQ ID NO 109
<211> LENGTH: 236
<212> TYPE: PRT
<213> ORGANISM: ARTIFICIAL SEQUENCE
<220> FEATURE:
<223> OTHER INFORMATION: Synthetic Construct

<400> SEQUENCE: 109

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Arg Arg Leu Ala Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asn Ser Phe Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 110
<211> LENGTH: 1398
<212> TYPE: DNA
<213> ORGANISM: ARTIFICIAL SEQUENCE
<220> FEATURE:
<223> OTHER INFORMATION: aDNP 3A4. IgG2  HC sequence
<220> FEATURE:
<221> NAME/KEY: CDS
<222> LOCATION: (1)..(1398)

<400> SEQUENCE: 110 atg gac atg agg gtg ccc gct cag ctc ctg ggg ctc ctg ctg ctg tgg      48
Met Asp Met Arg Val Pro Ala Gln Leu Leu Gly Leu Leu Leu Leu Trp
1               5                   10                  15 ctg aga ggt gcg cgc tgt cag gtg cag ctg gtg gag tct ggg gga ggc      96
Leu Arg Gly Ala Arg Cys Gln Val Gln Leu Val Glu Ser Gly Gly Gly
            20                  25                  30 gtg gtc cag cct ggg agg tcc ctg aga ctc tcc tgt gca gcg tct gga     144

```
                Val Val Gln Pro Gly Arg Ser Leu Arg Leu Ser Cys Ala Ala Ser Gly
                                 35                  40                  45 ttc acc ttc agt agc tat ggc atg cac tgg gtc cgc cag gct cca ggc         192
Phe Thr Phe Ser Ser Tyr Gly Met His Trp Val Arg Gln Ala Pro Gly
         50                  55                  60 aag ggg ctg gag tgg gtg gca gtt ata tgg tat gat gga agt aat aaa         240
Lys Gly Leu Glu Trp Val Ala Val Ile Trp Tyr Asp Gly Ser Asn Lys
 65                  70                  75                  80 tac tat gca gac tcc gtg aag ggc cga ttc act atc tcc aga gac aat         288
Tyr Tyr Ala Asp Ser Val Lys Gly Arg Phe Thr Ile Ser Arg Asp Asn
                 85                  90                  95 tcc aag aac acg ctg tat ctg caa atg aac agc ctg aga gcc gag gac         336
Ser Lys Asn Thr Leu Tyr Leu Gln Met Asn Ser Leu Arg Ala Glu Asp
            100                 105                 110 acg gct gtg tat tac tgt gcg agg tat aac tgg aac tac ggt atg gac         384
Thr Ala Val Tyr Tyr Cys Ala Arg Tyr Asn Trp Asn Tyr Gly Met Asp
            115                 120                 125 gtc tgg ggc caa ggg acc acg gtc acc gtc tct agt gcc tcc acc aag         432
Val Trp Gly Gln Gly Thr Thr Val Thr Val Ser Ser Ala Ser Thr Lys
        130                 135                 140 ggc cca tcg gtc ttc ccc ctg gcg ccc tgc tcc agg agc acc tcc gag         480
Gly Pro Ser Val Phe Pro Leu Ala Pro Cys Ser Arg Ser Thr Ser Glu
145                 150                 155                 160 agc aca gcg gcc ctg ggc tgc ctg gtc aag gac tac ttc ccc gaa ccg         528
Ser Thr Ala Ala Leu Gly Cys Leu Val Lys Asp Tyr Phe Pro Glu Pro
                165                 170                 175 gtg acg gtg tcg tgg aac tca ggc gct ctg acc agc ggc gtg cac acc         576
Val Thr Val Ser Trp Asn Ser Gly Ala Leu Thr Ser Gly Val His Thr
            180                 185                 190 ttc cca gct gtc cta cag tcc tca gga ctc tac tcc ctc agc agc gtg         624
Phe Pro Ala Val Leu Gln Ser Ser Gly Leu Tyr Ser Leu Ser Ser Val
            195                 200                 205 gtg acc gtg ccc tcc agc aac ttc ggc acc cag acc tac acc tgc aac         672
Val Thr Val Pro Ser Ser Asn Phe Gly Thr Gln Thr Tyr Thr Cys Asn
        210                 215                 220 gta gat cac aag ccc agc aac acc aag gtg gac aag aca gtt gag cgc         720
Val Asp His Lys Pro Ser Asn Thr Lys Val Asp Lys Thr Val Glu Arg
225                 230                 235                 240 aaa tgt tgt gtc gag tgc cca ccg tgc cca gca cca cct gtg gca gga         768
Lys Cys Cys Val Glu Cys Pro Pro Cys Pro Ala Pro Pro Val Ala Gly
                245                 250                 255 ccg tca gtc ttc ctc ttc ccc cca aaa ccc aag gac acc ctc atg atc         816
Pro Ser Val Phe Leu Phe Pro Pro Lys Pro Lys Asp Thr Leu Met Ile
            260                 265                 270 tcc cgg acc cct gag gtc acg tgc gtg gtg gtg gac gtg agc cac gaa         864
Ser Arg Thr Pro Glu Val Thr Cys Val Val Val Asp Val Ser His Glu
        275                 280                 285 gac ccc gag gtc cag ttc aac tgg tac gtg gac ggc gtg gag gtg cat         912
Asp Pro Glu Val Gln Phe Asn Trp Tyr Val Asp Gly Val Glu Val His
    290                 295                 300 aat gcc aag aca aag cca cgg gag gag cag ttc aac agc acg ttc cgt         960
Asn Ala Lys Thr Lys Pro Arg Glu Glu Gln Phe Asn Ser Thr Phe Arg
305                 310                 315                 320 gtg gtc agc gtc ctc acc gtt gtg cac cag gac tgg ctg aac ggc aag        1008
Val Val Ser Val Leu Thr Val Val His Gln Asp Trp Leu Asn Gly Lys
                325                 330                 335 gag tac aag tgc aag gtc tcc aac aaa ggc ctc cca gcc ccc atc gag        1056
Glu Tyr Lys Cys Lys Val Ser Asn Lys Gly Leu Pro Ala Pro Ile Glu
            340                 345                 350
```

```
aaa acc atc tcc aaa acc aaa ggg cag ccc cga gaa cca cag gtg tac      1104
Lys Thr Ile Ser Lys Thr Lys Gly Gln Pro Arg Glu Pro Gln Val Tyr
        355                 360                 365 acc ctg ccc cca tcc cgg gag gag atg acc aag aac cag gtc agc ctg      1152
Thr Leu Pro Pro Ser Arg Glu Glu Met Thr Lys Asn Gln Val Ser Leu
    370                 375                 380 acc tgc ctg gtc aaa ggc ttc tac ccc agc gac atc gcc gtg gag tgg      1200
Thr Cys Leu Val Lys Gly Phe Tyr Pro Ser Asp Ile Ala Val Glu Trp
385                 390                 395                 400 gag agc aat ggg cag ccg gag aac aac tac aag acc aca cct ccc atg      1248
Glu Ser Asn Gly Gln Pro Glu Asn Asn Tyr Lys Thr Thr Pro Pro Met
                405                 410                 415 ctg gac tcc gac ggc tcc ttc ttc ctc tac agc aag ctc acc gtg gac      1296
Leu Asp Ser Asp Gly Ser Phe Phe Leu Tyr Ser Lys Leu Thr Val Asp
            420                 425                 430 aag agc agg tgg cag cag ggg aac gtc ttc tca tgc tcc gtg atg cat      1344
Lys Ser Arg Trp Gln Gln Gly Asn Val Phe Ser Cys Ser Val Met His
        435                 440                 445 gag gct ctg cac aac cac tac acg cag aag agc ctc tcc ctg tct ccg      1392
Glu Ala Leu His Asn His Tyr Thr Gln Lys Ser Leu Ser Leu Ser Pro
    450                 455                 460 ggt aaa                                                              1398
Gly Lys
465

<210> SEQ ID NO 111
<211> LENGTH: 466
<212> TYPE: PRT
<213> ORGANISM: ARTIFICIAL SEQUENCE
<220> FEATURE:
<223> OTHER INFORMATION: Synthetic Construct

<400> SEQUENCE: 111

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Tyr Asn Trp Asn Tyr Gly Met Asp
        115                 120                 125

Val Trp Gly Gln Gly Thr Thr Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
```

```
            195                 200                 205
Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Ala Pro Pro Val Ala Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
                340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465

<210> SEQ ID NO 112
<211> LENGTH: 1398
<212> TYPE: DNA
<213> ORGANISM: ARTIFICIAL SEQUENCE
<220> FEATURE:
<223> OTHER INFORMATION: aDNP 3A4 W101F IgG2 HC sequence
<220> FEATURE:
<221> NAME/KEY: CDS
<222> LOCATION: (1)..(1398)

<400> SEQUENCE: 112 atg gac atg agg gtg ccc gct cag ctc ctg ggg ctc ctg ctg ctg tgg     48
Met Asp Met Arg Val Pro Ala Gln Leu Leu Gly Leu Leu Leu Leu Trp
1               5                   10                  15 ctg aga ggt gcg cgc tgt cag gtg cag ctg gtg gag tct ggg gga ggc     96
Leu Arg Gly Ala Arg Cys Gln Val Gln Leu Val Glu Ser Gly Gly Gly
            20                  25                  30 gtg gtc cag cct ggg agg tcc ctg aga ctc tcc tgt gca gcg tct gga    144
Val Val Gln Pro Gly Arg Ser Leu Arg Leu Ser Cys Ala Ala Ser Gly
        35                  40                  45 ttc acc ttc agt agc tat ggc atg cac tgg gtc cgc cag gct cca ggc    192
```

-continued

```
                Phe Thr Phe Ser Ser Tyr Gly Met His Trp Val Arg Gln Ala Pro Gly
                     50                   55                  60 aag ggg ctg gag tgg gtg gca gtt ata tgg tat gat gga agt aat aaa         240
Lys Gly Leu Glu Trp Val Ala Val Ile Trp Tyr Asp Gly Ser Asn Lys
 65              70                  75                  80 tac tat gca gac tcc gtg aag ggc cga ttc act atc tcc aga gac aat         288
Tyr Tyr Ala Asp Ser Val Lys Gly Arg Phe Thr Ile Ser Arg Asp Asn
                 85                  90                  95 tcc aag aac acg ctg tat ctg caa atg aac agc ctg aga gcc gag gac         336
Ser Lys Asn Thr Leu Tyr Leu Gln Met Asn Ser Leu Arg Ala Glu Asp
            100                 105                 110 acg gct gtg tat tac tgt gcg agg tat aac ttc aac tac ggt atg gac         384
Thr Ala Val Tyr Tyr Cys Ala Arg Tyr Asn Phe Asn Tyr Gly Met Asp
            115                 120                 125 gtc tgg ggc caa ggg acc acg gtc acc gtc tct agt gcc tcc acc aag         432
Val Trp Gly Gln Gly Thr Thr Val Thr Val Ser Ser Ala Ser Thr Lys
    130                 135                 140 ggc cca tcg gtc ttc ccc ctg gcg ccc tgc tcc agg agc acc tcc gag         480
Gly Pro Ser Val Phe Pro Leu Ala Pro Cys Ser Arg Ser Thr Ser Glu
145                 150                 155                 160 agc aca gcg gcc ctg ggc tgc ctg gtc aag gac tac ttc ccc gaa ccg         528
Ser Thr Ala Ala Leu Gly Cys Leu Val Lys Asp Tyr Phe Pro Glu Pro
                165                 170                 175 gtg acg gtg tcg tgg aac tca ggc gct ctg acc agc ggc gtg cac acc         576
Val Thr Val Ser Trp Asn Ser Gly Ala Leu Thr Ser Gly Val His Thr
            180                 185                 190 ttc cca gct gtc cta cag tcc tca gga ctc tac tcc ctc agc agc gtg         624
Phe Pro Ala Val Leu Gln Ser Ser Gly Leu Tyr Ser Leu Ser Ser Val
            195                 200                 205 gtg acc gtg ccc tcc agc aac ttc ggc acc cag acc tac acc tgc aac         672
Val Thr Val Pro Ser Ser Asn Phe Gly Thr Gln Thr Tyr Thr Cys Asn
            210                 215                 220 gta gat cac aag ccc agc aac acc aag gtg gac aag aca gtt gag cgc         720
Val Asp His Lys Pro Ser Asn Thr Lys Val Asp Lys Thr Val Glu Arg
225                 230                 235                 240 aaa tgt tgt gtc gag tgc cca ccg tgc cca gca cca cct gtg gca gga         768
Lys Cys Cys Val Glu Cys Pro Pro Cys Pro Ala Pro Pro Val Ala Gly
                245                 250                 255 ccg tca gtc ttc ctc ttc ccc cca aaa ccc aag gac acc ctc atg atc         816
Pro Ser Val Phe Leu Phe Pro Pro Lys Pro Lys Asp Thr Leu Met Ile
            260                 265                 270 tcc cgg acc cct gag gtc acg tgc gtg gtg gtg gac gtg agc cac gaa         864
Ser Arg Thr Pro Glu Val Thr Cys Val Val Val Asp Val Ser His Glu
            275                 280                 285 gac ccc gag gtc cag ttc aac tgg tac gtg gac ggc gtg gag gtg cat         912
Asp Pro Glu Val Gln Phe Asn Trp Tyr Val Asp Gly Val Glu Val His
    290                 295                 300 aat gcc aag aca aag cca cgg gag gag cag ttc aac agc acg ttc cgt         960
Asn Ala Lys Thr Lys Pro Arg Glu Glu Gln Phe Asn Ser Thr Phe Arg
305                 310                 315                 320 gtg gtc agc gtc ctc acc gtt gtg cac cag gac tgg ctg aac ggc aag        1008
Val Val Ser Val Leu Thr Val Val His Gln Asp Trp Leu Asn Gly Lys
                325                 330                 335 gag tac aag tgc aag gtc tcc aac aaa ggc ctc cca gcc ccc atc gag        1056
Glu Tyr Lys Cys Lys Val Ser Asn Lys Gly Leu Pro Ala Pro Ile Glu
            340                 345                 350 aaa acc atc tcc aaa acc aaa ggg cag ccc cga gaa cca cag gtg tac        1104
Lys Thr Ile Ser Lys Thr Lys Gly Gln Pro Arg Glu Pro Gln Val Tyr
            355                 360                 365
```

```
acc ctg ccc cca tcc cgg gag gag atg acc aag aac cag gtc agc ctg    1152
Thr Leu Pro Pro Ser Arg Glu Glu Met Thr Lys Asn Gln Val Ser Leu
370                 375                 380 acc tgc ctg gtc aaa ggc ttc tac ccc agc gac atc gcc gtg gag tgg    1200
Thr Cys Leu Val Lys Gly Phe Tyr Pro Ser Asp Ile Ala Val Glu Trp
385                 390                 395                 400 gag agc aat ggg cag ccg gag aac aac tac aag acc aca cct ccc atg    1248
Glu Ser Asn Gly Gln Pro Glu Asn Asn Tyr Lys Thr Thr Pro Pro Met
                405                 410                 415 ctg gac tcc gac ggc tcc ttc ttc ctc tac agc aag ctc acc gtg gac    1296
Leu Asp Ser Asp Gly Ser Phe Phe Leu Tyr Ser Lys Leu Thr Val Asp
            420                 425                 430 aag agc agg tgg cag cag ggg aac gtc ttc tca tgc tcc gtg atg cat    1344
Lys Ser Arg Trp Gln Gln Gly Asn Val Phe Ser Cys Ser Val Met His
        435                 440                 445 gag gct ctg cac aac cac tac acg cag aag agc ctc tcc ctg tct ccg    1392
Glu Ala Leu His Asn His Tyr Thr Gln Lys Ser Leu Ser Leu Ser Pro
450                 455                 460 ggt aaa                                                             1398
Gly Lys
465

<210> SEQ ID NO 113
<211> LENGTH: 466
<212> TYPE: PRT
<213> ORGANISM: ARTIFICIAL SEQUENCE
<220> FEATURE:
<223> OTHER INFORMATION: Synthetic Construct

<400> SEQUENCE: 113

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Tyr Asn Phe Asn Tyr Gly Met Asp
        115                 120                 125

Val Trp Gly Gln Gly Thr Thr Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220
```

```
Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Val Ala Gly
            245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
            275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465

<210> SEQ ID NO 114
<211> LENGTH: 1398
<212> TYPE: DNA
<213> ORGANISM: ARTIFICIAL SEQUENCE
<220> FEATURE:
<223> OTHER INFORMATION: aDNP 3A4 W101Y IgG2 HC sequence
<220> FEATURE:
<221> NAME/KEY: CDS
<222> LOCATION: (1)..(1398)

<400> SEQUENCE: 114 atg gac atg agg gtg ccc gct cag ctc ctg ggg ctc ctg ctg ctg tgg      48
Met Asp Met Arg Val Pro Ala Gln Leu Leu Gly Leu Leu Leu Leu Trp
1               5                   10                  15 ctg aga ggt gcg cgc tgt cag gtg cag ctg gtg gag tct ggg gga ggc      96
Leu Arg Gly Ala Arg Cys Gln Val Gln Leu Val Glu Ser Gly Gly Gly
            20                  25                  30 gtg gtc cag cct ggg agg tcc ctg aga ctc tcc tgt gca gcg tct gga     144
Val Val Gln Pro Gly Arg Ser Leu Arg Leu Ser Cys Ala Ala Ser Gly
        35                  40                  45 ttc acc ttc agt agc tat ggc atg cac tgg gtc cgc cag gct cca ggc     192
Phe Thr Phe Ser Ser Tyr Gly Met His Trp Val Arg Gln Ala Pro Gly
    50                  55                  60 aag ggg ctg gag tgg gtg gca gtt ata tgg tat gat gga agt aat aaa     240
```

```
                Lys Gly Leu Glu Trp Val Ala Val Ile Trp Tyr Asp Gly Ser Asn Lys
                 65              70                  75                  80 tac tat gca gac tcc gtg aag ggc cga ttc act atc tcc aga gac aat        288
Tyr Tyr Ala Asp Ser Val Lys Gly Arg Phe Thr Ile Ser Arg Asp Asn
                    85                  90                  95 tcc aag aac acg ctg tat ctg caa atg aac agc ctg aga gcc gag gac        336
Ser Lys Asn Thr Leu Tyr Leu Gln Met Asn Ser Leu Arg Ala Glu Asp
                100                 105                 110 acg gct gtg tat tac tgt gcg agg tat aac tac aac tac ggt atg gac        384
Thr Ala Val Tyr Tyr Cys Ala Arg Tyr Asn Tyr Asn Tyr Gly Met Asp
                115                 120                 125 gtc tgg ggc caa ggg acc acg gtc acc gtc tct agt gcc tcc acc aag        432
Val Trp Gly Gln Gly Thr Thr Val Thr Val Ser Ser Ala Ser Thr Lys
        130                 135                 140 ggc cca tcg gtc ttc ccc ctg gcg ccc tgc tcc agg agc acc tcc gag        480
Gly Pro Ser Val Phe Pro Leu Ala Pro Cys Ser Arg Ser Thr Ser Glu
145                 150                 155                 160 agc aca gcg gcc ctg ggc tgc ctg gtc aag gac tac ttc ccc gaa ccg        528
Ser Thr Ala Ala Leu Gly Cys Leu Val Lys Asp Tyr Phe Pro Glu Pro
                165                 170                 175 gtg acg gtg tcg tgg aac tca ggc gct ctg acc agc ggc gtg cac acc        576
Val Thr Val Ser Trp Asn Ser Gly Ala Leu Thr Ser Gly Val His Thr
                180                 185                 190 ttc cca gct gtc cta cag tcc tca gga ctc tac tcc ctc agc agc gtg        624
Phe Pro Ala Val Leu Gln Ser Ser Gly Leu Tyr Ser Leu Ser Ser Val
            195                 200                 205 gtg acc gtg ccc tcc agc aac ttc ggc acc cag acc tac acc tgc aac        672
Val Thr Val Pro Ser Ser Asn Phe Gly Thr Gln Thr Tyr Thr Cys Asn
            210                 215                 220 gta gat cac aag ccc agc aac acc aag gtg gac aag aca gtt gag cgc        720
Val Asp His Lys Pro Ser Asn Thr Lys Val Asp Lys Thr Val Glu Arg
225                 230                 235                 240 aaa tgt tgt gtc gag tgc cca ccg tgc cca gca cca cct gtg gca gga        768
Lys Cys Cys Val Glu Cys Pro Pro Cys Pro Ala Pro Pro Val Ala Gly
                245                 250                 255 ccg tca gtc ttc ctc ttc ccc cca aaa ccc aag gac acc ctc atg atc        816
Pro Ser Val Phe Leu Phe Pro Pro Lys Pro Lys Asp Thr Leu Met Ile
                260                 265                 270 tcc cgg acc cct gag gtc acg tgc gtg gtg gtg gac gtg agc cac gaa        864
Ser Arg Thr Pro Glu Val Thr Cys Val Val Val Asp Val Ser His Glu
            275                 280                 285 gac ccc gag gtc cag ttc aac tgg tac gtg gac ggc gtg gag gtg cat        912
Asp Pro Glu Val Gln Phe Asn Trp Tyr Val Asp Gly Val Glu Val His
        290                 295                 300 aat gcc aag aca aag cca cgg gag gag cag ttc aac agc acg ttc cgt        960
Asn Ala Lys Thr Lys Pro Arg Glu Glu Gln Phe Asn Ser Thr Phe Arg
305                 310                 315                 320 gtg gtc agc gtc ctc acc gtt gtg cac cag gac tgg ctg aac ggc aag       1008
Val Val Ser Val Leu Thr Val Val His Gln Asp Trp Leu Asn Gly Lys
                325                 330                 335 gag tac aag tgc aag gtc tcc aac aaa ggc ctc cca gcc ccc atc gag       1056
Glu Tyr Lys Cys Lys Val Ser Asn Lys Gly Leu Pro Ala Pro Ile Glu
                340                 345                 350 aaa acc atc tcc aaa acc aaa ggg cag ccc cga gaa cca cag gtg tac       1104
Lys Thr Ile Ser Lys Thr Lys Gly Gln Pro Arg Glu Pro Gln Val Tyr
            355                 360                 365 acc ctg ccc cca tcc cgg gag gag atg acc aag aac cag gtc agc ctg       1152
Thr Leu Pro Pro Ser Arg Glu Glu Met Thr Lys Asn Gln Val Ser Leu
        370                 375                 380
```

```
acc tgc ctg gtc aaa ggc ttc tac ccc agc gac atc gcc gtg gag tgg      1200
Thr Cys Leu Val Lys Gly Phe Tyr Pro Ser Asp Ile Ala Val Glu Trp
385                 390                 395                 400 gag agc aat ggg cag ccg gag aac aac tac aag acc aca cct ccc atg      1248
Glu Ser Asn Gly Gln Pro Glu Asn Asn Tyr Lys Thr Thr Pro Pro Met
            405                 410                 415 ctg gac tcc gac ggc tcc ttc ttc ctc tac agc aag ctc acc gtg gac      1296
Leu Asp Ser Asp Gly Ser Phe Phe Leu Tyr Ser Lys Leu Thr Val Asp
                420                 425                 430 aag agc agg tgg cag cag ggg aac gtc ttc tca tgc tcc gtg atg cat      1344
Lys Ser Arg Trp Gln Gln Gly Asn Val Phe Ser Cys Ser Val Met His
        435                 440                 445 gag gct ctg cac aac cac tac acg cag aag agc ctc tcc ctg tct ccg      1392
Glu Ala Leu His Asn His Tyr Thr Gln Lys Ser Leu Ser Leu Ser Pro
    450                 455                 460 ggt aaa                                                               1398
Gly Lys
465

<210> SEQ ID NO 115
<211> LENGTH: 466
<212> TYPE: PRT
<213> ORGANISM: ARTIFICIAL SEQUENCE
<220> FEATURE:
<223> OTHER INFORMATION: Synthetic Construct

<400> SEQUENCE: 115

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Tyr Asn Tyr Asn Tyr Gly Met Asp
        115                 120                 125

Val Trp Gly Gln Gly Thr Thr Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240
```

```
Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 116
<211> LENGTH: 1398
<212> TYPE: DNA
<213> ORGANISM: ARTIFICIAL SEQUENCE
<220> FEATURE:
<223> OTHER INFORMATION: aDNP 3A4-FSS IgG2 HC sequence
<220> FEATURE:
<221> NAME/KEY: CDS
<222> LOCATION: (1)..(1398)

<400> SEQUENCE: 116 atg gac atg agg gtg ccc gct cag ctc ctg ggg ctc ctg ctg ctg tgg      48
Met Asp Met Arg Val Pro Ala Gln Leu Leu Gly Leu Leu Leu Leu Trp
1               5                   10                  15 ctg aga ggt gcg cgc tgt cag gtg cag ctg gtg gag tct ggg gga ggc      96
Leu Arg Gly Ala Arg Cys Gln Val Gln Leu Val Glu Ser Gly Gly Gly
            20                  25                  30 gtg gtc cag cct ggg agg tcc ctg aga ctc tcc tgt gca gcg tct gga     144
Val Val Gln Pro Gly Arg Ser Leu Arg Leu Ser Cys Ala Ala Ser Gly
        35                  40                  45 ttc acc ttc agt agc tat ggc atg cac tgg gtc cgc cag gct cca ggc     192
Phe Thr Phe Ser Ser Tyr Gly Met His Trp Val Arg Gln Ala Pro Gly
    50                  55                  60 aag ggg ctg gag tgg gtg gca gtt ata tgg tat gat gga agt aat aaa     240
Lys Gly Leu Glu Trp Val Ala Val Ile Trp Tyr Asp Gly Ser Asn Lys
65                  70                  75                  80 tac tat gca gac tcc gtg aag ggc cga ttc act atc tcc aga gac aat     288
```

-continued

```
                Tyr Tyr Ala Asp Ser Val Lys Gly Arg Phe Thr Ile Ser Arg Asp Asn
                                85              90              95 tcc aag aac acg ctg tat ctg caa atg aac agc ctg aga gcc gag gac         336
Ser Lys Asn Thr Leu Tyr Leu Gln Met Asn Ser Leu Arg Ala Glu Asp
                100             105             110 acg gct gtg tat tac tgt gcg agg tat aac ttc aac tac ggt atg gac         384
Thr Ala Val Tyr Tyr Cys Ala Arg Tyr Asn Phe Asn Tyr Gly Met Asp
                115             120             125 gtc tgg ggc caa ggg acc acg gtc acc gtc tct agt gcc tcc acc aag         432
Val Trp Gly Gln Gly Thr Thr Val Thr Val Ser Ser Ala Ser Thr Lys
        130             135             140 ggc cca tcg gtc ttc ccc ctg gcg ccc tgc tcc agg agc acc tcc gag         480
Gly Pro Ser Val Phe Pro Leu Ala Pro Cys Ser Arg Ser Thr Ser Glu
145             150             155             160 agc aca gcg gcc ctg ggc tgc ctg gtc aag gac tac ttc ccc gaa ccg         528
Ser Thr Ala Ala Leu Gly Cys Leu Val Lys Asp Tyr Phe Pro Glu Pro
                165             170             175 gtg acg gtg tcg tgg aac tca ggc gct ctg acc agc ggc gtg cac acc         576
Val Thr Val Ser Trp Asn Ser Gly Ala Leu Thr Ser Gly Val His Thr
                180             185             190 ttc cca gct gtc cta cag tcc tca gga ctc tac tcc ctc agc agc gtg         624
Phe Pro Ala Val Leu Gln Ser Ser Gly Leu Tyr Ser Leu Ser Ser Val
                195             200             205 gtg acc gtg ccc tcc agc aac ttc ggc acc cag acc tac acc tgc aac         672
Val Thr Val Pro Ser Ser Asn Phe Gly Thr Gln Thr Tyr Thr Cys Asn
210             215             220 gta gat cac aag ccc agc aac acc aag gtg gac aag aca gtt gag cgc         720
Val Asp His Lys Pro Ser Asn Thr Lys Val Asp Lys Thr Val Glu Arg
225             230             235             240 aaa tct tct gtc gag tgc cca ccg tgc cca gca cca cct gtg gca gga         768
Lys Ser Ser Val Glu Cys Pro Pro Cys Pro Ala Pro Pro Val Ala Gly
                245             250             255 ccg tca gtc ttc ctc ttc ccc cca aaa ccc aag gac acc ctc atg atc         816
Pro Ser Val Phe Leu Phe Pro Pro Lys Pro Lys Asp Thr Leu Met Ile
                260             265             270 tcc cgg acc cct gag gtc acg tgc gtg gtg gtg gac gtg agc cac gaa         864
Ser Arg Thr Pro Glu Val Thr Cys Val Val Val Asp Val Ser His Glu
            275             280             285 gac ccc gag gtc cag ttc aac tgg tac gtg gac ggc gtg gag gtg cat         912
Asp Pro Glu Val Gln Phe Asn Trp Tyr Val Asp Gly Val Glu Val His
290             295             300 aat gcc aag aca aaa cca cgg gag gag cag ttc aac agc acg ttc cgt         960
Asn Ala Lys Thr Lys Pro Arg Glu Glu Gln Phe Asn Ser Thr Phe Arg
305             310             315             320 gtg gtc agc gtc ctc acc gtt gtg cac cag gac tgg ctg aac ggc aag        1008
Val Val Ser Val Leu Thr Val Val His Gln Asp Trp Leu Asn Gly Lys
                325             330             335 gag tac aag tgc aag gtc tcc aac aaa ggc ctc cca gcc ccc atc gag        1056
Glu Tyr Lys Cys Lys Val Ser Asn Lys Gly Leu Pro Ala Pro Ile Glu
                340             345             350 aaa acc atc tcc aaa acc aaa ggg cag ccc cga gaa cca cag gtg tac        1104
Lys Thr Ile Ser Lys Thr Lys Gly Gln Pro Arg Glu Pro Gln Val Tyr
                355             360             365 acc ctg ccc cca tcc cgg gag gag atg acc aag aac cag gtc agc ctg        1152
Thr Leu Pro Pro Ser Arg Glu Glu Met Thr Lys Asn Gln Val Ser Leu
                370             375             380 acc tgc ctg gtc aaa ggc ttc tac ccc agc gac atc gcc gtg gag tgg        1200
Thr Cys Leu Val Lys Gly Phe Tyr Pro Ser Asp Ile Ala Val Glu Trp
385             390             395             400
```

```
gag agc aat ggg cag ccg gag aac aac tac aag acc aca cct ccc atg      1248
Glu Ser Asn Gly Gln Pro Glu Asn Asn Tyr Lys Thr Thr Pro Pro Met
            405                 410                 415 ctg gac tcc gac ggc tcc ttc ttc ctc tac agc aag ctc acc gtg gac      1296
Leu Asp Ser Asp Gly Ser Phe Phe Leu Tyr Ser Lys Leu Thr Val Asp
        420                 425                 430 aag agc agg tgg cag cag ggg aac gtc ttc tca tgc tcc gtg atg cat      1344
Lys Ser Arg Trp Gln Gln Gly Asn Val Phe Ser Cys Ser Val Met His
    435                 440                 445 gag gct ctg cac aac cac tac acg cag aag agc ctc tcc ctg tct ccg      1392
Glu Ala Leu His Asn His Tyr Thr Gln Lys Ser Leu Ser Leu Ser Pro
450                 455                 460 ggt aaa                                                              1398
Gly Lys
465

<210> SEQ ID NO 117
<211> LENGTH: 466
<212> TYPE: PRT
<213> ORGANISM: ARTIFICIAL SEQUENCE
<220> FEATURE:
<223> OTHER INFORMATION: Synthetic Construct

<400> SEQUENCE: 117

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Tyr Asn Phe Asn Tyr Gly Met Asp
        115                 120                 125

Val Trp Gly Gln Gly Thr Thr Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Ser Ser Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
```

```
                260             265             270
Ser Arg Thr Pro Glu Val Thr Cys Val Val Asp Val Ser His Glu
        275             280             285

Asp Pro Glu Val Gln Phe Asn Trp Tyr Val Asp Gly Val Glu Val His
    290             295             300

Asn Ala Lys Thr Lys Pro Arg Glu Glu Gln Phe Asn Ser Thr Phe Arg
305             310             315             320

Val Val Ser Val Leu Thr Val Val His Gln Asp Trp Leu Asn Gly Lys
            325             330             335

Glu Tyr Lys Cys Lys Val Ser Asn Lys Gly Leu Pro Ala Pro Ile Glu
        340             345             350

Lys Thr Ile Ser Lys Thr Lys Gly Gln Pro Arg Glu Pro Gln Val Tyr
            355             360             365

Thr Leu Pro Pro Ser Arg Glu Glu Met Thr Lys Asn Gln Val Ser Leu
        370             375             380

Thr Cys Leu Val Lys Gly Phe Tyr Pro Ser Asp Ile Ala Val Glu Trp
385             390             395             400

Glu Ser Asn Gly Gln Pro Glu Asn Asn Tyr Lys Thr Thr Pro Pro Met
            405             410             415

Leu Asp Ser Asp Gly Ser Phe Phe Leu Tyr Ser Lys Leu Thr Val Asp
        420             425             430

Lys Ser Arg Trp Gln Gln Gly Asn Val Phe Ser Cys Ser Val Met His
            435             440             445

Glu Ala Leu His Asn His Tyr Thr Gln Lys Ser Leu Ser Leu Ser Pro
        450             455             460

Gly Lys
465

<210> SEQ ID NO 118
<211> LENGTH: 1398
<212> TYPE: DNA
<213> ORGANISM: ARTIFICIAL SEQUENCE
<220> FEATURE:
<223> OTHER INFORMATION: aDNP 3A4-YSS IgG2 HC sequence
<220> FEATURE:
<221> NAME/KEY: CDS
<222> LOCATION: (1)..(1398)

<400> SEQUENCE: 118 atg gac atg agg gtg ccc gct cag ctc ctg ggg ctc ctg ctg ctg tgg      48
Met Asp Met Arg Val Pro Ala Gln Leu Leu Gly Leu Leu Leu Leu Trp
1               5                   10                  15 ctg aga ggt gcg cgc tgt cag gtg cag ctg gtg gag tct ggg gga ggc      96
Leu Arg Gly Ala Arg Cys Gln Val Gln Leu Val Glu Ser Gly Gly Gly
            20                  25                  30 gtg gtc cag cct ggg agg tcc ctg aga ctc tcc tgt gca gcg tct gga     144
Val Val Gln Pro Gly Arg Ser Leu Arg Leu Ser Cys Ala Ala Ser Gly
        35                  40                  45 ttc acc ttc agt agc tat ggc atg cac tgg gtc cgc cag gct cca ggc     192
Phe Thr Phe Ser Ser Tyr Gly Met His Trp Val Arg Gln Ala Pro Gly
    50                  55                  60 aag ggg ctg gag tgg gtg gca gtt ata tgg tat gat gga agt aat aaa     240
Lys Gly Leu Glu Trp Val Ala Val Ile Trp Tyr Asp Gly Ser Asn Lys
65                  70                  75                  80 tac tat gca gac tcc gtg aag ggc cga ttc act atc tcc aga gac aat     288
Tyr Tyr Ala Asp Ser Val Lys Gly Arg Phe Thr Ile Ser Arg Asp Asn
                85                  90                  95 tcc aag aac acg ctg tat ctg caa atg aac agc ctg aga gcc gag gac     336
```

```
                Ser Lys Asn Thr Leu Tyr Leu Gln Met Asn Ser Leu Arg Ala Glu Asp
                            100                 105                 110 acg gct gtg tat tac tgt gcg agg tat aac tac aac tac ggt atg gac              384
Thr Ala Val Tyr Tyr Cys Ala Arg Tyr Asn Tyr Asn Tyr Gly Met Asp
            115                 120                 125 gtc tgg ggc caa ggg acc acg gtc acc gtc tct agt gcc tcc acc aag              432
Val Trp Gly Gln Gly Thr Thr Val Thr Val Ser Ser Ala Ser Thr Lys
130                 135                 140 ggc cca tcg gtc ttc ccc ctg gcg ccc tgc tcc agg agc acc tcc gag              480
Gly Pro Ser Val Phe Pro Leu Ala Pro Cys Ser Arg Ser Thr Ser Glu
145                 150                 155                 160 agc aca gcg gcc ctg ggc tgc ctg gtc aag gac tac ttc ccc gaa ccg              528
Ser Thr Ala Ala Leu Gly Cys Leu Val Lys Asp Tyr Phe Pro Glu Pro
                165                 170                 175 gtg acg gtg tcg tgg aac tca ggc gct ctg acc agc ggc gtg cac acc              576
Val Thr Val Ser Trp Asn Ser Gly Ala Leu Thr Ser Gly Val His Thr
            180                 185                 190 ttc cca gct gtc cta cag tcc tca gga ctc tac tcc ctc agc agc gtg              624
Phe Pro Ala Val Leu Gln Ser Ser Gly Leu Tyr Ser Leu Ser Ser Val
        195                 200                 205 gtg acc gtg ccc tcc agc aac ttc ggc acc cag acc tac acc tgc aac              672
Val Thr Val Pro Ser Ser Asn Phe Gly Thr Gln Thr Tyr Thr Cys Asn
    210                 215                 220 gta gat cac aag ccc agc aac acc aag gtg gac aag aca gtt gag cgc              720
Val Asp His Lys Pro Ser Asn Thr Lys Val Asp Lys Thr Val Glu Arg
225                 230                 235                 240 aaa tct tct gtc gag tgc cca ccg tgc cca gca cca cct gtg gca gga              768
Lys Ser Ser Val Glu Cys Pro Pro Cys Pro Ala Pro Pro Val Ala Gly
                245                 250                 255 ccg tca gtc ttc ctc ttc ccc cca aaa ccc aag gac acc ctc atg atc              816
Pro Ser Val Phe Leu Phe Pro Pro Lys Pro Lys Asp Thr Leu Met Ile
            260                 265                 270 tcc cgg acc cct gag gtc acg tgc gtg gtg gtg gac gtg agc cac gaa              864
Ser Arg Thr Pro Glu Val Thr Cys Val Val Val Asp Val Ser His Glu
        275                 280                 285 gac ccc gag gtc cag ttc aac tgg tac gtg gac ggc gtg gag gtg cat              912
Asp Pro Glu Val Gln Phe Asn Trp Tyr Val Asp Gly Val Glu Val His
    290                 295                 300 aat gcc aag aca aag cca cgg gag gag cag ttc aac agc acg ttc cgt              960
Asn Ala Lys Thr Lys Pro Arg Glu Glu Gln Phe Asn Ser Thr Phe Arg
305                 310                 315                 320 gtg gtc agc gtc ctc acc gtt gtg cac cag gac tgg ctg aac ggc aag             1008
Val Val Ser Val Leu Thr Val Val His Gln Asp Trp Leu Asn Gly Lys
                325                 330                 335 gag tac aag tgc aag gtc tcc aac aaa ggc ctc cca gcc ccc atc gag             1056
Glu Tyr Lys Cys Lys Val Ser Asn Lys Gly Leu Pro Ala Pro Ile Glu
            340                 345                 350 aaa acc atc tcc aaa acc aaa ggg cag ccc cga gaa cca cag gtg tac             1104
Lys Thr Ile Ser Lys Thr Lys Gly Gln Pro Arg Glu Pro Gln Val Tyr
        355                 360                 365 acc ctg ccc cca tcc cgg gag gag atg acc aag aac cag gtc agc ctg             1152
Thr Leu Pro Pro Ser Arg Glu Glu Met Thr Lys Asn Gln Val Ser Leu
    370                 375                 380 acc tgc ctg gtc aaa ggc ttc tac ccc agc gac atc gcc gtg gag tgg             1200
Thr Cys Leu Val Lys Gly Phe Tyr Pro Ser Asp Ile Ala Val Glu Trp
385                 390                 395                 400 gag agc aat ggg cag ccg gag aac aac tac aag acc aca cct ccc atg             1248
Glu Ser Asn Gly Gln Pro Glu Asn Asn Tyr Lys Thr Thr Pro Pro Met
                405                 410                 415
```

```
ctg gac tcc gac ggc tcc ttc ttc ctc tac agc aag ctc acc gtg gac    1296
Leu Asp Ser Asp Gly Ser Phe Phe Leu Tyr Ser Lys Leu Thr Val Asp
            420                 425                 430 aag agc agg tgg cag cag ggg aac gtc ttc tca tgc tcc gtg atg cat    1344
Lys Ser Arg Trp Gln Gln Gly Asn Val Phe Ser Cys Ser Val Met His
        435                 440                 445 gag gct ctg cac aac cac tac acg cag aag agc ctc tcc ctg tct ccg    1392
Glu Ala Leu His Asn His Tyr Thr Gln Lys Ser Leu Ser Leu Ser Pro
    450                 455                 460 ggt aaa                                                            1398
Gly Lys
465

<210> SEQ ID NO 119
<211> LENGTH: 466
<212> TYPE: PRT
<213> ORGANISM: ARTIFICIAL SEQUENCE
<220> FEATURE:
<223> OTHER INFORMATION: Synthetic Construct

<400> SEQUENCE: 119

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Val Arg Gln Ala Pro Gly
    50                  55                  60

Lys Gly Leu Glu Trp Val Ala Val Ile Trp Tyr Asp Gly Ser Asn Lys
65              70                  75                  80

Tyr Tyr Ala Asp Ser Val Lys Gly Arg Phe Thr Ile Ser Arg Asp Asn
            85                  90                  95

Ser Lys Asn Thr Leu Tyr Leu Gln Met Asn Ser Leu Arg Ala Glu Asp
        100                 105                 110

Thr Ala Val Tyr Tyr Cys Ala Arg Tyr Asn Tyr Asn Tyr Gly Met Asp
    115                 120                 125

Val Trp Gly Gln Gly Thr Thr Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
        180                 185                 190

Phe Pro Ala Val Leu Gln Ser Ser Gly Leu Tyr Ser Leu Ser Ser Val
    195                 200                 205

Val Thr Val Pro Ser Ser Asn Phe Gly Thr Gln Thr Tyr Thr Cys Asn
210                 215                 220

Val Asp His Lys Pro Ser Asn Thr Lys Val Asp Lys Thr Val Glu Arg
225                 230                 235                 240

Lys Ser Ser Val Glu Cys Pro Pro Cys Pro Ala Pro Pro Val Ala Gly
            245                 250                 255

Pro Ser Val Phe Leu Phe Pro Pro Lys Pro Lys Asp Thr Leu Met Ile
        260                 265                 270

Ser Arg Thr Pro Glu Val Thr Cys Val Val Val Asp Val Ser His Glu
    275                 280                 285
```

```
Asp Pro Glu Val Gln Phe Asn Trp Tyr Val Asp Gly Val Glu Val His
    290                 295                 300
Asn Ala Lys Thr Lys Pro Arg Glu Glu Gln Phe Asn Ser Thr Phe Arg
305                 310                 315                 320
Val Val Ser Val Leu Thr Val Val His Gln Asp Trp Leu Asn Gly Lys
                325                 330                 335
Glu Tyr Lys Cys Lys Val Ser Asn Lys Gly Leu Pro Ala Pro Ile Glu
            340                 345                 350
Lys Thr Ile Ser Lys Thr Lys Gly Gln Pro Arg Glu Pro Gln Val Tyr
        355                 360                 365
Thr Leu Pro Pro Ser Arg Glu Glu Met Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Met
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys
465

<210> SEQ ID NO 120
<211> LENGTH: 708
<212> TYPE: DNA
<213> ORGANISM: ARTIFICIAL SEQUENCE
<220> FEATURE:
<223> OTHER INFORMATION: aDNP 3B1 LC sequence
<220> FEATURE:
<221> NAME/KEY: CDS
<222> LOCATION: (1)..(708)

<400> SEQUENCE: 120 atg gac atg agg gtg ccc gct cag ctc ctg ggg ctc ctg ctg ctg tgg      48
Met Asp Met Arg Val Pro Ala Gln Leu Leu Gly Leu Leu Leu Leu Trp
1               5                   10                  15 ctg aga ggt gcg cgc tgt gac atc cag atg acc cag tct cca tcc tcc      96
Leu Arg Gly Ala Arg Cys Asp Ile Gln Met Thr Gln Ser Pro Ser Ser
            20                  25                  30 ctg tct gca tct gaa gga gac aga gtc acc atc act tgc cgg gca agt     144
Leu Ser Ala Ser Glu Gly Asp Arg Val Thr Ile Thr Cys Arg Ala Ser
        35                  40                  45 cag ggc att aga aat gat tta ggc tgg tat cag cag aaa cca ggg aaa     192
Gln Gly Ile Arg Asn Asp Leu Gly Trp Tyr Gln Gln Lys Pro Gly Lys
    50                  55                  60 gcc cct aag cgc ctg atc tat gct gca tcc agt ttg caa agt ggg gtc     240
Ala Pro Lys Arg Leu Ile Tyr Ala Ala Ser Ser Leu Gln Ser Gly Val
65                  70                  75                  80 cca tta agg ttc agc ggc agt gga tct ggg aca gaa ttc act ctc aca     288
Pro Leu Arg Phe Ser Gly Ser Gly Ser Gly Thr Glu Phe Thr Leu Thr
                85                  90                  95 atc agc agc ctg cag cct gaa gat ttt gca act tat tac tgt cta cag     336
Ile Ser Ser Leu Gln Pro Glu Asp Phe Ala Thr Tyr Tyr Cys Leu Gln
            100                 105                 110 tat aat agt tac ccg tgg acg ttc ggc caa ggg acc aag gtg gaa atc     384
```

```
Tyr Asn Ser Tyr Pro Trp Thr Phe Gly Gln Gly Thr Lys Val Glu Ile
            115                 120                 125 aaa cgt acg gtg gct gca cca tct gtc ttc atc ttc ccg cca tct gat      432
Lys Arg Thr Val Ala Ala Pro Ser Val Phe Ile Phe Pro Pro Ser Asp
        130                 135                 140 gag cag ttg aaa tct gga act gcc tct gtt gtg tgc ctg ctg aat aac      480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc      528
Phe Tyr Pro Arg Glu Ala Lys Val Gln Trp Lys Val Asp Asn Ala Leu
                165                 170                 175 caa tcg ggt aac tcc cag gag agt gtc aca gag cag gac agc aag gac      576
Gln Ser Gly Asn Ser Gln Glu Ser Val Thr Glu Gln Asp Ser Lys Asp
            180                 185                 190 agc acc tac agc ctc agc agc acc ctg acg ctg agc aaa gca gac tac      624
Ser Thr Tyr Ser Leu Ser Ser Thr Leu Thr Leu Ser Lys Ala Asp Tyr
        195                 200                 205 gag aaa cac aaa gtc tac gcc tgc gaa gtc acc cat cag ggc ctg agc      672
Glu Lys His Lys Val Tyr Ala Cys Glu Val Thr His Gln Gly Leu Ser
210                 215                 220 tcg ccc gtc aca aag agc ttc aac agg gga gag tgt                      708
Ser Pro Val Thr Lys Ser Phe Asn Arg Gly Glu Cys
225                 230                 235

<210> SEQ ID NO 121
<211> LENGTH: 236
<212> TYPE: PRT
<213> ORGANISM: ARTIFICIAL SEQUENCE
<220> FEATURE:
<223> OTHER INFORMATION: Synthetic Construct

<400> SEQUENCE: 121

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Glu Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80

Pro Leu Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

Tyr Asn Ser Tyr Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205
```

```
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235

<210> SEQ ID NO 122
<211> LENGTH: 1413
<212> TYPE: DNA
<213> ORGANISM: ARTIFICIAL SEQUENCE
<220> FEATURE:
<223> OTHER INFORMATION: aDNP 3B1 HC sequence
<220> FEATURE:
<221> NAME/KEY: CDS
<222> LOCATION: (1)..(1413)

<400> SEQUENCE: 122 atg gac atg agg gtg ccc gct cag ctc ctg ggg ctc ctg ctg ctg tgg      48
Met Asp Met Arg Val Pro Ala Gln Leu Leu Gly Leu Leu Leu Leu Trp
1               5                   10                  15 ctg aga ggt gcg cgc tgt cag gtg cag ctg cag gag tcg ggc cca gga      96
Leu Arg Gly Ala Arg Cys Gln Val Gln Leu Gln Glu Ser Gly Pro Gly
            20                  25                  30 ctg gtt aag cct tcg gag acc ctg tcc ctc acc tgc act gtc tct ggt     144
Leu Val Lys Pro Ser Glu Thr Leu Ser Leu Thr Cys Thr Val Ser Gly
        35                  40                  45 ggc tcc atc agt agt tac tac tgg agc tgg atc cgg cag ccc cca ggg     192
Gly Ser Ile Ser Ser Tyr Tyr Trp Ser Trp Ile Arg Gln Pro Pro Gly
    50                  55                  60 aag gga ctg gag tgg att ggg tat atc tat tac agt ggg aac acc aac     240
Lys Gly Leu Glu Trp Ile Gly Tyr Ile Tyr Tyr Ser Gly Asn Thr Asn
65                  70                  75                  80 tcc aac ccc tcc ctc aag agt cga gtc acc ata tca gta gac acg tcc     288
Ser Asn Pro Ser Leu Lys Ser Arg Val Thr Ile Ser Val Asp Thr Ser
                85                  90                  95 aag aac cag ttc tcc ctg aag ctg agc tct gtg acc gct gcg gac acg     336
Lys Asn Gln Phe Ser Leu Lys Leu Ser Ser Val Thr Ala Ala Asp Thr
            100                 105                 110 gcc gtg tat tac tgt gcg aga acc tac tat gat agt agt ggt tac tac     384
Ala Val Tyr Tyr Cys Ala Arg Thr Tyr Tyr Asp Ser Ser Gly Tyr Tyr
        115                 120                 125 tac cgt gct ttt gat atc tgg ggc caa ggg aca atg gtc acc gtc tct     432
Tyr Arg Ala Phe Asp Ile Trp Gly Gln Gly Thr Met Val Thr Val Ser
    130                 135                 140 agt gcc tcc acc aag ggc cca tcg gtc ttc ccc ctg gcg ccc tgc tcc     480
Ser Ala Ser Thr Lys Gly Pro Ser Val Phe Pro Leu Ala Pro Cys Ser
145                 150                 155                 160 agg agc acc tcc gag agc aca gcg gcc ctg ggc tgc ctg gtc aag gac     528
Arg Ser Thr Ser Glu Ser Thr Ala Ala Leu Gly Cys Leu Val Lys Asp
                165                 170                 175 tac ttc ccc gaa ccg gtg acg gtg tcg tgg aac tca ggc gct ctg acc     576
Tyr Phe Pro Glu Pro Val Thr Val Ser Trp Asn Ser Gly Ala Leu Thr
            180                 185                 190 agc ggc gtg cac acc ttc cca gct gtc cta cag tcc tca gga ctc tac     624
Ser Gly Val His Thr Phe Pro Ala Val Leu Gln Ser Ser Gly Leu Tyr
        195                 200                 205 tcc ctc agc agc gtg gtg acc gtg ccc tcc agc aac ttc ggc acc cag     672
Ser Leu Ser Ser Val Val Thr Val Pro Ser Ser Asn Phe Gly Thr Gln
    210                 215                 220 acc tac acc tgc aac gta gat cac aag ccc agc aac acc aag gtg gac     720
Thr Tyr Thr Cys Asn Val Asp His Lys Pro Ser Asn Thr Lys Val Asp
225                 230                 235                 240
```

| | | |
|---|---|---|
| aag aca gtt gag cgc aaa tgt tgt gtc gag tgc cca ccg tgc cca gca<br>Lys Thr Val Glu Arg Lys Cys Cys Val Glu Cys Pro Pro Cys Pro Ala<br>                      245                            250                      255 | 768 |
| cca cct gtg gca gga ccg tca gtc ttc ctc ttc ccc cca aaa ccc aag<br>Pro Pro Val Ala Gly Pro Ser Val Phe Leu Phe Pro Pro Lys Pro Lys<br>            260                            265                      270 | 816 |
| gac acc ctc atg atc tcc cgg acc cct gag gtc acg tgc gtg gtg gtg<br>Asp Thr Leu Met Ile Ser Arg Thr Pro Glu Val Thr Cys Val Val Val<br>       275                             280                            285 | 864 |
| gac gtg agc cac gaa gac ccc gag gtc cag ttc aac tgg tac gtg gac<br>Asp Val Ser His Glu Asp Pro Glu Val Gln Phe Asn Trp Tyr Val Asp<br>    290                            295                            300 | 912 |
| ggc gtg gag gtg cat aat gcc aag aca aag cca cgg gag gag cag ttc<br>Gly Val Glu Val His Asn Ala Lys Thr Lys Pro Arg Glu Glu Gln Phe<br>305                      310                            315                      320 | 960 |
| aac agc acg ttc cgt gtg gtc agc gtc ctc acc gtt gtg cac cag gac<br>Asn Ser Thr Phe Arg Val Val Ser Val Leu Thr Val Val His Gln Asp<br>            325                            330                      335 | 1008 |
| tgg ctg aac ggc aag gag tac aag tgc aag gtc tcc aac aaa ggc ctc<br>Trp Leu Asn Gly Lys Glu Tyr Lys Cys Lys Val Ser Asn Lys Gly Leu<br>                340                            345                      350 | 1056 |
| cca gcc ccc atc gag aaa acc atc tcc aaa acc aaa ggg cag ccc cga<br>Pro Ala Pro Ile Glu Lys Thr Ile Ser Lys Thr Lys Gly Gln Pro Arg<br>                    355                            360                      365 | 1104 |
| gaa cca cag gtg tac acc ctg ccc cca tcc cgg gag gag atg acc aag<br>Glu Pro Gln Val Tyr Thr Leu Pro Pro Ser Arg Glu Glu Met Thr Lys<br>    370                            375                            380 | 1152 |
| aac cag gtc agc ctg acc tgc ctg gtc aaa ggc ttc tac ccc agc gac<br>Asn Gln Val Ser Leu Thr Cys Leu Val Lys Gly Phe Tyr Pro Ser Asp<br>385                      390                            395                      400 | 1200 |
| atc gcc gtg gag tgg gag agc aat ggg cag ccg gag aac aac tac aag<br>Ile Ala Val Glu Trp Glu Ser Asn Gly Gln Pro Glu Asn Asn Tyr Lys<br>                405                            410                      415 | 1248 |
| acc aca cct ccc atg ctg gac tcc gac ggc tcc ttc ttc ctc tac agc<br>Thr Thr Pro Pro Met Leu Asp Ser Asp Gly Ser Phe Phe Leu Tyr Ser<br>                    420                            425                      430 | 1296 |
| aag ctc acc gtg gac aag agc agg tgg cag cag ggg aac gtc ttc tca<br>Lys Leu Thr Val Asp Lys Ser Arg Trp Gln Gln Gly Asn Val Phe Ser<br>                435                            440                      445 | 1344 |
| tgc tcc gtg atg cat gag gct ctg cac aac cac tac acg cag aag agc<br>Cys Ser Val Met His Glu Ala Leu His Asn His Tyr Thr Gln Lys Ser<br>    450                            455                            460 | 1392 |
| ctc tcc ctg tct ccg ggt aaa<br>Leu Ser Leu Ser Pro Gly Lys<br>465                    470 | 1413 |

```
<210> SEQ ID NO 123
<211> LENGTH: 471
<212> TYPE: PRT
<213> ORGANISM: ARTIFICIAL SEQUENCE
<220> FEATURE:
<223> OTHER INFORMATION: Synthetic Construct

<400> SEQUENCE: 123
```

Met Asp Met Arg Val Pro Ala Gln Leu Leu Gly Leu Leu Leu Leu Trp
1                 5                         10                         15

Leu Arg Gly Ala Arg Cys Gln Val Gln Leu Gln Glu Ser Gly Pro Gly
                   20                         25                         30

Leu Val Lys Pro Ser Glu Thr Leu Ser Leu Thr Cys Thr Val Ser Gly
                   35                         40                         45

-continued

```
Gly Ser Ile Ser Ser Tyr Tyr Trp Ser Trp Ile Arg Gln Pro Gly
 50                  55                  60

Lys Gly Leu Glu Trp Ile Gly Tyr Ile Tyr Tyr Ser Gly Asn Thr Asn
 65                  70                  75                  80

Ser Asn Pro Ser Leu Lys Ser Arg Val Thr Ile Ser Val Asp Thr Ser
                 85                  90                  95

Lys Asn Gln Phe Ser Leu Lys Leu Ser Ser Val Thr Ala Ala Asp Thr
                100                 105                 110

Ala Val Tyr Tyr Cys Ala Arg Thr Tyr Tyr Asp Ser Ser Gly Tyr Tyr
            115                 120                 125

Tyr Arg Ala Phe Asp Ile Trp Gly Gln Gly Thr Met Val Thr Val Ser
130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Leu
            340                 345                 350

Pro Ala Pro Ile Glu Lys Thr Ile Ser Lys Thr Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
450                 455                 460
```

```
Leu Ser Leu Ser Pro Gly Lys
465                 470

<210> SEQ ID NO 124
<211> LENGTH: 708
<212> TYPE: DNA
<213> ORGANISM: ARTIFICIAL SEQUENCE
<220> FEATURE:
<223> OTHER INFORMATION: aDNP 3C2 LC sequence
<220> FEATURE:
<221> NAME/KEY: CDS
<222> LOCATION: (1)..(708)

<400> SEQUENCE: 124 atg gac atg agg gtg ccc gct cag ctc ctg ggg ctc ctg ctg ctg tgg     48
Met Asp Met Arg Val Pro Ala Gln Leu Leu Gly Leu Leu Leu Leu Trp
1               5                   10                  15 ctg aga ggt gcg cgc tgt gac atc cag atg acc cag tct cca tcc tcc     96
Leu Arg Gly Ala Arg Cys Asp Ile Gln Met Thr Gln Ser Pro Ser Ser
            20                  25                  30 ctg tct gca tct gta gga gac aga gtc acc atc act tgc cgg gcg agt    144
Leu Ser Ala Ser Val Gly Asp Arg Val Thr Ile Thr Cys Arg Ala Ser
        35                  40                  45 cag ggc atg agc aat tat tta gcc tgg tat cag cag aaa cca agg aaa    192
Gln Gly Met Ser Asn Tyr Leu Ala Trp Tyr Gln Gln Lys Pro Arg Lys
    50                  55                  60 gtt cct aag ctc ctg atc tat gct gca tcc act ttg caa tca ggg gtc    240
Val Pro Lys Leu Leu Ile Tyr Ala Ala Ser Thr Leu Gln Ser Gly Val
65                  70                  75                  80 cca tct cgg ttc agt ggc agt gga tct ggg aca gat ttc act ctc acc    288
Pro Ser Arg Phe Ser Gly Ser Gly Ser Gly Thr Asp Phe Thr Leu Thr
                85                  90                  95 atc agc agc ctg cag ccg gaa gat gtt gca act tat tac tgt caa aag    336
Ile Ser Ser Leu Gln Pro Glu Asp Val Ala Thr Tyr Tyr Cys Gln Lys
            100                 105                 110 ttt aac agt gcc cca ttc act ttc ggc cct ggg acc aaa gtg gat atc    384
Phe Asn Ser Ala Pro Phe Thr Phe Gly Pro Gly Thr Lys Val Asp Ile
        115                 120                 125 aaa cgt acg gtg gct gca cca tct gtc ttc atc ttc ccg cca tct gat    432
Lys Arg Thr Val Ala Ala Pro Ser Val Phe Ile Phe Pro Pro Ser Asp
    130                 135                 140 gag cag ttg aaa tct gga act gcc tct gtt gtg tgc ctg ctg aat aac    480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc    528
Phe Tyr Pro Arg Glu Ala Lys Val Gln Trp Lys Val Asp Asn Ala Leu
                165                 170                 175 caa tcg ggt aac tcc cag gag agt gtc aca gag cag gac agc aag gac    576
Gln Ser Gly Asn Ser Gln Glu Ser Val Thr Glu Gln Asp Ser Lys Asp
            180                 185                 190 agc acc tac agc ctc agc agc acc ctg acg ctg agc aaa gca gac tac    624
Ser Thr Tyr Ser Leu Ser Ser Thr Leu Thr Leu Ser Lys Ala Asp Tyr
        195                 200                 205 gag aaa cac aaa gtc tac gcc tgc gaa gtc acc cat cag ggc ctg agc    672
Glu Lys His Lys Val Tyr Ala Cys Glu Val Thr His Gln Gly Leu Ser
    210                 215                 220 tcg ccc gtc aca aag agc ttc aac agg gga gag tgt                    708
Ser Pro Val Thr Lys Ser Phe Asn Arg Gly Glu Cys
225                 230                 235

<210> SEQ ID NO 125
<211> LENGTH: 236
```

```
<212> TYPE: PRT
<213> ORGANISM: ARTIFICIAL SEQUENCE
<220> FEATURE:
<223> OTHER INFORMATION: Synthetic Construct

<400> SEQUENCE: 125

Met Asp Met Arg Val Pro Ala Gln Leu Leu Gly Leu Leu Leu Trp
1               5                   10                  15

Leu Arg Gly Ala Arg Cys Asp Ile Gln Met Thr Gln Ser Pro Ser
            20                  25                  30

Leu Ser Ala Ser Val Gly Asp Arg Val Thr Ile Thr Cys Arg Ala Ser
        35                  40                  45

Gln Gly Met Ser Asn Tyr Leu Ala Trp Tyr Gln Lys Pro Arg Lys
    50                  55                  60

Val Pro Lys Leu Leu Ile Tyr Ala Ala Ser Thr Leu Gln Ser Gly Val
65                  70                  75                  80

Pro Ser Arg Phe Ser Gly Ser Gly Ser Gly Thr Asp Phe Thr Leu Thr
            85                  90                  95

Ile Ser Ser Leu Gln Pro Glu Asp Val Ala Thr Tyr Tyr Cys Gln Lys
            100                 105                 110

Phe Asn Ser Ala Pro Phe Thr Phe Gly Pro Gly Thr Lys Val Asp Ile
            115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 126
<211> LENGTH: 708
<212> TYPE: DNA
<213> ORGANISM: ARTIFICIAL SEQUENCE
<220> FEATURE:
<223> OTHER INFORMATION: aDNP 3H4 LC sequence
<220> FEATURE:
<221> NAME/KEY: CDS
<222> LOCATION: (1)..(708)

<400> SEQUENCE: 126 atg gac atg agg gtg ccc gct cag ctc ctg ggg ctc ctg ctg ctg tgg      48
Met Asp Met Arg Val Pro Ala Gln Leu Leu Gly Leu Leu Leu Leu Trp
1               5                   10                  15 ctg aga ggt gcg cgc tgt gac atc cag atg acc ctg tct cca tcc tcc      96
Leu Arg Gly Ala Arg Cys Asp Ile Gln Met Thr Leu Ser Pro Ser Ser
            20                  25                  30 ctg tct gca tct gta gga gac aga gtc acc atc act tgc cgg gca agt     144
Leu Ser Ala Ser Val Gly Asp Arg Val Thr Ile Thr Cys Arg Ala Ser
        35                  40                  45 cag ggc att aga aat gat tta ggc tgg tat cag cag aaa cca ggg aaa     192
Gln Gly Ile Arg Asn Asp Leu Gly Trp Tyr Gln Gln Lys Pro Gly Lys
```

|     |     |     |     |     |     |     |     |     |     |     |     |     |     |     |     | |
|---|---|---|---|---|---|---|---|---|---|---|---|---|---|---|---|---|
| | | 50 | | | | | 55 | | | | | 60 | | | | |
| gcc | cct | aag | cgc | ctg | atc | tat | gct | gca | tcc | agt | ttg | caa | agt | ggg | gtc | 240 |
| Ala | Pro | Lys | Arg | Leu | Ile | Tyr | Ala | Ala | Ser | Ser | Leu | Gln | Ser | Gly | Val | |
| 65 | | | | 70 | | | | | 75 | | | | | 80 | | |
| cca | tca | agg | ttc | agc | ggc | agt | gga | tct | ggg | aca | gaa | ttc | act | ctc | aca | 288 |
| Pro | Ser | Arg | Phe | Ser | Gly | Ser | Gly | Ser | Gly | Thr | Glu | Phe | Thr | Leu | Thr | |
| | | | | 85 | | | | | 90 | | | | | 95 | | |
| atc | agc | agc | ctg | cag | cct | gaa | gat | ttt | gca | act | tat | tac | tgt | cta | cag | 336 |
| Ile | Ser | Ser | Leu | Gln | Pro | Glu | Asp | Phe | Ala | Thr | Tyr | Tyr | Cys | Leu | Gln | |
| | | | 100 | | | | | 105 | | | | | 110 | | | |
| tat | aat | agt | tcc | ccg | tgg | acg | ttc | ggc | caa | ggg | acc | gag | gtg | gaa | atc | 384 |
| Tyr | Asn | Ser | Ser | Pro | Trp | Thr | Phe | Gly | Gln | Gly | Thr | Glu | Val | Glu | Ile | |
| | | 115 | | | | | 120 | | | | | 125 | | | | |
| aaa | cgt | acg | gtg | gct | gca | cca | tct | gtc | ttc | atc | ttc | ccg | cca | tct | gat | 432 |
| Lys | Arg | Thr | Val | Ala | Ala | Pro | Ser | Val | Phe | Ile | Phe | Pro | Pro | Ser | Asp | |
| | 130 | | | | | 135 | | | | | 140 | | | | | |
| gag | cag | ttg | aaa | tct | gga | act | gcc | tct | gtt | gtg | tgc | ctg | ctg | aat | aac | 480 |
| Glu | Gln | Leu | Lys | Ser | Gly | Thr | Ala | Ser | Val | Val | Cys | Leu | Leu | Asn | Asn | |
| 145 | | | | 150 | | | | | 155 | | | | | 160 | | |
| ttc | tat | ccc | aga | gag | gcc | aaa | gta | cag | tgg | aag | gtg | gat | aac | gcc | ctc | 528 |
| Phe | Tyr | Pro | Arg | Glu | Ala | Lys | Val | Gln | Trp | Lys | Val | Asp | Asn | Ala | Leu | |
| | | | | 165 | | | | | 170 | | | | | 175 | | |
| caa | tcg | ggt | aac | tcc | cag | gag | agt | gtc | aca | gag | cag | gac | agc | aag | gac | 576 |
| Gln | Ser | Gly | Asn | Ser | Gln | Glu | Ser | Val | Thr | Glu | Gln | Asp | Ser | Lys | Asp | |
| | | | 180 | | | | | 185 | | | | | 190 | | | |
| agc | acc | tac | agc | ctc | agc | agc | acc | ctg | acg | ctg | agc | aaa | gca | gac | tac | 624 |
| Ser | Thr | Tyr | Ser | Leu | Ser | Ser | Thr | Leu | Thr | Leu | Ser | Lys | Ala | Asp | Tyr | |
| | | 195 | | | | | 200 | | | | | 205 | | | | |
| gag | aaa | cac | aaa | gtc | tac | gcc | tgc | gaa | gtc | acc | cat | cag | ggc | ctg | agc | 672 |
| Glu | Lys | His | Lys | Val | Tyr | Ala | Cys | Glu | Val | Thr | His | Gln | Gly | Leu | Ser | |
| | 210 | | | | | 215 | | | | | 220 | | | | | |
| tcg | ccc | gtc | aca | aag | agc | ttc | aac | agg | gga | gag | tgt | | | | | 708 |
| Ser | Pro | Val | Thr | Lys | Ser | Phe | Asn | Arg | Gly | Glu | Cys | | | | | |
| 225 | | | | 230 | | | | | 235 | | | | | | | |

<210> SEQ ID NO 127
<211> LENGTH: 236
<212> TYPE: PRT
<213> ORGANISM: ARTIFICIAL SEQUENCE
<220> FEATURE:
<223> OTHER INFORMATION: Synthetic Construct

<400> SEQUENCE: 127

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Leu Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
            85                  90                  95

Ile Ser Ser Leu Gln Pro Glu Asp Phe Ala Thr Tyr Tyr Cys Leu Gln
        100                 105                 110

Tyr Asn Ser Ser Pro Trp Thr Phe Gly Gln Gly Thr Glu Val Glu Ile
    115                 120                 125

```
Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 128
<211> LENGTH: 1410
<212> TYPE: DNA
<213> ORGANISM: ARTIFICIAL SEQUENCE
<220> FEATURE:
<223> OTHER INFORMATION: aDNP 3H4 HC sequence
<220> FEATURE:
<221> NAME/KEY: CDS
<222> LOCATION: (1)..(1410)

<400> SEQUENCE: 128
```

| | | | | | | | | | | | | | | | | |
|---|---|---|---|---|---|---|---|---|---|---|---|---|---|---|---|---|
| atg | gac | atg | agg | gtg | ccc | gct | cag | ctc | ctg | ggg | ctc | ctg | ctg | ctg | tgg | 48 |
| Met | Asp | Met | Arg | Val | Pro | Ala | Gln | Leu | Leu | Gly | Leu | Leu | Leu | Leu | Trp | |
| 1 | | | | 5 | | | | | 10 | | | | | 15 | | |
| ctg | aga | ggt | gcg | cgc | tgt | cag | gtg | cag | ctg | cag | gag | tcg | ggc | cca | gga | 96 |
| Leu | Arg | Gly | Ala | Arg | Cys | Gln | Val | Gln | Leu | Gln | Glu | Ser | Gly | Pro | Gly | |
| | | | 20 | | | | | 25 | | | | | 30 | | | |
| ctg | gtg | aag | cct | tta | cag | acc | ctg | tcc | ctc | acc | tgc | act | gtc | tct | ggt | 144 |
| Leu | Val | Lys | Pro | Leu | Gln | Thr | Leu | Ser | Leu | Thr | Cys | Thr | Val | Ser | Gly | |
| | | 35 | | | | | 40 | | | | | 45 | | | | |
| ggc | tcc | atc | agc | agt | ggt | ggt | tat | tac | tgg | agc | tgg | atc | cgc | cag | cac | 192 |
| Gly | Ser | Ile | Ser | Ser | Gly | Gly | Tyr | Tyr | Trp | Ser | Trp | Ile | Arg | Gln | His | |
| 50 | | | | | 55 | | | | | 60 | | | | | | |
| cca | ggg | aag | ggc | ctg | gag | tgg | att | ggg | tac | atc | tat | tac | agt | agg | agc | 240 |
| Pro | Gly | Lys | Gly | Leu | Glu | Trp | Ile | Gly | Tyr | Ile | Tyr | Tyr | Ser | Arg | Ser | |
| 65 | | | | | 70 | | | | | 75 | | | | | 80 | |
| acc | tac | tac | aac | ccg | tcc | ctc | aag | agt | cga | gtt | acc | ata | tca | gta | gac | 288 |
| Thr | Tyr | Tyr | Asn | Pro | Ser | Leu | Lys | Ser | Arg | Val | Thr | Ile | Ser | Val | Asp | |
| | | | | 85 | | | | | 90 | | | | | 95 | | |
| acg | tct | aag | aac | cag | ttc | tcc | ctg | aag | ctg | agc | tct | gtg | aca | gcc | gcg | 336 |
| Thr | Ser | Lys | Asn | Gln | Phe | Ser | Leu | Lys | Leu | Ser | Ser | Val | Thr | Ala | Ala | |
| | | | 100 | | | | | 105 | | | | | 110 | | | |
| gac | acg | gcc | gtg | tat | tac | tgt | gcg | aga | acc | ggg | tat | agc | agt | ggc | tgg | 384 |
| Asp | Thr | Ala | Val | Tyr | Tyr | Cys | Ala | Arg | Thr | Gly | Tyr | Ser | Ser | Gly | Trp | |
| | | 115 | | | | | 120 | | | | | 125 | | | | |
| tac | cct | ttt | gac | tac | tgg | ggc | cag | gga | acc | ctg | gtc | acc | gtc | tct | agt | 432 |
| Tyr | Pro | Phe | Asp | Tyr | Trp | Gly | Gln | Gly | Thr | Leu | Val | Thr | Val | Ser | Ser | |
| | 130 | | | | | 135 | | | | | 140 | | | | | |
| gcc | tcc | acc | aag | ggc | cca | tcg | gtc | ttc | ccc | ctg | gcg | ccc | tgc | tcc | agg | 480 |
| Ala | Ser | Thr | Lys | Gly | Pro | Ser | Val | Phe | Pro | Leu | Ala | Pro | Cys | Ser | Arg | |
| 145 | | | | | 150 | | | | | 155 | | | | | 160 | |
| agc | acc | tcc | gag | agc | aca | gcg | gcc | ctg | ggc | tgc | ctg | gtc | aag | gac | tac | 528 |
| Ser | Thr | Ser | Glu | Ser | Thr | Ala | Ala | Leu | Gly | Cys | Leu | Val | Lys | Asp | Tyr | |
| | | | | 165 | | | | | 170 | | | | | 175 | | |

```
ttc ccc gaa ccg gtg acg gtg tcg tgg aac tca ggc gct ctg acc agc      576
Phe Pro Glu Pro Val Thr Val Ser Trp Asn Ser Gly Ala Leu Thr Ser
            180                 185                 190 ggc gtg cac acc ttc cca gct gtc cta cag tcc tca gga ctc tac tcc      624
Gly Val His Thr Phe Pro Ala Val Leu Gln Ser Ser Gly Leu Tyr Ser
        195                 200                 205 ctc agc agc gtg gtg acc gtg ccc tcc agc aac ttc ggc acc cag acc      672
Leu Ser Ser Val Val Thr Val Pro Ser Ser Asn Phe Gly Thr Gln Thr
    210                 215                 220 tac acc tgc aac gta gat cac aag ccc agc aac acc aag gtg gac aag      720
Tyr Thr Cys Asn Val Asp His Lys Pro Ser Asn Thr Lys Val Asp Lys
225                 230                 235                 240 aca gtt gag cgc aaa tgt tgt gtc gag tgc cca ccg tgc cca gca cca      768
Thr Val Glu Arg Lys Cys Cys Val Glu Cys Pro Pro Cys Pro Ala Pro
                245                 250                 255 cct gtg gca gga ccg tca gtc ttc ctc ttc ccc cca aaa ccc aag gac      816
Pro Val Ala Gly Pro Ser Val Phe Leu Phe Pro Pro Lys Pro Lys Asp
            260                 265                 270 acc ctc atg atc tcc cgg acc cct gag gtc acg tgc gtg gtg gtg gac      864
Thr Leu Met Ile Ser Arg Thr Pro Glu Val Thr Cys Val Val Val Asp
        275                 280                 285 gtg agc cac gaa gac ccc gag gtc cag ttc aac tgg tac gtg gac ggc      912
Val Ser His Glu Asp Pro Glu Val Gln Phe Asn Trp Tyr Val Asp Gly
    290                 295                 300 gtg gag gtg cat aat gcc aag aca aag cca cgg gag gag cag ttc aac      960
Val Glu Val His Asn Ala Lys Thr Lys Pro Arg Glu Glu Gln Phe Asn
305                 310                 315                 320 agc acg ttc cgt gtg gtc agc gtc ctc acc gtt gtg cac cag gac tgg     1008
Ser Thr Phe Arg Val Val Ser Val Leu Thr Val Val His Gln Asp Trp
                325                 330                 335 ctg aac ggc aag gag tac aag tgc aag gtc tcc aac aaa ggc ctc cca     1056
Leu Asn Gly Lys Glu Tyr Lys Cys Lys Val Ser Asn Lys Gly Leu Pro
            340                 345                 350 gcc ccc atc gag aaa acc atc tcc aaa acc aaa ggg cag ccc cga gaa     1104
Ala Pro Ile Glu Lys Thr Ile Ser Lys Thr Lys Gly Gln Pro Arg Glu
        355                 360                 365 cca cag gtg tac acc ctg ccc cca tcc cgg gag gag atg acc aag aac     1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tac ccc agc gac atc     1200
Gln Val Ser Leu Thr Cys Leu Val Lys Gly Phe Tyr Pro Ser Asp Ile
385                 390                 395                 400 gcc gtg gag tgg gag agc aat ggg cag ccg gag aac aac tac aag acc     1248
Ala Val Glu Trp Glu Ser Asn Gly Gln Pro Glu Asn Asn Tyr Lys Thr
                405                 410                 415 aca cct ccc atg ctg gac tcc gac ggc tcc ttc ttc ctc tac agc aag     1296
Thr Pro Pro Met Leu Asp Ser Asp Gly Ser Phe Phe Leu Tyr Ser Lys
            420                 425                 430 ctc acc gtg gac aag agc agg tgg cag cag ggg aac gtc ttc tca tgc     1344
Leu Thr Val Asp Lys Ser Arg Trp Gln Gln Gly Asn Val Phe Ser Cys
        435                 440                 445 tcc gtg atg cat gag gct ctg cac aac cac tac acg cag aag agc ctc     1392
Ser Val Met His Glu Ala Leu His Asn His Tyr Thr Gln Lys Ser Leu
    450                 455                 460 tcc ctg tct ccg ggt aaa                                             1410
Ser Leu Ser Pro Gly Lys
465                 470

<210> SEQ ID NO 129
<211> LENGTH: 470
```

```
<212> TYPE: PRT
<213> ORGANISM: ARTIFICIAL SEQUENCE
<220> FEATURE:
<223> OTHER INFORMATION: Synthetic Construct

<400> SEQUENCE: 129

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Pro Gly
            20                  25                  30

Leu Val Lys Pro Leu Gln Thr Leu Ser Leu Thr Cys Thr Val Ser Gly
        35                  40                  45

Gly Ser Ile Ser Ser Gly Gly Tyr Tyr Trp Ser Trp Ile Arg Gln His
    50                  55                  60

Pro Gly Lys Gly Leu Glu Trp Ile Gly Tyr Ile Tyr Tyr Ser Arg Ser
65                  70                  75                  80

Thr Tyr Tyr Asn Pro Ser Leu Lys Ser Arg Val Thr Ile Ser Val Asp
                85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Arg Thr Gly Tyr Ser Ser Gly Trp
        115                 120                 125

Tyr Pro Phe Asp Tyr Trp Gly Gln Gly Thr Leu Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380
```

```
Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 130
<211> LENGTH: 702
<212> TYPE: DNA
<213> ORGANISM: ARTIFICIAL SEQUENCE
<220> FEATURE:
<223> OTHER INFORMATION: aKLH 16.3.1 LC sequence
<220> FEATURE:
<221> NAME/KEY: CDS
<222> LOCATION: (1)..(702)

<400> SEQUENCE: 130 atg gac atg agg gtc cct gct cag ctc ctg ggg ctc ctg ctg ctc tgg    48
Met Asp Met Arg Val Pro Ala Gln Leu Leu Gly Leu Leu Leu Leu Trp
1               5                   10                  15 ctc tca ggt gcc aga tgt gac atc cag atg acc cag tct cca tcc tcc    96
Leu Ser Gly Ala Arg Cys Asp Ile Gln Met Thr Gln Ser Pro Ser Ser
            20                  25                  30 ctg tct gta tct gtg gga gac aga gtc acc atc act tgc cag gcg ggt   144
Leu Ser Val Ser Val Gly Asp Arg Val Thr Ile Thr Cys Gln Ala Gly
        35                  40                  45 cag gac att cgc aac tat tta aat tgg tat cag cag aaa cca ggg aaa   192
Gln Asp Ile Arg Asn Tyr Leu Asn Trp Tyr Gln Gln Lys Pro Gly Lys
    50                  55                  60 gcc cct aaa ctc ctg atc tac gat gca tcc aat ttg gaa aca ggg gtc   240
Ala Pro Lys Leu Leu Ile Tyr Asp Ala Ser Asn Leu Glu Thr Gly Val
65                  70                  75                  80 cca tca agg ttc agt gga agt gga tct ggg aca gct ttt act ttc acc   288
Pro Ser Arg Phe Ser Gly Ser Gly Ser Gly Thr Ala Phe Thr Phe Thr
                85                  90                  95 atc agc agc ctg cag cct gaa gat att gca aca tat tac tgt caa cag   336
Ile Ser Ser Leu Gln Pro Glu Asp Ile Ala Thr Tyr Tyr Cys Gln Gln
            100                 105                 110 tat gat aat ctc act ttt ggc cag ggg acc aaa ctg gag atc aaa cga   384
Tyr Asp Asn Leu Thr Phe Gly Gln Gly Thr Lys Leu Glu Ile Lys Arg
        115                 120                 125 act gtg gct gca cca tct gtc ttc atc ttc ccg cca tct gat gag cag   432
Thr Val Ala Ala Pro Ser Val Phe Ile Phe Pro Pro Ser Asp Glu Gln
    130                 135                 140 ttg aaa tct gga act gcc tct gtt gtg tgc ctg ctg aat aac ttc tat   480
Leu Lys Ser Gly Thr Ala Ser Val Val Cys Leu Leu Asn Asn Phe Tyr
145                 150                 155                 160 ccc aga gag gcc aaa gta cag tgg aag gtg gat aac gcc ctc caa tcg   528
Pro Arg Glu Ala Lys Val Gln Trp Lys Val Asp Asn Ala Leu Gln Ser
                165                 170                 175 ggt aac tcc cag gag agt gtc aca gag cag gac agc aag gac agc acc   576
Gly Asn Ser Gln Glu Ser Val Thr Glu Gln Asp Ser Lys Asp Ser Thr
            180                 185                 190
```

```
tac agc ctc agc agc acc ctg acg ctg agc aaa gca gac tac gag aaa      624
Tyr Ser Leu Ser Ser Thr Leu Thr Leu Ser Lys Ala Asp Tyr Glu Lys
            195                 200                 205 cac aaa gtc tac gcc tgc gaa gtc acc cat cag ggc ctg agc tcg ccc      672
His Lys Val Tyr Ala Cys Glu Val Thr His Gln Gly Leu Ser Ser Pro
    210                 215                 220 gtc aca aag agc ttc aac agg gga gag tgt                              702
Val Thr Lys Ser Phe Asn Arg Gly Glu Cys
225                 230
```

<210> SEQ ID NO 131  
<211> LENGTH: 234  
<212> TYPE: PRT  
<213> ORGANISM: ARTIFICIAL SEQUENCE  
<220> FEATURE:  
<223> OTHER INFORMATION: Synthetic Construct

<400> SEQUENCE: 131

```
Met Asp Met Arg Val Pro Ala Gln Leu Leu Gly Leu Leu Leu Leu Trp
1               5                   10                  15

Leu Ser Gly Ala Arg Cys Asp Ile Gln Met Thr Gln Ser Pro Ser Ser
            20                  25                  30

Leu Ser Val Ser Val Gly Asp Arg Val Thr Ile Thr Cys Gln Ala Gly
        35                  40                  45

Gln Asp Ile Arg Asn Tyr Leu Asn Trp Tyr Gln Gln Lys Pro Gly Lys
    50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Ala Phe Thr Phe Thr
                85                  90                  95

Ile Ser Ser Leu Gln Pro Glu Asp Ile Ala Thr Tyr Tyr Cys Gln Gln
            100                 105                 110

Tyr Asp Asn Leu Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 132  
<211> LENGTH: 1389  
<212> TYPE: DNA  
<213> ORGANISM: ARTIFICIAL SEQUENCE  
<220> FEATURE:  
<223> OTHER INFORMATION: aKLH 16.3.1 HC sequence  
<220> FEATURE:  
<221> NAME/KEY: CDS  
<222> LOCATION: (1)..(1389)

<400> SEQUENCE: 132

```
atg gaa ttg gga ctg agc tgg gtt ttc ctt ttt gct ata tta gaa ggt      48
Met Glu Leu Gly Leu Ser Trp Val Phe Leu Phe Ala Ile Leu Glu Gly
1               5                   10                  15 gtc cag tgt gag gtg cag ctg gtg gag tct ggg gga ggc ttg gta cag      96
Val Gln Cys Glu Val Gln Leu Val Glu Ser Gly Gly Gly Leu Val Gln
            20                  25                  30 cct ggg ggg tcc ctg aga ctc tcc tgt gca gcc tct gga ttc acc ttc     144
Pro Gly Gly Ser Leu Arg Leu Ser Cys Ala Ala Ser Gly Phe Thr Phe
        35                  40                  45 agt aac tac gac atg tac tgg gtc cgc caa act aca gga aaa ggt ctg     192
Ser Asn Tyr Asp Met Tyr Trp Val Arg Gln Thr Thr Gly Lys Gly Leu
    50                  55                  60 gag tgg gtc tca gct att ggt act gct ggt gac aca tac tat cca ggc     240
Glu Trp Val Ser Ala Ile Gly Thr Ala Gly Asp Thr Tyr Tyr Pro Gly
65                  70                  75                  80 tcc gtg aag ggc cga ttc acc atc tcc aga gaa aat gcc aag aac tcc     288
Ser Val Lys Gly Arg Phe Thr Ile Ser Arg Glu Asn Ala Lys Asn Ser
                85                  90                  95 ttg tat ctt caa atg aac agc ctg aga gcc ggg gac acg gct gtg tat     336
Leu Tyr Leu Gln Met Asn Ser Leu Arg Ala Gly Asp Thr Ala Val Tyr
            100                 105                 110 tac tgt gca aga gag aag tct agc acc tcg gcc ttt gac tac tgg ggc     384
Tyr Cys Ala Arg Glu Lys Ser Ser Thr Ser Ala Phe Asp Tyr Trp Gly
        115                 120                 125 cag gga acc ctg gtc acc gtc tcc tca gcc tcc acc aag ggc cca tcg     432
Gln Gly Thr Leu Val Thr Val Ser Ser Ala Ser Thr Lys Gly Pro Ser
    130                 135                 140 gtc ttc ccc ctg gcg ccc tgc tcc agg agc acc tcc gag agc aca gcg     480
Val Phe Pro Leu Ala Pro Cys Ser Arg Ser Thr Ser Glu Ser Thr Ala
145                 150                 155                 160 gcc ctg ggc tgc ctg gtc aag gac tac ttc ccc gaa ccg gtg acg gtg     528
Ala Leu Gly Cys Leu Val Lys Asp Tyr Phe Pro Glu Pro Val Thr Val
                165                 170                 175 tcg tgg aac tca ggc gct ctg acc agc ggc gtg cac acc ttc cca gct     576
Ser Trp Asn Ser Gly Ala Leu Thr Ser Gly Val His Thr Phe Pro Ala
            180                 185                 190 gtc cta cag tcc tca gga ctc tac tcc ctc agc agc gtg gtg acc gtg     624
Val Leu Gln Ser Ser Gly Leu Tyr Ser Leu Ser Ser Val Val Thr Val
        195                 200                 205 ccc tcc agc aac ttc ggc acc cag acc tac acc tgc aac gta gat cac     672
Pro Ser Ser Asn Phe Gly Thr Gln Thr Tyr Thr Cys Asn Val Asp His
    210                 215                 220 aag ccc agc aac acc aag gtg gac aag aca gtt gag cgc aaa tgt tgt     720
Lys Pro Ser Asn Thr Lys Val Asp Lys Thr Val Glu Arg Lys Cys Cys
225                 230                 235                 240 gtc gag tgc cca ccg tgc cca gca cca cct gtg gca gga ccg tca gtc     768
Val Glu Cys Pro Pro Cys Pro Ala Pro Pro Val Ala Gly Pro Ser Val
                245                 250                 255 ttc ctc ttc ccc cca aaa ccc aag gac acc ctc atg atc tcc cgg acc     816
Phe Leu Phe Pro Pro Lys Pro Lys Asp Thr Leu Met Ile Ser Arg Thr
            260                 265                 270 cct gag gtc acg tgc gtg gtg gtg gac gtg agc cac gaa gac ccc gag     864
Pro Glu Val Thr Cys Val Val Val Asp Val Ser His Glu Asp Pro Glu
        275                 280                 285 gtc cag ttc aac tgg tac gtg gac ggc gtg gag gtg cat aat gcc aag     912
Val Gln Phe Asn Trp Tyr Val Asp Gly Val Glu Val His Asn Ala Lys
    290                 295                 300 aca aag cca cgg gag gag cag ttc aac agc acg ttc cgt gtg gtc agc     960
Thr Lys Pro Arg Glu Glu Gln Phe Asn Ser Thr Phe Arg Val Val Ser
```

```
                305                 310                 315                 320
gtc ctc acc gtt gtg cac cag gac tgg ctg aac ggc aag gag tac aag     1008
Val Leu Thr Val Val His Gln Asp Trp Leu Asn Gly Lys Glu Tyr Lys
                        325                 330                 335 tgc aag gtc tcc aac aaa ggc ctc cca gcc ccc atc gag aaa acc atc     1056
Cys Lys Val Ser Asn Lys Gly Leu Pro Ala Pro Ile Glu Lys Thr Ile
                340                 345                 350 tcc aaa acc aaa ggg cag ccc cga gaa cca cag gtg tac acc ctg ccc     1104
Ser Lys Thr Lys Gly Gln Pro Arg Glu Pro Gln Val Tyr Thr Leu Pro
            355                 360                 365 cca tcc cgg gag gag atg acc aag aac cag gtc agc ctg acc tgc ctg     1152
Pro Ser Arg Glu Glu Met Thr Lys Asn Gln Val Ser Leu Thr Cys Leu
        370                 375                 380 gtc aaa ggc ttc tac ccc agc gac atc gcc gtg gag tgg gag agc aat     1200
Val Lys Gly Phe Tyr Pro Ser Asp Ile Ala Val Glu Trp Glu Ser Asn
385                 390                 395                 400 ggg cag ccg gag aac aac tac aag acc aca cct ccc atg ctg gac tcc     1248
Gly Gln Pro Glu Asn Asn Tyr Lys Thr Thr Pro Pro Met Leu Asp Ser
                405                 410                 415 gac ggc tcc ttc ttc ctc tac agc aag ctc acc gtg gac aag agc agg     1296
Asp Gly Ser Phe Phe Leu Tyr Ser Lys Leu Thr Val Asp Lys Ser Arg
                420                 425                 430 tgg cag cag ggg aac gtc ttc tca tgc tcc gtg atg cat gag gct ctg     1344
Trp Gln Gln Gly Asn Val Phe Ser Cys Ser Val Met His Glu Ala Leu
            435                 440                 445 cac aac cac tac acg cag aag agc ctc tcc ctg tct ccg ggt aaa         1389
His Asn His Tyr Thr Gln Lys Ser Leu Ser Leu Ser Pro Gly Lys
        450                 455                 460

<210> SEQ ID NO 133
<211> LENGTH: 463
<212> TYPE: PRT
<213> ORGANISM: ARTIFICIAL SEQUENCE
<220> FEATURE:
<223> OTHER INFORMATION: Synthetic Construct

<400> SEQUENCE: 133

Met Glu Leu Gly Leu Ser Trp Val Phe Leu Phe Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Asp Met Tyr Trp Val Arg Gln Thr Thr Gly Lys Gly Leu
    50                  55                  60

Glu Trp Val Ser Ala Ile Gly Thr Ala Gly Asp Thr Tyr Tyr Pro Gly
65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Ala Arg Glu Lys Ser Ser Thr Ser Ala Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
```

165                 170                 175
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 134
<211> LENGTH: 708
<212> TYPE: DNA
<213> ORGANISM: ARTIFICIAL SEQUENCE
<220> FEATURE:
<223> OTHER INFORMATION: aKLH 108.1.2 LC sequence
<220> FEATURE:
<221> NAME/KEY: CDS
<222> LOCATION: (1)..(708)

<400> SEQUENCE: 134 atg gaa acc cca gcg cag ctt ctc ttc ctc ctg cta ctc tgg ctc cca         48
Met Glu Thr Pro Ala Gln Leu Leu Phe Leu Leu Leu Leu Trp Leu Pro
1               5                   10                  15 gat acc acc gga gaa att gtg ttg acg cag tct cca ggc acc ctg tct         96
Asp Thr Thr Gly Glu Ile Val Leu Thr Gln Ser Pro Gly Thr Leu Ser
                20                  25                  30 ttg tct cca ggg gaa aga gcc acc ctc tcc tgt agg gcc agt cag aat        144
Leu Ser Pro Gly Glu Arg Ala Thr Leu Ser Cys Arg Ala Ser Gln Asn

```
                 35                  40                  45
att agc acc aac tac tta gcc tgg tac cag cag aaa cct ggc cag gct        192
Ile Ser Thr Asn Tyr Leu Ala Trp Tyr Gln Gln Lys Pro Gly Gln Ala
 50                  55                  60 ccc agg ttc ctc att tat ggt gca tcc agc agg gcc act ggc atc cca        240
Pro Arg Phe Leu Ile Tyr Gly Ala Ser Ser Arg Ala Thr Gly Ile Pro
65                  70                  75                  80 gac agg ttc agt ggc agt ggg tct ggg aca gac ttc act ctc acc atc        288
Asp Arg Phe Ser Gly Ser Gly Ser Gly Thr Asp Phe Thr Leu Thr Ile
                 85                  90                  95 agc aga ctg gag cct gaa gat ttt gca gtg tat tac tgt cag cag ttt        336
Ser Arg Leu Glu Pro Glu Asp Phe Ala Val Tyr Tyr Cys Gln Gln Phe
             100                 105                 110 ggg cgc tca cct cgg tgc agt ttt ggc cag ggg acc aag ctg gag atc        384
Gly Arg Ser Pro Arg Cys Ser Phe Gly Gln Gly Thr Lys Leu Glu Ile
         115                 120                 125 aaa cga act gtg gct gca cca tct gtc ttc atc ttc ccg cca tct gat        432
Lys Arg Thr Val Ala Ala Pro Ser Val Phe Ile Phe Pro Pro Ser Asp
130                 135                 140 gag cag ttg aaa tct gga act gcc tct gtt gtg tgc ctg ctg aat aac        480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc        528
Phe Tyr Pro Arg Glu Ala Lys Val Gln Trp Lys Val Asp Asn Ala Leu
                165                 170                 175 caa tcg ggt aac tcc cag gag agt gtc aca gag cag gac agc aag gac        576
Gln Ser Gly Asn Ser Gln Glu Ser Val Thr Glu Gln Asp Ser Lys Asp
            180                 185                 190 agc acc tac agc ctc agc agc acc ctg acg ctg agc aaa gca gac tac        624
Ser Thr Tyr Ser Leu Ser Ser Thr Leu Thr Leu Ser Lys Ala Asp Tyr
        195                 200                 205 gag aaa cac aaa gtc tac gcc tgc gaa gtc acc cat cag ggc ctg agc        672
Glu Lys His Lys Val Tyr Ala Cys Glu Val Thr His Gln Gly Leu Ser
210                 215                 220 tcg ccc gtc aca aag agc ttc aac agg gga gag tgt                        708
Ser Pro Val Thr Lys Ser Phe Asn Arg Gly Glu Cys
225                 230                 235

<210> SEQ ID NO 135
<211> LENGTH: 236
<212> TYPE: PRT
<213> ORGANISM: ARTIFICIAL SEQUENCE
<220> FEATURE:
<223> OTHER INFORMATION: Synthetic Construct

<400> SEQUENCE: 135

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Asn
        35                  40                  45

Ile Ser Thr Asn Tyr Leu Ala Trp Tyr Gln Gln Lys Pro Gly Gln Ala
    50                  55                  60

Pro Arg Phe Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Phe
```

```
                    100                 105                 110
Gly Arg Ser Pro Arg Cys Ser Phe Gly Gln Gly Thr Lys Leu Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
        180                 185                 190

Ser Thr Tyr Ser Leu Ser Ser Thr Leu Thr Leu Ser Lys Ala Asp Tyr
    195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 136
<211> LENGTH: 708
<212> TYPE: DNA
<213> ORGANISM: ARTIFICIAL SEQUENCE
<220> FEATURE:
<223> OTHER INFORMATION: aKLH 108.1.2 (N>Q, C>S) LC sequence
<220> FEATURE:
<221> NAME/KEY: CDS
<222> LOCATION: (1)..(708)

<400> SEQUENCE: 136 atg gaa acc cca gcg cag ctt ctc ttc ctc ctg cta ctc tgg ctc cca      48
Met Glu Thr Pro Ala Gln Leu Leu Phe Leu Leu Leu Leu Trp Leu Pro
1               5                   10                  15 gat acc acc gga gaa att gtg ttg acg cag tct cca ggc acc ctg tct      96
Asp Thr Thr Gly Glu Ile Val Leu Thr Gln Ser Pro Gly Thr Leu Ser
                20                  25                  30 ttg tct cca ggg gaa aga gcc acc ctc tcc tgt agg gcc agt cag caa     144
Leu Ser Pro Gly Glu Arg Ala Thr Leu Ser Cys Arg Ala Ser Gln Gln
            35                  40                  45 att agc acc aac tac tta gcc tgg tac cag cag aaa cct ggc cag gct     192
Ile Ser Thr Asn Tyr Leu Ala Trp Tyr Gln Gln Lys Pro Gly Gln Ala
        50                  55                  60 ccc agg ttc ctc att tat ggt gca tcc agc agg gcc act ggc atc cca     240
Pro Arg Phe Leu Ile Tyr Gly Ala Ser Ser Arg Ala Thr Gly Ile Pro
65                  70                  75                  80 gac agg ttc agt ggc agt ggg tct ggg aca gac ttc act ctc acc atc     288
Asp Arg Phe Ser Gly Ser Gly Ser Gly Thr Asp Phe Thr Leu Thr Ile
                85                  90                  95 agc aga ctg gag cct gaa gat ttt gca gtg tat tac tgt cag cag ttt     336
Ser Arg Leu Glu Pro Glu Asp Phe Ala Val Tyr Tyr Cys Gln Gln Phe
                100                 105                 110 ggg cgc tca cct cgg agc agt ttt ggc cag ggg acc aag ctg gag atc     384
Gly Arg Ser Pro Arg Ser Ser Phe Gly Gln Gly Thr Lys Leu Glu Ile
            115                 120                 125 aaa cga act gtg gct gca cca tct gtc ttc atc ttc ccg cca tct gat     432
Lys Arg Thr Val Ala Ala Pro Ser Val Phe Ile Phe Pro Pro Ser Asp
130                 135                 140 gag cag ttg aaa tct gga act gcc tct gtt gtg tgc ctg ctg aat aac     480
Glu Gln Leu Lys Ser Gly Thr Ala Ser Val Val Cys Leu Leu Asn Asn
145                 150                 155                 160
```

| | | | | | | | | | | | | | | | | |
|---|---|---|---|---|---|---|---|---|---|---|---|---|---|---|---|---|
| ttc | tat | ccc | aga | gag | gcc | aaa | gta | cag | tgg | aag | gtg | gat | aac | gcc | ctc | 528 |
| Phe | Tyr | Pro | Arg | Glu | Ala | Lys | Val | Gln | Trp | Lys | Val | Asp | Asn | Ala | Leu | |
| | | | | 165 | | | | | 170 | | | | | 175 | | |
| caa | tcg | ggt | aac | tcc | cag | gag | agt | gtc | aca | gag | cag | gac | agc | aag | gac | 576 |
| Gln | Ser | Gly | Asn | Ser | Gln | Glu | Ser | Val | Thr | Glu | Gln | Asp | Ser | Lys | Asp | |
| | | | 180 | | | | | 185 | | | | | 190 | | | |
| agc | acc | tac | agc | ctc | agc | agc | acc | ctg | acg | ctg | agc | aaa | gca | gac | tac | 624 |
| Ser | Thr | Tyr | Ser | Leu | Ser | Ser | Thr | Leu | Thr | Leu | Ser | Lys | Ala | Asp | Tyr | |
| | | | 195 | | | | | 200 | | | | | 205 | | | |
| gag | aaa | cac | aaa | gtc | tac | gcc | tgc | gaa | gtc | acc | cat | cag | ggc | ctg | agc | 672 |
| Glu | Lys | His | Lys | Val | Tyr | Ala | Cys | Glu | Val | Thr | His | Gln | Gly | Leu | Ser | |
| | 210 | | | | | 215 | | | | | 220 | | | | | |
| tcg | ccc | gtc | aca | aag | agc | ttc | aac | agg | gga | gag | tgt | | | | | 708 |
| Ser | Pro | Val | Thr | Lys | Ser | Phe | Asn | Arg | Gly | Glu | Cys | | | | | |
| 225 | | | | | 230 | | | | | 235 | | | | | | |

<210> SEQ ID NO 137
<211> LENGTH: 236
<212> TYPE: PRT
<213> ORGANISM: ARTIFICIAL SEQUENCE
<220> FEATURE:
<223> OTHER INFORMATION: Synthetic Construct

<400> SEQUENCE: 137

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Gln
            35                  40                  45

Ile Ser Thr Asn Tyr Leu Ala Trp Tyr Gln Gln Lys Pro Gly Gln Ala
        50                  55                  60

Pro Arg Phe Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Phe
            100                 105                 110

Gly Arg Ser Pro Arg Ser Ser Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 138
<211> LENGTH: 1410
<212> TYPE: DNA

```
<213> ORGANISM: ARTIFICIAL SEQUENCE
<220> FEATURE:
<223> OTHER INFORMATION: aKLH 108.1.2 HC sequence
<220> FEATURE:
<221> NAME/KEY: CDS
<222> LOCATION: (1)..(1410)

<400> SEQUENCE: 138 atg aag cac ctg tgg ttc ttc ctc ctg ctg gtg gcg gct ccc aga tgg      48
Met Lys His Leu Trp Phe Phe Leu Leu Leu Val Ala Ala Pro Arg Trp
1               5                   10                  15 gtc ctg tcc cag ctg cag ctg caa gag tcg ggc cca gga ctg atg aag      96
Val Leu Ser Gln Leu Gln Leu Gln Glu Ser Gly Pro Gly Leu Met Lys
            20                  25                  30 cct tcg gag acc ctg tcc ctc acc tgc act gtc tct ggt ggc tcc atc     144
Pro Ser Glu Thr Leu Ser Leu Thr Cys Thr Val Ser Gly Gly Ser Ile
        35                  40                  45 agc agt agt agt tac ttc tgg ggc tgg atc cgc cag ccc cca ggg aag     192
Ser Ser Ser Ser Tyr Phe Trp Gly Trp Ile Arg Gln Pro Pro Gly Lys
    50                  55                  60 gga ctg gag tgg att ggg agt atc tat tat agt ggg aac acc ttc tac     240
Gly Leu Glu Trp Ile Gly Ser Ile Tyr Tyr Ser Gly Asn Thr Phe Tyr
65                  70                  75                  80 aac ccg tcc ctc aag agt cga gtc acc ata tcc gtt gac acg tcc aag     288
Asn Pro Ser Leu Lys Ser Arg Val Thr Ile Ser Val Asp Thr Ser Lys
                85                  90                  95 aac cag ttc tcc ctg aag ctt aac tct atg acc gcc gca gac acg gct     336
Asn Gln Phe Ser Leu Lys Leu Asn Ser Met Thr Ala Ala Asp Thr Ala
            100                 105                 110 gtg tat ttc tgt gcg aga caa ggg ggt ata gca gct cgt acc gga tac     384
Val Tyr Phe Cys Ala Arg Gln Gly Gly Ile Ala Ala Arg Thr Gly Tyr
        115                 120                 125 tgg tac ttc gat ctc tgg ggc cgt ggc acc acg gtc acc gtc tcc tca     432
Trp Tyr Phe Asp Leu Trp Gly Arg Gly Thr Thr Val Thr Val Ser Ser
    130                 135                 140 gcc tcc acc aag ggc cca tcg gtc ttc ccc ctg gcg ccc tgc tcc agg     480
Ala Ser Thr Lys Gly Pro Ser Val Phe Pro Leu Ala Pro Cys Ser Arg
145                 150                 155                 160 agc acc tcc gag agc aca gcg gcc ctg ggc tgc ctg gtc aag gac tac     528
Ser Thr Ser Glu Ser Thr Ala Ala Leu Gly Cys Leu Val Lys Asp Tyr
                165                 170                 175 ttc ccc gaa ccg gtg acg gtg tcg tgg aac tca ggc gct ctg acc agc     576
Phe Pro Glu Pro Val Thr Val Ser Trp Asn Ser Gly Ala Leu Thr Ser
            180                 185                 190 ggc gtg cac acc ttc cca gct gtc cta cag tcc tca gga ctc tac tcc     624
Gly Val His Thr Phe Pro Ala Val Leu Gln Ser Ser Gly Leu Tyr Ser
        195                 200                 205 ctc agc agc gtg gtg acc gtg ccc tcc agc aac ttc ggc acc cag acc     672
Leu Ser Ser Val Val Thr Val Pro Ser Ser Asn Phe Gly Thr Gln Thr
    210                 215                 220 tac acc tgc aac gta gat cac aag ccc agc aac acc aag gtg gac aag     720
Tyr Thr Cys Asn Val Asp His Lys Pro Ser Asn Thr Lys Val Asp Lys
225                 230                 235                 240 aca gtt gag cgc aaa tgt tgt gtc gag tgc cca ccg tgc cca gca cca     768
Thr Val Glu Arg Lys Cys Cys Val Glu Cys Pro Pro Cys Pro Ala Pro
                245                 250                 255 cct gtg gca gga ccg tca gtc ttc ctc ttc ccc cca aaa ccc aag gac     816
Pro Val Ala Gly Pro Ser Val Phe Leu Phe Pro Pro Lys Pro Lys Asp
            260                 265                 270 acc ctc atg atc tcc cgg acc cct gag gtc acg tgc gtg gtg gtg gac     864
Thr Leu Met Ile Ser Arg Thr Pro Glu Val Thr Cys Val Val Val Asp
```

```
            275                 280                 285
gtg agc cac gaa gac ccc gag gtc cag ttc aac tgg tac gtg gac ggc    912
Val Ser His Glu Asp Pro Glu Val Gln Phe Asn Trp Tyr Val Asp Gly
    290                 295                 300 gtg gag gtg cat aat gcc aag aca aag cca cgg gag gag cag ttc aac    960
Val Glu Val His Asn Ala Lys Thr Lys Pro Arg Glu Glu Gln Phe Asn
305                 310                 315                 320 agc acg ttc cgt gtg gtc agc gtc ctc acc gtt gtg cac cag gac tgg   1008
Ser Thr Phe Arg Val Val Ser Val Leu Thr Val Val His Gln Asp Trp
                325                 330                 335 ctg aac ggc aag gag tac aag tgc aag gtc tcc aac aaa ggc ctc cca   1056
Leu Asn Gly Lys Glu Tyr Lys Cys Lys Val Ser Asn Lys Gly Leu Pro
            340                 345                 350 gcc ccc atc gag aaa acc atc tcc aaa acc aaa ggg cag ccc cga gaa   1104
Ala Pro Ile Glu Lys Thr Ile Ser Lys Thr Lys Gly Gln Pro Arg Glu
                355                 360                 365 cca cag gtg tac acc ctg ccc cca tcc cgg gag gag atg acc aag aac   1152
Pro Gln Val Tyr Thr Leu Pro Pro Ser Arg Glu Glu Met Thr Lys Asn
        370                 375                 380 cag gtc agc ctg acc tgc ctg gtc aaa ggc ttc tac ccc agc gac atc   1200
Gln Val Ser Leu Thr Cys Leu Val Lys Gly Phe Tyr Pro Ser Asp Ile
385                 390                 395                 400 gcc gtg gag tgg gag agc aat ggg cag ccg gag aac aac tac aag acc   1248
Ala Val Glu Trp Glu Ser Asn Gly Gln Pro Glu Asn Asn Tyr Lys Thr
                405                 410                 415 aca cct ccc atg ctg gac tcc gac ggc tcc ttc ttc ctc tac agc aag   1296
Thr Pro Pro Met Leu Asp Ser Asp Gly Ser Phe Phe Leu Tyr Ser Lys
            420                 425                 430 ctc acc gtg gac aag agc agg tgg cag cag ggg aac gtc ttc tca tgc   1344
Leu Thr Val Asp Lys Ser Arg Trp Gln Gln Gly Asn Val Phe Ser Cys
        435                 440                 445 tcc gtg atg cat gag gct ctg cac aac cac tac acg cag aag agc ctc   1392
Ser Val Met His Glu Ala Leu His Asn His Tyr Thr Gln Lys Ser Leu
450                 455                 460 tcc ctg tct ccg ggt aaa                                           1410
Ser Leu Ser Pro Gly Lys
465             470

<210> SEQ ID NO 139
<211> LENGTH: 470
<212> TYPE: PRT
<213> ORGANISM: ARTIFICIAL SEQUENCE
<220> FEATURE:
<223> OTHER INFORMATION: Synthetic Construct

<400> SEQUENCE: 139

Met Lys His Leu Trp Phe Phe Leu Leu Leu Val Ala Ala Pro Arg Trp
1               5                   10                  15

Val Leu Ser Gln Leu Gln Leu Gln Glu Ser Gly Pro Gly Leu Met Lys
            20                  25                  30

Pro Ser Glu Thr Leu Ser Leu Thr Cys Thr Val Ser Gly Gly Ser Ile
        35                  40                  45

Ser Ser Ser Ser Tyr Phe Trp Gly Trp Ile Arg Gln Pro Pro Gly Lys
    50                  55                  60

Gly Leu Glu Trp Ile Gly Ser Ile Tyr Tyr Ser Gly Asn Thr Phe Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Asn Ser Met Thr Ala Ala Asp Thr Ala
```

```
            100             105             110
Val Tyr Phe Cys Ala Arg Gln Gly Gly Ile Ala Ala Arg Thr Gly Tyr
            115             120             125

Trp Tyr Phe Asp Leu Trp Gly Arg Gly Thr Thr Val Thr Val Ser Ser
            130             135             140

Ala Ser Thr Lys Gly Pro Ser Val Phe Pro Leu Ala Pro Cys Ser Arg
145             150             155             160

Ser Thr Ser Glu Ser Thr Ala Ala Leu Gly Cys Leu Val Lys Asp Tyr
                165             170             175

Phe Pro Glu Pro Val Thr Val Ser Trp Asn Ser Gly Ala Leu Thr Ser
            180             185             190

Gly Val His Thr Phe Pro Ala Val Leu Gln Ser Ser Gly Leu Tyr Ser
            195             200             205

Leu Ser Ser Val Val Thr Val Pro Ser Ser Asn Phe Gly Thr Gln Thr
210             215             220

Tyr Thr Cys Asn Val Asp His Lys Pro Ser Asn Thr Lys Val Asp Lys
225             230             235             240

Thr Val Glu Arg Lys Cys Cys Val Glu Cys Pro Pro Cys Pro Ala Pro
            245             250             255

Pro Val Ala Gly Pro Ser Val Phe Leu Phe Pro Pro Lys Pro Lys Asp
            260             265             270

Thr Leu Met Ile Ser Arg Thr Pro Glu Val Thr Cys Val Val Val Asp
            275             280             285

Val Ser His Glu Asp Pro Glu Val Gln Phe Asn Trp Tyr Val Asp Gly
290             295             300

Val Glu Val His Asn Ala Lys Thr Lys Pro Arg Glu Glu Gln Phe Asn
305             310             315             320

Ser Thr Phe Arg Val Val Ser Val Leu Thr Val His Gln Asp Trp
            325             330             335

Leu Asn Gly Lys Glu Tyr Lys Cys Lys Val Ser Asn Lys Gly Leu Pro
            340             345             350

Ala Pro Ile Glu Lys Thr Ile Ser Lys Thr Lys Gly Gln Pro Arg Glu
            355             360             365

Pro Gln Val Tyr Thr Leu Pro Pro Ser Arg Glu Glu Met Thr Lys Asn
            370             375             380

Gln Val Ser Leu Thr Cys Leu Val Lys Gly Phe Tyr Pro Ser Asp Ile
385             390             395             400

Ala Val Glu Trp Glu Ser Asn Gly Gln Pro Glu Asn Asn Tyr Lys Thr
                405             410             415

Thr Pro Pro Met Leu Asp Ser Asp Gly Ser Phe Phe Leu Tyr Ser Lys
            420             425             430

Leu Thr Val Asp Lys Ser Arg Trp Gln Gln Gly Asn Val Phe Ser Cys
            435             440             445

Ser Val Met His Glu Ala Leu His Asn His Tyr Thr Gln Lys Ser Leu
450             455             460

Ser Leu Ser Pro Gly Lys
465             470

<210> SEQ ID NO 140
<211> LENGTH: 708
<212> TYPE: DNA
<213> ORGANISM: ARTIFICIAL SEQUENCE
<220> FEATURE:
<223> OTHER INFORMATION: aKLH 120.6 LC sequence
<220> FEATURE:
```

<221> NAME/KEY: CDS
<222> LOCATION: (1)..(708)

<400> SEQUENCE: 140

| | | | | | | | | | | | | | | | | |
|---|---|---|---|---|---|---|---|---|---|---|---|---|---|---|---|---|
| atg | gac | atg | agg | gtc | ccc | gct | cag | ctc | ctg | ggg | ctc | ctg | ctg | ctc | tgg | 48 |
| Met | Asp | Met | Arg | Val | Pro | Ala | Gln | Leu | Leu | Gly | Leu | Leu | Leu | Leu | Trp | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttc | cca | ggt | gcc | agg | tgt | gac | atc | cag | atg | acc | cag | tct | cca | tcc | tcc | 96 |
| Phe | Pro | Gly | Ala | Arg | Cys | Asp | Ile | Gln | Met | Thr | Gln | Ser | Pro | Ser | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| ctg | tct | gca | tct | gta | gga | gac | aga | gtc | acc | atc | act | tgc | cgg | gca | agt | 144 |
| Leu | Ser | Ala | Ser | Val | Gly | Asp | Arg | Val | Thr | Ile | Thr | Cys | Arg | Ala | Ser | |
| | | | 35 | | | | | 40 | | | | | 45 | | | |

| | | | | | | | | | | | | | | | | |
|---|---|---|---|---|---|---|---|---|---|---|---|---|---|---|---|---|
| cag | ggc | att | aga | aat | gat | tta | ggc | tgg | tat | cag | cag | aaa | cca | ggg | aaa | 192 |
| Gln | Gly | Ile | Arg | Asn | Asp | Leu | Gly | Trp | Tyr | Gln | Gln | Lys | Pro | Gly | Lys | |
| | 50 | | | | | 55 | | | | | 60 | | | | | |

| | | | | | | | | | | | | | | | | |
|---|---|---|---|---|---|---|---|---|---|---|---|---|---|---|---|---|
| gcc | cct | aaa | cgc | ctg | atc | tat | gct | gca | tcc | agt | ttg | caa | agt | ggg | gtc | 240 |
| Ala | Pro | Lys | Arg | Leu | Ile | Tyr | Ala | Ala | Ser | Ser | Leu | Gln | Ser | Gly | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cca | tca | agg | ttc | agc | ggc | agt | gga | tct | ggg | aca | gaa | ttc | act | ctc | aca | 288 |
| Pro | Ser | Arg | Phe | Ser | Gly | Ser | Gly | Ser | Gly | Thr | Glu | Phe | Thr | Leu | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| atc | agc | agc | ctg | cag | cct | gaa | gat | ttt | gca | act | tat | tac | tgt | cta | cag | 336 |
| Ile | Ser | Ser | Leu | Gln | Pro | Glu | Asp | Phe | Ala | Thr | Tyr | Tyr | Cys | Leu | Gln | |
| | | | 100 | | | | | 105 | | | | | 110 | | | |

| | | | | | | | | | | | | | | | | |
|---|---|---|---|---|---|---|---|---|---|---|---|---|---|---|---|---|
| cat | aat | agt | tac | ccg | ctc | act | ttc | ggc | gga | ggg | acc | aag | gtg | gag | atc | 384 |
| His | Asn | Ser | Tyr | Pro | Leu | Thr | Phe | Gly | Gly | Gly | Thr | Lys | Val | Glu | Ile | |
| | | | 115 | | | | | 120 | | | | | 125 | | | |

| | | | | | | | | | | | | | | | | |
|---|---|---|---|---|---|---|---|---|---|---|---|---|---|---|---|---|
| aaa | cga | act | gtg | gct | gca | cca | tct | gtc | ttc | atc | ttc | ccg | cca | tct | gat | 432 |
| Lys | Arg | Thr | Val | Ala | Ala | Pro | Ser | Val | Phe | Ile | Phe | Pro | Pro | Ser | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| gag | cag | ttg | aaa | tct | gga | act | gcc | tct | gtt | gtg | tgc | ctg | ctg | aat | aac | 480 |
| Glu | Gln | Leu | Lys | Ser | Gly | Thr | Ala | Ser | Val | Val | Cys | Leu | Leu | Asn | Asn | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ttc | tat | ccc | aga | gag | gcc | aaa | gta | cag | tgg | aag | gtg | gat | aac | gcc | ctc | 528 |
| Phe | Tyr | Pro | Arg | Glu | Ala | Lys | Val | Gln | Trp | Lys | Val | Asp | Asn | Ala | Leu | |
| | | | | 165 | | | | | 170 | | | | | 175 | | |

| | | | | | | | | | | | | | | | | |
|---|---|---|---|---|---|---|---|---|---|---|---|---|---|---|---|---|
| caa | tcg | ggt | aac | tcc | cag | gag | agt | gtc | aca | gag | cag | gac | agc | aag | gac | 576 |
| Gln | Ser | Gly | Asn | Ser | Gln | Glu | Ser | Val | Thr | Glu | Gln | Asp | Ser | Lys | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| agc | acc | tac | agc | ctc | agc | agc | acc | ctg | acg | ctg | agc | aaa | gca | gac | tac | 624 |
| Ser | Thr | Tyr | Ser | Leu | Ser | Ser | Thr | Leu | Thr | Leu | Ser | Lys | Ala | Asp | Tyr | |
| | | | 195 | | | | | 200 | | | | | 205 | | | |

| | | | | | | | | | | | | | | | | |
|---|---|---|---|---|---|---|---|---|---|---|---|---|---|---|---|---|
| gag | aaa | cac | aaa | gtc | tac | gcc | tgc | gaa | gtc | acc | cat | cag | ggc | ctg | agc | 672 |
| Glu | Lys | His | Lys | Val | Tyr | Ala | Cys | Glu | Val | Thr | His | Gln | Gly | Leu | Ser | |
| | 210 | | | | | 215 | | | | | 220 | | | | | |

| | | | | | | | | | | |
|---|---|---|---|---|---|---|---|---|---|---|
| tcg | ccc | gtc | aca | aag | agc | ttc | aac | agg | gga | gag | tgt | 708 |
| Ser | Pro | Val | Thr | Lys | Ser | Phe | Asn | Arg | Gly | Glu | Cys | |
| 225 | | | | | 230 | | | | | 235 | | |

<210> SEQ ID NO 141
<211> LENGTH: 236
<212> TYPE: PRT
<213> ORGANISM: ARTIFICIAL SEQUENCE
<220> FEATURE:
<223> OTHER INFORMATION: Synthetic Construct

<400> SEQUENCE: 141

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser

```
                    20                  25                  30
Leu Ser Ala Ser Val Gly Asp Arg Val Thr Ile Thr Cys Arg Ala Ser
            35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Ser Tyr Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 142
<211> LENGTH: 1392
<212> TYPE: DNA
<213> ORGANISM: ARTIFICIAL SEQUENCE
<220> FEATURE:
<223> OTHER INFORMATION: aKLH 120.6 HC sequence
<220> FEATURE:
<221> NAME/KEY: CDS
<222> LOCATION: (1)..(1392)

<400> SEQUENCE: 142 atg gac tgg acc tgg agg atc ctc ttc ttg gtg gca gca gcc aca gga    48
Met Asp Trp Thr Trp Arg Ile Leu Phe Leu Val Ala Ala Ala Thr Gly
1               5                   10                  15 gcc cac tcc cag gtg cag ctg gtg cag tct ggg gct gag gtg aag aag    96
Ala His Ser Gln Val Gln Leu Val Gln Ser Gly Ala Glu Val Lys Lys
                20                  25                  30 cct ggg gcc tca gtg aag gtc tcc tgc aag gct tct gga tac acc ttc    144
Pro Gly Ala Ser Val Lys Val Ser Cys Lys Ala Ser Gly Tyr Thr Phe
            35                  40                  45 acc ggc tac cac atg cac tgg gtg cga cag gcc cct gga caa ggg ctt    192
Thr Gly Tyr His Met His Trp Val Arg Gln Ala Pro Gly Gln Gly Leu
        50                  55                  60 gag tgg atg gga tgg atc aac cct aac agt ggt ggc aca aac tat gca    240
Glu Trp Met Gly Trp Ile Asn Pro Asn Ser Gly Gly Thr Asn Tyr Ala
65                  70                  75                  80 cag aag ttt cag ggc agg gtc acc atg acc agg gac acg tcc atc agc    288
Gln Lys Phe Gln Gly Arg Val Thr Met Thr Arg Asp Thr Ser Ile Ser
                85                  90                  95 aca gcc tac atg gag ctg agc agg ctg aga tct gac gac acg gcc gtg    336
```

```
                Thr Ala Tyr Met Glu Leu Ser Arg Leu Arg Ser Asp Asp Thr Ala Val
                        100                 105                 110 tat tac tgt gcg aga gat cgt ggg agc tac tac tgg ttc gac ccc tgg           384
Tyr Tyr Cys Ala Arg Asp Arg Gly Ser Tyr Tyr Trp Phe Asp Pro Trp
                115                 120                 125 ggc cag gga acc ctg gtc acc gtc tcc tca gcc tcc acc aag ggc cca           432
Gly Gln Gly Thr Leu Val Thr Val Ser Ser Ala Ser Thr Lys Gly Pro
        130                 135                 140 tcg gtc ttc ccc ctg gcg ccc tgc tcc agg agc acc tcc gag agc aca           480
Ser Val Phe Pro Leu Ala Pro Cys Ser Arg Ser Thr Ser Glu Ser Thr
145                 150                 155                 160 gcg gcc ctg ggc tgc ctg gtc aag gac tac ttc ccc gaa ccg gtg acg           528
Ala Ala Leu Gly Cys Leu Val Lys Asp Tyr Phe Pro Glu Pro Val Thr
                165                 170                 175 gtg tcg tgg aac tca ggc gct ctg acc agc ggc gtg cac acc ttc cca           576
Val Ser Trp Asn Ser Gly Ala Leu Thr Ser Gly Val His Thr Phe Pro
                180                 185                 190 gct gtc cta cag tcc tca gga ctc tac tcc ctc agc agc gtg gtg acc           624
Ala Val Leu Gln Ser Ser Gly Leu Tyr Ser Leu Ser Ser Val Val Thr
        195                 200                 205 gtg ccc tcc agc aac ttc ggc acc cag acc tac acc tgc aac gta gat           672
Val Pro Ser Ser Asn Phe Gly Thr Gln Thr Tyr Thr Cys Asn Val Asp
210                 215                 220 cac aag ccc agc aac acc aag gtg gac aag aca gtt gag cgc aaa tgt           720
His Lys Pro Ser Asn Thr Lys Val Asp Lys Thr Val Glu Arg Lys Cys
225                 230                 235                 240 tgt gtc gag tgc cca ccg tgc cca gca cca cct gtg gca gga ccg tca           768
Cys Val Glu Cys Pro Pro Cys Pro Ala Pro Pro Val Ala Gly Pro Ser
                245                 250                 255 gtc ttc ctc ttc ccc cca aaa ccc aag gac acc ctc atg atc tcc cgg           816
Val Phe Leu Phe Pro Pro Lys Pro Lys Asp Thr Leu Met Ile Ser Arg
                260                 265                 270 acc cct gag gtc acg tgc gtg gtg gtg gac gtg agc cac gaa gac ccc           864
Thr Pro Glu Val Thr Cys Val Val Val Asp Val Ser His Glu Asp Pro
        275                 280                 285 gag gtc cag ttc aac tgg tac gtg gac ggc gtg gag gtg cat aat gcc           912
Glu Val Gln Phe Asn Trp Tyr Val Asp Gly Val Glu Val His Asn Ala
        290                 295                 300 aag aca aag cca cgg gag gag cag ttc aac agc acg ttc cgt gtg gtc           960
Lys Thr Lys Pro Arg Glu Glu Gln Phe Asn Ser Thr Phe Arg Val Val
305                 310                 315                 320 agc gtc ctc acc gtt gtg cac cag gac tgg ctg aac ggc aag gag tac          1008
Ser Val Leu Thr Val Val His Gln Asp Trp Leu Asn Gly Lys Glu Tyr
                325                 330                 335 aag tgc aag gtc tcc aac aaa ggc ctc cca gcc ccc atc gag aaa acc          1056
Lys Cys Lys Val Ser Asn Lys Gly Leu Pro Ala Pro Ile Glu Lys Thr
                340                 345                 350 atc tcc aaa acc aaa ggg cag ccc cga gaa cca cag gtg tac acc ctg          1104
Ile Ser Lys Thr Lys Gly Gln Pro Arg Glu Pro Gln Val Tyr Thr Leu
        355                 360                 365 ccc cca tcc cgg gag gag atg acc aag aac cag gtc agc ctg acc tgc          1152
Pro Pro Ser Arg Glu Glu Met Thr Lys Asn Gln Val Ser Leu Thr Cys
        370                 375                 380 ctg gtc aaa ggc ttc tac ccc agc gac atc gcc gtg gag tgg gag agc          1200
Leu Val Lys Gly Phe Tyr Pro Ser Asp Ile Ala Val Glu Trp Glu Ser
385                 390                 395                 400 aat ggg cag ccg gag aac aac tac aag acc aca cct ccc atg ctg gac          1248
Asn Gly Gln Pro Glu Asn Asn Tyr Lys Thr Thr Pro Pro Met Leu Asp
                405                 410                 415
```

| tcc | gac | ggc | tcc | ttc | ttc | ctc | tac | agc | aag | ctc | acc | gtg | gac | aag | agc | 1296 |
|---|---|---|---|---|---|---|---|---|---|---|---|---|---|---|---|---|
| Ser | Asp | Gly | Ser | Phe | Phe | Leu | Tyr | Ser | Lys | Leu | Thr | Val | Asp | Lys | Ser | |
| | | 420 | | | | | 425 | | | | | 430 | | | | |

| agg | tgg | cag | cag | ggg | aac | gtc | ttc | tca | tgc | tcc | gtg | atg | cat | gag | gct | 1344 |
|---|---|---|---|---|---|---|---|---|---|---|---|---|---|---|---|---|
| Arg | Trp | Gln | Gln | Gly | Asn | Val | Phe | Ser | Cys | Ser | Val | Met | His | Glu | Ala | |
| | | 435 | | | | | 440 | | | | | 445 | | | | |

| ctg | cac | aac | cac | tac | acg | cag | aag | agc | ctc | tcc | ctg | tct | ccg | ggt | aaa | 1392 |
|---|---|---|---|---|---|---|---|---|---|---|---|---|---|---|---|---|
| Leu | His | Asn | His | Tyr | Thr | Gln | Lys | Ser | Leu | Ser | Leu | Ser | Pro | Gly | Lys | |
| | 450 | | | | | 455 | | | | | 460 | | | | | |

<210> SEQ ID NO 143
<211> LENGTH: 464
<212> TYPE: PRT
<213> ORGANISM: ARTIFICIAL SEQUENCE
<220> FEATURE:
<223> OTHER INFORMATION: Synthetic Construct

<400> SEQUENCE: 143

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Gly Tyr His Met His Trp Val Arg Gln Ala Pro Gly Gln Gly Leu
        50                  55                  60

Glu Trp Met Gly Trp Ile Asn Pro Asn Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Arg Gly Ser Tyr Tyr Trp Phe Asp Pro Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

-continued

```
Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
            325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 144
<211> LENGTH: 469
<212> TYPE: PRT
<213> ORGANISM: ARTIFICIAL SEQUENCE
<220> FEATURE:
<223> OTHER INFORMATION: aDNP 3A1 HC protein sequence

<400> SEQUENCE: 144

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Pro Gly
            20                  25                  30

Leu Val Lys Pro Ser Glu Thr Leu Ser Leu Thr Cys Thr Val Ser Gly
        35                  40                  45

Gly Ser Ile Ser His Tyr Tyr Trp Ser Trp Ile Arg Gln Pro Pro Gly
    50                  55                  60

Lys Gly Leu Gly Trp Ile Gly Tyr Ile Tyr Tyr Ser Gly Ser Thr Asn
65                  70                  75                  80

Tyr Asn Pro Ser Leu Lys Ser Arg Val Thr Ile Ser Val Asp Thr Ser
            85                  90                  95

Lys Asn Gln Phe Ser Leu Lys Leu Thr Ser Val Thr Ala Ala Asp Thr
        100                 105                 110

Ala Val Tyr Tyr Cys Ala Arg Ala Arg Gly Asp Gly Tyr Asn Tyr Pro
    115                 120                 125

Asp Ala Phe Asp Ile Trp Gly Gln Gly Thr Met Val Thr Val Ser Ser
130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
            165                 170                 175

Phe Pro Glu Pro Val Thr Val Ser Trp Asn Ser Gly Ala Leu Thr Ser
        180                 185                 190

Gly Val His Thr Phe Pro Ala Val Leu Gln Ser Ser Gly Leu Tyr Ser
    195                 200                 205
```

Leu Ser Ser Val Val Thr Val Pro Ser Ser Asn Phe Gly Thr Gln Thr
210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
            245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Gln Phe Asn Trp Tyr Val Asp Gly
290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
            325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
            355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly
465

<210> SEQ ID NO 145
<211> LENGTH: 465
<212> TYPE: PRT
<213> ORGANISM: ARTIFICIAL SEQUENCE
<220> FEATURE:
<223> OTHER INFORMATION: aDNP 3A4 HC protein sequence

<400> SEQUENCE: 145

Met Asp Met Arg Val Pro Ala Gln Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Tyr Asn Trp Asn Tyr Gly Met Asp
            115                 120                 125

Val Trp Gly Gln Gly Thr Thr Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Asn Phe Gly Thr Gln Thr Tyr Thr Cys Asn
            210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
            245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
            275                 280                 285

Asp Pro Glu Val Gln Phe Asn Trp Tyr Val Asp Gly Val Glu Val His
290                 295                 300

Asn Ala Lys Thr Lys Pro Arg Glu Glu Gln Phe Asn Ser Thr Phe Arg
305                 310                 315                 320

Val Val Ser Val Leu Thr Val His Gln Asp Trp Leu Asn Gly Lys
            325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
            450                 455                 460

Gly
465

<210> SEQ ID NO 146
<211> LENGTH: 25
<212> TYPE: PRT
<213> ORGANISM: ARTIFICIAL SEQUENCE
<220> FEATURE:
<223> OTHER INFORMATION: Linker sequence "L25"

```
<400> SEQUENCE: 146

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 147
<211> LENGTH: 20
<212> TYPE: PRT
<213> ORGANISM: ARTIFICIAL SEQUENCE
<220> FEATURE:
<223> OTHER INFORMATION: Linker sequence "L20"

<400> SEQUENCE: 147

Gly Gly Gly Gly Ser Gly Gly Gly Gly Ser Gly Gly Gly Gly Ser Gly
1               5                   10                  15

Gly Gly Gly Ser
            20

<210> SEQ ID NO 148
<211> LENGTH: 6
<212> TYPE: PRT
<213> ORGANISM: ARTIFICIAL SEQUENCE
<220> FEATURE:
<223> OTHER INFORMATION: Linker sequence
<220> FEATURE:
<221> NAME/KEY: MISC_FEATURE
<222> LOCATION: (1)..(2)
<223> OTHER INFORMATION: Xaa in positions 1 and 2 are each independently
      any amino acid residue
<220> FEATURE:
<221> NAME/KEY: MISC_FEATURE
<222> LOCATION: (4)..(5)
<223> OTHER INFORMATION: Xaa in positions 1 and 2 are each independently
      any amino acid residue

<400> SEQUENCE: 148

Xaa Xaa Asn Xaa Xaa Gly
1               5

<210> SEQ ID NO 149
<211> LENGTH: 4
<212> TYPE: PRT
<213> ORGANISM: ARTIFICIAL SEQUENCE
<220> FEATURE:
<223> OTHER INFORMATION: Linker sequence

<400> SEQUENCE: 149

Gly Gly Gly Gly
1

<210> SEQ ID NO 150
<211> LENGTH: 5
<212> TYPE: PRT
<213> ORGANISM: ARTIFICIAL SEQUENCE
<220> FEATURE:
<223> OTHER INFORMATION: Linker sequence

<400> SEQUENCE: 150

Gly Gly Gly Gly Gly
1               5

<210> SEQ ID NO 151
<211> LENGTH: 7
<212> TYPE: PRT
<213> ORGANISM: ARTIFICIAL SEQUENCE
```

```
<220> FEATURE:
<223> OTHER INFORMATION: Linker sequence

<400> SEQUENCE: 151

Gly Gly Gly Gly Gly Gly Gly
1               5

<210> SEQ ID NO 152
<211> LENGTH: 5
<212> TYPE: PRT
<213> ORGANISM: ARTIFICIAL SEQUENCE
<220> FEATURE:
<223> OTHER INFORMATION: Linker sequence "L5"

<400> SEQUENCE: 152

Gly Gly Gly Gly Ser
1               5

<210> SEQ ID NO 153
<211> LENGTH: 10
<212> TYPE: PRT
<213> ORGANISM: ARTIFICIAL SEQUENCE
<220> FEATURE:
<223> OTHER INFORMATION: Linker sequence

<400> SEQUENCE: 153

Gly Gly Gly Gly Ser Gly Gly Gly Gly Ser
1               5                   10

<210> SEQ ID NO 154
<211> LENGTH: 6
<212> TYPE: PRT
<213> ORGANISM: ARTIFICIAL SEQUENCE
<220> FEATURE:
<223> OTHER INFORMATION: Linker sequence

<400> SEQUENCE: 154

Gly Gly Gly Gly Gly Lys
1               5

<210> SEQ ID NO 155
<211> LENGTH: 7
<212> TYPE: PRT
<213> ORGANISM: ARTIFICIAL SEQUENCE
<220> FEATURE:
<223> OTHER INFORMATION: Linker sequence

<400> SEQUENCE: 155

Gly Gly Gly Gly Gly Lys Arg
1               5

<210> SEQ ID NO 156
<211> LENGTH: 8
<212> TYPE: PRT
<213> ORGANISM: ARTIFICIAL SEQUENCE
<220> FEATURE:
<223> OTHER INFORMATION: Linker sequence

<400> SEQUENCE: 156

Gly Gly Gly Asn Gly Ser Gly Gly
1               5

<210> SEQ ID NO 157
<211> LENGTH: 8
<212> TYPE: PRT
<213> ORGANISM: ARTIFICIAL SEQUENCE
<220> FEATURE:
```

<223> OTHER INFORMATION: Linker sequence

<400> SEQUENCE: 157

Gly Gly Gly Cys Gly Gly Gly Gly
1               5

<210> SEQ ID NO 158
<211> LENGTH: 5
<212> TYPE: PRT
<213> ORGANISM: ARTIFICIAL SEQUENCE
<220> FEATURE:
<223> OTHER INFORMATION: Linker sequence

<400> SEQUENCE: 158

Gly Pro Asn Gly Gly
1               5

<210> SEQ ID NO 159
<211> LENGTH: 8
<212> TYPE: PRT
<213> ORGANISM: ARTIFICIAL SEQUENCE
<220> FEATURE:
<223> OTHER INFORMATION: Linker sequence

<400> SEQUENCE: 159

Gly Gly Gly Lys Gly Gly Gly Gly
1               5

<210> SEQ ID NO 160
<211> LENGTH: 6
<212> TYPE: PRT
<213> ORGANISM: ARTIFICIAL SEQUENCE
<220> FEATURE:
<223> OTHER INFORMATION: Linker sequence

<400> SEQUENCE: 160

Gly Gly Glu Gly Gly Gly
1               5

<210> SEQ ID NO 161
<211> LENGTH: 8
<212> TYPE: PRT
<213> ORGANISM: ARTIFICIAL SEQUENCE
<220> FEATURE:
<223> OTHER INFORMATION: Linker sequence

<400> SEQUENCE: 161

Gly Gly Glu Glu Glu Gly Gly Gly
1               5

<210> SEQ ID NO 162
<211> LENGTH: 5
<212> TYPE: PRT
<213> ORGANISM: ARTIFICIAL SEQUENCE
<220> FEATURE:
<223> OTHER INFORMATION: Linker sequence

<400> SEQUENCE: 162

Gly Glu Glu Glu Gly
1               5

<210> SEQ ID NO 163
<211> LENGTH: 4
<212> TYPE: PRT
<213> ORGANISM: ARTIFICIAL SEQUENCE
<220> FEATURE:
<223> OTHER INFORMATION: Linker sequence

```
<400> SEQUENCE: 163

Gly Glu Glu Glu
1

<210> SEQ ID NO 164
<211> LENGTH: 6
<212> TYPE: PRT
<213> ORGANISM: ARTIFICIAL SEQUENCE
<220> FEATURE:
<223> OTHER INFORMATION: Linker sequence

<400> SEQUENCE: 164

Gly Gly Asp Gly Gly Gly
1               5

<210> SEQ ID NO 165
<211> LENGTH: 7
<212> TYPE: PRT
<213> ORGANISM: ARTIFICIAL SEQUENCE
<220> FEATURE:
<223> OTHER INFORMATION: Linker sequence

<400> SEQUENCE: 165

Gly Gly Asp Asp Asp Gly Gly
1               5

<210> SEQ ID NO 166
<211> LENGTH: 5
<212> TYPE: PRT
<213> ORGANISM: ARTIFICIAL SEQUENCE
<220> FEATURE:
<223> OTHER INFORMATION: Linker sequence

<400> SEQUENCE: 166

Gly Asp Asp Asp Gly
1               5

<210> SEQ ID NO 167
<211> LENGTH: 4
<212> TYPE: PRT
<213> ORGANISM: ARTIFICIAL SEQUENCE
<220> FEATURE:
<223> OTHER INFORMATION: Linker sequence

<400> SEQUENCE: 167

Gly Asp Asp Asp
1

<210> SEQ ID NO 168
<211> LENGTH: 21
<212> TYPE: PRT
<213> ORGANISM: ARTIFICIAL SEQUENCE
<220> FEATURE:
<223> OTHER INFORMATION: Linker sequence

<400> SEQUENCE: 168

Gly Gly Gly Gly Ser Asp Asp Ser Asp Glu Gly Ser Asp Gly Glu Asp
1               5                   10                  15

Gly Gly Gly Gly Ser
            20

<210> SEQ ID NO 169
<211> LENGTH: 5
<212> TYPE: PRT
<213> ORGANISM: ARTIFICIAL SEQUENCE
```

```
<220> FEATURE:
<223> OTHER INFORMATION: Linker sequence

<400> SEQUENCE: 169

Trp Glu Trp Glu Trp
1               5

<210> SEQ ID NO 170
<211> LENGTH: 5
<212> TYPE: PRT
<213> ORGANISM: ARTIFICIAL SEQUENCE
<220> FEATURE:
<223> OTHER INFORMATION: Linker sequence

<400> SEQUENCE: 170

Phe Glu Phe Glu Phe
1               5

<210> SEQ ID NO 171
<211> LENGTH: 6
<212> TYPE: PRT
<213> ORGANISM: ARTIFICIAL SEQUENCE
<220> FEATURE:
<223> OTHER INFORMATION: Linker sequence

<400> SEQUENCE: 171

Glu Glu Glu Trp Trp Trp
1               5

<210> SEQ ID NO 172
<211> LENGTH: 6
<212> TYPE: PRT
<213> ORGANISM: ARTIFICIAL SEQUENCE
<220> FEATURE:
<223> OTHER INFORMATION: Linker sequence

<400> SEQUENCE: 172

Glu Glu Glu Phe Phe Phe
1               5

<210> SEQ ID NO 173
<211> LENGTH: 7
<212> TYPE: PRT
<213> ORGANISM: ARTIFICIAL SEQUENCE
<220> FEATURE:
<223> OTHER INFORMATION: Linker sequence

<400> SEQUENCE: 173

Trp Trp Glu Glu Glu Trp Trp
1               5

<210> SEQ ID NO 174
<211> LENGTH: 7
<212> TYPE: PRT
<213> ORGANISM: ARTIFICIAL SEQUENCE
<220> FEATURE:
<223> OTHER INFORMATION: Linker sequence

<400> SEQUENCE: 174

Phe Phe Glu Glu Glu Phe Phe
1               5

<210> SEQ ID NO 175
<211> LENGTH: 6
<212> TYPE: PRT
<213> ORGANISM: ARTIFICIAL SEQUENCE
<220> FEATURE:
```

```
<223> OTHER INFORMATION: Linker sequence
<220> FEATURE:
<221> NAME/KEY: MISC_FEATURE
<222> LOCATION: (1)..(2)
<223> OTHER INFORMATION: Xaa in positions 1 and 2 are each independently
      any amino acid residue
<220> FEATURE:
<221> NAME/KEY: MISC_FEATURE
<222> LOCATION: (4)..(5)
<223> OTHER INFORMATION: Xaa in positions 1 and 2 are each independently
      any amino acid residue

<400> SEQUENCE: 175

Xaa Xaa Tyr Xaa Xaa Gly
1               5

<210> SEQ ID NO 176
<211> LENGTH: 6
<212> TYPE: PRT
<213> ORGANISM: ARTIFICIAL SEQUENCE
<220> FEATURE:
<223> OTHER INFORMATION: Linker sequence
<220> FEATURE:
<221> NAME/KEY: MISC_FEATURE
<222> LOCATION: (1)..(2)
<223> OTHER INFORMATION: Xaa in positions 1 and 2 are each independently
      any amino acid residue
<220> FEATURE:
<221> NAME/KEY: MISC_FEATURE
<222> LOCATION: (4)..(5)
<223> OTHER INFORMATION: Xaa in positions 1 and 2 are each independently
      any amino acid residue

<400> SEQUENCE: 176

Xaa Xaa Ser Xaa Xaa Gly
1               5

<210> SEQ ID NO 177
<211> LENGTH: 6
<212> TYPE: PRT
<213> ORGANISM: ARTIFICIAL SEQUENCE
<220> FEATURE:
<223> OTHER INFORMATION: Linker sequence
<220> FEATURE:
<221> NAME/KEY: MISC_FEATURE
<222> LOCATION: (1)..(2)
<223> OTHER INFORMATION: Xaa in positions 1 and 2 are each independently
      any amino acid residue
<220> FEATURE:
<221> NAME/KEY: MISC_FEATURE
<222> LOCATION: (4)..(5)
<223> OTHER INFORMATION: Xaa in positions 1 and 2 are each independently
      any amino acid residue

<400> SEQUENCE: 177

Xaa Xaa Thr Xaa Xaa Gly
1               5

<210> SEQ ID NO 178
<211> LENGTH: 22
<212> TYPE: PRT
<213> ORGANISM: ARTIFICIAL SEQUENCE
<220> FEATURE:
<223> OTHER INFORMATION: Linker sequence

<400> SEQUENCE: 178

Gly Ser Gly Ser Ala Thr Gly Gly Ser Gly Ser Thr Ala Ser Ser Gly
1               5                   10                  15

Ser Gly Ser Ala Thr His
            20
```

<210> SEQ ID NO 179
<211> LENGTH: 22
<212> TYPE: PRT
<213> ORGANISM: ARTIFICIAL SEQUENCE
<220> FEATURE:
<223> OTHER INFORMATION: Linker sequence

<400> SEQUENCE: 179

```
His Gly Ser Gly Ser Ala Thr Gly Gly Ser Gly Ser Thr Ala Ser Ser
1               5                   10                  15

Gly Ser Gly Ser Ala Thr
            20
```

<210> SEQ ID NO 180
<211> LENGTH: 19
<212> TYPE: PRT
<213> ORGANISM: ARTIFICIAL SEQUENCE
<220> FEATURE:
<223> OTHER INFORMATION: Linker sequence

<400> SEQUENCE: 180

```
Ala Glu Ala Ala Ala Lys Glu Ala Ala Ala Lys Glu Ala Ala Ala Lys
1               5                   10                  15

Ala Gly Gly
```

<210> SEQ ID NO 181
<211> LENGTH: 465
<212> TYPE: PRT
<213> ORGANISM: ARTIFICIAL SEQUENCE
<220> FEATURE:
<223> OTHER INFORMATION: aDNP 3A4 (W101Y) HC (H12) protein sequence

<400> SEQUENCE: 181

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Tyr Asn Tyr Asn Tyr Gly Met Asp
        115                 120                 125

Val Trp Gly Gln Gly Thr Thr Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205
```

```
Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
                275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
                340                 345                 350

Lys Thr Ile Ser Lys Thr Lys Gly Gln Pro Arg Glu Pro Gln Val Tyr
                355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
                435                 440                 445

Glu Ala Leu His Asn His Tyr Thr Gln Lys Ser Leu Ser Leu Ser Pro
    450                 455                 460

Gly
465

<210> SEQ ID NO 182
<211> LENGTH: 465
<212> TYPE: PRT
<213> ORGANISM: ARTIFICIAL SEQUENCE
<220> FEATURE:
<223> OTHER INFORMATION: H13 protein sequence

<400> SEQUENCE: 182

Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
                20                  25                  30

Val Val Gln Pro Gly Arg Ser Leu Arg Leu Ser Cys Ala Ala Ser Gly
                35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Thr Ile Ser Arg Asp Asn
                85                  90                  95
```

Ser Lys Asn Thr Leu Tyr Leu Gln Met Asn Ser Leu Arg Ala Glu Asp
            100                 105                 110

Thr Ala Val Tyr Tyr Cys Ala Arg Tyr Asn Phe Asn Tyr Gly Met Asp
            115                 120                 125

Val Trp Gly Gln Gly Thr Thr Val Thr Val Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Asn Phe Gly Thr Gln Thr Tyr Thr Cys Asn
            210                 215                 220

Val Asp His Lys Pro Ser Asn Thr Lys Val Asp Lys Thr Val Glu Arg
225                 230                 235                 240

Lys Ser Ser Val Glu Cys Pro Pro Cys Pro Ala Pro Pro Val Ala Gly
            245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
            275                 280                 285

Asp Pro Glu Val Gln Phe Asn Trp Tyr Val Asp Gly Val Glu Val His
            290                 295                 300

Asn Ala Lys Thr Lys Pro Arg Glu Glu Gln Phe Asn Ser Thr Phe Arg
305                 310                 315                 320

Val Val Ser Val Leu Thr Val His Gln Asp Trp Leu Asn Gly Lys
            325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
            405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
            450                 455                 460

Gly
465

<210> SEQ ID NO 183
<211> LENGTH: 465
<212> TYPE: PRT
<213> ORGANISM: ARTIFICIAL SEQUENCE
<220> FEATURE:

<223> OTHER INFORMATION: H14 protein sequence

<400> SEQUENCE: 183

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Tyr Asn Tyr Asn Tyr Gly Met Asp
        115                 120                 125

Val Trp Gly Gln Gly Thr Thr Val Thr Val Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Ser Ser Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400
```

```
Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly
465

<210> SEQ ID NO 184
<211> LENGTH: 470
<212> TYPE: PRT
<213> ORGANISM: ARTIFICIAL SEQUENCE
<220> FEATURE:
<223> OTHER INFORMATION: H15 protein sequence

<400> SEQUENCE: 184

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Pro Gly
            20                  25                  30

Leu Val Lys Pro Ser Glu Thr Leu Ser Leu Thr Cys Thr Val Ser Gly
        35                  40                  45

Gly Ser Ile Ser Ser Tyr Tyr Trp Ser Trp Ile Arg Gln Pro Pro Gly
    50                  55                  60

Lys Gly Leu Glu Trp Ile Gly Tyr Ile Tyr Tyr Ser Gly Asn Thr Asn
65                  70                  75                  80

Ser Asn Pro Ser Leu Lys Ser Arg Val Thr Ile Ser Val Asp Thr Ser
                85                  90                  95

Lys Asn Gln Phe Ser Leu Lys Leu Ser Ser Val Thr Ala Ala Asp Thr
            100                 105                 110

Ala Val Tyr Tyr Cys Ala Arg Thr Tyr Tyr Asp Ser Ser Gly Tyr Tyr
        115                 120                 125

Tyr Arg Ala Phe Asp Ile Trp Gly Gln Gly Thr Met Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285
```

```
Asp Val Ser His Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Leu
                340                 345                 350

Pro Ala Pro Ile Glu Lys Thr Ile Ser Lys Thr Lys Gly Gln Pro Arg
                355                 360                 365

Glu Pro Gln Val Tyr Thr Leu Pro Pro Ser Arg Glu Glu Met Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Met Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
                450                 455                 460

Leu Ser Leu Ser Pro Gly
465                 470

<210> SEQ ID NO 185
<211> LENGTH: 469
<212> TYPE: PRT
<213> ORGANISM: ARTIFICIAL SEQUENCE
<220> FEATURE:
<223> OTHER INFORMATION: H16 protein sequence

<400> SEQUENCE: 185

Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Pro Gly
                20                  25                  30

Leu Val Lys Pro Leu Gln Thr Leu Ser Leu Thr Cys Thr Val Ser Gly
                35                  40                  45

Gly Ser Ile Ser Ser Gly Gly Tyr Tyr Trp Ser Trp Ile Arg Gln His
50                  55                  60

Pro Gly Lys Gly Leu Glu Trp Ile Gly Tyr Ile Tyr Tyr Ser Arg Ser
65                  70                  75                  80

Thr Tyr Tyr Asn Pro Ser Leu Lys Ser Arg Val Thr Ile Ser Val Asp
                85                  90                  95

Thr Ser Lys Asn Gln Phe Ser Leu Lys Leu Ser Ser Val Thr Ala Ala
                100                 105                 110

Asp Thr Ala Val Tyr Tyr Cys Ala Arg Thr Gly Tyr Ser Ser Gly Trp
                115                 120                 125

Tyr Pro Phe Asp Tyr Trp Gly Gln Gly Thr Leu Val Thr Val Ser Ser
130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175
```

-continued

```
Phe Pro Glu Pro Val Thr Val Ser Trp Asn Ser Gly Ala Leu Thr Ser
            180                 185                 190
Gly Val His Thr Phe Pro Ala Val Leu Gln Ser Gly Leu Tyr Ser
        195                 200                 205
Leu Ser Ser Val Val Thr Val Pro Ser Ser Asn Phe Gly Thr Gln Thr
210                 215                 220
Tyr Thr Cys Asn Val Asp His Lys Pro Ser Asn Thr Lys Val Asp Lys
225                 230                 235                 240
Thr Val Glu Arg Lys Cys Cys Val Glu Cys Pro Pro Cys Pro Ala Pro
            245                 250                 255
Pro Val Ala Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
            275                 280                 285
Val Ser His Glu Asp Pro Glu Val Gln Phe Asn Trp Tyr Val Asp Gly
            290                 295                 300
Val Glu Val His Asn Ala Lys Thr Lys Pro Arg Glu Glu Gln Phe Asn
305                 310                 315                 320
Ser Thr Phe Arg Val Val Ser Val Leu Thr Val Val His Gln Asp Trp
                325                 330                 335
Leu Asn Gly Lys Glu Tyr Lys Cys Lys Val Ser Asn Lys Gly Leu Pro
            340                 345                 350
Ala Pro Ile Glu Lys Thr Ile Ser Lys Thr Lys Gly Gln Pro Arg Glu
            355                 360                 365
Pro Gln Val Tyr Thr Leu Pro Pro Ser Arg Glu Glu Met Thr Lys Asn
            370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Met Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
            435                 440                 445
Ser Val Met His Glu Ala Leu His Asn His Tyr Thr Gln Lys Ser Leu
    450                 455                 460
Ser Leu Ser Pro Gly
465

<210> SEQ ID NO 186
<211> LENGTH: 462
<212> TYPE: PRT
<213> ORGANISM: ARTIFICIAL SEQUENCE
<220> FEATURE:
<223> OTHER INFORMATION: H21 protein sequence

<400> SEQUENCE: 186

Met Glu Leu Gly Leu Ser Trp Val Phe Leu Phe Ala Ile Leu Glu Gly
1               5                   10                  15
Val Gln Cys Glu Val Gln Leu Val Glu Ser Gly Gly Gly Leu Val Gln
            20                  25                  30
Pro Gly Gly Ser Leu Arg Leu Ser Cys Ala Ala Ser Gly Phe Thr Phe
        35                  40                  45
Ser Asn Tyr Asp Met Tyr Trp Val Arg Gln Thr Thr Gly Lys Gly Leu
    50                  55                  60
```

-continued

```
Glu Trp Val Ser Ala Ile Gly Thr Ala Gly Asp Thr Tyr Tyr Pro Gly
 65                  70                  75                  80

Ser Val Lys Gly Arg Phe Thr Ile Ser Arg Glu Asn Ala Lys Asn Ser
             85                  90                  95

Leu Tyr Leu Gln Met Asn Ser Leu Arg Ala Gly Asp Thr Ala Val Tyr
        100                 105                 110

Tyr Cys Ala Arg Glu Lys Ser Ser Thr Ser Ala Phe Asp Tyr Trp Gly
    115                 120                 125

Gln Gly Thr Leu Val Thr Val Ser Ser Ala Ser Thr Lys Gly Pro Ser
130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly
    450                 455                 460

<210> SEQ ID NO 187
<211> LENGTH: 469
<212> TYPE: PRT
```

<213> ORGANISM: ARTIFICIAL SEQUENCE
<220> FEATURE:
<223> OTHER INFORMATION: H22 protein sequence

<400> SEQUENCE: 187

```
Met Lys His Leu Trp Phe Phe Leu Leu Val Ala Ala Pro Arg Trp
1               5                   10                  15

Val Leu Ser Gln Leu Gln Leu Gln Glu Ser Gly Pro Gly Leu Met Lys
            20                  25                  30

Pro Ser Glu Thr Leu Ser Leu Thr Cys Thr Val Ser Gly Gly Ser Ile
            35                  40                  45

Ser Ser Ser Ser Tyr Phe Trp Gly Trp Ile Arg Gln Pro Pro Gly Lys
50                  55                  60

Gly Leu Glu Trp Ile Gly Ser Ile Tyr Tyr Ser Gly Asn Thr Phe Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Asn Ser Met Thr Ala Ala Asp Thr Ala
            100                 105                 110

Val Tyr Phe Cys Ala Arg Gln Gly Gly Ile Ala Ala Arg Thr Gly Tyr
            115                 120                 125

Trp Tyr Phe Asp Leu Trp Gly Arg Gly Thr Thr Val Thr Val Ser Ser
130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Asn Phe Gly Thr Gln Thr
210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Gln Phe Asn Trp Tyr Val Asp Gly
290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
            355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
```

```
                    385                 390                 395                 400
Ala Val Glu Trp Glu Ser Asn Gly Gln Pro Glu Asn Asn Tyr Lys Thr
                    405                 410                 415

Thr Pro Pro Met Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
            450                 455                 460

Ser Leu Ser Pro Gly
465
```

<210> SEQ ID NO 188
<211> LENGTH: 5
<212> TYPE: PRT
<213> ORGANISM: ARTIFICIAL SEQUENCE
<220> FEATURE:
<223> OTHER INFORMATION: CDRH 1-1

<400> SEQUENCE: 188

```
His Tyr Tyr Trp Ser
1               5
```

<210> SEQ ID NO 189
<211> LENGTH: 5
<212> TYPE: PRT
<213> ORGANISM: ARTIFICIAL SEQUENCE
<220> FEATURE:
<223> OTHER INFORMATION: CDRH 1-2

<400> SEQUENCE: 189

```
Ser Tyr Gly Met His
1               5
```

<210> SEQ ID NO 190
<211> LENGTH: 5
<212> TYPE: PRT
<213> ORGANISM: ARTIFICIAL SEQUENCE
<220> FEATURE:
<223> OTHER INFORMATION: CDRH 1-3

<400> SEQUENCE: 190

```
Ser Tyr Tyr Trp Ser
1               5
```

<210> SEQ ID NO 191
<211> LENGTH: 7
<212> TYPE: PRT
<213> ORGANISM: ARTIFICIAL SEQUENCE
<220> FEATURE:
<223> OTHER INFORMATION: CDRH 1-4

<400> SEQUENCE: 191

```
Ser Gly Gly Tyr Tyr Trp Ser
1               5
```

<210> SEQ ID NO 192
<211> LENGTH: 16
<212> TYPE: PRT
<213> ORGANISM: ARTIFICIAL SEQUENCE
<220> FEATURE:
<223> OTHER INFORMATION: CDRH 2-1

<400> SEQUENCE: 192

```
Tyr Ile Tyr Tyr Ser Gly Ser Thr Asn Tyr Asn Pro Ser Leu Lys Ser
1               5                   10                  15
```

<210> SEQ ID NO 193
<211> LENGTH: 17
<212> TYPE: PRT
<213> ORGANISM: ARTIFICIAL SEQUENCE
<220> FEATURE:
<223> OTHER INFORMATION: CDRH 2-2

<400> SEQUENCE: 193

```
Val Ile Trp Tyr Asp Gly Ser Asn Lys Tyr Tyr Ala Asp Ser Val Lys
1               5                   10                  15

Gly
```

<210> SEQ ID NO 194
<211> LENGTH: 16
<212> TYPE: PRT
<213> ORGANISM: ARTIFICIAL SEQUENCE
<220> FEATURE:
<223> OTHER INFORMATION: CDRH 2-3

<400> SEQUENCE: 194

```
Tyr Ile Tyr Tyr Ser Gly Asn Thr Asn Ser Asn Pro Ser Leu Lys Ser
1               5                   10                  15
```

<210> SEQ ID NO 195
<211> LENGTH: 16
<212> TYPE: PRT
<213> ORGANISM: ARTIFICIAL SEQUENCE
<220> FEATURE:
<223> OTHER INFORMATION: CDRH 2-4

<400> SEQUENCE: 195

```
Tyr Ile Tyr Tyr Ser Arg Ser Thr Tyr Tyr Asn Pro Ser Leu Lys Ser
1               5                   10                  15
```

<210> SEQ ID NO 196
<211> LENGTH: 14
<212> TYPE: PRT
<213> ORGANISM: ARTIFICIAL SEQUENCE
<220> FEATURE:
<223> OTHER INFORMATION: CDRH 3-1

<400> SEQUENCE: 196

```
Ala Arg Gly Asp Gly Tyr Asn Tyr Pro Asp Ala Phe Asp Ile
1               5                   10
```

<210> SEQ ID NO 197
<211> LENGTH: 9
<212> TYPE: PRT
<213> ORGANISM: ARTIFICIAL SEQUENCE
<220> FEATURE:
<223> OTHER INFORMATION: CDRH 3-2

<400> SEQUENCE: 197

```
Tyr Asn Trp Asn Tyr Gly Met Asp Val
1               5
```

<210> SEQ ID NO 198
<211> LENGTH: 9
<212> TYPE: PRT
<213> ORGANISM: ARTIFICIAL SEQUENCE
<220> FEATURE:
<223> OTHER INFORMATION: CDRH 3-3

<400> SEQUENCE: 198

Tyr Asn Phe Asn Tyr Gly Met Asp Val
1               5

<210> SEQ ID NO 199
<211> LENGTH: 9
<212> TYPE: PRT
<213> ORGANISM: ARTIFICIAL SEQUENCE
<220> FEATURE:
<223> OTHER INFORMATION: CDRH 3-4

<400> SEQUENCE: 199

Tyr Asn Tyr Asn Tyr Gly Met Asp Val
1               5

<210> SEQ ID NO 200
<211> LENGTH: 15
<212> TYPE: PRT
<213> ORGANISM: ARTIFICIAL SEQUENCE
<220> FEATURE:
<223> OTHER INFORMATION: CDRH 3-5

<400> SEQUENCE: 200

Thr Tyr Tyr Asp Ser Ser Gly Tyr Tyr Arg Ala Phe Asp Ile
1               5                   10                  15

<210> SEQ ID NO 201
<211> LENGTH: 12
<212> TYPE: PRT
<213> ORGANISM: ARTIFICIAL SEQUENCE
<220> FEATURE:
<223> OTHER INFORMATION: CDRH 3-6

<400> SEQUENCE: 201

Thr Gly Tyr Ser Ser Gly Trp Tyr Pro Phe Asp Tyr
1               5                   10

<210> SEQ ID NO 202
<211> LENGTH: 11
<212> TYPE: PRT
<213> ORGANISM: ARTIFICIAL SEQUENCE
<220> FEATURE:
<223> OTHER INFORMATION: CDRL 1-1

<400> SEQUENCE: 202

Arg Ala Ser Gln Gly Ile Ser Asn Trp Leu Ala
1               5                   10

<210> SEQ ID NO 203
<211> LENGTH: 11
<212> TYPE: PRT
<213> ORGANISM: ARTIFICIAL SEQUENCE
<220> FEATURE:
<223> OTHER INFORMATION: CDRL 1-2

<400> SEQUENCE: 203

Arg Ala Ser Gln Gly Ile Ser Arg Arg Leu Ala
1               5                   10

<210> SEQ ID NO 204
<211> LENGTH: 11
<212> TYPE: PRT
<213> ORGANISM: ARTIFICIAL SEQUENCE
<220> FEATURE:
<223> OTHER INFORMATION: CDRL 1-3; CDRL 1-8

<400> SEQUENCE: 204

Arg Ala Ser Gln Gly Ile Arg Asn Asp Leu Gly
1               5                   10

<210> SEQ ID NO 205
<211> LENGTH: 11
<212> TYPE: PRT
<213> ORGANISM: ARTIFICIAL SEQUENCE
<220> FEATURE:
<223> OTHER INFORMATION: CDRL 1-4

<400> SEQUENCE: 205

Arg Ala Ser Gln Gly Met Ser Asn Tyr Leu Ala
1               5                   10

<210> SEQ ID NO 206
<211> LENGTH: 7
<212> TYPE: PRT
<213> ORGANISM: ARTIFICIAL SEQUENCE
<220> FEATURE:
<223> OTHER INFORMATION: CDRL 2-1; CDRL 2-5

<400> SEQUENCE: 206

Ala Ala Ser Ser Leu Gln Ser
1               5

<210> SEQ ID NO 207
<211> LENGTH: 7
<212> TYPE: PRT
<213> ORGANISM: ARTIFICIAL SEQUENCE
<220> FEATURE:
<223> OTHER INFORMATION: CDRL 2-2

<400> SEQUENCE: 207

Ala Ala Ser Thr Leu Gln Ser
1               5

<210> SEQ ID NO 208
<211> LENGTH: 9
<212> TYPE: PRT
<213> ORGANISM: ARTIFICIAL SEQUENCE
<220> FEATURE:
<223> OTHER INFORMATION: CDRL 3-1

<400> SEQUENCE: 208

Gln Gln Ala Ser Ser Phe Pro Trp Thr
1               5

<210> SEQ ID NO 209
<211> LENGTH: 9
<212> TYPE: PRT
<213> ORGANISM: ARTIFICIAL SEQUENCE
<220> FEATURE:
<223> OTHER INFORMATION: CDRL 3-2

<400> SEQUENCE: 209

Gln Gln Ala Asn Ser Phe Pro Phe Thr
1               5

<210> SEQ ID NO 210
<211> LENGTH: 9
<212> TYPE: PRT
<213> ORGANISM: ARTIFICIAL SEQUENCE
<220> FEATURE:
<223> OTHER INFORMATION: CDRL 3-3

<400> SEQUENCE: 210

Leu Gln Tyr Asn Ser Tyr Pro Trp Thr

```
<210> SEQ ID NO 211
<211> LENGTH: 9
<212> TYPE: PRT
<213> ORGANISM: ARTIFICIAL SEQUENCE
<220> FEATURE:
<223> OTHER INFORMATION: CDRL 3-4

<400> SEQUENCE: 211

Gln Lys Phe Asn Ser Ala Pro Phe Thr
 1               5

<210> SEQ ID NO 212
<211> LENGTH: 9
<212> TYPE: PRT
<213> ORGANISM: ARTIFICIAL SEQUENCE
<220> FEATURE:
<223> OTHER INFORMATION: CDRL 3-5

<400> SEQUENCE: 212

Leu Gln Tyr Asn Ser Ser Pro Trp Thr
 1               5

<210> SEQ ID NO 213
<211> LENGTH: 5
<212> TYPE: PRT
<213> ORGANISM: ARTIFICIAL SEQUENCE
<220> FEATURE:
<223> OTHER INFORMATION: CDRH 1-5

<400> SEQUENCE: 213

Asn Tyr Asp Met Tyr
 1               5

<210> SEQ ID NO 214
<211> LENGTH: 7
<212> TYPE: PRT
<213> ORGANISM: ARTIFICIAL SEQUENCE
<220> FEATURE:
<223> OTHER INFORMATION: CDRH 1-6

<400> SEQUENCE: 214

Ser Ser Ser Tyr Phe Trp Gly
 1               5

<210> SEQ ID NO 215
<211> LENGTH: 5
<212> TYPE: PRT
<213> ORGANISM: ARTIFICIAL SEQUENCE
<220> FEATURE:
<223> OTHER INFORMATION: CDRH 1-7

<400> SEQUENCE: 215

Gly Tyr His Met His
 1               5

<210> SEQ ID NO 216
<211> LENGTH: 16
<212> TYPE: PRT
<213> ORGANISM: ARTIFICIAL SEQUENCE
<220> FEATURE:
<223> OTHER INFORMATION: CDRH 2-5

<400> SEQUENCE: 216

Ala Ile Gly Thr Ala Gly Asp Thr Tyr Tyr Pro Gly Ser Val Lys Gly
 1               5                  10                  15
```

```
<210> SEQ ID NO 217
<211> LENGTH: 16
<212> TYPE: PRT
<213> ORGANISM: ARTIFICIAL SEQUENCE
<220> FEATURE:
<223> OTHER INFORMATION: CDRH 2-6

<400> SEQUENCE: 217

Ser Ile Tyr Tyr Ser Gly Asn Thr Phe Tyr Asn Pro Ser Leu Lys Ser
1               5                   10                  15

<210> SEQ ID NO 218
<211> LENGTH: 17
<212> TYPE: PRT
<213> ORGANISM: ARTIFICIAL SEQUENCE
<220> FEATURE:
<223> OTHER INFORMATION: CDRH 2-7

<400> SEQUENCE: 218

Trp Ile Asn Pro Asn Ser Gly Gly Thr Asn Tyr Ala Gln Lys Phe Gln
1               5                   10                  15
Gly

<210> SEQ ID NO 219
<211> LENGTH: 10
<212> TYPE: PRT
<213> ORGANISM: ARTIFICIAL SEQUENCE
<220> FEATURE:
<223> OTHER INFORMATION: CDRH 3-7

<400> SEQUENCE: 219

Glu Lys Ser Ser Thr Ser Ala Phe Asp Tyr
1               5                   10

<210> SEQ ID NO 220
<211> LENGTH: 15
<212> TYPE: PRT
<213> ORGANISM: ARTIFICIAL SEQUENCE
<220> FEATURE:
<223> OTHER INFORMATION: CDRH 3-8

<400> SEQUENCE: 220

Gln Gly Gly Ile Ala Ala Arg Thr Gly Tyr Trp Tyr Phe Asp Leu
1               5                   10                  15

<210> SEQ ID NO 221
<211> LENGTH: 10
<212> TYPE: PRT
<213> ORGANISM: ARTIFICIAL SEQUENCE
<220> FEATURE:
<223> OTHER INFORMATION: CDRH 3-9

<400> SEQUENCE: 221

Asp Arg Gly Ser Tyr Tyr Trp Phe Asp Pro
1               5                   10

<210> SEQ ID NO 222
<211> LENGTH: 11
<212> TYPE: PRT
<213> ORGANISM: ARTIFICIAL SEQUENCE
<220> FEATURE:
<223> OTHER INFORMATION: CDRL 1-5

<400> SEQUENCE: 222

Gln Ala Gly Gln Asp Ile Arg Asn Tyr Leu Asn
```

```
<210> SEQ ID NO 223
<211> LENGTH: 12
<212> TYPE: PRT
<213> ORGANISM: ARTIFICIAL SEQUENCE
<220> FEATURE:
<223> OTHER INFORMATION: CDRL 1-6

<400> SEQUENCE: 223

Arg Ala Ser Gln Asn Ile Ser Thr Asn Tyr Leu Ala
1               5                   10

<210> SEQ ID NO 224
<211> LENGTH: 12
<212> TYPE: PRT
<213> ORGANISM: ARTIFICIAL SEQUENCE
<220> FEATURE:
<223> OTHER INFORMATION: CDRL 1-7

<400> SEQUENCE: 224

Arg Ala Ser Gln Gln Ile Ser Thr Asn Tyr Leu Ala
1               5                   10

<210> SEQ ID NO 225
<211> LENGTH: 7
<212> TYPE: PRT
<213> ORGANISM: ARTIFICIAL SEQUENCE
<220> FEATURE:
<223> OTHER INFORMATION: CDRL 2-3

<400> SEQUENCE: 225

Asp Ala Ser Asn Leu Glu Thr
1               5

<210> SEQ ID NO 226
<211> LENGTH: 7
<212> TYPE: PRT
<213> ORGANISM: ARTIFICIAL SEQUENCE
<220> FEATURE:
<223> OTHER INFORMATION: CDRL 2-4

<400> SEQUENCE: 226

Gly Ala Ser Ser Arg Ala Thr
1               5

<210> SEQ ID NO 227
<211> LENGTH: 7
<212> TYPE: PRT
<213> ORGANISM: ARTIFICIAL SEQUENCE
<220> FEATURE:
<223> OTHER INFORMATION: CDRL 3-6

<400> SEQUENCE: 227

Gln Gln Tyr Asp Asn Leu Thr
1               5

<210> SEQ ID NO 228
<211> LENGTH: 10
<212> TYPE: PRT
<213> ORGANISM: ARTIFICIAL SEQUENCE
<220> FEATURE:
<223> OTHER INFORMATION: CDRL 3-7

<400> SEQUENCE: 228

Gln Gln Phe Gly Arg Ser Pro Arg Cys Ser
1               5                   10
```

<210> SEQ ID NO 229
<211> LENGTH: 10
<212> TYPE: PRT
<213> ORGANISM: ARTIFICIAL SEQUENCE
<220> FEATURE:
<223> OTHER INFORMATION: CDRL 3-8

<400> SEQUENCE: 229

Gln Gln Phe Gly Arg Ser Pro Arg Ser Ser
1               5                   10

<210> SEQ ID NO 230
<211> LENGTH: 9
<212> TYPE: PRT
<213> ORGANISM: ARTIFICIAL SEQUENCE
<220> FEATURE:
<223> OTHER INFORMATION: CDRL 3-9

<400> SEQUENCE: 230

Leu Gln His Asn Ser Tyr Pro Leu Thr
1               5

<210> SEQ ID NO 231
<211> LENGTH: 321
<212> TYPE: DNA
<213> ORGANISM: ARTIFICIAL SEQUENCE
<220> FEATURE:
<223> OTHER INFORMATION: VL1 coding sequence
<220> FEATURE:
<221> NAME/KEY: CDS
<222> LOCATION: (1)..(321)

<400> SEQUENCE: 231 gac atc cag atg acc cag tct cca tct tcc gtg tct gca tct gta ggt      48
Asp Ile Gln Met Thr Gln Ser Pro Ser Ser Val Ser Ala Ser Val Gly
1               5                   10                  15 gac aga gtc acc atc act tgt cgg gcg agt cag ggt att agc aac tgg      96
Asp Arg Val Thr Ile Thr Cys Arg Ala Ser Gln Gly Ile Ser Asn Trp
                20                  25                  30 tta gcc tgg tat cag cgg aaa cca ggg aaa gcc cct aag ctc ctg atc     144
Leu Ala Trp Tyr Gln Arg Lys Pro Gly Lys Ala Pro Lys Leu Leu Ile
            35                  40                  45 tat gct gca tcc agt ttg caa agt ggg gtc cca tca agg ttc agc ggc     192
Tyr Ala Ala Ser Ser Leu Gln Ser Gly Val Pro Ser Arg Phe Ser Gly
        50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
65                  70                  75                  80 gaa gat ttt gca gct tac tat tgt caa cag gct agc agt ttc ccg tgg     288
Glu Asp Phe Ala Ala Tyr Tyr Cys Gln Gln Ala Ser Ser Phe Pro Trp
                85                  90                  95 acg ttc ggc caa ggg acc agg gtg gaa atc aaa                         321
Thr Phe Gly Gln Gly Thr Arg Val Glu Ile Lys
            100                 105

<210> SEQ ID NO 232
<211> LENGTH: 107
<212> TYPE: PRT
<213> ORGANISM: ARTIFICIAL SEQUENCE
<220> FEATURE:
<223> OTHER INFORMATION: Synthetic Construct

<400> SEQUENCE: 232

Asp Ile Gln Met Thr Gln Ser Pro Ser Ser Val Ser Ala Ser Val Gly

```
                1               5                   10                  15
            Asp Arg Val Thr Ile Thr Cys Arg Ala Ser Gln Gly Ile Ser Asn Trp
                            20                  25                  30

Leu Ala Trp Tyr Gln Arg Lys Pro Gly Lys Ala Pro Lys Leu Leu Ile
                        35                  40                  45

Tyr Ala Ala Ser Ser Leu Gln Ser Gly Val Pro Ser Arg Phe Ser Gly
                    50                  55                  60

Ser Gly Ser Gly Thr Asp Phe Thr Leu Thr Ile Ser Ser Leu Gln Pro
            65                  70                  75                  80

Glu Asp Phe Ala Ala Tyr Tyr Cys Gln Gln Ala Ser Ser Phe Pro Trp
                            85                  90                  95

Thr Phe Gly Gln Gly Thr Arg Val Glu Ile Lys
                        100                 105

<210> SEQ ID NO 233
<211> LENGTH: 321
<212> TYPE: DNA
<213> ORGANISM: ARTIFICIAL SEQUENCE
<220> FEATURE:
<223> OTHER INFORMATION: VL2 coding sequence
<220> FEATURE:
<221> NAME/KEY: CDS
<222> LOCATION: (1)..(321)

<400> SEQUENCE: 233 gac atc cag atg acc cag tct cca tct tcc gtg tct gca tct gta gga         48
Asp Ile Gln Met Thr Gln Ser Pro Ser Ser Val Ser Ala Ser Val Gly
1               5                   10                  15 gac aga gtc acc atc act tgt cgg gcg agt cag ggt att agt agg agg         96
Asp Arg Val Thr Ile Thr Cys Arg Ala Ser Gln Gly Ile Ser Arg Arg
                20                  25                  30 tta gcc tgg tat cag cag aaa cca ggg aaa gcc cct aag ctc ctg atc       144
Leu Ala Trp Tyr Gln Gln Lys Pro Gly Lys Ala Pro Lys Leu Leu Ile
            35                  40                  45 tat gct gca tcc agt ttg caa agt ggg gtc cca tca agg ttc agc ggc       192
Tyr Ala Ala Ser Ser Leu Gln Ser Gly Val Pro Ser Arg Phe Ser Gly
        50                  55                  60 agt gga tct ggg aca gat ttc act ctc acc atc agc agc ctg cag cct       240
Ser Gly Ser Gly Thr Asp Phe Thr Leu Thr Ile Ser Ser Leu Gln Pro
65                  70                  75                  80 gaa gat ttt gca act tac tat tgt caa cag gct aac agt ttc cct ttc       288
Glu Asp Phe Ala Thr Tyr Tyr Cys Gln Gln Ala Asn Ser Phe Pro Phe
                85                  90                  95 act ttc ggc cct ggg acc aaa gtg gat atc aaa                           321
Thr Phe Gly Pro Gly Thr Lys Val Asp Ile Lys
            100                 105

<210> SEQ ID NO 234
<211> LENGTH: 107
<212> TYPE: PRT
<213> ORGANISM: ARTIFICIAL SEQUENCE
<220> FEATURE:
<223> OTHER INFORMATION: Synthetic Construct

<400> SEQUENCE: 234

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Arg
                20                  25                  30

Leu Ala Trp Tyr Gln Gln Lys Pro Gly Lys Ala Pro Lys Leu Leu Ile
            35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 235
<211> LENGTH: 321
<212> TYPE: DNA
<213> ORGANISM: ARTIFICIAL SEQUENCE
<220> FEATURE:
<223> OTHER INFORMATION: VL3 coding sequence
<220> FEATURE:
<221> NAME/KEY: CDS
<222> LOCATION: (1)..(321)

<400> SEQUENCE: 235 gac atc cag atg acc cag tct cca tcc tcc ctg tct gca tct gaa gga      48
Asp Ile Gln Met Thr Gln Ser Pro Ser Ser Leu Ser Ala Ser Glu Gly
1               5                   10                  15 gac aga gtc acc atc act tgc cgg gca agt cag ggc att aga aat gat      96
Asp Arg Val Thr Ile Thr Cys Arg Ala Ser Gln Gly Ile Arg Asn Asp
                20                  25                  30 tta ggc tgg tat cag cag aaa cca ggg aaa gcc cct aag cgc ctg atc     144
Leu Gly Trp Tyr Gln Gln Lys Pro Gly Lys Ala Pro Lys Arg Leu Ile
            35                  40                  45 tat gct gca tcc agt ttg caa agt ggg gtc cca tta agg ttc agc ggc     192
Tyr Ala Ala Ser Ser Leu Gln Ser Gly Val Pro Leu Arg Phe Ser Gly
        50                  55                  60 agt gga tct ggg aca gaa ttc act ctc aca atc agc agc ctg cag cct     240
Ser Gly Ser Gly Thr Glu Phe Thr Leu Thr Ile Ser Ser Leu Gln Pro
65                  70                  75                  80 gaa gat ttt gca act tat tac tgt cta cag tat aat agt tac ccg tgg     288
Glu Asp Phe Ala Thr Tyr Tyr Cys Leu Gln Tyr Asn Ser Tyr Pro Trp
                85                  90                  95 acg ttc ggc caa ggg acc aag gtg gaa atc aaa                         321
Thr Phe Gly Gln Gly Thr Lys Val Glu Ile Lys
            100                 105

<210> SEQ ID NO 236
<211> LENGTH: 107
<212> TYPE: PRT
<213> ORGANISM: ARTIFICIAL SEQUENCE
<220> FEATURE:
<223> OTHER INFORMATION: Synthetic Construct

<400> SEQUENCE: 236

Asp Ile Gln Met Thr Gln Ser Pro Ser Ser Leu Ser Ala Ser Glu Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Leu Arg Phe Ser Gly
        50                  55                  60

Ser Gly Ser Gly Thr Glu Phe Thr Leu Thr Ile Ser Ser Leu Gln Pro
65                  70                  75                  80
```

```
Glu Phe Ala Thr Tyr Tyr Cys Leu Gln Tyr Asn Ser Tyr Pro Trp
         85                  90                  95

Thr Phe Gly Gln Gly Thr Lys Val Glu Ile Lys
        100                 105

<210> SEQ ID NO 237
<211> LENGTH: 321
<212> TYPE: DNA
<213> ORGANISM: ARTIFICIAL SEQUENCE
<220> FEATURE:
<223> OTHER INFORMATION: VL4 coding sequence
<220> FEATURE:
<221> NAME/KEY: CDS
<222> LOCATION: (1)..(321)

<400> SEQUENCE: 237 gac atc cag atg acc cag tct cca tcc tcc ctg tct gca tct gta gga      48
Asp Ile Gln Met Thr Gln Ser Pro Ser Ser Leu Ser Ala Ser Val Gly
1               5                   10                  15 gac aga gtc acc atc act tgc cgg gcg agt cag ggc atg agc aat tat      96
Asp Arg Val Thr Ile Thr Cys Arg Ala Ser Gln Gly Met Ser Asn Tyr
            20                  25                  30 tta gcc tgg tat cag cag aaa cca agg aaa gtt cct aag ctc ctg atc     144
Leu Ala Trp Tyr Gln Gln Lys Pro Arg Lys Val Pro Lys Leu Leu Ile
        35                  40                  45 tat gct gca tcc act ttg caa tca ggg gtc cca tct cgg ttc agt ggc     192
Tyr Ala Ala Ser Thr Leu Gln Ser Gly Val Pro Ser Arg Phe Ser Gly
    50                  55                  60 agt gga tct ggg aca gat ttc acc ctc acc atc agc agc ctg cag ccg     240
Ser Gly Ser Gly Thr Asp Phe Thr Leu Thr Ile Ser Ser Leu Gln Pro
65                  70                  75                  80 gaa gat gtt gca act tat tac tgt caa aag ttt aac agt gcc cca ttc     288
Glu Asp Val Ala Thr Tyr Tyr Cys Gln Lys Phe Asn Ser Ala Pro Phe
                85                  90                  95 act ttc ggc cct ggg acc aaa gtg gat atc aaa                         321
Thr Phe Gly Pro Gly Thr Lys Val Asp Ile Lys
            100                 105

<210> SEQ ID NO 238
<211> LENGTH: 107
<212> TYPE: PRT
<213> ORGANISM: ARTIFICIAL SEQUENCE
<220> FEATURE:
<223> OTHER INFORMATION: Synthetic Construct

<400> SEQUENCE: 238

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Met Ser Asn Tyr
            20                  25                  30

Leu Ala Trp Tyr Gln Gln Lys Pro Arg Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Phe Asn Ser Ala Pro Phe
                85                  90                  95

Thr Phe Gly Pro Gly Thr Lys Val Asp Ile Lys
            100                 105
```

<210> SEQ ID NO 239
<211> LENGTH: 321
<212> TYPE: DNA
<213> ORGANISM: ARTIFICIAL SEQUENCE
<220> FEATURE:
<223> OTHER INFORMATION: VL5 coding sequence
<220> FEATURE:
<221> NAME/KEY: CDS
<222> LOCATION: (1)..(321)

<400> SEQUENCE: 239

```
gac atc cag atg acc ctg tct cca tcc tcc ctg tct gca tct gta gga      48
Asp Ile Gln Met Thr Leu Ser Pro Ser Ser Leu Ser Ala Ser Val Gly
1               5                   10                  15 gac aga gtc acc atc act tgc cgg gca agt cag ggc att aga aat gat      96
Asp Arg Val Thr Ile Thr Cys Arg Ala Ser Gln Gly Ile Arg Asn Asp
            20                  25                  30 tta ggc tgg tat cag cag aaa cca ggg aaa gcc cct aag cgc ctg atc     144
Leu Gly Trp Tyr Gln Gln Lys Pro Gly Lys Ala Pro Lys Arg Leu Ile
        35                  40                  45 tat gct gca tcc agt ttg caa agt ggg gtc cca tca agg ttc agc ggc     192
Tyr Ala Ala Ser Ser Leu Gln Ser Gly Val Pro Ser Arg Phe Ser Gly
    50                  55                  60 agt gga tct ggg aca gaa ttc act ctc aca atc agc agc ctg cag cct     240
Ser Gly Ser Gly Thr Glu Phe Thr Leu Thr Ile Ser Ser Leu Gln Pro
65                  70                  75                  80 gaa gat ttt gca act tat tac tgt cta cag tat aat agt tcc ccg tgg     288
Glu Asp Phe Ala Thr Tyr Tyr Cys Leu Gln Tyr Asn Ser Ser Pro Trp
                85                  90                  95 acg ttc ggc caa ggg acc gag gtg gaa atc aaa                         321
Thr Phe Gly Gln Gly Thr Glu Val Glu Ile Lys
            100                 105
```

<210> SEQ ID NO 240
<211> LENGTH: 107
<212> TYPE: PRT
<213> ORGANISM: ARTIFICIAL SEQUENCE
<220> FEATURE:
<223> OTHER INFORMATION: Synthetic Construct

<400> SEQUENCE: 240

```
Asp Ile Gln Met Thr Leu Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Ser Ser Pro Trp
                85                  90                  95

Thr Phe Gly Gln Gly Thr Glu Val Glu Ile Lys
            100                 105
```

<210> SEQ ID NO 241
<211> LENGTH: 315
<212> TYPE: DNA
<213> ORGANISM: ARTIFICIAL SEQUENCE
<220> FEATURE:
<223> OTHER INFORMATION: VL6 coding sequence
<220> FEATURE:

<221> NAME/KEY: CDS
<222> LOCATION: (1)..(315)

<400> SEQUENCE: 241

| | | | | | | | | | | | | | | | | |
|---|---|---|---|---|---|---|---|---|---|---|---|---|---|---|---|---|
| gac | atc | cag | atg | acc | cag | tct | cca | tcc | tcc | ctg | tct | gta | tct | gtg | gga | 48 |
| Asp | Ile | Gln | Met | Thr | Gln | Ser | Pro | Ser | Ser | Leu | Ser | Val | Ser | Val | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gac | aga | gtc | acc | atc | act | tgc | cag | gcg | ggt | cag | gac | att | cgc | aac | tat | 96 |
| Asp | Arg | Val | Thr | Ile | Thr | Cys | Gln | Ala | Gly | Gln | Asp | Ile | Arg | Asn | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| tta | aat | tgg | tat | cag | cag | aaa | cca | ggg | aaa | gcc | cct | aaa | ctc | ctg | atc | 144 |
| Leu | Asn | Trp | Tyr | Gln | Gln | Lys | Pro | Gly | Lys | Ala | Pro | Lys | Leu | Leu | Ile | |
| | | 35 | | | | | 40 | | | | | 45 | | | | |

| | | | | | | | | | | | | | | | | |
|---|---|---|---|---|---|---|---|---|---|---|---|---|---|---|---|---|
| tac | gat | gca | tcc | aat | ttg | gaa | aca | ggg | gtc | cca | tca | agg | ttc | agt | gga | 192 |
| Tyr | Asp | Ala | Ser | Asn | Leu | Glu | Thr | Gly | Val | Pro | Ser | Arg | Phe | Ser | Gly | |
| 50 | | | | | 55 | | | | | 60 | | | | | | |

| | | | | | | | | | | | | | | | | |
|---|---|---|---|---|---|---|---|---|---|---|---|---|---|---|---|---|
| agt | gga | tct | ggg | aca | gct | ttt | act | ttc | acc | atc | agc | agc | ctg | cag | cct | 240 |
| Ser | Gly | Ser | Gly | Thr | Ala | Phe | Thr | Phe | Thr | Ile | Ser | Ser | Leu | Gln | Pro | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gaa | gat | att | gca | aca | tat | tac | tgt | caa | cag | tat | gat | aat | ctc | act | ttt | 288 |
| Glu | Asp | Ile | Ala | Thr | Tyr | Tyr | Cys | Gln | Gln | Tyr | Asp | Asn | Leu | Thr | Phe | |
| | | | 85 | | | | | 90 | | | | | 95 | | | |

| | | | | | | | | |
|---|---|---|---|---|---|---|---|---|
| ggc | cag | ggg | acc | aaa | ctg | gag | atc | aaa | 315 |
| Gly | Gln | Gly | Thr | Lys | Leu | Glu | Ile | Lys | |
| | | 100 | | | | | 105 | | |

<210> SEQ ID NO 242
<211> LENGTH: 105
<212> TYPE: PRT
<213> ORGANISM: ARTIFICIAL SEQUENCE
<220> FEATURE:
<223> OTHER INFORMATION: Synthetic Construct

<400> SEQUENCE: 242

Asp Ile Gln Met Thr Gln Ser Pro Ser Ser Leu Ser Val Ser Val Gly
1               5                   10                  15

Asp Arg Val Thr Ile Thr Cys Gln Ala Gly Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Ala Phe Thr Phe Thr Ile Ser Ser Leu Gln Pro
65                  70                  75                  80

Glu Asp Ile Ala Thr Tyr Tyr Cys Gln Gln Tyr Asp Asn Leu Thr Phe
                85                  90                  95

Gly Gln Gly Thr Lys Leu Glu Ile Lys
            100                 105

<210> SEQ ID NO 243
<211> LENGTH: 327
<212> TYPE: DNA
<213> ORGANISM: ARTIFICIAL SEQUENCE
<220> FEATURE:
<223> OTHER INFORMATION: VL7 coding sequence
<220> FEATURE:
<221> NAME/KEY: CDS
<222> LOCATION: (1)..(327)

<400> SEQUENCE: 243

| | | | | | | | | | | | | | | | | |
|---|---|---|---|---|---|---|---|---|---|---|---|---|---|---|---|---|
| gaa | att | gtg | ttg | acg | cag | tct | cca | ggc | acc | ctg | tct | ttg | tct | cca | ggg | 48 |
| Glu | Ile | Val | Leu | Thr | Gln | Ser | Pro | Gly | Thr | Leu | Ser | Leu | Ser | Pro | Gly | |

```
                1               5                    10                        15
gaa aga gcc acc ctc tcc tgt agg gcc agt cag aat att agc acc aac        96
Glu Arg Ala Thr Leu Ser Cys Arg Ala Ser Gln Asn Ile Ser Thr Asn
            20                      25                      30 tac tta gcc tgg tac cag cag aaa cct ggc cag gct ccc agg ttc ctc        144
Tyr Leu Ala Trp Tyr Gln Gln Lys Pro Gly Gln Ala Pro Arg Phe Leu
            35                      40                      45 att tat ggt gca tcc agc agg gcc act ggc atc cca gac agg ttc agt        192
Ile Tyr Gly Ala Ser Ser Arg Ala Thr Gly Ile Pro Asp Arg Phe Ser
        50                      55                      60 ggc agt ggg tct ggg aca gac ttc act ctc acc atc agc aga ctg gag        240
Gly Ser Gly Ser Gly Thr Asp Phe Thr Leu Thr Ile Ser Arg Leu Glu
65                      70                      75                  80 cct gaa gat ttt gca gtg tat tac tgt cag cag ttt ggg cgc tca cct        288
Pro Glu Asp Phe Ala Val Tyr Tyr Cys Gln Gln Phe Gly Arg Ser Pro
                    85                      90                      95 cgg tgc agt ttt ggc cag ggg acc aag ctg gag atc aaa                    327
Arg Cys Ser Phe Gly Gln Gly Thr Lys Leu Glu Ile Lys
                100                     105
```

<210> SEQ ID NO 244
<211> LENGTH: 109
<212> TYPE: PRT
<213> ORGANISM: ARTIFICIAL SEQUENCE
<220> FEATURE:
<223> OTHER INFORMATION: Synthetic Construct

<400> SEQUENCE: 244

```
Glu Ile Val Leu Thr Gln Ser Pro Gly Thr Leu Ser Leu Ser Pro Gly
1               5                   10                      15

Glu Arg Ala Thr Leu Ser Cys Arg Ala Ser Gln Asn Ile Ser Thr Asn
            20                      25                      30

Tyr Leu Ala Trp Tyr Gln Gln Lys Pro Gly Gln Ala Pro Arg Phe Leu
            35                      40                      45

Ile Tyr Gly Ala Ser Ser Arg Ala Thr Gly Ile Pro Asp Arg Phe Ser
        50                      55                      60

Gly Ser Gly Ser Gly Thr Asp Phe Thr Leu Thr Ile Ser Arg Leu Glu
65                      70                      75                  80

Pro Glu Asp Phe Ala Val Tyr Tyr Cys Gln Gln Phe Gly Arg Ser Pro
                    85                      90                      95

Arg Cys Ser Phe Gly Gln Gly Thr Lys Leu Glu Ile Lys
                100                     105
```

<210> SEQ ID NO 245
<211> LENGTH: 327
<212> TYPE: DNA
<213> ORGANISM: ARTIFICIAL SEQUENCE
<220> FEATURE:
<223> OTHER INFORMATION: VL8 coding sequence
<220> FEATURE:
<221> NAME/KEY: CDS
<222> LOCATION: (1)..(327)

<400> SEQUENCE: 245

```
gaa att gtg ttg acg cag tct cca ggc acc ctg tct ttg tct cca ggg        48
Glu Ile Val Leu Thr Gln Ser Pro Gly Thr Leu Ser Leu Ser Pro Gly
1               5                   10                      15 gaa aga gcc acc ctc tcc tgt agg gcc agt cag caa att agc acc aac        96
Glu Arg Ala Thr Leu Ser Cys Arg Ala Ser Gln Gln Ile Ser Thr Asn
            20                      25                      30 tac tta gcc tgg tac cag cag aaa cct ggc cag gct ccc agg ttc ctc        144
Tyr Leu Ala Trp Tyr Gln Gln Lys Pro Gly Gln Ala Pro Arg Phe Leu
```

```
                Tyr Leu Ala Trp Tyr Gln Gln Lys Pro Gly Gln Ala Pro Arg Phe Leu
                            35                  40                  45 att tat ggt gca tcc agc agg gcc act ggc atc cca gac agg ttc agt        192
Ile Tyr Gly Ala Ser Ser Arg Ala Thr Gly Ile Pro Asp Arg Phe Ser
 50                  55                  60 ggc agt ggg tct ggg aca gac ttc act ctc acc atc agc aga ctg gag        240
Gly Ser Gly Ser Gly Thr Asp Phe Thr Leu Thr Ile Ser Arg Leu Glu
 65                  70                  75                  80 cct gaa gat ttt gca gtg tat tac tgt cag cag ttt ggg cgc tca cct        288
Pro Glu Asp Phe Ala Val Tyr Tyr Cys Gln Gln Phe Gly Arg Ser Pro
                    85                  90                  95 cgg agc agt ttt ggc cag ggg acc aag ctg gag atc aaa                    327
Arg Ser Ser Phe Gly Gln Gly Thr Lys Leu Glu Ile Lys
                   100                 105
```

<210> SEQ ID NO 246
<211> LENGTH: 109
<212> TYPE: PRT
<213> ORGANISM: ARTIFICIAL SEQUENCE
<220> FEATURE:
<223> OTHER INFORMATION: Synthetic Construct

<400> SEQUENCE: 246

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Gln Ile Ser Thr Asn
                20                  25                  30

Tyr Leu Ala Trp Tyr Gln Gln Lys Pro Gly Gln Ala Pro Arg Phe Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Arg Ser Pro
                    85                  90                  95

Arg Ser Ser Phe Gly Gln Gly Thr Lys Leu Glu Ile Lys
                   100                 105
```

<210> SEQ ID NO 247
<211> LENGTH: 321
<212> TYPE: DNA
<213> ORGANISM: ARTIFICIAL SEQUENCE
<220> FEATURE:
<223> OTHER INFORMATION: VL9 coding sequence
<220> FEATURE:
<221> NAME/KEY: CDS
<222> LOCATION: (1)..(321)

<400> SEQUENCE: 247

```
gac atc cag atg acc cag tct cca tcc tcc ctg tct gca tct gta gga         48
Asp Ile Gln Met Thr Gln Ser Pro Ser Ser Leu Ser Ala Ser Val Gly
 1               5                  10                  15 gac aga gtc acc atc act tgc cgg gca agt cag ggc att aga aat gat         96
Asp Arg Val Thr Ile Thr Cys Arg Ala Ser Gln Gly Ile Arg Asn Asp
                20                  25                  30 tta ggc tgg tat cag cag aaa cca ggg aaa gcc cct aaa cgc ctg atc        144
Leu Gly Trp Tyr Gln Gln Lys Pro Gly Lys Ala Pro Lys Arg Leu Ile
            35                  40                  45 tat gct gca tcc agt ttg caa agt ggg gtc cca tca agg ttc agc ggc        192
Tyr Ala Ala Ser Ser Leu Gln Ser Gly Val Pro Ser Arg Phe Ser Gly
 50                  55                  60
```

| | | |
|---|---|---|
| agt gga tct ggg aca gaa ttc act ctc aca atc agc agc ctg cag cct<br>Ser Gly Ser Gly Thr Glu Phe Thr Leu Thr Ile Ser Ser Leu Gln Pro<br>65                           70                      75                     80 | 240 |
| gaa gat ttt gca act tat tac tgt cta cag cat aat agt tac ccg ctc<br>Glu Asp Phe Ala Thr Tyr Tyr Cys Leu Gln His Asn Ser Tyr Pro Leu<br>                      85                      90                      95 | 288 |
| act ttc ggc gga ggg acc aag gtg gag atc aaa<br>Thr Phe Gly Gly Gly Thr Lys Val Glu Ile Lys<br>            100                    105 | 321 |

<210> SEQ ID NO 248
<211> LENGTH: 107
<212> TYPE: PRT
<213> ORGANISM: ARTIFICIAL SEQUENCE
<220> FEATURE:
<223> OTHER INFORMATION: Synthetic Construct

<400> SEQUENCE: 248

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 249
<211> LENGTH: 366
<212> TYPE: DNA
<213> ORGANISM: ARTIFICIAL SEQUENCE
<220> FEATURE:
<223> OTHER INFORMATION: VH1 coding sequence
<220> FEATURE:
<221> NAME/KEY: CDS
<222> LOCATION: (1)..(366)

<400> SEQUENCE: 249

| | |
|---|---|
| cag gtg cag ctg cag gag tcg ggc cca gga ctg gtg aag cct tcg gag<br>Gln Val Gln Leu Gln Glu Ser Gly Pro Gly Leu Val Lys Pro Ser Glu<br>1               5                   10                 15 | 48 |
| acc ctg tcc ctc acc tgc act gtc tct ggt ggc tcc atc agt cat tac<br>Thr Leu Ser Leu Thr Cys Thr Val Ser Gly Gly Ser Ile Ser His Tyr<br>            20                   25                  30 | 96 |
| tac tgg agc tgg atc cgg cag ccc cca ggg aag gga ctg ggt gga att<br>Tyr Trp Ser Trp Ile Arg Gln Pro Pro Gly Lys Gly Leu Gly Trp Ile<br>        35                  40                   45 | 144 |
| ggg tat atc tat tac agt ggg agc acc aac tac aac ccc tcc ctc aag<br>Gly Tyr Ile Tyr Tyr Ser Gly Ser Thr Asn Tyr Asn Pro Ser Leu Lys<br>50                      55                    60 | 192 |
| agt cga gtc acc ata tca gta gac acg tcc aag aac cag ttc tcc ctg<br>Ser Arg Val Thr Ile Ser Val Asp Thr Ser Lys Asn Gln Phe Ser Leu<br>65                          70                    75                    80 | 240 |
| aag ctg acc tct gtg acc gct gcg gac acg gcc gtg tat tac tgt gcg<br>Lys Leu Thr Ser Val Thr Ala Ala Asp Thr Ala Val Tyr Tyr Cys Ala<br>                    85                      90                    95 | 288 |

```
agg gcc cgg gga gat ggc tac aat tac cct gat gct ttt gat atc tgg     336
Arg Ala Arg Gly Asp Gly Tyr Asn Tyr Pro Asp Ala Phe Asp Ile Trp
            100                 105                 110 ggc caa ggg aca atg gtc acc gtc tct agt                             366
Gly Gln Gly Thr Met Val Thr Val Ser Ser
        115                 120
```

<210> SEQ ID NO 250
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 250

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser His Tyr
            20                  25                  30

Tyr Trp Ser Trp Ile Arg Gln Pro Pro Gly Lys Gly Leu Gly Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Ala Arg Gly Asp Gly Tyr Asn Tyr Pro Asp Ala Phe Asp Ile Trp
            100                 105                 110

Gly Gln Gly Thr Met Val Thr Val Ser Ser
        115                 120
```

<210> SEQ ID NO 251
<211> LENGTH: 354
<212> TYPE: DNA
<213> ORGANISM: ARTIFICIAL SEQUENCE
<220> FEATURE:
<223> OTHER INFORMATION: VH2 coding sequence
<220> FEATURE:
<221> NAME/KEY: CDS
<222> LOCATION: (1)..(354)

<400> SEQUENCE: 251

```
cag gtg cag ctg gtg gag tct ggg gga ggc gtg gtc cag cct ggg agg    48
Gln Val Gln Leu Val Glu Ser Gly Gly Gly Val Val Gln Pro Gly Arg
1               5                   10                  15 tcc ctg aga ctc tcc tgt gca gcg tct gga ttc acc ttc agt agc tat    96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg    144
Gly Met His Trp Val Arg Gln Ala Pro Gly Lys Gly Leu Glu Trp Val
        35                  40                  45 gca gtt ata tgg tat gat gga agt aat aaa tac tat gca gac tcc gtg    192
Ala Val Ile Trp Tyr Asp Gly Ser Asn Lys Tyr Tyr Ala Asp Ser Val
    50                  55                  60 aag ggc cga ttc act atc tcc aga gac aat tcc aag aac acg ctg tat    240
Lys Gly Arg Phe Thr Ile Ser Arg Asp Asn Ser Lys Asn Thr Leu Tyr
65                  70                  75                  80 ctg caa atg aac agc ctg aga gcc gag gac acg gct gtg tat tac tgt    288
Leu Gln Met Asn Ser Leu Arg Ala Glu Asp Thr Ala Val Tyr Tyr Cys
                85                  90                  95
```

```
gcg agg tat aac tgg aac tac ggt atg gac gtc tgg ggc caa ggg acc      336
Ala Arg Tyr Asn Trp Asn Tyr Gly Met Asp Val Trp Gly Gln Gly Thr
            100                 105                 110 acg gtc acc gtc tct agt                                              354
Thr Val Thr Val Ser Ser
        115
```

<210> SEQ ID NO 252
<211> LENGTH: 118
<212> TYPE: PRT
<213> ORGANISM: ARTIFICIAL SEQUENCE
<220> FEATURE:
<223> OTHER INFORMATION: Synthetic Construct

<400> SEQUENCE: 252

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Trp Asn Tyr Gly Met Asp Val Trp Gly Gln Gly Thr
            100                 105                 110

Thr Val Thr Val Ser Ser
        115
```

<210> SEQ ID NO 253
<211> LENGTH: 354
<212> TYPE: DNA
<213> ORGANISM: ARTIFICIAL SEQUENCE
<220> FEATURE:
<223> OTHER INFORMATION: CH3 coding sequence
<220> FEATURE:
<221> NAME/KEY: CDS
<222> LOCATION: (1)..(354)

<400> SEQUENCE: 253

```
cag gtg cag ctg gtg gag tct ggg gga ggc gtg gtc cag cct ggg agg       48
Gln Val Gln Leu Val Glu Ser Gly Gly Gly Val Val Gln Pro Gly Arg
1               5                   10                  15 tcc ctg aga ctc tcc tgt gca gcg tct gga ttc acc ttc agt agc tat       96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg      144
Gly Met His Trp Val Arg Gln Ala Pro Gly Lys Gly Leu Glu Trp Val
        35                  40                  45 gca gtt ata tgg tat gat gga agt aat aaa tac tat gca gac tcc gtg      192
Ala Val Ile Trp Tyr Asp Gly Ser Asn Lys Tyr Tyr Ala Asp Ser Val
    50                  55                  60 aag ggc cga ttc act atc tcc aga gac aat tcc aag aac acg ctg tat      240
Lys Gly Arg Phe Thr Ile Ser Arg Asp Asn Ser Lys Asn Thr Leu Tyr
65                  70                  75                  80 ctg caa atg aac agc ctg aga gcc gag gac acg gct gtg tat tac tgt      288
Leu Gln Met Asn Ser Leu Arg Ala Glu Asp Thr Ala Val Tyr Tyr Cys
                85                  90                  95
```

```
gcg agg tat aac ttc aac tac ggt atg gac gtc tgg ggc caa ggg acc      336
Ala Arg Tyr Asn Phe Asn Tyr Gly Met Asp Val Trp Gly Gln Gly Thr
            100                 105                 110 acg gtc acc gtc tct agt                                              354
Thr Val Thr Val Ser Ser
        115
```

<210> SEQ ID NO 254
<211> LENGTH: 118
<212> TYPE: PRT
<213> ORGANISM: ARTIFICIAL SEQUENCE
<220> FEATURE:
<223> OTHER INFORMATION: Synthetic Construct

<400> SEQUENCE: 254

```
Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Phe Asn Tyr Gly Met Asp Val Trp Gly Gln Gly Thr
            100                 105                 110

Thr Val Thr Val Ser Ser
        115
```

<210> SEQ ID NO 255
<211> LENGTH: 354
<212> TYPE: DNA
<213> ORGANISM: ARTIFICIAL SEQUENCE
<220> FEATURE:
<223> OTHER INFORMATION: VH4 coding sequence
<220> FEATURE:
<221> NAME/KEY: CDS
<222> LOCATION: (1)..(354)

<400> SEQUENCE: 255

```
cag gtg cag ctg gtg gag tct ggg gga ggc gtg gtc cag cct ggg agg       48
Gln Val Gln Leu Val Glu Ser Gly Gly Gly Val Val Gln Pro Gly Arg
 1               5                   10                  15 tcc ctg aga ctc tcc tgt gca gcg tct gga ttc acc ttc agt agc tat       96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg      144
Gly Met His Trp Val Arg Gln Ala Pro Gly Lys Gly Leu Glu Trp Val
        35                  40                  45 gca gtt ata tgg tat gat gga agt aat aaa tac tat gca gac tcc gtg      192
Ala Val Ile Trp Tyr Asp Gly Ser Asn Lys Tyr Tyr Ala Asp Ser Val
    50                  55                  60 aag ggc cga ttc act atc tcc aga gac aat tcc aag aac acg ctg tat      240
Lys Gly Arg Phe Thr Ile Ser Arg Asp Asn Ser Lys Asn Thr Leu Tyr
65                  70                  75                  80 ctg caa atg aac agc ctg aga gcc gag gac acg gct gtg tat tac tgt      288
Leu Gln Met Asn Ser Leu Arg Ala Glu Asp Thr Ala Val Tyr Tyr Cys
                85                  90                  95
```

```
gcg agg tat aac tac aac tac ggt atg gac gtc tgg ggc caa ggg acc      336
Ala Arg Tyr Asn Tyr Asn Tyr Gly Met Asp Val Trp Gly Gln Gly Thr
            100                 105                 110 acg gtc acc gtc tct agt                                              354
Thr Val Thr Val Ser Ser
        115

<210> SEQ ID NO 256
<211> LENGTH: 118
<212> TYPE: PRT
<213> ORGANISM: ARTIFICIAL SEQUENCE
<220> FEATURE:
<223> OTHER INFORMATION: Synthetic Construct

<400> SEQUENCE: 256

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Tyr Asn Tyr Gly Met Asp Val Trp Gly Gln Gly Thr
            100                 105                 110

Thr Val Thr Val Ser Ser
        115

<210> SEQ ID NO 257
<211> LENGTH: 369
<212> TYPE: DNA
<213> ORGANISM: ARTIFICIAL SEQUENCE
<220> FEATURE:
<223> OTHER INFORMATION: VH5 coding sequence
<220> FEATURE:
<221> NAME/KEY: CDS
<222> LOCATION: (1)..(369)
<223> OTHER INFORMATION: VH5 coding sequence

<400> SEQUENCE: 257 cag gtg cag ctg cag gag tcg ggc cca gga ctg gtt aag cct tcg gag      48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc agt agt tac      96
Thr Leu Ser Leu Thr Cys Thr Val Ser Gly Gly Ser Ile Ser Ser Tyr
            20                  25                  30 tac tgg agc tgg atc cgg cag ccc cca ggg aag gga ctg gag tgg att      144
Tyr Trp Ser Trp Ile Arg Gln Pro Pro Gly Lys Gly Leu Glu Trp Ile
        35                  40                  45 ggg tat atc tat tac agt ggg aac acc aac tcc aac ccc tcc ctc aag      192
Gly Tyr Ile Tyr Tyr Ser Gly Asn Thr Asn Ser Asn Pro Ser Leu Lys
    50                  55                  60 agt cga gtc acc ata tca gta gac acg tcc aag aac cag ttc tcc ctg      240
Ser Arg Val Thr Ile Ser Val Asp Thr Ser Lys Asn Gln Phe Ser Leu
65                  70                  75                  80 aag ctg agc tct gtg acc gct gcg gac acg gcc gtg tat tac tgt gcg      288
Lys Leu Ser Ser Val Thr Ala Ala Asp Thr Ala Val Tyr Tyr Cys Ala
```

```
                   85                  90                  95
aga acc tac tat gat agt agt ggt tac tac tac cgt gct ttt gat atc    336
Arg Thr Tyr Tyr Asp Ser Ser Gly Tyr Tyr Tyr Arg Ala Phe Asp Ile
                100                 105                 110 tgg ggc caa ggg aca atg gtc acc gtc tct agt                        369
Trp Gly Gln Gly Thr Met Val Thr Val Ser Ser
            115                 120

<210> SEQ ID NO 258
<211> LENGTH: 123
<212> TYPE: PRT
<213> ORGANISM: ARTIFICIAL SEQUENCE
<220> FEATURE:
<223> OTHER INFORMATION: Synthetic Construct

<400> SEQUENCE: 258

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Asn Ser Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr Tyr Tyr Asp Ser Ser Gly Tyr Tyr Tyr Arg Ala Phe Asp Ile
            100                 105                 110

Trp Gly Gln Gly Thr Met Val Thr Val Ser Ser
        115                 120

<210> SEQ ID NO 259
<211> LENGTH: 366
<212> TYPE: DNA
<213> ORGANISM: ARTIFICIAL SEQUENCE
<220> FEATURE:
<223> OTHER INFORMATION: VH6 coding sequence
<220> FEATURE:
<221> NAME/KEY: CDS
<222> LOCATION: (1)..(366)

<400> SEQUENCE: 259 cag gtg cag ctg cag gag tcg ggc cca gga ctg gtg aag cct tta cag    48
Gln Val Gln Leu Gln Glu Ser Gly Pro Gly Leu Val Lys Pro Leu Gln
1               5                   10                  15 acc ctg tcc ctc acc tgc act gtc tct ggt ggc tcc atc agc agt ggt    96
Thr Leu Ser Leu Thr Cys Thr Val Ser Gly Gly Ser Ile Ser Ser Gly
            20                  25                  30 ggt tat tac tgg agc tgg atc cgc cag cac cca ggg aag ggc ctg gag    144
Gly Tyr Tyr Trp Ser Trp Ile Arg Gln His Pro Gly Lys Gly Leu Glu
        35                  40                  45 tgg att ggg tac atc tat tac agt agg agc acc tac tac aac ccg tcc    192
Trp Ile Gly Tyr Ile Tyr Tyr Ser Arg Ser Thr Tyr Tyr Asn Pro Ser
    50                  55                  60 ctc aag agt cga gtt acc ata tca gta gac acg tct aag aac cag ttc    240
Leu Lys Ser Arg Val Thr Ile Ser Val Asp Thr Ser Lys Asn Gln Phe
65                  70                  75                  80 tcc ctg aag ctg agc tct gtg aca gcc gcg gac acg gcc gtg tat tac    288
Ser Leu Lys Leu Ser Ser Val Thr Ala Ala Asp Thr Ala Val Tyr Tyr
```

```
            85                  90                  95
tgt gcg aga acc ggg tat agc agt ggc tgg tac cct ttt gac tac tgg     336
Cys Ala Arg Thr Gly Tyr Ser Ser Gly Trp Tyr Pro Phe Asp Tyr Trp
            100                 105                 110 ggc cag gga acc ctg gtc acc gtc tct agt                             366
Gly Gln Gly Thr Leu Val Thr Val Ser Ser
        115                 120
```

<210> SEQ ID NO 260
<211> LENGTH: 122
<212> TYPE: PRT
<213> ORGANISM: ARTIFICIAL SEQUENCE
<220> FEATURE:
<223> OTHER INFORMATION: Synthetic Construct

<400> SEQUENCE: 260

```
Gln Val Gln Leu Gln Glu Ser Gly Pro Gly Leu Val Lys Pro Leu Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Arg Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Thr Gly Tyr Ser Ser Gly Trp Tyr Pro Phe Asp Tyr Trp
            100                 105                 110

Gly Gln Gly Thr Leu Val Thr Val Ser Ser
        115                 120
```

<210> SEQ ID NO 261
<211> LENGTH: 354
<212> TYPE: DNA
<213> ORGANISM: ARTIFICIAL SEQUENCE
<220> FEATURE:
<223> OTHER INFORMATION: VH7 coding sequence
<220> FEATURE:
<221> NAME/KEY: CDS
<222> LOCATION: (1)..(354)

<400> SEQUENCE: 261

```
gag gtg cag ctg gtg gag tct ggg gga ggc ttg gta cag cct ggg ggg     48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt aac tac     96
Ser Leu Arg Leu Ser Cys Ala Ala Ser Gly Phe Thr Phe Ser Asn Tyr
            20                  25                  30 gac atg tac tgg gtc cgc caa act aca gga aaa ggt ctg gag tgg gtc     144
Asp Met Tyr Trp Val Arg Gln Thr Thr Gly Lys Gly Leu Glu Trp Val
        35                  40                  45 tca gct att ggt act gct ggt gac aca tac tat cca ggc tcc gtg aag     192
Ser Ala Ile Gly Thr Ala Gly Asp Thr Tyr Tyr Pro Gly Ser Val Lys
    50                  55                  60 ggc cga ttc acc atc tcc aga gaa aat gcc aag aac tcc ttg tat ctt     240
Gly Arg Phe Thr Ile Ser Arg Glu Asn Ala Lys Asn Ser Leu Tyr Leu
65                  70                  75                  80 caa atg aac agc ctg aga gcc ggg gac acg gct gtg tat tac tgt gca     288
Gln Met Asn Ser Leu Arg Ala Gly Asp Thr Ala Val Tyr Tyr Cys Ala
```

```
              85                  90                  95
aga gag aag tct agc acc tcg gcc ttt gac tac tgg ggc cag gga acc    336
Arg Glu Lys Ser Ser Thr Ser Ala Phe Asp Tyr Trp Gly Gln Gly Thr
            100                 105                 110 ctg gtc acc gtc tcc tca                                           354
Leu Val Thr Val Ser Ser
        115

<210> SEQ ID NO 262
<211> LENGTH: 118
<212> TYPE: PRT
<213> ORGANISM: ARTIFICIAL SEQUENCE
<220> FEATURE:
<223> OTHER INFORMATION: Synthetic Construct

<400> SEQUENCE: 262

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Tyr Trp Val Arg Gln Thr Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Lys Ser Ser Thr Ser Ala Phe Asp Tyr Trp Gly Gln Gly Thr
            100                 105                 110

Leu Val Thr Val Ser Ser
        115

<210> SEQ ID NO 263
<211> LENGTH: 375
<212> TYPE: DNA
<213> ORGANISM: ARTIFICIAL SEQUENCE
<220> FEATURE:
<223> OTHER INFORMATION: VH8 coding sequence
<220> FEATURE:
<221> NAME/KEY: CDS
<222> LOCATION: (1)..(375)

<400> SEQUENCE: 263 cag ctg cag ctg caa gag tcg ggc cca gga ctg atg aag cct tcg gag    48
Gln Leu Gln Leu Gln Glu Ser Gly Pro Gly Leu Met Lys Pro Ser Glu
1               5                   10                  15 acc ctg tcc ctc acc tgc act gtc tct ggt ggc tcc atc agc agt agt    96
Thr Leu Ser Leu Thr Cys Thr Val Ser Gly Gly Ser Ile Ser Ser Ser
            20                  25                  30 agt tac ttc tgg ggc tgg atc cgc cag ccc cca ggg aag gga ctg gag   144
Ser Tyr Phe Trp Gly Trp Ile Arg Gln Pro Pro Gly Lys Gly Leu Glu
        35                  40                  45 tgg att ggg agt atc tat tat agt ggg aac acc ttc tac aac ccg tcc   192
Trp Ile Gly Ser Ile Tyr Tyr Ser Gly Asn Thr Phe Tyr Asn Pro Ser
    50                  55                  60 ctc aag agt cga gtc acc ata tcc gtt gac acg tcc aag aac cag ttc   240
Leu Lys Ser Arg Val Thr Ile Ser Val Asp Thr Ser Lys Asn Gln Phe
65                  70                  75                  80 tcc ctg aag ctt aac tct atg acc gcc gca gac acg gct gtg tat ttc   288
Ser Leu Lys Leu Asn Ser Met Thr Ala Ala Asp Thr Ala Val Tyr Phe
```

```
                85                  90                  95
tgt gcg aga caa ggg ggt ata gca gct cgt acc gga tac tgg tac ttc    336
Cys Ala Arg Gln Gly Gly Ile Ala Ala Arg Thr Gly Tyr Trp Tyr Phe
            100                 105                 110 gat ctc tgg ggc cgt ggc acc acg gtc acc gtc tcc tca                375
Asp Leu Trp Gly Arg Gly Thr Thr Val Thr Val Ser Ser
        115                 120                 125

<210> SEQ ID NO 264
<211> LENGTH: 125
<212> TYPE: PRT
<213> ORGANISM: ARTIFICIAL SEQUENCE
<220> FEATURE:
<223> OTHER INFORMATION: Synthetic Construct

<400> SEQUENCE: 264

Gln Leu Gln Leu Gln Glu Ser Gly Pro Gly Leu Met Lys Pro Ser Glu
1               5                   10                  15

Thr Leu Ser Leu Thr Cys Thr Val Ser Gly Gly Ser Ile Ser Ser Ser
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Asn Thr Phe Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Met Thr Ala Ala Asp Thr Ala Val Tyr Phe
                85                  90                  95

Cys Ala Arg Gln Gly Gly Ile Ala Ala Arg Thr Gly Tyr Trp Tyr Phe
            100                 105                 110

Asp Leu Trp Gly Arg Gly Thr Thr Val Thr Val Ser Ser
        115                 120                 125

<210> SEQ ID NO 265
<211> LENGTH: 357
<212> TYPE: DNA
<213> ORGANISM: ARTIFICIAL SEQUENCE
<220> FEATURE:
<223> OTHER INFORMATION: VH9 coding sequence
<220> FEATURE:
<221> NAME/KEY: CDS
<222> LOCATION: (1)..(357)

<400> SEQUENCE: 265 cag gtg cag ctg gtg cag tct ggg gct gag gtg aag aag cct ggg gcc    48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac    96
Ser Val Lys Val Ser Cys Lys Ala Ser Gly Tyr Thr Phe Thr Gly Tyr
            20                  25                  30 cac atg cac tgg gtg cga cag gcc cct gga caa ggg ctt gag tgg atg    144
His Met His Trp Val Arg Gln Ala Pro Gly Gln Gly Leu Glu Trp Met
        35                  40                  45 gga tgg atc aac cct aac agt ggt ggc aca aac tat gca cag aag ttt    192
Gly Trp Ile Asn Pro Asn Ser Gly Gly Thr Asn Tyr Ala Gln Lys Phe
    50                  55                  60 cag ggc agg gtc acc atg acc agg gac acg tcc atc agc aca gcc tac    240
Gln Gly Arg Val Thr Met Thr Arg Asp Thr Ser Ile Ser Thr Ala Tyr
65                  70                  75                  80 atg gag ctg agc agg ctg aga tct gac gac acg gcc gtg tat tac tgt    288
Met Glu Leu Ser Arg Leu Arg Ser Asp Asp Thr Ala Val Tyr Tyr Cys
```

```
                        85                  90                  95
gcg aga gat cgt ggg agc tac tac tgg ttc gac ccc tgg ggc cag gga         336
Ala Arg Asp Arg Gly Ser Tyr Tyr Trp Phe Asp Pro Trp Gly Gln Gly
            100                 105                 110 acc ctg gtc acc gtc tcc tca                                             357
Thr Leu Val Thr Val Ser Ser
        115
```

<210> SEQ ID NO 266
<211> LENGTH: 119
<212> TYPE: PRT
<213> ORGANISM: ARTIFICIAL SEQUENCE
<220> FEATURE:
<223> OTHER INFORMATION: Synthetic Construct

<400> SEQUENCE: 266

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

His Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Arg Gly Ser Tyr Tyr Trp Phe Asp Pro Trp Gly Gln Gly
            100                 105                 110

Thr Leu Val Thr Val Ser Ser
        115
```

<210> SEQ ID NO 267
<211> LENGTH: 281
<212> TYPE: PRT
<213> ORGANISM: ARTIFICIAL SEQUENCE
<220> FEATURE:
<223> OTHER INFORMATION: aKLH 120.6 kappa LC-ShK[1-35, Q16K] fusion
    protein

<400> SEQUENCE: 267

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Ser Tyr Pro Leu Thr Phe Gly Gly Gly Thr Lys Val Glu Ile
        115                 120                 125
```

```
Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys Gly Gly Gly Gly
225                 230                 235                 240

Ser Gly Gly Gly Gly Ser Arg Ser Cys Ile Asp Thr Ile Pro Lys Ser
                245                 250                 255

Arg Cys Thr Ala Phe Lys Cys Lys His Ser Met Lys Tyr Arg Leu Ser
                260                 265                 270

Phe Cys Arg Lys Thr Cys Gly Thr Cys
            275                 280
```

<210> SEQ ID NO 268
<211> LENGTH: 280
<212> TYPE: PRT
<213> ORGANISM: ARTIFICIAL SEQUENCE
<220> FEATURE:
<223> OTHER INFORMATION: aKLH 120.6 kappa LC-ShK[1-35, Q16K] fusion protein

<400> SEQUENCE: 268

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Ser Tyr Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205
```

-continued

Glu Lys His Lys Val Tyr Ala Cys Glu Val Thr His Gln Gly Leu Ser
    210                 215                 220

Ser Pro Val Thr Lys Ser Phe Asn Arg Gly Glu Cys Gly Gly Gly Gly
225                 230                 235                 240

Ser Gly Gly Gly Ser Ser Cys Ile Asp Thr Ile Pro Lys Ser Arg
                245                 250                 255

Cys Thr Ala Phe Lys Cys Lys His Ser Met Lys Tyr Arg Leu Ser Phe
            260                 265                 270

Cys Arg Lys Thr Cys Gly Thr Cys
        275                 280

<210> SEQ ID NO 269
<211> LENGTH: 34
<212> TYPE: DNA
<213> ORGANISM: ARTIFICIAL SEQUENCE
<220> FEATURE:
<223> OTHER INFORMATION: Primer sequence

<400> SEQUENCE: 269
aacaggggag agtgtggagg aggaggatcc ggag                              34

<210> SEQ ID NO 270
<211> LENGTH: 22
<212> TYPE: DNA
<213> ORGANISM: ARTIFICIAL SEQUENCE
<220> FEATURE:
<223> OTHER INFORMATION: Primer sequence

<400> SEQUENCE: 270
catgcggccg ctcattagca gg                                           22

<210> SEQ ID NO 271
<211> LENGTH: 26
<212> TYPE: DNA
<213> ORGANISM: ARTIFICIAL SEQUENCE
<220> FEATURE:
<223> OTHER INFORMATION: Forward primer sequence

<400> SEQUENCE: 271
ggacactgac atggactgaa ggagta                                       26

<210> SEQ ID NO 272
<211> LENGTH: 21
<212> TYPE: DNA
<213> ORGANISM: ARTIFICIAL SEQUENCE
<220> FEATURE:
<223> OTHER INFORMATION: Reverse primer sequence

<400> SEQUENCE: 272
ctcctgggag ttacccgatt g                                            21

<210> SEQ ID NO 273
<211> LENGTH: 40
<212> TYPE: DNA
<213> ORGANISM: ARTIFICIAL SEQUENCE
<220> FEATURE:
<223> OTHER INFORMATION: Reverse primer sequence

<400> SEQUENCE: 273
gatgggccct tggtggaggc tgaggagacg gtgaccgtgg                        40

<210> SEQ ID NO 274
<211> LENGTH: 36

-continued

```
<212> TYPE: DNA
<213> ORGANISM: ARTIFICIAL SEQUENCE
<220> FEATURE:
<223> OTHER INFORMATION: Primer sequence

<400> SEQUENCE: 274
aagctcgagg tcgactagac caccatggac atgagg                              36

<210> SEQ ID NO 275
<211> LENGTH: 41
<212> TYPE: DNA
<213> ORGANISM: ARTIFICIAL SEQUENCE
<220> FEATURE:
<223> OTHER INFORMATION: Primer sequence

<400> SEQUENCE: 275
aaccgtttaa acgcggccgc tcaacactct ccctgttga a                         41

<210> SEQ ID NO 276
<211> LENGTH: 41
<212> TYPE: DNA
<213> ORGANISM: ARTIFICIAL SEQUENCE
<220> FEATURE:
<223> OTHER INFORMATION: Primer sequence

<400> SEQUENCE: 276
aagctcgagg tcgactagac caccatggaa ttgggactga g                        41

<210> SEQ ID NO 277
<211> LENGTH: 41
<212> TYPE: DNA
<213> ORGANISM: ARTIFICIAL SEQUENCE
<220> FEATURE:
<223> OTHER INFORMATION: Primer sequence

<400> SEQUENCE: 277
aaccgtttaa acgcggccgc tcatttaccc ggagacaggg a                        41

<210> SEQ ID NO 278
<211> LENGTH: 37
<212> TYPE: DNA
<213> ORGANISM: ARTIFICIAL SEQUENCE
<220> FEATURE:
<223> OTHER INFORMATION: Primer sequence

<400> SEQUENCE: 278 tttttttgc gcgctgtgac atccagatga cccagtc                              37

<210> SEQ ID NO 279
<211> LENGTH: 32
<212> TYPE: DNA
<213> ORGANISM: ARTIFICIAL SEQUENCE
<220> FEATURE:
<223> OTHER INFORMATION: Primer sequence

<400> SEQUENCE: 279
aaaaaacgta cgtttgatat ccactttggt cc                                  32

<210> SEQ ID NO 280
<211> LENGTH: 50
<212> TYPE: DNA
<213> ORGANISM: ARTIFICIAL SEQUENCE
<220> FEATURE:
<223> OTHER INFORMATION: Primer sequence

<400> SEQUENCE: 280
```
ctgtgtatta ctgtgcgagg tataacttca actacggtat ggacgtctgg    50

<210> SEQ ID NO 281
<211> LENGTH: 50
<212> TYPE: DNA
<213> ORGANISM: ARTIFICIAL SEQUENCE
<220> FEATURE:
<223> OTHER INFORMATION: Primer sequence

<400> SEQUENCE: 281
ccagacgtcc ataccgtagt tgaagttata cctcgcacag taatacacag    50

<210> SEQ ID NO 282
<211> LENGTH: 50
<212> TYPE: DNA
<213> ORGANISM: ARTIFICIAL SEQUENCE
<220> FEATURE:
<223> OTHER INFORMATION: Primer sequence

<400> SEQUENCE: 282
ctgtgtatta ctgtgcgagg tataactaca actacggtat ggacgtctgg    50

<210> SEQ ID NO 283
<211> LENGTH: 50
<212> TYPE: DNA
<213> ORGANISM: ARTIFICIAL SEQUENCE
<220> FEATURE:
<223> OTHER INFORMATION: Primer sequence

<400> SEQUENCE: 283
ccagacgtcc ataccgtagt tgtagttata cctcgcacag taatacacag    50

<210> SEQ ID NO 284
<211> LENGTH: 59
<212> TYPE: DNA
<213> ORGANISM: ARTIFICIAL SEQUENCE
<220> FEATURE:
<223> OTHER INFORMATION: Primer sequence

<400> SEQUENCE: 284
aagctcgagg tcgactagac caccatggac atgagggtgc ccgctcagct cctggggct    59

<210> SEQ ID NO 285
<211> LENGTH: 41
<212> TYPE: DNA
<213> ORGANISM: ARTIFICIAL SEQUENCE
<220> FEATURE:
<223> OTHER INFORMATION: Primer sequence

<400> SEQUENCE: 285
aaccgtttaa acgcggccgc tcatttaccc ggagacaggg a    41

<210> SEQ ID NO 286
<211> LENGTH: 50
<212> TYPE: DNA
<213> ORGANISM: ARTIFICIAL SEQUENCE
<220> FEATURE:
<223> OTHER INFORMATION: Primer sequence

<400> SEQUENCE: 286
ggacaagaca gttgagcgca aatcttctgt cgagtgccca ccgtgcccag    50

<210> SEQ ID NO 287
<211> LENGTH: 50
<212> TYPE: DNA
<213> ORGANISM: ARTIFICIAL SEQUENCE

```
<220> FEATURE:
<223> OTHER INFORMATION: Primer sequence

<400> SEQUENCE: 287
ctgggcacgg tgggcactcg acagaagatt tgcgctcaac tgtcttgtcc          50

<210> SEQ ID NO 288
<211> LENGTH: 59
<212> TYPE: DNA
<213> ORGANISM: ARTIFICIAL SEQUENCE
<220> FEATURE:
<223> OTHER INFORMATION: Primer sequence

<400> SEQUENCE: 288
aagctcgagg tcgactagac caccatggac atgagggtgc ccgctcagct cctggggct    59

<210> SEQ ID NO 289
<211> LENGTH: 41
<212> TYPE: DNA
<213> ORGANISM: ARTIFICIAL SEQUENCE
<220> FEATURE:
<223> OTHER INFORMATION: Primer sequence

<400> SEQUENCE: 289
aaccgtttaa acgcggccgc tcatttaccc ggagacaggg a                   41

<210> SEQ ID NO 290
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 290

His Gly Glu Gly Thr Phe Thr Ser Asp Gln Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 291
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 291

His Gly Glu Gly Thr Phe Thr Ser Asp Gln Ser Ser Tyr Leu Glu Gly
 1               5                  10                  15

Gln Ala Ala Lys Glu Phe Ile Ala Trp Leu Gln Lys Gly Arg Gly
            20                  25                  30

<210> SEQ ID NO 292
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 292

His Gly Glu Gly Thr Phe Thr Ser Asp Val Ser Ser Tyr Gln Glu Gly
 1               5                  10                  15

Gln Ala Ala Lys Glu Phe Ile Ala Trp Leu Val Lys Gly Arg Gly
            20                  25                  30
```

<210> SEQ ID NO 293
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 293

His Gly Glu Gly Thr Phe Thr Ser Asp Val Ser Ser Tyr Leu Glu Gly
 1               5                  10                  15

Gln Ala Ala Lys Glu Phe Ile Ala Gln Leu Val Lys Gly Arg Gly
            20                  25                  30

<210> SEQ ID NO 294
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 294

His Gly Glu Gly Thr Phe Thr Ser Asp Val Ser Ser Tyr Leu Glu Gly
 1               5                  10                  15

Gln Ala Ala Lys Glu Phe Ile Ala Gln Leu Gln Lys Gly Arg Gly
            20                  25                  30

<210> SEQ ID NO 295
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 295

His Gly Glu Gly Thr Phe Thr Ser Asp Val Ser Ser Tyr Leu Glu Gly
 1               5                  10                  15

Gln Ala Ala Lys Glu Phe Ile Ala Trp Leu Gln Lys Gly Arg Gly
            20                  25                  30

<210> SEQ ID NO 296
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 296

His Asn Glu Thr Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 297
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 297

His Gly Glu Gly Thr Phe Thr Ser Asp Val Ser Ser Tyr Leu Glu Asn
 1               5                  10                  15

Gln Thr Ala Lys Glu Phe Ile Ala Trp Leu Val Lys Gly Arg Gly
            20                  25                  30

```
<210> SEQ ID NO 298
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 298

His Gly Glu Gly Thr Phe Thr Ser Asp Val Ser Ser Tyr Leu Glu Gly
1               5                   10                  15

Asn Ala Thr Lys Glu Phe Ile Ala Trp Leu Val Lys Gly Arg Gly
            20                  25                  30

<210> SEQ ID NO 299
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 299

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Asn Gly Thr Gly
            20                  25                  30

<210> SEQ ID NO 300
<211> LENGTH: 31
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 300

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Asn Arg Thr
            20                  25                  30

<210> SEQ ID NO 301
<211> LENGTH: 33
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 301

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Asn Gly
            20                  25                  30

Thr

<210> SEQ ID NO 302
<211> LENGTH: 37
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 302

His Gly Glu Gly Thr Phe Thr Ser Asp Val Ser Ser Tyr Leu Glu Gly
1               5                   10                  15
```

-continued

```
Gln Ala Ala Lys Glu Phe Ile Ala Trp Leu Val Lys Gly Arg Gly Gly
             20                  25                  30

Thr Gly Asn Gly Thr
        35

<210> SEQ ID NO 303
<211> LENGTH: 37
<212> TYPE: PRT
<213> ORGANISM: ARTIFICIAL SEQUENCE
<220> FEATURE:
<223> OTHER INFORMATION: GLP-1 mimetic polypeptide sequence

<400> SEQUENCE: 303

His Gly Glu Gly Thr Phe Thr Ser Asp Val Ser Ser Tyr Leu Glu Gly
1               5                  10                  15

Gln Ala Ala Lys Glu Phe Ile Ala Trp Leu Val Lys Gly Arg Gly Gly
             20                  25                  30

Ser Gly Asn Gly Thr
        35

<210> SEQ ID NO 304
<211> LENGTH: 511
<212> TYPE: PRT
<213> ORGANISM: ARTIFICIAL SEQUENCE
<220> FEATURE:
<223> OTHER INFORMATION: aKLH 120.6 IgG2-ShK[1-35, R1A, I4A, Q16K]
      fusion protein

<400> SEQUENCE: 304

Met Asp Met Arg Val Pro Ala Gln Leu Leu Gly Leu Leu Leu Leu Trp
1               5                  10                  15

Leu Arg Gly Ala Arg Cys Gln Val Gln Leu Val Gln Ser Gly Ala Glu
             20                  25                  30

Val Lys Lys Pro Gly Ala Ser Val Lys Val Ser Cys Lys Ala Ser Gly
         35                  40                  45

Tyr Thr Phe Thr Gly Tyr His Met His Trp Val Arg Gln Ala Pro Gly
     50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                 85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220
```

```
Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Gly Gly Gly Ser Gly Gly Gly Ser Ala Ser Cys Ala
465                 470                 475                 480

Asp Thr Ile Pro Lys Ser Arg Cys Thr Ala Phe Lys Cys Lys His Ser
                485                 490                 495

Met Lys Tyr Arg Leu Ser Phe Cys Arg Lys Thr Cys Gly Thr Cys
            500                 505                 510
```

<210> SEQ ID NO 305
<211> LENGTH: 511
<212> TYPE: PRT
<213> ORGANISM: ARTIFICIAL SEQUENCE
<220> FEATURE:
<223> OTHER INFORMATION: aKLH 120.6 IgG2-ShK[1-35, R1A, Q16K, K30E]
    fusion protein

<400> SEQUENCE: 305

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80
```

-continued

Asn Tyr Ala Gln Lys Phe Gln Gly Arg Val Thr Met Thr Arg Asp Thr
            85              90                  95

Ser Ile Ser Thr Ala Tyr Met Glu Leu Ser Arg Leu Arg Ser Asp Asp
            100             105                 110

Thr Ala Val Tyr Tyr Cys Ala Arg Asp Arg Gly Ser Tyr Tyr Trp Phe
            115             120                 125

Asp Pro Trp Gly Gln Gly Thr Leu Val Thr Val Ser Ser Ala Ser Thr
130             135                 140

Lys Gly Pro Ser Val Phe Pro Leu Ala Pro Cys Ser Arg Ser Thr Ser
145                 150                 155             160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
                340                 345                 350

Glu Lys Thr Ile Ser Lys Thr Lys Gly Gln Pro Arg Glu Pro Gln Val
                355                 360                 365

Tyr Thr Leu Pro Pro Ser Arg Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Gly Gly Gly Ser Gly Gly Gly Ser Ala Ser Cys Ile
465                 470                 475             480

Asp Thr Ile Pro Lys Ser Arg Cys Thr Ala Phe Lys Cys Lys His Ser
                485                 490                 495

```
Met Lys Tyr Arg Leu Ser Phe Cys Arg Glu Thr Cys Gly Thr Cys
            500                 505                 510
```

<210> SEQ ID NO 306
<211> LENGTH: 511
<212> TYPE: PRT
<213> ORGANISM: ARTIFICIAL SEQUENCE
<220> FEATURE:
<223> OTHER INFORMATION: aKLH 120.6 HC IgG2 -ShK[1-35, R1H, I4A, Q16K] fusion protein

<400> SEQUENCE: 306

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350
```

```
Glu Lys Thr Ile Ser Lys Thr Lys Gly Gln Pro Arg Glu Pro Gln Val
            355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Gly Gly Gly Ser Gly Gly Gly Ser His Ser Cys Ala
465                 470                 475                 480

Asp Thr Ile Pro Lys Ser Arg Cys Thr Ala Phe Lys Cys Lys His Ser
                485                 490                 495

Met Lys Tyr Arg Leu Ser Phe Cys Arg Lys Thr Cys Gly Thr Cys
            500                 505                 510

<210> SEQ ID NO 307
<211> LENGTH: 511
<212> TYPE: PRT
<213> ORGANISM: ARTIFICIAL SEQUENCE
<220> FEATURE:
<223> OTHER INFORMATION: aKLH 120.6 IgG2-ShK[1-35, R1H, Q16K, K30E]
      fusion protein

<400> SEQUENCE: 307

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
```

```
            195                 200                 205
Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
    275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
            325                 330                 335

Lys Glu Tyr Lys Cys Lys Val Ser Asn Lys Gly Leu Pro Ala Pro Ile
        340                 345                 350

Glu Lys Thr Ile Ser Lys Thr Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Met Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Gly Gly Gly Ser Gly Gly Gly Ser His Ser Cys Ile
465                 470                 475                 480

Asp Thr Ile Pro Lys Ser Arg Cys Thr Ala Phe Lys Cys Lys His Ser
            485                 490                 495

Met Lys Tyr Arg Leu Ser Phe Cys Arg Glu Thr Cys Gly Thr Cys
        500                 505                 510

<210> SEQ ID NO 308
<211> LENGTH: 511
<212> TYPE: PRT
<213> ORGANISM: ARTIFICIAL SEQUENCE
<220> FEATURE:
<223> OTHER INFORMATION: aKLH 120.6 HC (IgG2)-ShK[1-35, R1K, I4A, Q16K]
      fusion protein

<400> SEQUENCE: 308

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45
```

```
Tyr Thr Phe Thr Gly Tyr His Met His Trp Val Arg Gln Ala Pro Gly
 50                  55                  60

Gln Gly Leu Glu Trp Met Gly Trp Ile Asn Pro Asn Ser Gly Gly Thr
 65                  70                  75                  80

Asn Tyr Ala Gln Lys Phe Gln Gly Arg Val Thr Met Thr Arg Asp Thr
                 85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
            115                 120                 125

Asp Pro Trp Gly Gln Gly Thr Leu Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Asn Phe Gly Thr Gln Thr Tyr Thr Cys
210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Gln Phe Asn Trp Tyr Val Asp Gly Val Glu Val
290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
            355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Gly Gly Gly Gly Ser Gly Gly Gly Gly Ser Lys Ser Cys Ala
```

-continued

```
                465                 470                 475                 480
Asp Thr Ile Pro Lys Ser Arg Cys Thr Ala Phe Lys Cys Lys His Ser
                    485                 490                 495
Met Lys Tyr Arg Leu Ser Phe Cys Arg Lys Thr Cys Gly Thr Cys
                    500                 505                 510

<210> SEQ ID NO 309
<211> LENGTH: 511
<212> TYPE: PRT
<213> ORGANISM: ARTIFICIAL SEQUENCE
<220> FEATURE:
<223> OTHER INFORMATION: aKLH 120.6 IgG2-ShK[1-35, R1K, Q16K, K30E]
      fusion protein

<400> SEQUENCE: 309

Met Asp Met Arg Val Pro Ala Gln Leu Leu Gly Leu Leu Leu Leu Trp
1               5                   10                  15
Leu Arg Gly Ala Arg Cys Gln Val Gln Leu Val Gln Ser Gly Ala Glu
                20                  25                  30
Val Lys Lys Pro Gly Ala Ser Val Lys Val Ser Cys Lys Ala Ser Gly
                35                  40                  45
Tyr Thr Phe Thr Gly Tyr His Met His Trp Val Arg Gln Ala Pro Gly
            50                  55                  60
Gln Gly Leu Glu Trp Met Gly Trp Ile Asn Pro Asn Ser Gly Gly Thr
65                  70                  75                  80
Asn Tyr Ala Gln Lys Phe Gln Gly Arg Val Thr Met Thr Arg Asp Thr
                85                  90                  95
Ser Ile Ser Thr Ala Tyr Met Glu Leu Ser Arg Leu Arg Ser Asp Asp
                100                 105                 110
Thr Ala Val Tyr Tyr Cys Ala Arg Asp Arg Gly Ser Tyr Tyr Trp Phe
            115                 120                 125
Asp Pro Trp Gly Gln Gly Thr Leu Val Thr Val Ser Ser Ala Ser Thr
130                 135                 140
Lys Gly Pro Ser Val Phe Pro Leu Ala Pro Cys Ser Arg Ser Thr Ser
145                 150                 155                 160
Glu Ser Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
            195                 200                 205
Val Val Thr Val Pro Ser Ser Asn Phe Gly Thr Gln Thr Tyr Thr Cys
        210                 215                 220
Asn Val Asp His Lys Pro Ser Asn Thr Lys Val Asp Lys Thr Val Glu
225                 230                 235                 240
Arg Lys Cys Cys Val Glu Cys Pro Pro Cys Pro Ala Pro Pro Val Ala
                245                 250                 255
Gly Pro Ser Val Phe Leu Phe Pro Pro Lys Pro Lys Asp Thr Leu Met
                260                 265                 270
Ile Ser Arg Thr Pro Glu Val Thr Cys Val Val Val Asp Val Ser His
            275                 280                 285
Glu Asp Pro Glu Val Gln Phe Asn Trp Tyr Val Asp Gly Val Glu Val
        290                 295                 300
His Asn Ala Lys Thr Lys Pro Arg Glu Glu Gln Phe Asn Ser Thr Phe
305                 310                 315                 320
```

```
Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Gly Gly Gly Ser Gly Gly Gly Ser Lys Ser Cys Ile
465                 470                 475                 480

Asp Thr Ile Pro Lys Ser Arg Cys Thr Ala Phe Lys Cys Lys His Ser
                485                 490                 495

Met Lys Tyr Arg Leu Ser Phe Cys Arg Glu Thr Cys Gly Thr Cys
            500                 505                 510

<210> SEQ ID NO 310
<211> LENGTH: 37
<212> TYPE: DNA
<213> ORGANISM: ARTIFICIAL SEQUENCE
<220> FEATURE:
<223> OTHER INFORMATION: Primer sequence

<400> SEQUENCE: 310
aggaggagga agcgccagct gcgccgacac catcccc                              37

<210> SEQ ID NO 311
<211> LENGTH: 37
<212> TYPE: DNA
<213> ORGANISM: ARTIFICIAL SEQUENCE
<220> FEATURE:
<223> OTHER INFORMATION: Primer sequence

<400> SEQUENCE: 311
ggggatggtg tcggcgcagc tggcgcttcc tcctcct                              37

<210> SEQ ID NO 312
<211> LENGTH: 30
<212> TYPE: DNA
<213> ORGANISM: ARTIFICIAL SEQUENCE
<220> FEATURE:
<223> OTHER INFORMATION: Primer sequence

<400> SEQUENCE: 312
gaggaggagg aagcgccagc tgcatcgaca                                      30

<210> SEQ ID NO 313
<211> LENGTH: 27
<212> TYPE: DNA
<213> ORGANISM: ARTIFICIAL SEQUENCE
<220> FEATURE:
<223> OTHER INFORMATION: Primer sequence
```

```
<400> SEQUENCE: 313
gagcttctgc cgcgagacct gcggcac                                27

<210> SEQ ID NO 314
<211> LENGTH: 27
<212> TYPE: DNA
<213> ORGANISM: ARTIFICIAL SEQUENCE
<220> FEATURE:
<223> OTHER INFORMATION: Primer sequence

<400> SEQUENCE: 314
cgatgcagct ggcgcttcct cctcctc                                27

<210> SEQ ID NO 315
<211> LENGTH: 27
<212> TYPE: DNA
<213> ORGANISM: ARTIFICIAL SEQUENCE
<220> FEATURE:
<223> OTHER INFORMATION: Primer sequence

<400> SEQUENCE: 315
gtgccgcagg tctcgcggca gaagctc                                27

<210> SEQ ID NO 316
<211> LENGTH: 36
<212> TYPE: DNA
<213> ORGANISM: ARTIFICIAL SEQUENCE
<220> FEATURE:
<223> OTHER INFORMATION: Primer sequence

<400> SEQUENCE: 316
ggaggaggaa gccacagctg cgccgacacc atcccc                      36

<210> SEQ ID NO 317
<211> LENGTH: 36
<212> TYPE: DNA
<213> ORGANISM: ARTIFICIAL SEQUENCE
<220> FEATURE:
<223> OTHER INFORMATION: Primer sequence

<400> SEQUENCE: 317
ggggatggtg tcggcgcagc tgtggcttcc tcctcc                      36

<210> SEQ ID NO 318
<211> LENGTH: 27
<212> TYPE: DNA
<213> ORGANISM: ARTIFICIAL SEQUENCE
<220> FEATURE:
<223> OTHER INFORMATION: Primer sequence

<400> SEQUENCE: 318
ggaggaggaa gccacagctg catcgac                                27

<210> SEQ ID NO 319
<211> LENGTH: 27
<212> TYPE: DNA
<213> ORGANISM: ARTIFICIAL SEQUENCE
<220> FEATURE:
<223> OTHER INFORMATION: Primer sequence

<400> SEQUENCE: 319
gtcgatgcag ctgtggcttc ctcctcc                                27

<210> SEQ ID NO 320
```

<210> SEQ ID NO 321
<211> LENGTH: 45
<212> TYPE: DNA
<213> ORGANISM: ARTIFICIAL SEQUENCE
<220> FEATURE:
<223> OTHER INFORMATION: Primer sequence

<400> SEQUENCE: 320
ccggaggagg aggaagcaag agctgcgccg acaccatccc caaga    45

<210> SEQ ID NO 321
<211> LENGTH: 45
<212> TYPE: DNA
<213> ORGANISM: ARTIFICIAL SEQUENCE
<220> FEATURE:
<223> OTHER INFORMATION: Primer sequence

<400> SEQUENCE: 321
tcttggggat ggtgtcggcg cagctcttgc ttcctcctcc tccgg    45

<210> SEQ ID NO 322
<211> LENGTH: 35
<212> TYPE: DNA
<213> ORGANISM: ARTIFICIAL SEQUENCE
<220> FEATURE:
<223> OTHER INFORMATION: Primer sequence

<400> SEQUENCE: 322
cggaggagga ggaagcaaga gctgcatcga cacca    35

<210> SEQ ID NO 323
<211> LENGTH: 33
<212> TYPE: DNA
<213> ORGANISM: ARTIFICIAL SEQUENCE
<220> FEATURE:
<223> OTHER INFORMATION: Primer sequence

<400> SEQUENCE: 323
tggtgtcgat gcagctcttg cttcctcctc ctc    33

<210> SEQ ID NO 324
<211> LENGTH: 493
<212> TYPE: PRT
<213> ORGANISM: ARTIFICIAL SEQUENCE
<220> FEATURE:
<223> OTHER INFORMATION: aKLH 120.6 IgG2 HC-Amp5 fusion protein

<400> SEQUENCE: 324

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125
```

```
Asp Pro Trp Gly Gln Gly Thr Leu Val Thr Val Ser Ser Ala Ser Thr
            130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Trp Tyr Val Asp Gly Val Glu Val His
                245                 250                 255

Asn Ala Lys Thr Lys Pro Arg Glu Glu Gln Phe Asn Ser Thr Phe Arg
            260                 265                 270

Val Val Ser Val Leu Thr Val Val His Gln Asp Trp Leu Asn Gly Lys
        275                 280                 285

Glu Tyr Lys Cys Lys Val Ser Pro Pro Cys Pro Ala Pro Pro Val Ala
    290                 295                 300

Gly Pro Ser Val Phe Leu Phe Pro Pro Lys Pro Lys Asp Thr Leu Met
305                 310                 315                 320

Ile Ser Arg Thr Pro Glu Val Thr Cys Val Val Val Asp Val Ser His
                325                 330                 335

Glu Asp Pro Glu Val Gln Phe Asn Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Gly Gly Gly Gly Gln Gly Cys Ser Ser Gly Gly Pro Thr
465                 470                 475                 480

Leu Arg Glu Trp Gln Gln Cys Arg Arg Ala Gln His Ser
                485                 490

<210> SEQ ID NO 325
<211> LENGTH: 59
<212> TYPE: DNA
<213> ORGANISM: ARTIFICIAL SEQUENCE
<220> FEATURE:
<223> OTHER INFORMATION: Forward primer sequence

<400> SEQUENCE: 325
```
aagctcgagg tcgactagac caccatggac atgagggtgc ccgctcagct cctggggct    59

<210> SEQ ID NO 326
<211> LENGTH: 51
<212> TYPE: DNA
<213> ORGANISM: ARTIFICIAL SEQUENCE
<220> FEATURE:
<223> OTHER INFORMATION: Reverse primer sequence

<400> SEQUENCE: 326
gccgctgctg cagccctgac caccacctcc accacccgga gacagggaga g    51

<210> SEQ ID NO 327
<211> LENGTH: 474
<212> TYPE: PRT
<213> ORGANISM: ARTIFICIAL SEQUENCE
<220> FEATURE:
<223> OTHER INFORMATION: VK1sp-KLH-120.6 IgG2 HC DesK-G5 fusion fragment

<400> SEQUENCE: 327

Met Asp Met Arg Val Pro Ala Gln Leu Leu Gly Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

-continued

```
Glu Asp Pro Glu Val Gln Phe Asn Trp Tyr Val Asp Gly Val Glu Val
            290                 295                 300
His Asn Ala Lys Thr Lys Pro Arg Glu Glu Gln Phe Asn Ser Thr Phe
305                 310                 315                 320
Arg Val Val Ser Val Leu Thr Val Val His Gln Asp Trp Leu Asn Gly
                325                 330                 335
Lys Glu Tyr Lys Cys Lys Val Ser Asn Lys Gly Leu Pro Ala Pro Ile
            340                 345                 350
Glu Lys Thr Ile Ser Lys Thr Lys Gly Gln Pro Arg Glu Pro Gln Val
        355                 360                 365
Tyr Thr Leu Pro Pro Ser Arg Glu Glu Met Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Met Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Gly Gly Gly Gly Gln Gly Cys
465                 470
```

<210> SEQ ID NO 328
<211> LENGTH: 51
<212> TYPE: DNA
<213> ORGANISM: ARTIFICIAL SEQUENCE
<220> FEATURE:
<223> OTHER INFORMATION: Forward primer sequence

<400> SEQUENCE: 328
ctctccctgt ctccgggtgg tggaggtggt ggtcagggct gcagcagcgg c        51

<210> SEQ ID NO 329
<211> LENGTH: 35
<212> TYPE: DNA
<213> ORGANISM: ARTIFICIAL SEQUENCE
<220> FEATURE:
<223> OTHER INFORMATION: Reverse primer sequence

<400> SEQUENCE: 329
ctactagcgg ccgctcagct atgctgagcg cggcg        35

<210> SEQ ID NO 330
<211> LENGTH: 33
<212> TYPE: PRT
<213> ORGANISM: ARTIFICIAL SEQUENCE
<220> FEATURE:
<223> OTHER INFORMATION: G5-AMP5 fusion fragment

<400> SEQUENCE: 330

```
Leu Ser Leu Ser Pro Gly Gly Gly Gly Gly Gln Gly Cys Ser Ser
1               5                   10                  15
Gly Gly Pro Thr Leu Arg Glu Trp Gln Gln Cys Arg Arg Ala Gln His
                20                  25                  30
Ser
```

```
<210> SEQ ID NO 331
<211> LENGTH: 493
<212> TYPE: PRT
<213> ORGANISM: ARTIFICIAL SEQUENCE
<220> FEATURE:
<223> OTHER INFORMATION: IgG2 DesK HC-AMP5 fusion polypeptide

<400> SEQUENCE: 331
```

| | | | | | | | | | | | | | | | |
|---|---|---|---|---|---|---|---|---|---|---|---|---|---|---|---|
| Met | Asp | Met | Arg | Val | Pro | Ala | Gln | Leu | Leu | Gly | Leu | Leu | Leu | Leu | Trp |
| 1 | | | | 5 | | | | | 10 | | | | | 15 | |
| Leu | Arg | Gly | Ala | Arg | Cys | Gln | Val | Gln | Leu | Val | Gln | Ser | Gly | Ala | Glu |
| | | | 20 | | | | | 25 | | | | | 30 | | |
| Val | Lys | Lys | Pro | Gly | Ala | Ser | Val | Lys | Val | Ser | Cys | Lys | Ala | Ser | Gly |
| | | 35 | | | | | 40 | | | | | 45 | | | |
| Tyr | Thr | Phe | Thr | Gly | Tyr | His | Met | His | Trp | Val | Arg | Gln | Ala | Pro | Gly |
| | 50 | | | | | 55 | | | | | 60 | | | | |
| Gln | Gly | Leu | Glu | Trp | Met | Gly | Trp | Ile | Asn | Pro | Asn | Ser | Gly | Gly | Thr |
| 65 | | | | | 70 | | | | | 75 | | | | | 80 |
| Asn | Tyr | Ala | Gln | Lys | Phe | Gln | Gly | Arg | Val | Thr | Met | Thr | Arg | Asp | Thr |
| | | | | 85 | | | | | 90 | | | | | 95 | |
| Ser | Ile | Ser | Thr | Ala | Tyr | Met | Glu | Leu | Ser | Arg | Leu | Arg | Ser | Asp | Asp |
| | | | 100 | | | | | 105 | | | | | 110 | | |
| Thr | Ala | Val | Tyr | Tyr | Cys | Ala | Arg | Asp | Arg | Gly | Ser | Tyr | Tyr | Trp | Phe |
| | | 115 | | | | | 120 | | | | | 125 | | | |
| Asp | Pro | Trp | Gly | Gln | Gly | Thr | Leu | Val | Thr | Val | Ser | Ser | Ala | Ser | Thr |
| | 130 | | | | | 135 | | | | | 140 | | | | |
| Lys | Gly | Pro | Ser | Val | Phe | Pro | Leu | Ala | Pro | Cys | Ser | Arg | Ser | Thr | Ser |
| 145 | | | | | 150 | | | | | 155 | | | | | 160 |
| Glu | Ser | Thr | Ala | Ala | Leu | Gly | Cys | Leu | Val | Lys | Asp | Tyr | Phe | Pro | Glu |
| | | | | 165 | | | | | 170 | | | | | 175 | |
| Pro | Val | Thr | Val | Ser | Trp | Asn | Ser | Gly | Ala | Leu | Thr | Ser | Gly | Val | His |
| | | | 180 | | | | | 185 | | | | | 190 | | |
| Thr | Phe | Pro | Ala | Val | Leu | Gln | Ser | Ser | Gly | Leu | Tyr | Ser | Leu | Ser | Ser |
| | | 195 | | | | | 200 | | | | | 205 | | | |
| Val | Val | Thr | Val | Pro | Ser | Ser | Asn | Phe | Gly | Thr | Gln | Thr | Tyr | Thr | Cys |
| | 210 | | | | | 215 | | | | | 220 | | | | |
| Asn | Val | Asp | His | Lys | Pro | Ser | Asn | Thr | Lys | Val | Asp | Lys | Thr | Val | Glu |
| 225 | | | | | 230 | | | | | 235 | | | | | 240 |
| Arg | Lys | Cys | Cys | Val | Glu | Cys | Pro | Pro | Cys | Pro | Ala | Pro | Pro | Val | Ala |
| | | | | 245 | | | | | 250 | | | | | 255 | |
| Gly | Pro | Ser | Val | Phe | Leu | Phe | Pro | Pro | Lys | Pro | Lys | Asp | Thr | Leu | Met |
| | | | 260 | | | | | 265 | | | | | 270 | | |
| Ile | Ser | Arg | Thr | Pro | Glu | Val | Thr | Cys | Val | Val | Val | Asp | Val | Ser | His |
| | | 275 | | | | | 280 | | | | | 285 | | | |
| Glu | Asp | Pro | Glu | Val | Gln | Phe | Asn | Trp | Tyr | Val | Asp | Gly | Val | Glu | Val |
| | 290 | | | | | 295 | | | | | 300 | | | | |
| His | Asn | Ala | Lys | Thr | Lys | Pro | Arg | Glu | Glu | Gln | Phe | Asn | Ser | Thr | Phe |
| 305 | | | | | 310 | | | | | 315 | | | | | 320 |
| Arg | Val | Val | Ser | Val | Leu | Thr | Val | Val | His | Gln | Asp | Trp | Leu | Asn | Gly |
| | | | | 325 | | | | | 330 | | | | | 335 | |
| Lys | Glu | Tyr | Lys | Cys | Lys | Val | Ser | Asn | Lys | Gly | Leu | Pro | Ala | Pro | Ile |
| | | | 340 | | | | | 345 | | | | | 350 | | |
| Glu | Lys | Thr | Ile | Ser | Lys | Thr | Lys | Gly | Gln | Pro | Arg | Glu | Pro | Gln | Val |
| | | 355 | | | | | 360 | | | | | 365 | | | |
| Tyr | Thr | Leu | Pro | Pro | Ser | Arg | Glu | Glu | Met | Thr | Lys | Asn | Gln | Val | Ser |

```
                    370                 375                 380
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
                450                 455                 460

Pro Gly Gly Gly Gly Gly Gln Gly Cys Ser Ser Gly Gly Pro Thr
465                 470                 475                 480

Leu Arg Glu Trp Gln Gln Cys Arg Arg Ala Gln His Ser
                485                 490

<210> SEQ ID NO 332
<211> LENGTH: 497
<212> TYPE: PRT
<213> ORGANISM: ARTIFICIAL SEQUENCE
<220> FEATURE:
<223> OTHER INFORMATION: AMP5-aKLH120.6-IgG2 Heavy Chain(HC)

<400> SEQUENCE: 332

Met Asp Met Arg Val Pro Ala Gln Leu Leu Gly Leu Leu Leu Leu Trp
1               5                   10                  15

Leu Arg Gly Ala Arg Cys Gln Gly Cys Ser Ser Gly Gly Pro Thr Leu
                20                  25                  30

Arg Glu Trp Gln Gln Cys Arg Arg Ala Gln His Ser Gly Gly Gly Gly
            35                  40                  45

Gly Gln Val Gln Leu Val Gln Ser Gly Ala Glu Val Lys Lys Pro Gly
        50                  55                  60

Ala Ser Val Lys Val Ser Cys Lys Ala Ser Gly Tyr Thr Phe Thr Gly
65                  70                  75                  80

Tyr His Met His Trp Val Arg Gln Ala Pro Gly Gln Gly Leu Glu Trp
                85                  90                  95

Met Gly Trp Ile Asn Pro Asn Ser Gly Gly Thr Asn Tyr Ala Gln Lys
                100                 105                 110

Phe Gln Gly Arg Val Thr Met Thr Arg Asp Thr Ser Ile Ser Thr Ala
            115                 120                 125

Tyr Met Glu Leu Ser Arg Leu Arg Ser Asp Asp Thr Ala Val Tyr Tyr
        130                 135                 140

Cys Ala Arg Asp Arg Gly Ser Tyr Tyr Trp Phe Asp Pro Trp Gly Gln
145                 150                 155                 160

Gly Thr Leu Val Thr Val Ser Ser Ala Ser Thr Lys Gly Pro Ser Val
                165                 170                 175

Phe Pro Leu Ala Pro Ser Ser Lys Ser Thr Ser Gly Gly Thr Ala Ala
                180                 185                 190

Leu Gly Cys Leu Val Lys Asp Tyr Phe Pro Glu Pro Val Thr Val Ser
            195                 200                 205

Trp Asn Ser Gly Ala Leu Thr Ser Gly Val His Thr Phe Pro Ala Val
        210                 215                 220

Leu Gln Ser Ser Gly Leu Tyr Ser Leu Ser Ser Val Val Thr Val Pro
225                 230                 235                 240

Ser Ser Ser Leu Gly Thr Gln Thr Tyr Ile Cys Asn Val Asn His Lys
```

```
                    245                 250                 255
Pro Ser Asn Thr Lys Val Asp Lys Arg Val Glu Pro Lys Ser Cys Asp
            260                 265                 270

Lys Thr His Thr Cys Pro Pro Cys Pro Ala Pro Glu Leu Leu Gly Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Gln Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
    370                 375                 380

Lys Thr Ile Ser Lys Ala Lys Gly Gln Pro Arg Glu Pro Gln Val Tyr
385                 390                 395                 400

Thr Leu Pro Pro Ser Arg Glu Glu Met Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Lys Leu Thr Val Asp
    450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly

<210> SEQ ID NO 333
<211> LENGTH: 38
<212> TYPE: DNA
<213> ORGANISM: ARTIFICIAL SEQUENCE
<220> FEATURE:
<223> OTHER INFORMATION: Reverse primer sequence

<400> SEQUENCE: 333
gccgctgctg cagccctgac atctggcacc tctcaacc                              38

<210> SEQ ID NO 334
<211> LENGTH: 28
<212> TYPE: PRT
<213> ORGANISM: ARTIFICIAL SEQUENCE
<220> FEATURE:
<223> OTHER INFORMATION: PCR-generated fusion peptide

<400> SEQUENCE: 334

Met Asp Met Arg Val Pro Ala Gln Leu Leu Gly Leu Leu Leu Leu Trp
1               5                   10                  15

Leu Arg Gly Ala Arg Cys Gln Gly Cys Ser Ser Gly
            20                  25

<210> SEQ ID NO 335
```

```
<211> LENGTH: 38
<212> TYPE: DNA
<213> ORGANISM: ARTIFICIAL SEQUENCE
<220> FEATURE:
<223> OTHER INFORMATION: Reverse primer sequence

<400> SEQUENCE: 335
ggttgagagg tgccagatgt cagggctgca gcagcggc                              38

<210> SEQ ID NO 336
<211> LENGTH: 42
<212> TYPE: DNA
<213> ORGANISM: ARTIFICIAL SEQUENCE
<220> FEATURE:
<223> OTHER INFORMATION: Reverse primer sequence

<400> SEQUENCE: 336
cagctgcacc tgaccaccac ctccaccgct atgctgagcg cg                         42

<210> SEQ ID NO 337
<211> LENGTH: 39
<212> TYPE: PRT
<213> ORGANISM: ARTIFICIAL SEQUENCE
<220> FEATURE:
<223> OTHER INFORMATION: Fusion polypeptide sequence

<400> SEQUENCE: 337

Trp Leu Arg Gly Ala Arg Cys Gln Gly Cys Ser Ser Gly Gly Pro Thr
1               5                   10                  15

Leu Arg Glu Trp Gln Gln Cys Arg Arg Ala Gln His Ser Gly Gly Gly
            20                  25                  30

Gly Gly Gln Val Gln Leu Val
        35

<210> SEQ ID NO 338
<211> LENGTH: 42
<212> TYPE: DNA
<213> ORGANISM: ARTIFICIAL SEQUENCE
<220> FEATURE:
<223> OTHER INFORMATION: Forward primer sequence

<400> SEQUENCE: 338
cgcgctcagc atagcggtgg aggtggtggt caggtgcagc tg                         42

<210> SEQ ID NO 339
<211> LENGTH: 34
<212> TYPE: DNA
<213> ORGANISM: ARTIFICIAL SEQUENCE
<220> FEATURE:
<223> OTHER INFORMATION: Reverse primer sequence

<400> SEQUENCE: 339
ctactagcgg ccgctcaacc cggagacagg gaga                                  34

<210> SEQ ID NO 340
<211> LENGTH: 458
<212> TYPE: PRT
<213> ORGANISM: ARTIFICIAL SEQUENCE
<220> FEATURE:
<223> OTHER INFORMATION: Fusion polypeptide sequence

<400> SEQUENCE: 340

Arg Ala Gln His Ser Gly Gly Gly Gly Gln Val Gln Leu Val Gln
1               5                   10                  15

Ser Gly Ala Glu Val Lys Lys Pro Gly Ala Ser Val Lys Val Ser Cys
```

-continued

```
                20                  25                  30
Lys Ala Ser Gly Tyr Thr Phe Thr Gly Tyr His Met His Trp Val Arg
             35                  40                  45
Gln Ala Pro Gly Gln Gly Leu Glu Trp Met Gly Trp Ile Asn Pro Asn
         50                  55                  60
Ser Gly Gly Thr Asn Tyr Ala Gln Lys Phe Gln Gly Arg Val Thr Met
 65                  70                  75                  80
Thr Arg Asp Thr Ser Ile Ser Thr Ala Tyr Met Glu Leu Ser Arg Leu
                 85                  90                  95
Arg Ser Asp Asp Thr Ala Val Tyr Tyr Cys Ala Arg Asp Arg Gly Ser
             100                 105                 110
Tyr Tyr Trp Phe Asp Pro Trp Gly Gln Gly Thr Leu Val Thr Val Ser
         115                 120                 125
Ser Ala Ser Thr Lys Gly Pro Ser Val Phe Pro Leu Ala Pro Ser Ser
    130                 135                 140
Lys Ser Thr Ser Gly Gly Thr Ala Ala Leu Gly Cys Leu Val Lys Asp
145                 150                 155                 160
Tyr Phe Pro Glu Pro Val Thr Val Ser Trp Asn Ser Gly Ala Leu Thr
                 165                 170                 175
Ser Gly Val His Thr Phe Pro Ala Val Leu Gln Ser Ser Gly Leu Tyr
             180                 185                 190
Ser Leu Ser Ser Val Val Thr Val Pro Ser Ser Ser Leu Gly Thr Gln
         195                 200                 205
Thr Tyr Ile Cys Asn Val Asn His Lys Pro Ser Asn Thr Lys Val Asp
    210                 215                 220
Lys Arg Val Glu Pro Lys Ser Cys Asp Lys Thr His Thr Cys Pro Pro
225                 230                 235                 240
Cys Pro Ala Pro Glu Leu Leu Gly Gly Pro Ser Val Phe Leu Phe Pro
                 245                 250                 255
Pro Lys Pro Lys Asp Thr Leu Met Ile Ser Arg Thr Pro Glu Val Thr
             260                 265                 270
Cys Val Val Val Asp Val Ser His Glu Asp Pro Glu Val Lys Phe Asn
         275                 280                 285
Trp Tyr Val Asp Gly Val Glu Val His Asn Ala Lys Thr Lys Pro Arg
    290                 295                 300
Glu Glu Gln Tyr Gln Ser Thr Tyr Arg Val Val Ser Val Leu Thr Val
305                 310                 315                 320
Leu His Gln Asp Trp Leu Asn Gly Lys Glu Tyr Lys Cys Lys Val Ser
                 325                 330                 335
Asn Lys Ala Leu Pro Ala Pro Ile Glu Lys Thr Ile Ser Lys Ala Lys
             340                 345                 350
Gly Gln Pro Arg Glu Pro Gln Val Tyr Thr Leu Pro Pro Ser Arg Glu
         355                 360                 365
Glu Met Thr Lys Asn Gln Val Ser Leu Thr Cys Leu Val Lys Gly Phe
    370                 375                 380
Tyr Pro Ser Asp Ile Ala Val Glu Trp Glu Ser Asn Gly Gln Pro Glu
385                 390                 395                 400
Asn Asn Tyr Lys Thr Thr Pro Pro Val Leu Asp Ser Asp Gly Ser Phe
                 405                 410                 415
Phe Leu Tyr Ser Lys Leu Thr Val Asp Lys Ser Arg Trp Gln Gln Gly
             420                 425                 430
Asn Val Phe Ser Cys Ser Val Met His Glu Ala Leu His Asn His Tyr
         435                 440                 445
```

Thr Gln Lys Ser Leu Ser Leu Ser Pro Gly
        450                 455

<210> SEQ ID NO 341
<211> LENGTH: 496
<212> TYPE: PRT
<213> ORGANISM: ARTIFICIAL SEQUENCE
<220> FEATURE:
<223> OTHER INFORMATION: aKLH 120.6 hIgG1 N297Q-Amp5 Fc(CH3) Loop fusion

<400> SEQUENCE: 341

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Gln Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Gly Gly
        370                 375                 380

Gln Gly Cys Ser Ser Gly Gly Pro Thr Leu Arg Glu Trp Gln Gln Cys
385                 390                 395                 400

Arg Arg Ala Gln His Ser Gly Gly Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

<210> SEQ ID NO 342
<211> LENGTH: 263
<212> TYPE: PRT
<213> ORGANISM: ARTIFICIAL SEQUENCE
<220> FEATURE:
<223> OTHER INFORMATION: Amp5-KLH-120.6 kappa LC fusion protein

<400> SEQUENCE: 342

Met Asp Met Arg Val Pro Ala Gln Leu Leu Gly Leu Leu Leu Leu Trp
1               5                   10                  15

Leu Arg Gly Ala Arg Cys Gln Cys Ser Ser Gly Gly Pro Thr Leu
            20                  25                  30

Arg Glu Trp Gln Gln Cys Arg Arg Ala Gln His Ser Gly Gly Gly Gly
        35                  40                  45

Gly Asp Ile Gln Met Thr Gln Ser Pro Ser Ser Leu Ser Ala Ser Val
    50                  55                  60

Gly Asp Arg Val Thr Ile Thr Cys Arg Ala Ser Gln Gly Ile Arg Asn
65                  70                  75                  80

Asp Leu Gly Trp Tyr Gln Gln Lys Pro Gly Lys Ala Pro Lys Arg Leu
                85                  90                  95

Ile Tyr Ala Ala Ser Ser Leu Gln Ser Gly Val Pro Ser Arg Phe Ser
            100                 105                 110

Gly Ser Gly Ser Gly Thr Glu Phe Thr Leu Thr Ile Ser Ser Leu Gln
        115                 120                 125

Pro Glu Asp Phe Ala Thr Tyr Tyr Cys Leu Gln His Asn Ser Tyr Pro
    130                 135                 140

Leu Thr Phe Gly Gly Gly Thr Lys Val Glu Ile Lys Arg Thr Val Ala
145                 150                 155                 160

Ala Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Glu Val Thr His Gln Gly Leu Ser Ser Pro Val Thr Lys
            245                 250                 255

Ser Phe Asn Arg Gly Glu Cys
        260

<210> SEQ ID NO 343
<211> LENGTH: 30
<212> TYPE: DNA
<213> ORGANISM: ARTIFICIAL SEQUENCE
<220> FEATURE:
<223> OTHER INFORMATION: Primer sequence

<400> SEQUENCE: 343
cattctagaa ccaccatgga catgagggtg                                    30

<210> SEQ ID NO 344
<211> LENGTH: 48
<212> TYPE: DNA
<213> ORGANISM: ARTIFICIAL SEQUENCE
<220> FEATURE:
<223> OTHER INFORMATION: Primer sequence

<400> SEQUENCE: 344
ctgggtcatc tggatgtcac caccacctcc accgctatgc tgagcgcg               48

<210> SEQ ID NO 345
<211> LENGTH: 40
<212> TYPE: PRT
<213> ORGANISM: ARTIFICIAL SEQUENCE
<220> FEATURE:
<223> OTHER INFORMATION: Fusion peptide sequence

<400> SEQUENCE: 345

Trp Leu Arg Gly Ala Arg Cys Gln Gly Cys Ser Ser Gly Gly Pro Thr
1               5                   10                  15

Leu Arg Glu Trp Gln Gln Cys Arg Arg Ala Gln His Ser Gly Gly Gly
            20                  25                  30

Gly Gly Asp Ile Gln Met Thr Gln
        35                  40

<210> SEQ ID NO 346
<211> LENGTH: 48
<212> TYPE: DNA
<213> ORGANISM: ARTIFICIAL SEQUENCE
<220> FEATURE:
<223> OTHER INFORMATION: Forward primer sequence

<400> SEQUENCE: 346
cgcgctcagc atagcggtgg aggtggtggt gacatccaga tgacccag                48

<210> SEQ ID NO 347
<211> LENGTH: 41
<212> TYPE: DNA
<213> ORGANISM: ARTIFICIAL SEQUENCE
<220> FEATURE:
<223> OTHER INFORMATION: Reverse primer sequence

<400> SEQUENCE: 347
aaccgtttaa acgcggccgc tcaacactct ccctgttga a                        41

<210> SEQ ID NO 348

```
<211> LENGTH: 224
<212> TYPE: PRT
<213> ORGANISM: ARTIFICIAL SEQUENCE
<220> FEATURE:
<223> OTHER INFORMATION: Fusion peptide sequence

<400> SEQUENCE: 348
```

Arg Ala Gln His Ser Gly Gly Gly Gly Asp Ile Gln Met Thr Gln
1               5                   10                  15

Ser Pro Ser Ser Leu Ser Ala Ser Val Gly Asp Arg Val Thr Ile Thr
            20                  25                  30

Cys Arg Ala Ser Gln Gly Ile Arg Asn Asp Leu Gly Trp Tyr Gln Gln
        35                  40                  45

Lys Pro Gly Lys Ala Pro Lys Arg Leu Ile Tyr Ala Ala Ser Ser Leu
    50                  55                  60

Gln Ser Gly Val Pro Ser Arg Phe Ser Gly Ser Gly Ser Gly Thr Glu
65                  70                  75                  80

Phe Thr Leu Thr Ile Ser Ser Leu Gln Pro Glu Asp Phe Ala Thr Tyr
                85                  90                  95

Tyr Cys Leu Gln His Asn Ser Tyr Pro Leu Thr Phe Gly Gly Gly Thr
            100                 105                 110

Lys Val Glu Ile Lys Arg Thr Val Ala Ala Pro Ser Val Phe Ile Phe
        115                 120                 125

Pro Pro Ser Asp Glu Gln Leu Lys Ser Gly Thr Ala Ser Val Val Cys
    130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Glu Cys
    210                 215                 220

```
<210> SEQ ID NO 349
<211> LENGTH: 39
<212> TYPE: PRT
<213> ORGANISM: Homo sapiens
<220> FEATURE:
<221> NAME/KEY: MISC_FEATURE
<223> OTHER INFORMATION: Exendin 4 polypeptide

<400> SEQUENCE: 349
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

```
<210> SEQ ID NO 350
<211> LENGTH: 273
<212> TYPE: PRT
<213> ORGANISM: ARTIFICIAL SEQUENCE
<220> FEATURE:
<223> OTHER INFORMATION: (VK-1 SP)-C681-KLH-120.6 IgG2 variable HC
      fusion polypeptide
```

-continued

<400> SEQUENCE: 350

```
Met Asp Met Arg Val Pro Ala Gln Leu Leu Gly Leu Leu Leu Leu Trp
1               5                   10                  15

Leu Arg Gly Ala Arg Cys Ser Gly Gly Ser Cys Leu Pro Asp Gln Phe
            20                  25                  30

Arg Cys Gly Asn Gly Gln Cys Ile Pro Leu Asp Trp Val Cys Asp Gly
        35                  40                  45

Val Asn Asp Cys Pro Asp Ser Asp Glu Glu Gly Cys Pro Pro Arg
    50                  55                  60

Thr Cys Ala Pro Ser Gln Phe Gln Cys Gly Ser Gly Tyr Cys Ile Ser
65                  70                  75                  80

Gln Arg Trp Val Cys Asp Gly Glu Asn Asp Cys Glu Asp Gly Ser Asp
                85                  90                  95

Glu Ala Asn Cys Ala Gly Ser Val Pro Thr Cys Pro Ser Asp Glu Phe
            100                 105                 110

Arg Cys Arg Asn Gly Arg Cys Ile Pro Arg Ala Trp Arg Cys Asp Gly
        115                 120                 125

Val Asn Asp Cys Ala Asp Asn Ser Asp Glu Glu Asp Cys Thr Glu His
    130                 135                 140

Thr Gly Gly Gly Gly Gln Val Gln Leu Val Gln Ser Gly Ala Glu
145                 150                 155                 160

Val Lys Lys Pro Gly Ala Ser Val Lys Val Ser Cys Lys Ala Ser Gly
                165                 170                 175

Tyr Thr Phe Thr Gly Tyr His Met His Trp Val Arg Gln Ala Pro Gly
            180                 185                 190

Gln Gly Leu Glu Trp Met Gly Trp Ile Asn Pro Asn Ser Gly Gly Thr
        195                 200                 205

Asn Tyr Ala Gln Lys Phe Gln Gly Arg Val Thr Met Thr Arg Asp Thr
    210                 215                 220

Ser Ile Ser Thr Ala Tyr Met Glu Leu Ser Arg Leu Arg Ser Asp Asp
225                 230                 235                 240

Thr Ala Val Tyr Tyr Cys Ala Arg Asp Arg Gly Ser Tyr Tyr Trp Phe
                245                 250                 255

Asp Pro Trp Gly Gln Gly Thr Leu Val Thr Val Ser Ser Ala Ser Thr
            260                 265                 270

Lys
```

<210> SEQ ID NO 351
<211> LENGTH: 267
<212> TYPE: DNA
<213> ORGANISM: ARTIFICIAL SEQUENCE
<220> FEATURE:
<223> OTHER INFORMATION: SalI (5') and BamHI (3')DNA Fragment

<400> SEQUENCE: 351

```
gtcgactaga ccaccatgga catgagggtc cccgctcagc tcctggggct cctgctattg      60
tggttgagag gtgccagatg tcatggggag gaacattta caagcgatct gagcaaacaa     120
atggaggaag aggcagttag actgttcatt gaatggctca gaacggcgg accgagtagt     180 ggtgctccgc ctcccagcgg atctggcagc gctactggtg gatctggatc gggtgcatcc     240
tctggatctg gaagcgctac cggatcc                                         267
```

<210> SEQ ID NO 352
<211> LENGTH: 29
<212> TYPE: DNA

```
<213> ORGANISM: ARTIFICIAL SEQUENCE
<220> FEATURE:
<223> OTHER INFORMATION: Primer sequence

<400> SEQUENCE: 352
aatggatccg acatccagat gacccagtc                                29

<210> SEQ ID NO 353
<211> LENGTH: 23
<212> TYPE: DNA
<213> ORGANISM: ARTIFICIAL SEQUENCE
<220> FEATURE:
<223> OTHER INFORMATION: Primer sequence

<400> SEQUENCE: 353
aatgcggccg ctcaacactc tcc                                      23

<210> SEQ ID NO 354
<211> LENGTH: 920
<212> TYPE: DNA
<213> ORGANISM: ARTIFICIAL SEQUENCE
<220> FEATURE:
<223> OTHER INFORMATION: Ex-4-1kG-KLH-120.6 kappa LC coding sequence
      construct

<400> SEQUENCE: 354
gtcgactaga ccaccatgga catgagggtc cccgctcagc tcctggggct cctgctattg    60
tggttgagag gtgccagatg tcatggggag ggaacattta caagcgatct gagcaaacaa   120
atggaggaag aggcagttag actgttcatt gaatggctca agaacggcgg accgagtagt   180
ggtgctccgc ctcccagcgg atctggcagc gctactggtg atctggatc gggtgcatcc    240 tctggatctg gaagcgctac cggatccgac atccagatga cccagtctcc atcctccctg   300
tctgcatctg taggagacag agtcaccatc acttgccggg caagtcaggg cattagaaat   360
gatttaggct ggtatcagca gaaaccaggg aaagccccta acgcctgat ctatgctgca    420 tccagtttgc aaagtggggt cccatcaagg ttcagcggca gtggatctgg gacagaattc   480
actctcacaa tcagcagcct gcagcctgaa gattttgcaa cttattactg tctacagcat   540
aatagttacc cgctcacttt cggcggaggg accaaggtgg agatcaaacg aactgtggct   600
gcaccatctg tcttcatctt cccgccatct gatgagcagt tgaaatctgg aactgcctct   660
gttgtgtgcc tgctgaataa cttctatccc agagaggcca agtacagtg gaaggtggat    720 aacgccctcc aatcgggtaa ctcccaggag agtgtcacag agcaggacag caaggacagc   780
acctacagcc tcagcagcac cctgacgctg agcaaagcag actacgagaa acacaaagtc   840
tacgcctgcg aagtcaccca tcagggcctg agctcgcccg tcacaaagag cttcaacagg   900
ggagagtgtt gagcggccgc                                              920

<210> SEQ ID NO 355
<211> LENGTH: 298
<212> TYPE: PRT
<213> ORGANISM: ARTIFICIAL SEQUENCE
<220> FEATURE:
<223> OTHER INFORMATION: (VK-1 SP)-Ex-4-1kG-KLH-120.6 kappa LC

<400> SEQUENCE: 355

Met Asp Met Arg Val Pro Ala Gln Leu Leu Gly Leu Leu Leu Leu Trp
1               5                   10                  15

Leu Arg Gly Ala Arg Cys His Gly Glu Gly Thr Phe Thr Ser Asp Leu
            20                  25                  30
```

```
Ser Lys Gln Met Glu Glu Ala Val Arg Leu Phe Ile Glu Trp Leu
         35                  40                  45
Lys Asn Gly Gly Pro Ser Ser Gly Ala Pro Pro Ser Gly Ser Gly
 50                  55                  60
Ser Ala Thr Gly Ser Gly Ser Gly Ala Ser Ser Gly Ser Gly Ser
 65                  70                  75                  80
Ala Thr Gly Ser Asp Ile Gln Met Thr Gln Ser Pro Ser Ser Leu Ser
                 85                  90                  95
Ala Ser Val Gly Asp Arg Val Thr Ile Thr Cys Arg Ala Ser Gln Gly
                100                 105                 110
Ile Arg Asn Asp Leu Gly Trp Tyr Gln Gln Lys Pro Gly Lys Ala Pro
                115                 120                 125
Lys Arg Leu Ile Tyr Ala Ala Ser Ser Leu Gln Ser Gly Val Pro Ser
                130                 135                 140
Arg Phe Ser Gly Ser Gly Ser Gly Thr Glu Phe Thr Leu Thr Ile Ser
145                 150                 155                 160
Ser Leu Gln Pro Glu Asp Phe Ala Thr Tyr Tyr Cys Leu Gln His Asn
                165                 170                 175
Ser Tyr Pro Leu Thr Phe Gly Gly Gly Thr Lys Val Glu Ile Lys Arg
                180                 185                 190
Thr Val Ala Ala Pro Ser Val Phe Ile Phe Pro Pro Ser Asp Glu Gln
                195                 200                 205
Leu Lys Ser Gly Thr Ala Ser Val Val Cys Leu Leu Asn Asn Phe Tyr
                210                 215                 220
Pro Arg Glu Ala Lys Val Gln Trp Lys Val Asp Asn Ala Leu Gln Ser
225                 230                 235                 240
Gly Asn Ser Gln Glu Ser Val Thr Glu Gln Asp Ser Lys Asp Ser Thr
                245                 250                 255
Tyr Ser Leu Ser Ser Thr Leu Thr Leu Ser Lys Ala Asp Tyr Glu Lys
                260                 265                 270
His Lys Val Tyr Ala Cys Glu Val Thr His Gln Gly Leu Ser Ser Pro
                275                 280                 285
Val Thr Lys Ser Phe Asn Arg Gly Glu Cys
                290                 295
```

<210> SEQ ID NO 356
<211> LENGTH: 594
<212> TYPE: PRT
<213> ORGANISM: ARTIFICIAL SEQUENCE
<220> FEATURE:
<223> OTHER INFORMATION: (VK-1 SP)-C681-aKLH 120.6 IgG2 HC fusion

<400> SEQUENCE: 356

```
Met Asp Met Arg Val Pro Ala Gln Leu Leu Gly Leu Leu Leu Leu Trp
 1               5                  10                  15
Leu Arg Gly Ala Arg Cys Ser Gly Gly Ser Cys Leu Pro Asp Gln Phe
                 20                  25                  30
Arg Cys Gly Asn Gly Gln Cys Ile Pro Leu Asp Trp Val Cys Asp Gly
                 35                  40                  45
Val Asn Asp Cys Pro Asp Asp Ser Asp Glu Glu Gly Cys Pro Pro Arg
 50                  55                  60
Thr Cys Ala Pro Ser Gln Phe Gln Cys Gly Ser Gly Tyr Cys Ile Ser
 65                  70                  75                  80
Gln Arg Trp Val Cys Asp Gly Glu Asn Asp Cys Glu Asp Gly Ser Asp
                 85                  90                  95
```

```
Glu Ala Asn Cys Ala Gly Ser Val Pro Thr Cys Pro Ser Asp Glu Phe
                100                 105                 110

Arg Cys Arg Asn Gly Arg Cys Ile Pro Arg Ala Trp Arg Cys Asp Gly
            115                 120                 125

Val Asn Asp Cys Ala Asp Asn Ser Asp Glu Glu Asp Cys Thr Glu His
        130                 135                 140

Thr Gly Gly Gly Gly Gln Val Gln Leu Val Gln Ser Gly Ala Glu
145                 150                 155                 160

Val Lys Lys Pro Gly Ala Ser Val Lys Val Ser Cys Lys Ala Ser Gly
                165                 170                 175

Tyr Thr Phe Thr Gly Tyr His Met His Trp Val Arg Gln Ala Pro Gly
            180                 185                 190

Gln Gly Leu Glu Trp Met Gly Trp Ile Asn Pro Asn Ser Gly Gly Thr
        195                 200                 205

Asn Tyr Ala Gln Lys Phe Gln Gly Arg Val Thr Met Thr Arg Asp Thr
210                 215                 220

Ser Ile Ser Thr Ala Tyr Met Glu Leu Ser Arg Leu Arg Ser Asp Asp
225                 230                 235                 240

Thr Ala Val Tyr Tyr Cys Ala Arg Asp Arg Gly Ser Tyr Tyr Trp Phe
                245                 250                 255

Asp Pro Trp Gly Gln Gly Thr Leu Val Thr Val Ser Ser Ala Ser Thr
            260                 265                 270

Lys Gly Pro Ser Val Phe Pro Leu Ala Pro Cys Ser Arg Ser Thr Ser
        275                 280                 285

Glu Ser Thr Ala Ala Leu Gly Cys Leu Val Lys Asp Tyr Phe Pro Glu
290                 295                 300

Pro Val Thr Val Ser Trp Asn Ser Gly Ala Leu Thr Ser Gly Val His
305                 310                 315                 320

Thr Phe Pro Ala Val Leu Gln Ser Ser Gly Leu Tyr Ser Leu Ser Ser
                325                 330                 335

Val Val Thr Val Pro Ser Ser Asn Phe Gly Thr Gln Thr Tyr Thr Cys
            340                 345                 350

Asn Val Asp His Lys Pro Ser Asn Thr Lys Val Asp Lys Thr Val Glu
        355                 360                 365

Arg Lys Cys Cys Val Glu Cys Pro Pro Cys Pro Ala Pro Pro Val Ala
370                 375                 380

Gly Pro Ser Val Phe Leu Phe Pro Pro Lys Pro Lys Asp Thr Leu Met
385                 390                 395                 400

Ile Ser Arg Thr Pro Glu Val Thr Cys Val Val Val Asp Val Ser His
                405                 410                 415

Glu Asp Pro Glu Val Gln Phe Asn Trp Tyr Val Asp Gly Val Glu Val
            420                 425                 430

His Asn Ala Lys Thr Lys Pro Arg Glu Glu Gln Phe Asn Ser Thr Phe
        435                 440                 445

Arg Val Val Ser Val Leu Thr Val His Gln Asp Trp Leu Asn Gly
450                 455                 460

Lys Glu Tyr Lys Cys Lys Val Ser Asn Lys Gly Leu Pro Ala Pro Ile
465                 470                 475                 480

Glu Lys Thr Ile Ser Lys Thr Lys Gly Gln Pro Arg Glu Pro Gln Val
                485                 490                 495

Tyr Thr Leu Pro Pro Ser Arg Glu Glu Met Thr Lys Asn Gln Val Ser
            500                 505                 510

Leu Thr Cys Leu Val Lys Gly Phe Tyr Pro Ser Asp Ile Ala Val Glu
```

```
            515                 520                 525
Trp Glu Ser Asn Gly Gln Pro Glu Asn Tyr Lys Thr Thr Pro Pro
    530                 535                 540

Met Leu Asp Ser Asp Gly Ser Phe Phe Leu Tyr Ser Lys Leu Thr Val
545                 550                 555                 560

Asp Lys Ser Arg Trp Gln Gln Gly Asn Val Phe Ser Cys Ser Val Met
                565                 570                 575

His Glu Ala Leu His Asn His Tyr Thr Gln Lys Ser Leu Ser Leu Ser
            580                 585                 590

Pro Gly

<210> SEQ ID NO 357
<211> LENGTH: 594
<212> TYPE: PRT
<213> ORGANISM: ARTIFICIAL SEQUENCE
<220> FEATURE:
<223> OTHER INFORMATION: aKLH 120.6 IgG2 HC-C681 fusion polypeptide

<400> SEQUENCE: 357

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
                20                  25                  30

Val Lys Lys Pro Gly Ala Ser Val Lys Val Ser Cys Lys Ala Ser Gly
            35                  40                  45

Tyr Thr Phe Thr Gly Tyr His Met His Trp Val Arg Gln Ala Pro Gly
        50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285
```

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Gly Gly Gly Gly Ser Gly Gly Ser Cys Leu Pro Asp Gln
465                 470                 475                 480

Phe Arg Cys Gly Asn Gly Gln Cys Ile Pro Leu Asp Trp Val Cys Asp
                485                 490                 495

Gly Val Asn Asp Cys Pro Asp Asp Ser Asp Glu Glu Gly Cys Pro Pro
            500                 505                 510

Arg Thr Cys Ala Pro Ser Gln Phe Gln Cys Gly Ser Gly Tyr Cys Ile
        515                 520                 525

Ser Gln Arg Trp Val Cys Asp Gly Glu Asn Asp Cys Glu Asp Gly Ser
530                 535                 540

Asp Glu Ala Asn Cys Ala Gly Ser Val Pro Thr Cys Pro Ser Asp Glu
545                 550                 555                 560

Phe Arg Cys Arg Asn Gly Arg Cys Ile Pro Arg Ala Trp Arg Cys Asp
                565                 570                 575

Gly Val Asn Asp Cys Ala Asp Asn Ser Asp Glu Glu Asp Cys Thr Glu
            580                 585                 590

His Thr

<210> SEQ ID NO 358
<211> LENGTH: 217
<212> TYPE: PRT
<213> ORGANISM: ARTIFICIAL SEQUENCE
<220> FEATURE:
<223> OTHER INFORMATION: C681 avimer polypeptide sequence

<400> SEQUENCE: 358

Met Thr Lys Asn Gln Val Ser Leu Thr Cys Leu Val Lys Gly Phe Tyr
1               5                   10                  15

Pro Ser Asp Ile Ala Val Glu Trp Glu Ser Asn Gly Gln Pro Glu Asn
            20                  25                  30

Asn Tyr Lys Thr Thr Pro Pro Met Leu Asp Ser Asp Gly Ser Phe Phe
        35                  40                  45

```
Leu Tyr Ser Lys Leu Thr Val Asp Lys Ser Arg Trp Gln Gln Gly Asn
             50                  55                  60

Val Phe Ser Cys Ser Val Met His Glu Ala Leu His Asn His Tyr Thr
 65                  70                  75                  80

Gln Lys Ser Leu Ser Leu Ser Pro Gly Gly Gly Gly Gly Ser Gly
                 85                  90                  95

Gly Ser Cys Leu Pro Asp Gln Phe Arg Cys Gly Asn Gly Gln Cys Ile
                100                 105                 110

Pro Leu Asp Trp Val Cys Asp Gly Val Asn Asp Cys Pro Asp Asp Ser
                115                 120                 125

Asp Glu Glu Gly Cys Pro Pro Arg Thr Cys Ala Pro Ser Gln Phe Gln
130                 135                 140

Cys Gly Ser Gly Tyr Cys Ile Ser Gln Arg Trp Val Cys Asp Gly Glu
145                 150                 155                 160

Asn Asp Cys Glu Asp Gly Ser Asp Glu Ala Asn Cys Ala Gly Ser Val
                165                 170                 175

Pro Thr Cys Pro Ser Asp Glu Phe Arg Cys Arg Asn Gly Arg Cys Ile
                180                 185                 190

Pro Arg Ala Trp Arg Cys Asp Gly Val Asn Asp Cys Ala Asp Asn Ser
                195                 200                 205

Asp Glu Glu Asp Cys Thr Glu His Thr
210                 215

<210> SEQ ID NO 359
<211> LENGTH: 364
<212> TYPE: PRT
<213> ORGANISM: ARTIFICIAL SEQUENCE
<220> FEATURE:
<223> OTHER INFORMATION: C681-aKLH 120.6 kappa LC fusion

<400> SEQUENCE: 359

Met Asp Met Arg Val Pro Ala Gln Leu Leu Gly Leu Leu Leu Leu Trp
 1               5                  10                  15

Leu Arg Gly Ala Arg Cys Ser Gly Gly Ser Cys Leu Pro Asp Gln Phe
                 20                  25                  30

Arg Cys Gly Asn Gly Gln Cys Ile Pro Leu Asp Trp Val Cys Asp Gly
             35                  40                  45

Val Asn Asp Cys Pro Asp Asp Ser Asp Glu Glu Gly Cys Pro Pro Arg
 50                  55                  60

Thr Cys Ala Pro Ser Gln Phe Gln Cys Gly Ser Gly Tyr Cys Ile Ser
 65                  70                  75                  80

Gln Arg Trp Val Cys Asp Gly Glu Asn Asp Cys Glu Asp Gly Ser Asp
                 85                  90                  95

Glu Ala Asn Cys Ala Gly Ser Val Pro Thr Cys Pro Ser Asp Glu Phe
                100                 105                 110

Arg Cys Arg Asn Gly Arg Cys Ile Pro Arg Ala Trp Arg Cys Asp Gly
            115                 120                 125

Val Asn Asp Cys Ala Asp Asn Ser Asp Glu Glu Asp Cys Thr Glu His
                130                 135                 140

Thr Gly Gly Gly Gly Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Gly Ile Arg Asn Asp Leu Gly Trp Tyr Gln Gln Lys Pro Gly Lys
                180                 185                 190
```

Ala Pro Lys Arg Leu Ile Tyr Ala Ala Ser Ser Leu Gln Ser Gly Val
            195                 200                 205

Pro Ser Arg Phe Ser Gly Ser Gly Ser Gly Thr Glu Phe Thr Leu Thr
        210                 215                 220

Ile Ser Ser Leu Gln Pro Glu Asp Phe Ala Thr Tyr Tyr Cys Leu Gln
225                 230                 235                 240

His Asn Ser Tyr Pro Leu Thr Phe Gly Gly Gly Thr Lys Val Glu Ile
                245                 250                 255

Lys Arg Thr Val Ala Ala Pro Ser Val Phe Ile Phe Pro Pro Ser Asp
            260                 265                 270

Glu Gln Leu Lys Ser Gly Thr Ala Ser Val Val Cys Leu Leu Asn Asn
        275                 280                 285

Phe Tyr Pro Arg Glu Ala Lys Val Gln Trp Lys Val Asp Asn Ala Leu
        290                 295                 300

Gln Ser Gly Asn Ser Gln Glu Ser Val Thr Glu Gln Asp Ser Lys Asp
305                 310                 315                 320

Ser Thr Tyr Ser Leu Ser Ser Thr Leu Thr Leu Ser Lys Ala Asp Tyr
                325                 330                 335

Glu Lys His Lys Val Tyr Ala Cys Glu Val Thr His Gln Gly Leu Ser
            340                 345                 350

Ser Pro Val Thr Lys Ser Phe Asn Arg Gly Glu Cys
        355                 360

<210> SEQ ID NO 360
<211> LENGTH: 261
<212> TYPE: PRT
<213> ORGANISM: ARTIFICIAL SEQUENCE
<220> FEATURE:
<223> OTHER INFORMATION: (VK-1 SP)-C681-(G5)-aKLH 120.6 kappa variable
      LC fusion polypeptide

<400> SEQUENCE: 360

Met Asp Met Arg Val Pro Ala Gln Leu Leu Gly Leu Leu Leu Leu Trp
1               5                   10                  15

Leu Arg Gly Ala Arg Cys Ser Gly Gly Ser Cys Leu Pro Asp Gln Phe
            20                  25                  30

Arg Cys Gly Asn Gly Gln Cys Ile Pro Leu Asp Trp Val Cys Asp Gly
        35                  40                  45

Val Asn Asp Cys Pro Asp Ser Asp Glu Glu Gly Cys Pro Arg
    50                  55                  60

Thr Cys Ala Pro Ser Gln Phe Gln Cys Gly Ser Gly Tyr Cys Ile Ser
65                  70                  75                  80

Gln Arg Trp Val Cys Asp Gly Glu Asn Asp Cys Glu Asp Gly Ser Asp
                85                  90                  95

Glu Ala Asn Cys Ala Gly Ser Val Pro Thr Cys Pro Ser Asp Glu Phe
            100                 105                 110

Arg Cys Arg Asn Gly Arg Cys Ile Pro Arg Ala Trp Arg Cys Asp Gly
        115                 120                 125

Val Asn Asp Cys Ala Asp Asn Ser Asp Glu Glu Asp Cys Thr Glu His
    130                 135                 140

Thr Gly Gly Gly Gly Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Gly Ile Arg Asn Asp Leu Gly Trp Tyr Gln Gln Lys Pro Gly Lys
            180                 185                 190

Ala Pro Lys Arg Leu Ile Tyr Ala Ala Ser Ser Leu Gln Ser Gly Val
            195                 200                 205

Pro Ser Arg Phe Ser Gly Ser Gly Ser Gly Thr Glu Phe Thr Leu Thr
        210                 215                 220

Ile Ser Ser Leu Gln Pro Glu Asp Phe Ala Thr Tyr Tyr Cys Leu Gln
225                 230                 235                 240

His Asn Ser Tyr Pro Leu Thr Phe Gly Gly Gly Thr Lys Val Glu Ile
                245                 250                 255

Lys Arg Thr Val Ala
            260

<210> SEQ ID NO 361
<211> LENGTH: 35
<212> TYPE: PRT
<213> ORGANISM: Stichodactyla helianthus

<400> SEQUENCE: 361

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
                20                  25                  30

Gly Thr Cys
        35

<210> SEQ ID NO 362
<211> LENGTH: 36
<212> TYPE: PRT
<213> ORGANISM: ARTIFICIAL SEQUENCE
<220> FEATURE:
<223> OTHER INFORMATION: [Lys16]ShK-Ala

<400> SEQUENCE: 362

Arg Ser Cys Ile Asp Thr Ile Pro Lys Ser Arg Cys Thr Ala Phe Lys
1               5                   10                  15

Cys Lys His Ser Met Lys Tyr Arg Leu Ser Phe Cys Arg Lys Thr Cys
                20                  25                  30

Gly Thr Cys Ala
        35

<210> SEQ ID NO 363
<211> LENGTH: 35
<212> TYPE: PRT
<213> ORGANISM: Stichodactyla helianthus
<220> FEATURE:
<221> NAME/KEY: MISC_FEATURE
<223> OTHER INFORMATION: PEGylated

<400> SEQUENCE: 363

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
                20                  25                  30

Gly Thr Cys
        35

<210> SEQ ID NO 364
<211> LENGTH: 35
<212> TYPE: PRT
<213> ORGANISM: ARTIFICIAL SEQUENCE
<220> FEATURE:
<223> OTHER INFORMATION: ShK PEGylated toxin peptide

```
<220> FEATURE:
<221> NAME/KEY: MISC_FEATURE
<222> LOCATION: (1)..(1)
<223> OTHER INFORMATION: PEGylated

<400> SEQUENCE: 364

Arg Ser Cys Ile Asp Thr Ile Pro Lys Ser Arg Cys Thr Ala Phe Lys
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 365
<211> LENGTH: 36
<212> TYPE: PRT
<213> ORGANISM: ARTIFICIAL SEQUENCE
<220> FEATURE:
<223> OTHER INFORMATION: PEGylated toxin peptide analog
<220> FEATURE:
<221> NAME/KEY: MISC_FEATURE
<222> LOCATION: (1)..(1)
<223> OTHER INFORMATION: 20kDa PEG-[Lys16]ShK-Ala

<400> SEQUENCE: 365

Arg Ser Cys Ile Asp Thr Ile Pro Lys Ser Arg Cys Thr Ala Phe Lys
1               5                   10                  15

Cys Lys His Ser Met Lys Tyr Arg Leu Ser Phe Cys Arg Lys Thr Cys
            20                  25                  30

Gly Thr Cys Ala
        35

<210> SEQ ID NO 366
<211> LENGTH: 463
<212> TYPE: PRT
<213> ORGANISM: ARTIFICIAL SEQUENCE
<220> FEATURE:
<223> OTHER INFORMATION: H23 sequence

<400> SEQUENCE: 366

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr His Met His Trp Val Arg Gln Ala Pro Gly Gln Gly Leu
    50                  55                  60

Glu Trp Met Gly Trp Ile Asn Pro Asn Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Asp Arg Gly Ser Tyr Tyr Trp Phe Asp Pro Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160
```

```
Ala Ala Leu Gly Cys Leu Val Lys Asp Tyr Phe Pro Glu Pro Val Thr
            165                 170                 175

Val Ser Trp Asn Ser Gly Ala Leu Thr Ser Gly Val His Thr Phe Pro
        180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly
    450                 455                 460

<210> SEQ ID NO 367
<211> LENGTH: 467
<212> TYPE: PRT
<213> ORGANISM: ARTIFICIAL SEQUENCE
<220> FEATURE:
<223> OTHER INFORMATION: H24 sequence

<400> SEQUENCE: 367

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr His Met His Trp Val Arg Gln Ala Pro Gly
    50                  55                  60
```

```
Gln Gly Leu Glu Trp Met Gly Trp Ile Asn Pro Asn Ser Gly Gly Thr
 65                  70                  75                  80

Asn Tyr Ala Gln Lys Phe Gln Gly Arg Val Thr Met Thr Arg Asp Thr
                 85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Asp Arg Gly Ser Tyr Tyr Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

```
<210> SEQ ID NO 368
<211> LENGTH: 659
<212> TYPE: DNA
<213> ORGANISM: ARTIFICIAL SEQUENCE
<220> FEATURE:
<223> OTHER INFORMATION: BamHI (5') to NotI (3') DNA fragment

<400> SEQUENCE: 368
ggatccgaca tccagatgac ccagtctcca tcctccctgt ctgcatctgt aggagacaga      60
gtcaccatca cttgccgggc aagtcagggc attagaaatg atttaggctg gtatcagcag     120
aaaccaggga aagcccctaa acgcctgatc tatgctgcat ccagtttgca aagtggggtc     180
ccatcaaggt tcagcggcag tggatctggg acagaattca ctctcacaat cagcagcctg     240
cagcctgaag attttgcaac ttattactgt ctacagcata atagttaccc gctcactttc     300
ggcggaggga ccaaggtgga gatcaaacga actgtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata acgcctccaa atcgggtaac     480
tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
cagggcctga gctcgcccgt cacaaagagc ttcaacaggg gagagtgttg agcggccgc      659
```